(12) United States Patent
Roos et al.

(10) Patent No.: US 7,645,588 B2
(45) Date of Patent: Jan. 12, 2010

(54) COMPOSITION COMPRISING A CELL COMPRISING A STIM1 PROTEIN AND AN AGENT THAT MODULATES INTRACELLULAR CALCIUM AND METHODS OF USE

(75) Inventors: Jack Roos, San Diego, CA (US); Kenneth A. Stauderman, San Diego, CA (US); Gonul Velicelebi, San Diego, CA (US); Paul J. Digregorio, San Diego, CA (US); Kari Lynn Ohlsen, San Diego, CA (US)

(73) Assignee: CalciMedica, Inc., La Jolla, CA (US)

( * ) Notice: Subject to any disclaimer, the term of this patent is extended or adjusted under 35 U.S.C. 154(b) by 0 days.

(21) Appl. No.: 10/547,720

(22) PCT Filed: Mar. 3, 2004

(86) PCT No.: PCT/US2004/006542

§ 371 (c)(1),
(2), (4) Date: Jul. 18, 2006

(87) PCT Pub. No.: WO2004/078995

PCT Pub. Date: Sep. 16, 2004

(65) Prior Publication Data
US 2007/0031814 A1    Feb. 8, 2007

Related U.S. Application Data

(60) Provisional application No. 60/451,958, filed on Mar. 4, 2003.

(51) Int. Cl.
*G01N 33/53* (2006.01)
*C12P 21/02* (2006.01)
*C07K 14/435* (2006.01)
*A61K 33/06* (2006.01)

(52) U.S. Cl. .............. 435/7.2; 435/69.1; 530/350; 424/682

(58) Field of Classification Search ............... 435/7.2, 435/69.1; 530/350; 424/682
See application file for complete search history.

(56) References Cited

U.S. PATENT DOCUMENTS 4,716,150 A * 12/1987 Van Eldik et al. ............ 514/14
6,171,864 B1 * 1/2001 Coughlan et al. ........... 435/469
2002/0034728 A1   3/2002 Normant et al.

FOREIGN PATENT DOCUMENTS

WO    WO-99-32619 A1   7/1999
WO    WO-02-30976 A1   4/2002

OTHER PUBLICATIONS

Petersen et al., "The role of endoplasmic reticulum calcium pumps during cytosolic calcium spiking in pancreatic acinar cells," J Biol Chem 268(30):22262-22264, 1993.*
Williams et al., "Identification and characterization of the STIM (stromal interaction molecule) gene family: coding for a novel class of transmembrane proteins," Biochem J 357:673,685, 2001.*
Williams et al., "Identification and characterization of the STIM (stromal interaction molecule) gene family: coding for a novel class of transmembrane proteins," Biochem J 367:673-685, 2001.*
Michalak et al., "Ca2+ signaling and calcium binding chaperones of the endoplasmic reticulum," Cell Calcium 32:26-278, 2002.*

(Continued)

*Primary Examiner*—Karen Cochrane Carlson
*Assistant Examiner*—Rosanne Kosson
(74) *Attorney, Agent, or Firm*—Wilson Sonsini Goodrich & Rosati

(57) ABSTRACT

Methods are provided for identifying agents that modulate intracellular calcium. Also provided are methods of modulating calcium within cells and methods of identifying proteins involved in modulating intracellular calcium.

13 Claims, 4 Drawing Sheets

OTHER PUBLICATIONS

Figure 1:
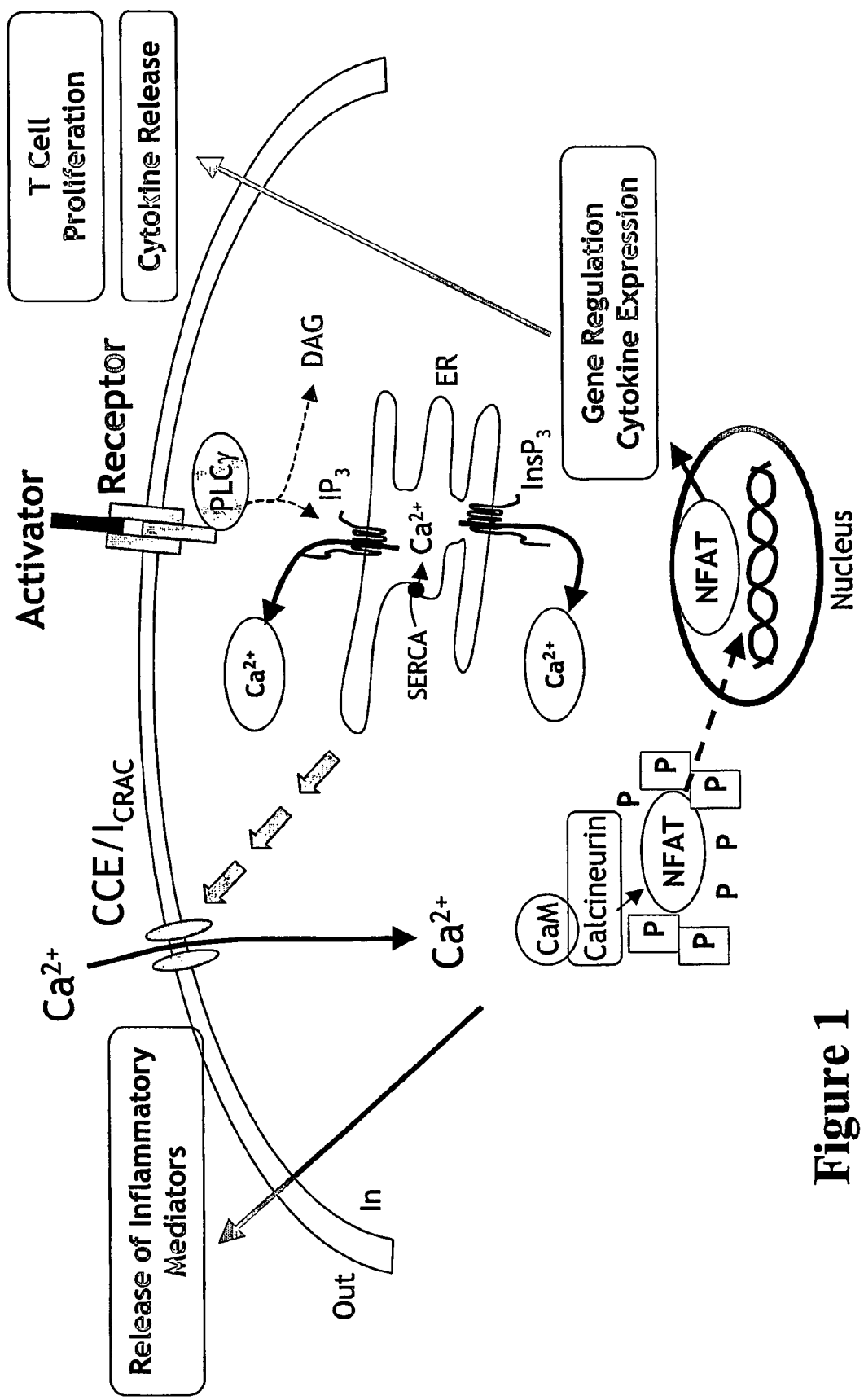

Wikipedia entry for HEK cells, http://en.wikipedia.org/wiki/Hek293#Origins_of_HEK_Cells, printed on May 2, 2008.*

Williams et al., "Stromal interaction molecule 1 (STIM1), a transmembrane protein with growth suppressor activity, contains an extracellular SAM domain modified by N-linked glycosylation," Biochim Biophys Acta 1596:131-137, Apr. 1, 2002.*

Cahill, J., "Protein and antibody arrays and their medical applications," Immunol. Meth. 250:81-91 (2001).

Clemens et al., "Use of double-stranded RNA interference in *Drosophila* cell lines to dissect signal transduction pathways," PNAS USA 97:6499-6503 (2000).

Eroshkin et al., "Algorithm and computer program Pro_Anal for analysis of relationship between structure and activity in a family of proteins or peptides," Comput. Appl. Biosci. 9:491-497 (1993).

Fanger et al., "Characterization of T Cell Mutants with Defects in Capacitative Calcium Entry: Genetic Evidence for the Physiological Roles of CRAC Channels," J. Cell Biol. 131:655-657 (1995).

Feske et al., "Gene regulation mediated by calcium signals in T lymphocytes," Nature Immunol. 2:316-324 (2001).

Hanes and Pluckthun, "In vitro selection and evoluation of functional proteins by using ribosome display," PNAS USA 13:4937-4942 (1997).

Karvonen et al., "Psoriasis and Altered Calcium Metabolism: Downregulated Capacitative Calcium Influx and Defective Calcium-Mediated Cell Signaling in Cultured Psoriatic Keratinocytes," J. Invest. Dermatol. 114:693-700 (2000).

Koi et al., "Tumor Cell Growth Arrest Caused by Subchromosomal Transferable DNA Fragments from Chromosome 11," Science 260:361-364 (1993).

LeDeist et al., "A primary T-cell immunodeficiency associated with defective transmembrane calcium influx," Blood 85:1053-1062 (1995).

Martin et al., "Relation between Phosphatidylserine Exposure and Store-Operated Ca2+ Entry in Stimulated Cells," Biochem. Biophys. Res. Commun. 279:639-645 (2000).

Martinez et al., "Significance of Capacitative Ca Entry in the Regulation of Phosphatidylserine Expression at the Surface of Stimulated Cells," Biochem. 38:10092-10098 (1999).

Oritani and Kincade, "Identification of Stromal Cell Products That Interact with Pre-B Cells," J. Cell Biol. 134:771-782 (1996).

Partiseti et al., "The Calcium Current Activated by T Cell Receptor and Store Depletion in Human Lymphocytes Is Absent in a Primary Immunodeficiency," J. Biol. Chem. 269:32327-32335 (1994).

Rodi et al., "One from col. A and two from col. B: the benefits of phage display in molecular-recognition studies," Curr. Opin. Chem. Biol. 6:92-96 (2002).

Rubinson et al., "A lentivirus-based system to functionally silence genes in primary mammalian cells, stem cells and transgenic mice by RNA interference," Nature Genet. 33:401-406(2003) and Corrigendum, vol. 39(6):803 (2007).

Tiscornia et al., "A general method for gene knockdown in mice by using lentiviral vectors expressing small interfering RNA," PNAS 100:1844-1848 (2003).

Williams et al., "Stromal interaction molecule 1 (STIM1), a transmembrane protein with growth suppressor activity, contains an extracellular SAM domain modified by N-linked glycosylation," Biochim. Biophys. Acta 1596:131-137 (2002).

* cited by examiner

COMPOSITION COMPRISING A CELL COMPRISING A STIM1 PROTEIN AND AN AGENT THAT MODULATES INTRACELLULAR CALCIUM AND METHODS OF USE

RELATED APPLICATIONS

This application is the U.S. national phase of International Application No. PCT/US04/06542, filed on Mar. 3, 2004. The International Application claims priority to U.S. Provisional Application Ser. No. 60/451,958, filed Mar. 4, 2003, entitled "Methods of Modulating and Identifying Agents that Modulate Intracellular Calcium." Where permitted, the subject matter and contents, including sequence listing, of this provisional application are incorporated by reference herein in their entirety.

FIELD OF THE INVENTION

The present invention relates to methods of identifying agents that modulate intracellular calcium. The invention further relates to methods of modulating calcium within cells and treating disease by modulating intracellular calcium. The invention also relates to methods of screening for candidate intracellular calcium-modulating proteins and nucleic acids encoding such proteins and methods of identifying intracellular calcium-modulating proteins and nucleic acids encoding such proteins.

BACKGROUND OF THE INVENTION

Calcium plays a vital role in cell function and survival. For example, calcium is a key element in the transduction of signals into and within cells. Cellular responses to growth factors, neurotransmitters, hormones and a variety of other signal molecules are initiated through calcium-dependent processes. Many proteins are activated by binding calcium and in turn affect other proteins in signal cascade mechanisms in cells. The normal basal concentration of free calcium in the cytoplasm of cells is about 50-100 nM whereas the extracellular calcium concentration is typically about 2 mM. Therefore, intracellular calcium levels and fluctuations thereof are tightly regulated by cells.

Calcium regulation by cells is accomplished through a variety of mechanisms, some of which are associated with particular cell types. For example, excitable cells, such as muscle and nerve cells in which calcium signals are essential to functions including contraction and transmission of nerve impulses, contain voltage-gated calcium channels spanning the cell membrane. These channels respond to depolarization of the potential difference across the membrane and can open to permit an influx of calcium from the extracellular medium and a rapid increase in intracellular calcium concentrations.

Nonexcitable cells, e.g., blood cells, fibroblasts and epithelial cells, as well as many excitable cells, contain channels that span intracellular membranes and that can open to permit an influx of calcium into the cytoplasm from calcium-storing organelles, such as the endoplasmic reticulum. One such intracellular ion channel is the inositol 1,4,5-triphosphate ($IP_3$) receptor located in the membrane of the endoplasmic reticulum. The $IP_3$ receptor functions as a ligand-gated ion channel that permits passage of calcium upon binding of $IP_3$ released through hydrolysis of membrane phospholipids by activated phospholipase C (PLC). PLC can be activated through agonist binding to a surface membrane G protein-coupled receptor. Activation of the $IP_3$ receptor results in the release of calcium stored in the endoplasmic reticulum into the cytoplasm. Reduced endoplasmic reticulum calcium concentration resulting from release of calcium therefrom provides a signal for influx of calcium from the extracellular medium into the cell. It appears that this influx of calcium does not rely on voltage-gated plasma membrane channels and does not involve activation of calcium channels by calcium. This calcium influx mechanism has been referred to as capacitative calcium entry (CCE) or store-operated calcium entry (SOCE). The actual factor that directly activates influx of calcium across the plasma membrane in CCE is unknown, as is the identity of the molecule or molecules that provide for mobilization of calcium across the plasma membrane and into the cell.

Because of the vital role that calcium plays in cell function and survival, dysregulation of calcium in cells can have deleterious effects on cell structure and function. Alterations in intracellular calcium homeostasis have been implicated in a variety of diseases.

There is a need, therefore, to elucidate the factors, structures and mechanisms involved in calcium regulation in cells, which may be targets for therapeutic intervention in diseases associated with calcium dysregulation. There is also a need for agents that modulate intracellular calcium and methods of identifying such agents as possible therapeutic compounds for treatment of diseases associated with calcium dysregulation.

SUMMARY

Methods for identifying an agent that modulates intracellular calcium are provided. In one embodiment, the methods include the steps of: contacting one or more test cells or a portion thereof comprising one or more proteins with a test agent, wherein the one or more proteins is/are (a) at least about 45% homologous to the protein encoded by *Drosophila* gene CG9126 and/or a stromal interacting molecule (STIM) or STIM-like protein over at least about 52% of the protein or (b) a portion of a protein that is at least about 45% homologous to the protein encoded by *Drosophila* gene CG9126 and/or a stromal interacting molecule (STIM) or STIM-like protein over at least about 52% of the protein; assessing the effect(s) of the test agent on intracellular calcium; and identifying a test agent as an agent that modulates intracellular calcium if it has an effect on intracellular calcium.

In another embodiment, the methods include the steps of: contacting one or more test cells or a portion thereof comprising a stromal interacting molecule (STIM) protein or portion thereof; assessing the effect(s) of the test agent on intracellular calcium; and identifying a test agent as an agent that modulates intracellular calcium if it has an effect on intracellular calcium.

In a further embodiment, the methods include the steps of: assessing the effects of an agent on intracellular calcium, wherein the agent modulates an activity of, an interaction of, the level of or binds to or interacts with a protein that is at least about 45% homologous to the protein encoded by *Drosophila* gene CG9126 and/or a stromal interacting molecule (STIM) protein over at least about 52% of the protein; and identifying a test agent as an agent that modulates intracellular calcium if it has an effect on intracellular calcium.

In another embodiment, the methods include the steps of: assessing the effects of an agent on intracellular calcium, wherein the agent modulates an activity of, an interaction of, the level of or binds to or interacts with a STIM or STIM-like protein; and identifying a test agent as an agent that modulates intracellular calcium if it has an effect on intracellular calcium.

In a further embodiment, the methods include the steps of: assessing the effects of a test agent on (a) a protein that is at least about 45% homologous to the protein encoded by *Drosophila* gene CG9126 and/or a stromal interacting molecule (STIM) protein over at least about 52% of the protein or (b) a portion of a protein that is at least about 45% homologous to the protein encoded by *Drosophila* gene CG9126 and/or a stromal interacting molecule (STIM) protein over at least about 52% of the protein, wherein the test agent modulates intracellular calcium; and identifying a test agent as an agent that modulates intracellular calcium if it has an effect on a protein, or portion thereof, that is at least about 45% homologous to the protein encoded by *Drosophila* gene CG9126 and/or a stromal interacting molecule (STIM) protein over at least about 52% of the protein.

In another embodiment, the methods include the steps of: assessing the effects of a test agent on a stromal interacting molecule (STIM) or STIM-like protein, or portion thereof, wherein the test agent modulates intracellular calcium; and identifying a test agent as an agent that modulates intracellular calcium if it has an effect on a STIM or STIM-like protein, or portion thereof.

In methods of identifying an agent that modulates intracellular calcium, at least one of the one or more proteins can be STIM1 or a STIM2 protein; a protein at least about 50% homologous, or at least about 62% homologous, to the protein encoded by *Drosophila* gene CG9126 over at least about 77% of the encoded protein; a protein at least about 67% homologous to a mammalian STIM1 protein over at least about 86% of the protein; a protein at least about 67% homologous to the amino acid sequence set forth as SEQ ID NO: 90 over at least about 86% of the sequence; or a STIM or STIM-like protein containing one or more of the following domains: (a) a sterile "α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezrin/radixin/moesin domain, and (e) a diacylglycerol kinase accessory domain. At least one of the one or more proteins can be involved in, participate in and/or provide for store-operated calcium entry. At least one of the one or more proteins can be an ion transport protein or a component of an ion transport protein complex.

In methods of identifying an agent that modulates intracellular calcium that include a step of assessing the effects of an agent on intracellular calcium, the step can involve assessing the effect(s) of the test agent on store-operated calcium entry, the calcium level in an intracellular calcium store, the movement of an ion into, out of or within an intracellular calcium store, cytosolic calcium buffering and/or resting cytosolic calcium levels. The step can involve assessing the effect of test agent on intracellular and/or extracellular a) ion movement, b) ion flux or c) ion levels of the one or more test cells.

In methods of identifying an agent that modulates intracellular calcium that include a step of assessing the effects of a test agent on a protein or portion thereof, the step can involve assessing binding or interaction of the test agent with the protein or portion thereof; assessing the effect of the test agent on homotypic binding of the protein or portion thereof or on binding of the protein or portion thereof to a second protein; assessing the effect of the test agent on the level or size of the protein, or portion thereof, in a cell or portion thereof; assessing the effect of the test agent on the level or size of nucleic acid encoding the protein, or portion thereof, in a cell, or portion thereof; assessing the effect of the test agent on the level of expression of a nucleic acid sequence operatively linked to a promoter from a gene encoding the protein; assessing the effect of the test agent on STIM protein, or a portion thereof, interaction with an immune system cell, or portion thereof; assessing the effect of the test agent on STIM-dependent augmentation of pre-B cell proliferation; assessing the effect of the test agent on STIM-dependent suppression of tumor cell growth; or assessing the effect of a test agent on Notch signaling.

Also provided are systems that can be used, for example, in methods of identifying an agent or a molecule that modulates intracellular calcium. In one embodiment, the systems include: a cell, or portion thereof, comprising one or more heterologous proteins and/or heterologous nucleic acid encoding one or more proteins that is/are (a) at least about 45% homologous to the protein encoded by *Drosophila* gene CG9126 and/or a stromal interacting molecule (STIM) or STIM-like protein over at least about 52% of the protein or (b) a portion of a protein that is at least about 45% homologous to the protein encoded by *Drosophila* gene CG9126 and/or a stromal interacting molecule (STIM) or STIM-like protein over at least about 52% of the protein; and an agent that provides for reduction of calcium levels in an intracellular calcium store.

In another embodiment, the systems include: a cell, or portion thereof, comprising one or more heterologous STIM of STIM-like proteins, or a portion thereof and/or heterologous nucleic acid encoding one or more STIM or STIM-like proteins, or a portion thereof; and an agent that provides for reduction of calcium levels in an intracellular calcium store.

In a further embodiment, the systems include: a cell, or portion thereof, comprising one or more heterologous proteins and/or heterologous nucleic acid encoding one or more proteins that is/are (a) at least about 45% homologous to the protein encoded by *Drosophila* gene CG9126 and/or a stromal interacting molecule (STIM) or STIM-like protein over at least about 52% of the protein or (b) a portion of a protein that is at least about 45% homologous to the protein encoded by *Drosophila* gene CG9126 and/or a stromal interacting molecule (STIM) or STIM-like protein over at least about 52% of the protein; and a molecule used in monitoring or measuring calcium and/or calcium movement.

In another embodiment, the systems include: a cell, or portion thereof, comprising one or more heterologous STIM or STIM-like proteins, or a portion thereof, and/or heterologous nucleic acid encoding one or more STIM of STIM-like proteins, or a portion thereof; and a molecule used in monitoring or measuring calcium and/or calcium movement.

In such systems, the protein can be STIM1 or a STIM2 protein; a protein at least about 50% homologous, or at least about 62% homologous, to the protein encoded by *Drosophila* gene CG9126 over at least about 77% of the encoded protein; a protein at least about 67% homologous to a mammalian STIM1 protein over at least about 86% of the protein; a protein at least about 67% homologous to the amino acid sequence set forth as SEQ ID NO: 90 over at least about 86% of the sequence; or a STIM or STIM-like protein containing one or more of the following domains: (a) a sterile "α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezrin/radixin/moesin domain, and (e) a diacylglycerol kinase accessory domain. The protein can be involved in, participate in and/or provide for store-operated calcium entry. The protein can be an ion transport protein or a component of an ion transport protein complex. Also provided are methods of identifying a molecule involved in modulating intracellular calcium.

In one embodiment, the methods involve the step of: assessing the effect of a test molecule on intracellular calcium, wherein the test molecule interacts with a protein that is (a) at least about 45% homologous to the protein encoded by *Drosophila* gene CG9126 and/or a stromal interacting molecule (STIM) or STIM-like protein over at least about 52% of the protein or (b) a portion of a protein that is at least about 45% homologous to the protein encoded by *Drosophila* gene CG9126 and/or a stromal interacting molecule (STIM) or STIM-like protein over at least about 52% of the protein; and identifying a test molecule as a molecule involved in modulating intracellular calcium if it has an effect on intracellular calcium.

In another embodiment, the methods involve the step of: assessing the effect of a test molecule on intracellular calcium, wherein the test molecule interacts with a STIM or STIM-like protein, or portion thereof; and identifying a test molecule as a molecule involved in modulating intracellular calcium if it has an effect on intracellular calcium.

In the methods of identifying a molecule that modulates intracellular calcium, the protein can be STIM1 or a STIM2 protein; a protein at least about 50% homologous, or at least about 62% homologous, to the protein encoded by *Drosophila* gene CG9126 over at least about 77% of the encoded protein; a protein at least about 67% homologous to a mammalian STIM1 protein over at least about 86% of the protein; a protein at least about 67% homologous to the amino acid sequence set forth as SEQ ID NO: 90 over at least about 86% of the sequence; or a STIM or STIM-like protein containing one or more of the following domains: (a) a sterile "α-motif (SAM) domain comprising one or more N-linked glycosylation sites and, optionally, an N-liked glycosylation site in the amino acid sequence on either side of the SAM domain, (b) a dibasic sequence of a proteolytic cleavage site, (c) an ATP synthase B/B' domain, (d) an ezxrin/radixin/moesin domain, and (e) a diacylglycerol kinase accessory domain. The protein can be involved in, participate in and/or provide for store-operated calcium entry. The protein can be an ion transport protein or a component of an ion transport protein complex. In methods of identifying a molecule that modulates intracellular calcium that include a step of assessing the effects of a test molecule on intracellular calcium, the step can involve assessing the effect(s) of the molecule on store-operated calcium entry, the calcium level in an intracellular calcium store, the movement of an ion into, out of or within an intracellular calcium store, cytosolic calcium buffering and/or resting cytosolic calcium levels.

Also provided is a method of modulating intracellular calcium, comprising modulating in a cell, or portion thereof, one or more proteins, or nucleic acid encoding one or more proteins, that is (are) at least about 45% homologous to the protein encoded by *Drosophila* gene CG9126 and/or a stromal interacting molecule (STIM) or STIM-like protein over at least about 52% of the protein, thereby modulating intracellular calcium in a cell or portion thereof.

In this method, intracellular calcium, for example, can be altered in the cell or portion thereof. In embodiments of this method, store-operated calcium entry, calcium buffering, calcium levels in and intracellular calcium store and/or movement of calcium into, out of or within an intracellular calcium store can be altered in the cell or portion thereof.

In this method, modulating includes modulating the level of, expression of, activity of or molecular interactions of one or more proteins or nucleic acid encoding one or more proteins. In certain embodiments, modulating includes increasing the level of, expression of, activity of or molecular interactions of one or more proteins or nucleic acid encoding one or more proteins. In other embodiments, modulating includes reducing the level of, expression of, activity of or molecular interactions of one or more proteins or nucleic acid encoding one or more proteins.

The cells include mammalian cells, such as but are limited to rodents and human cells. A portion of a cell in these methods includes a plasma membrane, a cell organelle, an intracellular store or a membrane of a cell organelle or intracellular store. In embodiments of these methods, at least one of the one or more proteins is a STIM1 or a STIM2 protein. In particular embodiments, the protein is at least about 50%, or at least about 62%, homologous to the protein encoded by *Drosophila* gene CG9126 over at least about 77% of the encoded protein. The protein can be at least about 67% homologous to a mammalian STIM1 protein over at least about 86% of the protein. For example, the protein can be least about 67% homologous to the amino acid sequence set forth as SEQ ID NO: 90 over at least about 86% of the sequence.

In other embodiments of these methods, the protein is a STIM or STIM-like protein containing one or more of the following domains: (a) a sterile α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezxrin/radixin/moesin domain, and (e) a diacylglycerol kinase accessory domain. The protein can be one that is involved in, participates in and/or provides for store-operated calcium entry, and can be, for example, an ion transport protein or a component of an ion transport protein complex. The protein can be a mammalian protein, such as a rodent or human protein. In all methods, test molecules can be any molecules, including proteins; the mammals include humans and rodents.

Also provided are isolated nucleic acid molecules that encode a rodent reference STIM1. In one exemplary embodiment, the isolated nucleic acid molecules contain a sequence of nucleotides encoding rat STIM1 (SEQ ID NO: 97). In another exemplary embodiment, the isolated nucleic acid molecules contain a sequence of nucleotides encoding hamster STIM1 (SEQ ID NO: 95). In one exemplary embodiment, the isolated nucleic acid molecules contain a sequence of nucleotides encoding reference STIM1 (SEQ ID NO: 52) or a portion thereof such as mature reference STIM1 (amino acids 23-685 of SEQ ID NO: 52) or a polypeptide with no greater than 16 amino acid substitutions relative to the mature reference STIM1, which retains at least one biological activity of STIM1. In another embodiment, the isolated nucleic acid molecules contain a sequence of nucleotides encoding a polypeptide hamster or rat STIM1 (SEQ ID NO: 96 and 98).

In another embodiment, the isolated nucleic acid molecules contain a sequence of nucleotides selected from among a) a nucleotide sequence encoding rodent reference STIM1 extracellular domain; b) a nucleotide sequence encoding a polypeptide with no greater than 3 amino acid substitutions relative to a), which retains at least one biological activity of STIM1 extracellular domain; c) a nucleotide sequence encoding rodent reference STIM1 cytoplasmic domain; d) a nucleotide sequence encoding a polypeptide with no greater than 13 amino acid substitutions relative to c), which retains at least one biological activity of STIM1 cytoplasmic domain; e) a sequence of nucleotides encoding rodent reference STIM1 Glu-rich domain; and f) a nucleotide sequence encoding rodent reference STIM1 Pro-Ser rich domain.

In one embodiment, the isolated nucleic acid molecules are operatively linked to a promoter of gene expression. In another embodiment, the nucleic acid molecules are contained in a vector. The nucleic acid molecules or a vector containing the nucleic acid molecules can be present in a host cell.

Also provided are isolated oligonucleotides containing at least 17 contiguous nucleotides of SEQ ID NO: 51, wherein the contiguous nucleotides include a position selected from among positions 15, 63, 69, 84, 103, 108, 112, 120, 150, 183, 201, 207, 210, 213, 240, 300, 303, 312, 330, 357, 402, 441, 474, 570, 621, 660, 697, 738, 783, 795, 861, 873, 874, 895, 951, 1051, 1062, 1107, 1200, 1224, 1228, 1278, 1299, 1392, 1395, 1452, 1580, 1652, 1654, 1675, 1747, 1749, 1173, 1854, 1855, 1881, 1884, 1888, 1896, 2001 and 2025 of SEQ ID NO:51 or a corresponding position in rodent reference STIM1 sequences as set forth in SEQ ID NOs: 95 and 97. Also provided are isolated oligonucleotides that specifically hybridizes to SEQ ID NO:51, but do not specifically hybridize to SEQ ID NO:3, SEQ ID NO:9 or SEQ ID NO:82.

Also provided are isolated STIM1 polypeptides and portions thereof. In one embodiment, the polypeptides contain reference STIM1 (SEQ ID NO:52) or mature reference STIM1 (amino acids 23-685 of SEQ ID NO: 52) or an amino acid sequence with no greater than 13 amino acid substitutions relative to a rodent reference STIM1, such as set forth in SEQ ID NO:52, SEQ ID NO:96; and SEQ ID NO:98. In another embodiment, the polypeptides contain a sequence of amino acids set forth in SEQ ID NO: 96 or SEQ ID NO: 98.

In another embodiment, the polypeptides contain a polypeptide selected from among: a) rodent reference STIM1 extracellular domain; b) a polypeptide with no greater than 3 amino acid substitutions relative to a), which retains at least one biological activity of STIM1 extracellular domain; c) rodent reference STIM1 cytoplasmic domain; d) a polypeptide with no greater than 13 amino acid substitutions relative to c), which retains at least one biological activity of STIM1 cytoplasmic domain; e) rodent reference STIM1 Glu-rich domain; and f) rodent reference STIM1 Pro-Ser rich domain.

Also provided are isolated peptides containing at least 8 contiguous amino acids of SEQ ID NO: 52, wherein the contiguous amino acids include a position selected from positions 21, 35, 38, 292, 527, 551, 552, 583 or 619 of SEQ ID NO: 52 or a corresponding position in SEQ ID NOS: 96 and 98.

Also provided are antibodies that specifically bind to isolated rodent reference STIM1 peptides. In particular, the antibodies that specifically bind to a rodent reference STIM1 bind to the rodent reference STIM1 with at least 2-, 5, 10- or greater-fold affinity than to a STIM1 from human or mouse. For example, provided is an antibody that specifically binds to a polypeptide comprising the sequence of amino acids set forth in SEQ ID NOS: 52, 96 or 98 but does not specifically bind to a polypeptide comprising the sequence of amino acids set forth in SEQ ID NO: 83, SEQ ID NO: 84 or SEQ ID NO: 85.

Provided are methods of modulating intracellular calcium by modulating in a cell, or portion thereof, one or more proteins, or nucleic acid encoding one or more proteins, that is (are) at least about 45% homologous to the protein encoded by Drosophila gene CG9126 and/or a stromal interacting molecule (STIM) or STIM-like protein over at least about 52% of the protein.

The protein includes those that are involved in, participates in and/or provides for store-operated calcium entry. The proteins include STIM1 and STIM2 proteins, particularly STIM1. The methods include those in which least one of the one or more proteins is a STIM1 protein. Also included are methods in which at least one of the proteins is at least about 50% homologous, or at least about 62% homologous, to the protein encoded by Drosophila gene CG9126 over at least about 77% of the encoded protein. In other embodiments, the protein is at least about 67% homologous to a mammalian STIM1 protein over at least about 86% of the protein.

In others, the protein is at least about 67% homologous to the amino acid sequence set forth as SEQ ID NO: 90 over at least about 86% of the sequence. In certain embodiments, at least one or more proteins is a STIM or STIM-like protein comprising one or more of the following domains: (a) a sterile α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezrin/radixin/moesin domain, and (e) a diacylglycerol kinase accessory domain. Included among the proteins is an ion transport protein or a component of an ion transport protein complex. The protein can be a mammalian protein, including, for example, a rodent or human protein.

The cell or portion thereof in which the one or more proteins, or nucleic acid encoding one or more proteins, is modulated exhibits altered intracellular calcium. The altered intracellular calcium activity can be altered store-operated calcium entry, altered calcium buffering, altered calcium levels in an intracellular calcium store and/or altered movement of calcium into, out of or within an intracellular calcium store, such as, for example, altered store-operated calcium entry. The portion of a cell can be plasma membrane, a cell organelle, an intracellular store or a membrane of a cell organelle or intracellular store. The cells include eukaryotic cells, such as mammalian cells. Mammalian cells include rodent and human cells.

Modulating can include modulating the level of, expression of, activity of or molecular interactions of one or more proteins or nucleic acid encoding one or more proteins. For example, modulating includes increasing the level of, expression of, activity of or molecular interactions of one or more proteins or nucleic acid encoding one or more proteins. Alternatively, modulating can include reducing the level of, expression of, activity of or molecular interactions of one or more proteins or nucleic acid encoding one or more proteins.

Also provided are methods for identifying an agent that modulates intracellular calcium, comprising: assessing the effects of a test agent on intracellular calcium of a test cell or portion thereof; and identifying a test agent as an agent that modulates intracellular calcium if it has an effect on intracellular calcium of the test cell. In these methods the test cell or a portion thereof comprises a polymorphic form of one or more proteins and/or a polymorphic form of a gene or nucleic acid encoding one or more proteins with a test agent, wherein the one or more proteins is/are (a) at least about 45% homologous to the protein encoded by Drosophila gene CG9126 and/or a stromal interacting molecule (STIM) or STIM-like protein over at least about 52% of the protein or (b) a portion of a protein that is at least about 45% homologous to the protein encoded by Drosophila gene CG9126 and/or a stromal interacting molecule (STIM) or STIM-like protein over at least about 52% of the protein; and intracellular calcium of the test cell differs from intracellular calcium of a cell, or portion thereof, that contains a wild-type form of the protein. Also provided are methods for identifying an agent that modulates intracellular calcium, comprising: assessing the effects of a test agent on intracellular calcium of a test cell or portion thereof; and identifying a test agent as an agent that modulates intracellular calcium if it has an effect on intracellular calcium of the test cell. The test cell or a portion thereof comprises a polymorphic form of one or more STIM or STIM-like proteins and/or a polymorphic form of a gene or nucleic acid encoding one or more STIM or STIM-like proteins; and intracellular calcium of the test cell differs from intracellular calcium of a cell, or portion thereof, that contains a wild-type form of the protein(s).

In these methods, provided are embodiments where one or more of the following differs in the test cell and a cell that contains a wild-type form of the protein: store-operated calcium entry, cytosolic calcium buffering, calcium level of an intracellular calcium store, movement of calcium into, out of or within an intracellular calcium store and resting cytosolic calcium level.

Also provided are methods for identifying an agent that modulates intracellular calcium, by assessing the effects of a test agent on intracellular calcium of a test cell, or portion thereof, that exhibits calcium dyshomeostasis; and identifying a test agent as an agent that modulates intracellular calcium if it has an effect on intracellular calcium of the test cell. The test agent modulates an activity of, an interaction of, the level of or binds to or interacts with a protein that is at least about 45% homologous to the protein encoded by *Drosophila* gene CG9126 and/or a stromal interacting molecule (STIM) protein over at least about 52% of the protein. Also provided are methods for identifying an agent that modulates intracellular calcium, by assessing the effects of a test agent on intracellular calcium of a test cell, or portion thereof, that exhibits calcium dyshomeostasis; and identifying a test agent as an agent that modulates intracellular calcium if it has an effect on intracellular calcium of the test cell. The test agent modulates an activity of, an interaction of, the level of or binds to or interacts with a STIM or STIM-like protein.

In these methods the test cell exhibits an alteration in one or more of the following relative to a substantially similar cell that does not exhibit calcium dyshomeostasis: store-operated calcium entry, cytosolic calcium buffering, calcium levels of an intracellular calcium store, movement of calcium into, out of or within an intracellular calcium store and resting cytosolic calcium levels. The test cell can be any suitable cell, and is generally a eukaryotic cell, such as an immune system cell, a skin cell, a blood cell, a renal cell and a muscle cell. Exemplary of immune system cells are lymphocytes, such as T cells, including a T cells that exhibit a defect in activation. Also exemplary of test cells are keratinocytes, including, for example, psoriatic keratinocytes. Other cells are mesangial cells, airway smooth muscle cells. The test cells can be those that exhibit altered store-operated calcium entry relative to a substantially similar cell that does not exhibit calcium dyshomeostasis.

A protein in all of the methods includes those that are involved in, participates in and/or provides for store-operated calcium entry. The proteins include STIM1 and STIM2 proteins, particularly STIM1. The methods include those in which least one of the one or more proteins is a STIM1 protein. Also included are methods in which at least one of the proteins is at least about 50% homologous, or at least about 62% homologous, to the protein encoded by *Drosophila* gene CG9126 over at least about 77% of the encoded protein. In other embodiments, the protein is at least about 67% homologous to a mammalian STIM1 protein over at least about 86% of the protein.

In others, the protein is at least about 67% homologous to the amino acid sequence set forth as SEQ ID NO: 90 over at least about 86% of the sequence. In certain embodiments, at least one or more proteins is a STIM or STIM-like protein comprising one or more of the following domains: (a) a sterile α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezxrin/radixin/moesin domain, and (e) a diacylglycerol kinase accessory domain. Included among the proteins is an ion transport protein or a component of an ion transport protein complex. The protein can be a mammalian protein, including, for example, a rodent or human protein.

In all of these methods the portion of the cell can include a plasma membrane, a cell organelle, an intracellular store or a membrane of a cell organelle or intracellular store.

In all methods, the test cells include mammalian cells, such as a rodent or human cell. In the methods, the protein can be encoded by nucleic acid that is heterologous to the cell. The test cell can be a recombinant cell and the gene or nucleic acid encoding the protein can heterologous to the cell. In these methods, the protein or at least one of the one or more proteins is overexpressed in the test cell.

Also provided are methods for identifying an agent for treating or preventing a disease or disorder involving an alteration in intracellular calcium, by assessing the effects of a test agent on intracellular calcium of a test cell or portion thereof; and identifying a test agent as an agent for treating or preventing a disease or disorder if it has an effect on intracellular calcium of the test cell. The test cell is a cell of an animal that comprises a polymorphic form of one or more proteins and/or a polymorphic form of a gene, or portion thereof, or nucleic acid encoding one or more proteins with a test agent, wherein the one or more proteins is/are (a) at least about 45% homologous to the protein encoded by *Drosophila* gene CG9126 and/or a stromal interacting molecule (STIM) or STIM-like protein over at least about 52% of the protein or (b) a portion of a protein that is at least about 45% homologous to the protein encoded by *Drosophila* gene CG9126 and/or a stromal interacting molecule (STIM) or STIM-like protein over at least about 52% of the protein. The cell comprises a polymorphic form of the one or more proteins and/or the polymorphic form of a gene, or portion thereof, or nucleic acid encoding the one or more proteins exhibits calcium dyshomeostasis.

Also provided are methods for identifying an agent for treating or preventing a disease or disorder involving an alteration in intracellular calcium, by assessing the effects of a test agent on intracellular calcium of a test cell or portion thereof; and identifying a test agent as an agent for treating or preventing a disease or disorder if it has an effect on intracellular calcium of the test cell. The test cell is a cell of an animal comprising a polymorphic form of one or more STIM or STIM-like proteins and/or a polymorphic form of a gene, or portion thereof, or nucleic acid encoding one or more STIM or STIM-like proteins. A cell comprising the polymorphic form of the one or more proteins and/or the polymorphic form of a gene, or portion thereof, or nucleic acid encoding the one or more proteins exhibits calcium dyshomeostasis.

In these methods, one or more of the following is altered in a cell comprising a polymorphic form of the one or more proteins or a polymorphic form of a gene, or portion thereof, or nucleic acid encoding the one or more proteins: store-operated calcium entry, cytosolic calcium buffering, calcium level of an intracellular calcium store, movement of calcium into, out of or within an intracellular calcium store and resting cytosolic calcium level.

Also provided are methods for identifying an agent for treating or preventing a disease or disorder involving an alteration in intracellular calcium, by assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a protein that is at least about 45% homologous to the protein encoded by Drosophila gene CG9126 and/or a stromal interacting molecule (STIM) protein over at least about 52% of the protein; and the organism comprises one or more cells that exhibit calcium dyshomeostasis.

Also provided are methods for identifying an agent for treating or preventing a disease or disorder involving an alteration in intracellular calcium, by assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a STIM or STIM-like protein; and the organism comprises one or more cells that exhibit calcium dyshomeostasis.

Also provided are methods for identifying an agent for treating or preventing a disease or disorder involving an alteration in intracellular calcium, by: assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a protein that is at least about 45% homologous to the protein encoded by Drosophila gene CG9126 and/or a stromal interacting molecule (STIM) protein over at least about 52% of the protein; and the organism exhibits a phenotype associated with a disease or disorder that involves or is characterized at least in part by calcium dyshomeostasis.

Also provided are methods for identifying an agent for treating or preventing a disease or disorder involving an alteration in intracellular calcium, by assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a STIM or STIM-like protein; and the organism exhibits a phenotype associated with a disease or disorder that involves or is characterized at least in part by calcium dyshomeostasis.

Also provided are methods for identifying an agent for treating or preventing a disease or disorder, by: assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a protein that is at least about 45% homologous to the protein encoded by Drosophila gene CG9126 and/or a stromal interacting molecule (STIM) protein over at least about 52% of the protein; and the organism exhibits a phenotype associated with a disease or disorder selected from the group consisting of an immune system-related disease, a disease involving inflammation, a renal system disease, a neurodegenerative disease, pain and liver disease.

Also provided are methods for identifying an agent for treating or preventing a disease or disorder, by: assessing the effects of a test agent on a phenotype of an organism; and identifying a test agent as an agent for treating or preventing a disease or disorder if it has an effect on a phenotype of the organism. The test agent modulates an activity of, an interaction of, the level of or binds to or interacts with a STIM or STIM-like protein; and the organism exhibits a phenotype associated with a disease or disorder selected from the group consisting of an immune system-related disease, a disease involving inflammation, a renal system disease, a neurodegenerative disease, pain and liver disease.

Diseases in the above methods include autoimmune diseases, diseases that involve an immunodeficiency, diseases that involve glomerulonephritis. Diseases include, but are not limited to, psoriasis, asthma, and arthritis. The disease can involve exocrinopathy. Other diseases or disorders include, but are not limited to, Sjogren's syndrome and neuropathic pain.

In all of the above methods, modulating one or more proteins, and/or nucleic acid encoding one or more proteins, can comprise exposing the cell, or portion thereof, to one or more agents that modulate the one or more proteins, and/or a gene or nucleic acid encoding the one or more proteins. The one or more agents can modulate the level, expression, functioning, molecular interactions and/or activity of the one or more proteins, and/or a gene or nucleic acid encoding the one or more proteins.

Also provided are methods for preventing a disease or disorder, by modulating in a subject having a disease or disorder, or at risk for developing a disease or disorder, one or more proteins, and/or a gene or nucleic acid encoding one or more proteins, that is (are) at least about 45% homologous to the protein encoded by Drosophila gene CG9126 and/or a stromal interacting molecule (STIM) or STIM-like protein over at least about 52% of the protein. The disease or disorder involves, or is characterized at least in part by: (1) altered intracellular calcium, altered intracellular calcium regulation or calcium dyshomeostasis or dysregulation and/or (2) an alteration or defect in, or aberrant functioning of, a cellular process which relies on or is regulated by intracellular calcium. For example, the disease or disorder can involve, or is characterized at least in part, by altered store-operated calcium entry, altered calcium buffering, altered calcium levels in an intracellular calcium store, and/or altered movement of calcium into, out of or within an intracellular calcium store, such as, for example, by altered store-operated calcium entry. In these methods, modulating includes modulating the level of, expression of activity of or molecular interactions of one or more proteins and/or a gene or nucleic acid encoding one or more proteins. Modulating includes increasing the level of, expression of, activity of or molecular interactions of one or more proteins and/or a gene or nucleic acid encoding one or more proteins. Modulating also includes reducing the level of, expression of, activity of or molecular interactions of one or more proteins and/or a gene or nucleic acid encoding one or more proteins. In these methods, at least one of the one or more proteins is a STIM1 or a STIM2 protein. Included is a protein that is at least about 50% homologous to the protein encoded by Drosophila gene CG9126 over at least about 77% of the encoded protein or at least about 62% homologous to the protein encoded by Drosophila gene CG9126 over at least about 77% of the encoded protein. The protein can be least about 67% homologous to a mammalian STIM1 protein over at least about 86% of the protein, including a protein that is at least about 67% homologous to the amino acid sequence set forth as SEQ ID NO: 90 over at least about 86% of the sequence. The protein can be a STIM or STIM-like protein comprising one or more of the following domains: (a) a sterile α-motif (SAM) domain comprising one or more N-linked glycosylation sites and, optionally, an N-linked glycosylation site in the amino acid sequence on either side of the SAM domain, (b) a dibasic sequence of a proteolytic cleavage site, (c) an ATP synthase B/B' domain, (d) an ezxrin/radixin/moesin domain, and (e) a diacylglycerol kinase accessory domain. Exemplary of the proteins is a protein that is involved in, participates in and/or provides for store-operated calcium entry. The protein can be an ion transport protein or a component of an ion transport protein complex. The proteins include human proteins.

In these methods, modulating one or more proteins, and/or a gene or nucleic acid encoding one or more proteins, can include the steps of: administering to the subject one or more agents that modulate the one or more proteins, and/or a gene or nucleic acid encoding the one or more proteins. The one or more agents can modulate the level, expression, functioning, molecular interactions and/or activity of the one or more proteins, and/or a gene or nucleic acid encoding the one or more proteins. An agent can bind to or interact with one of the proteins and/or a gene or nucleic acid encoding one of the proteins. Exemplary agents are selected among: proteins, peptides, antibodies or fragments thereof and nucleic acids. Other exemplary agents are DNA or RNA.

The one or more proteins, and/or a gene or nucleic acid encoding one or more proteins is/are modulated in cells, which include: immune cells, fibroblasts, skin cells, blood cells, renal cells, muscle cells, exocrine cells and secretory cells, such as, but are not limited to, lymphocytes, keratinocytes, mesangial cells, airway smooth muscle cells, lung cells, salivary gland cells and lacrimal gland cells.

The disease or disorder includes: immune system-related diseases/disorders, diseases/disorders involving inflammation, glomerulonephritis, hepatic diseases/disorders, renal diseases/disorders, neurodegenerative diseases/disorders, aging-related diseases/disorders, sensitivity to pain or touch, chronic obstructive pulmonary disease, rheumatoid arthritis, inflammatory bowel disease, neuroinflammatory diseases, Alzheimer's disease, amytrophic lateral sclerosis, traumatic brain injury, multiple sclerosis, vasculitis, inflammatory bowel disease, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis (e.g., Hashimoto's and autoimmune thyroiditis), myasthenia gravis, autoimmune hemolytic anemia, cystic fibrosis, chronic relapsing hepatitis, primary biliary cirrhosis, allergic conjunctivitis, hepatitis and atopic dermatitis, such as but are not limited to, asthma, Sjogren's syndrome, Scott syndrome, glomerulonephritis, autoimmune diseases/disorders and immunodeficiency-related diseases/disorders. The disease or disorder includes a primary immunodeficiency or a severe combined immunodeficiency.

Also provided are methods of identifying an agent that modulates intracellular calcium. The methods include contacting, with a test agent, one or more test cells overexpressing a mammalian STIM1 protein or a portion thereof that retains at least one biological activity of a mammalian STIM1 protein, assessing the effect of the test agent on intracellular calcium, and identifying a test agent as an agent that modulates intracellular calcium if it has an effect on intracellular. In another embodiment, the method includes contacting one or more test cells with a test agent, wherein the test agent modulates an activity of, modulates an interaction of or modulates the level of, or binds to or interacts with a mammalian STIM1 protein or a portion thereof that retains at least one biological activity of a mammalian STIM1 protein, assessing the effect of the test agent on intracellular calcium, and identifying a test agent as an agent that modulates intracellular calcium if it has an effect on intracellular calcium. In another embodiment, the method includes assessing the effect of the test agent on an activity of, an interaction of or the level of a mammalian STIM1 protein or a portion thereof that retains at least one biological activity of a mammalian STIM1 protein, or on binding to or interaction with mammalian STIM1 protein or a portion thereof that retains at least one biological activity of a mammalian STIM1 protein, wherein the test agent modulates intracellular calcium, and identifying an agent that modulates the STIM1 protein or portion thereof if it has an effect on an activity of, an interaction of or the level of STIM1, or binds to or interacts with the STIM1 protein or portion thereof.

In the methods herein the test cell can be an immune cell. In the methods, the STIM1 can be human STIM1. The step of assessing in the methods herein can include assessing the effect(s) of the test agent on a calcium entry-mediated event. In one embodiment of the methods, the test agent that modulates intracellular calcium modulates a calcium entry-mediated event. In another embodiment, the calcium entry-mediated event is selected from the group consisting of cytokine expression, cytokine secretion, NFAT dephosphorylation, NFAT nuclear localization, NFAT transcriptional activation, calcineurin phosphatase activity, and inflammatory mediator release. The cytokine can be IL-2 or TNFα. The inflammatory mediator can be β-hexosaminidase.

Also provided herein are methods of identifying an agent that modulates cytokine expression or secretion. The methods include contacting, with a test agent, one or more test cells overexpressing a mammalian STIM1 protein or a portion thereof that retains at least one biological activity of a mammalian STIM1, assessing the effect of the test agent on cytokine expression or secretion; and identifying a test agent that modulates cytokine expression or secretion. In one embodiment, the method includes contacting one or more test cells with a test agent, wherein the test agent modulates an activity of, modulates an interaction of or modulates the level of, or binds to or interacts with a mammalian STIM1 protein or a portion thereof that retains at least one biological activity of a mammalian STIM1 protein, assessing the effect of the test agent on cytokine expression or secretion; and identifying a test agent that modulates cytokine expression or secretion. In the methods the cytokine can be interleukin-2 (IL-2). In the methods, the test cell can be an immune cell.

Also provided herein are systems. In one embodiment, the system includes a cell, or portion thereof, overexpressing one or more mammalian STIM1 proteins or a portion thereof that retains at least one biological activity of a mammalian STIM1 protein, and a molecule used in monitoring, measuring or detecting a calcium-entry mediated event. In the systems, the STIM1 can be human STIM1. In the systems, the cell can be an immune cell. In another embodiment, the system includes a cell, or portion thereof, containing a heterologous nucleic acid molecule comprising one or more mammalian STIM1 nucleic acid molecules or a portion thereof, wherein the expression of STIM1 in the cell or portion thereof is reduced, and a molecule for monitoring, measuring or detecting a calcium-entry mediated event. In the systems, the heterologous nucleic acid can be an interference nucleic acid molecule such as a double-stranded RNA (dsRNA), an antisense RNA, siRNA or RNAi.

FIGURE DESCRIPTIONS

FIG. 1 shows exemplary calcium entry-mediated events in immune cells. For example, as depicted, receptor activation leads to depletion of ER calcium stores, which activates capacitative calcium entry through $I_{crac}$ channels. Calcium entry activates calmodulin-dependent enzymes including the serine phosphatase calcineurin, which leads to release of inflammatory mediators in mast cells. Activation of calcineurin also leads to dephosphorylation, nuclear translocation and activation of transcription factors such as NFAT. NFAT activation results in expression and release of cytokines and T cell proliferation. Abbreviations: CCE, calcium capacitative entry; $I_{CRAC}$, calcium release activated calcium channel current; PLCγ, phospholipase C gamma; $IP_3$, Inositol 1,4,5-triphosphate; SERCA, sarcoplasmic/endoplasmic reticulum calcium ATPase; DAG, diacyl glycerol; ER, endoplasmic reticulum; CaM, Calmodulin; NFAT, nuclear factor of activated T cells.

Figure 2:
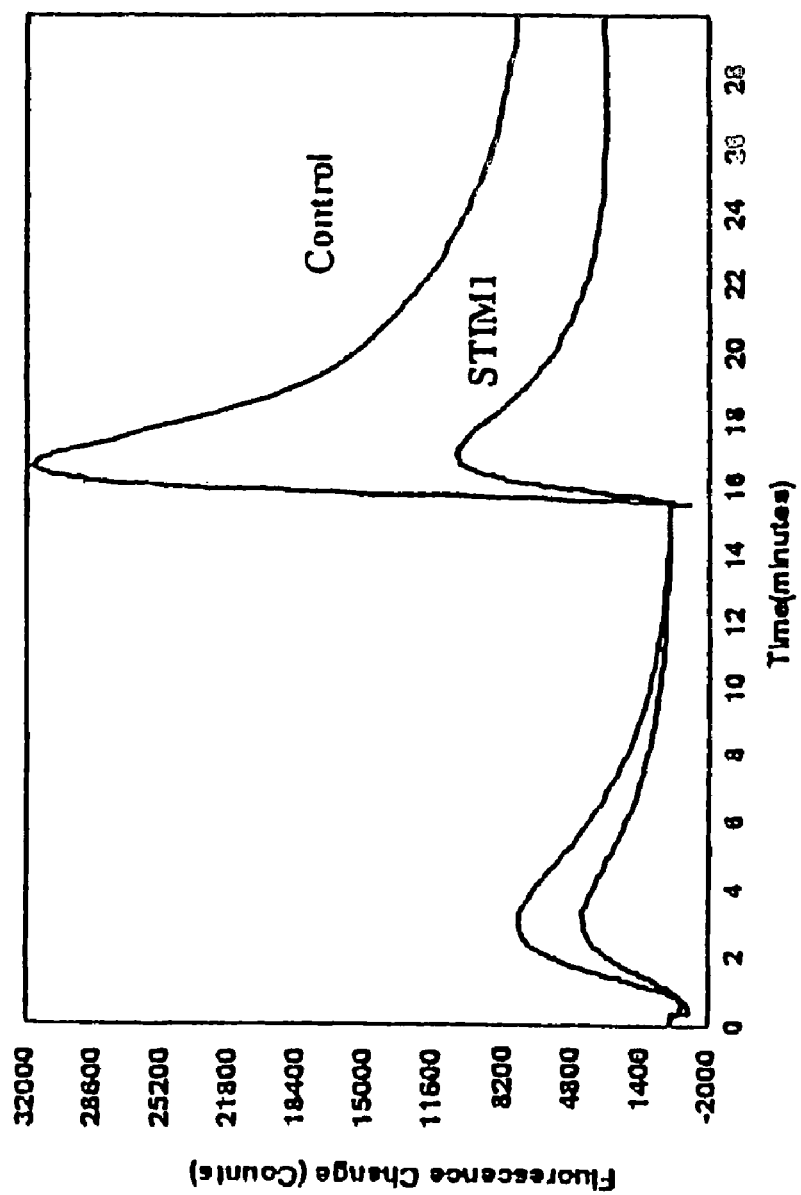

FIG. 2 is a graph showing fluorescence vs. time as measured in HEK293 cells which had been loaded with a fluorescent indicator and subjected to conditions designed to assess store-operated calcium entry into the cell (see EXAMPLES for details of the methods). The curve labeled as "STIM1" reflects fluorescence levels in a cell in which STIM1 protein and mRNA expression had been reduced to non-detectable levels using siRNA-based interference methods described herein. The curve labeled "Control" reflects fluorescence levels in a cell that had been treated with control RNAs as described herein. At time "0", 1 μM thapsigargin was added to the essentially calcium-free medium. The increase in fluorescence upon addition of thapsigargin reflects an increase (followed by decrease) in calcium levels in the cytosol due to release of calcium from intracellular calcium stores. At about 16 minutes, 1.8 mM calcium was added to the medium. The increase in fluorescence upon addition of calcium to the medium reflects store-operated calcium entry into the cytosol.

Figure 3:
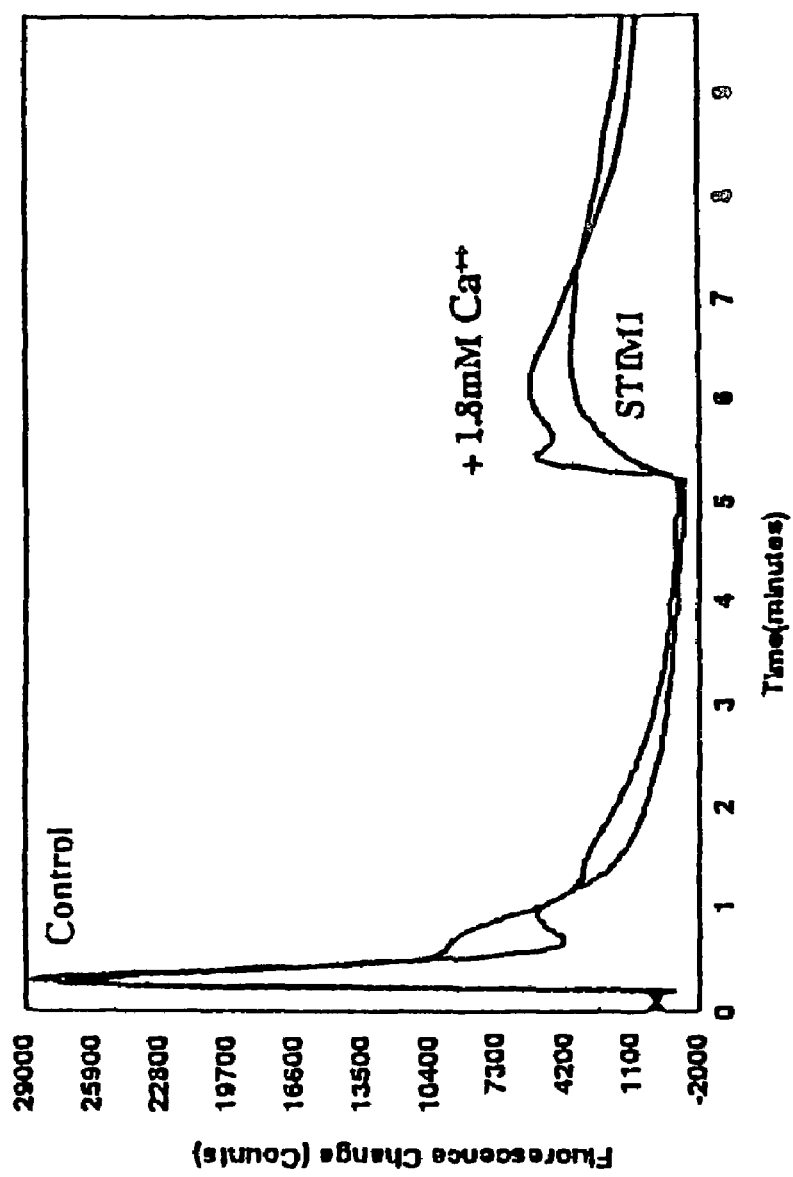

FIG. 3 is a graph showing fluorescence vs. time as measured in HEK293 cells which had been loaded with a fluorescent indicator and subjected to conditions designed to assess store-operated calcium entry into the cell (see EXAMPLES for details of the methods). The curve labeled as "STIM1" reflects fluorescence levels in a cell in which STIM1 protein and mRNA expression had been reduced to non-detectable levels using siRNA-based interference methods described herein. The curve labeled "Control" reflects fluorescence levels in a cell that had been treated with control RNAs as described herein. At time "0", 300 μM methylcholine was added to the essentially calcium-free medium. The increase in fluorescence upon addition of thapsigargin reflects an increase (followed by decrease) in calcium levels in the cytosol due to release of calcium from intracellular calcium stores. At about 5 minutes, 1.8 mM calcium was added to the medium. The increase in fluorescence upon addition of calcium to the medium reflects calcium influx into the cell that includes store-operated calcium entry.

Figure 4:
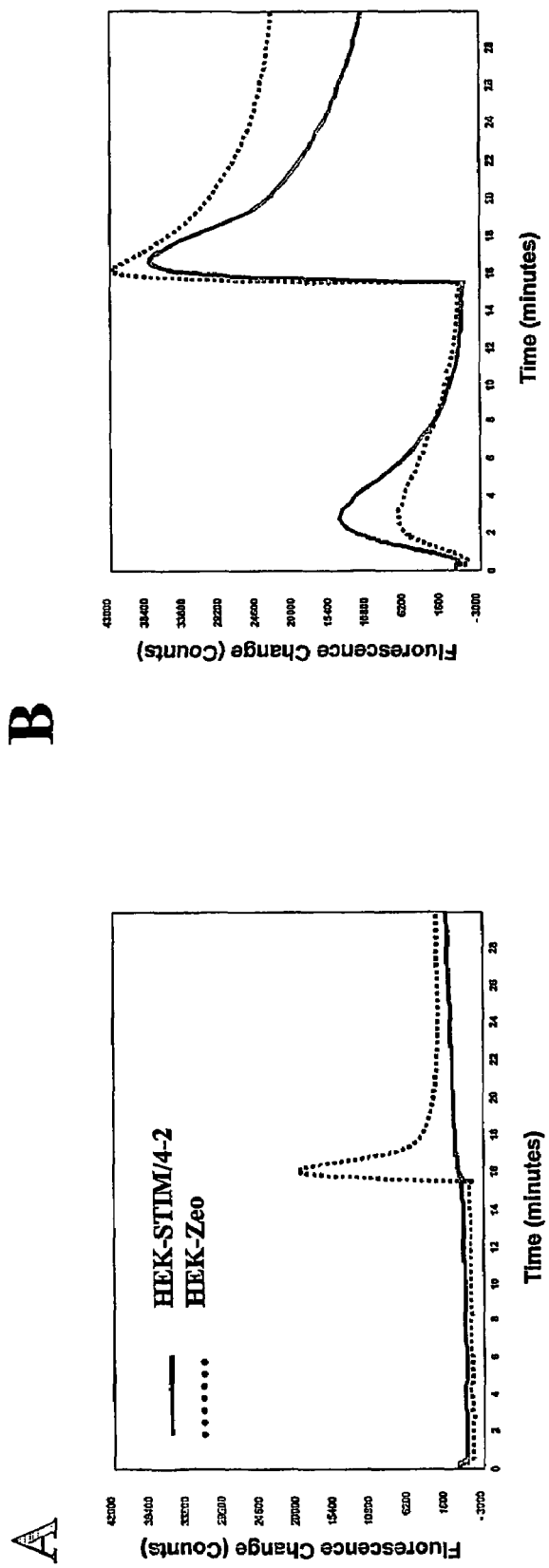

FIG. 4 is a graph showing fluorescence vs. time as measured in HEK293 cells which had been loaded with a fluorescent indicator and subjected to conditions designed to assess store-operated calcium entry (SOCE) into the cell (see EXAMPLES for details of the methods). The curves labeled as "STIM1" (dotted line) reflects fluorescence levels in a cell overexpressing STIM1 (HEK[STIM1]). The curves labeled "Control" (solid line) reflect fluorescence levels in a control HEK293 cell. At time "0", either DMSO (Panel A) or 1 μM thapsigargin (Panel B) was added to the essentially calcium-free medium. At about 15 minutes, 1.8 mM calcium was added to the medium. Overexpression of STIM1 results in constitutive activation of $Ca^{2+}$ entry, enhanced thapsigargin-activated $Ca^{2+}$ entry, and a reduction in the amplitude and kinetics of the thapsigargin-mediated release of calcium from the internal stores.

DETAILED DESCRIPTION OF PARTICULAR EMBODIMENTS

A. Definitions

Unless defined otherwise, all technical and scientific terms used herein have the same meaning as is commonly understood by one of skill in the art to which this invention belongs. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "calcium homeostasis" refers to the maintenance of an overall balance in intracellular calcium levels and movements, including calcium signaling, within a cell.

As used herein, "calcium dyshomeostasis" refers to altered, abnormal or impaired calcium homeostasis. For example, calcium dyshomeostasis can be imbalances or disturbances in intracellular calcium levels or movements such as may result from altered calcium regulation in a cell.

As used herein, "intracellular calcium" refers to calcium located in a cell without specification of a particular cellular location. In contrast, "cytosolic" or "cytoplasmic" with reference to calcium refers to calcium located in the cell cytoplasm. Intracellular calcium can be free calcium and/or bound calcium.

As used herein, an "effect on intracellular calcium" is any alteration of any aspect of intracellular calcium, including but not limited to, an alteration in intracellular calcium levels, calcium location and movement of calcium into, out of or within a cell or intracellular calcium store or organelle. For example, an effect on intracellular calcium can be an alteration of the properties, such as, for example, the kinetics, sensitivities, rate, amplitude, and electrophysiological characteristics of calcium flux or movement that occurs in a cell or portion thereof. An effect on intracellular calcium can be an alteration in any intracellular calcium-modulating process, including, store-operated calcium entry, cytosolic calcium buffering, and calcium levels in or movement of calcium into, out of or within an intracellular calcium store. Any of these aspects can be assessed in a variety of ways including, but not limited to, evaluation of calcium or other ion particularly cation) levels, movement of calcium or other ion (particularly cation), fluctuations in calcium or other ion (particularly cation) levels, kinetics of calcium or other ion particularly cation) fluxes and/or transport of calcium or other ion particularly cation) through a membrane. An alteration can be any such change that is statistically significant. Thus, for example if intracellular calcium in a test cell and a control cell is said to differ, such difference can be a statistically significant difference.

As used herein, "calcium entry-mediated event" is an effect on intracellular calcium, and refers to any cellular process regulated by store-operated calcium entry. Processes regulated by store-operated calcium entry include, but are not limited to, calmodulin activation, calcineurin activation, mast cell degranulation and release of inflammatory mediators, activation of calcium-dependent transcription factors (e.g. nuclear factor of activated T cells (NFAT), nuclear factor kappa B (NFκB), and/or c-Jun N-terminal kinase (JNK)), NFAT dephosphorylation, NFAT nuclear translocation, NFAT-dependent gene regulation, expression, release and/or activity of molecules regulated by such transcription factors (e.g. cytokine expression, release or activity cytokine release). Exemplary calcium entry-mediated events are shown, for example, in FIG. 1.

An effect on intracellular calcium can be assessed by detecting a calcium-entry mediated event. For example, an effect on intracellular calcium can be assessed by detecting or determining activity of calcium-regulated proteins, such as calmodulin and calcineurin; regulation, localization and/or activity of calcium regulated transcription factors such as NFAT, JNK and NFκB; and effects on gene expression, such as genes regulated by calcium-regulated transcription factors, for example, cytokine gene expression such as expression of IL-2, IL-3, IL-4, IL-5, IL-8, IL-13, as well as tumor necrosis factor alpha (TNFα), granulocyte colony-stimulating factor (GCSF), and gamma-interferon (γ-IFN) and/or reporter genes linked to promoters or regulatory elements of such genes. An effect on intracellular calcium can also be assessed by detecting or determining secretion and/or release of peptides and proteins, such as secretion of cytokines such as IL-2, and degranulation and release of inflammatory mediators such as histamine and β-hexosaminidase.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the amplitude or kinetics of calcium movements or fluxes into, out of and within cells. Modulation includes, for example, increases, up-regulation, induction, stimulation, potentiation, relief of inhibition, reduction, inhibition, down-regulation and suppression.

As used herein, "protein involved in modulating intracellular calcium" refers to any cellular protein that is involved in regulating, controlling and/or altering intracellular calcium. For example, such a protein can be involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein involved in modulating intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins. When a protein is referred to as being "involved in" a particular aspect of intracellular calcium or intracellular calcium regulation it can be a protein which has the following property: when expression or activity of the protein in a cell is reduced, altered or eliminated, there is a concomitant or associated alteration (including, for example, reduction, elimination, increase or other alteration) of one or more aspects of intracellular calcium or intracellular calcium regulation. Such an alteration or reduction in expression or activity can occur by virtue of an alteration of expression of a gene encoding the protein or by altering the levels of the protein. A protein involved in an aspect of intracellular calcium, such as, for example, store-operated calcium entry, thus, can be one that provides for or participates in an aspect of intracellular calcium or intracellular calcium regulation. For example, a protein that provides for store-operated calcium entry can be an ion transport protein that forms the pore of a calcium channel and a protein that participates in store-operated calcium entry can be a regulatory protein that modulates a store-operated calcium entry channel. A protein that participates in store-operated calcium entry can be a protein that is not necessarily a component of the store-operated calcium entry channel but is directly or indirectly associated with its activity, such as, for example, a non pore-forming subunit or ligand or other modulatory or regulatory protein that modulates its activity.

As used herein, a "protein that is a component of a calcium channel" is a protein that participates in a multi-protein complex that forms the channel.

As used herein, "basal" or "resting" with reference to cytosolic calcium levels refers to the concentration of calcium in the cytoplasm of a cell, such as, for example, an unstimulated cell, that has not been subjected to a condition that results in movement of calcium into or out of the cell or within the cell. The basal or resting cytosolic calcium level can be the concentration of free calcium (i.e., calcium that is not bound to a cellular calcium-binding substance) in the cytoplasm of a cell, such as, for example, an unstimulated cell, that has not been subjected to a condition that results in movement of calcium into or out of the cell.

As used herein, "movement" with respect to ions, including cations, e.g., calcium, refers to movement or relocation, such as for example flux, of ions into, out of, or within a cell. Thus, movement of ions can be, for example, movement of ions from the extracellular medium into a cell, from within a cell to the extracellular medium, from within an intracellular organelle or storage site to the cytosol, from the cytosol into an intracellular organelle or storage site, from one intracellular organelle or storage site to another intracellular organelle or storage site, from the extracellular medium into an intracellular organelle or storage site, from an intracellular organelle or storage site to the extracellular medium and from one location to another within the cell cytoplasm.

As used herein, "cation entry" or "calcium entry" into a cell refers to entry of cations, such as calcium, into an intracellular location, such as the cytoplasm of a cell or into the lumen of an intracellular organelle or storage site. Thus, cation entry can be, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "agent that modulates intracellular calcium" refers to any substance that can modulate intracellular calcium. Examples of agents include, but are not limited to, small organic molecules, large organic molecules, amino acids, peptides, polypeptides, nucleotides, nucleic acids (including DNA, cDNA, RNA, antisense RNA and any double- or single-stranded forms of nucleic acids), polynucleotides, carbohydrates, lipids, lipoproteins, glycoproteins, inorganic ions (including, for example, $Gd^{3+}$, lead and lanthinum).

As used herein, a "STIM protein" includes any STIM protein, including but not limited to, STIM1, a STIM, DSTIM, CSTIM and STIM-like proteins. STIM1, STIM2, DSTIM and STIM-like protein are described in detail below. A STIM-like protein can be one that has similar homology to STIM1 and STIM2 proteins and that is at least about 45% homologous to the protein encoded by Drosophila gene CG9126 over at least about 52% of the protein.

As used herein, a "biological activity of a STIM1 protein" includes any activity known to those of skill in the art to be associated with STIM1, and also the intracellular calcium modulating activity described herein. STIM1 biological activities known to those of skill in the art, include, but are not limited to, binding to pre-B cells and differentiated B lymphocytes, augmentation of IL-7-dependent proliferation of pre-B cells, modulation of cell morphology and suppression of tumor growth.

As used herein, "mammalian STIM1 proteins" refer collectively to mammalian STIM1 proteins such as those as set forth and/or encoded by SEQ ID NOs: 3, 4, 9, 10, 49-56, 85, 95, 96, 97, 98 and proteins with at least 90% homology over at least 70% of the protein with human STIM1 and/or SEQ ID NO: 4. Mammalian STIM1 proteins include naturally occurring variants of STIM1 proteins found in mammals as well as variants constructed synthetically or recombinantly that retain at least 90% homology over at least 70% of the protein with human STIM1 and/or SEQ ID NO: 4.

As used herein, "reference STIM1" refers to nucleotide sequence as set forth in SEQ ID NO: 52 encoding reference STIM1 protein set forth in SEQ ID NO: 52. Reference STIM1 contains a hamster partial STIM1 cDNA that was extended with 5' and 3' sequences from the rat Rattus norvegicus chromosome 1 WGS supercontig sequence having GenBank Accession No. NW_043388.

As used herein, "rodent reference STIM1" refers collectively to rat, hamster and reference STIM1. Rodent reference STIM1 nucleotide sequences refers collectively to rat, hamster and reference STIM1 nucleotide sequences and include SEQ ID NOs: 51, 95 and 97. Rodent reference STIM1 proteins or amino acid sequences refer collectively to rat, hamster and reference STIM1 proteins or amino acid sequences, and include SEQ ID NOs: 52, 96 and 98 and proteins as encoded by SEQ ID NOs: 51, 95 and 97.

As used herein, "overexpression" refers to the expression of a protein in a test cell such that it is greater than the expression of the protein in a reference cell. The reference cell can be a cell that is substantially the same but lacks the means for overexpressing the protein. For example, the test cell can contain one or more heterologous nucleic acid molecules encoding a protein not present or not expressed in the reference cell. The test cell can be induced by a agent or condition resulting in expression of a protein and the reference cell can be an uninduced cell. The reference cell and test cell are not required to be assessed simultaneously. They can be assessed separately, under substantially the same conditions. The reference cell can also be represented by a collection of data, for example stored in a database; the data can be collected from experiments of cells and conditions from one or more experiments which can be used for comparison with a test cell.

As used herein, "test agent," in the context of methods for identifying agents that modulate intracellular calcium, refers to any substance that is being evaluated as a possible agent that modulates intracellular calcium.

As used herein, "agent that modulates the level and/or activity of a protein" refers to any substance that can modulate the amount of and/or activity of a protein. Such agents include, but are not limited to, small and large organic molecules, amino acids, peptides, polypeptides, nucleotides, nucleic acids (including DNA, cDNA, expression vectors, RNA, antisense RNA, and any double- or single-stranded forms of nucleic acids), polynucleotides, carbohydrates, lipids, lipoproteins and glycoproteins.

As used herein, "amelioration" refers to an improvement in a disease or condition or at least a partial relief of symptoms associated with a disease or condition.

As used herein, "cell response" refers to any cellular response that results from ion movement into or out of a cell or within a cell. The cell response may be associated with any cellular activity that is dependent, at least in part, on ions such as, for example, calcium. Such activities may include, for example, cellular activation, gene expression, endocytosis, exocytosis, cellular trafficking and apoptotic cell death.

As used herein, "nucleic acid" or "nucleic acid molecule" refers to both deoxyribonucleic acid (DNA) and ribonucleic acid (RNA) molecules, as well as modified polynucleotides. Modified polynucleotides include polynucleotides having, for example, modifications to the base, sugar, or the phosphate portion, or that contain a modified phosphodiester linkage. The term "nucleic acid" includes both single-stranded and double-stranded nucleic acids, which can correspond to the sense strand, antisense strand or both of a reference sequence. The term includes molecules with various conformations, including linear, circular, hairpin and branched molecules.

As used herein, "heterologous" or "foreign" with reference to nucleic acids, cDNA, DNA and RNA are used interchangeably and refer to nucleic acid, DNA or RNA that does not occur naturally as part of the genome in which it is present or which is found in a location(s) or in an amount in the genome that differs from that in which it occurs in nature. It can be nucleic acid that has been exogenously introduced into the cell. Thus, heterologous nucleic acid is nucleic acid not normally found in the host genome in an identical context. Examples of heterologous nucleic acids include, but are not limited to, DNA that encodes a gene product or gene product(s) of interest, introduced, for example, for purposes of gene therapy or for production of an encoded protein. Other examples of heterologous DNA include, but are not limited to, DNA that encodes a selectable marker, DNA that encodes therapeutically effective substances, such as enzymes and hormones, and DNA that encodes other types of proteins, such as antibodies.

As used herein, "expression" refers to the process by which nucleic acid, e.g., DNA, is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, "vector" or "plasmid" refers to discrete elements that are used to introduce heterologous nucleic acids into cells. Typically, vectors are used to transfer heterologous nucleic acids into cells for either expression of the heterologous nucleic acid or for replication of the heterologous nucleic acid. Selection and use of such vectors and plasmids are well within the level of skill of the art.

As used herein, "transformation" or "transfection" refers to the process by which nucleic acids are introduced into cells. Transfection refers to the taking up of exogenous nucleic acid, e.g., an expression vector, by a host cell whether or not any coding sequences are in fact expressed. Numerous methods of transfection are known to the ordinarily skilled artisan. Successful transfection is generally recognized by detection of the presence of the heterologous nucleic acid within the transfected cell, such as, for example, any visualization of the heterologous nucleic acid or any indication of the operation of a vector within the host cell.

As used herein, the "amino acids," which occur in the various amino acid sequences appearing herein, are identified according to their well-known, three-letter or one-letter abbreviations (see Table 1). The nucleotides, which occur in the various DNA fragments, are designated with the standard single-letter designations used routinely in the art.

As used herein, "amino acid residue" refers to an amino acid formed upon chemical digestion hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243:3552-59 (1969) and adopted at 37 C.F.R. §§. 1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxyl-terminal group such as COOH.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

Such substitutions may be made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, "similarity" between two proteins or nucleic acids refers to the relatedness between the amino acid sequences of the proteins or the nucleotide sequences of the nucleic acids. Similarity can be based on the degree of identity and/or homology of sequences and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g.: *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)).

As used herein, "homology" with reference to proteins or nucleic acids refers to shared sequence similarity that takes into account both identical residues and residues that may substitute for one another. Substitutions may include, for example, conserved amino acids and frequent substitutions based on statistical analyses and evolutionary distance.

Percent identity and percent homology may be determined, for example, by comparing sequence information using any of a number of computer algorithms known in the art. The GAP program uses the alignment method of Needleman and Wunsch (*J. Mol. Biol.* 48:443 (1970)), as revised by Smith and Waterman (*Adv. Appl. Math.* 2:482 (1981)). Briefly, the GAP program defines similarity as the number of aligned symbols (i.e., nucleotides or amino acids) which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov and Burgess, Nucl. Acids Res. 14:6745 (1986), as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Whether any two protein or nucleic acid molecules have amino acid or nucleotide sequences that are at least, for example, 20%, 30%, 40%, or 50%, "identical" can be determined using known computer algorithms such as the "FAST A" program, using for example, the default parameters as in Pearson and Lipman, *Proc. Natl. Acad. Sci. USA* 85:2444 (1988). The BLAST function of the National Center for Biotechnology Information database may be used to determine identity. By way of example, in a comparison of a test and reference polypeptide, wherein the length of the reference polypeptide is 100 amino acids, a level of 90% or more identity between the polypeptides is indicative of having no more than 10% (i.e., 10 out of 100) amino acids in the test polypeptide differing from that of the reference polypeptide. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). The BLinK tool ("BLAST Link") displays the results of precomputed BLAST searches (Altschul et al. (19990) *J. Mol. Biol.* 215:403-410) that have been done for protein sequences in the Entrez Proteins data domain against the non-redundant (nr) database (e.g., GenBank).

Methods commonly employed to determine identity or homology between two sequences include, but are not limited to, those disclosed in *Guide to Huge Computers*, Martin J. Bishop, ed., Academic Press, San Diego, 1994, and Carillog, H. & Lipton, D., *SIAM J Applied Math* 48:1073 (1988). Methods to determine identity and homology are codified in computer programs. Computer program methods to determine identity and homology between two sequences include, but are not limited to, GCG program package (Devereux, J., et al., *Nucleic Acids Research* 12(1):387 (1984)), BLASTP, BLASTN, FASTA (Atschul, S. F., et al., *J Molec Biol* 215:403 (1990)).

Therefore, as used herein, the terms "identity" and "homology" represent a comparison between two polypeptides or polynucleotides. Typically, a "test" polypeptide or polynucleotide is compared to a "reference" molecule to determine if there is a significant level of similarity (including identity and/or homology) between the test and reference molecules.

As used herein, the terms at least "X % homology over X % of the protein" or "X % identity over X % of the protein" with reference to a comparison of protein A with protein B refers to protein A having X % homology or X % identity to protein B over X % of the amino acid sequence of protein B. The term "over the protein" means over the length of the amino acid sequence of the protein, but not necessarily over a contiguous sequence of amino acids of the protein. Thus, for example, protein B may be 40% homologous to protein A over 60% of protein B; however, the 60% of the amino acids in protein B to which protein A has homology may be located in multiple, separate sequences (e.g., regions or domains) of protein B.

As used herein, protein "homologs" refers to similar proteins encoded by related but different genes either within a species or between species. Protein "orthologs" refers to similar proteins in different species that arose from a common ancestral gene.

As used herein, all assays and procedures, such as hybridization reactions and antibody-antigen reactions, unless otherwise specified, are conducted under conditions recognized by those of skill in the art as standard conditions.

As used herein, a "nucleotide sequence" or "sequence of nucleotides" (or reference to a nucleic acid molecule designated by a SEQ ID NO:) refers to a single-stranded nucleic acid molecule having the reference sequence, to its reverse complement, or to a double-stranded or partially double-stranded molecule containing the reference sequence base-paired to its reverse complement. Accordingly, a nucleic acid molecule that hybridizes to a reference nucleotide sequence can hybridize to the reference sequence or to its reverse complement.

As used herein, "isolated," with reference to an invention biomolecule, such as a nucleic acid molecule, oligonucleotide, -polypeptide or antibody, indicates that the molecule has been altered by the hand of man from how it is found in its natural environment. For example, a molecule produced by and/or contained within a recombinant host cell is considered "isolated." Likewise, a molecule that has been purified, partially or substantially, from a native source or recombinant host cell, or produced by synthetic methods, is considered "isolated." Depending on the intended application, an isolated molecule can be present in any form, such as in an animal, cell or extract thereof; dehydrated, in vapor, solution or suspension; or immobilized on a solid support.

As used herein, an "amino acid substitution relative to" a reference sequence, refers to a difference between the amino acid residue in the reference sequence and the amino acid residue at the "corresponding position" in the second sequence. Corresponding positions can be determined by comparing and aligning sequences to maximize the number of identical residues. The position of interest is then given the position number assigned to the aligned residue in the reference sequence. An amino acid substitution can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

As used herein, "position," with regard to a specified nucleotide or amino acid, refers to the numerical location of the nucleotide or amino acid in the reference sequence, with the 5'-most nucleotide, or the N-terminal amino acid, designated as position 1.

As used herein, "operatively linked" indicates that the recited nucleotide sequences are positioned such that there is a functional relationship between the sequences. In the context of RNA transcription, the term "operatively linked" indicates that a regulatory sequence(s), such as a promoter, is positioned in such a manner to permit or modulate transcription of RNA using the linked sequence as a template, when appropriate molecules of the transcriptional machinery are bound to the regulatory sequence(s). Two sequences that are "operatively linked" are not necessarily contiguous. Methods for operatively linking a nucleic acid to a promoter are well known in the art and include, for example, cloning the nucleic acid into a vector containing the desired promoter, or appending the promoter to a nucleic acid sequence using PCR.

As used herein, "promoter of gene expression" refers to those nucleotide sequences containing binding sites for RNA polymerase and other transcription factors necessary for transcription. The choice of promoter to operatively link to an invention nucleic acid molecule will depend on the intended application, and can be determined by those skilled in the art. For example, it may be desirable to link the invention nucleic acid molecule to a regulated promoter, such that gene expression can be turned on or off. Alternatively, it may be preferred to have expression driven by either a weak or strong constitutive promoter. Exemplary promoters suitable for bacterial and in vitro transcription systems include, for example, T7, T3 and SP6 promoters. Promoters suitable for mammalian cell systems include, for example, SV40 early promoter, cytomegalovirus (CMV) promoter, Rous sarcoma virus (RSV) promoter, adenovirus major late promoter, and Moloney murine leukemia virus (MMLV) promoter. Regulated promoters can include inducible and repressible elements, such as ecdysone-responsive elements, steroid-responsive elements, lac or trp inducible elements, and the like.

As used herein, "oligonucleotide" refers to a short nucleic acid molecule, such as a nucleic acid molecule that contains, or consists of, at least about 16, 17, 18, 19, 20, 21, 22, 24, 26, 28, 30, 35, 40, 45, 50 or more nucleotides. An oligonucleotide can optionally contain, or consist of, no more than about 500, 400, 350, 300, 250, 200, 150, 100, 75, 50, 45, 40, 35, 30 or 25 nucleotides. An oligonucleotide can be entirely single-stranded or double-stranded, or partially single-stranded and partially double-stranded, as appropriate for the intended application.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that a given nucleic acid molecule can serve as both a "probe" and as a "primer." A primer can be used in a variety of methods, including polymerase chain reaction (PCR), reverse-transcriptase (RT)-PCR, RNA PCR, LCR, multiplex PCR, panhandle PCR, capture PCR, expression PCR, 3' and 5' RACE, in situ PCR, and ligation-mediated PCR.

As used herein, "primer pair" refers to a set of primers that includes a 5' (upstream) primer that hybridizes with the 5' end of a sequence to be amplified (e.g. by PCR) and a 3' (downstream) primer that hybridizes with the complement of the 3' end of the sequence to be amplified.

As used herein, "specifically hybridizes" refers to annealing, by complementary base-pairing, of a nucleic acid molecule (e.g. an invention oligonucleotide) to a target nucleic acid molecule. Those of skill in the art are familiar with both in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1× SSPE, 0.1% SDS, 65° C., and at medium stringency are 0.2× SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application.

As used herein, "inhibitory oligonucleotide" refers to an oligonucleotide that specifically hybridizes to a target nucleic acid molecule in a cell, thereby specifically reduces the amount of target mRNA or its encoded protein present in the cell. Inhibitory oligonucleotides can be used, for example, in functional genomics approaches to determine the biological activities of a target gene, or to treat conditions associated with expression of the target mRNA. Examples of inhibitory oligonucleotides include, but are not limited to, interference nucleic acid molecules, antisense nucleic acid molecules and catalytic nucleic acid molecules. As with other oligonucleotides described herein, inhibitory oligonucleotides can be produced synthetically, or can be produced recombinantly by either in vitro or in vivo transcription, by methods known in the art. Methods of using inhibitory oligonucleotides in ex vivo and in vivo applications are also well known in the art, and such methods can be used to reduce the amount of target mRNA or protein.

As used herein, "interference nucleic acid molecule" refers to a molecule that acts through a complex known as the RNA-induced silencing complex (RISC) to specifically induce the degradation of cognate mRNA. Interference nucleic acid molecules may additionally or alternatively act to inhibit mRNA translation through the same or a different complex. Interference nucleic acid molecules include, but are not limited to, long double-stranded RNAs (dsRNA) that can be cleaved intracellularly into short inhibitory RNAs (siRNA); siRNAs, which are about 21-23 nucleotide double-stranded RNA molecules, generally with 2 nucleotide single stranded overhangs (Hannon (2002) *Nature* 418:244-251); short hairpin RNAs (shRNA), which are similar to small temporal RNAs (stRNAs) and micro-RNAs (miRNAs) (McManus et al. (2002) *RNA* 8:842-850); and mRNA-cDNA hybrids (D-RNAi; Lin et al. (2001) *Biochem. Biophys. Res. Commun.* 281:639-644). Interference molecules can thus be completely or partially double-stranded.

As used herein, "antisense nucleic acid molecule" refers to a molecule that base pairs with cognate mRNA and inhibit its translation. The antisense-bound mRNA is then degraded by RnaseH, or alternatively forms a stable complex that blocks a cell's translational machinery. Antisense molecules can be DNA or RNA, and commonly contain modified bases, sugars or linkages to enhance their stability. Methods of making antisense nucleic acids by synthetic and recombinant methods are known in the art (e.g. Phillips (ed.) (1999) "Antisense Technology, Part A (Methods in Enzymology, Volume 313)" Academic Press).

As used herein, "catalytic nucleic acid molecule" refers a molecule that base-pairs with, and enzymatically cleaves, target RNA. Catalytic nucleic acid molecules include, for example, hairpin ribozymes, hammerhead ribozymes, hepatitis delta virus ribozymes, and lead-dependent ribozymes (Doherty and Doudna (2001) *Annu. Rev. Biophys. Biomol. Struct.* 30:457-475). Methods of making catalytic nucleic acid molecules by synthetic and recombinant methods are known in the art (e.g. Gibson (ed.) (2002) "Antisense and Ribozyme Methodology: Laboratory Companion" John Wiley & Sons).

As used herein, "domain" refers to a region of a polypeptide that is capable of maintaining its structure or function in a context other than in the full-length polypeptide, such as when expressed alone or as a fusion protein. A structural domain can comprise one or more beta sheets, alpha helices, loops, folds or other structural motifs, and can correspond, for example, to one or more extracellular domains, transmembrane domains or intracellular domains. A functional domain can, but need not, correspond exactly to a structural domain. Exemplary functional domains include an epitope, a ligand or effector binding site, a modification site (e.g. a site of phosphorylation, acylation or glycosylation), an enzyme active site, and the like. Regions of a polypeptide that comprise structural or functional domains can be determined using methods known in the art. For example, the boundaries of a single exon, or of several contiguous exons, are often identical to the boundaries of a structural or functional domain. Domains can also be identified by their homology to proteins known to contain particular structural or functional domains, for example, by using the search and alignment resources of the pfam database (pfam.wustl.edu/; Bateman et al. (2002) Nucleic Acids: Research 30: 276-280). Domains can also be identified by producing polypeptide fragments and directly analyzing their structural or functional properties.

As used herein, "mature" with respect to a STIM1 polypeptide, refers to the polypeptide with the presumptive signal peptide (amino acids 1-22 of human, mouse or reference STIM1) removed.

As used herein, "extracellular domain of STIM1" refers to the portion of the mature polypeptide that is N-terminal to the presumptive transmembrane domain (e.g. N-terminal to the position corresponding to position 214 of human, mouse or reference STIM1). It will be appreciated that the "extracellular domain" may not necessarily be localized extracellularly in all instances, and thus may alternatively be localized intralumenally or intracytoplasmically (e.g. during protein synthesis, sorting, or degradation, or when synthesized as a recombinant fusion protein).

As used herein, "cytoplasmic domain of STIM1" refers to the portion of the mature polypeptide that is C-terminal to the presumptive transmembrane domain (e.g. C-terminal to the position corresponding to position 234 of human, mouse or reference STIM1). It will be appreciated that the "cytoplasmic domain" may not necessarily be localized to the cytoplasm in all instances, and thus may alternatively be localized intralumenally or extracellularly (e.g. during protein synthesis, sorting, or degradation, or when synthesized as a recombinant fusion protein).

As used herein, "polypeptide" includes naturally and non-naturally occurring peptides and proteins. A polypeptide can be a core protein, or can be a post-translationally modified form of a protein such as a phosphoprotein, glycoprotein, proteoglycan, lipoprotein or nucleoprotein. Polypeptides may include one or more D-amino acids, one or more chemically or enzymatically derivatized amino acids (e.g. derivatized by replacement of a hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation), one or more amino acid analogs or mimetics (described, for example, in Sawyer, "Peptide Based Drug Design," ACS, Washington (1995)), or one or more labeled (e.g. radiolabeled or fluorescently labeled) amino acids.

As used herein, "peptide" refers to a short polypeptide, such as a polypeptide that contains, or consists of, at least about 8, 9, 10, 12, 14, 16, 18, 20, 25, 30, 35, 40 or more amino acids. A peptide can optionally contain, or consist of, no more than about 200, 150, 100, 75, 50, 45, 40, 35, 30, 25 or 20 amino acids.

As used herein, "antibody" is intended to refer to both polyclonal and monoclonal antibodies, as well as molecules containing one or more antigen binding fragments of such antibodies (e.g. complementarity determining regions (CDRs), Fab, F(ab')$_2$, Fd and Fv fragments and the like). In addition, the term "antibody" is intended to encompass non-natural antibodies, including, for example, single chain antibodies, chimeric antibodies, bifunctional antibodies, humanized antibodies, CDR-grafted antibodies and CDR-grafted alternative scaffolds, as well as antigen-binding fragments thereof. Also encompassed are detectably labeled antibodies, such as antibodies labeled with a radioactive isotope, fluorochrome, ferromagnetic substance, luminescent agent, enzyme or ligand.

As used herein, "specifically binds," in the context of an antibody-antigen interaction, refers to a binding interaction between the antibody and the target antigen that has a $K_d$ of about $10^{-6}$ M or less, such as about $10^{-7}$ M or less, including about $10^{-8}$ M, $10^{-9}$ M or $10^{-10}$ M or less. In contrast, the term "does not bind," in the context of an antibody-antigen interaction, refers to a binding interaction between the antibody and the target antigen that has a $K_d$ of about $10^{-5}$ M or higher. Methods of determining binding affinity between antibodies and antigens are well known in the art (see, for example, Harlow and Lane (1989) "Antibodies: A Laboratory Manual," Cold Spring Harbor Press (New York)).

As used herein, "kit" refers to a product that includes at least one container having disposed therein an amount of an invention molecule (e.g. nucleic acid molecule, polypeptide, peptide, antibody, agent, etc.) sufficient for an intended use of the kit. The container can be of any convenient material and shape, including those customarily used in laboratories and clinics, and can serve to provide a contaminant-free or sterile environment for the contained molecule. A kit can further include a tangible description of the amount or concentration of the molecule, and/or guidance regarding its formulation and use. A kit can further include additional containers, such as containers having disposed therein buffers, carriers, solvents and the like, useful for formulating the molecule, and/or containers having disposed therein additional molecules used in conjunction with the molecules provided herein.

As used herein, "substrate" refers to any suitable solid or semi-solid support, such as membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which an invention molecule (e.g. nucleic acid molecule, polypeptide, peptide, antibody, agent, etc.) can be bound.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that can alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

As used herein, "a system" is used interchangeably with the term "combination" and refers to any association between or among two or more items. The combination can be two or more separate items, can be a mixture thereof or any variation thereof.

B. Cellular Signaling and Calcium Modulation

All living cells sense and respond to their environment by a set of mechanisms termed cell signaling. These mechanisms are part of a complex system of communication that governs basic cellular activities and coordinates the actions of cells. Living cells must respond appropriately to their environment, whether they are free-living in the soil or part of a tissue. Cell communication is necessary for the existence of multicellular organisms. The ability of cells to perceive and correctly respond to their microenvironment is the basis of development, tissue repair, and immunity as well as normal tissue homeostasis.

Cells, through a class of proteins known as receptors, receive information from their environment. The information is then processed through signaling pathways and decoded in the nucleus and other areas of the cell. The spatial and temporal dynamics of both receptors and the components of the signaling pathways are important in the transfer of the message from the extracellular to the intracellular environment. The components of the signaling pathway, their location either inside or on the surface of the cell, the role of each component in the transduction of the signal, and interactions among the components of the system in order to transduce the signal are required to elucidate the cause, mechanism and effect of the signal transduction on the cell. Molecules that can serve as components of a signaling pathway include, but are not limited to, an organic compound, inorganic compound, metal complex, receptor, enzyme, antibody, protein, nucleic acid, peptide nucleic acid, DNA, RNA, polynucleotide, oligonucleotide, oligosaccharide, lipid, lipoprotein, amino acid, peptide, polypeptide, peptidomimetic, carbohydrate, cofactor, drug, prodrug, lectin, sugar, glycoprotein, hormone, steroid, biomolecule, macromolecule, biopolymer, polymer, sub-cellular structure, sub-cellular compartment or any combination, portion, salt, or derivative thereof, a virus, such as a viral vector or viral capsid with or without packaged nucleic acid, phage, including a phage vector or phage capsid, with or without encapsulated nucleic acid, a cell, including eukaryotic and prokaryotic cells or fragments thereof, a liposome or micellar agent or other packaging particle, and other such biological materials. The interactions among the components of the signaling system include, but are not limited to, protein:protein, protein:nucleic acid, nucleic acid:nucleic acid, protein:lipid, lipid:lipid, protein:small molecule, receptor:signal, antibody:antigen, peptide nucleic acid:nucleic acid, and small molecule:nucleic acid.

There are many signaling pathways; such pathways include, but are not limited to, the Notch pathway; G-protein signaling and activation of phospholipase C (PLC); nuclear factor κB (NFκB) pathway; T cell activation; activation of protein kinase C (PKC) and protein kinase A (PKA); Ahr signal transduction pathway; anthrax toxin mechanism of action; ataxia telangiectasia-mutated gene (ATM) signaling pathway; bioactive peptide induced signaling pathway; co-activator-associated arginine methyltransferase 1 (CARM1) and regulation of the estrogen receptor; CBL mediated ligand-induced down-regulation of EGF receptors; control of skeletal myogenesis by HDAC and calcium/calmodulin-dependent kinase; CXCR4 signaling pathway; cyclins and cell cycle regulation; the cytokine network; D4-GDI (GDP dissociation inhibitor) signaling pathway; mitogen activated protein kinase (MAPK) pathway; Erk1/Erk2 MAPK signaling pathway; FAS signaling pathway; Fc Epsilon Receptor I signaling; growth hormone signaling pathway; ErbB4 signaling; interferon signaling, such as, interferon alpha (IFNα) and IFNγ signaling; insulin-like growth factor 1 (IFG-1) signaling; interleukin (IL) signaling, such as, IL-17, IL-18, IL-2, IL-3, IL-4, IL-5, IL-6 and IL-22 signaling; insulin signaling pathway; integrin signaling pathway; phorbal esters signaling pathway; tumor necrosis factor receptor 5 (TMFR-5) pathway; p53 signaling pathway; CCR5 signaling pathway; phospholipase C and phospholipase C epsilon pathways; RAC1 cell motility signaling pathway; RAS signaling pathway; reelin signaling pathway; RHO cell motility signaling pathway; ubiquitin-proteasomal pathway; signal transducers and activators of transcription 3 (STAT-3) pathway; transforming growth factor β (TFGβ) signaling pathway; TNF/Stress related signaling pathways; TNFR1 and TNFR2 signaling pathways; TRKA receptor signaling pathway; lymphocyte signaling; Atk signaling; and chromatin regulation.

Errors in cellular information processing contribute to numerous diseases, including, but not limited to, cancer, autoimmunity, and diabetes. In order to effectively treat these diseases, knowledge of the mechanism by which the signal is transduced is required. Identifying the components of the signaling pathway and the message that it transmits allows for the alteration, blocking or amplification of the message and possible prevention of the undesired cellular response or activation of desired cellular response. This information can also be used in other ways such as, but not limited to, controlling the behavior of individual cells and permitting the creation of artificial tissues.

A key component in some signaling pathways is calcium. Intracellular calcium concentration is tightly regulated, and numerous cellular constituents, e.g., proteins, and processes are calcium sensitive. Thus, many signal transduction mechanisms involve transient calcium flux across the plasma membrane and membranes of intracellular organelles.

1. Calcium Homeostasis

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space can enter the cell through various calcium channels and a sodium/calcium exchanger and is actively extruded from the cell by calcium pumps and sodium/calcium exchangers. Calcium can also be released from internal stores through inositol trisphosphate or ryanodine receptors and can be taken up by these organelles by means of calcium pumps.

Endocytosis provides another process by which cells can take up calcium from the extracellular medium through endosomes. In addition, some cells, e.g., exocrine cells, can release calcium via exocytosis.

a. Basal or Resting Cytosolic Calcium Levels

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leaks in the endoplasmic reticulum and plasma membrane. Disturbance of resting cytosolic calcium levels can effect transmission of such signals and give rise to defects in a number of cellular processes. For example, cell proliferation involves a prolonged calcium signaling sequence. Other cellular processes, including but not limited to, secretion, fertilization and learning, involve calcium signaling.

b. Store-Operated Calcium Entry

One mechanism for movement of calcium into cells through the plasma membrane is commonly referred to as store-operated calcium entry. Reduced calcium concentration in intracellular calcium stores such as the endoplasmic reticulum resulting from release of calcium therefrom provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism has been referred to as capacitative calcium entry (CCE), calcium release-activated, store-operated or depletion-operated calcium entry. Store-operated calcium entry can be recorded as an ionic current with distinctive properties. In some instances, this current is referred to as $I_{SOC}$ (store-operated current) or $I_{CRAC}$ (calcium release-activated current).

i. Regulation of Store-Operated Calcium Entry by Intracellular Calcium Stores

Store-operated calcium entry is regulated by the level of calcium within an intracellular calcium store. Intracellular calcium stores can be characterized by sensitivity to agents, which can be physiological or pharmacological, that activate release of calcium from the stores or inhibit uptake of calcium into the stores. Different cells have been studied in characterization of intracellular calcium stores, and stores have been characterized as sensitive to various agents, including, but not limited to, $IP_3$ and compounds that effect the $IP_3$ receptor, thapsigargin, ionomycin and/or cyclic ADP-ribose (cADPR) (see, e.g., Berridge (1993) Nature 361:315-325; Churchill and Louis (1999) Am. J. Physiol. 276:C426-C434; Dargie et al. (1990) Cell Regul. 1:279-290; Gerasimenko et al. (1996) Cell 84:473-480; Gromoda et al. (1995) FEBS Lett. 360:303-306; Guse et al. (1999) Nature 398:70-73).

The identities and/or cellular locations of calcium stores can be determined, for example, by isolation and characterization of organelles or imaging of cells using calcium-sensitive indicators which localize in storage organelles. Mag-fura 2, an example of one such indicator, is a UV light-excitable, ratiometric, low-affinity fluorescent calcium indicator. The moderate calcium affinity of mag-fura-2 and the tendency of its acetoxymethyl (AM) ester to accumulate in subcellular compartments makes this indicator particularly useful in monitoring of or assessing calcium stores (see, e.g., Hofer and Machen (1993) Proc. Natl. Acad. Sci. U.S.A. 90:2598-2602; Hofer et al. (1998) EMBO J. 17:1986-1995; Hofer et al. (1998) J. Cell Biol. 140:325-334; Churchill and Louis (1999) Am. J. Physiol. 276:C426-C434). Intracellular calcium stores include the endoplasmic reticulum and sarcoplasmic reticulum, which are sensitive to $IP_3$ or caffeine/ryanodine and thapsigargin/cyclopiazonic acid (CPA) (see, e.g., Pozzan et al. (1994) Physiol. Rev. 74:595-637; Meldolesi and Pozzan (1998) J. Cell Biol. 142:1395-1398; Meldolesi and Pozzan (1998) Trends Biochem. Sci. 23:10-14; Golovina and Blaustein (2000) Glia 31:15-28), and isolated zymogen granules and the envelope of isolated nuclei, which are sensitive to cADPR and $IP_3$ (see, e.g., Gerasimenko et al. (1996) Cell 84:473-480; Gerasimenko et al. (1995) Cell 80:439-444).

Basal free calcium concentrations in calcium stores can be orders of magnitude, e.g., $10^3$-fold, greater than the free calcium concentration in the cytosol. For example, the basal free calcium concentration measured in the endoplasmic reticulum of HEK293 cells ranges between about 200-700 µM, with an average of about 500 µM, whereas the basal free calcium concentration in the cytosol is about 50 nM (Yu and Hinkle (2000) J. Biol. Chem. 275:23648-23653).

Free calcium concentrations in the endoplasmic reticulum can be measured in a variety of ways such as, for example, using various calcium-sensitive indicators (see, e.g., Yu and Hinkle (2000) J. Biol. Chem. 275:23648-23653) including mag-fura 2 (see, e.g., Hofer and Schulz (1996) Cell Calcium 20:235-242), endoplasmic reticulum-targeted aequorin (see, e.g., Montero et al. (1995) EMBO J. 14:5467-5475) and endoplasmic reticulum-targeted "cameleons" (i.e., fluorescent calcium indicators based on fluorescence resonance energy transfer between two modified green fluorescent proteins (GFPs) contained in a protein with calmodulin and a calmodulin-binding peptide; see, e.g., Miyawaki et al. (1997) Nature 388:882-887 and Yu and Hinkle (2000) J. Biol. Chem. 275:23648-23653).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium (Yu and Hinkle (2000) J. Biol. Chem. 275: 23648-23653; Hofer et al. (1998) EMBO J. 17:1986-1995).

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by IP$_3$ formed in the break down of plasma membrane phosphoinositides through the action of phospholipase C activated by binding of an agonist to a plasma membrane G protein-coupled receptor. Ryanodine receptor-mediated calcium release is triggered by an increase in cytoplasmic calcium and is referred to as calcium-induced calcium release (CICR). The activity of ryanodine receptors (which have affinity for ryanodine and caffeine) may also be regulated by cyclic ADP-ribose.

Thus, the calcium levels in the stores, and in the cytoplasm, fluctuate. For example, ER free calcium can decrease from a range of about 60-400 µM to about 1-50 µM when HeLa cells are treated with histamine, an agonist of PLC-linked histamine receptors (Miyawaki et al. (1997) *Nature* 388:882-887). Store-operated calcium entry is activated as the free calcium concentration of the intracellular stores is reduced. Depletion of store calcium, as well as a concomitant increase in cytosolic calcium concentration, can thus regulate store-operated calcium entry into cells.

ii. Store-Operated Ionic Currents

Electrophysiological analysis of store-operated or calcium release-activated currents reveals distinct biophysical properties (see, e.g., Parekh and Penner (1997) *Physiol. Rev.* 77:901-930) of these currents. For example, the current can be activated by depletion of intracellular calcium stores (e.g., by nonphysiological activators such as thapsigargin, CPA, ionomycin and BAPTA, and physiological activators such as IP$_3$) and can be selective for divalent cations, such as calcium, over monovalent ions in physiological solutions or conditions, can be influenced by changes in cytosolic calcium levels, and can show altered selectivity and conductivity in the presence of low extracellular concentrations of divalent cations. The current may also be blocked or enhanced by 2-APB (depending on concentration) and blocked by SKF96365 and Gd3+ and generally can be described as a calcium current that is not strictly voltage-gated.

c. Cytoplasmic Calcium Buffering

Agonist activation of signaling processes in cells can involve dramatic increases in the calcium permeability of the endoplasmic reticulum, for example, through opening of IP$_3$ receptor channels, and the plasma membrane through store-operated calcium entry. These increases in calcium permeability are associated with an increase in cytosolic calcium concentration that can be separated into two components: a "spike" of calcium release from the endoplasmic reticulum during activation of the IP$_3$ receptor and a plateau phase which is a sustained elevation of calcium levels resulting from entry of calcium into the cytoplasm from the extracellular medium. Upon stimulation, the resting intracellular free calcium concentration of about 100 nM can rise globally to greater than 1 µM. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria can act as calcium buffers by taking up calcium during periods of activation and slowly releasing it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase (PMR1/ATP2C1). Additionally, there is evidence that a significant amount of the calcium released upon IP$_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions can be bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels can be reduced are proteins that are involved in, participate in and/or provide for cytoplasmic calcium buffering.

d. Receptor-Mediated and Second Messenger-Operated Cation Movement

Receptor-mediated cation channels are gated in response to ligand binding to a membrane receptor distinct from the channel protein itself. Some receptor-mediated cation channels are activated downstream of tyrosine kinases and others via G protein signaling cascades. Receptor-mediated channels are expressed in a number of both excitable and nonexcitable cells, including smooth muscle, mast cells, epidermis and renal mesangial cells.

One way in which receptor-mediated cation channels are regulated is through second messengers induced in response to ligand-binding to a membrane receptor. Such cation channels are referred to as second messenger-operated channels. For example, cyclic nucleotides generated by adenylyl and guanylyl cyclases can directly activate cation-permeable channels. Such cyclic nucleotide-gated channels are predominantly expressed in sensory tissues, for example the retina and in olfactory/gustatory epithelia. Calcium is another second messenger that can mediate ion channel function. Examples of calcium-mediated channels include calcium-activated potassium and chloride channels as well as cation channels in neutrophils, smooth muscle and mast cells.

Inositol phosphates generated upon activation of phospholipase C (PLC) can also act as second messengers that activate certain channels. For example, channels responsive to inositol-1,4,5-triphosphate (IP$_3$) include the intracellular IP$_3$ receptor of the endoplasmic reticulum as well as plasma membrane channels such as those expressed in T-lymphocytes, mast cells and epidermal cells. The intracellular IP$_3$ receptor functions as a ligand-gated ion channel that permits passage of calcium upon binding of IP$_3$ released through hydrolysis of membrane phospholipids by activated phospholipase C (PLC). PLC can be activated through agonist binding to a surface membrane G protein-coupled receptor. Activation of the IP$_3$ receptor results in the release of calcium stored in the endoplasmic reticulum into the cytoplasm which produces a transient "peak" increase in cytosolic calcium concentration. In addition, although no cation channels have been identified in components of the endocytic pathway, e.g., endosomes and lysosomes, IP$_3$-dependent agonists appear to be associated with calcium release from lysosomes in MDCK cells (see Haller et al. (1996) *Biochem. J.* 319:909-912).

Lipids and polyunsaturated fatty acids (PUFAs) may also act as second messengers for the activation of ion channels. For example, arachidonic acid and its metabolites, as well as linolenic acid, can activate receptor-mediated ion channels. In addition, phospholipids, such as lysophospholipids (e.g., lysophosphatidic acid (LPA), lysophosphatidylcholine (LPC), sphingosylphosphoryl choline (SPC) and sphingosine 1-phosphate (SIP)) can be ligands for plasma membrane receptors such as G-protein-coupled receptors (GPCRs)

involved in a second messenger cascade process in cells (see, e.g., Hla et al. (2001) *Science* 294:1875). PLC generates not only $IP_3$ but also diacylglycerol (DAG) which is a potential precursor for polyunsaturated fatty acids. PUFAs can be released from DAG by the action of DAG lipase.

e. Calcium Uptake and Release by Endosomes and Lysosomes

Endocytosis is a process whereby contents of the cell plasma membrane and extracellular medium are transported into the interior of the cell. Not only does endocytosis serve "house-keeping" functions of a cell, it plays crucial roles in cell signaling, development, and the regulation of varied biological processes including, for example, synaptogenesis, neural plasticity, generation of morphogen gradients and programmed cell death. Endocytosis may have both negative and positive influences on signaling. For example, endocytosis can regulate the number of receptors on the plasma membrane. In addition, endocytosis plays a positive role in signaling mediated by the Notch signaling pathway which acts to determine cell-type specificity during development.

The endocytic process involves several components, including endosomes and lysosomes which are intracellular compartments along the endocytic pathway. Endosomes are morphologically heterogeneous and constitute a pleiomorphic smooth membrane system of tubular and vesicular elements. The vesicular elements contain intra-organelle vesicles and are described as multivesicular bodies. Endocytosed macromolecules are delivered first to early endosomes and then to late endosomes. Early endosomes are tubular with varicosities and many are located peripherally within the cell close to the plasma membrane. Late endosomes are more spherical and have the appearance of multivesicular bodies. They are mostly juxtanuclear being concentrated near the microtubule organizing center. Early and late endosomes are characterized by different lumenal pHs, different protein compositions and association with different small GTPases of the Rab family. The early endosome is the major sorting compartment of the endocytic pathway where many ligands dissociate from their receptors and from which many of the receptors recycle to the cell surface.

Lysosomes are membrane-bound organelles containing hydrolytic enzymes and are regarded as the terminal degradation compartment of the endocytic pathway. Lysosomes also play an important role in phagocytosis, autophagy, crinophagy and proteolysis of some cytosolic proteins that are transported across the lysosomal membrane. In many cell types, lysosomes secrete their contents after fusion with the plasma membrane. The limiting membrane of lysosomes contains a set of highly glycosylated lysosomal-associated membrane proteins (LAMPs). Additional lysosomal membrane proteins mediate transport of ions, amino acids, and other solutes across the lysosomal membrane.

In mammalian cells, the organelles of the late endocytic pathway interact with each other and are in dynamic equilibrium. Content mixing and/or exchange of membrane proteins occurs between late endosomes, lysosomes and between late endosomes and lysosomes. Delivery of endocytosed macromolecules to lysosomes occurs by content mixing between late endosomes and lysosomes as a result of transient as well as direct fusion which can form hybrid organelles. Cell-free heterotypic fusion of mammalian late endosomes and lysosomes requires calcium which may mediate its effects via calmodulin. The calcium is derived and released from the endocytic organelle lumen and is required in a late step in fusion. Although the calcium release pathway has not yet been elucidated, docking of endocytic organelles is thought to trigger release of endocytosed calcium from the lumen of endocytic organelles into the cytoplasm. This calcium release is believed to mediate membrane fusion events at several stages on the endocytic pathway. Lysosomes contain a mobilizable calcium pool. Furthermore, although no cation transport molecule has been identified in endosomes or lysosomes, both endosomal and lysosomal membranes provide for calcium transport. Thus, uptake and release of calcium from endosomes and lysosomes can impact intracellular and cytosolic calcium levels.

2. Molecules Involved in Intracellular Calcium Modulation and Calcium-Entry Mediated Events Fluctuations in the level of calcium ions, including free and bound calcium, in cells provide important biological signals involved in processes such as, for example, protein secretion, muscle contraction, cell death and development. The movement of cations, such as calcium, into, within and out of cells thus plays a critical role in the operation and survival of cells. Calcium binding and movement into, out of and within cells can act as a signal that is highly organized in space, frequency and amplitude due in part to localization of the movements and tight regulation of the processes through which calcium movement occurs in cells.

Altered calcium regulation or calcium dyshomeostasis or dysregulation in cells is associated with a number of diseases and disorders. Altered calcium regulation can be the result of alterations in the elements involved in movement of calcium ions, and/or in the regulation thereof. It is, therefore, desirable to identify cellular constituents, such as proteins, that modulate intracellular calcium, including, for example, proteins that provide for and/or regulate the movement of cations, such as calcium, into, within and out of cells, and to identify agents that modulate intracellular calcium. Identification of molecules, e.g., proteins, involved in modulating intracellular calcium makes possible the elucidation of the molecular and cellular mechanisms underlying modulatory processes such as calcium binding and movement. An example of one such process is store-operated calcium entry, a fundamental and essential process of many cells. The identities of the molecular components that are involved in, participate in and/or provide for store-operated calcium entry, and, in particular, the identities of the ion transport proteins or channels that provide for store-operated calcium entry, are largely unknown and may differ for many cell types. Identification of such molecules provides molecular targets for the regulation of this specific and critical process in calcium-dependent cellular functions.

Furthermore, identification of molecules involved in modulating intracellular calcium assists in the dissection of complex signaling processes and facilitates the elucidation of the elements involved in regulation of these processes. Such processes include, but are not limited to, receptor-mediated, store-operated, and second messenger-operated cation entry into the cytoplasm or intracellular organelles. Knowledge of the number and structure of such molecules, as well as a comparison of their properties, permits the identification and design of agents that specifically interact with and/or affect or regulate molecules, such as, for example, ion transport proteins, that modulate intracellular calcium. Such agents have many uses. For example, they can be used to assess function and distribution of proteins that modulate intracellular calcium. The specific identified proteins may also be used as targets in methods for identifying agents that modulate intracellular, such as cytosolic, calcium and candidate therapeutic agents. Furthermore, the identified proteins, as well as nucleic acids encoding the proteins, may be used to modulate intracellular calcium, for example, by recombinant expression of nucleic acid encoding such a protein in a cell, or by reducing, altering, eliminating or interfering with expression of such a protein in a cell.

Molecules that can be involved in modulating intracellular calcium include, but are not limited to, calcium-binding proteins, ion transport proteins that are involved in providing for movement of cations, such as calcium, into, out of or within cells, receptors and proteins that regulate ion transport proteins, receptors or calcium-binding proteins. A molecule involved in modulating intracellular calcium can do so at any level and in connection with any of a number of processes within a cell. For example, a molecule involved in modulating intracellular calcium may participate in the maintenance of resting cytosolic calcium levels, store-operated calcium entry into cells, receptor-mediated calcium movement, second messenger-operated calcium movement, calcium influx into or efflux from a cell, and/or calcium uptake into or release from intracellular compartments, including, for example, the endoplasmic reticulum, endosomes and lysosomes. A molecule involved in modulating intracellular calcium may function alone (e.g., as a single unit or as a homo-multimer of two or more of proteins) or in combination with other molecules, e.g., proteins (e.g., in a heteromeric configuration), and may be involved in regulating proteins that bind and/or transport calcium or receptors, particularly receptors involved in receptor-mediated cation movement or cell signaling.

a. Ion Transport Proteins

Ion transport proteins are proteins involved in providing for the transport of ions into, within, or out of cells. Ion transport proteins involved in modulating intracellular calcium are involved in providing for the transport of calcium. Such ion transport proteins may be relatively specific for calcium ion transport.

i. Structural Features of Ion Transport Proteins

An ion transport protein may function to transport cations in a number of ways. For example, the proteins may form and/or contribute to a complex that forms a pore or channel for the transport of cations through a membrane. The proteins may instead provide for a translocation of cations through ion binding and release processes as is characteristic of a transporter. Ion transport proteins may function to transport ions as a single unit or may be one unit of a multi-component structure that transports ions. A multi-component structure may be a homo-multimer of two or more of the same proteins or a hetero-multimer containing two or more different proteins (and which may also contain two or more of the same proteins).

Ion transport proteins involved in providing for movement of ions via a channel-like or pore structure typically contain one or multiple regions that have characteristics of transmembrane domains, which may possibly participate in channel formation. Transmembrane domains tend to include a sequence of amino acids, typically of about 10 to about 30 or more amino acids, about 15 to about 30 or more amino acids, about 20 to about 30 or more amino acids, or about 20 to about 25 amino acids, of high hydrophobicity. The hydrophobicity scale is defined from the transfer free energy of amino acids between organic solvents and water, and statistics on the distribution of residues in proteins. Hydropathy plots of the hydrophobicity of adjacent amino acid residues averaged over a moving window of suitable length are commonly used to assess proteins for such sequences of amino acids (see, e.g., Kyte and Doolittle (1982) *J. Mol. Biol.* 157:105-134; Argos et al. (1982) *Eur. J. Biochem.* 128:565-575 and Engelman et al. (1984) *Ann. Rev. Biophys. Biophys. Chem.* 15:321-353). Although transmembrane domains may be in an α-helical and/or β-sheet conformation, the transmembrane domain structure of most major families of ion channel proteins appears to be α-helical.

Pore-lining segments of ion transport protein channel transmembrane domains, such as regions lining aqueous channels, may have a partly hydrophilic face and appear as amphipathic segments. Amphipathic segments may be identified based on the hydrophobic moment (see, e.g., Eisenberg et al. (1984) *J. Mol. Biol.* 179:125-142; and Finer-Moore and Stroud (1984) *Proc. Natl. Acad. U.S.A.* 81:155-159).

The number of transmembrane domains contained in an ion transport protein that includes a channel-like structure can vary. For example, there can be at least one transmembrane domain contained in a protein involved in providing for ion transport. Thus, for example, there can be one, two, three, four, five, six or more transmembrane domains contained in a protein involved in providing for ion transport. Typically, there are at least about 1 to about 25 or more transmembrane domains, about 2 to about 25 or more transmembrane domains, about 4 to about 25 or more transmembrane domains, about 6 to about 25 or more transmembrane domains, about 8 to about 25 or more transmembrane domains, or about 1 or 2 to about 8 transmembrane domains or about 6 or more transmembrane domains. For example, an ion transport protein that includes a channel-like structure and is capable of providing for the movement of cations through a membrane may contain at least one, or at least two, or at least three or at least 4 or more groups of six transmembrane helices.

Multimeric complexes form the complete structure of many ion transport channels. These complexes can contain two or more different subunits. Typically, at least one subunit of a complex is designated the pore subunit, which may be able to flux ions in the absence of other subunits. Other subunits of such complexes, which alone may not be able to flux ions, are typically required for normal kinetics and modulation, e.g., gating, activation, and deactivation) of the channel. Such subunits have been referred to as auxiliary subunits of a channel complex. For example, voltage-gated sodium channels contain an α subunit, which has a functional pore sufficient for functional expression of sodium currents, and two auxiliary subunits, β1 and β2 subunits, which are required for normal kinetics and the voltage-dependence of gating of sodium channels. The α subunit is larger and contains multiple domains containing multiple α-helical transmembrane segments, whereas the β subunits have a single transmembrane segment, a large, glycosylated extracellular domain and a small intracellular domain (see, e.g., Catterall (2000) *Neuron* 26:13-25).

ii. Calcium Transport

Ion transport proteins that modulate intracellular calcium are involved in the transport of calcium. Calcium transport may be assessed in a variety ways. For example, cells expressing an ion transport protein may be evaluated for uptake of labeled calcium, such as $45Ca^{2+}$, into the cells. RNA coding for an ion transport protein may also be introduced into a cell, e.g., *Xenopus laevis* oocytes, which may be evaluated for $^{45}Ca^{2+}$ uptake.

Calcium transport properties of an ion transport protein may also be assessed using calcium indicator-based assays of the intracellular calcium levels of cells expressing the protein. Such assays utilize calcium-sensitive indicators which facilitate detection of transient alterations in intracellular calcium levels. These indicators provide a detectable signal, e.g., fluorescence or bioluminescence, upon binding of calcium and therefore can be correlated to calcium levels in cells. Methods of measuring intracellular calcium using calcium indicators are well known in the art (see, e.g., Takahashi et al. (1999) *Physiol. Rev.* 79:1089-1125).

Electrophysiological analysis of cells expressing an ion transport protein also can be used to assess calcium transport by a transport protein. For example, whole-cell, patch-clamp, voltage clamp and single-channel recording methods may be used to detect and measure calcium or other cation currents across membranes of cells to which calcium or another cation has been applied. A variety of cells may be used for such electrophysiological analysis, including, but not limited to, *X. laevis* oocytes into which RNA encoding an ion transport protein has been injected.

Ion transport protein(s) involved in calcium regulation in cells may be more permeable to calcium than to monovalent ions under physiological conditions. Thus, for example, such types of proteins can be able to flux calcium through a membrane more readily than monovalent ions. For example, the permeability of an ion transport protein to calcium may be more than about 1.5-fold, more than about 2-fold, more than about 3-fold, more than about 4-fold, more than about 5-fold, more than about 6-fold, more than about 7-fold, more than about 8-fold, more than about 9-fold or more than about 10-fold greater than the permeability to monovalent ions. Ion transport proteins may be selective for calcium under physiological conditions.

b. Modulatory or Regulatory Molecules

In addition to ion transport proteins, there may be cellular molecules that are involved in modulating intracellular calcium but that are not directly involved in providing for the transport of ions into or out of the cytosol as would, for example, a channel protein or pore-forming subunit of a channel protein. Such molecules, which can be referred to as modulatory or regulatory molecules (i.e., modulators or regulators), encompass a diverse array of structures and include receptors, enzymes and calcium-binding proteins. Modulator or regulator molecules can, for example, function in processing a signal in a cell (e.g., signaling pathway components) or regulate the activity of an enzyme or ion channel.

For example, some calcium-binding proteins can be involved in modulating intracellular calcium. Included among the calcium-binding proteins are proteins that contain a calcium binding motif referred to as an EF-hand (see, e.g., Kretsinger (1997) *Nat. Struct. Biol.* 4:514-516; Ikura (1996) *Trends Biochem. Sci.* 21:14-17; Kawasaki et al. (1995) *Protein Profile* 2:297-490). Typically, an EF-hand motif contains a loop of about 12 amino acid residues flanked on either side by an alpha helix of about 12 amino acid residues. Position 12 of the loop typically contains a Glu or Asp. The helix-loop-helix motif can be repeated from about 2 to about 12 times. The motifs may coordinate calcium to side-chain oxygens of invariant residues occupying positions 1, 3, 5 and 12 of the loop, and to a carbonyl oxygen of a less conserved residue at position 7. EF hand-containing proteins may undergo a conformational change upon binding calcium, and thus some of these proteins can pass signaling information on to targets to which such proteins can bind. EF hand proteins can function in a number of ways. For example, they can function as a separate subunit of a single protein (e.g., enzyme), as a subunit that reversibly associates with different proteins (e.g., calmodulin) or as an integral portion of the sequence of an enzyme (e.g., calpain).

Neuronal calcium sensor (NCS) proteins are examples of proteins containing EF hand motifs. These proteins are expressed predominantly or solely in retinal photoreceptors or neurons. Five subfamilies of NCS proteins have been described: two expressed in retinal photoreceptors (recovering, which inhibit rhodopsin kinase, and the guanylate cyclase-activating proteins (GCAPs)) and three expressed in central neurons and neuroendocrine cells (frequenins, visinin-like proteins and the Kv channel-interacting proteins) (see, e.g., Burgoyne and Weiss (2002) *Biochem. J.* 353:1-12). The latter three subfamilies may regulate neurotransmitter release, polyphosphoinositide biosynthesis, cyclic nucleotide metabolism and the activity of type A potassium channels. The NCS proteins undergo conformational changes upon binding calcium and have thus been referred to as calcium sensors or switches. Most NCS proteins are N-terminally myristoylated, and, after binding of calcium, the myristoyl residue and hydrophobic portions of the sequence are exposed favoring interaction with membranes or target proteins.

Another family of EF hand-containing proteins is the calpain family of intracellular cysteine proteases. These proteins modulate biological activities of their substrates by limited proteolysis. The protease core region of the µ isoform of calpain appears to also contain two non-EF hand calcium-binding sites. Binding of calcium at these sites aligns the active site cleft and converts the core into an active enzyme with calpain-like specificity (see, e.g., Moldoveanu et al. (2002) *Cell* 108:649-660). Thus, there are at least three different types of calcium-binding sites in calpains: EF-hand, C2-like domain and protease domain sites.

Another example of an EF hand protein is calmodulin (CaM). Calmodulin interacts with numerous diverse proteins, including, for example, CaM-dependent serine/threonine kinases, CaM kinase II, CaM kinase kinase and myosin light chain kinase, calcineurin, CaM-calcium-activated potassium channel and anthrax adenylyl cyclase. The roles of CaM binding to such target proteins include, for example, release of autoinhibitory domains of kinases, CaM tethering and calcium-dependent inactivation of the target protein, active site remodeling of adenylyl cyclase, dimerization and activation of channel proteins. CaM recruitment motifs of CaM-binding domains of CaM-dependent proteins have been predicted (see, e.g. Rhoads and Friedberg (1997) *FASEB J.* 11:331-340; Hoeflich and Ikura (2002) *Cell* 108:739-742 and calcium.uhnres.utoronto.ca). An example of a CaM-binding motif is an "IQ motif" having the following consensus sequence which can be present in tandem repeats: IQXXXRGXXXR.

c. Downstream Calcium Entry-Mediated Events

In addition to intracellular changes in calcium stores, store-operated calcium entry affects a multitude of events that are consequent to or in addition to the store-operated changes. For example $Ca^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF2 and NFκB. NFAT transcription factors play important roles in many cell types, including immune cells. There are four calcium-regulated members of the NFAT family. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFa), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NFAT is a sensitive indicator of intracellular calcium levels.

C. Identification of Molecules Involved in Modulating Intracellular Calcium

Described herein is the identification of cellular proteins involved in modulating intracellular calcium. Proteins identified herein as being involved in modulating intracellular calcium may participate in one or more of a number of processes that affect intracellular calcium, including, but not limited to, receptor-mediated or second messenger-operated calcium movement, calcium uptake and/or release by intracellular organelles (e.g., endoplasmic reticulum, endosomes and lysosomes), cytosolic calcium buffering and store-operated calcium entry into cells. A direct participation of a protein in a particular process or pathway not only affects that process but can also indirectly affect one or more other processes or pathways. Thus, for example, a protein that has a direct role in a G-protein-coupled receptor signaling pathway may also indirectly affect store-operated calcium entry into a cell by affecting the release of calcium from the endoplasmic reticulum, which is involved in providing a signal for calcium entry via store-operated ion channels.

Proteins identified as being involved in modulating intracellular calcium include, but are not limited to, proteins that are homologous to a protein encoded by a *Drosophila* or mammalian (e.g., human or rodent such as rat, hamster or mouse) gene that, when altered in its expression in a cell, results in altered intracellular calcium. The protein can be one that is homologous to a protein encoded by a *Drosophila* or mammalian gene that, when altered in its expression, results in altered store-operated calcium entry, altered calcium levels in, or movement of calcium into, out of or within an intracellular organelle or calcium store (e.g., endoplasmic reticulum), altered cytoplasmic calcium buffering and/or altered basal cytosolic calcium levels. The identified cellular proteins include mammalian proteins, e.g., rodent and human proteins, nematode, e.g., *C. elegans*, proteins and insect, e.g., *Drosophila*, proteins. The proteins include modulatory proteins, receptors and proteins that are involved in, participate in and/or provide for the movement of calcium, such as, for example, an ion transport protein, or a component of an ion transport protein complex, that is involved in, participates in and/or provides for store-operated calcium entry.

Also provided herein are methods for identifying additional elements (e.g., proteins and other cellular or cell-associated molecules) involved in modulating intracellular calcium, identifying agents that modulate intracellular calcium and methods for modulating intracellular calcium and for treating diseases and disorders. Such methods can utilize or target the proteins identified herein as being involved in modulating intracellular calcium, such as, for example, by modulating or by participating in store-operated calcium entry.

1. Stromal Interacting Molecule (STIM) Proteins

As described herein, proteins identified as being involved in modulating intracellular calcium include stromal interacting molecules (also referred to as STIM, SIM and GOK) or STIM-like proteins or portions thereof. Proteins identified herein as proteins involved in modulating intracellular calcium include proteins homologous to a protein encoded by the coding sequence of *Drosophila* gene CG9126 (GenBank Accession no. NM_078633, gi22832319 and AF328906; see also SEQ ID NO. 1 for gene coding sequence and SEQ ID NO. 2 and GenBank Accession no. NP_523357, AAF48542, AAK82338 and P83094 for amino acid sequence) and/or a mammalian stromal interacting molecule (STIM) protein (see, e.g., SEQ ID NO: 90 for a mammalian STIM1 consensus amino acid sequence), such as, for example, human STIM1 (GenBank protein Accession nos. Q13586, NP-003147, AAC51627 and nucleotide Accession nos. NM_003156, gi2264345, gi2264346; see also SEQ ID NOS:82 and 3 for nucleic acid coding sequences and SEQ ID NOS:84, 83 and 4 for amino acid sequences), Chinese hamster STIM1 (see SEQ ID NO: 95 for a partial nucleic acid coding sequence and SEQ ID NO: 96 for a partial amino acid sequence), rat STIM1 (see SEQ ID NO: 97 for a partial nucleic acid coding sequence and SEQ ID NO: 98 for a partial amino acid sequence) and also reference STIM sequence. (see SEQ ID NO: 51 for a nucleic acid coding sequence and SEQ ID NO: 52 for an amino acid sequence). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum). Particular proteins include stromal interacting molecule (STIM) proteins and STIM-like proteins, including, but not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. Proteins identified herein as being involved in modulating intracellular calcium include proteins that are at least about 45% homologous to the protein encoded by the coding sequence of *Drosophila* gene CG9126 and/or a mammalian stromal interacting molecule (STIM) protein over at least about 52% of the protein.

STIM proteins are type I transmembrane phosphoproteins with a single transmembrane segment separating the extracellular portion from the cytosolic domain. Vertebrates have two forms of the STIM protein, STIM1 and STIM2, while invertebrates have only one genetic form, e.g., D-STIM in *Drosophila melanogaster*. Comparison of the vertebrate and invertebrate STIM proteins demonstrates a conserved genomic organization, indicating that the two STIM genes found in vertebrates likely arose from a single ancestral gene (Williams et al. (2001) *Biochem. J.* 357: 673-685).

STIM proteins include, but are not limited to, STIM1 (SEQ ID NO. 4 for *homo sapiens* STIM1, SEQ ID NO: 52 for *rattus norvegicus* STIM1, and SEQ ID NO. 10 for *Mus musculus* STIM1) and STIM2 (SEQ ID NO. 6 for *Homo sapiens* and SEQ ID NO. 28 for *Mus musculus*) in humans and other vertebrates, D-STIM (SEQ ID NO. 2) in *Drosophila melanogaster*, and C-STIM in *caenorhabditis elegans* (SEQ ID NOs. 24 and 26). Partial sequences for STIM proteins include seq id no. 98 (rat) and SEQ ID NO. 96 (hamster). Other potential orthologs of STIM proteins were identified in tblastn searches of Genbank databases. Expressed sequence tags (ests) were identified for STIM1 genes in rat (*Rattus norvegicus*; Genbank accession nos. AA996745 and AI763957), bovine (*bos* taurus; genbank accession nos. AV609285 and AW669469) and swine (*Sus scrofa*; Genbank accession nos. AW787215 and BE663170). ESTs representing STIM2 homologs were identified in mouse (*mus musculus*; Genbank accession nos. AA088943, AI194208, AW106055, AW910374, be652414 and bf463756), rat (*Rattus norvegicus*; Genbank accession nos. AA944338, BF286659 and BF296660), bovine (*Bos taurus*; Genbank accession no. Be482998), amphibian (*Xenopus laevis*; Genbank accession nos. Aw633493, AW639117 and BF427891) and avian (*Gallus gallus*; Genbank accession no. AI981296).

Sources of nucleic acid molecules encoding STIM proteins in humans include human tissues, cancerous cells and cell lines, including, but not limited to, prostate; uterus; colon; testis; kidney, breast; placenta; heart; mammary gland; muscle (skeletal); lung; whole brain; marrow; ovary; nervous; liver; fetal eyes; sciatic nerve; cerebellum; pooled adenocarcinoma with signet ring cell features; pooled human melanocyte, fetal heart, and pregnant uterus; B-cell, chronic lymphotic leukemia; lymphoma, follicular mixed small and large cell; thymus, pooled; anaplastic oligodendroglioma; adenocarcinoma; serous papillary carcinoma; carcinoma in situ from retromolar trigone; renal cell tumor; glioblastoma; corresponding non cancerous liver tissue; adenocarcinoma (cell line); follicular carcinoma; large cell carcinoma, undifferentiated; melanotic melanoma; senescent fibroblast; epithelioid carcinoma; cervical carcinoma (cell line); choriocarcinoma; prostate tumor; anaplastic oligodendroglioma with 1p/19q loss; neuroblastoma; renal carcinoma (ascites); lymphoma; nervous tumor; melanocyte; lung tumor; renal cell adenocarcinoma; neuroblastoma (cell line); primary B-cells from tonsils (cell line); embryonal carcinoma (cell line); melanotic melanoma, high MDR (cell line); epithelioid carcinoma (cell line); Islets of Langerhans; leiomyosarcoma; natural killer cells (cell line); fetal eyes, lens, eye anterior segment, optic nerve, retina, Retina Foveal and Macular, RPE and Choroid; leukopheresis; colon tumor; parathyroid tumor; ascites; astrocytoma grade IV, cell line; Primary Lung Cystic Fibrosis Epithelial Cells; Lung Focal Fibrosis; Chondrosarcoma Grade II; duodenal adenocarcinoma (cell line); epidermoid carcinoma (cell line); teratocarcinoma (cell line); moderately-differentiated endometrial adenocarcinoma, 3 pooled tumors; metastatic prostate bone lesion; pooled germ cell tumors; schizophrenic brain S-11 frontal lobe; kidney tumor; and carcinoid.

The STIM1 gene (also referred to as GOK) has been identified as being part of a set of genes that maps to the human chromosome region 11p15.5 which is associated with adult and childhood tumors (Manji et al. (2000) *Biochem. Biophys. Acta* 1481: 147-155; Sabbioni et al. (1999) *Cytogenet. Cell Genet.* 86: 214-218). Functional studies have indicated that the 11p15 region includes tumor and growth suppressive functions (Dowdy et al. (1991) *Science* 254: 293-295; Koi et al. (1993) *Science* 260: 361-364; Negrini et al. (1994) *Cancer Res.* 55: 2904-2909; Reid et al. (1996) *Hum. Mol. Genet.* 5: 239-247; Satoh et al. (1993) o: 157-164), and genetic studies have identified at least three regions of loss of heterozygosity within the chromosome band (Negrini et al. (1995) *Cancer Res.* 55: 3003-3007). Transfection experiments have shown that STIM1 may act as a growth suppressor in the rhabdomyosarcoma and rhabdoid tumor cell lines RD and G401 (Sabbioni et al. (1997) *Cancer Res.* 57: 4493-4497). The expression of STIM1 within these cells lines induced growth arrest and degeneration, indicating that down-modulation of STIM1 expression could be the mechanism leading to cell immortalization. The STIM1 gene promoter has been identified within a 1.8-kb SacI fragment at the 5' end of the gene (Sabbioni et al. (1999) *Cytogenet. Cell Genet.* 86:214-218; see also GenBank Accession no. AF139917 and SEQ ID NO:93). Transient transfection of RD cells with a vector containing the STIM1 promoter sequence upstream of DNA encoding a luciferase reporter molecule (pGL3-STIM1.B; see Sabbioni et al. (1999) *Cytogenet. Cell Genet.* 86:214-218) which had been methylated in vitro results in a reduction of luciferase activity compared to that of cells transfected with non-methylated vector.

On the other hand, STIM1 has also been identified as a stromal cell product that binds to the surface of hematopoietic cells, such as pre-B lymphoid cells, and can promote proliferation of these cells (Oritani and Kincade (1996) *J. Cell Biol.* 134:771-782). Additionally, overexpression of STIM in PC12 (overexpression of both STIM1 and STIM2) cells has been reported to alter cell phenotype in vivo (including elongated morphology and increased migratory behavior) and generate a phenotype in transgenic *Drosophila* (overexpressing DSTIM) with similarity to *Drosophila* Delta and Notch mutants indicating an antagonist effect of STIM on the Notch signaling pathway (see PCT Application publication no. WO02/30976).

a. STIM and STIM-Like Protein Features

Although DSTIM, STIM1 and STIM2 share some conserved features, there are also areas in which the proteins diverge. The three STIM proteins differ in length from about 570 amino acids for the *Drosophila* STIM protein (including signal peptide) to about 685 amino acids for STIM1 (including signal peptide) and about 746 amino acids (including signal peptide) for STIM2. Each STIM protein contains a transmembrane domain located within the first one-third to one-half of the protein which is bounded on either side by N-terminal and C-terminal portions of the protein. The N-terminal portion of STIM may be a putative extracellular domain, whereas the C-terminal portion may be a putative cytoplasmic domain.

The N-terminal putative extracellular domains of DSTIM, STIM1 and STIM2 contain an N-terminal signal peptide followed by approximately 271, 190 and 203 amino acid residues, respectively. The signal peptide of human STIM1 and DSTIM, which is cleaved to yield a mature protein, corresponds to the sequence of the first approximately 22-23 amino acids of the protein (see, e.g., the first 22 amino acids of a human STIM1 amino acid sequence (SEQ ID NO: 4 and the first 23 amino acids of a DSTIM amino acid sequence (SEQ ID NO: 2). In contrast, the signal peptide of human STIM2 contains about 14 amino acids (see the first 14 amino acids of SEQ ID NO: 6), which is about 60% of the length of the signal peptides of human STIM1 and DSTIM.

The N-terminal domain of all three STIM proteins contains two closely spaced cysteine residues that can be involved in intra- or inter-chain disulfide binding (see, e.g., residues corresponding to positions 126 and 133 of DSTIM (SEQ ID NO: 2) 49 and 56 of human STIM1 (SEQ ID NO: 4) and 53 and 60 of human STIM2 (SEQ ID NO: 6)). The N-terminal domain of D-STIM has an additional 70-80 amino acid region (relative to STIM1 and STIM2 proteins) between the signal peptide and two closely spaced cysteine residues. Beyond the signal sequence for all three proteins, the extracellular domain also includes an EF hand domain (see, e.g., residues corresponding to positions 155-166 of DSTIM (SEQ ID NO: 2), 76-87 of human STIM1 (SEQ ID NO: 4) and 80-91 of human STIM2 (SEQ ID NO: 6)) and a sterile α-motif (SAM) domain (see, e.g., residues corresponding to positions 213-281 of DSTIM (SEQ ID NO: 2), 129-196 of human STIM1 (SEQ ID NO: 4) and 136-204 of human STIM2 (SEQ ID NO: 6)). SAM domains are generally compact five helical bundles with a conserved hydrophobic core and are found in a wide variety of eukaryotic signaling, scaffolding and adaptor molecules and transcription regulators. These domains have also been implicated in mediating protein-protein interaction via the formation of homo- and heterotypic oligomers in signaling molecules and transcriptional regulators (Thanos et al. (1996) J. Biol. Chem. 274: 37301-37306). The location of a SAM domain in the putative extracellular region of STIM proteins appears to be a unique feature of this family (Williams et al. (2001) Biochem. J. 357: 673-685). An N-linked glycosylation site occurs at or very near the N-terminal limit of the SAM domain in all three STIM proteins (see, e.g., residue corresponding to position 212 in DSTIM (SEQ ID NO: 2), 131 in human STIM1 (SEQ ID NO: 4) and 135 in human STIM2 (SEQ ID NO: 6)), while STIM1 possesses a unique second N-linked glycosylation site within the SAM domain (see, e.g., residue corresponding to position 171 in human STIM1 (SEQ ID NO: 4)). The modification of a SAM domain by N-linked glycosylation also appears to be unique to STIM1 (Williams et al. (2002) Biochim. Biophys. Acta 1596:131-137). Another feature that occurs in the N-terminal (putative extracellular) region of STIM1 that is not present in DSTIM or STIM2 is a possible enzymatic cleavage site (see, e.g., residues corresponding to positions 207-209 of human STIM1 (SEQ ID NO: 4)). This site, which is a three-amino-acid sequence of ARG-HIS-ASN in STIM1, is reminiscent of other proteolytic sites.

A single predicted transmembrane domain is present in all STIM proteins (see, e.g., residues corresponding to positions 295-312 of DSTIM (SEQ ID NO: 2), 213 (or 214)-234 of human STIM1 (SEQ ID NO: 4) and 218-235 of human STIM2 (SEQ ID NO: 6)) and contains a single cysteine residue.

The C-terminal putative intracellular or cytoplasmic domain is approximately 451 amino acid residues in length for STIM1 (see, e.g., residues corresponding to positions 235-685 of human STIM1 (SEQ ID NO: 4)), approximately 511 amino acid residues in length for STIM2 (see, e.g., residues corresponding to positions 236-746 of human STIM2 (SEQ ID NO: 6)) and approximately 258 amino acid residues in length for D-STIM (see, e.g., residues corresponding to positions 313-570 of DSTIM (SEQ ID NO: 2)). For STIM1 and STIM2 proteins, this portion of the polypeptide contains (1) a potential consensus sequence (YYNI) (see, e.g., residues corresponding to positions 361-364 of human STIM1 (SEQ ID NO: 4) and 365-368 of human STIM2 (SEQ ID NO: 6)) for phosphorylation-dependent binding of Src homology type 2 (SH2) domains, such as, for example, the SH2 domain of the growth factor receptor bound protein 2 (GRB2), (2) two coiled-coil domains (see, e.g. residues corresponding approximately to positions 238-343 and 362-390 of human STIM1 (SEQ ID NO: 4) and 242-344 and 358-394 of human STIM2 (SEQ ID NO: 6)) which is a principal subunit oligomerization motif (typically involving a heptad repeat pattern of primarily apolar residues, and (3) a proline- and serine-rich (STIM1; see, e.g., residues corresponding to positions 600-629 of human STIM1 (SEQ ID NO: 4)) or proline- and histidine-rich (STIM2; see, e.g., residues corresponding to positions 533-559 of human STIM2 (SEQ ID NO: 6)) domain that contains several potential proline-directed serine/threonine phosphorylation sites (which are potential targets for by members of the proline-directed protein kinase (PDPK) family, such as the MAP/ERK kinases and cyclin-dependent kinases (Cdk)) and a potential consensus binding sequence for 14-3-3 proteins. Also within this general region of STIM1 and STIM2 are several potential SH3 domain binding motifs, which have a minimum consensus sequence of PXXP (see, e.g., the region of residues corresponding to positions 573-629 of human STIM1 (SEQ ID NO: 4) and 521-559 of human STIM2 (SEQ ID NO: 6)). The two STIM proteins diverge significantly distal to their proline-rich regions with the exception of lysine-rich tails at their respective C-termini. The cytoplasmic region of D-STIM is half the length of those of STIM1 and STIM2. The domain structure of D-STIM is similar to that seen for STIM1 and STIM2 in that there is a significant degree of α-helical structure (coiled-coils) (see, e.g., residues corresponding approximately to positions 310-407 and 420-462 of DSTIM (SEQ ID NO: 2)), however, there appears to be no homologous GRB2 consensus sequence nor a proline-rich region.

The C-terminal putative cytoplasmic region of STIM1 also contains several additional domains that are not found in STIM2 and DSTIM proteins. For example, STIM1 contains ATP synthase B/B' (pfam00430), ezrin/radixin/moesin (ERM; pfam00769) and diacylglycerol kinase accessory (DAGKa; smart00045) domains. The ATP synthase B/B' domain (see, e.g., residues corresponding approximately to positions 249-337 of human STIM1 (SEQ ID NO: 4)) is a domain that is also found as a part of the CF(0) (base unit) of ATP synthase which may translocate protons through membranes (e.g., the mitochondrial inner membrane). STIM proteins contain a domain (referred to as an SMC domain; COG1196) at a similar region of the C-terminal portion of the protein (see, e.g., residues corresponding to positions 238-340 of human STIM2 (SEQ ID NO: 2)) which is found in Smc chromosome segregation ATPases. The ezrin/radixin/moesin domain (see, e.g., residues corresponding approximately to positions 253-424 of human STIM1 (SEQ ID NO: 4)) is a domain also found in the ERM family of proteins which contain a band 4.1 domain (pfam00373) at the amino terminus. The DAGKa domain (see, e.g., residues corresponding approximately to positions 422-484 of human STIM1 (SEQ ID NO: 4)) which is also found in kinases that are activated by diacylglycerol (DAG), e.g., protein kinase C.

DSTIM, which has the shortest C-terminal putative cytoplasmic region of the STIM proteins, contains a myosin tail domain (see, e.g., residues corresponding approximately to positions 324-491 of DSTIM (SEQ ID NO: 2)) that is not present in STIM1 and STIM2 proteins.

STIM proteins undergo post-translational modification. STIM1 and STIM2 are modified by N-linked glycosylation and phosphorylation which occurs predominantly on serine residues. Differing levels of phosphorylation of STIM2 may account for two molecular mass isoforms (approximately 105 and 115 kDa) of the protein. In contrast, the molecular mass of STIM1 is approximately 90 kDa, which decreases to about 84 kDa when N-linked glycosylation is inhibited by tunicamycin. D-STIM (an approximately 65 kDa protein), like STIM1 and STIM2, is modified by N-linked glycosylation (Williams et al. (2001) Biochem. J. 357: 673-685) as evidenced by mobility shift experiments.

b. STIM and STIM-Like Protein Sequences

In particular embodiments of the methods for screening for or identifying agents and molecules that modulate intracellular calcium, a protein (and/or nucleic acid, or portion(s) thereof, encoding a protein) used in the method (or on which the method is based) is a STIM, STIM1, STIM2 or STIM-like protein or portion(s) thereof. Examples of such proteins include the following: STIM1 from Homo sapiens (SEQ ID NO. 4); STIM1 from Mus musculus (SEQ ID NO. 10); D-STIM from Drosophila melanogaster (SEQ ID NO. 2); C-STIM from Caenorhabditis elegans (SEQ ID NO. 26); STIM2 from Homo sapiens (SEQ ID NO. 6); STIM2 from Mus musculus (SEQ ID NO. 28); and a homolog from Anopheles gambiae str. PEST (SEQ ID NO. 8). In other embodiments, other proteins that may be used in the methods provided herein include, but are not limited to, proteins involved in intracellular calcium modulation that are substantially homologous to the above-listed proteins. These listed proteins and their sequences exemplify proteins that are useful for methods, materials and systems provided herein. Naturally occurring and synthesized alternative forms of these proteins such as allelic forms, isoforms, muteins, and mutated derivatives will have sequence changes that do not abolish their operation in intracellular calcium modulation and are useful in embodiments. Mutations and allelic forms of these proteins are known and are contemplated as embodiments.

In a particular embodiment of the methods of screening for or identifying an agent or molecule that modulates intracellular calcium, a protein (or nucleic acid, or portion(s) thereof, encoding a protein) involved in modulating intracellular calcium that is used in the method (or on which the method is based) is a STIM or STIM1 protein or portion(s) thereof. In one embodiment of the methods, the protein is one that is homologous to a DSTIM protein over at least about 77%, or at least about 78%, or at least about 79% or at least about 80% or at least about 85%, or at least about 90%, or at least about 95% or more of the DSTIM protein. For example, the protein can be one that is at least about 50%, or at least about 51%, or at least about 52%, or at least about 54%, or at least about 55%, or at least about 58%, or at least about 60%, or at least about 65%, or at least about 62%, or at least about 70% or more homologous to a DSTIM protein over the specified extent of the DSTIM protein. In another embodiment, the protein is one that is homologous to a STIM1 protein (e.g., a mammalian STIM1 protein (see SEQ ID NO: 90 for a mammalian STIM1 consensus sequence of amino acids), such as a human or rodent STIM1 protein) over at least about 86%, or at least about 87%, or at least about 88%, or at least about 89%, or at least about 90%, or at least about 92%, or at least about 95%, or at least about 97% or more of the STIM1 protein. For example, the protein can be one that is at least about 67%, or at least about 68%, or at least about 69%, or at least about 70%, or at least about 72%, or at least about 75%, or at least about 77%, or at least about 80%, or at least about 82%, or at least about 85%, or at least about 90%, or at least about 95% or more homologous to a STIM1 protein over the specified extent of the STIM1 protein.

In another embodiment of the method for screening for or identifying an agent or molecule that modulates intracellular calcium, a protein (or nucleic acid, or portion(s) thereof, encoding a protein) used in the method (or on which the method is based) is a STIM or STIM-like protein (or portion(s) thereof) that contains one or more or all of the following structural features or sequences: (1) an amino acid sequence containing a SAM domain that contains within it one or more N-linked glycosylation sites and, optionally, an N-linked glycosylation site in the amino acid sequence on either side of the SAM domain, (2) an amino acid sequence containing a dibasic sequence that could serve as a proteolytic cleavage site (see, e.g., residues corresponding to positions 207-209 of human STIM1 (SEQ ID NO: 4)), and, in particular embodiments, the consecutive two- or three-amino-acid sequence of ARG-HIS or ARG-HIS-ASN, (3) an amino acid sequence containing a sequence homologous to an ATP synthase B/B' domain (pfam00430), (4) an amino acid sequence containing a sequence homologous to an ezxrin/radixin/moesin domain (ERM; pfam00769), and (5) an amino acid sequence containing a sequence homologous to a diacylglycerol kinase accessory (DAGKa; smart00045) domain.

2. Rodent STIM Proteins and Nucleic Acid Encoding Rodent STIM Proteins a. Nucleic Acid Molecules Provided herein are isolated nucleic acid molecules encoding sequences for rodent STIM, including hamster, rat and reference STIM1 sequences (collectively referred to herein as rodent reference STIM and STIM sequences). Also provided are isolated nucleic acid molecules that encode domains of rodent reference STIM1, or encode polypeptides with substitutions relative to rodent reference STIM1 or its domains that retain at least one biological activity of STIM1 or the domain. Such nucleic acid molecules generally retain sufficient homology such that the resulting encoded polypeptide or domain retains a biological activity.

Also provided are nucleic acid molecules encoding polypeptides with one or several amino acid substitutions relative to mature reference STIM1, or encoding polypeptides with one or several amino acid substitutions relative to various domains of rodent reference STIM1 described herein, which retain at least one biological activity of STIM1 or of the particular domain. Incorporating amino acid substitutions into rodent reference STIM1 polypeptides and domains may be advantageous, for example, in enhancing the stability, expression level, immunogenicity, or a biological activity of the polypeptide. Exemplary substitutions include substitutions at positions that differ between mouse and rodent reference STIM1, or between human and rodent reference STIM1, since these positions are likely to be tolerant of conservative or non-conservative substitutions without substantially affecting a STIM1 biological activity. Computer programs known in the art that predict three-dimensional protein structure can also provide guidance in predicting which amino acid residues can be modified while retaining the function of the polypeptide (see, for example, Eroshkin et al. (1993) *Comput. Appl. Biosci.* 9:491-497).

Such nucleic acid molecules include, but are not limited to, nucleic acid molecules that encode a rodent reference STIM1 that has at least 60%, 70%, 80%, 90% or about 95% sequence identity with the rodent reference STIM1s exemplified herein, or that hybridize along their full length or along at least about 70%, 80% or 90% of the full length to the exemplified sequence of nucleotides or domain-encoding portion thereof, particularly under conditions of moderate, generally high, stringency.

SEQ ID NO:51 sets forth an exemplary sequence of nucleotides encoding full-length reference STIM1 (SEQ ID NO:52). SEQ ID NO: 97 sets forth an exemplary sequence of nucleotides encoding a partial rat STIM1. SEQ ID NO: 95 sets forth an exemplary sequence of nucleotides encoding a partial hamster STIM1. Reference STIM contains a fusion of rat and hamster STIM sequences using the partial hamster STIM1 sequence and constructing a full-length reference sequence using the 5' and 3'ends of rat STIM1. It will be appreciated that due to the degeneracy of the genetic code, the skilled person can select alternative sequences of nucleotides that encode SEQ ID NOS:51, 95 and 97. The exemplary sequence of nucleotides set forth in SEQ BD NO:51 differs from SEQ ID NOS:3 and 82, which encode a human STIM1, differs from SEQ ID NO:9, which encodes a mouse STIM1 at nucleotide positions 15, 63, 69, 84, 103, 108, 112, 120, 150, 183, 201, 207, 210, 213, 240, 300, 303, 312, 330, 357, 402, 441, 474, 570, 621, 660, 697, 738, 783, 795, 861, 873, 874, 895, 951, 1051, 1062, 1107, 1200, 1224, 1228, 1278, 1299, 1392, 1395, 1452, 1580, 1652, 1654, 1675, 1747, 1749, 1173, 1854, 1855, 1881, 1884, 1888, 1896, 2001 and 2025 of SEQ ID NO:51. Exemplary of the nucleic acid molecules encoding full-length reference STIM is that set forth in SEQ ID NO:51, as well as mature reference STIM1.

Also provided are nucleic acid molecules (and the encoded polypeptides) encoding domains of mature rodent reference STIM1, including the extracellular, transmembrane, cytoplasmic, SAM, coiled-coil, Glu-rich, Pro-Ser-rich, ezrin/radixin/moesin (ERM), diacylglycerol kinase accessory domain (DAGKa) and Lys-rich domains. Such nucleic acid molecules can be used in place of nucleic acid molecules encoding full-length or mature reference STIM1 in many of the applications for STIM1 described herein. It will be understood that for such applications, nucleic acid molecules encoding polypeptides with several additional, or several fewer, amino acids at either or both termini relative to the STIM1 domain boundaries indicated herein will likely have equivalent structures and functions, and are thus contemplated herein.

The nucleic acid molecules can be used, for example, in screening applications described herein or to express rodent reference STIM1 polypeptides and domains. They also can be used as probes and primers to detect and/or quantify expression of rodent reference STIM1 mRNA in rat and hamster tissues and cell lines. Other applications will be apparent to those skilled in the art.

Also provided are nucleic acid constructs contain the nucleic acid molecules encoding STIM1 operatively linked to a promoter of gene expression. The promoter can be a heterologous promoter known in the art to promote transcription of operatively linked genes. The choice of heterologous promoter will depend, for example, on whether it is desired to turn on or off gene expression (in which case a regulated promoter would be chosen), the desired level of gene expression (determining the choice of strong or weak promoter), and the type of host cell or in vitro transcription system (e.g. mammalian, bacterial, yeast, Drosophila, C. elegans, etc.). The promoter can alternatively be a STIM promoter, such as a rat, hamster or other mammalian STIM1 promoter. STIM1 promoter sequences can be identified by those skilled in the art as regions within about 1000 nucleotides, such as within about 500, 200, 100 or 50 nucleotides, of the transcriptional start of STIM1. Nucleic acid molecules operatively linked to a promoter of gene expression can be used, for example, to express rodent STIM1, domains therefrom, and polypeptides with substitutions thereto, in a desired host cell or in vitro transcription-translation system. Methods for operatively linking a nucleic acid to a promoter are well known in the art and include, for example, cloning the nucleic acid into a vector containing the desired promoter, or appending the promoter to a nucleic acid sequence using PCR.

Also provided are vectors containing the nucleic acid molecules. The type of vector will depend on the intended application. For example, in order to amplify, subclone or genetically engineer a nucleic acid molecule, a suitable cloning vector compatible with the host cell can be used, which may not have the capability to express the inserted nucleic acid molecules. In order to express mRNA or encoded polypeptides, the nucleic acid molecules can further be operatively linked to a promoter of gene expression, as described above, which may be a component of the vector or present in the inserted nucleic acid molecule. Factors involved in ensuring compatibility between various host cells and vectors are well known in the art.

Further provided are cells containing nucleic acid molecules provided herein. Isolated nucleic acid molecule is generally contained within a vector, which can be maintained episomally, or incorporated into the host cell genome. Cells can be used, for example, for molecular biology applications such as to amplify, subclone or genetically engineer a nucleic acid molecule. For such applications, bacterial cells, such as laboratory strains of E. coli are useful. The cells also advantageously can be used to express the encoded polypeptide for screening applications, or to purify the encoded polypeptide. For such applications bacterial cells, insect cells (e.g. Drosophila), yeast cells (e.g. S. cerevisiae, S. pombe, or Pichia pastoris), and vertebrate cells (e.g. mammalian primary cells and established cell lines; and amphibian cells, such as Xenopus embryos and oocytes), are useful.

Also provided are isolated oligonucleotides that contain at least 17 contiguous nucleotides of SEQ ID NO:51 (or its complement) or SEQ ID NO:95 (or its complement), or SEQ ID NO:97 (or its complement), including at least one position selected from positions 15, 63, 69, 84, 103, 108, 112, 120, 150, 183, 201, 207, 210, 213, 240, 300, 303, 312, 330, 357, 402, 441, 474, 570, 621, 660, 697, 738, 783, 795, 861, 873, 874, 895, 951, 1051, 1062, 1107, 1200, 1224, 1228, 1278, 1299, 1392, 1395, 1452, 1580, 1652, 1654, 1675, 1747, 1749, 1173, 1854, 1855, 1881, 1884, 1888, 1896, 2001 and 2025 of SEQ ID NO:51 or a position in SEQ ID NOS:95 or 97 that corresponds to the listed positions. The recited positions are those where the nucleotide of SEQ ID NO:51 differs from the corresponding position in SEQ ID NOS:2 and 82. One of skill in the art can use nucleotide alignment of one or more sequences with SEQ ID NO:51 to determine corresponding positions.

An oligonucleotide can contain the rodent reference, rat or hamster STIM1-specific nucleotide at the 5' or 3' end of the contiguous nucleotides of SEQ ID NO:51, or at any position within the contiguous nucleotides of SEQ ID NO:51. An oligonucleotide can contain several rodent reference STIM1-specific nucleotide positions. For example, it can include, among the at least 17 contiguous nucleotides of SEQ ID NO:51, nucleotides 63-69, or 103-120, or 201-213, or 300-312, or 861-874, or 1224-1228, or 1392-1395, or 1652-1654, or 1747-1749, or 1854-1855, or 1881-1896.

Also provided are fragments thereof or oligonucleotides that can be used as probes or primers and that contain at least about 10, 14, 16 nucleotides, generally less than 1000 or less than or equal to 100; or contain at least about 30 nucleotides (or the complement thereof) or contain oligonucleotides that hybridize along their full length or along at least about 70%, 80% or 90% of the full length to any such fragments or oligonucleotides. The length of the fragments is a function of the purpose for which they are used and/or the complexity of the genome of interest. Generally probes and primers contain less than about 500, 150, 100 nucleotides.

In particular, oligonucleotides that include one or more nucleotides that are specific to rodent reference STIM1 nucleic acid molecules can specifically hybridize to endogenous rat STIM1 DNA or mRNA, while not specifically hybridizing to STIM1 nucleic acid molecules of other species. Such oligonucleotides can be used, for example, as probes or primers to determine the presence or amount of a rat STIM1-encoding nucleic acid molecule in a sample. Such oligonucleotides can also be prepared as inhibitory oligonucleotide molecules, such as RNA interference, antisense or catalytic molecules, and used to specifically reduce expression of a STIM1 nucleic acid molecule in vitro or in vivo.

It will be understood that 5' or 3' to the specified number of nucleotides of rat STIM1, a nucleic acid molecule or oligonucleotide can optionally contain heterologous nucleotide sequences, such as, but not limited to, linkers or restriction sites useful in cloning applications; regulatory sequences useful in gene expression; sequences encoding epitope tags or fusion proteins useful in protein purification and analysis.

The isolated nucleic acid molecules, including molecules encoding rodent reference STIM1, domains therefrom, and oligonucleotides, can be prepared by methods known in the art (see, for example, Sambrook and Russell (2000) "Molecular Cloning: A Laboratory Manual" Cold Spring Harbor Laboratory Press; Ausubel et al. (eds.) (current edition) "Current Protocols in Molecular Biology" John Wiley & Sons.

An exemplary method for preparing an isolated rodent reference STIM1 nucleic acid molecule or oligonucleotide involves amplification of the nucleic acid molecule using STIM1-specific primers and the polymerase chain reaction (PCR). Using PCR, a rat STIM1 nucleic acid molecule having any desired boundaries can be amplified exponentially starting from only a few DNA or RNA molecules, such as from a single cell.

Alternatively, an isolated rodent reference STIM1 nucleic acid molecule or oligonucleotide can be prepared by screening a library, such as a cDNA library or expression library, with a detectably labeled rodent reference STIM1 nucleic acid molecule or antibody. Libraries are commercially available or can be produced from cells of interest. The library clones identified as containing rodent reference STIM1 nucleic acid molecules can be isolated, subcloned and/or sequenced by methods known in the art.

Furthermore, an isolated rodent reference STIM1 nucleic acid molecule or oligonucleotide can be prepared by chemical or recombinant synthesis. For example, a single stranded nucleic acid molecule can be chemically synthesized in one piece, or in several pieces, by automated synthesis methods. The complementary strand can likewise be synthesized in one or more pieces, and a double-stranded molecule made by annealing the complementary strands. Direct synthesis is particularly advantageous for producing oligonucleotides, and also for producing nucleic acid molecules containing modified nucleotides or linkages. A rodent reference STIM1 RNA (including an inhibitory RNA) can also be prepared recombinantly by in vitro or in vivo transcription of a template DNA molecule.

It will be understood that rodent reference STIM1 nucleic acid molecules and oligonucleotides provide herein do not include, for example, identical sequences, including Expressed Sequence Tags (ESTs), Sequence Tagged Sites (STSs), genomic fragments and other such fragments, that may have been previously deposited in public databases such as the NCBI nr, dbest, dbsts, gss, pat and htgs databases (see, e.g., www.ncbi.nlm.nih.gov/blast/). In particular, specifically excluded from the nucleic acid molecules provided herein are nucleic acid molecule having the exact, specific and complete nucleic acid molecule sequence corresponding to the accession numbers that follow:
gi|11632030|gb|BF524063.1|BF524063;
gi|14950288|gb|BI291079.1|BI291079;
gi|4280511|gb|AA996745.1|AA996745;
gi|14947181|gb|BI289522.1|BI289522;
gi|977818|gb|H32401.1|H32401; and
gi|5209892|gb|AI763957.1|AI763957.

Vectors containing the nucleic acids encoding rodent reference STIM1 and cells containing the vectors are provided. Nucleic acid molecules, promoters, vectors and cells suitable for recombinantly producing polypeptides and peptides having any desired boundaries, have been described above. Rodent reference STIM1 polypeptides and domains therefrom can also be prepared by biochemical procedures. A rat or hamster STIM1 polypeptide can be isolated from tissues or cells that naturally express the polypeptide, or from recombinant cells or transgenic animals that express the polypeptide, by biochemical procedures routinely used in the art, including fractionation, chromatography, electrophoresis and affinity methods. Protein purification procedures are described, for example, in Rosenberg, I. M. (1996) "Protein Analysis and Purification: Benchtop Techniques" Springer Verlag; and Scopes, R. K. (1994) "Protein Purification: Principles and Practice" Springer Verlag. For example, a rodent reference STIM1 polypeptide can be isolated by immunoaffinity methods using the antibodies described herein.

b. Polypeptides

Also provided are mature rodent reference STIM1 polypeptides, domains of rodent STIM1, and polypeptides with substitutions relative to rodent reference STIM1 or its domains, which retain at least one biological activity of STIM1 or the domain. Rodent reference STIM1 polypeptide domain boundaries, types of substitutions and biological activities have been described above with to nucleic acid molecules encoding such polypeptides. The polypeptides can be used, for example, in screening applications described herein, and to produce rodent reference STIM1 antibodies. Isolated peptides provided herein as well as rodent reference STIM1 domain polypeptides, further can be used as agents that block interactions between STIM1 and its oligomeric partners.

An exemplary rat STIM polypeptide is set forth in SEQ ID NO. 98. An exemplary hamster STIM polypeptide is set forth in SEQ ID NO. 96. An exemplary reference STIM polypeptide is set forth in SEQ ID NO. 52. As noted also contemplated are rodent reference STIM polypeptides that have a specified homology and/or retain a biological activity. Included among such variants are those encoded by the nucleic acid molecules described above. Variants include, but are not limited to, a polypeptide encoded by the sequence of nucleotides set forth in SEQ ID NOs. 51, 95 and 97; a polypeptide encoded by a sequence of nucleotides that hybridizes under conditions of low, moderate or high stringency to the sequence of nucleotides set forth in SEQ ID NOs. 51, 95 and 97; a polypeptide that comprises the sequence of amino acids set forth in SEQ ID NO. 51, 96 or 98; a polypeptide that comprises a sequence of amino acids having at least about 60%, 70%, 80%, 90% or about 95% or more sequence identity with the sequence of amino acids set forth in SEQ ID NO. 52, 96 or 98; and/or a polypeptide encoded by a splice variant of a sequence of nucleotides that encodes a rodent reference STIM1 polypeptide. SEQ ID NO:52 sets forth the amino acid sequence of a full-length reference STIM1, as encoded by SEQ ID NO:51. Reference STIM1 differs from human STIM1 (SEQ ID NOS:4 and 83) and mouse STIM1 (SEQ ID NOS:10 and 85) at amino acid positions 21, 35, 38, 292, 527, 551, 552, 583 and 619. The exemplified reference STIM1 differs from a human STIM1 polypeptides at a total of 25 positions, and from a mouse STIM1 at a total of 17 positions. Rat and hamster STIM1 differ from human STIM1 (SEQ ID NOS:4 and 83) and mouse STIM1 (SEQ ID NOS:10 and 85) at multiple amino acid positions, which can be determined by an alignment of the sequences.

Domains of hamster, rat and reference STIM1 can be determined by an alignment with the relevant domains of human and mouse STIM1. Such domains include, for example, the extracellular, transmembrane, cytoplasmic, SAM, coiled-coil, Glu-rich, Pro-Ser-rich, ezrin/radixin/moesin (ERM), diacylglycerol kinase accessory domain (DAGKa) and Lys-rich domains.

In the exemplary reference STIM polypeptide set forth in SEQ ID NO: 52, amino acids 1-22 of SEQ ID NO:52 correspond to the signal peptide domain, whereas amino acids 23-685 correspond to the mature reference STIM1 polypeptide. Amino acids 23-213 correspond to the extracellular domain, amino acids 214-234 correspond to the transmembrane domain, and amino acids 235-685 correspond to the cytoplasmic domain of reference STIM1.

Within the extracellular domain, amino acids 132-200 correspond to a SAM (sterile alpha motif) domain. Because SAM domains in other proteins are involved in binding to SH2-containing polypeptides and in homodimerization, it is contemplated herein that the SAM domain of rodent reference STIM1 may mediate oligomerization with STIM1, STIM2 and/or other polypeptides.

Within the cytoplasmic domain, amino acids 238-343 and 362-390 correspond to coiled-coil domains. Amino acids 270-336 of the first coiled-coiled domain are rich in glutamic acid residues, and thus this region is designated as a Glu-rich domain. Because the coiled-coil motif is involved in oligomerization in many other proteins, it is contemplated herein that either or both of the coiled-coiled domains of rodent reference STIM1 (or the region corresponding from amino acids 238-390 of reference STIM1), or the Glu-rich domain within its first coiled-coil domain, may mediate oligomerization with STIM1, STIM2 and/or other polypeptides.

Also within the cytoplasmic domain, amino acids 600-629 correspond to a proline-serine (Pro-Ser) rich domain. Because proline-rich and serine-rich domains are involved in oligomerization in many other proteins, it is contemplated herein that the Pro-Ser rich domain of rodent reference STIM1 may mediate oligomerization with STIM1, STIM2 and/or other polypeptides.

Additional domains within the cytoplasmic domain of reference STIM1 include an ezrin/radixin/moesin family "ERM" domain (amino acids 253-424), a diacylglycerol kinase accessory domain "DAGKa" domain (amino acids 422-484), and a lysine-rich domain (amino acids 672-685).

Also provided are isolated peptides that contain contiguous amino acids of SEQ ID NO:52 that include a position selected from among positions 21, 35, 38, 292, 527, 551, 552, 583 or 619 of SEQ ID NO:52 (or corresponding positions). The recited positions are those where the amino acid residue in reference STIM1 differs from the corresponding residue in a human and mouse STIM1.

A polypeptide provided herein can contain the rodent reference STIM1-specific amino acid at the N- or C-terminus of the contiguous amino acids of SEQ ID NO:52, or at any position within the contiguous amino acids of SEQ ID NO:52. It can contain several rodent reference STIM1-specific amino acid positions. For example, a polypeptide can include, among the at least 8 contiguous amino acids of SEQ ID NO:52, amino acids 35-38, or amino acids 551 and 552.

The polypeptides can be used, for example, in inducing and/or purifying STIM1 antibodies, including antibodies that specifically bind rodent reference STIM1 and not human or mouse STIM1. Rat, hamster and reference STIM1 peptides that are likely to be immunogenic, and thus useful for such applications, can be predicted using methods and algorithms known in the art and described, for example, in Irnaten et al. (1998) *Protein Eng.* 11:949-955, and Savoie et al. (1999) *Pac. Symp. Biocomput.* 1999:82-189. Immunogenicity can be tested or confirmed by methods known in the art, such as by delayed-type hypersensitivity response assays in an animal sensitized to a STIM1 polypeptide, or by direct or competitive ELISA assays.

The number of substitutions to an encoded rodent reference STIM1 polypeptide or domain therefrom that retains at least one biological activity of the reference polypeptide or domain can be 1, 2, 3, 4 or more, including any unit increment up to the total number of amino acid differences minus one between the rat and mouse or human sequence of the domain of interest.

Rodent reference STIM1 polypeptide domains also can be produced by enzymatic or chemical cleavage of a longer rodent reference STIM1 polypeptide. Methods for enzymatic and chemical cleavage and for purification of the resultant fragments are well known in the art. Furthermore, rodent reference STIM1 domains and peptides can be produced by chemical synthesis methods known in the art (e.g. Grant, G. A. (ed) "Synthetic Peptides: A User's Guide" 2nd ed. Oxford University Press).

Biological activities of other STIM1 species (e.g. human, mouse and *Drosophila*), and methods of assessing such biological activities in vitro or in vivo, are known in the art and/or described elsewhere herein in detail. Because of the high degree of similarity between STIM1 polypeptides across species, it will be appreciated that biological activities of STIM1 from other species will be identical or substantially equivalent to the rat STIM1 polypeptides. It will also be appreciated that many of the biological activities of mature rodent reference STIM1, including the ability to oligomerize, will be exhibited by the domains described herein, either alone or when expressed as chimeric proteins.

Assays that can be performed to confirm that a polypeptide with substitutions relative to mature rodent reference STIM1 (or a domain therefrom) retains at least one biological activity of STIM1 (or of a domain therefrom) include, for example, assays that detect in vitro or in vivo homooligomerization; assays that detect in vitro or in vivo heterooligomerization with other polypeptides (e.g. STIM2); assays that detect binding to pre-B cells or differentiated B lymphocytes; assays that detect augmentation of IL-7-dependent proliferation following expression in pre-B cells; assays that detect modulation of cell morphology following expression in 293T cells; assays that detect suppression of cell growth following expression in tumor cells; and assays that detect modulation of intracellular calcium signaling.

c. Antibodies

Also provided are antibodies that specifically bind to isolated rat, hamster or reference STIM1 peptides, and antibodies that specifically bind to rat, hamster or reference STIM1 but not to either mouse STIM1 or human STIM1 or bind with substantially (at least 2, 5, 10-fold) less affinity. These antibodies have a variety of applications, such as, for example, to detect rat and hamster STIM1 polypeptides expressed in tissues or cells. Such antibodies are also used for purifying rodent reference STIM1 polypeptides by immunoaffinity methods. Furthermore, such antibodies can be used to interfere with the biological activity of STIM1 polypeptides or to deliver moieties to cells or tissues expressing STIM1 polypeptides.

Methods of preparing and isolating antibodies, including polyclonal and monoclonal antibodies and fragments therefrom, using rodent reference STIM1 polypeptides and peptides, as described above, are well known in the art. Methods of preparing and isolating non-natural antibodies are also well known in the art. For example, non-natural antibodies can be constructed using solid phase peptide synthesis or can be produced recombinantly, using nucleotide and amino acid sequence information of the antigen binding sites of antibodies that specifically bind the target polypeptide. Non-natural antibodies can also be obtained by screening combinatorial libraries containing of variable heavy chains and variable light chains, or of antigen-binding portions thereof. Methods of preparing, isolating and using polyclonal, monoclonal and non-natural antibodies are reviewed, for example, in Kontermann and Dubel, eds. (2001) "Antibody Engineering" Springer Verlag; Howard and Bethell, eds. (2001) "Basic Methods in Antibody Production and Characterization" CRC Press; and O'Brien and Aitkin, eds. (2001) "Antibody Phage Display" Humana Press.

D. Methods for Screening Agents and Molecules

Provided herein are methods of screening for or identify agents and molecules that modulate intracellular calcium. The methods include screening for or identifying a test agent that modulate intracellular calcium. The methods also include identifying new molecules, e.g., proteins and/or nucleic acids encoding new proteins, that were previously unknown, and for identifying known molecules (e.g., proteins) as being involved in intracellular calcium modulation. The test agents and identified molecules can be used in the methods provided herein for screening for agents for the treatment of a disease or disorder and additionally in methods of treating diseases and disorders. The test agents and identified molecules can also be used to in methods such as provided herein for modulating intracellular calcium.

1. Methods of Screening for or Identifying an Agent that Modulates Intracellular Calcium Methods of screening for or identifying agents that modulate intracellular calcium are provided herein. The methods are based in directly or indirectly monitoring of or assessing the effect of test agents on intracellular calcium and/or in assessing the interaction of a test agent with, or the effect of a test agent on, a protein involved in modulating intracellular calcium. In particular embodiments, the methods involve monitoring of or assessing store-operated calcium entry, calcium levels of (and/or movement of ions into, out of or within) intracellular organelles or calcium stores (e.g., the endoplasmic reticulum), cytosolic calcium buffering and/or resting cytosolic calcium levels. The effect(s) of test agents on intracellular calcium can be assessed in a variety of ways including, but not limited to, evaluation of calcium or other ion (particularly cation) levels, movement of calcium or other ions particularly cations), fluctuations in calcium or other ion (particularly cation) levels, kinetics of calcium or other ion particularly cation) fluxes and/or transport of calcium or other ion (particularly cation) through a membrane. The effect(s) of a test agent can also be assessed by assays, such as described herein, to monitor a calcium-entry mediated event.

In one embodiment, the methods can be conducted using a particular test agent: one that binds to, interacts with and/or modulates interactions, activities, levels or any physical, structural or other property of a protein involved in modulating intracellular calcium. In this embodiment, the method includes monitoring or assessing the effects of such a particular test agent on intracellular calcium (and, in particular embodiments, the effects on store-operated calcium entry, calcium levels in or movement of ions (such as calcium) into, out of or within an intracellular organelle (or calcium store), cytosolic calcium buffering and/or resting cytosolic calcium levels and/or effects on a calcium-entry mediated event). The method can optionally include a step of identifying an agent that can bind to, interact with and/or modulate interactions, activities, levels or any physical, structural or other property of a protein involved in modulating intracellular calcium. This optional step can be performed prior to or concurrently with the step of monitoring or assessing the effects of the agent on intracellular calcium.

In another embodiment, the methods can be performed using a test agent that modulates intracellular calcium and assessing the interaction of the test agent with, or the effect of the test agent on, a protein involved in modulating intracellular calcium. In particular embodiments, the binding of test agent with a protein involved in modulating intracellular calcium can be assessed. In other embodiments, the effect of a test agent on interactions, activities, levels or any physical, structural or other property of a protein involved in modulating intracellular calcium can be assessed. The method can optionally include a step of identifying a test agent that modulates intracellular calcium prior to (or concurrently with) the step of assessing the interaction of the test agent with, or the effect of the test agent on, a protein involved in modulating intracellular calcium.

In another embodiment, the methods can be performed by contacting any test agent with (1) one or more proteins involved in modulating intracellular calcium, e.g., a component of an ion transport protein complex or a modulatory protein, and/or (2) a cell, or portion thereof, e.g., a membrane, containing one or more proteins involved in modulating intracellular calcium, and/or nucleic acid (e.g. a gene or coding sequence such as cDNA or RNA), or portion(s) thereof, encoding such proteins. The effect of the test agent on intracellular calcium (and, in particular embodiments, the effect on store-operated calcium entry, calcium levels in or movement of ions (such as calcium) into, out of or within an intracellular organelle (or calcium store), cytosolic calcium buffering and/or resting cytosolic calcium levels) is monitored or assessed. In this embodiment of the methods, the test agent can be any agent, and is not necessarily one that is known to modulate (or has been identified as one that modulates) intracellular calcium, or that binds to, interacts with and/or modulates interactions, activities, levels or any physical, structural or other property of a protein involved in modulating intracellular calcium.

In particular embodiments of any of the methods of screening for or identifying an agent that modulates intracellular calcium provided herein, the protein(s) involved in modulating intracellular calcium can be a protein that is involved in, participates in and/or provides for store-operated calcium entry, cytosolic calcium buffering, maintenance of resting cytosolic calcium levels and/or modulation of calcium levels in, or movement of cations into, out of or within an intracellular organelle or calcium store, such as, for example, the endoplasmic reticulum. In particular embodiments, the protein involved in modulating intracellular calcium is an ion transport protein, such as, for example, an ion transport protein that is involved in, participates in and/or provides for store-operated calcium entry or movement of calcium into, out of or within the endoplasmic reticulum or other calcium store. In one embodiment, the protein involved in modulating intracellular calcium is a component of a store-operated calcium entry channel complex (e.g., a multimeric complex containing multiple subunits of the same and/or different proteins). In another embodiment the protein involved in modulating intracellular calcium is a modulatory protein. A protein involved in modulating intracellular calcium (and/or nucleic acid, or portion(s) thereof, encoding a protein involved in modulating intracellular calcium) may be contained in a cell or portion thereof, such as, for example, a cell membrane (e.g., plasma membrane or an intracellular membrane). The methods may be performed in particular embodiments under conditions that permit specific evaluation of store-operated ion flux or movement, resting cytosolic calcium levels, cytoplasmic calcium buffering and/or cation levels in, or movement into, out of or within an intracellular organelle or calcium store, such as, for example, the endoplasmic reticulum.

A protein involved in modulating intracellular calcium that is used in the methods (or on which a method is based) can be a full-length or complete protein (e.g., a protein that contains the complete amino acid sequence encoded by a gene, cDNA or RNA or a complete amino acid sequence that lacks sequences that are removed during processing of the protein, including removal of a signal sequence, such as may occur in transport of a protein to a particular cellular location, or processing to remove a pre- and/or pro-sequence of a protein) or a portion of a complete protein. In embodiments of the methods that involve assessing a functional activity of the protein, the protein used in the method can be a portion of a full-length protein that is associated with, or exhibits or is sufficient for producing the functional activity, e.g., an intracellular calcium-modulating activity. In embodiments of the methods that involve assessing a property of the protein that is not necessarily the intracellular calcium-modulating activity of the protein, the protein used in the method can be a portion of a full-length protein that is associated with the particular property being assessed, e.g., binding properties, and can be, for example, a particular domain of the protein. Similarly, when a nucleic acid, or portion(s) thereof, encoding a protein involved in modulating intracellular calcium is used in the methods, the nucleic acid can be a complete gene, e.g., including transcriptional regulatory sequences, a complete protein coding sequence, e.g., cDNA or RNA, or portion(s) of these (e.g., a portion encoding a functional domain of a protein).

a. Proteins (and/or Nucleic Acids Encoding Proteins) Involved in Modulating Intracellular Calcium The methods provided herein for screening for or identifying agents that modulate intracellular calcium are related to proteins (and/or nucleic acids, or portions thereof, that encode proteins) that are involved in modulating intracellular calcium. Some embodiments of the methods involve monitoring or assessing the effect on intracellular calcium of a test agent that binds to, interacts with and/or in some way modulates such a protein. Other embodiments involve the actual use of such proteins. For example, one embodiment involves assessing the interaction of a particular test agent with, or the effect of a particular test agent on, such a protein. Another embodiment involves contacting a test agent with (1) one or more proteins involved in modulating intracellular calcium, e.g., a component of an ion transport protein complex or a modulatory protein, and/or (2) a cell, or portion thereof, e.g., a membrane, containing one or more such proteins, and/or nucleic acid (e.g., a gene or coding sequence such as cDNA or RNA), or portion(s) thereof, encoding such proteins.

Proteins involved in modulating intracellular calcium can be, for example, ion transport proteins, a component of an ion transport protein complex, calcium-binding proteins, modulatory proteins, receptors and regulatory proteins that regulate ion transport proteins, receptors or calcium-binding proteins. Proteins (or nucleic acids, or portion(s) thereof, encoding proteins) that can be used in the methods of screening for or identifying agents that modulate intracellular calcium provided herein (or proteins on which the methods are based) include proteins that are homologous to a protein encoded by a *Drosophila* or mammalian (e.g. human or rodent, such as rat, hamster or mouse) gene that, when altered in its expression in a cell, results in altered intracellular calcium. An alteration in intracellular calcium can be any alteration in calcium level, movement, location, or other calcium alteration, in a cell. An alteration of intracellular calcium can be any change in intracellular calcium compared to a control cell (e.g., a *Drosophila* or mammalian cell that does not have altered expression of the gene).

In particular embodiments, the protein can be one that is homologous to a protein encoded by a *Drosophila* or mammalian (e.g., human or rodent, such as rat or mouse) gene that when altered in its expression in a cell (e.g., a *Drosophila* cell or mammalian, such as human or rodent, cell), results in altered store-operated calcium entry into the cell, altered calcium levels in or altered calcium movement into, within or out of an intracellular organelle or calcium store, altered cytosolic calcium buffering and/or altered basal or resting cytosolic calcium levels. An alteration of store-operated calcium entry or of movement into, out of or within an intracellular organelle or calcium store (e.g., endoplasmic reticulum) can be a complete or nearly complete elimination of the activity, a reduction of the activity, an alteration in properties or characteristics of the activity (e.g., current properties or sensitivities) or an increase in the activity, e.g., relative to the activity in a control cell (e.g., a *Drosophila* or mammalian cell), that has not been altered in its store-operated ion flux activity.

An alteration in the calcium level within an intracellular organelle or an alteration of resting cytosolic calcium levels can be, for example, a reduction, depletion, elimination of, or increase in calcium levels, e.g., relative to the levels in a control cell (e.g., a *Drosophila* or mammalian cell) that has not been altered in its intracellular organelle or basal cytosolic calcium levels. An alteration in the calcium level of an organelle or calcium store or an alteration in basal cytosolic calcium level can be effected in a number of ways, including, for example, by alterations in calcium movement across a cellular membrane (e.g., plasma membrane or membrane of an intracellular organelle or calcium store).

An alteration in cytosolic calcium buffering can be, for example, a complete or nearly complete elimination of the activity, a reduction of the activity, an alteration in properties or characteristics of the activity (e.g., rates, kinetics or timing) or an increase in the activity, e.g., relative to the activity in a control cell (e.g., a *Drosophila* or mammalian cell) that has not been altered with respect to its calcium buffering activity. Thus, for example, an alteration in calcium buffering can be a reduction or increase in the rate at which cytosolic calcium levels return to basal levels after activation of calcium influx into the cytoplasm. The alteration can be an overall time course of cytosolic calcium level adjustment that differs from that in a control cell. In another example, an alteration in calcium buffering can be a delay in onset of the adjustment of cytosolic calcium levels to return to basal levels after activation of calcium influx into the cytoplasm. In another example, an alteration in calcium buffering can be an adjustment in cytosolic calcium levels after activation of calcium influx that does not result in a return of calcium levels to a basal level, but instead to a level that is higher or lower than the basal level. In yet a further example, an alteration in calcium buffering can be a complete or near complete absence of an adjustment in cytosolic calcium levels following activation of calcium influx into the cytoplasm.

Similarly, an alteration in gene expression may be complete or nearly complete elimination of the expression of a gene, a reduction in the expression of a gene, an increase in the expression of a gene, or an alteration in the protein encoded by the gene (such as truncation or other alteration that effectively renders the protein nonfunctional or provides for aberrant functioning of the protein), e.g., relative to the expression of the gene in a cell that has not been altered in its expression of the gene.

In a particular embodiment of the methods of screening for or identifying an agent that modulates intracellular calcium, the protein used in the method (and/or protein encoded by a nucleic acid, or portion(s) thereof, used in the method) can be one that is homologous to a protein encoded by a *Drosophila* or mammalian (e.g., human or rodent such as rat, hamster or mouse) gene that, when altered in its expression in (e.g., a *Drosophila* or mammalian cell), results in alterations in one or more, or all, of the following: (1) store-operated calcium entry into the cell, (2) calcium levels in an intracellular organelle or calcium store, (3) calcium movement into, within or out of an intracellular organelle or calcium store and (4) cytosolic calcium buffering.

Particular proteins that are homologous to a protein encoded by a *Drosophila* or mammalian gene that, when altered in its expression, results in altered intracellular calcium include proteins that are involved in, participate in and/or provide for the movement of calcium. Such proteins may be relatively specific for calcium ion transport. For example, the protein can be an ion transport protein, or a component of an ion transport protein complex, that is involved in, participates in and/or provides for store-operated calcium entry.

In one embodiment of the methods of screening for or identifying agents that modulate intracellular calcium provided herein, a protein used in the method, or on which the method is based, is involved in modulating intracellular calcium (and, in particular embodiments, is involved in, participates in and/or provides for store-operated calcium entry, movement of calcium into, out of or within an intracellular organelle, modulation of intracellular organelle calcium level, and/or cytosolic calcium buffering) and is homologous to a protein encoded by the coding sequence of *Drosophila* gene CG9126 (GenBank Accession no. NM_078633, gi22832319 and AF328906; see also SEQ ID NO:1 for a coding sequence and SEQ ID NO: 2 and GenBank Accession no. NP_523357, AAF48542, AAK82338 and P83094 for amino acid sequence) and/or a mammalian stromal interacting molecule (STIM) protein (see, e.g., SEQ ID NO:90 for a mammalian STIM1 consensus amino acid sequence), such as, for example, human STIM1 (GenBank protein Accession nos. Q13586, NP_003147, AAC51627 and nucleotide Accession nos. NM_003156, gi2264345, gi2264346; see also SEQ ID NOS:3, 82 for nucleic acid coding sequences and SEQ ID NOS: 4 and 83 for amino acid sequences), rat STIM 1 (see SEQ ID NO: 97 for a nucleic acid coding sequence and SEQ ID NO: 98 for an amino acid sequence, hamster STIM1 (see SEQ ID NO: 95 for a nucleic acid coding sequence and SEQ ID NO: 96 for an amino acid sequence) and reference STIM1 (see SEQ ID NO: 51 for a nucleic acid coding sequence and SEQ ID NO: 52 for an amino acid sequence). As described herein (see the EXAMPLES), alteration, and, in particular, reduction, of the expression of CG9126 in *Drosophila* S2 cells or of the expression of the gene encoding mammalian STIM1 proteins in mammalian cells (e.g., human SH-SY5Y and HEK293 cells, rat basophilic leukemia (RBL-2H3) cells and Chinese hamster ovary (CHO) cells) is associated with a reduction in store-operated calcium entry into the cells, a reduction in calcium levels in the endoplasmic reticulum, a reduction in movement of calcium out of the endoplasmic reticulum and/or alteration of calcium buffering following activation of release of calcium from intracellular calcium stores. Accordingly, the protein encoded by CG9126, and mammalian (e.g., human and rodent, such as rat) STIM proteins, as well as proteins homologous with CG9126 and mammalian (e.g., human and rodent, such as rat and hamster) STIM proteins, are identified herein as being involved in modulating intracellular calcium. In particular, such proteins are identified herein as being involved in, participating in and/or providing for store-operated calcium entry, modulation of calcium levels in or movement of calcium into, out of, or within intracellular calcium stores (e.g., endoplasmic reticulum) and/or calcium buffering. In particular embodiments, a protein used in the method (or on which the method is based) that is involved in modulating intracellular calcium and is homologous to a specified protein is an ion transport protein, a component of an ion transport protein complex, a modulatory protein, or a receptor.

A protein used in the methods of screening for or identifying an agent that modulates intracellular calcium can be, for example, one that is involved in modulating intracellular calcium (and, in particular embodiments, is involved in, participates in and/or provides for store-operated calcium entry, movement of calcium into, out of or within an intracellular organelle, modulation of intracellular organelle calcium level, and/or cytosolic calcium buffering) and that has an amino acid sequence that is at least about 20%, or at least about 25%, or at least about 30%, or least about 35%, or at least about 39%, or at least about 40%, or at least about 45%, or at least about 47%, or at least about 50%, or at least about 55%, or at least about 60%, or at least about 65%, or at least about 70%, or at least about 75%, or at least about 80%, or at least about 85%, or at least about 90%, or at least about 95% or more homologous to an amino acid sequence of the protein encoded by the coding sequence of *Drosophila* gene CG9126 and/or a mammalian stromal interacting molecule (STIM) protein, e.g., human or rodent (such as rat or hamster) STIM1. The particular homology can depend on the particular protein, e.g., species, that is homologous to the specified proteins and the extent of a specified protein to which the particular protein is homologous. In particular embodiments, the protein is at least 45% or more homologous to the protein encoded by the coding sequence of *Drosophila* gene CG9126 and/or a mammalian stromal interacting molecule (STIM) protein, e.g., human or rodent (such as rat or hamster) STIM1. Such exemplary proteins may be homologous to the specified proteins over at least about 25%, or at least about 30%, or at least about 35%, or at least about 40%, or at least about 45%, or at least about 50%, or at least about 52%, or least about 55%, or at least about 60%, or at least about 65%, or at least about 70%, or at least about 75%, or at least about 80%, or at least about 84%, or at least about 85%, or at least about 90%, or at least about 95% or more of the protein encoded by the coding sequence of a specified protein. In particular embodiments, the protein is homologous to the specified proteins over at least about 52% or more of a specified protein.

In particular embodiment of the methods for screening for or identifying agents that modulate intracellular calcium, a protein used in the method (or proteins encoded by nucleic acids, or portion(s) thereof, used in the method) is one that is involved in modulating intracellular calcium (and, in particular embodiments, is involved in, participates in and/or provides for store-operated calcium entry, movement of calcium into, out of or within an intracellular organelle or calcium store, modulation of intracellular organelle (or calcium store) calcium level, and/or cytosolic calcium buffering) and that has an amino acid sequence that is at least about 45% homologous over at least about 52% of a specified protein.

Proteins homologous to the protein encoded by the coding sequence of *Drosophila* gene CG9126 and/or a mammalian stromal interacting molecule (STIM) protein, e.g., human or rodent STIM1, include, but are not limited to, the proteins listed in Table 3.

TABLE 3

Examples of Proteins

| PROTEIN(GenBank Protein; Nucleic Acid Accession Numbers) | Homology (Identity) To Protein Encoded By *Drosophila* Gene CG9126 | Homology (Identity) To Human STIM1 | Homology (Identity) To Reference STIM1 |
|---|---|---|---|
| Protein Encoded By *Drosophila* Gene CG9126 SEQ ID NOS: 2, 75-81 (NP_523357, AAF48542, AAK82338, P83094 and AAL39831; NM_078633, gi22832319, AF328906 and AY069686) | 100% (100%) over 100% of the protein | 58% (39%) over 70% of the protein | 58% (39%) over 70% of the protein |
| *Homo sapiens* STIM1 SEQ ID NOS: 3, 4, 82-84 (Q13586, NP_003147, AAC51627; NM_003156, U52456, gi2264346) | 58% (39%) over 84% of the protein | 100% (100%) over 100% of the protein | 97% (96%) over 100% of the protein |
| Reference STIM1 SEQ ID NOS: 51 and 52 | 58% (39%) over 85% of the protein | 97% (96%) over 100% of the protein | 100% (100%) over 100% of the protein |
| *Mus musculus* STIM1 SEQ ID NOS: 9, 10 and 85 (NP_033313.1 and P70302; NM_009287) | 58% (39%) over 84% of the protein | 97% (96%) over 100% of the protein | 98% (97%) over 100% of the protein |
| *Homo sapiens* unknown protein for MGC: 29566 SEQ ID NOS: 49 and 50 (AAH21300; BC021300) | 58% (39%) over 84% of the protein | 99% (99%) over 100% of the protein | 97% 96%) over 100% of the protein |
| *Mus musculus* stromal cell protein SEQ ID NOS: 56 and 55 (AAC52715; U47323) | 58% (39%) over 84% of the protein | 97% (96%) over 100% of the protein | 98% (97%) over 100% of the protein |
| *Homo sapiens* KIAA1482 protein SEQ ID NOS: 59 and 60 (BAA96006; AB040915) | 61% (41%) over 75% of the protein | 66% (53%) over 84% of the protein | 67% (59%) over 80% of the protein |
| *Homo sapiens* STIM2 SEQ ID NOS: 5, 6, 86-88 (AAK82337, NP_065911, Q9P246; AF328905, NM_020860) | 61% (41%) over 75% of the protein | 66% (53%) over 84% of the protein | 68% (53%) over 80% of the protein |
| *Mus musculus* STIM2 SEQ ID NOS: 11, 12, 67, 68 (XP_132038, AAK82339; XM_132038, AF328907) | 60% (41%) over 66% of the protein | 64% (52%) over 80% of the protein | 65% (53%) over 80% of the protein |
| *Rattus norvegicus* protein similar to STIM2 SEQ ID NOS: 72, 73 (XP_223454; XM_223454) | 58% (40%) over 63% of the protein | 71% (58%) over 63% of the protein | 72% (59%) over 61% of the protein |
| *Homo sapiens* protein similar to STIM2 SEQ ID NOS: 61 and 62 (AAH15659; BC015659) | 58% (40%) over 53% of the protein | 67% (56%) over 59% of the protein | 71% (60%) over 52% of the protein |
| *Anopheles gambiae* str. PEST ebiP8103 SEQ ID NOS: 6 and 7 (EAA06485; AAAB1008846) | 85% (73%) over 84% of the protein | 59% (40%) over 71% of the protein | 60% (42%) over 68% of the protein |

TABLE 3-continued

Examples of Proteins

| PROTEIN(GenBank Protein; Nucleic Acid Accession Numbers) | Homology (Identity) To Protein Encoded By *Drosophila* Gene CG9126 | Homology (Identity) To Human STIM1 | Homology (Identity) To Reference STIM1 |
| --- | --- | --- | --- |
| *Mus musculus* protein for MGC: 13964SEQ ID NOS: 53 and 54(AAH21644; BC021644) | 58% (39%) over 84% of the protein | 97% (96%) over 100% of the protein | 98% (97%) over 100% of the protein |
| *Homo sapiens* hypothetical protein SEQ ID NOS: 57 and 58(CAB66512; AL136577) | 61% (41%) over 75% of the protein | 66% (53%) over 84% of the protein | 67% (55%) over 80% of the protein |
| *Caenorhabditis elegans* Y55B1M.1.p protein SEQ ID NOS: 13 and 14(NP_497197; NM_064796) | 50% (31%) over 74% of the protein | 52% (31%) over 56% of the protein | 52% (31%) over 56% of the protein |
| *Caenorhabditis elegans* putative membrane protein SEQ ID NOS: 73 and 74(NP_741073; NM_171065) | 51% (32%) over 67% of the protein | 49% (29%) over 68% of the protein | 47% (28%) over 74% of the protein |
| *Caenorhabditis elegans* hypothetical protein Y55B1BM.1aSEQ ID NOS: 63 and 64(AAF59596; AC024823) | 50% (31%) over 74% of the protein | 52% (31%) over 56% of the protein | 52% (31%) over 56% of the protein |
| *Caenorhabditis elegans* hypothetical protein Y55B1BM.1bSEQ ID NOS: 65 and 66(AAL32257; AC024823) | 51% (32%) over 67% of the protein | 49% (29%) over 68% of the protein | 47% (28%) over 75% of the protein |

In other embodiments, other proteins that may be used in the methods provided herein include, but are not limited to, proteins involved in intracellular calcium modulation that are substantially homologous to the above-listed proteins.

These listed proteins and their amino acid sequences, and nucleic acids encoding such proteins (including the listed nucleotide sequences), exemplify proteins and nucleic acids that are useful for methods, materials and systems provided herein. Naturally occurring and synthesized alternative forms of these proteins such as allelic forms, isoforms, muteins, and mutated derivatives will have sequence changes that do not abolish their operation in intracellular calcium modulation and are useful in embodiments. Mutations, polymorphisms and allelic forms of these proteins are known and are contemplated as embodiments.

Proteins used in the methods for screening for or identifying an agent that modulates intracellular calcium include synthetic proteins, proteins endogenously expressed by a cell, and recombinant proteins. The protein can, for example, be isolated from a source containing the protein or can be contained within a cell, virus or organism or portion(s) thereof, e.g., a membrane. Nucleic acids used in the methods include synthetic nucleic acids, recombinant nucleic acids and nucleic acids isolated from a source containing the nucleic acid. A variety of methods, some of which are described herein, can be employed for protein and nucleic acid synthesis and isolation, and recombinant expression of nucleic acids and proteins. Many such methods are well known in the art.

b. Test Agents

Generally, agents tested in the methods of screening for or identifying agents that modulate intracellular calcium provided herein can be of any physical type. Examples of agents include, but are not limited to, biomolecules, including, but not limited to, amino acids, peptides, polypeptides, peptiomimetics, nucleotides, nucleic acids (including DNA, cDNA, RNA, antisense RNA and any double- or single-stranded forms of nucleic acids and derivatives and structural analogs thereof), polynucleotides, saccharides, fatty acids, steroids, carbohydrates, lipids, lipoproteins and glycoproteins. Such biomolecules can be substantially purified, or can be present in a mixture, such as a cell extract or supernate. Test agents further include synthetic or natural chemical compounds, such as simple or complex organic molecules, metal-containing compounds and inorganic ions. Also included are pharmacological compounds, which optionally can be subjected to directed or random chemical modifications, such as acylation, alkylation, esterification, amidation, etc., to produce structural analogs.

Test agents suitable for use in the methods can optionally be contained in compound libraries. Methods for producing compound libraries by random or directed synthesis of a wide variety of organic compounds and biomolecules are known in the art, and include expression of randomized oligonucleotides and oligopeptides. Methods of producing natural compounds in the form of bacterial, fungal, plant and animal extracts are also known in the art. Additionally, synthetically produced or natural compounds and compound libraries can be readily modified through conventional chemical, physical and biochemical means to produce combinatorial libraries. Compound libraries are also available from commercial sources.

c. Methods Based on Testing an Agent that Binds to, Interacts with and/or Modulates Interactions, Activities or Levels of a Protein Involved in Modulating Intracellular Calcium (and/or Nucleic Acid, or Portion(s) Thereof, Encoding such Proteins)

In one embodiment of the methods for screening for or identifying agents that modulate intracellular calcium provided herein, the test agent is one that binds to, interacts with and/or modulates interactions, activities, levels or any physical, structural or other property of a protein (e.g., an ion transport protein, a component of an ion transport protein complex, a modulatory protein, or a receptor) involved in modulating intracellular calcium and/or portion(s) thereof. This embodiment of the methods includes a step of assessing or monitoring or assessing the effects of such a test agent on intracellular calcium (and, in particular embodiments, the effects on store-operated calcium entry, calcium levels in or movement of calcium into, out of or within an intracellular organelle (or calcium store), cytosolic calcium buffering and/or resting cytosolic calcium levels). Such particular test agents used in this embodiment include agents that are known to be or that have already been identified as agents that can bind to, interact with and/or modulate interactions, activities, levels or any physical, structural or other property of a protein involved in modulating intracellular calcium. Optionally, this embodiment of the methods can include a step of identifying an agent that can bind to, interact with and/or modulate interactions, activities, levels or any physical, structural or other property of a protein involved in modulating intracellular calcium.

The protein involved in modulating intracellular calcium that the test agent binds to, interacts with and/or modulates (e.g., the interactions, activities, levels or any physical, structural or other property of the protein) can be a protein as provided herein and described above (and elsewhere herein). In particular embodiments, the protein is one that is involved in, participates in, and/or provides for store-operated calcium entry, movement of calcium into, out of or within an intracellular organelle or calcium store, modulation of intracellular organelle (or calcium store) calcium level, and/or cytosolic calcium buffering. In particular embodiments, the protein is one of the proteins (or is substantially homologous to one of the proteins) listed in Table 3. The protein can be a STIM or STIM-like protein, including a STIM1, STIM2, DSTIM or CSTIM protein. In one embodiment of the methods, the protein is a STIM1 protein, for example, a mammalian STIM1 protein. In a particular embodiment, the effect of test agent on store-operated calcium entry is monitored or assessed.

i. Identification of Particular Test Agents

Test agents suitable for use in this embodiment of the methods for screening for or identifying agents that modulate intracellular calcium can be identified in a number of ways using techniques described herein and/or known in the art.

(a) Binding and Interaction Assays

A number of in vitro and cell-based binding assays are known in the art and can be modified as needed by one of skill in the art to identify agents that bind to or interact with a protein involved in modulating intracellular calcium and/or portion(s) thereof. Test agents that bind to a protein involved in modulating intracellular calcium include molecules that physically interact with the protein and/or portion(s) thereof with relatively high affinity and selectivity. For example, an agent that binds to a protein involved in modulating intracellular calcium can bind with a $K_d$ of about $10^{-4}$ M or less, such as about $10^{-6}$ M or less, including about $10^{-8}$ M or about $10^{-9}$ M or less. In contrast, under the same conditions, the agent can bind a protein that is not the particular protein involved in modulating intracellular calcium with an affinity that is at least 10-fold lower, such as at least 100-fold or 1000-fold lower.

In vitro methods for identifying molecules that bind to or interact with a protein involved in modulating intracellular calcium include both direct methods, e.g., in which binding between the agent and the polypeptide is detected or measured, and competitive methods, in which the ability of an agent to displace binding between a bound molecule and the polypeptide is detected or measured. For example, antibodies, such as monoclonal antibodies, that specifically recognize a protein of interest or portion thereof can be used to compete for binding of the protein or portion thereof.

Exemplary in vitro methods include co-purification assays (e.g., GST pull-down assays, co-immunoprecipitation assay, chromatographic assays), phage display (see, e.g., Rodi et al. (2002) *Curr. Opin. Chem. Biol.* 6:92-96), ribozyme display (Hanes and Pluckthun (1997) *Proc. Natl. Acad. Sci. U.S.A.* 13:4937-4942), and protein arrays (Cahill (2001) *J. Immunol. Meth.* 250:81-91). Antibodies that recognize a particular protein can be used to immunoprecipitate the protein and any molecule(s) bound to the protein. Lambda phage expression libraries can also be screened, using methods known in the art, for proteins that bind to a protein of interest or portion thereof.

Detection of in vitro binding or interaction between an agent and a protein involved in modulating intracellular calcium and/or portion(s) thereof can involve a variety of approaches, such as, for example, nuclear magnetic resonance (NMR) (Hadjuk et al. (1999) *J. Med. Chem.* 42:2315-2317), mass spectroscopy (Siegel (2002) *Curr. Top. Med. Chem.* 2:13-33), fluorescence spectroscopy (Winkler et al. (1999) *Proc. Natl. Acad. Sci. U.S.A.* 96:1375-01378), scintillation proximity assays (SPQ) (Fernandes (1998) *Curr. Opin. Chem. Biol.* 2:597-603), surface plasmon resonance assays (available commercially from BIACORE; /www.biacore.se/proteomics/), and others. Many of these methods are amenable to high-throughput screening of test agents.

The protein involved in modulating intracellular calcium, the agent, or both, used in an in vitro binding or interaction assay can be in gas phase, in solution, in suspension, or attached to a solid support, as appropriate for the assay method. The protein, agent, or both can be detectably labeled. Methods for preparing the protein or test agent in a form suitable for the particular assay are known in the art. For example, the protein, or a portion thereof, can be prepared synthetically, isolated from a source of the protein, enzymatically or otherwise cleaved to yield desired protein or peptide fragments, or produced by recombinant methods, such as by expression of a nucleic acid construct encoding the protein (or portion thereof) in a host cell (e.g., bacteria, yeast, or mammalian cell or other cells) and secretion or isolation therefrom.

Cell-based binding assays include, for example, yeast two-hybrid assays (see, e.g., U.S. Pat. Nos. 5,283,173, 5,468,614 and 5,667,973 and PCT Application Publication Nos. WO01/25420 and WO02/079493); bacterial two-hybrid assays (Juong (2001) *J. Cell Biochem. Suppl.* 37:53-57), and others. Such assays are particularly suitable for identifying polypeptides that interact with a protein involved in modulating intracellular calcium. Two-hybrid assays are based on the modular nature of most transcription factors, which consist of separable DNA-binding and activation domains. Briefly, such assays use two different DNA constructs, one that codes for the polypeptide of interest (i.e., a protein involved in modulating intracellular calcium or portion thereof) fused to a gene or nucleic acid encoding the DNA binding domain of a known transcription factor. In the other construct, a DNA sequence, from a library of sequences, that encodes a potential test agent polypeptide is fused to a gene or nucleic acid that codes for the activation domain of the known transcription factor. If the polypeptide of interest and the test polypeptide interact, the DNA-binding and activation domains are brought into close proximity, which allows transcription of a reporter gene that is operably linked to a transcriptional regulatory site responsive to the transcription factor. Expression of the reporter gene can be detected, and cell colonies containing the functional transcription factor isolated. From these colonies, the nucleic acid molecule encoding the test polypeptide that binds or interacts with the protein involved in intracellular calcium modulation can be isolated.

Another cell-based assay for identification of molecules that interact with a protein, such as a protein involved in modulating intracellular calcium, is the tandem affinity purification (TAP) method (see, e.g., Rigaut et al. (1999) *Nature Biotech.* 17:1030-1032; Puig et al. (2001) *Methods* 24:218-229). The method involves a two-step process for the affinity purification of protein complexes from cells, e.g., yeast, when expressed at relatively normal levels under native conditions. The method employs a tag that is fused to the protein of interest (e.g., a protein involved in modulating intracellular calcium), or portion(s) thereof, through recombinant expression of the fusion protein in order to facilitate affinity purification using two different selection molecules. The tag can be a fusion of protein A IgG-binding domains (for use in a first affinity purification by an IgG matrix) and a calmodulin-binding peptide (for use in a second affinity purification by calmodulin-coated beads) separated by a TEV protease cleavage site (to eluate protein complexes bound to the IgG matrix). Thus, the protein of interest is expressed in cells as a fusion with the tag and then extracts of the cells are mixed with the IgG matrix, bound complexes are eluted by cleavage with TEV protease, and the eluate is mixed with calmodulin-coated beads in the presence of calcium. The complexes are released from the beads with EGTA. The purified complex can be used for protein identification, functional or structural studies. Analytical methods that can be applied include analytical gel electrophoresis and mass spectrometry. The method can be used to identify a variety of interacting agents, including, for example, proteins, nucleic acids, lipids and peptides.

Assays that generally can be used for identifying test agents that modulate the binding or interaction of a protein of interest (e.g., a protein involved in intracellular calcium modulation), or portion(s) thereof, with other molecules are also known in the art. In these assays, a complex of the protein of interest and a binding/interaction partner (or portion(s) thereof) is typically contacted with or exposed to a potential test agent and the binding or interaction of the complex is assessed (for example, for an effect of the potential test agent on the binding, such as decreased, increased or other alterations in the interaction) using standard analytical techniques as described herein and known in the art. For example, one such technique involves measuring fluorescence resonance energy transfer (FRET) between an energy donor molecule linked to one binding partner and an energy acceptor molecule linked to the other binding partner in the presence of an agent. An agent that alters the interaction of the binding partners can be detected as a difference (e.g., increase or fluorescent energy of a different wavelength) in the fluorescence of the sample. Suitable donor and acceptable molecules and conditions for conducting such assays are known in the art (see, e.g., U.S. Pat. Nos. 6,348,322 and 4,868,103). FRET assays may also be used to identify molecules that interact with or bind to a protein of interest (e.g., a protein involved in modulating intracellular calcium) or portion(s) thereof. Other methods that can be used to assess binding between binding partners include ELISA and radioligand binding assays.

As described above, a protein involved in modulating intracellular calcium that is used in the methods for screening for or identifying an agent that modulates intracellular calcium (or a protein on which the method is based) can be a full-length or complete protein or a portion of a complete protein. Portions of complete proteins include portions that are associated with, exhibit or that are sufficient for producing a particular activity or function of the complete protein, and portions that are associated with a particular property or feature of the complete protein, such as a binding portion or a particular domain, or any random portion of the protein. Similarly, nucleic acids that encode proteins that can be used in the methods (or on which a method is based) can encode a complete protein or portion(s) thereof.

In the embodiment of the methods that involve assessing the effects on intracellular calcium of an agent that binds to or interacts with a protein involved in modulating intracellular calcium, the test agent can be one that is identified, for example, using any such binding/interaction assay as described above (or known in the art) that employs a complete or full-length protein of interest or portion(s) thereof. Portions of proteins can be obtained using a variety of methods (e.g., synthetically, through recombinant production methods) described herein and/or known in the art and can be random or selected for a particular feature. Methods for identifying particular features of proteins are known in the art. For example, particular domains (e.g., protein interaction domains, calcium-binding domains, catalytic domains, phosphorylation domains and others) can be identified by comparing the primary structure of a protein to known motifs and domains, particularly through computer-assisted comparisons utilizing protein motif databases (see, e.g., computer-assisted proteome analysis programs such as that available through www.ebi.ak.uk/proteome, and searchable amino acid sequence pattern information available and searchable through other databases, including InterPro (see www.ebi-.ac.uk/interpro/) as well as SWISS-PROT, TrEMBL, PROSITE, PRINTS, Pfam and Prodom; see also the domain identification and Conserved Domain Architecture Retrieval Tool (CDART) programs available through the National Center for Biotechnology Information (NCBI) Entrez Search and Retrieval system (www.ncbi.nlm.nih.gov)).

In a particular embodiment of these methods of screening for or identifying an agent that modulates intracellular calcium, a protein used in the method (or on which the method is based) is a STIM or STIM-like protein (e.g., a STIM1 or STIM2 or DSTIM protein). The test agent can be one that binds to or interacts with a STIM or STIM-like protein or portion(s) thereof or that modulates the interaction or binding of such a protein with a binding partner. Such agents can be any agent known to bind to or interact with such proteins (or known to modulate the binding or interaction of such proteins) or can be one identified using methods described herein and/or known in the art. Any portion of a STIM or STIM-like protein can be used in methods of identifying an agent that binds to or interacts with the protein, including the complete protein, the mature protein (lacking signal sequence) and any portion thereof. Particular domains of STIM and STIM-like proteins are described herein and/or can be identified using methods described herein and/or known in the art. For example, sterile a motif (SAM) and coiled-coil domains contained in N-terminal and C-terminal regions, respectively, of STIM proteins are domains implicated in protein-protein interactions and subunit oligomerization. Examples of nucleic acids encoding STIM proteins and portions thereof are also described herein or can be designed based on amino acid sequences such as those described herein.

In a particular embodiment of these methods, a test agent is one that modulates the interaction of two or more STIM or STIM-like proteins (or portion(s) thereof). For example, human STIM1 and STIM2 proteins form co-precipitable oligomeric associations in K562 cells (chronic myeloid leukemia cells) and in 293T cells transfected with nucleic acids encoding human STIM1 and STIM2 proteins (Williams et al. (2001) Biochem. J. 357:673-685). In addition, STIM1 homotypic interactions occur in human 293T cells transfected with nucleic acid encoding human STIM1 and nucleic acid encoding a fusion protein containing the transmembrane and cytoplasmic (i.e., the C-terminal) region of human STIM1 (Williams et al. (2002) Biochim. Biophys. Acta 1596:131-137). Thus, STIM1-STIM1 homotypic interactions are mediated via the C-terminal domain of the protein. Methods of assaying the interaction of STIM proteins include methods described by Williams et al. ((2001) Biochem. J. 357:673-685; and Biochim. Biophys. Acta 1596:131-137), including cotransfection and immunoprecipitation assays. For example, interaction of STIM1 proteins can be detected by cotransfection of cells (e.g., human 293T cells) with nucleic acid encoding human STIM1 and nucleic acid encoding a fusion protein containing a detectable marker (e.g., the extracellular region of the GCSF (granulocyte colony stimulating factor) receptor) protein fused to the transmembrane and cytoplasmic (i.e., C-terminal) region of human STIM1 and immunoprecipitation of the homo-multimer from cellular lysates with an anti-marker protein antibody followed by immunoblotting of the immune complexes with antibody that recognizes the C-terminal region of STIM1. Similarly, interaction of STIM1 and STIM2 proteins can be detected by cotransfection of cells (e.g., human 293T cells) with nucleic acid encoding STIM1 and STIM2 and immunoprecipitation of the hetero-multimer from cellular lysates with an antibody that recognizes STIM1 or STIM2 and immunoblotting of the complexes with an antibody that recognizes both STIM1 and STIM2. Thus, an agent that modulates (e.g., disrupts, inhibits or alters) interactions of STIM proteins can be identified by assaying agents for an effect on the immune complex (e.g., a decrease or elimination of the complex).

Antibodies that recognize STIM proteins (and/or portions thereof) are described herein and/or known in the art and can be produced using standard techniques known to those of skill in the art. For example, antibodies generated against human STIM1 include a monoclonal antibody prepared to amino acids 25-139 of human GOK (STIM1) (Transduction Laboratories, San Diego, Calif., U.S.A., catalog no. G72120), a polyclonal antibody prepared in sheep against an N-terminal peptide (amino acids 22-37) of human STIM1 (LSHSH-SEKATGTSSG-C) with cysteine added for conjugation, and a polyclonal antibody prepared in rabbits against a C-terminal peptide (amino acids 657-685) of human STIM1 (C-DNGSI-GEETDSSPGRKKFPLKIFKKPLKK) with cysteine added for conjugation (see, e.g., Williams et al. (2001) Biochem. J. 357:673-685). Antibodies generated against human STIM2 include peptide affinity-purified antibodies prepared by immunizing sheep with a 22-amino-acid peptide based on the C-terminal region of human STIM2 (CHNGEKSKKPSKIK-SLFKKKSK) (see, e.g., Williams et al. (2001) Biochem. J. 357:673-685). Antibody pools reactive with mammalian and invertebrate STIM proteins include Pan-STIM antibodies prepared against multiple peptides simultaneously in sheep. In one example, four peptides have been used to prepare a Pan-STIM antibody pool: (1) HKLMDDDANGDVDVEES-DEFLR-COOH (SEQ ID NO: 101; human STIM1), (2) HKQMDDDKDGGIEVEESDEFIR-COOH (SEQ ID NO: 102; human STIM2), (3) HRQLDDDDNGNIDLSESD-DFLR-COOH (SEQ ID NO: 103; D. melanogaster STIM and (4) HRDMDDDHSGSIDRNESFQFMK-COOH (SEQ ID NO: 104; C. elegans STIM) (see, e.g., Williams et al. (2001) Biochem. J. 357:673-685).

(b) Level and Activity Assays

A number of in vitro and cell-based assays are known in the art and can be modified as needed by one of skill in the art to identify agents that alter the level and/or activity of proteins. The assay used can depend on the protein of interest and its activities. Thus, for example, if the protein of interest is an ion transport protein, one method for assessing activity is the analysis of the electrophysiological properties of the channel activity using procedures described herein and known in the art. If the protein of interest has an enzymatic activity, then one method for assessing activity is the analysis of substrate interaction and reaction. For example, if the protein of interest has a protease activity, it typically can be assessed by analysis of substrate cleavage. Potential test agents that modulate an activity of a protein involved in intracellular calcium modulation can be identified by evaluating the effect of such an agent on the particular activity of the protein.

In a particular embodiment of these methods of screening for or identifying an agent that modulates intracellular calcium, a protein used in the method (or on which the method is based) is a STIM or STIM-like protein (e.g., a STIM1, STIM2, DSTIM or CSTIM protein). The test agent can be one that modulates the level or activity of a STIM or STIM-like protein or portion(s) thereof. Such agents can be any agent known to modulate the level or activity of such proteins or can be one identified using methods described herein and/or known in the art. Activities of a mammalian STIM1 protein include binding of pre-B cells and differentiated B lymphocytes (facilitated by divalent cations such as $Mn^{2+}$), augmentation of interleukin 7-dependent proliferation of pre-B cells, and modulation of the morphology of 293T cells, i.e., a human renal carcinoma cell line transfected with large T antigen (see, e.g., Oritani and Kincade (1996) J. Cell Biol. 134:771-782). Thus, an agent that modulates an activity of mammalian STIM1 can be identified by assaying agents for an effect on any of these activities. Methods of assaying for these activities include methods described by Oritani and Kincade ((1996) J. Cell Biol. 134:771-782), such as a flow cytometry-based assay for binding of a human Ig-mouse STIM1 fusion protein (soluble fusion protein purified on Protein A columns) to mouse pre-B cells stained with an FITC-conjugated anti-Ig antibody, a semisolid agar colony-forming assay to enumerate IL-7 responsive B lymphocyte precursors (CFU-IL7), and a cell morphology-based assay using 293T cells overexpressing mouse STIM1 through transfection with nucleic acid encoding full-length mouse STIM1. Thus, an agent that, for example, enhances or reduces (1) binding of STIM1 to pre-B cells, or (2) the augmentation of B lymphocyte precursor proliferation by STIM1 or (3) the induction of a rounded morphology and detachment of 293Tcells overexpressing STIM1 is an agent that modulates an activity of STIM.

Another activity of STIM1 is the suppression of tumor growth. The expression of human STIM1 (GOK cDNA) in rhabdomyoscarcoma and rhabdoid tumor cell lines RD and G401 induces growth arrest and degeneration (Sabbioni et al.

(1997) *Cancer Res.* 57: 4493-4497). Thus, an agent that modulates an activity of STIM can be identified by assaying agents for an effect on this growth suppression activity. Methods for assaying this activity include methods described by Sabbioni et al. ((1997) *Cancer Res.* 57: 4493-4497). Such methods include, for example, a cell morphology- or phenotype-based assay using assessing rhabdomyosarcoma (e.g., A204, A673, Hs729, RD, SJCRH30, TE125.T and TE611 cells available from the American Type Culture Collection (ATCC)) or rhabdoid tumor cells (e.g., G401 cells available from ATCC) transfected with nucleic acid encoding full-length human STIM1. Thus, an agent that, for example, enhances or reduces the STIM-dependent induction of the growth-suppressed phenotype (e.g., rounded and detached or enlarged and degenerating cells) of such cells is one that modulates an activity of STIM.

A further activity of STIM proteins is modulation of the Notch signaling pathway. Cell-cell signaling mediated by activation of the Notch receptor results in proteolytic cleavage of the intracellular domain of Notch which translocates to the nucleus where it associates with DNA-binding proteins and activates gene expression which in turn affects regulation of downstream target genes to influence cell differentiation, proliferation and apoptotic events. The modulation of Notch signaling by STIM proteins can include a possible antagonistic effect based on the generation of a phenotype in transgenic *Drosophila* (overexpressing DSTIM) with similarity to *Drosophila* Delta and Notch mutants (see PCT Application publication no. WO02/30976). Thus, an agent that, for example, alters (e.g., enhances or reduces) the modulation of Notch signaling by STIM proteins can be one that modulates an activity of STIM. One method for assessing whether an agent has an effect on STIM-dependent modulation of Notch signaling involves contacting a cell that exhibits altered Notch signaling due to overexpression of a STIM protein with a test agent and determining whether the agent reverses, at least partially, or enhances the STIM-dependent effect on or modulation of Notch signaling. Methods of monitoring Notch signaling are known in the art (see, e.g., PCT Patent Application Publication No. WO02/12890, U.S. Pat. No. 6,436,650 and Karlstrom et al. (2002) *J. Biol. Chem.* 277: 6763-6766).

Potential test agents that modulate the levels and/or expression of a protein involved in intracellular calcium modulation can be identified using a number of techniques known in the art. For example, potential agents that modulate the levels of expression of a protein can be identified in cell-based assays in which the level of the protein (either an endogenous protein or a recombinant or reporter protein) is assessed upon exposure of the cell to a potential test agent. Thus, for example, if the protein of interest is endogenously or recombinantly expressed in a cell using transcription regulatory sequences (e.g., promoters, enhancers) from the gene that encodes the protein, it is possible to identify test agents that modulate expression of the gene by evaluating protein levels of the cell. Alternatively, the transcription regulatory sequences of the gene can be operably linked to DNA encoding a readily measurable reporter protein and the levels of reporter protein measured as an indication of the effect of a potential test agent on expression levels of the protein of interest. Methods of measuring protein levels are well known in the art, including, for example, quantitative electrophoretic analyses and immunoassays, e.g., ELISA and other assays (such as activity/property assays, e.g., reporter protein activity, fluorescence, bioluminescence). The levels of the mRNA transcript of a protein of interest can also be determined upon exposure of a cell to a potential test agent to identify agents that modulate expression of the protein. Methods of evaluating mRNA levels as an indication of levels of gene and/or protein expression are also well known in the art, including, for example, northern blotting and RT-PCR.

In a particular embodiment of these methods of screening for or identifying an agent that modulates intracellular calcium, a test agent can be one that modulates the level or expression of a STIM or STIM-like protein or portion(s) thereof. Such agents can be identified in a number of ways. For example, the effect of a potential test agent on the level of STIM mRNA or protein in a cell expressing a STIM protein (e.g., endogenously or recombinantly) can be assessed to identify an agent associated with changes in protein or mRNA levels relative to a cell that has not been exposed to the potential test agent. Reagents (e.g., STIM mRNA-specific nucleic acid probes and primers and STIM-specific antibodies) and techniques are described herein and/or known in the art for detecting STIM mRNA and protein. Alternatively, a reporter molecule-based assay can be used to identify agents that modulate expression of the gene and protein. A STIM gene promoter sequence can be operably linked to a reporter molecule (e.g., nucleic acid encoding luciferase, a fluorescent protein, an enzyme that catalyzes a reaction that yields a readily detectable product) and expressed in a host cell which is contacted with or exposed to potential test agents to monitor or assess the effect of agents on reporter molecule levels. In one example, a STIM gene promoter sequence can be cloned upstream of DNA encoding luciferase in the vector pGL3-Basic (Promega, Madison, Wis.) (see, e.g., vector pGL3-STIM1.B described by Sabbioni et al. (1999) *Cytogenet. Cell Genet.* 86:214-218). STIM gene promoter sequences include the human STIM1 (GOK) gene promoter sequence (see, e.g., GenBank accession no. AF139917 and Sabbioni et al. (1999) *Cytogenet. Cell Genet.* 86:214-218).

ii. Monitoring or Assessing the Effects of Test Agent on Intracellular Calcium

In this embodiment of the methods of screening for or identifying an agent that modulates intracellular calcium, the effects of a test agent (which is one that binds to, interacts with and/or modulates interactions, activities, levels or any physical, structural or other property of a protein involved in modulating intracellular) on intracellular calcium are monitored or assessed. A test agent is identified as an agent that modulates intracellular calcium if it has an effect on intracellular calcium. In particular embodiments, the effect of test agent on store-operated calcium entry, calcium levels in or movement of calcium into, within or out of an intracellular organelle or calcium store (e.g., endoplasmic reticulum) cytosolic calcium buffering and/or resting cytosolic calcium levels is monitored or assessed.

Generally, in monitoring or assessing the effect of a test agent on intracellular calcium in any of the screening/identification methods provided herein, including this particular embodiment, some direct or indirect evaluation or measurement of cellular (including cytosolic and intracellular organelle or compartment) calcium and/or movement of ions into, within or out of a cell, organelle, or portions thereof (e.g., a membrane) is conducted. A variety of methods are described herein (see detailed descriptions provided below and elsewhere herein) and/or known in the art for evaluating calcium levels and ion movements or flux, and for monitoring calcium entry-mediated events. The particular method used and the conditions employed can depend on whether a particular aspect of intracellular calcium is being monitored. For example, as described herein, reagents and conditions are known, and can be used, for specifically evaluating store-operated calcium entry, calcium levels or movement of calcium into, out of or within an intracellular organelle or calcium store, calcium buffering and resting cytosolic calcium levels. The effect of test agent on intracellular calcium can be monitored or assessed using, for example, a cell, an intracellular organelle or storage compartment, a membrane (including, e.g., a detached membrane patch or a lipid bilayer) or a cell-free (e.g. outside-out membrane vesicle) assay system. Generally, some aspect of intracellular calcium is monitored or assessed in the presence of test agent and compared to a control, including intracellular calcium in the absence of test agent.

In a particular embodiment of these methods, the effect of test agent on intracellular calcium is monitored or assessed using a cell. The cell can be one that contains the particular protein involved in intracellular calcium modulation that the test agent binds to, interacts with, and/or modulates (e.g., the interactions, activities, levels or any physical, structural or other property of the protein). Alternatively, the cell can be one that does not contain the particular protein involved in intracellular calcium modulation. If the test agent is a cellular protein, for example a cellular protein that binds to a protein involved in modulating intracellular calcium, then the effect of the test agent on intracellular calcium can also be assessed by altering the expression or level of the cellular protein in a cell that expresses the protein and monitoring or assessing the effect of the alteration on intracellular calcium. Methods for altering protein expression and/or levels in a cell are described herein and/or known in the art.

In one embodiment of these methods, the cell used in the method is a cell that exhibits store-operated calcium entry, and the effect of the test agent on store-operated calcium entry is monitored or assessed.

d. Methods Based on Assessing the Interaction of a Test Agent with, or the Effect of a Test Agent on, a Protein Involved in Modulating Intracellular Calcium In one embodiment of the methods for screening for or identifying an agent that modulates intracellular calcium provided herein, the test agent is one that modulates intracellular calcium. In particular embodiments, the test agent is one that modulates store-operated calcium entry, calcium levels in or movement of calcium into, within or out of an intracellular organelle (or calcium store, e.g. endoplasmic reticulum), cytosolic calcium buffering and/or resting cytosolic calcium levels. This embodiment of the methods includes a step of assessing the interaction of the test agent with, or the effect of the test agent on, a protein involved in modulating intracellular calcium. A test agent is identified as one involved in modulating intracellular calcium if it interacts with and/or otherwise affects a protein involved in modulating intracellular calcium. Thus, this embodiment of the screening/identifying methods can be used to identify intracellular calcium-modulating agents that modulate calcium through a process that involves and that may be specific for an interaction or effect on a particular protein or proteins. Test agents suitable for use in this embodiment of the screening/identification methods can be agents already known to modulate intracellular calcium or can be identified as such in a number of ways using techniques described herein and/or known in the art for evaluating intracellular calcium. Agents that have been reported to modulate intracellular calcium include, for example, stearoylethanolamide (SEA; see, e.g., Maccarrone et al. (2002) *Biochem. J.* 366:137-144) and reported store-operated calcium entry inhibitors (for example, statins in the δ-lactone form (e.g., lovastatin, mevastatin and simvastatin) and other compounds (see, e.g., PCT Patent Application Publication WO02/096416)). The method can optionally include a step of identifying a test agent that modulates intracellular calcium prior to (or concurrently with) the step of assessing the interaction of the test agent with, or the effect of the test agent on, a protein involved in modulating intracellular calcium.

The protein involved in modulating intracellular calcium that is used in assessing a test agent with respect to whether the agent interacts with or affects the protein can be a protein as provided herein and described above (and elsewhere herein). In particular embodiments, the protein is one that is involved in, participates in, and/or provides for store-operated calcium entry, movement of calcium into, out of or within an intracellular organelle or calcium store, modulation of intracellular organelle (or calcium store) calcium level, and/or cytosolic calcium buffering. In particular embodiments, the protein is one of the proteins (or is substantially homologous to one of the proteins) listed in Table 3. The protein can be a STIM or STIM-like protein, including a STIM1, STIM2, DSTIM or CSTIM protein. In one embodiment of the methods, the protein is a STIM1 protein, for example, a mammalian, such as a human, STIM1 protein. In a particular embodiment, the protein is one that is involved in, participates in and/or provides for store-operated calcium entry.

As described above, a protein involved in modulating intracellular calcium that is used in the methods for screening for or identifying an agent that modulates intracellular calcium (or a protein on which the method is based) can be a full-length or complete protein or a portion of a complete protein. Portions of complete proteins include portions that are associated with, exhibit or that are sufficient for producing a particular activity or function of the complete protein, and portions that are associated with a particular property or feature of the complete protein, such as a binding portion or a particular domain, or any random portion of the protein. Similarly, nucleic acids that encode proteins that can be used in the methods (or on which a method is based) can encode a complete protein or portion(s) thereof.

In this embodiment of the methods that involves assessing a test agent for interaction with, or effects on, a protein involved in modulating intracellular calcium, the assessment can be conducted using a complete or full-length protein involved in modulating intracellular calcium or portion(s) thereof. Portions of proteins can be obtained using a variety of methods (e.g., synthetically, through recombinant production methods) described herein and/or known in the art and can be random or selected for a particular feature. Methods for identifying particular features of proteins are described herein and/or known in the art.

The test agent can be evaluated for any effect on a protein involved in modulating intracellular calcium. For example, the test agent can be assessed for binding to a protein, interaction with a protein, or modulation of interactions, activities, levels or any physical, structural or other property of a protein involved in modulating intracellular calcium. Reagents and procedures for assessing protein binding, interactions, activities, levels and other protein properties are described herein (see, e.g., above sections entitled "Binding and interaction assays" and "Level and activity assays") and/or known in the art. For example, methods for assessing binding or interaction of a test agent with a protein involved in modulating intracellular calcium include NMR, mass spectroscopy, fluorescence spectroscopy, scintillation proximity assays, surface plasmon resonance assays and others. Examples of methods for assessing modulation of interactions, activities, levels or any physical, structural or other property of a protein involved in modulating intracellular calcium include, but are not limited to, FRET assays to assess effects on protein interactions, NMR, X-ray crystallography and circular dichroism to assess effects on protein interactions and on physical and structural properties of a protein, and activity assays suitable for assessing a particular activity of a protein.

In a particular embodiment of these methods of screening for or identifying an agent that modulates intracellular calcium, a protein used in the method (or on which the method is based) is a STIM or STIM-like protein (e.g., a STIM1, STIM2, DSTIM or CSTIM) or portion thereof. Any portion of a STIM or STIM-like protein can be used in the methods, including the complete protein, the mature protein (e.g., lacking a signal sequence) and any portion thereof. Particular domains of STIM and STIM-like proteins are described herein and/or can be identified using methods described herein and/or known in the art. Examples of nucleic acids encoding such proteins and portions thereof are also described herein or can be designed based on amino acid sequences such as those described herein. Methods of assessing binding or interaction of an agent with a STIM protein and modulation of STIM protein interactions or activities are described herein. For example, a method for assessing the effect of a test agent on STIM protein homotypic or heterotypic interactions can include evaluating STIM protein immune complex formation and/or levels in lysates of cells that express (e.g., endogenously or recombinantly) STIM proteins (and/or STIM fusion proteins). Thus, for example, a test agent identified as one that modulates intracellular calcium in this embodiment of the methods can be one that disrupts, inhibits, enhances or otherwise alters STIM protein complexes as can be detected in immunoprecipitation assays. Methods for assessing the effect of a test agent on STIM protein activity can include, for example, evaluating the effect of a test agent on STIM protein binding to pre-B cells and differentiated B lymphocytes, STIM augmentation of IL-7-dependent proliferation of pre-B cells, STIM modulation of cell morphology and STIM suppression of tumor growth. Thus, for example, a test agent identified as one that modulates intracellular calcium in this embodiment of the methods can be one that reduces, enhances or otherwise alters these activities of STIM proteins. Examples of particular reagents and procedures that can be used in assessing such activities are described herein. Methods of assessing the effect of a test agent on STIM protein levels or expression can include, for example, evaluating the effect of a test agent on the level of STIM mRNA or protein in a cell expressing a STIM protein (e.g., endogenously or recombinantly) or on the level of reporter molecule or activity in a cell expressing a STIM gene promoter sequence operably linked to a nucleic acid encoding a reporter molecule. Thus, for example, a test agent identified as one that modulates intracellular calcium in this embodiment of the methods can be one that reduces, enhances or otherwise alters expression of STIM protein or mRNA or of a reporter molecule. Examples of particular reagents and procedures that can be used in assessing protein and mRNA expression are described herein.

e. Methods Based on Testing the Effect of any Test Agent on Intracellular Calcium In another embodiment of the methods for screening for or identifying agents that modulate intracellular calcium provided herein, the effect of any test agent on intracellular calcium (and, in particular embodiments, the effect on store-operated calcium entry, calcium levels in (and/or movement of calcium into, out of or within) intracellular organelles or calcium stores (e.g., endoplasmic reticulum), cytosolic calcium buffering and/or resting cytosolic calcium levels) is monitored, assessed or evaluated. In this embodiment of the methods, the test agent can be any agent, and is not necessarily one that (or has been identified as one that) binds to, interacts with and/or modulates (e.g., interactions, activities, levels or any physical, structural or other property) a protein involved in modulating intracellular calcium. Generally, in this embodiment, the method can be performed by contacting any test agent with (1) one or more proteins involved in modulating intracellular calcium (e.g. an ion transport protein, a component of an ion transport protein complex, or a modulatory protein) and/or (2) a cell, or portion thereof, e.g., a membrane, containing one or more proteins involved in modulating intracellular calcium and/or nucleic acid (e.g., a gene or coding sequence such as cDNA or RNA), or portion(s) thereof, encoding such proteins. The one or more proteins involved in modulating intracellular calcium that are used in these methods can be proteins as provided herein and described above (and elsewhere herein). In particular embodiments, the one or more proteins is (are) one that is involved in, participates in, and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering. In particular embodiments, the protein(s) is (or is substantially homologous to) one of the proteins listed in Table 3. The protein can be, for example, a STIM or STIM-like protein (including a STIM1, STIM2, DSTIM and CSTIM protein). In one embodiment, the protein is a STIM1 protein, for example, a mammalian, such as human or rodent, STIM1 protein. In a particular embodiment of the methods, the effect of test agent on store-operated calcium entry is monitored or assessed.

As described above, a protein involved in modulating intracellular calcium that is used in the methods for screening for or identifying an agent that modulates intracellular calcium (or a protein on which the method is based) can be a full-length or complete protein or a portion of a complete protein. Portions of complete proteins include portions that are associated with, exhibit or that are sufficient for producing a particular activity or function of the complete protein. The activity or function of the complete protein is one that is involved in modulating intracellular calcium. Similarly, nucleic acids that encode proteins that can be used in the methods (or on which a method is based) can encode a complete protein or portion(s) thereof.

The monitoring, evaluation or assessment of intracellular calcium in these embodiments of the methods can be conducted in a variety of ways which can be used for all embodiments of the screening/identification methods as described herein. The monitoring or assessing typically involves some direct or indirect evaluation or measurement of cellular (including cytosolic and intracellular organelle or compartment) calcium and/or movement of ions into, within or out of a cell, organelle, or portions thereof (e.g., a membrane). A variety of methods are described herein (see detailed descriptions provided below and elsewhere herein) and/or known in the art for evaluating calcium levels and ion movements or flux. The particular method used and the conditions employed can depend on whether a particular aspect of intracellular calcium is being monitored or assessed. For example, as described herein, reagents and conditions are known, and can be used, for specifically evaluating store-operated calcium entry, calcium levels or movement of calcium into, out of or within an intracellular organelle or calcium store, calcium buffering and resting cytosolic calcium levels. The effect of test agent on intracellular calcium can be monitored or assessed using, for example, a cell, an intracellular organelle or storage compartment, a membrane (including, e.g., a detached membrane patch or a lipid bilayer) or a cell-free (e.g., outside-out membrane vesicle) assay system. Generally, some aspect of intracellular calcium is monitored or assessed in the presence of test agent and compared to a control, e.g., intracellular calcium in the absence of test agent.

Generally, a test agent is identified as an agent, or candidate agent, that modulates intracellular calcium if there is a detectable effect of the agent on intracellular calcium levels and/or ion movement or flux, such as a detectable difference in levels or flux in the presence of the test agent. A test agent can also be identified as an agent, or candidate agent, that modulates intracellular calcium if there is a detectable effect of the agent on a calcium-entry mediated event. Effects of a test agent on a calcium entry-mediated event can be detected using assays known in the art, including assays such as provided and described herein. In particular embodiments, a test agent is identified as one that produces at least a 50% difference in any aspect or parameter of intracellular calcium (e.g., store-operated calcium entry, calcium buffering, calcium levels of or movement into, out of or within an intracellular organelle or calcium store) relative to control (e.g., absence of compound, i.e., vehicle only). In particular embodiments, the effect or differences can be substantial or statistically significant.

2. Methods of Identifying Molecules Involved in Modulating Intracellular Calcium Proteins (and/or nucleic acids encoding proteins) involved in modulating intracellular calcium, as described herein, further provide the basis for additional methods of identifying molecules involved in modulating intracellular calcium, as well as for methods of elucidating pathways, and elements thereof, of intracellular calcium modulation. Once a protein has been identified as one involved in modulating intracellular calcium, it can be used to identify molecules, in particular cellular components, that interact with or bind to it and potentially function in the modulation of intracellular calcium. Cellular components that can be modulators of intracellular calcium include, but are not limited to, molecules such as proteins (e.g., enzymes, receptors, modulatory proteins, ion transport proteins), nucleic acids, lipids and soluble second messengers (e.g., $IP_3$, cADPR, cGMP and cAMP). Additionally, the identification of molecules that interact with proteins involved in intracellular calcium modulation, facilitates the dissection and elucidation of pathways and mechanisms of cellular calcium regulation and signaling. The elucidation of such pathways provides additional targets that can be modulated in methods of modulating intracellular calcium and for use in methods of identifying agents for modulating intracellular calcium. Because the dissection of such pathways also elucidates components of the pathway and interactions between the components, it further makes possible the refinement of methods of modulating intracellular calcium by the balanced targeting of modulation of one or more components and/or interactions of the pathway.

Particular proteins (and/or nucleic acids encoding proteins) involved in modulating intracellular calcium (and, in particular, proteins that are involved in, participate in and/or provide for store-operated calcium entry, movement of calcium into, out of or within an intracellular calcium store or organelle, modulation of calcium levels in intracellular calcium stores or organelles, and/or cytosolic calcium buffering) are provided herein. These proteins can thus be used in methods of identifying molecules, and, in particular, cellular components, that interact with or bind to the proteins and that may be involved in modulating intracellular calcium.

Provided herein are methods of identifying a molecule or candidate molecule involved in modulating intracellular calcium (and, in particular, a molecule that is involved in, participates in and/or provides for store-operated calcium entry, movement of calcium into, out of or within an intracellular calcium store or organelle, modulation of calcium levels in intracellular calcium stores or organelles, and/or cytosolic calcium buffering). The methods are useful in identifying new molecules, e.g., proteins and/or nucleic acids encoding new proteins, that were previously unknown, and for identifying known molecules (e.g., proteins) as being involved in intracellular calcium modulation. The methods include a step of assessing the effect on intracellular calcium of a candidate or test molecule (e.g., a cellular component, such as a protein) that interacts with a protein involved in modulating intracellular calcium, or portion thereof. Assessing the effect on intracellular calcium can involve assessing the effect that modulation of the molecule and/or its interaction with the protein has on intracellular calcium. The methods can optionally include a step of identifying a candidate or test molecule, such as, for example, a cellular component, that interacts with a protein involved in intracellular calcium modulation, or portion thereof.

Generally, in assessing the effect of a candidate or test molecule on intracellular calcium, some direct or indirect evaluation or measurement of cellular (including cytosolic and intracellular organelle or calcium store) calcium and/or movement of ions into, within or out of a cell, calcium store, organelle, or portions thereof (e.g., a membrane) is conducted. A variety of methods are described herein (see detailed descriptions provided above and elsewhere herein) and/or known in the art for evaluating calcium levels and ion movements or flux. The particular method used and the conditions employed can depend on whether a particular aspect of intracellular calcium is being monitored or assessed. For example, as described herein, reagents and conditions are known, and can be used, for specifically evaluating store-operated calcium entry, calcium levels or movement of calcium into, out of or within an intracellular organelle or calcium store, calcium buffering and resting cytosolic calcium levels. The effect of a candidate or test molecule on intracellular calcium can be monitored using, for example, a cell, an intracellular organelle, calcium store or storage compartment, a membrane (including, e.g., a detached membrane patch or a lipid bilayer) or a cell-free (e.g., outside-out membrane vesicle) assay system.

Generally, in determining whether a test or candidate molecule has an effect on intracellular calcium, some aspect of intracellular calcium can be compared under differing conditions of the test molecule. Thus, for example, an interaction of, an activity of and/or the level or size of the test molecule can be altered or modulated and intracellular calcium can be compared under the different conditions (i.e., unaltered (control) vs. altered interaction, activity, level or size of the test molecule). In a particular embodiment of these methods, the effect of a test or candidate molecule on intracellular calcium is assessed using a cell, or portion thereof. The cell, or portion thereof, can be one that contains the test molecule, or portion thereof, and may or may not contain the particular protein involved in intracellular calcium modulation with which the test molecule binds to or interacts. Thus, for example, one embodiment of the methods includes comparing intracellular calcium of a control cell (or portion thereof) containing the test molecule (or portion thereof) and intracellular calcium of a test cell (or portion thereof) that differs from the control cell by an alteration of an interaction, activity, size and/or level of the test molecule relative to the control cell. In one embodiment, the interaction between a test molecule (or portion thereof) and the protein with which it interacts (or portion thereof) is altered in the test cell (or portion thereof) relative to a control cell (or portion thereof).

a. Proteins Involved in Intracellular Calcium Modulation

Methods of identifying a molecule involved in modulating intracellular calcium provided herein involve assessing the effect of a candidate molecule that interacts with a protein involved in modulating intracellular calcium (or portion thereof) on intracellular calcium. The protein can be a protein involved in modulating intracellular calcium as provided herein and described above (and elsewhere herein). Thus, for example, the protein can be one that is homologous to an amino acid sequence of the protein encoded by the coding sequence of *Drosophila* gene CG9126 and/or to a mammalian stromal interacting molecule (STIM) protein, e.g., human or rodent (such as rat) STIM1. In particular embodiments, the protein is one that is involved in, participates in and/or provides for store-operated calcium entry, movement of calcium into, out of or within an intracellular calcium store or organelle, modulation of calcium levels in intracellular calcium stores or organelles, and/or cytosolic calcium buffering. In particular embodiments, the protein is one of the proteins (or is substantially homologous to one of the proteins) listed in Table 3. The protein can be, for example, a STIM or STIM4-like protein, including a STIM1, STIM2, DSTIM or CSTIM protein. In one embodiment of the methods, the protein is a STIM1 protein, for example, a mammalian STIM1 protein.

The protein involved in modulating intracellular calcium with which a candidate or test molecule interacts or binds can be a complete protein (e.g., the entire amino acid sequence encoded by a gene or mRNA transcript which can include a signal sequence), a mature, processed protein (e.g., lacking signal sequence) or any fragment or portion of a complete or mature protein that is made up of less than all of the amino acid sequence of a complete or mature protein can be used. Portions of complete proteins include portions that are associated with, exhibit or that are sufficient for producing a particular activity or function of the complete protein, and portions that are associated with a particular property or feature (e.g., structural feature) of the complete protein, such as a binding portion or a particular domain. Domains thus include, for example, beta sheets, alpha helices, loops, folds, hydrophobic domains, amphipathic domains, extracellular, cytoplasmic, intralumenal and transmembrane domains, an epitope, a ligand- or effector-binding site, a modification site (e.g., a site of phosphorylation, acylation, or glycosylation), and an enzyme active site. There are numerous methods known in the art for identifying domains within a protein. For example, transmembrane domains can be identified through analysis of hydropathy plots of the hydrophobicity of adjacent amino acid residues (commonly used to assess proteins for transmembrane domains; see, e.g., Kyte and Doolittle (1982) *J. Mol. Biol.* 157:105-134; Argos et al. (1982) *Eur. J. Biochem.* 128:565-575 and Engelman et al. (1984) *Ann. Rev. Biophys. Biophys. Chem.* 15:321-353) and through the use of programs such as TMpred (see, e.g., www.ch.embnet.org/software/TMpred_form.html which can be accessed via the ExPASy Molecular Biology Server (www.expasy.ch)). The TMpred program predicts membrane-spanning regions and their orientation through use of an algorithm generated by statistical analysis of naturally occurring transmembrane proteins (i.e., proteins contained in the TMbase database; see Hofman and Stoffel (1993) *Biol. Chem. Hoppe-Seyler* 374: 166). Domains can also be identified by homology to proteins known to contain particular structural or functional domains, for example, by using the search and alignment resources of conserved domain databases, such as the Pfam database (pfam.wustl.edu/; Bateman et al. (2002) *Nuc. Acids Res.* 30:276-280), the Simple Module Architecture Research Tool (SMART; accessible through smart.embl-heidelberg.de; see also Letunic et al. (2002) *Nuc. Acids Res.* 30:242-244) and the Clusters of Orthologous Groups (COG) database (a phylogenetic classification of proteins from complete genomes accessible through www.ncbi.nlm.nih.gov/cog; see also Tatusov et al. (2001) *Nuc. Acids Res.* 29:22-28) which groups proteins into clusters (or COGs) of very similar proteins with an ancient conserved domain found in at least three species. These databases of conserved domains assign identifying numbers (which begin with database identifiers such as "Pfam," "smart" and "COG") to particular domains that have been characterized in proteins.

Particular portions of a STIM protein with which a candidate or test molecule can interact or bind include, but are not limited to, the following domains: N-terminal (putative extracellular), transmembrane, C-terminal (putative cytoplasmic), signal peptide, N-terminal closely spaced cysteine residues, EF hand, sterile α-motif (SAM) and coiled-coil domains. Particular portions of STIM1 and STIM2 proteins that may distinguish them from DSTIM proteins include a consensus sequence (YYNI) for phosphorylation-dependent binding of Src homology type 2 (SH2) domains, proline/serine-rich (STIM1) or proline/histidine-rich (STIM2) domains, potential SH3 domain binding motifs (PXXP) and a lysine-rich domain. In contrast, DSTIM contains a myosin tail domain not present in STIM1 or STIM2 as well as an N-terminal domain that has no equivalent in STIM1 or STIM2. Particular portions of a STIM1 protein that may distinguish it from a DSTIM or STIM2 protein include an N-linked glycosylation site within the SAM domain, a dibasic proteolytic cleavage site, ATP synthase B/B☐ domain (pfam00430), ezrin/radixin/moesin (ERM; pfam00769) domain and a diacylglycerol kinase accessory (DAGKa; smart00045) domain. A particular portion of a STIM2 protein that may distinguish it from a DSTIM or STIM1 protein is an SMC domain (COG1196). Table 4 provides examples of STIM protein domains with reference to particular *Drosophila* DSTIM, human and rat STIM1, and human STIM2 proteins.

TABLE 4

STIM Protein Domains

| DOMAIN | HUMAN STIM1 (SEQ ID NOS: 4, 83, 84) Approximate Amino Acid Positions | Reference STIM1 (SEQ ID NO: 52) Approximate Amino Acid Positions | HUMAN STIM2 (SEQ ID NOS: 6, 87, 88) Approximate Amino Acid Positions | DSTIM (SEQ ID NOS: 2, 76, 78, 80, 81) Approximate Amino Acid Positions |
|---|---|---|---|---|
| N-Terminal | 1-212 | 1-213 | 1-217 | 1-294 |
| N-Terminal (without signal peptide) | 23-212 | 23-213 | 15-217 | 24-294 |
| Transmembrane | 213-234 | 214-234 | 218-235 | 295-312 |
| C-Terminal | 235-685 | 235-685 | 236-746 | 313-570 |
| Signal Peptide | 1-22 | 1-22 | 1-14 | 1-23 |
| N-Terminal Subdomain | | | | 27-125 |
| Closely Spaced Cysteine Residues | 49-56 | 49-56 | 53-60 | 126-133 |
| EF Hand | 76-87 | 76-87 | 80-91 | 155-166 |
| Sterile α-motif (SAM) | 136-204 | 213-281 | 129-196 | 132-200 |

TABLE 4-continued

STIM Protein Domains

| DOMAIN | HUMAN STIM1 (SEQ ID NOS: 4, 83, 84) Approximate Amino Acid Positions | Reference STIM1 (SEQ ID NO: 52) Approximate Amino Acid Positions | HUMAN STIM2 (SEQ ID NOS: 6, 87, 88) Approximate Amino Acid Positions | DSTIM (SEQ ID NOS: 2, 76, 78, 80, 81) Approximate Amino Acid Positions |
|---|---|---|---|---|
| Dibasic Proteolytic Cleavage Site | 207-209 | 207-209 | | |
| Coiled-Coil | 238-343 and 362-390 | 238-343 and 362-390 | 242-344 and 358-394 | 310-407 and 420-462 |
| Coiled-Coil and ERM | 238-424 | 238-424 | | |
| Consensus Sequence for SH2 Domain Binding | 361-364 | 361-364 | 365-368 | |
| Proline/Serine-or Proline/Histidine-Rich | 600-629 | 600-629 | 533-559 | |
| SH3 Domain-Binding Region | 573-629 | 573-629 | 521-559 | |
| Lysine-Rich | 672-685 | 672-685 | 730-746 | |
| Proline/Serine- and Lysine-Rich | 591-685 | 591-685 | | |
| Myosin Tail Domain | | | | 324-491 |
| ATP synthase B/B☐ domain (pfam00430) | 249-337 | 249-337 | | |
| ERM (pfam00769) | 253-424 | 253-424 | | |
| DAGKa (smart00045) | 422-484 | 422-484 | | |
| SMC domain (COG1196) | | | 238-340 | |

A portion or fragment of a protein can be obtained using a number of processes known in the art. For example, a portion of a protein can be obtained by synthetic methods, by degradation of a complete protein and by recombinant expression of a nucleic acid encoding the amino acid sequence of the portion.

A candidate or test molecule, such as a cellular component, that interacts with or binds to a protein involved in modulating intracellular calcium, or portion thereof, can be one that is known to interact with or bind to such a protein (or portion thereof) or can be one that is identified (but not previously known) as one that interacts with or binds to such a protein (or portion thereof).

b. Identifying Candidate or Test Molecules

Candidate or test molecules (such as cellular components, e.g., a protein) suitable for use in the methods for identifying a molecule involved in modulating intracellular calcium can be identified in a number of ways using techniques described herein and/or known in the art for detecting an interaction or binding between a protein and a molecule. The interaction can be any direct or indirect physical, biochemical, chemical or other interaction between a molecule and a protein (or portion thereof) involved in intracellular calcium modulation, such as those described herein. Interactions between a molecule and a protein (or portion thereof) involved in modulating intracellular calcium include, for example, covalent, non-covalent, ionic, electrostatic, hydrophobic, hydrogen bonding, disulfide bonding and other interactions.

Several methods for identifying a molecule that interacts with a protein are described herein with respect to the methods of screening for or identifying agents that modulate intracellular calcium. For example, binding assays can be used to identify an interaction between a molecule and a protein involved in intracellular calcium modulation, or portion thereof. A number of in vitro and cell-based binding assays are known in the art and can be modified as needed by one of skill in the art to identify molecules that bind to or interact with a protein (or portion thereof) involved in modulating intracellular calcium. In one such assay, the protein (or portion thereof) involved in intracellular calcium modulation is contacted with cellular components (within the context of a cell or in isolation), cell medium, a cell and/or a cell extract and assayed for binding of a molecule to the protein (or portion thereof) involved in modulating intracellular calcium. Binding can be evaluated and detected using any of several methods known in the art for detecting binding of molecules to proteins, including, but not limited to, affinity chromatography (including Biacore and Ciphergen technologies), immunoprecipitation, ELISA assays, far-western blotting and other methods. Immunoassays to detect binding of molecules to a protein involved in intracellular calcium modulation can utilize antibodies (e.g., monoclonal and polyclonal) prepared against the protein or portions thereof. Methods of generating and testing antibodies against proteins are well known in the art. Interactions between a protein (or portion thereof) involved in intracellular calcium modulation and a candidate molecule involved in modulating intracellular calcium can also be identified using assays such as co-purification assays (e.g., GST pull-down assays, co-immunoprecipitation assay, chromatographic assays), phage display, ribozyme display, and protein arrays. Detection of in vitro binding or interaction between a candidate molecule and a protein involved in modulating intracellular calcium can involve a variety of approaches, such as, for example, nuclear magnetic resonance (NMR), mass spectroscopy, fluorescence spectroscopy, scintillation proximity assays (SPQ), surface plasmon resonance assays (available commercially from BIACORE; www.biacore.se/proteomics/), and others. Cell-based binding assays include, for example, yeast two-hybrid assays (see, e.g., U.S. Pat. Nos. 5,283,173, 5,468,614 and 5,667,973 and PCT Application Publication Nos. WO01/25420 and WO02/079493); bacterial two-hybrid assays (Juong (2001) *J. Cell Biochem. Suppl.* 37:53-57), and others. Such assays are particularly suitable for identifying polypeptides that interact with a protein involved in modulating intracellular calcium. Another cell-based assay for identification of molecules that interact with a protein, such as a protein involved in modulating intracellular calcium, is the tandem affinity purification (TAP) method (see, e.g., Rigaut et al. (1999) *Nature Biotech.* 17:1030-1032; Puig et al. (2001) *Methods* 24:218-229).

Methods are also known in the art for identifying interaction of a protein (or portion thereof) with a lipid. For example, centrifugation and FRET (fluorescence resonance energy transfer) assays can be used to assess protein binding to phospholipid vesicles (see, e.g., Ou-Yang et al. (Jan. 21, 2003) *J. Biol. Chem.* Manuscript M212606200; Bazzi and Nelsestuen (1991) *Biochemistry* 29:7624-7630; Rietveld et al. (1986) *J. Biol. Chem.* 261:3846-3856). Immunoassays (such as ELISA assays) can also be used to assess binding of a protein to phospholipid (see, e.g., Ghosh et al. (1996) *J. Biol. Chem.* 271:8472-8480) or other cellular components.

A molecule that has bound to or otherwise interacted with the protein (or portion thereof) involved in intracellular calcium modulation can be characterized and identified using methods that are also well known in the art, including, for example, HPLC, FPLC, amino acid sequencing if the molecule is a protein, and cloning of nucleic acid encoding a molecule that is a protein.

c. Assessment of the Effects of a Candidate or Test Molecule on Intracellular Calcium A molecule that interacts or binds with a protein (or portion thereof) involved in modulating intracellular calcium is evaluated to assess its effects on intracellular calcium. A candidate or test molecule (e.g., a cellular component such as a protein) is identified as one that modulates intracellular calcium if it has an effect on intracellular calcium. In particular embodiments, the effect of a candidate or test molecule on store-operated calcium entry, calcium level in or movement of calcium into, out of or within an intracellular calcium store or organelle, cytosolic calcium buffering and/or basal cytosolic calcium levels is monitored or assessed.

There are a number of ways in which the effect of a candidate or test molecule on intracellular calcium can be assessed. For example, a cell, or portion thereof (e.g., a membrane, intracellular organelle or intracellular calcium store) comprising the interacting molecule and the protein involved in modulating intracellular calcium can be used for such evaluations. The interaction between the molecule and the protein involved in intracellular calcium modulation can be altered or disrupted or inhibited in the cell, or portion thereof, and then intracellular calcium can be monitored to determine if intracellular calcium is effected by the alteration in the interaction. Intracellular calcium can be assessed using any methods known in the art and/or described herein.

In another process for assessing the effect of a candidate or test molecule on intracellular calcium, the amount and/or activity of the molecule in a cell, or portion thereof, can be altered, for example, increased, decreased or the molecule can be eliminated in the cell, or portion thereof, and the effects of such an alteration or elimination on intracellular calcium can be assessed. For example, the synthesis and/or degradation of the molecule can be altered (e.g., increased, reduced or inhibited) in the cell or portion thereof. One method for altering the amount of the molecule in the cell, if the molecule is a protein or nucleic acid produced by the cell, is to alter the expression of the protein or nucleic acid in the cell. This can be accomplished using a variety of methods, including methods described herein and/or known in the art, such as for example, RNA interference, antisense RNA methods, gene knock-out procedures and gene insertion/over-expression processes. Many such methods can require knowledge of at least a portion of the nucleotide sequence of the molecule (if the molecule is a nucleic acid) or of the gene or transcript or coding sequence encoding the molecule (e.g., if the molecule is a protein). If the nucleic acid or protein is one that is found in a cell of an organism for which much of the genome sequence is available, then at least a portion of the nucleotide sequence may be publicly available for use in altering the expression of the gene. If the nucleotide sequence of a gene (or portion of a gene) encoding a candidate or test molecule is not known, then cloning methods well known in the art can be used to obtain at least a portion of the nucleotide sequence. It is also possible to assess the effect on intracellular calcium of a candidate or test molecule of one species by altering expression of a homologous gene (e.g., an ortholog) of a different organism (e.g., an organism for which genomic sequence is readily available) and assessing the effects of the alteration on intracellular calcium of a cell of the different organism.

i. Reduction, Alteration or Elimination of the Expression of a Gene in a Cell

One process for assessing the effect of a candidate or test molecule on intracellular calcium involves reduction, alteration or elimination of the expression of a gene encoding the candidate molecule in a cell and the assessment of intracellular calcium (e.g., intracellular/cytosolic calcium levels and/or calcium movement into, within or out of the cell) to determine the effects of reduction, alteration or elimination of gene expression on intracellular calcium (and, in particular, on store-operated calcium entry, calcium levels in or movement of calcium into, out of or within an intracellular calcium store or organelle, and/or cytosolic calcium buffering). A molecule (such as a protein) that is involved in modulating intracellular calcium (and nucleic acid encoding such a protein) can be identified by a cell in which reduction, alteration or elimination of the expression of a gene encoding the molecule is accompanied by an alteration in intracellular calcium (e.g., intracellular calcium levels and/or calcium ion movement into, out of or within a cell). Following and/or simultaneously with the alteration of gene expression in a cell, the cell (or portion thereof) is analyzed to evaluate the effect, if any, on intracellular calcium.

These methods for assessing the effect of a candidate or test molecule, such as a protein (and/or nucleic acid encoding a protein), on intracellular calcium are function-based and specific; that is, they provide a direct, one-to-one correlation between a molecule that can be expressed in its native cellular environment and cell calcium. The correlation is determined by the association of altered expression of a gene with alterations in intracellular calcium. In particular embodiments, a molecule involved in modulating intracellular calcium is identified by a gene that, when expressed in an altered fashion (including a reduction or elimination of expression), results in altered cytosolic calcium buffering, altered basal cytosolic calcium levels, altered calcium levels in an intracellular calcium store and/or altered, reduced or eliminated store-operated calcium entry ion or movement of calcium into, out of or within an intracellular calcium store. The molecule, such as a protein, encoded by the gene is thereby identified as a molecule that is involved in, participates in and/or provides for modulation of calcium levels in or movement of calcium into, out of or within an intracellular calcium store or organelle, cytosolic calcium buffering and/or store-operated calcium entry.

Techniques for altering gene expression in a cell are known in the art and described herein. Any such procedures may be used in the methods of identifying a molecule involved in modulating intracellular calcium provided herein. With respect to these methods, the alteration in gene expression need only be such that any associated alteration in intracellular calcium (e.g., intracellular calcium levels and/or calcium movement into, out of or within a cell) is detectable. An alteration in gene expression may be complete or nearly complete elimination of expression of a gene, a reduction in the expression of a gene, an increase in the expression of a gene (overexpression), or an alteration in the protein encoded by the gene (such as a truncation or other alteration that effectively renders the protein nonfunctional or provides for aberrant functioning of the protein), e.g., relative to the expression of the gene in a cell that has not been altered in its expression of the gene. Methods for assessing the type and extent of an alteration in gene expression are known in the art. For example, the level and characteristics (e.g., size) of a transcript (e.g., mRNA) generated from a gene can be evaluated by Northern blot analysis employing nucleic acid probes that specifically hybridize to the transcript or by reverse transcriptase PCR (RT-PCR) nucleic acid amplification. The level and characteristics (e.g., size and immunoreactivity) of a protein encoded by a gene can be evaluated by western blot or other immunoassays employing antibodies that specifically bind the protein.

For example, a complete or nearly complete elimination of expression of a gene encoding a molecule that is principally involved in providing for store-operated calcium entry in the cell may identify the molecule as such by a complete or nearly complete elimination of store-operated calcium entry in a cell. If the molecule substantially participates in but is not principally involved in providing for store-operated calcium entry, then elimination of the expression of the gene encoding the molecule may result in an alteration and/or reduction, but perhaps not elimination, of store-operated calcium entry in the cell. For example, if the molecule is an ion transport protein that is involved in store-operated calcium entry by being a component, such as a subunit, of a multi-subunit complex (e.g., heteromeric complex) providing for store-operated calcium entry, then complete or near complete elimination of expression of the gene encoding the molecule may result in altered store-operated ion current properties, e.g., ion selectivity and/or conductance, reduced, or even increased store-operated entry into the cell. In another example, if expression of a gene is reduced, but not eliminated, and the gene encodes a molecule (e.g., a protein) that is principally involved in providing for store-operated calcium influx in the cell, then the molecule may be identified as such by a partial reduction of store-operated calcium entry in the cell. If the gene encodes a molecule that substantially participates in but is not principally involved in providing for store-operated calcium entry, then partial elimination of expression of the gene may identify the molecule as such by an alteration and/or reduction of store-operated calcium entry in the cell.

If the molecule is involved in modulation of intracellular calcium store calcium levels or maintenance of resting cytosolic calcium levels, then it may be identified as such, for example, by an alteration in calcium levels (intracellular calcium store or resting cytosolic calcium levels) in a cell in which expression of the gene encoding the molecule has been altered or eliminated. An alteration of these calcium levels can be, for example, a reduction, depletion, elimination of, or increase in calcium levels, e.g., relative to the levels in a control cell (e.g., one that has not been altered with respect to expression of the gene encoding the molecule).

If the molecule is involved in modulation of cytosolic calcium buffering, then it may be identified as such, for example, by an alteration in cytosolic calcium buffering in a cell in which expression of the gene encoding the molecule has been altered or eliminated. An alteration in cytosolic calcium buffering can be, for example, a complete or nearly complete elimination of the activity, a reduction of the activity, an alteration in properties or characteristics of the activity (e.g., rates, kinetics or timing) or an increase in the activity, e.g., relative to the activity in a control cell (e.g., a cell that has not been altered with respect to expression of the gene encoding the molecule). Thus, for example, an alteration in calcium buffering can be a reduction or increase in the rate at which cytosolic calcium levels return to basal levels after activation of calcium influx into the cytoplasm. The alteration can be an overall time course of cytosolic calcium level adjustment that differs from that in a control cell. In another example, an alteration in calcium buffering can be a delay in onset of the adjustment of cytosolic calcium levels to return to basal levels after activation of calcium influx into the cytoplasm. In another example, an alteration in calcium buffering can be an adjustment in cytosolic calcium levels after activation of calcium influx that does not result in a return of calcium levels to a basal level, but instead to a level that is higher or lower than the basal level. In yet a further example, an alteration in calcium buffering can be a complete or near complete absence of an adjustment in cytosolic calcium levels following activation of calcium influx into the cytoplasm.

Although any cell may be used in the methods, cells that are particularly suitable are those that exhibit a number of calcium transport processes and/or those in which calcium levels and/or movement may readily be assessed. Choice of cell for use in the methods may also depend on whether a particular aspect of intracellular calcium (e.g., store-operated calcium entry, calcium levels in or movement of calcium into, out of or within an intracellular calcium store, and/or cytosolic calcium buffering) is being evaluated to assess the effect of altering gene expression. In instances in which a particular aspect of intracellular calcium is assessed, a cell used in the method can be one which is particularly amenable to analysis of that aspect of intracellular calcium or one that exhibits the particular aspect of intracellular calcium modulation. For example, selection of a cell that exhibits store-operated calcium entry is described herein and can be accomplished using procedures known in the art.

Another feature of a cell that is particularly suitable for use in the methods that utilize alteration of gene expression for assessing the effect of a candidate molecule on intracellular calcium is amenability to gene expression alteration. A number of techniques for altering gene expression in cells are known in the art and described herein. The relative ease with which these techniques may be applied to a cell to effect reduction, alteration, increase or elimination of expression of a gene in the cell is a consideration in selection of cells for use in the methods provided herein. Amenability to gene expression alteration and analysis of ion flux particularly may be considerations.

(a) Antisense RNA Methods

Introduction into a cell of RNA complementary to an RNA transcript encoded by a gene within the cell can be used to alter expression of the gene. Such an approach may be referred to as an "antisense" RNA method when a single-stranded RNA molecule is introduced into a cell (see, e.g., Izant and Weintraub (1984) *Cell* 36:1007-1015). RNA can be synthesized from, for example, phagemid clones containing DNA corresponding to a gene to be targeted for alteration of expression, using T3 and T7 polymerase. DNA templates may be removed by DNase treatments. Antisense RNA is then introduced into a cell, and, after an appropriate period, intracellular calcium (e.g., intracellular calcium levels and/or calcium movement into, out of or within the cell) is evaluated and compared to intracellular calcium prior to introduction of antisense RNA or to intracellular calcium in a substantially similar cell that has not received antisense RNA. Antisense RNA may also be expressed in a cell by transfecting the cell with a plasmid containing nucleic acid coding for antisense RNA.

(b) RNA Interference (RNAi) Methods

RNA interference (RNAi) is a method of gene silencing which involves the introduction of double-stranded RNA (dsRNA) into cells. The basic premise of RNAi is the ability of double-stranded RNA (dsRNA) to specifically block expression of its homologous gene when present in cells. Thus, in performing RNAi, a dsRNA construct containing a nucleotide sequence with homology to or identical to a portion of the target gene to be silenced can be introduced into a cell (including introduction from outside of the cell and introduction by generating the dsRNA within a cell) containing the target gene. Generally, in the RNAi reaction, both strands (sense and antisense) of the dsRNA are processed to small RNA fragments or segments of from about 21-23 nucleotides (nt) in length. Processing of the dsRNA to the small RNA fragments does not require the targeted mRNA, which demonstrates that the small RNA species is generated by processing of the dsRNA and not as a product of dsRNA-targeted mRNA degradation. The mRNA is cleaved only within the region of identity with the dsRNA. Cleavage occurs at sites 21-23 nucleotides apart, the same interval observed for the dsRNA itself, suggesting that the 21-23 nucleotide fragments from the dsRNA are guiding mRNA cleavage. The RNAi phenomenon is mediated by a set of enzyme activities that are evolutionarily conserved in eukaryotes ranging from plants to mammals. After partial purification, a multi-component nuclease (RISC nuclease) co-fractionates with the dsRNA fragments which may confer specificity to the nuclease through homology to the substrate mRNAs. It is believed that the dsRNA fragments instruct the RISC nuclease to destroy specific mRNAs corresponding to the dsRNA sequences. An additional enzyme, Dicer, has been identified that can produce the guide RNAs. Dicer is a member of the RNAse III family of nucleases that specifically cleave dsRNA and is evolutionarily conserved in worms, flies, plants, fungi and mammals. The enzyme has a distinctive structure which includes a helicase domain and dual RNAse III motifs. Dicer also contains a region of homology to the RDE1/QDE2/ARGONAUTE family, which have been genetically linked to RNAi in lower eukaryotes. Activation, or overexpression, of Dicer and/or Argonaute is, thus, useful for facilitating RNAi in cells, such as cultured eukaryotic cells, or mammalian cells in culture or in whole organisms.

Mammalian cells exhibit an interferon-mediated antiviral response to long dsRNA that results in diminished protein synthesis. This response makes it difficult to utilize long dsRNA in RNA interference of mammalian cells. Thus, for RNAi of mammalian cells, short interfering dsRNAs of about 21 nucleotides can be used which do not activate the antiviral response (see, e.g., Elbashir et al. (2001) *Nature* 411:494-498). Additionally, cells can be treated with an agent(s) that inhibits the double-stranded RNA-dependent protein known as PKR (protein kinase RNA-activated). Part of the interferon response is the activation of the PKR response. PKR phosphorylates and inactivates eIF2α. Inactivation of eIF2α results in inhibition of protein synthesis and ultimately apoptosis. This sequence-independent PKR response can be overcome in favor of the sequence-specific RNAi response without altering the activity of PKR; however, in certain instances, it may be desirable to treat the cells with agents which inhibit expression of PKR, cause its destruction, and/or inhibit the kinase activity of PKR. Likewise, overexpression of an agent which ectopically activates eIF2α can be used.

The double-stranded structure may be formed by a single self-complementary RNA strand or two complementary RNA strands. The dsRNA construct may include modifications to either the phosphate-sugar backbone or the nucleoside. The backbone may be modified for stability or for other reasons. The phosphodiester linkages may be modified to include at least one of a nitrogen or sulfur heteroatom. RNA duplex formation may be initiated either inside or outside the cell. The RNA may be introduced in an amount which allows delivery of at least one copy per cell. Higher doses (e.g., at least 5, 10, 100, 500, or 1000 copies per cell) of double-stranded material may yield more effective inhibition; lower doses may be useful for specific applications. Inhibition is sequence-specific in that nucleotide sequences corresponding to the duplex region of the RNA are targeted for genetic inhibition.

Double-stranded RNA constructs containing a nucleotide sequence identical to a portion of the target gene are generally most effective in the inhibition of target gene expression. RNA sequences with insertions, deletions, and single point mutations relative to the target sequence have also been found to be effective for inhibition. Sequence identity may be optimized by sequence comparison and alignment algorithms known in the art (see e.g., Gribskov and Devereux, Sequence Analysis Primer, Stickton Press, 1991) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, generally provides for the greatest inhibition; however, it is not required for inhibition. The RNAi method is able to tolerate sequence variations that might be expected due to genetic mutation, strain polymorphism, or evolutionary divergence. Alternatively, the duplex region of the RNA may be defined functionally as a nucleotide sequence that is capable of hybridizing with a portion of the target gene transcript. The length of the identical nucleotide sequences may be, for example, at least 25, 50, 100, 200, 300, or 400 bases.

The dsRNA construct may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the dsRNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The dsRNA construct may be chemically or enzymatically synthesized by manual or automated reactions. The dsRNA construct may be synthesized by a cellular RNA polymerase or a bacteriophage RNA polymerase (e.g., T3, T7, SP6). The use and production of an expression construct are known in the art (see, e.g., WO97/32016; U.S. Pat. Nos. 5,593,874, 5,698,425, 5,712,135, 5,789,214, and 5,804,693). If synthesized chemically or by in vitro enzymatic synthesis, the RNA may be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

RNAi can be used to alter gene expression in a cell derived from or contained in any organism. The organism may be a plant, animal, protozoan, bacterium, virus, or fungus. For example, such organisms include, but are not limited to *Drosophila*, trypanosomes, lanaria, hydra, zebrafish, *Cae-* norhabditis elegans, mice, rats, humans and other mammals. The cell may be from, for example, the germ line or somatic, totipotent or pluripotent, dividing or non-dividing, parenchyma or epithelium, immortalized or transformed, a stem cell or a differentiated cell. The cell may be any individual cell of the early embryo, and may be a blastocyte, or, alternatively, it may be an oocyte (see, e.g., Fire et al. (1998) *Nature* 391:806; Clemens et al. (2000) *Proc. Natl. Acad. Sci. U.S.A.* 97:6499-6503; PCT International Application Publication Nos. WO01/36646, WO99/32619, WO01/68836, WO01/29058 and WO01/75164).

The dsRNA may be directly injected into the cell or may be introduced by bathing the cell in a solution containing RNA. Other methods for introducing dsRNA into a cell include bombardment by particles covered by the RNA, for example gene gun technology in which the dsRNA is immobilized on gold particles and fired directly at the site, and electroporation of cell membranes in the presence of the RNA. Precise conditions for electroporation depend on the device used to produce the electro-shock and the dimensions of the chamber used to hold the cells. This method permits RNAi on a large scale. Any known gene therapy technique can also be used to administer the RNA. A viral construct packaged into a viral particle would accomplish both efficient introduction of an expression construct into the cell and transcription of RNA encoded by the expression construct. In a particular example, a lentivirus-based vector can be used to introduce siRNAs into primary cells (e.g., T lymphocytes) (see, e.g., Qin et al. (2003) *Proc. Natl. Acad. Sci. U.S.A.* 100:183-188). Other methods known in the art for introducing nucleic acids into cells may be used, such as lipid-mediated carrier transport, chemical-mediated transport, such as calcium phosphate, and the like. Thus, the RNA may be introduced along with components that perform one or more of the following activities: enhance RNA uptake by the cell, promote annealing of the duplex strands, stabilize the annealed strands, or otherwise increase inhibition of the target gene. A transgenic animal that expresses RNA from a recombinant construct may be produced by introducing the construct into a zygote, an embryonic stem cell, or another multipotent cell derived from the appropriate animal.

RNAi may also be performed on an organismal level. Mammalian cells can respond to extracellular dsRNA, and RNAi can act systemically; therefore a specific transport mechanism for dsRNA may exist (see, e.g., Asher et al. (1969) *Nature* 223:715-717; WO01/36646; WO01/68836). Consequently, injection of dsRNA into one tissue can inhibit gene function in cells throughout the animal. Thus, dsRNA may be administered extracellularly into a cavity, interstitial space, into the circulation of a mammal, introduced orally, or may be introduced by bathing an organism in a solution containing RNA. Methods for oral introduction include direct mixing of the RNA with food of the organism, as well as engineered approaches in which a species that is used as food is engineered to express the RNA, then fed to the organism to be affected. For example, food bacteria, such as *Lactococcus lactis*, may be transformed to produce the dsRNA (see, e.g., WO97/17117, WO97/14806). Methods of injection include injection into vascular or extravascular circulation, the blood or lymph systems and the cerebrospinal fluid are sites where the RNA may be injected.

*Drosophila* cells are particularly well-suited for RNAi-based alteration of gene expression. Many *Drosophila* cell lines have been established and can be biochemically characterized for use in studying various cellular processes. *Drosophila* cell lines that are known to respond to dsRNAs by ablating expression of the target protein include S2, KC, BG2-C6, and Shi cells. Many signal transduction pathways and other cellular processes have been highly conserved from *Drosophila* to mammals, making it possible to study complex biochemical problems in a genetically tractable model organism. Importantly, results obtained from the cell culture studies can be confirmed in the whole organism, because *Drosophila* is very amenable to RNAi analyses at the organismal level. The use of dsRNA in *Drosophila* cell culture to silence expression of specific genes is technically simple, efficacious, and highly reproducible. The dsRNAs are efficiently internalized by the cells, thereby circumventing the problems generated by variable transfection efficiencies. Also, the gene silencing effect can be sustained through many cell divisions.

Compared to antisense technology, RNAi has been reported to achieve greater than 95% reduction in gene product. This effect can be manifested over a period of 6-7 days, thus allowing for many data points and repetition of the assay over time (Caplen et al. (2000) *Gene* 252:95-105).

(c) Gene Knock Out or Deletion

Direct gene "knock-out" procedures may also be used to alter the expression of a gene in a cell. In these methods, homologous recombination between DNA in a cell and heterologous nucleic acid introduced into the cell results in elimination of a targeted gene from the genome or alteration of the gene such that it does not produce functional protein. Methods of designing nucleic acid constructs for use in targeted gene disruption or deletion are well known in the art (see, e.g., Capecchi (1989) *Science* 244:1288; Capecchi et al. (1990) *Nature* 344:105; Koller et al. (1990) *Science* 248:1227).

(d) Gene Insertion

Transfection methods may be used to introduce a gene, or portion thereof, into a host cell. The nucleic acid(s) transferred into the host cell may encode a wild-type or altered protein or a domain, derivative, fragment or homolog thereof. Transfer of nucleic acid(s) into a host cell can be accomplished by a variety of procedures. Such procedures include, but are not limited to, direct uptake using calcium phosphate ($CaPO_4$; see, e.g., Wigler et al. (1979) *Proc. Natl. Acad. Sci. U.S.A.* 76:1373-1376), polyethylene glycol (PEG)-mediated DNA uptake, electroporation, lipofection (see, e.g., Strauss (1996) *Meth. Mol. Biol.* 54:307-327), microcell fusion (see, e.g., Lambert (1991) *Proc. Natl. Acad. Sci. U.S.A.* 88:5907-5911; U.S. Pat. No. 5,396,767, Sawford et al. (1987) *Somatic Cell Mol. Genet.* 13:279-284; Dhar et al. (1984) *Somatic Cell Mol. Genet.* 10:547-559; and McNeill-Killary et al. (1995) *Meth. Enzymol.* 254:133-152), lipid-mediated carrier systems (see, e.g., Teifel et al. (1995) *Biotechniques* 19:79-80; Albrecht et al. (1996) *Ann. Hematol.* 72:73-79, Holmen et al. (1995) In vitro Cell Dev. Biol. Anim. 31:347-351; Remy et al. (1994) *Bioconjug. Chem.* 5:647-654; Le Bolch et al. (1995) *Tetrahedron Lett.* 3:6681-6684; Loeffler et al. (1993) *Meth. Enzymol.* 217:599-618), liposome-mediated delivery (see, e.g., Philip et al. (1993) *J. Biol. Chem.* 268:16087-16090 and Aksentijevich et al. (1996) *Hum. Gen. Ther.* 7:1111-1122), adenovirus infection (see, e.g., Ragot et al. (1993) *Nature* 361:647-650), retroviral transduction (see, e.g., Cochlovius et al. (1998) *Cancer Immunol. Immunother.* 46:61-66, Bunnell et al. (1995) *Proc. Natl. Acad. Sci. U.S.A.* 92:7739 and Finer et al. (1994) *Blood* 83:43), electroporation (see, e.g., Hughes et al. (1996) *J. Biol. Chem.* 271:5369-5377 and Cron et al. (1997) *J. Immunol Meth.* 205:145-150), particle bombardment (see, e.g., Yang et al. (1990) *Proc. Natl. Acad. Sci.*

U.S.A. 87:9568-9572), direct local injection of the DNA (for in vivo transfer of DNA) (see, e.g., Wolff et al. (1990) *Science* 247:1465-1468; and Zhu et al. (1993) *Science* 261:209-211), antibody-based methods (Mannino and Gould-Fogerite (1988) *Biotechniques* 6:682-690), retroviruses (Roux et al. (1989) *Proc. Natl. Acad. Sci. U.S.A.* 86:9079-9083), and antifection (see, e.g., Hirsch et al. (1993) *Transpl. Proc.* 25:138-139 and Poncet et al. (1996) *Gene Therapy* 3:731-738).

The nucleic acid encoding a molecule (e.g., protein) of interest can be operably linked to elements that facilitate expression of the nucleic acid in host cells. Such elements include promoters, enhancers and terminators that are functional in the recipient host cell and are known to those of skill in the art.

For transfer of nucleic acid of interest into cells, the nucleic acid may be contained within a vector. Any vector known in the art for transfer and expression of nucleic acids in cells may be used, including plasmids, cosmids and artificial chromosomes. For simultaneous co-transfection, nucleic acid encoding more than one molecule (e.g., protein) of interest may be contained on separate vectors or on the same vector in which they can be operably linked to elements that facilitate expression of the nucleic acids in host cells. Multiple sequences, such as nucleic acids expressing multiple elements in a calcium flux pathway, contained on the same vector may be controlled either by a single promoter or by multiple promoters. In a specific embodiment, the promoter is not native to the gene(s) expressing the protein(s).

Any methods known to those of skill in the art for the insertion of DNA fragments into a vector may be used to construct expression vectors containing a nucleic acid of interest and appropriate transcriptional/translational control signals and/or other protein coding sequences. These methods may include in vitro recombinant DNA and synthetic techniques and in vivo recombinants (genetic recombination).

d. Determining Effects of Alteration of Gene Expression on Intracellular Calcium Following and/or simultaneously with the alteration of gene expression in a cell, the cell (or portion thereof) is analyzed to evaluate the effect, if any, on intracellular calcium. Intracellular calcium may be evaluated in any of a number of ways, including any of the methods described herein or known in the art. For example, intracellular calcium can be evaluated by assessment of cytosolic or intracellular calcium store or organelle calcium levels and/or fluxes or by assessment of calcium movement into or out of the cell following reduction, alteration or elimination of the expression of a gene encoding a candidate or test molecule. Cells can be exposed to conditions (e.g., intracellular and/or extracellular calcium buffering, including use of calcium chelators, and exposure to agents that activate, inhibit or otherwise modulate various cation entry/flux processes) that facilitate assessment of intracellular calcium. In particular embodiments of the methods provided herein for identifying intracellular calcium-modulating proteins, cytosolic calcium buffering, calcium store, organelle or resting cytosolic calcium levels, movement of calcium into, out of or within a calcium store or intracellular organelle and/or store-operated calcium entry are evaluated during and/or following alteration of gene expression. For example, calcium levels and/or calcium release from an intracellular calcium store (e.g., endoplasmic reticulum) can directly be assessed using mag-fura 2, endoplasmic reticulum-targeted aequorin or cameleons. One method for indirect assessment of calcium levels or release is monitoring cytosolic calcium levels (for example, using fluorescence-based methods) after exposing a cell to an agent that effects calcium release (e.g., non-physiological activators such as thapsigargin, and physiological activators such as IP$_3$) from the organelle in the absence of extracellular calcium.

Resting cytosolic calcium levels, intracellular calcium store or organelle calcium levels and cation movement may be assessed using any of the methods described herein or known in the art (see, e.g., descriptions herein of calcium sensitive indicator-based measurements, such as fluo-3, mag-fura 2 and ER-targeted aequorin, labelled calcium (such as $^{45}Ca^{2+}$)-based measurements, and electrophysiological measurements). Particular aspects of ion flux that may be assessed include, but are not limited to, a reduction (including elimination) or increase in the amount of ion flux, altered biophysical properties of the ion current, and altered sensitivities of the flux to activators or inhibitors of calcium flux processes, such as, for example, store-operated calcium entry.

A protein, e.g., an ion transport protein, that is involved in, participates in and/or provides for store-operated calcium entry, and/or nucleic acid encoding such a protein, can be identified by a cell in which reduction, alteration or elimination of the expression of a gene is accompanied by an alteration, e.g., reduction, elimination, increase or other modification, of store-operated calcium entry in the cell. A protein, e.g., an ion transport protein, involved in maintenance of resting cytosolic calcium levels, and/or nucleic acid encoding such a protein, can be identified by a cell in which reduction, alteration or elimination of the expression of a gene is accompanied by an alteration, e.g., increase, decrease or other modification, of resting cytosolic calcium levels. A protein, e.g., an ion transport protein, that is involved in, participates in, or provides for modulation of calcium levels in or movement of calcium into, out of or within an intracellular calcium store or organelle (and/or nucleic acid encoding such a protein) can be identified by a cell in which reduction, alteration or elimination of the expression of a gene is accompanied by an alteration, e.g., increase, decrease, reduction, elimination or other modification, of the calcium level of an intracellular calcium store or organelle or of movement of cations (or other charge carrier) into, out of or within an intracellular calcium store or organelle.

3. Assays and Tools for Use with Screening Methods

A wide variety of assay methods can be used with the screening/identification methods described herein. Any assays that detect, monitor or measure an effect on intracellular calcium, including calcium entry-mediated events can be used. Such assays include, but are not limited to, assays monitoring, measuring and/or detecting intracellular calcium levels, modulation of calcium levels, and movement of calcium into, out of or within cells and intracellular organelles. Assays can also include monitoring, measuring and/or detecting calcium entry-mediated events and molecules involved in calcium entry-mediated events such as, but not limited to, signal transduction molecules, transcription factors, secreted molecules and other molecules that are affected by changes in calcium homeostasis a. Cells In embodiments of the screening/identification methods that involve the use of cells, any cell that can be evaluated for intracellular calcium can be used. A wide variety of cell types for such assays are available. Exemplary cells and assays are described herein. In a particular embodiment, the cell is one in which store-operated calcium entry occurs or that can be manipulated such that store-operated calcium entry occurs in the cell. In particular embodiments, the cell contains one or more proteins involved in modulating intracellular calcium (and, in particular, is involved in, participates in and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering), such as those provided herein. In particular embodiments, the protein(s) is (or is substantially homologous to) one of the proteins listed in Table 3. The protein can be, for example, a STIM or STIM-like protein (including a STIM1, STIM2, DSTIM and CSTIM protein). In one embodiment, the protein is a STIM1 protein, for example, a mammalian, such as human or rodent, STIM1 protein. The cell may endogenously express the protein(s) or recombinantly express the protein(s), e.g., through introduction of heterologous nucleic acid encoding the protein(s) into the cell using methods known in the art and described herein.

In particular embodiments, the cell is a recombinant cell wherein at least some of the protein(s) are encoded by nucleic acid that is heterologous to the cell. The cell can be a recombinant cell that expresses at least some of the protein(s) as heterologous protein(s). Such cells may overexpress the protein(s), e.g., relative to any level of expression of the protein(s) in the same cell which has not be treated so as to introduce heterologous nucleic acid encoding the protein(s). For example, a recombinant cell may be one that endogenously expresses the protein(s) and that also has been transfected with additional copies of nucleic acid encoding the protein(s). In a particular example, the host cell used in generating the recombinant cell may be one that endogenously expresses little to no store-operated calcium entry activity (e.g., CHO-K1 cells that do not exhibit a current with biophysical properties characteristic of a store-operated calcium entry current), or a host cell in which endogenous store-operated calcium entry activity has been reduced or eliminated (e.g., through gene knock-out or silencing, such as RNA interference, methods or by inhibition with an agent that does not inhibit store-operated calcium entry activity of the heterologous protein(s)).

Cells or less differentiated precursor cells having an endogenous protein involved in modulating intracellular calcium can be used. Cells or less differentiated precursor cells may be recombinant cells stably or transiently transfected with intracellular calcium-modulating protein(s) in vitro or in an organism. In vitro transfection is followed by cell expansion through culturing prior to use.

Cells for use in the methods may be of any species. In one embodiment, the cells can be eukaryotic cells. In a particular embodiment, the cells can be yeast, insect (e.g., *Drosophila* or *Anopheles*), or mammalian cells. Mammalian cells include, but are not limited to, rodent (e.g., mouse, rat and hamster), primate, monkey, dog, bovine, rabbit and human cells. A variety of cell types can be used in the methods, including, for example, neuronal, nervous system, brain, immune system cells, e.g., T lymphocytes and B cells, primary cells, blood and hematopoietic cells, stromal cells, myeloid cells, lymphoid cells, and a variety of tumor and cancer cells. Particular cells include *Drosophila* Schneider 2 or S2 cells, human embryonic kidney (HEK293) cells, rat basophilic leukemia (RBL-2H3) cells, Jurkat cells, epithelial cells, rhabdomyosarcoma cells, rhabdoid cells, retinoblastoma cells, neuroepithelioma cells, neuroblastoma cells, osteosarcoma cells, fibroblasts, bone marrow stroma cells, erythroleukemia cells and lymphoblast cells. Other cell lines include HEK 293 and 293T, CHO (including CHO-K1), LTK-, N2A, H6, and HGB. Many such cells and cell lines are available through cell depositories such as, for example, the American Type Culture Collection (ATCC, Manassas, Va.). Primary cells can be obtained by isolation from tissue sources. For example, dorsal root ganglion cells can be isolated by dissection from the spinal cord of rats using procedures known in the art. The generation, maintenance and use of such cells and cell lines is well known. The host cell for generation of a recombinant cell may be a less differentiated precursor cell, and may be one that is readily stably or transiently transfected.

In particular embodiments, neuronal, neuroendocrine, brain, or nervous system (e.g., CNS) or tissue-derived cells can be used in the method for screening for or identifying an agent that modulates intracellular calcium. Such a cell can be one that contains (endogenously and/or as heterologous components, e.g., recombinantly) one or more proteins involved in modulating intracellular calcium (as described above, including proteins listed in Table 3 or substantially homologous to proteins listed in Table 3). Cells from a known cell line can be used, such as neuroblastoma SH-SY5Y cells, pheochromocytoma PC12 cells, neuroblastoma SK-N-BE(2)C or SK-N-SH cells, human SK-N-MC neuroepithelioma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells. Primary cells, e.g., dorsal root ganglion and other primary neuronal or CNS-derived cells, can also be used in the methods.

In another particular embodiment, myeloid cells and cell lines may be used in the methods for screening for or identifying an agent that modulates intracellular calcium. Such a cell can be one that contains (endogenously and/or as heterologous components, e.g., recombinantly) one or more proteins involved in modulating intracellular calcium (as described above, including proteins listed in Table 3 or substantially homologous to proteins listed in Table 3). Such cells include, but are not limited to, chronic myeloid leukemia cells (e.g., human K562 cells), promyelocytic leukemia cells (e.g., HL60 cells) and histiocytic lymphoma cells (e.g., U937 cells).

In one embodiment, epithelial-type cells and cell lines may be used in the methods of screening for or identifying agents that modulate intracellular calcium. Such a cell can be one that contains (endogenously and/or as heterologous components, e.g., recombinantly) one or more proteins involved in modulating intracellular calcium (as described above, including proteins listed in Table 3 or substantially homologous to proteins listed in Table 3). Such cells include, but are not limited to, rhabdoid tumor cells (e.g., human kidney rhabdoid tumor cells, such as G401 cells) and rhabdomyosarcoma cells (e.g., human muscle rhabdomyosarcoma cells, such as A204 cells).

In another embodiment, lymphoid cells and cell lines may be used in the methods of identifying agents that modulate intracellular calcium. Such a cell can be one that contains (endogenously and/or as heterologous components, e.g., recombinantly) one or more proteins involved in modulating intracellular calcium (as described above, including proteins listed in Table 3 or substantially homologous to proteins listed in Table 3). Such cells include, but are not limited to, Burkitt's lymphoma cells (e.g., CA46 cells), B-cells (e.g., NALM6), acute lymphoblastic leukemia cells (e.g., MOLT4cells), T cells (e.g. Jurkat cells) and early T-ALL (e.g., DU528) cells.

The choice of a cell for use in practicing any of the methods for screening for or identifying an agent involved in modulating intracellular calcium can involve several considerations, including, for example, a particular protein that is being used in the method and a particular aspect or activity of intracellular calcium modulation that is being monitored or assessed in the method. For example, different cells (e.g., different cell types or cells of the same type from different species of organisms) may have different sets of molecules, including proteins and ion transport proteins, that participate in various aspects (e.g., store-operated calcium entry, receptor-mediated calcium movement, second messenger-operated calcium movement, calcium uptake, storage and/or release from intracellular compartments or stores, calcium buffering) of intracellular calcium modulation. Accordingly, a cell used in the methods can be selected to be one that provides (e.g., endogenously and/or recombinantly) a cellular environment conducive for functioning of any particular protein(s) (such as those provided herein and described above, including proteins listed in or substantially homologous to protein listed in Table 3) being used in the method or supportive of any particular activity in intracellular calcium modulation that is being specifically monitored or assessed in the methods. A cell may also be selected based on relative amounts of particular proteins expressed by the cell. For example, in some embodiments of the methods, it may be desirable to utilize a cell that contains more STIM1 than STIM2 protein (e.g., a PC12 cell). Additionally, some cells may be more amenable to various manipulations that may be a part of some embodiments of the methods, e.g., recombinant expression of proteins, growth in culture, electrophysiological analysis, etc. Cells that are particularly suitable for specific embodiments of the methods can be determined empirically by those of skill in the art.

For example, particular embodiments of the methods for screening for or identifying agents that modulate intracellular calcium include a step of monitoring or assessing the effect of a test agent on store-operated calcium entry. These methods can involve the use of cells for assessing effects on store-operated calcium entry. Cells typically used in such methods exhibit store-operated calcium entry either naturally or through manipulation of the cells. Cells that endogenously exhibit store-operated calcium entry include some excitable cells and most non-excitable cells and can be identified using methods described herein and/or known in the art. Any method of determining the occurrence of calcium entry into a cell that distinguishes store-operated calcium entry from other types of calcium influx (e.g., entry through voltage-gated calcium channels or other channels that are not dependent on depletion of calcium stores) can be used to determine if a cell exhibits store-operated calcium entry. It may also be possible to manipulate some cells that exhibit low levels or undetectable levels of store-operated calcium entry such that they produce store-operated calcium entry activity, or exhibit more readily detectable levels of store-operated calcium entry activity. For example, transfer and expression of nucleic acids encoding one or more proteins (or portions thereof) described herein as proteins involved in intracellular calcium modulation (including STIM, STIM-like proteins and proteins listed in or proteins substantially homologous to proteins listed in Table 3) into such cells may result in store-operated calcium entry activity or increased stored-operated calcium entry activity in the recombinant cells. Such cells can be evaluated to determine the presence or level of store-operated calcium entry activity using procedures described herein and/or known in the art.

In embodiments of the screening/identification methods that include a step of monitoring or assessing the effect of a test agent on store-operated calcium entry, it may be desirable to utilize a cell that contains components of signaling and messenger systems that can effect release of calcium from intracellular stores. For example, cells containing components of receptor-mediated phospholipase C (PLC) activation systems can be used for physiological activation (via generation of $IP_3$) of store depletion to facilitate monitoring of store-operated calcium entry. Receptor-mediated PLC activation occurs through distinct coupling mechanisms: PLC-β activation by G protein-coupled receptors (GPCRs) and PLC-γ activation by tyrosine kinase receptors and nonreceptor tyrosine kinases. Components of receptor-mediated PLC activation systems include GPCRs (e.g., muscarinic acetylcholine receptors, purinergic receptors, β-adrenergic receptors and serotonin receptors), tyrosine kinase receptors (e.g., growth factor receptors, including EGF, FGF, PDGF and NGF receptors), nonreceptor tyrosine kinases (e.g., Src, Syk and Tec which can be activated by antigen and Ig receptors, such as the T-cell antigen and B-cell antigen receptors) and G proteins. Thus, cells containing a receptor-mediated PLC-activation system can be monitored or assessed for store-operated calcium entry upon agonist activation of one or more receptors known to participate in the system. A cell can contain an endogenous receptor-mediated PLC-activation system or can be manipulated (e.g., by introduction and expression of heterologous nucleic) to express such a system. For example, store-operated calcium entry can be monitored or assessed in PC12 cells upon activation of purinergic P2Y receptors (e.g., by UTP), in cultured hippocampal neurons, human neuroblastoma cells (e.g., SH-SY5Y cells) and human embryonic kidney (e.g., HEK 293) cells upon activation with the cholinergic agonists carbachol or methacholine (see e.g., Bouron (2000) FEBS Lett 470:269-272) and in DT40 chicken B lymphocyte cells (which express PLC-β) and *Drosophila* S2 cells upon activation of G protein-coupled muscarinic (e.g., M5 or *Drosophila* M1) receptors (e.g., by carbachol) recombinantly expressed through transfection of the cells with nucleic acid encoding a muscarinic receptor (see, e.g., Millar et al. (1995) *J. Exp. Biol.* 198:1843-1850; Yagodin et al. (1998) *Cell Calcium* 23:219-228; Yagodin et al. (1999) *Cell Calcium* 25:429-438; and Patterson et al. (2002) *Cell* 111:1-20). Cells containing receptor-mediated PLC-activation systems, and reagents (e.g., nucleic acids encoding receptors, such as muscarinic acetylcholine receptors, and other elements of receptor-mediated PLC-activation systems) and methods for use in generating such systems, are known in the art.

b. Monitoring or Assessing Effects on Intracellular Calcium

In monitoring or assessing the effect of a test agent or molecule on intracellular calcium in any of the screening/identification methods provided herein, a direct or indirect evaluation or measurement of cellular (including cytosolic and intracellular organelle or compartment) calcium and/or movement of ions into, within or out of a cell, organelle, calcium store or portions thereof (e.g., a membrane) can be conducted. A variety of methods are described herein and/or known in the art for evaluating calcium levels and ion movements or flux. The particular method used and the conditions employed can depend on whether a particular aspect of intracellular calcium is being monitored or assessed. For example, as described herein, reagents and conditions are known, and can be used, for specifically evaluating store-operated calcium entry, resting cytosolic calcium levels, calcium buffering and calcium levels and uptake by or release from intracellular organelles and calcium stores. The effect of a test agent or molecule on intracellular calcium can be monitored or assessed using, for example, a cell, an intracellular organelle or calcium storage compartment, a membrane (including, e.g., a detached membrane patch or a lipid bilayer) or a cell-free assay system (e.g., outside-out membrane vesicle).

Generally, monitoring or assessing the effect of a test agent or molecule on intracellular calcium involves contacting a test agent with (1) a protein (and/or nucleic acid, or portion(s) thereof, encoding a protein) involved in modulating intracellular calcium (in particular, a protein provided herein) and/or (2) a cell, or portion(s) thereof (e.g., a membrane or intracellular structure or organelle) or cell-free system that may or may not contain a protein (and/or nucleic acid, or portion(s) thereof, encoding a protein) involved in modulating intracellular calcium. A cell can be one that exhibits one or more aspects of intracellular modulation, such as, for example, store-operated calcium entry. Before, during and/or after the contacting of test agent or molecule, a direct or indirect assessment of intracellular calcium can be made. An indirect assessment can be, for example, evaluation or measurement of current through an ion transport protein (e.g., a store-operated calcium channel), or detection of the expression of a reporter protein operably linked to a calcium-sensitive promoter. A direct assessment can be, for example, evaluation or measurement of intracellular (e.g., cytosolic or intracellular organelle) calcium.

The assessment of intracellular calcium is made in such a way as to be able to determine an effect of an agent on intracellular calcium. Typically, this involves comparison of intracellular calcium in the presence of a test agent or molecule with a control for intracellular calcium. For example, one control is a comparison of intracellular calcium in the presence and absence of the test agent or molecule or in the presence of varying amounts of a test agent or molecule. Thus, one method for monitoring or assessing an effect on intracellular calcium involves comparing intracellular calcium before and after contacting a test agent or molecule with a test cell or portion thereof (e.g., a cell, or portion thereof, containing a protein (and/or nucleic acid encoding a protein) involved in modulating intracellular calcium), or comparing intracellular calcium with respect to a test cell (or portion thereof) that has been contacted with or exposed to test agent and with respect to a cell (or portion thereof) that has not been contacted with or exposed to test agent or molecule (i.e., a control cell or system). Generally, the control cell (or portion thereof) is substantially identical to, if not the same as, the test cell (or portion thereof), except it is the cell (or portion thereof) in the absence of test agent. A difference in intracellular calcium of a test cell (or portion thereof) in the presence and absence of test agent or molecule or a difference in intracellular calcium of a test cell (or portion thereof) and a control cell (or portion thereof) indicates that the agent or molecule is one that modulates intracellular calcium.

In embodiments of the screening/identification methods that involve exposing a test cell (or portion thereof) containing a protein (or portion thereof) involved in modulating intracellular calcium to a test agent, another type of control cell (or portion thereof) can be used in the methods. Such a control cell (or portion thereof) is substantially similar to the test cell but contains a different amount or level of the particular protein (or activity of the particular protein) involved in modulating intracellular calcium than the amount or level of the protein (or activity of the protein) contained in the test cell. For example, the control cell (or portion thereof) can contain more of the protein (or greater activity of the protein) involved in modulating intracellular calcium or less of the protein (or reduced activity of the protein) compared to the amount of the protein (or the activity level of the protein) contained in the test cell (or portion thereof).

Such control cells (or portions thereof) can be generated in a number of ways. For example, a substantially similar control cell of this type could be generated by altering the expression of a particular protein involved in modulating intracellular calcium in a test cell using methods described herein and/or known in the art. Expression-reducing (or eliminating) techniques include RNA interference, antisense RNA and gene knock-out methods. Expression-increasing techniques include introduction of additional copies of nucleic acid encoding the particular protein into a test cell (e.g., over-expression of the particular protein). A control cell generated by altering expression of a protein in a test cell is substantially similar to the test cell except that it contains more or less of the protein (or protein activity) than the test cell. In another example, a control cell can also be one that is not manipulated in the same way as a test cell. For example, if the test cell containing the protein involved in intracellular calcium modulation is a recombinant cell generated by transfer of nucleic acid encoding the protein into a host cell, then one possible control cell is a host cell that has not been transfected with nucleic acid encoding the protein. If the host cell is one that does not contain nucleic acid encoding the protein, then the control cell is substantially similar to the test cell except that it lacks the particular protein involved in modulating intracellular calcium. If the host cell is one that does express some level of the particular protein, then the control cell is substantially similar to the test cell except that it contains less nucleic acid encoding the particular protein (and less of the particular protein) than the test cell. Thus, a control cell may contain, e.g., endogenously, the particular protein involved in modulating intracellular calcium, in which case the test cell would contain higher levels of (or overexpress) the particular protein.

When a control cell (or portion thereof) used in the method is one that is substantially similar to a test cell but contains a different amount or level of the particular protein (or activity of the particular protein) involved in modulating intracellular calcium than the amount or level of the protein (or activity of the protein) contained in the test cell, an effect of test agent on intracellular calcium can be monitored or assessed by comparing intracellular calcium of the test and control cell in the presence of test agent. This type of control comparison is particularly of use when it is desired to identify an agent that specifically modulates intracellular calcium via an effect on, or modulation of, a particular protein (and/or nucleic acid, or portion(s) thereof, encoding a particular protein). Thus, for example, if there is no detectable or substantial difference in intracellular calcium in the test and control cells in the presence of the agent, it is not likely that the agent has an effect on intracellular calcium that is specifically mediated via the particular protein (or nucleic acid encoding the protein). If there is a detectable or substantial difference in intracellular calcium in the test and control cells in the presence of the test agent, then the test agent may be a candidate agent that specifically modulates intracellular calcium via an effect on or modulation of the particular protein. A candidate agent can be subjected to further control assays to compare intracellular calcium in test cells in the presence and absence of test agent and/or to compare intracellular calcium in control cells in the presence and absence of test agent, which can aid in determination of whether a candidate agent is an agent that modulates intracellular calcium. For example, any difference in intracellular calcium in a control cell in the presence and absence of test agent can be compared to any difference in intracellular calcium in a test cell in the presence and absence of test agent. If the relative differences in intracellular calcium for the test and control cells are similar or do not differ substantially, then it may not be likely that the agent has an effect on intracellular calcium that is mediated via the particular protein.

An assessment of intracellular calcium conducted to monitor the effect of test agent or molecule on intracellular calcium can be made under a variety of conditions. Conditions can be selected to evaluate the effect of test agent on a specific aspect of intracellular calcium. For example, as described herein, reagents and conditions are known, and can be used, for specifically evaluating store-operated calcium entry, resting cytosolic calcium levels, calcium buffering, and calcium levels of and calcium uptake by or release from intracellular organelles. Resting cytosolic calcium levels, intracellular organelle calcium levels and cation movement may be assessed using any of the methods described herein or known in the art (see, e.g., descriptions herein of calcium-sensitive indicator-based measurements, such as fluo-3, mag-fura 2 and ER-targeted aequorin, labelled calcium (such as $^{45}Ca^{2+}$)-based measurements, and electrophysiological measurements). Particular aspects of ion flux that may be assessed include, but are not limited to, a reduction (including elimination) or increase in the amount of ion flux, altered biophysical properties of the ion current, and altered sensitivities of the flux to activators or inhibitors of calcium flux processes, such as, for example, store-operated calcium entry. Reagents and conditions for use in specifically evaluating receptor-mediated calcium movement and second messenger-operated calcium movement are also available.

i. Evaluation of Store-Operated Calcium Entry

In particular embodiments of the methods for screening for or identifying agents and molecules that modulate intracellular calcium, the methods are conducted under conditions that permit store-operated calcium entry to occur. Such conditions are described herein and are known in the art. Test agents can be contacted with a protein and/or nucleic acid encoding, or regulating the expression of, a protein (such as the proteins and nucleic acids provided herein) involved in modulating intracellular calcium and/or a cell (or portion thereof) containing such a protein (or nucleic acid) under these appropriate conditions.

For example, in one method for detecting or monitoring store-operated transport of calcium across the plasma membrane, cells may be treated to reduce the calcium levels of intracellular calcium stores and then analyzed for evidence of ion (particularly cation, e.g., calcium) influx in response thereto. Techniques for reducing calcium levels of intracellular stores and for analyzing cells for evidence of ion (particularly cation, e.g., calcium) influx are known in the art and described herein.

In other methods, diffusible signals may be used to activate store-operated calcium entry in methods of detecting and monitoring the same. One such signal is referred to as calcium influx factor (CIF) (see, e.g., Randriamampita and Tsien (1993) Nature 364:809-814; Parekh et al. (1993) Nature 364: 814-818; Csutora et al. (1999) Proc. Natl. Acad. Sci. U.S.A. 96:121-126), which may be a small (~<500 D) phosphate-containing anion. A CIF activity from thapsigargin-treated Jurkat cells, as well as a similar activity from calcium pump-deficient yeast, can activate calcium influx in Xenopus oocytes and in Jurkat cells. When included in the patch pipette during whole-cell patch clamp of Jurkat cells, the extracts activate an inward current resembling $I_{CRAC}$.

In other methods, electrophysiological analysis of currents across a cell-detached plasma membrane patch or an outside-out membrane vesicle may be used to detect or monitor store-operated channel currents (e.g., $I_{CRAC}$)

(a) Reduction of Calcium Levels of Intracellular Stores

A variety of treatments may be used to reduce calcium levels in intracellular calcium stores. Generally, the treatments can be viewed as either an active, direct reduction in calcium levels, such as by removal of free calcium from the stores (i.e., "active" depletion), or a passive reduction in calcium levels, such as by leak of calcium from the stores either by a reduction in the availability of free calcium for filling or replenishing the stores or by preventing filling or replenishing of stores (i.e., "passive" depletion).

(1) Passive Depletion

One method of reducing the availability of calcium for the internal calcium stores is to decrease the calcium concentration of the extracellular medium and/or cytoplasm. Calcium concentrations of these fluids can be decreased using cation, and particularly calcium, chelators including, but not limited to EGTA and 1,2-bis(2-amino-phenoxy)ethane-N,N,N,N'-tetraacetic acid (BAPTA). For example, cells may be equilibrated in 10 mM external calcium with strong buffering of cytosolic calcium, for example, through dialysis with 10 mM EGTA. Alternatively, reduction of external calcium may also deplete intracellular calcium stores in many types of cells. For example, cells may be incubated in nominally free calcium solution, e.g., 10 μM external calcium, or essentially calcium-free solution, e.g., ~1 nM external calcium with strongly (e.g., 10 mM EGTA) buffered cytosolic calcium.

A membrane-permeant cation chelator that can chelate calcium within internal stores may also be used to reduce free calcium levels of the stores. One such chelator is N,N,N,N'-tetrakis(2-pyridylmethyl)ethylene diamine (TPEN), which, in its uncomplexed form, diffuses across cell membranes (see, e.g., Hofer et al. (1998) J. Cell Biol. 140:325-334). Because this multivalent cation chelator has a low affinity for calcium, it should not significantly influence calcium levels in the cytoplasm or other cell compartments where the steady-state calcium concentration is in the nanomolar or low micromolar range. In cell compartments where the calcium concentration is comparable to its Kd, such as, for example, the endoplasmic reticulum, TPEN should bind calcium to rapidly reduce free calcium levels. Removal of TPEN from the cell medium should provide for increases in free calcium levels in such cell compartments due to rapid unbinding of the chelator from calcium ions and diffusion of the free form of TPEN from the compartment. Thus, TPEN may be used to reversibly manipulate store calcium levels without interfering with other aspects of calcium homeostasis.

Reduction of calcium in intracellular calcium stores can also be accomplished by application of an agent that blocks endoplasmic reticulum calcium ATPase pumps (SERCAs), thereby reducing or preventing refilling of the endoplasmic reticulum with calcium and providing for leak of calcium from the ER into the cytoplasm resulting in a reduction of ER free calcium concentration. For example, ER free calcium concentration may decrease from about 500 μM to about 50-100 μM as has been observed in HEK293 cells (Yu and Hinkle (2000) J. Biol. Chem. 275:23648-23653). Such agents include, but are not limited to, thapsigargin, cyclopiazonic acid (CPA), and di-tert-butyl-hydroquinone (tBHQ). Agents such as these are referred to as nonphysiological activators of calcium store depletion.

(2) Active Depletion

Active reduction of calcium levels in intracellular calcium stores can be experimentally implemented in a number of ways. For example, exposure of endoplasmic reticulum inositol-1,4,5-triphosphate ($IP_3$) receptors to $IP_3$ or derivatives or analogs thereof provides for release of calcium from this calcium store and serves to reduce calcium levels therein. $IP_3$ or derivatives or analogs thereof can be provided to the endoplasmic reticulum through direct intracellular application, through application to the plasma membrane (using membrane-permeable derivatives of $IP_3$) or by contacting cells with or exposing cells to an agent that activates the phosphoinositide cascade to generate $IP_3$. Such activating agents include agonists of plasma membrane receptors linked to activation of PLC and agents that activate PLC downstream of the plasma membrane in the signaling cascade. Examples of G protein-coupled receptor agonists include histamine, muscarine, carbachol, substance P, bradykinin, serotonin, uridine triphosphate (UTP) and glutamate. Additionally, inhibition of catabolic enzymes involved in degradation of $IP_3$ can serve to provide $IP_3$ for interaction with its receptor. $IP_3$ and agents that activate the phosphoinositide cascade are referred to as physiological activators of calcium store depletion.

Ionophores, e.g., ionomycin (a $Ca^{2+}$/proton ionophore), also may be used for active depletion of intracellular calcium stores by embedding in the ER membrane and providing a pore-like mechanism for movement of calcium out of the ER.

(b) Analysis of Ion Flux

Many methods for monitoring or detecting store-operated calcium entry include a step of detecting and/or analyzing ion flux into a cell or across a membrane. Techniques for detection and analysis of ion flux into and within cells and across membranes are well known in the art. Typically, a cell or membrane can be exposed to conditions that activate store-operated calcium entry or store-operated calcium channels, including conditions described herein, such as treatment with an agonist that results in generation of $IP_3$, internal perfusion with $IP_3$, treatment with a physiological or non-physiological store-depletion agent e.g., thapsigargin, buffering of cytoplasmic calcium or treatment with a CIF, and then analyzed for evidence of movement of ions across a membrane and/or into a cell. Depending on the assay conditions, the ion may be calcium or other cation, for example sodium or manganese, that can be transported via a store-operated channel.

When it is desired to specifically monitor only store-operated calcium entry or ion flux, particular conditions and/or methods can be used in the analysis. For example, as described herein and in the art, store-operated channel currents (e.g., $I_{CRAC}$) have distinct features that can be detected through electrophysiological analysis methods and used to distinguish store-operated calcium entry or ion flux. In addition, non-physiological activators of store depletion (e.g., thapsigargin) can be used to specifically activate store-operated calcium entry without possible interference by other fluxes (calcium or other ion) that may possibly be induced by physiological activators (e.g., activators of receptor-mediated PLC activation). It may be possible to detect interfering fluxes (e.g., through receptor-operated channels which are not dependent on calcium store depletion for activation) by using a control cell in which store depletion that would occur upon treatment with a physiological activator is reduced or eliminated by an antagonist of the $IP_3$ receptor (e.g. 2-aminoethoxydiphenylborate (2-APB)). Changes in intracellular calcium or other ion levels, or calcium (or other ion) movement into such a control cell (or across a control cell membrane) upon treatment with a physiological activator would not be reflective of store-operated channel activity or store-operated calcium entry.

Ion flux, such as occurs in store-operated calcium entry, can be measured electrophysiologically, for example, using patch clamp methods (see, e.g. Hamil et al. (1981) *Pflugers Arch.* 391:85-100); Hoffman et al. (1999) *Nature* 397:259-263; and Krause et al. (1999) *J. Biol. Chem.* 274:36957-36962) to record the inward $Ca^{2+}$ (or other ion or charge carrier) current. The current may be highly selective for $Ca^{2+}$ divalent ions, may display negative feedback regulation by $Ca^{2+}$ (see, e.g. Zweifach and Lewis (1995) *J. Gen. Physiol.* 105:209-226), and may be inhibited by divalent and trivalent metal ions such as $Zn^{2+}$, $Ni^{2+}$, $Gd^{3+}$ and $La^{3+}$ (Parekh and Penner (1997) *Physiol. Rev.* 77: 901-930). Negative feedback by $Ca^{2+}$ can be eliminated by the inclusion of very high concentrations of $Ca^{2+}$ buffers in the patch pipette. In the absence of these buffers or with buffers of lower capacity, the current may be too small to be detected, although $Ca^{2+}$ entry clearly occurs. The current may be strongly inwardly rectifying and may lose its property of inward rectification in the complete absence of divalent cations. It may be possible to determine the time course of activation of the current in single cells followed by passive store depletion via patch pipettes containing $Ca^{2+}$ chelating reagent BAPTA in the whole cell configuration using $Na^{2+}$ used as the charge carrier (Kerschbaum and Cahalan (1999) *Science* 283:836).

The electrophysiological measurement/recording of store-operated ion flux through a membrane can provide for the assessment of such biophysiological properties as kinetics, voltage dependence and ionic selectivity. The electrophysiological measurement can be performed by using whole cell patch clamp methods which can allow for the reliable and precise determination of the conditions under which $Ca^{2+}$ influx occurs. As described by Hofman et al. ((1999) *Nature* 397:259-263), the patch clamp technique can be used in whole-cell, cell-attached, inside-out and outside-out mode.

Additionally patch clamp methods can be performed in a perforated-patch whole cell, configuration. Variations of the patch-clamp technique or other methods for detecting and analyzing ionic activity of cells, which are routine in the art, can also be used.

Measurement of changes of intracellular ions, such as cations including $Ca^{2+}$, can also can also be performed using fluorescence imaging, such as fluorescence videomicroscopy, digital imaging or ratioimaging techniques. Measurement of changes in intracellular $Ca^{2+}$ $((Ca^{2+})i)$ in individual cells by fluorescence videomicroscopy can be performed using a digital imaging system, such as, for example, that produced by T.I.L.L. Photonics, or the Attofluor Digital Imaging and Photometry attachment of a Carl Zeis axiovert inverted microscope. Typically, cells can be grown on coverslips, rinsed and incubated with 5 µM fura2/AM (Molecular Probes) at 37° C. for 30 minutes and then washed with HPSS. The coverslips with the cells are then typically clamped into a circular open-bottom chamber and mounted onto the stage of a microscope. $(Ca^{2+})i$ can be calculated from fluorescence ratios obtained at 340 nm and 380 nm excitation wavelengths (Garcia et. al (1994) *J. Neurosci.* 14:1233-1246). Modified protocols such as those described by Zitt et. al. ((1997) *J. Cell Biol.* 138: 1333-1341) and alternate forms of fluorescence ratio imaging may also be used.

Calcium-sensitive indicators, such as fluo-3 (Catalog No. F-1241, Molecular Probes, Inc., Eugene, Oreg.) and fluo-4, are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence.

Additionally, calcium flux in a cell may be monitored using a reporter gene expression system. In such a system, the cell in which calcium levels and fluctuations therein are monitored may contain a reporter gene encoding a detectable signal, such as luciferase, which is linked to a transcription regulatory element, e.g., promoter, that is induced by calcium-dependent factors.

For example, in conducting one method for screening for or identifying an agent that modulates intracellular calcium under conditions selected for evaluating store-operated calcium entry, intracellular calcium levels of test cells are monitored over time using a fluorescent calcium indicator (e.g., FLUO-4). Store-operated calcium entry into the cells is detected as an increase in fluorescence (i.e., increase in intracellular calcium levels) in response to conditions under which store-operated calcium entry occurs. The conditions include addition of a store-depletion agent, e.g., thapsigargin (which inhibits the ER calcium pump and discharges calcium stores) to the media of cell that has been incubated in $Ca^{2+}$-free buffer, incubation with thapsigargin for about 5-15 minutes, addition of test compound (or vehicle control) to the media and incubation of the cell with test agent for about 5-15 minutes, followed by addition of external calcium to the media to a final concentration of about 1.8 mM. By adding thapsigargin to the cell in the absence of external calcium, it is possible to delineate the transient increase in intracellular calcium levels due to calcium release from calcium stores and the more sustained increase in intracellular calcium levels due to calcium influx into the cell from the external medium (i.e., store-operated calcium entry through the plasma membrane that is detected when calcium is added to the medium). Because the fluorescence-based assay allows for essentially continuous monitoring of intracellular calcium levels during the entire period from prior to addition of thapsigargin until well after addition of calcium to the medium, not only can "peak" or maximal calcium levels (as well as total calcium entry) resulting from store-operated calcium entry be assessed in the presence and absence of test agent, a number of other parameters of the calcium entry process may also be evaluated, as described herein. For example, the kinetics of store-operated calcium entry can be assessed by evaluation of the time required to reach peak intracellular calcium levels, the up slope and rate constant associated with the increase in calcium levels, and the decay slope and rate constant associated with the decrease in calcium levels as store-operated calcium entry discontinues. Any of these parameters can be evaluated and compared in the presence and absence of test agent to determine whether the agent has an effect on store-operated calcium entry, and thus on intracellular calcium. In other embodiments, store-operated calcium entry can be evaluated by, for example, assessing a current across a membrane or into a cell that is characteristic of a store-operated calcium entry current (e.g., responsiveness to reduction in calcium levels of intracellular stores) or assessing transcription of reporter construct that includes a calcium-sensitive promoter element. In particular embodiments, a test agent is identified as one that produces at least a 50% difference in any aspect or parameter of store-operated calcium entry relative to control (e.g., absence of compound, i.e., vehicle only).

ii. Evaluation of Intracellular Calcium Stores

In particular embodiments of the methods for screening for or identifying agents that modulate intracellular calcium, the method is conducted under conditions that permit evaluation or monitoring of intracellular calcium stores, such as, for example, the endoplasmic reticulum. Such conditions are described herein and are known in the art. A cell (or portion thereof, e.g., an intracellular organelle or calcium store) can be contacted with or exposed to an agent under these appropriate conditions. The cell can be one, for example, that contains a protein (or nucleic acid encoding, or regulating the expression of, a protein) involved in modulating intracellular calcium (such as proteins provided herein, including STIM and STIM-like proteins and proteins listed in Table 3).

For example, in one method for detecting or monitoring intracellular calcium stores, calcium levels and/or calcium uptake by or release from the endoplasmic reticulum can directly be assessed using mag-fura 2, endoplasmic reticulum-targeted aequorin or cameleons. One method for indirect assessment of calcium levels in, or calcium release from, an intracellular store involves monitoring or assessing intracellular calcium levels, such as cytosolic calcium levels and time course of changes therein (for example using fluorescence-based methods), after exposing a cell to an agent that effects calcium release (actively, e.g., $IP_3$ or caffeine, or passively, e.g., thapsigargin) from the calcium store or organelle in the absence of extracellular calcium. The amplitude and rate of the increase in cytosolic calcium levels are indicative of the calcium levels in and calcium release process of the intracellular calcium store.

In particular methods of screening for or identifying an agent that modulates intracellular calcium provided herein, the effect of a test agent (which is one that interacts with, binds to and/or modulates interactions, activities, levels or any physical, structural or other property of a protein involved in modulating intracellular calcium) on intracellular calcium store calcium level and/or calcium release is monitored or assessed. In another embodiment, the effect of a test agent on intracellular calcium store calcium level and/or calcium release is monitored or assessed in a cell that contains a protein involved in modulating intracellular calcium. In either of these particular embodiments, the protein involved in modulating intracellular calcium can be one of the proteins described herein above, such as a STIM or STIM-like protein, or a protein listed in Table 3 or substantially homologous to a protein listed in Table 3. For example, the protein can be a STIM1 protein, such as a mammalian, and in particular, human, STIM1 protein. As described herein, calcium release from thapsigargin-sensitive calcium stores may be altered in human embryonic kidney (HEK293) and neuroblastoma (SH-SY5Y) cells in which STIM1 gene expression is reduced (as evidenced by decreased mRNA and protein levels) by RNA interference methods. This finding suggests STIM1 may be involved in regulation of calcium store (e.g., endoplasmic reticulum) calcium levels and/or release of calcium from calcium stores. Thus, in particular embodiments of the methods for screening for identifying an agent that modulates intracellular calcium, the effect of a test agent on intracellular calcium store calcium level and/or calcium release is monitored or assessed, wherein the test agent is one that interacts with and/or modulates a STIM1 protein or the test cell is one that contains a STIM1 protein.

iii. Evaluation of Calcium Buffering

In particular embodiments of the methods for screening for or identifying agents that modulate intracellular calcium, the method is conducted under conditions that permit evaluation or monitoring of intracellular (e.g., cytosolic) calcium buffering. Such conditions are described herein and/or are known in the art. A cell can be contacted with or exposed to a test agent under these appropriate conditions. The cell can be, for example, one that contains a protein (or nucleic acid encoding, or regulating the expression of, a protein) involved in modulating intracellular calcium (such as proteins provided herein, including STIM and STIM-like proteins and proteins listed in Table 3).

For example, in one method for detecting or monitoring calcium buffering, involves monitoring or assessing intracellular calcium levels, such as cytosolic calcium levels and time course of changes therein (for example using fluorescence-based methods), after exposing a cell to an agent that effects calcium release (actively, e.g., $IP_3$ or caffeine, or passively, e.g., thapsigargin) from a calcium store or organelle in the absence of extracellular calcium. The properties or characteristics (e.g., rates, kinetics or timing) of the decrease in cytosolic calcium levels is indicative of the buffering of calcium (e.g., by uptake of calcium into intracellular organelles or calcium stores and by transfer of calcium from the cytoplasm to the extracellular medium, such as by extrusion from the cell through the action of the plasma membrane calcium ATPase). Thus, for example, monitoring of or assessing calcium buffering can involve evaluating the rate at which cytosolic calcium levels return to basal levels after activation of calcium influx into the cytoplasm, the overall time course of cytosolic calcium level adjustment, timing of the onset of the adjustment of cytosolic calcium levels to return to basal levels after activation of calcium influx into the cytoplasm, and the final cytosolic calcium level (e.g., basal level) attained upon adjustment of calcium levels after activation of calcium influx.

In particular methods of screening for or identifying an agent that modulates intracellular calcium provided herein, the effect of a test agent (which is one that interacts with, binds to and/or modulates interactions, activities, levels or any physical, structural or other property of a protein involved in modulating intracellular calcium) on calcium buffering is monitored or assessed. In another embodiment, the effect of a test agent on calcium buffering is monitored or assessed in a cell that contains a protein involved in modulating intracellular calcium. In either of these particular embodiments, the protein involved in modulating intracellular calcium can be one of the proteins described herein above, such as a STIM or STIM-like protein, or a protein listed in Table 3 or substantially homologous to a protein listed in Table 3. For example, the protein can be a STIM1 protein, such as a mammalian, and in particular, human, STIM1 protein. As described herein, calcium buffering capacity is altered in human embryonic kidney (HEK293) cells in which STIM1 gene expression is reduced (as evidenced by decreased mRNA and protein levels) by RNA interference methods. For example, the rate and kinetics of the adjustment (i.e., decrease) in cytosolic calcium levels following methylcholine-induced calcium release from intracellular calcium stores in such cells is altered relative to HEK293 cells in which STIM1 expression has not been reduced. This finding indicates involvement of STIM1 in calcium buffering (e.g., by uptake of calcium into intracellular organelles or extrusion of calcium to the exterior of the cell). Thus, in particular embodiments of the methods for screening for identifying an agent that modulates intracellular calcium, the effect of a test agent on calcium buffering is monitored or assessed, wherein the test agent is one that interacts with and/or modulates a STIM1 protein or the test cell is one that contains a STIM1 protein.

iv. Evaluation of Resting Cytosolic Calcium Levels

In particular embodiments of the methods for screening for or identifying an agent that modulates intracellular calcium, the method is conducted under conditions that permit evaluation or monitoring of basal or resting cytosolic calcium levels. Such conditions are described herein and/or known in the art. A cell can be contacted with or expose to a test agent under these appropriate conditions. The cell can be one, for example, that contains a protein (or nucleic acid encoding, or regulating the expression of, a protein) involved in modulating intracellular calcium (such as proteins provided herein, including STIM and STIM-like proteins and proteins listed in Table 3).

For example, resting cytosolic calcium levels can be evaluated using any techniques for detecting or measuring cytosolic calcium known in the art and/or described herein, including fluorescent calcium indicators. The evaluation is conducted while a cell is at rest with respect to cytosolic calcium. A cell is at rest with respect to cytosolic calcium when it has not been subjected to conditions that result in activation of calcium flux into the cytoplasm from the external medium or calcium release from intracellular calcium stores into the cytoplasm.

c. Evaluation of Calcium Entry-Mediated Events

A number of molecules involved in calcium-regulated pathways are known (see for example, FIG. 1 which shows exemplary molecules involved in calcium-entry mediated events in immune cells). Evaluation of molecules involved in calcium-entry mediated events can be used to monitor intracellular calcium, and can be used, for example in screening assays described herein to monitor the effects of, or identify, test agents and molecules. Examples of assays include but are not limited to assays which detect, or determine the presence, levels, alteration of levels, production, modification (such as phosphorylation and dephosphorylation), translocation, degradation and activity of molecules involved in calcium-entry mediated events (see for example, Trevillyan et al. (2001) *J. Biol. Chem.* 276:48118-26). The assays described herein can be used with cells that have been treated with or contacted with a test agent, or that express an altered amount of a test molecule (such as a molecule involved in calcium regulation, including a STIM or STIM-like protein), or with control cells. The assays can also be conducted in cells that have been stimulated with a physiological or non-physiological activator, or in unstimulated cells. The following are representative assays for molecules involved in calcium-entry mediated events and are meant to be exemplary only. Other assays for these molecules and assays for other molecules involved in calcium-entry mediated events can also be employed in any of the screening and/or modulation methods described herein.

β-hexosaminidase Release

In mast cells, $Ca^{2+}$ influx results in degranulation and release of inflammatory mediators such as heparin, histamine and enzymes such as β-hexosaminidase. Detecting and/or measuring release of such molecules can thus be used to monitor intracellular calcium. For example, media from mast cells can be collected. A suitable substrate for β-hexosaminidase (e.g. p-nitrophenyl-acetyl-glucosamide) can then be added and the absorbance of the resulting mixture assessed to measure the relative amount of β-hexosaminidase activity in the samples (see for example, Example 10, and also, Funaba et al. (2003) *Cell Biol. International* 27:879-85).

Calcium/Calmodulin-Dependent CaN Phosphatase Activity

The phosphatase calcineurin (CaN) dephosphorylates various proteins, affecting their activity and localization. CaN activity can be assessed by incubating purified CaN and a CaN substrate, for example a radiolabeled peptide corresponding to a sequence in the $R_{II}$ subunit of cAMP-dependent kinase, either with or without a test agent or test molecule (see, Trevillyan et al. (2001) *J. Biol. Chem* 276:48118-26). The level of radiolabeled peptide and/or the amount of free inorganic phosphate released can be measured to assess CaN dephosphorylation activity.

NFAT Transcriptional Activity

The NFAT (nuclear factor of activated T cells) transcription factor regulates a number of genes in response to intracellular calcium levels. For example, NFAT proteins regulate the transcription of cytokine genes involved in the immune response. Promoters from NFAT-regulated genes, and/or regulatory regions and elements from these genes, can be used to monitor NFAT regulated expression and thereby monitor intracellular calcium. Reporter gene fusions can be constructed with NFAT regulated promoters or NFAT-regulated elements operably linked to a reporter gene such as luciferase, β-galactosidase, green fluorescent protein (GFP) or any other known reporter in the art (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular $Ca^{2+}$, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT can be monitored for example, by expressing a detectably tagged NFAT protein in cells, such as a $His_6$ tagged-NFAT. Tagged NFAT can be purified from cells using $Ni^{2+}$ chromatography and subjected to gel electrophoresis and staining or western blotting. More highly phosphorylated forms of NFAT can be distinguished by their slower migration. The state of phosphorylated NFAT can be used as a measure of NFAT activation (see, Trevillyan et al. (2001) *J. Biol. Chem* 276:48118-26).

NFAT Nuclear Localization

NFAT localization between the cytoplasm and nucleus is regulated by the phosphorylation state of NFAT. Phosphorylation of NFAT prevents nuclear localization by masking the nuclear localization sequence. NFAT nuclear localization can be monitored, for example, by expressing fluorescently tagged NFAT, for example, GFP-NFAT, in cells. Confocal microscopy can be used to monitor nuclear localization of the tagged NFAT (see, Trevillyan et al. (2001) *J. Biol. Chem* 276:48118-26).

Cytokine Secretion

Cytokine secretion, such as IL-2 secretion, can be monitored using protein detection assays. For example, supernatant can be collected from immune cells. An ELISA assay or other suitable format with IL-2 antibodies can be used to detect and/or measure the amount of IL-2 secreted as compared to control cells (see EXAMPLE 9). Secretion of other cytokines, for example, TNFα, can also be detected in similar assays.

Cytokine Expression

Expression of cytokines, such as IL-2, can be assessed either directly or indirectly in cells. For example, in indirect methods, an IL-2 promoter can be operably linked to a reporter gene such as luciferase or β-galactosidase, and the reporter construct introduced into cells. Reporter gene expression can be monitored and compared to gene expression in control cells (see, Trevillyan et al. (2001) *J. Biol. Chem* 276:48118-26). Alternatively, expression of endogenous or recombinant IL-2 mRNA or protein can be assessed.

T Cell Proliferation

Cytokines such as IL-2 are necessary for T-cell proliferation in response to mitogen or alloantigen stimulation, and thus T-cell proliferation is altered by changes in cytokine expression or secretion. T cells can be induced, such as with concanavalin A or alloreactive lymphocytes and T cell proliferation measured, for example, by subjecting cells to a pulse of $^3$H-thymidine and measuring $^3$H-thymidine incorporation (see, Trevillyan et al. (2001) *J. Biol. Chem* 276:48118-26).

d. Systems

Also provided herein are systems for use in identifying an agent that modulates intracellular, including, for example, cytoplasmic, calcium. Such systems include a protein or portion thereof (and/or nucleic acid encoding a protein or portion thereof) involved in modulating intracellular calcium that has an amino acid sequence homologous to an amino acid sequence of a mammalian, e.g., rodent or human, stromal interacting molecule (STIM) protein and/or a protein encoded by a *Drosophila* gene that, when altered in its expression in a *Drosophila* cell, results in altered store-operated calcium entry into the cell, altered calcium levels in or movement of calcium into, out of or within an intracellular calcium store and/or altered cytosolic calcium buffering. One such *Drosophila* gene is CG9216. In a particular embodiment, the protein is one that is involved in modulating intracellular calcium (and, in particular embodiments is involved in, participates in and/or provides for store-operated calcium entry, movement of calcium into, out of or within an intracellular organelle or calcium store, modulation of intracellular store or organelle calcium level, and/or cytosolic calcium buffering) and that has an amino acid sequence that is at least about 20%, or at least about 25%, or at least about 30%, or least about 35%, or at least about 39%, or at least about 40%, or at least about 45%, or at least about 47%, or at least about 50%, or at least about 55%, or at least about 60%, or at least about 65%, or at least about 70%, or at least about 75%, or at least about 80%, or at least about 85%, or at least about 90%, or at least about 95% or more homologous to an amino acid sequence of the protein encoded by the coding sequence of *Drosophila* gene CG9126 and/or a mammalian STIM protein, e.g., human or rodent (such as rat) STIM1. The particular homology can depend on the particular protein, e.g., species, that is homologous to the specified proteins and the extent of the specified proteins to which the particular protein is homologous. In particular embodiments, the protein is at least 45% or more homologous to the protein encoded by the coding sequence of *Drosophila* gene CG9126 and/or a mammalian STIM protein, e.g., human or rodent (such as rat) STIM1. Such proteins may be homologous to the specified proteins over at least about 25%, or at least about 30%, or at least about 35%, or at least about 40%, or at least about 45%, or at least about 50%, or at least about 52%, or least about 55%, or at least about 60%, or at least about 65%, or at least about 70%, or at least about 75%, or at least about 80%, or at least about 84%, or at least about 85%, or at least about 90%, or at least about 95% or more of a specified protein. In particular embodiments, the protein is homologous to a specified protein over at least about 52% or more of a specified protein.

In another particular embodiment of the above systems, a protein, or portion thereof (and/or nucleic acid encoding a protein or portion thereof), of the system is involved in intracellular calcium modulation (and in particular embodiments, is involved in, participates in and/or provides for store-operated calcium entry, movement of calcium into, out of or within an intracellular organelle or calcium store, modulation of intracellular store or organelle calcium level, and/or cytosolic calcium buffering) that is at least about 45% homologous over at least about 52% of the protein encoded by the coding sequence of *Drosophila* gene CG9126 and/or a mammalian STIM protein, e.g., human or rodent (such as rat) STIM1. Proteins homologous to the protein encoded by the coding sequence of *Drosophila* gene CG9126 and/or a mammalian STIM protein, e.g., human or rodent (such as rat) STIM1, include, but are not limited to, the proteins listed in Table 3. In other embodiments, other proteins that may be used in the systems provided herein include, but are not limited to, proteins involved in intracellular calcium modulation that are substantially homologous to the proteins listed in Table 3.

In one embodiment of the systems for use in identifying an agent that modulates intracellular calcium, the system includes a cell, or portion thereof, containing one or more STIM proteins or STIM-like proteins, or portion thereof. Examples of STIM or STIM-like proteins include, but are not limited to, the following: STIM proteins (e.g., of *Drosophila* (SEQ ID NOS: 2, 76, 78, 80 and 81) and *C. elegans* (SEQ ID NO: 14)); STIM1 or STIM1-like proteins (e.g., of *Homo sapiens* (SEQ ID NOS: 4, 50, 83, 84), reference STIM1 (SEQ ID NO: 52) and *Mus musculus* (SEQ ID NOS:10, 56 and 85)); STIM2 or STIM2-like proteins (e.g., of *Homo sapiens* (SEQ ID NOS: 6, 62, 87 and 88), *Mus musculus* (SEQ ID NOS: 12 and 68), rat (SEQ ID NO: 72) and partial protein sequences from hamster SEQ ID NO:96 and from rat (SEQ ID NO:98)).

In a particular embodiment of the system, the protein can be contained in a cell, or portion thereof (e.g., a membrane or intracellular organelle). A cell of the system can be an isolated cell (or can be in a cell culture) that endogenously expresses such protein(s) and/or can express such proteins from heterologous nucleic acid (e.g., recombinant expression) as described above with respect to the methods for identifying agents. In a particular embodiment, the cell is one that overexpresses the protein. Systems in which the cell recombinantly expresses the protein can be such that the cell is an isolated cell or is in a cell culture or are contained within an animal, in particular, a non-human animal, e.g., a non-human mammal.

The protein, or portion thereof (and/or nucleic acid encoding a protein or portion thereof), and/or cell, or portion thereof, of particular embodiments of the systems can be contained in a medium that contains an agent that provides for passive or active intracellular calcium store reduction or depletion (e.g., thapsigargin or other non-physiological activator of calcium store depletion) and/or that contains a molecule or molecules that facilitate monitoring or measurement of intracellular calcium and/or calcium movement. Such molecules include fluorescent (or otherwise labeled) calcium indicators, trivalent cations, divalent cations other than calcium and calcium-buffering agents, e.g., calcium chelators.

E. Methods of Modulating Intracellular Calcium

Provided herein are methods for modulating intracellular calcium. Modulation of intracellular calcium can be any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In particular embodiments, intracellular calcium modulation can involve alteration or adjustment of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium can involve an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

1. Modulating a Protein(s), and/or Nucleic Acid Encoding a Protein, Involved in Modulating Intracellular Calcium Methods of modulating intracellular calcium include a step of modulating a protein involved in modulating intracellular calcium. Thus, methods of modulating intracellular calcium provided herein can be methods of specifically or selectively modulating intracellular calcium, in contrast to modulation of intracellular calcium that may occur as one of several effects that a general, non-specific manipulation of a cell may elicit. Modulating a protein involved in modulating intracellular calcium can include, for example, modulating the level, expression, functioning, molecular interactions and/or activity of a protein or portion thereof (and/or nucleic acid encoding one or more proteins or portion thereof) involved in modulating intracellular calcium. The protein involved in modulating intracellular calcium can be, for example, an ion transport protein, a component of an ion transport protein complex, a modulatory or regulatory protein, a receptor, a calcium-binding protein or a protein that regulates any such proteins.

In one embodiment, the method includes a step of specifically modulating a particular protein involved in modulating intracellular calcium. In specifically modulating a particular protein involved in modulating intracellular calcium, the particular protein is targeted for modulation. Specific modulation of a particular protein involves selectively (and typically directly) modulating the protein and thus also modulating any particular intracellular calcium modulation process or pathway in which the particular protein may be involved. In embodiments of the methods for modulating intracellular calcium in which a particular protein is specifically modulated, the modulation of the protein can be such that the associated modulation of intracellular calcium occurs through a process that is primarily initiated through a direct effect on the particular protein. Specific modulation of a particular protein can be such that the particular protein, and thus a particular pathway or cascade or intracellular calcium-modulating process in which it is involved, is directly modulated, altered or affected to a greater extent than other proteins that are not involved in the particular intracellular calcium-modulating process or signaling pathway that the particular protein is involved in.

In one embodiment, the method may include a step of contacting or exposing a cell, or portion thereof (e.g., a membrane or intracellular calcium store or organelle), with an agent that modulates the level, expression, functioning, molecular interactions and/or activity of one or more proteins (or a gene or nucleic acid encoding one or more proteins) involved in modulating intracellular calcium. In particular embodiments, the agent is one that specifically modulates a particular protein involved in modulating intracellular calcium. The cell, or portion thereof, can be one that contains the protein involved in modulating intracellular calcium. The cell can be one, for example, that exhibits altered intracellular calcium. The cell can be an isolated cell, a cell in culture, in a tissue or in an organism.

Particular proteins (and/or nucleic acids encoding proteins) involved in modulating intracellular calcium (and, in particular, that are involved in, participate in, and/or provide for store-operated calcium entry, movement of calcium into, out of or within an intracellular calcium store or organelle, modulation of calcium levels in intracellular calcium stores or organelles, and/or cytosolic calcium buffering) are provided herein. The proteins provided herein and described above (and elsewhere herein) can be used in methods of modulating intracellular calcium provided herein. Thus, for example, the protein can be one that is homologous to an amino acid sequence of the protein encoded by the coding sequence of *Drosophila* gene CG9126 and/or to a mammalian stromal interacting molecule (STIM) protein, e.g., human or rodent (such as rat) STIM1. In particular embodiments, the protein is one that is involved in, participates in and/or provides for store-operated calcium entry, movement of calcium into, out of or within an intracellular calcium store or organelle, modulation of calcium levels in intracellular calcium stores or organelles, and/or cytosolic calcium buffering. In particular embodiments, the protein is one of the proteins (or is substantially homologous to one of the proteins) listed in Table 3. The protein can be, for example, a STIM or STIM-like protein, including a STIM1, STIM2, DSTIM or CSTIM protein. In one embodiment of the methods, the protein is a STIM1 protein, for example, a mammalian STIM1 protein.

The step of modulating one or more proteins involved in modulating intracellular calcium can be performed in a variety of ways and may involve the use of a number of agents. Agents that can be used in the methods include agents described herein for modulating a protein involved in modulating intracellular calcium as well as agents that can be identified using the methods provided herein for screening for or identifying particular agents (e.g., agents that interact with or modulate the level, activity and/or interactions of proteins provided herein) that modulate intracellular calcium. In particular embodiments, the agent is one that specifically modulates a particular protein involved in modulating intracellular calcium. For example, the agent can be one that specifically or selectively binds to or interacts with a protein involved in modulating intracellular calcium or a gene (or portion thereof) or nucleic acid encoding such a protein and/or that is based on a specific feature, e.g., amino acid or nucleic acid sequence, of the protein. Included among such agents are compounds that specifically or selectively bind to or interact with such a protein, antibodies that specifically or selectively recognize such a protein, peptides that specifically alter (e.g., disrupt or inhibit) interaction of such a protein with another molecule, and nucleic acids that specifically bind to or hybridize with a gene, or portion thereof, or nucleic acid (e.g., DNA, RNA, mRNA) encoding such a protein.

In one example of modulating such proteins, the level and/or expression of a protein (and/or nucleic acid encoding a protein) involved in modulating intracellular calcium can be altered, e.g., in a cell or portion thereof. For example, the level and/or expression of a protein (and/or nucleic acid encoding a protein) involved in modulating intracellular calcium can be increased or reduced. In a particular embodiment, the level and/or expression of a protein (and/or nucleic acid encoding a protein) involved in modulating intracellular calcium is specifically or selectively altered.

In one method for altering the level of a protein in a cell or portion thereof, the level of expression of nucleic acid encoding the protein is altered. The level of expression of nucleic acid encoding the protein can be specifically or selectively altered. Agents for use in altering nucleic acid expression include agents that functionally bind to transcription regulatory sequences that are operably linked to nucleic acid encoding a protein, and nucleic acids. Nucleic acid agents can also be used to alter protein levels. Such nucleic acid agents include inhibitory nucleic acids that reduce the level of and/or reduce or prevent the translation of mRNA coding for a protein. Such agents include RNA, e.g., antisense RNA and molecules that can be used in RNA interference-based processes, such as double-stranded RNA (dsRNA) and small interfering RNAs. Expression of a nucleic acid encoding a protein can also be reduced or eliminated by introducing a nucleic acid, such as a cDNA or expression vector, that serves to disrupt (e.g., through homologous recombination) the already present DNA encoding the protein such that the level of the protein is decreased in a cell or the protein that is produced is altered (e.g., truncated) such that it is not functional or active with respect to its intracellular calcium-modulating activity. The level of a protein in a cell can also be altered by altering, e.g., increasing, the number of copies of nucleic acid encoding the protein present in the cell. Thus, for example, an agent can be a nucleic acid, e.g., genomic DNA, cDNA or expression vector, that is introduced into the cell for expression of the protein therein, thereby increasing the level of the protein in the cell.

Agents that can affect expression of a nucleic acid encoding particular proteins provided herein are described herein and/or can be identified and produced using methods described herein and/or known in the art. For example, an agent that modulates transcription regulatory elements of a STIM1 gene can be identified as an agent that alters the level of expression of a reporter molecule operably linked to STIM1 gene promoter sequences. In addition, numerous examples of nucleic acids encoding STIM and STIM-like proteins (and portions thereof) are provided herein and can be used in designing and producing cDNAs, expression vectors, antisense RNAs and dsRNAs using methods known in the art.

In another example of modulating a protein involved in modulating intracellular calcium, an activity of a protein (and/or nucleic acid encoding a protein) involved in modulating intracellular calcium can be altered, e.g., in a cell or portion thereof, by methods other than through altering protein (and/or nucleic acid) levels. For example, an activity of a protein (and/or nucleic acid encoding a protein) involved in modulating intracellular calcium can be increased or reduced. An activity of a protein (and/or nucleic acid encoding a protein) involved in modulating intracellular calcium can be specifically or selectively altered. For example, the activity of a particular protein (and/or nucleic acid encoding a particular protein) can be altered to a greater extent than the activity of other proteins such as proteins that are not involved in a particular intracellular calcium-modulating process or pathway that the particular protein is involved in. The activity can be one that is involved in modulating intracellular calcium either directly (e.g., has an immediate direct effect) or indirectly (e.g., an upstream event in a pathway that ultimately affects intracellular calcium). Alterations in an activity of the protein include, but are not limited to, increases and decreases in an activity and/or functioning of the protein. Activities of calcium-modulating proteins include, but are not limited to, calcium transport, calcium binding, other interactions (e.g., protein-protein interactions) and regulation of calcium-modulating proteins. Thus, agents that modulate these activities, or any other activity involved in intracellular calcium modulation, can be used in the methods provided herein. For example, antibodies or other proteins that specifically bind to the protein and modulate such activities can be agents used in the methods. Examples of particular antibodies that recognize and bind to STIM proteins are described herein. An antibody or other protein may, for instance, bind to a site of a regulatory protein and reduce or eliminate its binding to the protein it regulates, thereby reducing its regulatory activity. A peptide based on a particular amino acid sequence of a protein (e.g., the sequence of a protein-protein interaction domain) can be an agent that may, for example, alter (e.g., disrupt or inhibit) interaction of a protein with a binding or interacting partner. Examples of a number of domains, including protein-protein interaction domains, of STIM proteins are described herein and with reference to particular STIM amino acid sequences. Molecules, such as small organic molecules, can also be agents that may, for example, reduce or increase calcium transport by an ion transport protein and thus can be agents used in the methods. Agents that modulate particular proteins provided herein can also be identified using methods described herein and/or known in the art. Such methods include binding and interaction assays and assays for detecting disruption or inhibition of binding (e.g., STIM1 homotypic and STIM1/STIM2 hetero-oligomeric interactions) described above.

2. Altered Intracellular Calcium

In one embodiment of the methods of modulating intracellular calcium, one or more proteins (and/or nucleic acid encoding one or more proteins) involved in modulating intracellular calcium is (are) modulated in a particular cell (or portion thereof): a cell (or portion thereof) that exhibits altered intracellular calcium. Altered intracellular calcium in a cell can be differences in intracellular calcium relative to a cell recognized as normal with respect to intracellular calcium, e.g. a cell that exhibits overall calcium homeostasis and controlled, regulated calcium responses to activation of processes that involve calcium mobilization. Thus, altered intracellular calcium can be aberrant, abnormal, or defective intracellular calcium or intracellular calcium regulation. This embodiment of the methods can involve providing or selecting a cell that exhibits altered intracellular calcium. A variety of methods are described herein and/or known in the art for assessing intracellular calcium, and numerous aspects of intracellular calcium regulation or modulation, in a cell or portion thereof to determine if a cell exhibits altered intracellular calcium.

Altered intracellular calcium at a basic level can be an alteration in calcium levels and/or calcium location in a cell and/or movement of calcium into, out of or within a cell or intracellular organelle. Thus, in one example, an alteration in intracellular calcium can be an alteration in the calcium level within an intracellular organelle or calcium storage compartment or an alteration in basal or resting cytosolic calcium levels. Altered intracellular calcium can occur through an alteration in any one or more aspects of intracellular calcium modulation, including alterations in store-operated calcium entry, calcium buffering, receptor-mediated and second messenger-operated ion (e.g., calcium) movement. For example, an alteration of store-operated ion flux into a cell can be a complete or nearly complete elimination of the activity, a reduction of the activity, an alteration in properties or characteristics (e.g., current properties or sensitivities) of the activity or an increase in the activity relative to the activity in a cell that does not have altered store-operated calcium entry activity.

Cells that have altered intracellular calcium can have phenotypes indicative of the alteration(s). For example, T cells, fibroblasts, and in some cases B cells, from patients with a primary T cell immunodeficiency or severe-combined immunodeficiency (SCID) having a principal defect in T cell activation show a strong defect in store-operated calcium entry (Feske et al. (2001) *Nature Immunol.* 2:316-324; Paratiseti et al. (1994) *J. Biol. Chem.* 269:32327-32335; and Le Deist et al. (1995) *Blood* 85:1053-1062). In another example, psoriatic keratinocytes (from patients with plague-type psoriasis) have disturbed (down-regulated) store-operated calcium entry and slightly lower calcium levels in calcium stores relative to normal keratinocytes (Karvonen et al. (2000) *J. Invest. Dermatol.* 114:693-700). In a further example, B cells from a patient with Scott syndrome (an inherited disorder of the migration of phosphatidylserine toward the exoplasmic leaflet of the plasma membrane of stimulated white blood cells) show an alteration (reduction) in store-operated calcium entry (Martin et al. (2000) *Biochem. Biophys. Res. Commun.* 279:639-645; Martinez et al. (1999) *Biochemistry* 38:10092-10098).

Provided herein are methods of modulating intracellular calcium in a particular selected cell which is one that has altered intracellular calcium. The methods include a step of modulating one or more proteins (and/or a gene or nucleic acid encoding one or more proteins) involved in modulating intracellular calcium, and, in particular, proteins provided herein, including STIM and STIM-like proteins. In particular embodiments, the selected cell is one that exhibits altered store-operated calcium entry, calcium buffering, and/or calcium levels in or movement of calcium into, out of or within an intracellular calcium store or organelle. In particular embodiments, the cell is an immune system cell (e.g., a lymphocyte, white blood cell, T cell, B cell), a fibroblast (or a cell derived from a fibroblast), or an epidermal, dermal or skin cell (e.g., a keratinocyte). The step of modulating one or more proteins (or nucleic acid encoding one or more proteins) involved in modulating intracellular calcium can involve, for example, increasing or reducing the level, expression of, an activity of, function of and/or molecular interactions of a protein. For instance, if a cell exhibits a deficit in some aspect of intracellular calcium, e.g., store-operated calcium entry, then modulating may involve increasing the level of, expression of, an activity or function of or a molecular interaction of a protein (and/or nucleic acid encoding a protein). If a cell exhibits an increase in calcium levels or lack of regulation of an aspect of intracellular calcium modulation, then modulating may involve reducing the level of, expression of, an activity or function of or a molecular interaction of a protein (and/or nucleic acid encoding a protein).

F. Methods of Screening for or Identifying Agents for the Treatment of a Disease or Disorder Provided herein are methods for screening for or identifying agents or candidate agents for the treatment or prevention of diseases or disorders. Many of these methods are also methods for screening for or identifying an agent that modulates intracellular calcium. In a first embodiment, the methods provided herein and described above (and elsewhere herein) for screening for or identifying an agent that modulates intracellular calcium can be used to identify agents and candidate agents for the treatment of diseases and disorders involving or characterized at least in part by calcium dyshomeostasis or dysregulation or alterations in intracellular calcium, including, for example, alterations in calcium signaling. Therapeutic potential of candidate agents can be further evaluated in disease models, which include cell- and organism-based systems. Models for diseases and disorders involving alteration of intracellular calcium are described herein and/or known in the art.

Methods provided herein of identifying or screening for agents that modulate intracellular calcium, and methods provided herein of identifying or screening for agents or candidate agents for the treatment or prevention of diseases/disorders also include methods which utilize particular cells and/or organisms, i.e., cells and/or organisms that have altered intracellular calcium (or that exhibit calcium dysregulation) and/or that are models of diseases or disorders that (1) involve or are characterized at least in part by calcium dyshomeostasis or dysregulation or alterations in intracellular calcium or (2) involve an alteration or aberrant functioning of a cellular process which relies on or is regulated by intracellular calcium. Such cells or organisms are known in the art and/or described herein. In one embodiment of such methods, the effect of a test agent on intracellular calcium is directly or indirectly monitored or assessed using a cell, or portion thereof, containing a polymorphic form of one or more proteins (or portion thereof) involved in modulating intracellular calcium (and/or a polymorphic form of a nucleic acid, such as a gene, cDNA or RNA, or portion(s) thereof, encoding such protein) that is not a wild-type form of the protein (or nucleic acid) and that is associated with an alteration in intracellular calcium in the cell, or portion thereof. The alteration in intracellular calcium can be relative to intracellular calcium in a cell, or portion thereof, that contains a wild-type or reference form of the one or more proteins (or nucleic acid, or portion thereof, encoding a protein) involved in modulating intracellular calcium. In particular embodiments, the alteration in intracellular calcium can be an alteration of store-operated calcium entry, cytosolic calcium buffering, calcium levels in or movement of calcium into, out of or within an intracellular calcium store or organelle (e.g., endoplasmic reticulum) and/or maintenance of resting cytosolic calcium levels. In a particular embodiment, the effect(s) of a test agent on store-operated calcium entry, cytosolic calcium buffering, calcium levels in or movement of calcium into, out of or within an intracellular calcium store or organelle (e.g., endoplasmic reticulum) and/or resting cytosolic calcium levels is (are) assessed. In this embodiment, the test agent can be any agent. The cell, or portion thereof, used in the method can be an isolated cell, one or more cells in a culture or collection of cells or can be in a tissue or organism (e.g., an animal model).

In another embodiment of the methods for screening for or identifying an agent or candidate agent for the treatment of a disease or disorder, the method can be conducted using a particular test agent: one that binds to, interacts with and/or modulates interactions, activities, levels or any physical, structural or other property of a protein involved in modulating intracellular calcium. In this embodiment, the method includes monitoring or assessing the effects of such a test agent on intracellular calcium and/or a disease/disorder phenotype of a cell- or organism-based model of a disease or disorder that (1) involves or is characterized at least in part by calcium dyshomeostasis or dysregulation or alterations in intracellular calcium (including, for example, alterations in calcium signaling) or (2) involves an alteration or aberrant functioning of a cellular process which relies on or is regulated by intracellular calcium. In particular embodiments, the effect(s) of a test agent on store-operated calcium entry, cytosolic calcium buffering, calcium levels in or movement of calcium into, out of or within an intracellular calcium store or organelle (e.g., endoplasmic reticulum) and/or resting cytosolic calcium levels is (are) assessed. Test agents used in this embodiment of the methods can be agents that are already known to bind to, interact with and/or modulate a particular protein involved in modulating intracellular calcium or can be identified as such using methods described herein and/or known in the art. Methods for identifying such test agents include methods described herein above, such as, for example, binding, interaction, level and activity assays (and, in particular, STIM protein binding and interaction assays, activity assays and assays for detecting disruption or inhibition of binding, e.g., STIM1 homotypic and STIM1/STIM2 hetero-oligomeric interactions, described above.) The method can optionally include a step of identifying an agent that can bind to, interact with and/or modulate interactions, activities, levels or any physical, structural or other property involved in modulating intracellular calcium. This optional step can be performed prior to or concurrently with the step of monitoring the effects of the test agent on intracellular calcium and/or a disease/disorder phenotype.

In particular embodiments of any of the methods of screening for or identifying an agent or candidate agent for the treatment of a disease or disorder provided herein, the protein(s) involved in modulating intracellular calcium can be a protein that is involved in, participates in and/or provides for store-operated calcium entry, cytosolic calcium buffering, maintenance of resting cytosolic calcium levels and/or modulation of calcium levels in, or movement of cations into, out of or within an intracellular organelle or calcium store, such as, for example, the endoplasmic reticulum. In particular embodiments, the protein involved in modulating intracellular calcium is an ion transport protein, such as, for example, an ion transport protein that is involved in, participates in and/or provides for store-operated calcium entry or movement of calcium into, out of or within the endoplasmic reticulum or other calcium store. In one embodiment, the protein involved in modulating intracellular calcium is a component of a store-operated calcium entry channel complex (e.g., a multimeric complex containing multiple subunits of the same and/or different proteins). In another embodiment the protein involved in modulating intracellular calcium is a modulatory protein. A protein involved in modulating intracellular calcium (and/or nucleic acid, or portion(s) thereof, encoding a protein involved in modulating intracellular calcium) may be contained in a cell or portion thereof, such as, for example, a cell membrane (e.g., plasma membrane or an intracellular membrane). The methods may be performed in particular embodiments under conditions that permit specific evaluation of store-operated ion flux or movement, resting cytosolic calcium levels, cytoplasmic calcium buffering and/or cation levels in, or movement into, out of or within an intracellular organelle or calcium store, such as, for example, the endoplasmic reticulum.

A protein involved in modulating intracellular calcium that is used in the methods (or on which a method is based) can be a full-length or complete protein (e.g., a protein that contains the complete amino acid sequence encoded by a gene, cDNA or RNA or a complete amino acid sequence that lacks sequences that are removed during processing of the protein, including removal of a signal sequence, such as may occur in transport of a protein to a particular cellular location, or processing to remove a pre- and/or pro-sequence of a protein) or a portion of a complete protein. In embodiments of the methods that involve assessing a functional activity of the protein, the protein used in the method can be a portion of a full-length protein that is associated with, or exhibits or is sufficient for producing the functional activity, e.g., an intracellular calcium-modulating activity. In embodiments of the methods that involve assessing a property of the protein that is not necessarily the intracellular calcium-modulating activity of the protein, the protein used in the method can be a portion of a full-length protein that is associated with the particular property being assessed, e.g., binding properties, and can be, for example, a particular domain of the protein. Similarly, when a nucleic acid, or portion(s) thereof, encoding a protein involved in modulating intracellular calcium is used in the methods, the nucleic acid can be a complete gene, e.g., including transcriptional regulatory sequences, a complete protein coding sequence, e.g., cDNA or RNA, or portion(s) of these (e.g., a portion encoding a functional domain of a protein).

In particular embodiments of the methods for screening for or identifying an agent or candidate agent for the treatment of a disease or disorder, a protein involved in modulating intracellular calcium can be a protein (or portion thereof) involved in modulating intracellular calcium as provided herein and described above (and elsewhere herein). Thus, for example, the protein can be one that is homologous to an amino acid sequence of the protein encoded by the coding sequence of Drosophila gene CG9126 and/or to a mammalian stromal interacting molecule (STIM) protein, e.g., human or rodent (such as rat) STIM1. In particular embodiments, the protein is one that is involved in, participates in and/or provides for store-operated calcium entry, movement of calcium into, out of or within an intracellular calcium store or organelle, modulation of calcium levels in intracellular calcium stores or organelles, and/or cytosolic calcium buffering. In particular embodiments, the protein is one of the proteins (or is substantially homologous to one of the proteins) listed in Table 3. The protein can be, for example, a STIM or STIM-like protein, including a STIM1, STIM2, DSTIM or CSTIM protein. In one embodiment of the methods, the protein is a STIM1 protein, for example, a mammalian STIM1 protein.

1. Cells and Cell Models

Cell that can be used in embodiments of the methods for screening for or identifying agents or candidate agents for the treatment of diseases and disorders include cells that exhibit an alteration in intracellular calcium or that exhibit calcium dysregulation or dyshomeostasis. Such cells can also be used in elucidating the mechanisms underlying calcium dyshomeostasis or altered calcium signaling in a cell as well as in dissecting processes involved in intracellular calcium regulation. Cells for use in the methods also include cell models of diseases or disorders involving or characterized at least in part by calcium dyshomeostasis or dysregulation or alterations in intracellular calcium, including, for example, alterations in calcium signaling.

Cells that exhibit an alteration in intracellular calcium or that exhibit calcium dysregulation or dyshomeostasis can include cells that contain a polymorphic form of one or more proteins (or portion thereof) involved in modulating intracellular calcium (and/or a polymorphic form of a nucleic acid, such as a gene, cDNA or RNA, or portion(s) thereof, encoding such protein) that is not a wild-type or reference form of the protein (or nucleic acid). A polymorphic form of a protein or nucleic acid is a form that varies in amino acid or nucleotide sequence relative to a reference or wild-type form. With respect to cells that exhibit altered intracellular calcium and that contain a polymorphic form of a protein and/or nucleic acid, a wild-type or reference form of the protein or nucleic acid can be one that occurs in a cell that does not exhibit altered intracellular calcium or calcium dyshomeostasis. A wild-type form of a nucleic acid or protein can often be a predominant form in a population. A polymorphic or mutant protein can be one that has an altered activity or function or one that has no activity or is non-functional, particularly relative to a wild-type, reference or predominant form of the protein. Cells that contain a polymorphic form of one or more proteins (or portion thereof) involved in modulating intracellular calcium (and/or a polymorphic form of a nucleic acid, such as a gene, cDNA or RNA, or portion(s) thereof, encoding such protein) that is not a wild-type form of the protein (or nucleic acid) can be evaluated using methods described herein and/or known in the art to identify cells that exhibit an alteration in intracellular calcium in the cell (or portion thereof). For example, an alteration in intracellular calcium can be identified through comparison of intracellular calcium of the cell to intracellular calcium of a cell, or portion thereof, that contains a wild-type or reference form of the one or more proteins (or nucleic acid, or portion thereof, encoding a protein) involved in modulating intracellular calcium. Wild-type or reference proteins (and nucleic acids encoding such proteins) include proteins (and nucleic acids) described herein and listed in Table 3. In particular embodiments, the alteration in intracellular calcium can be an alteration of store-operated calcium entry, cytosolic calcium buffering, calcium levels in or movement of calcium into, out of or within an intracellular calcium store or organelle (e.g., endoplasmic reticulum) and/or maintenance of resting cytosolic calcium levels.

A polymorphic form of a sequence of nucleotides or amino acids can be any difference in the sequence relative to a reference or wild-type sequence. For example, a difference in sequence can be a single nucleotide change (e.g., a SNP), a single amino acid change, a deletion or insertion of a single nucleotide or amino acid, or can be an alteration of two or more consecutive nucleotides or amino acids (e.g., insertions and deletions of a sequence of two or more nucleotides or amino acids). A polymorphic form of a protein can also be one which is shorter (or truncated) relative to a reference or wild-type amino acid sequence. A polymorphic form of a gene that encodes a particular protein can be one that differs from a reference or wild-type form in a non-coding portion of the gene sequence (e.g., transcriptional regulatory regions, such as promoters or enhancers, introns, and untranslated sequences). Polymorphisms located in the primary RNA transcript-encoding portion of a gene may affect the processing of the transcript into mature RNA. For example, single nucleotide changes can disrupt the function of splicing enhancers located within coding sequences. Enhancers can be disrupted by single nonsense, missense or translationally silent point mutations. Single nucleotide polymorphisms that function as exon splicing silencers have also been described which could alter splicing patterns of primary RNA transcripts.

Polymorphisms or mutations of particular proteins involved in modulating intracellular calcium provided herein (or polymorphic genes or nucleic acids encoding such proteins or portions thereof) are known (see, e.g., NCBI database of single nucleotide polymorphisms (SNPs) accessible at www.ncbi.nlm.nih.gov/SNP/index.html). Cells containing a particular polymorphic form of a protein (and/or gene or nucleic acid encoding a protein) provided herein (e.g., a STIM or STIM-like protein, including proteins listed in Table 3) can be cells that endogenously contain such proteins (and/or nucleic acids) or that are generated through recombinant processes, such as, for example, through transfer of a polymorphic nucleic acid (or nucleic acid encoding a polymorphic protein or portion thereof) into a host cell or through disruption of an endogenous gene encoding a wild-type form of a protein. Thus, cell models include recombinant cells that contain heterologous nucleic acid encoding a polymorphic form of one or more proteins involved in intracellular calcium modulation.

Cell models that exhibit an alteration in intracellular calcium or that exhibit calcium dysregulation or dyshomeostasis can also include recombinant cells in which expression of a protein involved in intracellular calcium modulation (which is either endogenously expressed in the cell or is expressed in the cell from a heterologous nucleic acid) has been altered or eliminated, such as by replacing or modifying the promoter region or other regulatory region driving expression of nucleic acid encoding the protein. Such a cell can be produced, using methods known in the art and/or described herein, by introduction into a cell of heterologous nucleic acid that either targets and alters DNA regulatory sequences associated with an endogenous gene or that links DNA encoding the protein to a particular expression regulation sequence(s). Cell models including a recombinant cell in which expression of an endogenous protein involved in intracellular calcium modulation as identified above has been reduced or eliminated can be produced by disruption or elimination (e.g., through gene knock-out, antisense RNA or RNA interference methods) of the gene or RNA encoding the protein in the cell.

Any cell may be used in generating a cell models. In particular embodiments of the cell models, the cell is a neuronal, nervous system- or tissue-derived cell or a brain cell. For example, cells from a known cell line can be used, such as from neuroblastoma SH-SY5Y cells, pheochromocytoma PC12 cells, neuroblastoma SK-N-BE(2)C cells, human SK-N-MC neuroblastoma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells. Cell lines include HEK 293, CHO (including CHO-K1), LTK-, N2A, H6, HGB, and *Drosophila* S2 cells. In another embodiment, the cell can be an immune cell (e.g., lymphocyte, white blood cell, T cell or B cell), a fibroblast (or a cell derived from a fibroblast), an epidermal, dermal or skin cell (e.g. a keratinocyte), a blood cell, a kidney or renal cell (e.g., mesangial cell), a muscle cell (e.g., a smooth muscle cell such as an airway (tracheal or bronchial) smooth muscle cell) or an exocrine or secretory (e.g., salivary, including parotid acinar and submandibular gland) cell. The generation, maintenance and use of such cell lines is well known.

Other cell models of particular diseases/disorders for use in the methods include (1) cells (e.g., T cells, fibroblasts, and B cells) from subjects with a primary T cell immunodeficiency or severe-combined immunodeficiency (SCID) having a principal defect in T cell activation show a strong defect in store-operated calcium entry (Feske et al. (2001) *Nature Immunol.* 2:316-324; Partiseti et al. (1994) *J. Biol. Chem.* 269:32327-32335; and Le Deist et al. (1995) *Blood* 85:1053-1062); (2) cells (e.g., psoriatic keratinocytes) from subjects with psoriasis (e.g., plague-type psoriasis) which have disturbed store-operated calcium entry and/or slightly lower calcium levels in calcium stores relative to normal keratinocytes (Karvonen et al. (2000) *J. Invest. Dermatol.* 114:693-700); (3) cells (e.g., B cells) from subjects with Scott syndrome (an inherited disorder of the migration of phosphatidylserine toward the exoplasmic leaflet of the plasma membrane of stimulated white blood cells) which show an alteration (reduction) in store-operated calcium entry (Martin et al. (2000) *Biochem. Biophys. Res. Commun.* 279:639-645; Martinez et al. (1999) *Biochemistry* 38:10092-10098); and (4) T cell (e.g., Jurkat T cell) mutants with defective store-operated calcium entry (Fanger et al. (1995) *J. Cell Biol.* 131:655-657). Cell models also include cells derived from animal models of particular diseases/disorders, including, for example, those described herein below (and elsewhere herein).

2. Animal Models

Animal models that can be used in embodiments of the methods for screening for or identifying agents or candidate agents for the treatment of diseases and disorders include animals (particularly non-human animals) that have an alteration in intracellular calcium or that have calcium dysregulation or dyshomeostasis. Animal models for use in the methods also include any animal model of a disease or disorder involving or characterized at least in part by calcium dyshomeostasis or dysregulation or alterations in intracellular calcium, including, for example, alterations in calcium signaling.

Animal models that can be used in embodiments of the methods further include animals (particularly non-human animals) that have, in at least some of their cells, an alteration or defect in, or aberrant functioning of, a cellular process which relies on or is regulated by intracellular calcium. Such cells need not have altered intracellular calcium or calcium dyshomeostasis; yet, because intracellular calcium (and regulation thereof) plays an important role in such cellular processes, modulating intracellular calcium of such cells can be an effective treatment by compensating for the defect, counteracting the defect, reversing the defect or alleviating or eliminating the defect. Cellular processes that rely on or are regulated by intracellular calcium include, for example, cellular activation, gene expression, cellular trafficking, and apoptosis. Diseases/disorders that involve defects that may be at least partially compensated for by modulation of intracellular calcium include, but are not limited to: Autoimmune disorders, including Sjogren's syndrome (cytokines associated with lymphocyte invasion of salivary epithelial cells can reduce calcium mobilization in parotid cells; also, T-cell activation, including activation of transcription factors, cytokine gene expression and cell proliferation, depends on sustained elevation of intracellular calcium level provided by store-operated calcium influx), asthma (store-operated calcium entry may play an important role in mediating bronchial chonstriction and bronchial smooth muscle cell proliferation), glomerulonephritis and glomerular inflammation (changes in intracellular calcium, such as by store-operated calcium entry, signal monocyte adhesion in a co-culture model of glomerular inflammation).

The animal models can also be used in elucidating the mechanisms underlying calcium dyshomeostasis or altered calcium signaling in animal cells as well as in dissecting processes involved in intracellular calcium regulation. Types of animal models include, but are not limited to, non-human animals, such as non-human invertebrates and vertebrates and non-human mammals, rodents (e.g., mice, rat and hamster), cows, chickens, pigs, goats, dogs, sheep, insects, *Drosophila*, nematodes, worms, *C. elegans*, monkeys, gorillas, and other primates.

Animal models that exhibit an alteration in intracellular calcium or that exhibit calcium dysregulation or dyshomeostasis can include animals that contain a polymorphic form one or more proteins (or portion thereof) involved in modulating intracellular calcium (and/or a polymorphic form of a nucleic acid, such as a gene, cDNA or RNA, or portion(s) thereof, encoding such protein) that is not a wild-type or reference form of the protein (or nucleic acid). Such a polymorphic or mutant protein can be one that has an altered activity or function or one that has no activity or is non-functional, particularly relative to a wild-type, reference or predominant form of the protein. Such animals can be generated, for example, using methods known in the art for producing transgenic animals that express an introduced transgene. For example, such animals can be prepared by "knock-in" methods in which the endogenous form (e.g., "normal") of a gene encoding the protein(s) is replaced by a variant, such a mutant, or other form. It is also possible to replace one species', such as a rodent's, endogenous gene with a gene from another species, such as from a human. Transgenic animals also can be produced by non-homologous recombination into other sites in a chromosome; including animals that have a plurality of integration events.

In another example of animal models that can be used in the methods, the expression of nucleic acid encoding one or more proteins involved in modulating intracellular calcium (e.g., particular proteins identified herein above) is altered or eliminated in at least some cells in the animal. Alteration or elimination of expression of the protein(s) can be achieved in a number of ways. For example, expression can be altered by replacing or modifying the promoter region or other regulatory region of an endogenous gene encoding the protein(s) in the animal. Such an animal can be produced using methods known in the art, e.g., by promoting recombination between endogenous nucleic acid and an exogenous nucleic acid.

Increased expression of one or more of the proteins in a transgenic animal can be achieved by altering or replacing an endogenous promoter or by introducing additional copies of nucleic acid encoding the protein(s) into the animal. Reduction or elimination of expression of one or more of the proteins can be achieved by disruption or "knockout" of endogenous genes in the animal. For example, such an animal can initially be produced by promoting homologous recombination between a gene of interest in its chromosome and the corresponding exogenous gene of interest that has been rendered biologically inactive (typically by insertion of a heterologous sequence, e.g., an antibiotic resistance gene). In many organisms, e.g. *C. elegans*, it is possible to reduce or eliminate expression of a gene encoding a protein by introduction of double-stranded RNA that contains sequence identical or complementary to at least a portion of the sequence of the gene of interest into the animal.

Introduction of nucleic acids into cells for generation of transgenic animals can be conducted using any known method of nucleic acid delivery, including, but not limited to, microinjection, lipofection and other modes of nucleic acid delivery. The nucleic acids can be introduced into cells such as, for example, germline cells or somatic cells, such as an embryonic stem cell. For example, the nucleic acid can be introduced into a cell, such as an embryonic stem cell (ES), followed by injecting the ES cells into a blastocyst, and implanting the blastocyst into a foster mother, which is followed by the birth of a transgenic animal. Nuclear transfer methods can also be used to generate transgenic animals. In these methods, nucleic acid being used to generate a transgenic animal is introduced into a nuclear donor cell containing a totipotent nucleus, followed by transfer of the donor nucleus into a recipient cell, e.g., an enucleated oocyte, which can be transferred to a recipient female for development into a transgenic animal.

In one method of generating a "knock-out" transgenic animal, homologous recombination is performed by transforming embryo-derived stem (ES) cells with a vector containing the insertionally inactivated gene of interest, such that homologous recombination occurs, followed by injecting the ES cells into a blastocyst, and implanting the blastocyst into a foster mother, followed by the birth of the chimeric animal ("knockout animal") in which a gene of interest has been inactivated (see Capecchi, *Science* 244: 1288-1292 (1989)). The chimeric animal can be bred to produce homozygous knockout animals, which can then be used to produce additional knockout animals. Knockout animals include, but are not limited to, mice, hamsters, sheep, pigs, cattle, and other non-human mammals. The resulting animals can serve as models of diseases involving altered expression of a protein involved in intracellular calcium modulation. Such knockout animals can be used to screen for agents or candidate therapeutic agents or to test molecules that have already been identified as candidate therapeutic agents for the ability to treat or prevent such diseases or disorders.

Animal models also include non-transgenic animals. One example of such an animal model that can be used in particular embodiments of the methods is SCID-human skin chimera mouse model of psoriasis and cutaneous inflammation (see, e.g., Raychaudhuri et al. (2001) *British J. Dermatol.* 144:931-939 and Nickoloff et al. (1995) *Am. J. Pathol.* 146:580-588). This xenograft model can be generated by transplantation of psoriasis plaques onto a severe combined immunodeficient (SCID) mouse. Test agents can be delivered at the site of the lesion, and a therapeutic response can be determined, for example, through examination and comparison of clinical, morphological and histological features of the lesions of animals that are treated and not treated with the test agent. Another example of an animal model that can be used in particular embodiments of the methods is a rodent model of airway hyperresponsiveness (AHR), a characteristic of asthma. This model can be generated, for example, by sensitization through immunization with ovalbumin followed by exposure to aerosolized ovalbumin and challenge by cholinergic stimulation (e.g., via administration of methacholine or acetylcholine) (see, e.g., Xu et al. (2002) *J. Appl. Physiol.* 93:1833-1840; Humbles et al (2002) *Proc. Natl. Acad. Sci.* 99:1479-1484). Airway hyperresponsiveness (which can be evaluated using methods known in the art, e.g., using barometric plethysmography to record respiratory pressure curves and through measurement of pulmonary parameters such as pulmonary conductance and pulmonary compliance) can be assessed and compared in animals treated and not treated with test agent. A further example of an animal model that can be used in particular embodiments of the methods is a rodent model of mesangial proliferative glomerulonephritis, which can be generated, for example, by administration of anti-Thy1.1 antibody (see, e.g., Jefferson and Johnson (1999) *J. Nephrol.* 12:297-307). Any number of parameters indicative of glomerulonephritis or renal dysfunction (e.g., mesangial cell proliferation, blood pressure, urinary protein excretion, creatinine clearance, glomerulosclerosis index and other parameters) can be evaluated and compared in animals treated with and not treated with test agent. The non-obese diabetic (NOD) mouse, an inbred mouse strain that spontaneously develops an autoimmune diabetes that shares many immunogenetic features with Type 1 diabetes mellitus, is another example of an animal model that can be used in a particular embodiment of the methods. These mice also manifest many characteristics of autoimmune exocrinopathy (such as Sjorgen's syndrome) including declining exocrine tissue secretory function (see, e.g., Humphreys-Beher and Peck (1999) *Arch. Oral Biol.* 44 Suppl 1:S21-25 and Brayer et al. (2000) *J Rheumatol.* 27:1896-1904). Characteristics relevant to Sjorgen's syndrome (e.g., lymphocytic infiltrates in exocrine glands (e.g., salivary and lacrimal glands), presence of dendritic cells and macrophages in submandibular glands, integrity of the lacrimal gland by measurement of basal and stimulated tear secretion, saliva flow rates and amylase activity) can be evaluated and compared in animals treated with and not treated with test agent. An animal (e.g., rodent) model of autoimmune disease can also be used in particular embodiments of the methods. Such animals include rat models available through the National Institutes of Health (NIH) Autoimmune Rat Model Repository and Development Center (Bethesda, Md.; accessible at www.ors.od.nih.gov/dirs/vrp/ratcenter). One rat model of rheumatoid arthritis (RA) and related chronic/inflammatory autoimmune diseases is the collagen-induced arthritis (CIA) model (see, e.g., Griffiths and Remmers (2001) *Immunol. Rev.* 184:172-183). Characteristic phenotypes of autoimmune disease (e.g. altered levels of immune reactivity to self-antigens, chronic inflammation of autoantigen-expressing target organs, and activation and participation of invading mononuclear cells and tissue fibroblasts in organ damage) can be evaluated and compared in animals treated with and not treated with test agent. An animal (e.g., rodent) model of neuropathic or inflammatory pain can also be used in a particular embodiment of the methods. For example, one rat model of neuropathic pain involves development of tactile allodynia (exaggerated response to otherwise innocuous stimuli) after ligation of lumbar spinal nerves (see, e.g., Chaplan et al. (1994) *J. Neurosci. Methods*

53:55-63 and Luo et al. (2001) *J. Neurosci.* 21:1868-1875). Tactile allodynia, one characteristic feature of neuropathic pain, can be evaluated (e.g., by evaluating paw withdrawal threshold in response to application of pressure) and compared in animals treated and not treated with test agent.

Animal (e.g., rodent) models of neurodegenerative diseases (e.g. Alzheimer's disease) can also be used in a particular embodiment of the methods. Numerous transgenic mice exhibiting various characteristics of AD and other neurodegenerative diseases are available. These have been made using APP, PS1, PS2, Tau, APOE and other genes, alone and in combinations (see www.alzforum.org/members/resources/transgenic/index.html). Characteristic phenotypes of neurodegenerative disease (e.g., senile plaques, neuritic plaques, and components of each, neurofibrillary tangles, tau protein and abnormal phosphorylation of tau protein, amyloid precursor protein (APP) and processing thereof, Aβ protein, α-, β- and γ-secretases, presenilin proteins, amyloid deposition, memory or learning deficits (which can be tested in rodents by the Morris water maze (Stewart and Morris (1993) "Behavioral Neuroscience," IRL Press, R. Saghal ed. 107) and the Y-maze (Brits et al. (1981) *Brain Res. Bull.* 6:71) can be evaluated and compared in model animals treated with and not treated with test agent.

3. Evaluation of Models and Effects of Test Agents Thereon

Cell and animal models of altered intracellular calcium (e.g., calcium dysregulation or dyshomeostasis) and/or of diseases and disorders involving or characterized at least in part by calcium dyshomeostasis or dysregulation or alterations in intracellular calcium have a number of uses. For example, by evaluating the cellular or organismal phenotypes associated with the altered expression of proteins involved in intracellular calcium modulation (and/or with the expression of a polymorphic form of such proteins) in the cells/organisms and correlating such phenotypes with specific cellular molecules and processes, the disease/disorder models can be used in elucidating the mechanisms underlying calcium dyshomeostasis in a cell as well as in dissecting processes and pathways involved in intracellular calcium regulation. In addition, by evaluating the effects of test agents or candidate therapeutic agents on intracellular calcium and the phenotypic manifestations of the model cells/organisms, the models can be used in screening agents and testing candidate agents for the treatment of diseases and disorders that involve alterations in intracellular calcium or calcium dyshomeostasis.

In particular embodiments of the methods of screening for or identifying an agent or candidate agent for the treatment or prevention of diseases and disorders, a model cell and/or organism, or portion(s) thereof, is contacted with or exposed to a test or candidate agent. The effect of the test or candidate agent on (1) intracellular calcium (and, in particular, store-operated calcium entry, cytosolic calcium buffering, calcium levels in or movement of calcium into, out of or within an intracellular calcium store and/or resting cytosolic calcium levels) and/or (2) a phenotypic manifestation of a disease or disorder, or of altered intracellular calcium or calcium dyshomeostasis, is monitored or assessed. A variety of methods may be used for evaluating such parameters and are described herein and/or known in the art. The evaluation method used can depend on the aspect of intracellular calcium being assessed or the particular phenotype being assessed. In one embodiment of the methods, the effect of a test agent on intracellular calcium or a phenotypic manifestation of altered intracellular calcium or a disease/disorder can be assessed by comparing intracellular calcium or phenotypes of a cell or organism that has been exposed to or contacted or treated with test agent (test cell or organism) and a cell or organism that has not been exposed to or contacted or treated with test agent (control cell or organism). The control cell or organism can be, for example, the test cell or organism prior to contact with or exposure to test agent or can be substantially similar to the test cell or organism. In general, a test agent can be identified as an agent or candidate agent for use in treating or preventing a disease or disorder if the parameter being assessed and compared differs in the test cell or organism and the control cell or organism.

For example, in some embodiments of the methods, a test or candidate agent that alters intracellular calcium (e.g., calcium levels and/or movement of calcium into, out of or within a cell) of a model or test cell (or portion thereof) is identified as an agent or candidate agent for the treatment or prevention of a disease or disorder involving an alteration in intracellular calcium or calcium dyshomeostasis. In one embodiment, the test cell is one that exhibits calcium dyshomeostasis. Thus, for example, in such an embodiment, a test agent may be identified as an agent for use in treating or preventing a disease calcium homeostasis of a test cell is restored in the presence of the test agent (or after exposure to or contact or treatment with the test agent). In another embodiment, the test or model cell is one that contains a polymorphic form of a protein (or of a gene, or portion thereof, or nucleic acid encoding a protein) that is involved in modulating intracellular calcium. In this embodiment, a test agent may be identified as an agent for use in treating or preventing a disease, for example, if intracellular calcium of a test cell is altered in the presence of the test agent (or after exposure to or contact or treatment with the test agent) such that there is less of a difference between intracellular calcium of the test cell and a cell that contains a wild-type or reference form of the protein (or gene or nucleic acid or portion thereof).

In other embodiments of the methods, a test or candidate agent that alters a phenotype (e.g., a phenotype associated with a disease or disorder, including, e.g., a disease or disorder that involves or is characterized at least in part by altered intracellular calcium or calcium dyshomeostasis) of a model or test organism is identified as an agent or candidate agent for the treatment or prevention of a disease or disorder. An alteration or effect on a phenotype can be, for example, at least a partial reversal or reduction, or an elimination of a disease trait or phenotype exhibited by a model or test organism, or a partial or complete restoration of calcium homeostasis or modulation of calcium signaling or movement to compensate for disease-associated abnormalities in intracellular calcium. A disease trait or phenotype can be any one or more feature(s) of an organism that has a disease or disorder or altered intracellular calcium which contribute to the characterization of the organism as differing from an organism that does not have the disease or disorder or altered intracellular calcium. Thus, there are numerous and varied disease traits or phenotypes depending on the disease or disorder (e.g., particular clinical, morphological and histological features, and altered blood pressure, saliva flow rates, allodynia). A test agent can be identified as an agent or candidate agent for use in treatment of a disease or disorder if it ameliorates or eliminates the symptoms and/or manifestations of an inherited or acquired disease or disorder in a model cell and/or organism. A test agent can be identified as an agent or candidate agent for use in preventing or curing the disease or disorder if it at least partially restores the wild-type phenotype. This may include modulation of store-operated calcium entry, resting cytosolic calcium levels, calcium buffering, and/or calcium levels in or movement of calcium into, out of or within an intracellular calcium store in model cells and/or organisms. Intracellular calcium or a phenotype of a test or model cell or organism that has been contacted with or exposed to a test agent can also be compared to intracellular calcium or a phenotype of a control cell or organism that is considered a normal or non-disease cell or organism.

G. Methods of Treating a Disease or Disorder

Proteins described herein as being involved in modulating intracellular calcium, as well as agents that modulate intracellular calcium (including agents described herein and that are identified using methods provided herein), are useful in elucidating cellular processes for calcium homeostasis and signaling. The proteins involved in modulating, and the agents that modulate, intracellular calcium provided herein, are also useful in the development of methods for treating or preventing diseases and disorders.

Because of the important role that calcium regulation plays in many cellular processes including cellular activation, gene expression, cellular trafficking and apoptotic cell death, calcium dyshomeostasis is implicated in the many diseases and disorders involving such cellular activities. In addition, because any of a number of components (including components that are not direct regulators of intracellular calcium or that are involved downstream of a calcium signal in a cell) of such critical cellular processes can be altered or defective in diseases and disorders, altering of intracellular calcium in cells that have such defects (but that do not necessarily have calcium dyshomeostasis or dysregulation) can be an effective treatment by compensating for the defect, counteracting the defect, reversing the defect, or alleviating or eliminating the defect. Such cells need not have altered intracellular calcium or calcium dyshomeostasis; yet, because intracellular calcium (and regulation thereof) plays an important role in such cellular processes, modulating intracellular calcium of such cells can be an effective treatment or prophylatic method. Diseases/disorders that involve defects that may be at least partially compensated for by modulation of intracellular calcium include, but are not limited to: autoimmune disorders, including Sjogren's syndrome, asthma, glomerulonephritis and glomerular inflammation, neurological, neurodegenerative, immune system-related, inflammatory, liver and kidney diseases and disorders, aging-related disorders, and sensitivity to pain and touch.

Provided herein are methods for treating or preventing a disease or disorder. The disease or disorder can be one that involves, or is characterized at least in part by, (1) altered intracellular calcium, altered intracellular calcium regulation or calcium dyshomeostasis or dysregulation or (2) an alteration or defect in, or aberrant functioning of, a cellular process which relies on or is regulated by intracellular calcium. The disease or disorder can also be any such disease or disorder that is not cancer or a neoplastic disease. Such methods can include a step of therapeutically modulating a protein (and/or a gene or nucleic acid encoding a protein) involved in modulating intracellular calcium in a subject having such a disease or disorder or at risk of developing such a disease or disorder. Therapeutic modulation can be modulation that is associated with an effective reduction, amelioration or elimination of a symptom or manifestation of the disease or disorder or that cures the disease or disorder. The step can be a step of specifically or selectively modulating a particular protein (and/or gene or nucleic acid encoding a particular protein) involved in modulating intracellular calcium in a subject.

In particular embodiments, the level of, expression of, a molecular interaction of and/or an activity or function of a protein (and/or gene, or portion thereof, or nucleic acid encoding a protein) involved in modulating intracellular calcium is modulated in a subject having such a disease or disorder. In one embodiment, the method includes a step of administering to a subject having such a disease or disorder, or at risk for developing such a disease or disorder, an agent that modulates a protein (and/or a gene or nucleic acid encoding a protein) involved in modulating intracellular calcium. The agent can be a therapeutic agent, e.g., drug, pharmacological agent, pharmaceutical agent, that is a therapeutically active substance that can be delivered to a living organism to produce a desired, usually beneficial, effect. Agents include, but are not limited to, amino acids, peptides, polypeptides, peptiomimetics, nucleotides, nucleic acids (including DNA, cDNA, RNA, antisense RNA, interfering RNA, such as siRNA, and any double- or single-stranded forms of nucleic acids and derivatives and structural analogs thereof), polynucleotides, saccharides, fatty acids, steroids, carbohydrates, lipids, lipoproteins, glycoproteins, synthetic or natural chemical compounds, such as simple or complex organic molecules and metal-containing compounds. The agent can be one that specifically or selectively modulates a protein (and/or a gene or nucleic acid encoding a protein) involved in modulating intracellular calcium. In particular embodiments, the agent modulates the level of, expression of, a molecular interaction of and/or an activity or function of a protein (and/or gene, or portion thereof, or nucleic acid encoding a protein) involved in modulating intracellular calcium. In particular embodiments, the disease or disorder involves altered store-operated calcium entry, altered resting cytosolic calcium levels, altered calcium buffering, and/or altered calcium levels in or movement of calcium into, out of or within an intracellular calcium store (e.g., endoplasmic reticulum).

In one embodiment of the methods for treating or preventing a disease or disorder, the protein that is being modulated, or that is modulated by an agent being administered, is a protein involved in modulating intracellular calcium provided herein and described above (and elsewhere herein). Thus, for example, the protein can be one that is homologous to an amino acid sequence of the protein encoded by the coding sequence of *Drosophila* gene CG9126 and/or to a mammalian stromal interacting molecule (STIM) protein, e.g., human or rodent (such as rat or hamster) STIM1. In a particular example, the protein can be at least about 45% homologous to a specified protein over at least about 52% of the protein. In particular embodiments, the protein is one that is involved in, participates in and/or provides for store-operated calcium entry, movement of calcium into, out of or within an intracellular calcium store or organelle, modulation of calcium levels in intracellular calcium stores or organelles, and/or cytosolic calcium buffering. In particular embodiments, the protein is one of the proteins (or is substantially homologous to one of the proteins) listed in Table 3. The protein can be, for example, a STIM or STIM-like protein, including a STIM1, STIM2, DSTIM-like or CSTIM-like protein. In one embodiment of the methods, the protein is a STIM1 protein, for example, a mammalian (such as human) STIM1 protein.

Methods of modulating the level of, expression of, a molecular interaction of, an activity of and/or a function of a protein (and/or gene, or portion thereof, or nucleic acid encoding a protein) involved in modulating intracellular calcium, and, in particular, the proteins provided herein above, are described herein. Also, agents that modulate the level of, expression of, a molecular interaction of, an activity of and/or a function of a protein (and/or gene, or portion thereof, or nucleic acid encoding a protein) involved in modulating intracellular calcium, and, in particular, the proteins provided herein above, are described herein and/or can be identified using methods of screening for intracellular calcium-modulating or treatment agents provided herein. In particular embodiments, the agent is one that specifically modulates a particular protein involved in modulating intracellular calcium. For example, the agent can be one that specifically or selectively binds to or interacts with a protein involved in modulating intracellular calcium or a gene (or portion thereof) or nucleic acid encoding such a protein and/or that is based on a specific feature, e.g., amino acid or nucleic acid sequence, of the protein. Included among such agents are compounds that specifically or selectively bind to or interact with such a protein, antibodies that specifically or selectively recognize such a protein, peptides that specifically alter (e.g., disrupt or inhibit) interaction of such a protein with another molecule, and nucleic acids that specifically bind to or hybridize with a gene, or portion thereof, or nucleic acid (e.g., DNA, RNA, mRNA) encoding such a protein.

In one embodiment, the level and/or expression of a protein (and/or gene or nucleic acid encoding a protein) involved in modulating intracellular calcium can be altered (e.g., increased or reduced) or modulated. For example, an agent that modulates (e.g., increases or decreases) the level and/or expression of a protein (and/or gene or nucleic acid encoding a protein) involved in modulating intracellular calcium can be administered to a subject in such methods. In a particular embodiment, the level and/or expression of a protein (and/or gene or nucleic acid encoding a protein) involved in modulating intracellular calcium is specifically or selectively altered.

In one method, the level of a protein in a cell of a subject can be altered, for example, by altering the level of expression of nucleic acid encoding the protein. The level of expression of nucleic acid encoding the protein can be specifically or selectively altered. Agents for use in altering nucleic acid expression include agents that functionally bind to or otherwise modulate transcription regulatory sequences that are operably linked to nucleic acid encoding a protein. Such agents can be of any physical type, including peptides, compounds and nucleic acids. Nucleic acid agents can also be used to alter protein levels in other ways. Such nucleic acid agents include inhibitory nucleic acids that reduce the level of and/or reduce or prevent the translation of mRNA coding for a protein. Such agents include RNA, e.g., antisense RNA and molecules that can be used in RNA interference-based processes, such as double-stranded RNA (dsRNA) and small interfering RNAs. The level of a protein in a subject can also be altered by altering, e.g., increasing, the number of copies of nucleic acid encoding the protein present in cells within the subject. Thus, for example, an agent can be a nucleic acid, e.g., genomic DNA, cDNA or expression vector, that is introduced into a subject for expression of the protein in cells in the subject, thereby increasing the level of the protein in the subject.

Agents that can affect expression of a nucleic acid encoding particular proteins provided herein are described herein and/or can be identified and produced using methods described herein and/or known in the art. For example, an agent that modulates transcription regulatory elements of a STIM1 gene can be identified as an agent that alters the level of expression of a reporter molecule operably linked to STIM1 gene promoter sequences. In addition, numerous examples of nucleic acids encoding STIM and STIM-like proteins (and portions thereof) are provided herein and can be used in designing and producing cDNAs, expression vectors, antisense RNAs and dsRNAs (e.g., siRNAs) using methods known in the art.

In another example of modulating a protein involved in modulating intracellular calcium, an activity of a protein (and/or a gene or nucleic acid encoding a protein) involved in modulating intracellular calcium can be altered in a subject by methods other than through altering protein (and/or nucleic acid) levels. For example, an activity of a protein (and/or gene or nucleic acid encoding a protein) involved in modulating intracellular calcium can be increased or reduced. An activity of a protein (and/or gene or nucleic acid encoding a protein) involved in modulating intracellular calcium can be specifically or selectively altered. In one embodiment, an agent that modulates an activity of a protein (and/or gene or nucleic acid encoding a protein) involved in modulating intracellular calcium can be administered to a subject. The activity can be one that is involved in modulating intracellular calcium either directly (e.g., has an immediate direct effect on intracellular calcium) or indirectly (e.g., an upstream event in a pathway that ultimately affects intracellular calcium). Alterations in an activity of the protein include, but are not limited to, increases and decreases in an activity and/or functioning of the protein. Activities of calcium-modulating proteins include, but are not limited to, calcium transport, calcium binding, other interactions (e.g., protein-protein interactions) and regulation of calcium-modulating proteins. Thus, agents that modulate these activities, or any other activity involved in intracellular calcium modulation, can be used in the methods provided herein. For example, antibodies or other proteins that specifically bind to the protein and modulate such activities can be agents used in the methods. An antibody or other protein may, for instance, bind to a site of a regulatory protein and reduce or eliminate its binding to the protein it regulates, thereby reducing its regulatory activity. Antibodies may also specifically disrupt or inhibit any number of molecular interactions of a protein involved in modulating intracellular calcium. A peptide based on a particular amino acid sequence of a protein (e.g., the sequence of a protein-protein interaction domain) can be an agent that may, for example, alter (e.g. disrupt or inhibit) interaction of a protein with a binding or interaction partner. Examples of a number of domains, including protein-protein interaction domains and regulatory domains, of STIM proteins are described herein and with reference to particular STIM amino acid sequences. Agents that modulate particular proteins provided herein can also be identified using methods described herein and/or known in the art. Such methods include binding and interaction assays and assays for detecting disruption or inhibition of binding (e.g., STIM1 homotypic and STIM1/STIM2 hetero-oligomeric interactions) described above.

Antibody-based agents include antibodies (e.g., monoclonal and polyclonal) and fragments of antibodies, e.g., an antigen-binding portion. Fragments include fragments that retain the ability to specifically bind to an antigen, such as, for example, Fab, F(ab')$_2$, Fd, Fv, dAb and CDR (complementarity determining region) fragments. Methods of producing antibodies and fragments thereof are known in the art. Particular antibodies for use in the methods include antibodies specific for a STIM or STIM-like protein (or a portion thereof), such as a STIM1 or STIM2 protein or portion thereof (including antibodies described herein). In particular embodiments, an agent for use in the method is an antibody, or fragment thereof, specific for STIM1, such as human STIM1, or a portion thereof. Human monoclonal antibodies directed against human proteins can be generated using transgenic mice whose genomes include the human immunoglobulin loci instead of the murine loci. Splenocytes from these transgenic mice immunized with the antigen of interest are used to produce hybridomas that secrete human monoclonal antibodies with specific affinities for epitopes from a human protein. Mouse (or other animal) antibodies and chimeric (e.g., mouse-human) antibodies can also be humanized using methods known in the art. Such methods include methods in which at least a portion of a CDR of a human antibody is replaced with a CDR derived from a non-human antibody.

Peptide or protein fragment agents, e.g., peptides or fragments based on a particular amino acid sequence of a protein (e.g., the sequence of a protein-protein interaction domain) can also be generated using techniques known in the art. Such agents include peptides and biologically active analogs thereof. Biologically active analogs are peptide analogs that retain the ability to modulate a protein involved in modulating intracellular calcium. Examples of peptide analogs are peptides modified to increase peptide stability (e.g., modified with a non-peptide bond, D-amino acids or non-naturally occurring amino acids) and to make the peptide non-hydrolyzable (through, e.g., peptide backbone modifications). Peptides and protein fragments can be produced by a variety of methods known in the art, including, for example, recombinantly, by proteolytic digestion, or by chemical synthesis.

In particular embodiments of the methods for treating diseases and disorders provided herein, the disease or disorder can be, for example, a neurodegenerative disease or disorder, e.g., Alzheimer's disease (AD), Parkinson's disease, Huntington's disease, amyotrophic lateral sclerosis (ALS), and other brain disorders caused by trauma or other insults including aging, an immune system-related disease (e.g., an autoimmune disease or an immunodeficiency disorder or disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, and disorders of the immune system), cancer or other proliferative disease, kidney disease and liver disease.

1. Diseases a. Neurodegenerative Diseases and Disorders

Diseases or disorders that can be treated or prevented using the methods provided herein include neurodegenerative diseases and disorders. In particular embodiments, the neurodegenerative disease or disorder is not a cancer or neoplastic disease or disorder. Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) *Proc. Natl. Acad. Sci. U.S.A.* 91:534-538; Gibson et al. (1996) *Biochem. Biophys. ACTA* 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase $IP_3$-mediated $Ca^{2+}$ release from internal stores (Guo et al. (1996) *Neuro Report*, 8:379-383; Leissring et al. (1999) *J. Neurochemistry*, 72:1061-1068; Leissring et al. (1999) *J. Biol. Chem.* 274(46): 32535-32538; Leissring et al. (2000) *J. Biol. Chem.* 149(4): 793-797; Leissring et al. (2000) *Proc. Natl. Acad. Sci. U.S.A.* 97(15):8590-8593). Furthermore, mutations in PS1 or PS2 associated with an increase in amyloidogenic amyloid β peptide generation in AD are reported to be associated with a decrease in store-operated calcium entry (Yoo et al. (2000) *Neuron*, 27(3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels including store-operated channels. It has been further shown that channel blockers may be beneficial in the treatment of neurological motor dysfunction when administered in the acute posttraumatic period (Cheney et al. (2000) *J. Neurotrauma*, 17(1):83-91).

b. Diseases/Disorders Involving Inflammation and Diseases/Disorders Related to the Immune System Diseases or disorders that can be treated or prevented using the methods provided herein include diseases and disorders involving inflammation and/or that are related to the immune system. In particular embodiments, the disease or disorder involving inflammation or the immune system is not a cancer or neoplastic disease or disorder. These diseases include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration (($Ca^{2+}$)i). Store-operated calcium influx in particular is thought to play an important role in PMN activation. It has been shown that trauma increases PMN store-operated calcium influx (Hauser et al. (2000) *J. Trauma Injury Infection and Critical Care* 48 (4):592-598) and that prolonged elevations of ($Ca^2$)i due to enhanced store-operated calcium influx may alter stimulus-response coupling to chemotaxins and contribute to PMN dysfunction after injury. Modulation of PMN ($Ca^{2+}$)i through store-operated calcium channels might therefore be useful in regulating PMN-mediated inflammation and spare cardiovascular function after injury, shock or sepsis (Hauser et al. (2001) *J. Leukocyte Biology* 69 (1):63-68).

Calcium plays a critical role in lymphocyte activation. Activation of lymphocytes, e.g., by antigen stimulation, results in rapid increases in intracellular free calcium concentrations and activation of transcription factors, including nuclear factor of activated T cells (NFAT), NF-kappaB, JNK1, MEF2 and CREB. NFAT is a key transcriptional regulator of the IL-2 (and other cytokine) genes (see, e.g. Lewis (2001) *Annu. Rev. Immunol* 19:497-521). A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, modulation of intracellular calcium, and particularly store-operated calcium entry (e.g., reduction in, elimination of and enhancement of store-operated calcium entry), in lymphocytes can be a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example treatment of an automimmune disease/disorder might involve reducing, blocking or eliminating store-operated calcium entry in lymphocytes. Treatment of an immunodeficiency might involve enhancing store-operated calcium entry in lymphocytes. Examples of immune disorders include immunodeficiency or severe-combined immunodeficiency (SCID), psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In a particular embodiment of the methods for treating or preventing a disease/disorder provided herein, the disease or disorder is an immunodeficiency, such as a primary immunodeficiency, T-cell immunodeficiency or severe combined immunodeficiency (SCID). In one embodiment, the immunodeficiency is one characterized by a defect in calcium influx, and, in particular, store-operated calcium entry, into lymphocytes, such as T lymphocytes (see, e.g., Feske et al. (2001) *Nature Immunol.* 2:316-324; Partiseti et al. (1994) *J. Biol. Chem.* 269:32327-32335; and Le Deist et al. (1995) *Blood* 85:1053-1062). The method includes a step of modulating in a cell (or portion thereof) of a subject having such an immunodeficiency (or at risk for developing such an immunodeficiency), a protein (and/or gene or nucleic acid encoding a protein) involved in modulating intracellular calcium. The protein can be one that is homologous to an amino acid sequence of the protein encoded by the coding sequence of *Drosophila* gene CG9126 and/or to a mammalian stromal interacting molecule (STIM) protein, e.g., human or rodent (such as rat) STIM1. In a particular example, the protein can be at least about 45% homologous to a specified protein over at least about 52% of the protein. In particular embodiments, the protein is one that is involved in, participates in and/or provides for store-operated calcium entry, movement of calcium into, out of or within an intracellular calcium store or organelle, modulation of calcium levels in intracellular calcium stores or organelles, and/or cytosolic calcium buffering. In particular embodiments, the protein is one of the proteins (or is substantially homologous to one of the proteins) listed in Table 3. The protein can be, for example, a STIM or STIM-like protein, including a STIM1, STIM2, DSTIM-like or CSTIM-like protein. In one embodiment of the methods, the protein is a STIM1 protein. In particular, the protein is a human protein.

In one embodiment, the protein (or gene or nucleic acid encoding the protein) is specifically or selectively modulated in a cell of a subject having an immunodeficiency or at risk for developing such an immunodeficiency. In a particular embodiment, the cell is an immune cell, such as a lymphocyte, e.g., a T lymphocyte. The protein can be modulated in a number of ways as described herein. For example, the level of, expression of, a molecular interaction of and/or an activity or function of the protein (and/or gene, or portion thereof, or nucleic acid encoding a protein) involved in modulating intracellular calcium can be modulated. The step of modulating the protein can include administering to a subject an agent that modulates the protein. The agent can be one that specifically or selectively modulates the protein. Agents include, for example, but are not limited to, a peptide or polypeptide having an amino acid sequence of all or part of the protein, a nucleic acid having a nucleotide sequence of, or complementary to, a sequence in a gene or nucleic acid (e.g., cDNA or RNA transcript) encoding the protein, and a composition that modulates expression of a gene encoding the protein and/or an intracellular calcium-modulating activity of the protein. Examples of nucleotide and amino acid sequences are provided herein (see, e.g., Table 3 and listed SEQ ID NOS.).

Agents that modulate expression of a gene encoding the protein and/or an intracellular calcium-modulating activity of the protein can be identified using methods described herein. In a particular embodiment, the method of treating or preventing an immunodeficiency involves administering to a subject having an immunodeficiency (or at risk for developing an immunodeficiency) the particular protein involved in modulating intracellular calcium, a nucleic acid encoding a protein involved in modulating intracellular calcium, and/or an agent that up-regulates or enhances expression of a gene encoding the protein, thereby increasing the level and/or activity of the protein in a cell or cells of the subject. Procedures and reagents for use in delivering such agents to a subject are described herein and/or known in the art.

C. Cancer and Other Proliferative Diseases

Methods provided herein may also be used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry may play an important role in cell proliferation in cancer cells (Weiss et al. (2001) *International Journal of Cancer* 92 (6): 877-882).

d. Liver Diseases and Disorders

Diseases or disorders that can be treated or prevented using the methods provided herein include hepatic or liver diseases and disorders. In particular embodiments, the hepatic or liver disease or disorder is not a cancer or neoplastic disease or disorder. These diseases and disorders include but are not limited to alcoholic liver disease, liver injury, for example, due to transplantation, hepatitis and cirrhosis.

Store-operated calcium entry has been implicated in chronic liver disease (Tao et al. (1999) *J. Biol. Chem.*, 274 (34):23761-23769) as well as transplantation injury after cold preservation-warm reoxygenation (Elimadi et al. (2001) *Am J. Physiology*, 281(3 Part 1):G809-G815. Chronic ethanol consumption has been shown to impair liver regeneration, in part, by modulating store-operated calcium entry (Zhang et al. (1996) *J. Clin. Invest.* 98(5):1237-1244).

e. Kidney Diseases and Disorders

Diseases or disorders that can be treated or prevented using the methods provided herein include kidney or renal diseases and disorders. In particular embodiments, the kidney or renal disease or disorder is not a cancer or neoplastic disease or disorder. Mesangial cell hyperplasia is often a key feature of such diseases and disorders. Such diseases and disorders may be caused by immunological or other mechanisms of injury, including IgAN, membranoproliferative glomerulonephritis or lupus nephritis. Imbalances in the control of mesangial cell replication also appear to play a key role in the pathogenesis of progressive renal failure.

The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis can result. Data have indicated that regulators of mesangial cell growth, particularly growth factors, may act by regulating store-operated calcium channels (Ma et al. (2001) *J Am. Soc. of Nephrology*, 12:(1) 47-53). Modulators of store-operated calcium influx may aid in the treatment of glomerular diseases by inhibiting mesangial cell proliferation.

2. Agents for Treatment

Agents for use in the methods of treating a disease or disorder can be any substance or combination of substances that modulates the level of, expression of, a molecular interaction of and/or an activity of a protein involved in modulating intracellular calcium as provided herein. Examples of agents include, but are not limited to, chemical compounds, small organic molecules, amino acids, peptides, polypeptides, nucleotides, nucleic acids, polynucleotides, carbohydrates, lipids, lipoproteins and glycoproteins. Generally, an agent for treatment of a disease or disorder is a composition, such as a compound or combination of compounds, that when administered to a subject having a disease or disorder effectively reduces, ameliorates or eliminates a symptom or manifestation of the disease or disorder or that cures the disease or disorder. An agent can also be a composition that, when administered to a subject predisposed to a disease or disorder who does not yet manifest a symptom of the disease or disorder, prevents or delays development of the symptoms. The agent can have such effects alone or in combination with other agents, or may function to enhance a therapeutic effect of another agent.

3. Methods of Delivering an Agent for Treatment

Agents for use in the methods of treating or preventing a disease or disorder as provided herein may be delivered to a subject using any methods known in the art or described herein, particularly methods that provide for delivery of agent to target cells in which intracellular calcium may be altered. Typically, delivery of an agent involves the administration of an effective amount (e.g., a therapeutically effective amount) of agent or a pharmaceutically acceptable salt or derivatives thereof. The agent may be administered with a pharmaceutically acceptable, non-toxic, excipient, including solid, semi-solid, liquid or aerosol dosage forms.

Administration of the agent can be via a variety of modes and formulations for administering compounds to subjects. For example, the agent may be administered orally, by injection (e.g., intravenous, intradermal, subcutaneous, intramuscular or intraperitoneal), by inhalation, nasally, intrabronchially, rectally, parenterally, intravascularly, transdermally (including electrotransport), by implantation (e.g., insertion of implantable drug delivery systems such as microspheres, hydrogels, polymeric reservoirs, cholesterol matrices, polymeric systems and non-polymeric systems) or topically, in the form of a solid, semi-solid, lyophilized powder, or liquid dosage forms, such as, for example, tablets, suppositories, pills, capsules, powders, solutions, suspensions, emulsions, creams, lotions, aerosols, ointments, injectables and gels, preferably in unit dosage forms suitable for simple administration of precise dosages. The compositions can include a pharmaceutical carrier or excipient and an active compound (i.e., the agent or pharmaceutically acceptable salt or derivative thereof), and, in addition, may include other medicinal agents, pharmaceutical agent carriers, adjuvants and other such substances.

For oral administration, a pharmaceutically acceptable, non-toxic composition may be formed by the incorporation of excipients, such as, for example, pharmaceutical grades of mannitol, lactose, starch, magnesium stearate, sodium saccharine, talcum, cellulose, glucose, gelatin, sucrose and magnesium carbonate. Such compositions may take several forms, such as solutions, suspensions, tablets, pills, capsules, powders and sustained release formulations. The composition may contain, along with the active ingredient, a diluent, such as lactose, sucrose, dicalcium phosphate, a disintegrant, such as starch or derivatives thereof, a lubricant, such as magnesium stearate, and a binder, such as starch, gum acacia, polyvinylpyrrolidone, gelatin, cellulose and derivatives thereof.

Liquid formulations may, for example, be prepared by dissolving, dispersing an active agent or compound (for example, about 0.1% to about 95%, or 0.1% to about 50%, or about 0.5% to about 20%) and optional pharmaceutical adjuvants in a carrier, such as water, saline, aqueous dextrose, glycerol, and ethanol, to thereby form a solution or suspension. Actual methods of preparing such dosage forms are known, or will be apparent, to those skilled in the art; for example, see Remington's Pharmaceutical Sciences, Mack Publishing Company, Easton, Pa., 15th ed., 1975.

For parenteral administration, the agent may be mixed with a carrier, such as, for example, an oily ester such as ethyl oleate and isopropyl myristate. Sterile liquid pharmaceutical compositions, solutions or suspensions can be utilized by, for example, intraperitoneal injection, subcutaneous injection, intramuscular injection or intravenously.

Transdermal administration of the agent may be conducted through the use of a patch containing the agent and a carrier that is inert to the agent, is non-toxic to the skin and allows delivery of the agent for systemic absorption into the blood stream via the skin. Carriers for transdermal absorption may include pastes, e.g., absorptive powders dispersed in petroleum or hydrophilic petroleum containing the agent with or without a carrier or a matrix containing the agent; creams and ointments, e.g., viscous liquid or semi-solid emulsions, gels and occlusive devices.

Generally, an agent is administered to achieve an amount effective for amelioration of, or prevention of the development of symptoms of, the disease or disorder (i.e., a therapeutically effective amount). Thus, a therapeutically effective amount can be an amount which is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies. A therapeutically effective amount can be determined empirically by those of skill in the art.

An agent can be administered prior to, concurrently with and subsequent to the appearance of symptoms of a disease or disorder. In particular embodiments, an agent is administered to a subject with a family history of the disease or disorder, or who has a phenotype that may indicate a predisposition to a disease or disorder, or who has a genotype which predisposes the subject to the disease or disorder.

The particular delivery system used can depend on a number of factors, including, for example, the intended target and the route of administration, e.g., local or systemic. Targets for delivery can be specific cells which are causing or contributing to a disease or disorder, including, for example, cells that have altered intracellular calcium or calcium dysregulation or dyshomeostasis, and cells that do not have altered intracellular calcium but that may have some alteration, defect or deficiency that can be, at least in part, compensated, counteracted, reversed or alleviated or eliminated by altering intracellular calcium of the cell. Particular cells include, for example, immune cells (e.g., lymphocytes, T cells, B cells, white blood cells), fibroblasts (or cells derived from a fibroblast), epidermal, dermal or skin cells (e.g., a keratinocytes), blood cells, kidney or renal cells (e.g., mesangial cells), muscle cells (e.g., a smooth muscle cell such as an airway (tracheal or bronchial) smooth muscle cell) and exocrine or secretory (e.g., salivary, including parotid acinar and submandibular gland) cells. For example, a target cell can be resident or infiltrating cells in the lungs or airways that contribute to an asthmatic illness or disease, resident or infiltrating cells in the nervous system contributing to a neurological, neurodegenerative or demyelinating disease or disorder, resident or infiltrating cells involved in rejection of a kidney graft, grafted cells that when activated lead to graft-versus-host disease, resident or infiltrating cells involved in rejection of a kidney graft, resident or infiltrating cells, activation of which contributes to inflammation, e.g., in arthritis, resident or infiltrating cells in the kidney or renal system (e.g., mesangial cells) involved in neuropathy and glomerulonephritis and resident or infiltrating cells in exocrine glands (e.g., salivary and lacrimal glands) involved in autoimmune disorders (e.g., Sjogren's disease). Administration of an agent can be directed to one or more cell types or subsets of a cell type by methods known to those of skill in the art. For example, an agent can be coupled to an antibody, ligand to a cell surface receptor or a toxin, or can be contained in a particle that is selectively internalized into cells, e.g., liposomes or a virus in which the viral receptor binds specifically to a certain cell type, or a viral particle lacking the viral nucleic acid, or can be administered locally.

Nucleic acid agents (including RNA and DNA) for use in the methods can be delivered to a subject in a number of ways known in the art, including through the use of gene therapy vectors and methods. If the nucleic acid is one to be expressed in the subject, it can be operably linked to transcription regulatory nucleotide sequences such as promoter elements and 5' and 3' untranslated sequences. Regulatory sequences can be those naturally associated in a genome with the expression of the nucleic acid sequence or can be from another gene. For example, it may be desired to provide for a particular type of inducible expression of the nucleic acid in a subject or a tissue- or cell-specific expression that is other than the natural expression pattern of the nucleic acid, in which case regulatory elements from another gene may be operably linked to the nucleic acid. Nucleic acids that can be expressed in a subject include nucleic acids that encode a protein, peptide and/or an RNA molecule. RNA molecules include inhibitory molecules. For example, small interfering RNA molecules (siRNA) can be produced within a cell as, for example, hairpin transcripts (short hairpins or shRNA) (see, e.g., Qin et al. (2003) Proc. Natl. Acad. Sci. 100:183-188; Tiscornia et al. (2003) Proc. Natl. Acad. Sci. 100:1844-1848; and Robinson et al. (Feb. 18, 2003) Nature Genet. doi:10.1038/ng117). The nucleic acid can be contained within a vector that can be one useful in gene therapy, for example, a vector that can be transferred to the cells of a subject and provide for expression of the therapeutic nucleic acid agent therein. Such vectors include chromosomal vectors (e.g., artificial chromosomes), non-chromosomal vectors and synthetic nucleic acids. Vectors include plasmids, viruses and phage, such as retroviral vectors, lentiviral vectors, adenoviral vectors and adeno-associated vectors.

Nucleic acid agents can be transferred into a subject using ex vivo or in vivo methods. Ex vivo methods involve transfer of the nucleic acid into cells in vitro (e.g., by transfection, infection or injection) that are then transferred into or administered to the subject. The cells can be, for example, cells derived from the subject (e.g., lymphocytes) or allogeneic cells. For example, the cells can be implanted directly in to a specific tissue of the subject or implanted after encapsulation within an artificial polymer matrix. Examples of sites of implantation include the lungs or airways, skin, conjunctiva, central nervous system, peripheral nerve, a grafted kidney or an inflamed joint. Nucleic acids can also be delivered into a subject in vivo. For example, nucleic acids can be administered in an effective carrier, e.g., any formulation or composition capable of effectively delivering the nucleic acid to cells in vivo. Nucleic acids contained within viral vectors can be delivered to cells in vivo by infection or transduction using virus. Nucleic acids and vectors can also be delivered to cells by physical means, e.g., by electroporation, lipids, cationic lipids, liposomes, DNA gun, calcium phosphate precipitation, injection or delivery of naked nucleic acid.

The following examples are included for illustrative purposes only and are not intended to limit the scope of the invention.

H. EXAMPLES

Example 1

Evaluation of CG9126 Gene in Intracellular Calcium Modulation

This Example describes procedures used to silence the CG9126 Drosophila gene in S2 cells using RNA interference (RNAi) and to assess the effects of CG9126 gene silencing on basal cytosolic calcium levels and store-operated calcium entry. The results obtained are consistent with the CG9126 gene product being involved in modulating intracellular calcium.

A. RNAi Protocol

1. Cell Culture

S2 cells (Invitrogen) were propagated in Drosophila expression system (DES) media (Invitrogen) supplemented with 12.5% FBS, and 200 U/L penicillin/streptomycin (DES complete media). Cells were plated at a density of 1×106 cells/ml until they became ~90% confluent in a 75-cm2 T-flask. Cells were incubated at 22° C.

2. Double-Stranded RNA (dsRNA) Production

PCR primers were designed based on the CG9126 coding sequence (GenBank Accession No. AF328906). CG9126 DNA was amplified from S2 cells using the EXPAND Long Template PCR system (Roche) as per manufacturer's protocols with the following primers (both internal designations and sequence identifiers are given for each primer).

The sense strand primers contained a 5' T7 RNA polymerase binding site (GAATTAATACGACTCACTATAGGGAGA; SEQ ID NO: 47) followed by a sequence specific for the CG9126 gene.

Sense-Strand Primers:

| | |
|---|---|
| Dm000223U2 | (SEQ ID NO: 15) |
| Dm000223U55 | (SEQ ID NO: 17) |
| Dm000223U3 | (SEQ ID NO: 19) |
| Dm000223U4 | (SEQ ID NO: 21) |

The antisense-strand primers contained a 5' T3 RNA polymerase binding site (AATTAACCCTCACTAAAGGGAGA; SEQ ID NO: 48) followed by sequence specific for the CG9126 gene.

Antisense-Strand Primers:

```
Dm000223L2        (SEQ ID NO: 16)
Dm000223L556      (SEQ ID NO: 18)
Dm000223L3        (SEQ ID NO: 20)
Dm000223L4        (SEQ ID NO: 22)
```

Double-stranded RNA (dsRNA) was generated from the PCR amplification products (SEQ ID Nos. 23 and 24) using the T7 Megascript and T3 Megascript Kits (Ambion, Austin, Tex.). Duplex RNA was achieved by heating equivalent amounts of sense and antisense stands to 65° C. for 30 minutes and then slow cooling to room temperature. The concentration of dsRNA was determined by spectrophotometry (optical density at 260 nm). Double-stranded RNA was stored at −20° C.

3. Conditions for RNAi in *Drosophila* Cell Culture

*Drosophila* S2 cells were diluted to a final concentration of 1×106 cells/ml in DES complete medium. Six milliliters of cells were plated in a 75 cm2 T-flask. The cells were allowed to attach to the flask, and the DES complete media was replaced with 6 ml DES serum-free media. dsRNA was added directly to the media to an approximate final concentration of 37 nM and mixed by agitation. The cells were incubated for 30 min at room temperature followed by addition of 12 ml of DES complete media. The cells were treated with the dsRNA on day 0 of the time course. The cells were incubated and analyzed over a 4-day period to determine turnover of the target gene.

B. Analysis of CG9126 Gene Silencing

To confirm dsRNA-mediated silencing of CG9126, RNA was isolated from the S2 cells using an RNeasy™ kit from Qiagen, and RT-PCR used to monitor CG9126 mRNA levels. A reduction in CG9126 mRNA levels in cells treated with CG9126 dsRNA relative to control cells was observed starting on day 1. By day 2, CG9126 mRNA levels in cells treated with CG9126 dsRNA were reduced to less than 10% of control cells. CG9126 mRNA levels in dsRNA-treated cells remained at less than 10% of control cells on days 3 and 4 of the time course analysis.

C. Measurement of Cytosolic Calcium

Control S2 cells and S2 cells subjected to RNAi for the silencing of CG9126 were analyzed for possible effects of gene silencing on cytosolic calcium using a fluorescence-based assay.

1. Fluorescence-Based Assay Protocol

S2 cells, and S2 cells treated with CG9126 dsRNA, as described above, were seeded in a 96-well plate at a density of 100,000 cells/well (100 µl of 106 cells/ml stock). The following day, the media was removed and cells were washed with 2 mM $Ca^{2+}$ buffer (120 mM NaCl, 5 mM KCl, 4 mM $MgCl_2.6H_2O$, 2 mM $CaCl_2.2H_2O$, 10 mM HEPES, pH 7.4). Cells were loaded with 50 µl of 10 µM FLUO-4-AM dye (a $Ca^{2+}$-sensitive fluorescent dye) in 2 mM $Ca^{2+}$ buffer supplemented with 2.5 mM probenecid and incubated for 60 minutes at room temperature in the dark. The dye was removed and cells were washed with nominally $Ca^{2+}$-free buffer (120 mM NaCl, 5 mM KCl, 4 mM $MgCl_2.6H_2O$, 10 mM HEPES, pH 7.4). Cells were then incubated in 90 µl $Ca^{2+}$ free buffer supplemented with 2.5 mM probenecid. Probenecid inhibits the multidrug resistance transporter, which otherwise would transport loaded dye out of the cell.

Fluorescence of the dye-loaded cells was measured using an excitation wavelength of 485 nm and an emission wavelength of 510 nm on a FluoroSkan Ascent fluorimeter (Lab Systems). Both an Fmax and cellular fluorescence were measured for each well. The Fmax is the maximum fluorescence of FLUO-4, derived after lysis of cells, which is measured 10 minutes after adding 10 µl of 1% Triton X-100 to each well at the end of the experiment. The Fmax provides a measure of the relative amount of dye loaded in each well of the 96-well plate, and is proportional to the total number of cells in each well. By taking Fmax into account, any differences in fluorescence of different wells due to well-to-well variability that may arise during the plating procedure can be factored out of the analysis. Cellular fluorescence is the FLUO-4-dependent fluorescence from intact cells of a well.

2. Evaluation of Basal Cytosolic Calcium

Initial basal, resting calcium levels were determined in the absence of external $Ca^{2+}$ by measuring the fluorescence of the wells prior to adding any type of agent (e.g., store-depletion agent) or manipulating the medium (e.g., altering the calcium concentration of the medium) in order to evaluate store-operated calcium entry as described below. To determine basal calcium levels, the cellular fluorescence of a well was divided by the Fmax for that well at the beginning of each experiment. The cellular fluorescence/Fmax values of different wells containing control cells and cells subjected to RNAi to silence CG9126 gene expression were compared.

The results of these comparisons revealed that the basal, resting cytosolic calcium levels of S2 cells on day 4 after treatment with dsRNA corresponding to CG9126 gene sequence was nearly the same as the resting cytosolic calcium levels of control cells.

3. Evaluation of Store-Operated Calcium Entry

Store-operated calcium channels have specific pharmacological characteristics that are distinct from other ion channels. Store-operated calcium channels are activated in response to depletion of intracellular calcium stores, which is one feature that distinguishes them from other ion channels such as voltage-gated channels. Store-operated calcium entry can thus be monitored by using store depletion to activate channel activity. Either passive or active store depletion may be used to activate store-operated channel activity. Passive intracellular store depletion can be achieved using a buffering agent such as EGTA or chelator such as TPEN. Active intracellular $Ca^{2+}$ store depletion can be achieved using inositol-1,4,5-triphosphate (InsP3) to release $Ca^{2+}$ from the stores directly, or by using an agonist that activates a receptor leading to an increase in InsP3. Thapsigargin or thapsigargin-like compounds and compounds such as ionomycin, BHQ, and cyclopiazonic acid may also be used to actively deplete $Ca^{2+}$ from intracellular stores. Thapsigargin (Tg) acts to inhibit the ER $Ca^{2+}$ pump and discharge intracellular $Ca^{2+}$ stores. In the absence of external $Ca^{2+}$, thapsigargin elicits a transient elevation in cytosolic free $Ca^{2+}$ concentration ($[Ca^{2+}]i$), which is believed to result from release of stored $Ca^{2+}$, followed by removal or buffering of cytosolic $Ca^{2+}$ back to prestimulation levels. Following measurement of basal calcium, S2 cells were incubated with either 10 µl of 0.1% DMSO (control) or 10 µl of 10 µM thapsigargin (final concentration of 1 µM) for 5 minutes at room temperature. Ten microliters of 20 mM $Ca^{2+}$ buffer (120 mM NaCl, 5 mM KCl, 4 mM $MgCl_2.6H_2O$, 20 mM $CaCl_2.2H_2O$, 10 mM HEPES, pH 7.4) was then added to the cells, and the cells were incubated for 3 minutes at room temperature. Cytosolic calcium levels were then evaluated by measuring fluorescence of the wells.

To evaluate any cytosolic calcium level increases due to store-operated entry of calcium into the cell from the extracellular medium independently of any increased cytosolic calcium levels induced by non store-operated means, the basal fluorescence (measured as described above) was subtracted from the cellular fluorescence measured after treatment with or without thapsigargin and incubation in calcium-containing medium. The adjusted fluorescence value was then divided by Fmax for the particular well. These manipulations distinguish an effect on non store-operated calcium from an effect on store-operated calcium entry (i.e., thapsigargin-dependent calcium entry).

Analysis of these fluorescence values revealed that thapsigargin-dependent entry of calcium was significantly reduced in S2 cells that had been subjected to RNAi-mediated silencing of CG9126 gene compared to control cells.

Example 2

Evaluation of STIM1 in Intracellular Calcium Modulation

This Example describes procedures used to silence the STIM1 gene in human and rodent cell lines using RNA interference (RNAi) and to determine the effects of STIM1 gene silencing on thapsigargin-induced and agonist-induced store-operated calcium entry. The results obtained are consistent with STIM1 being involved in modulating intracellular calcium.

A. RNAi Protocol
  1. Cell Culture

HEK293 human embryonic kidney cells were propagated in HEK complete media (90% DMEM, 10% FBS, 2 mM L-glutamine, 1.5 mg/l sodium bicarbonate, 0.1 mM non-essential amino acids and 1.0 mM sodium pyruvate). SH-SY5Y human neuroblastoma cells were propagated in SY5Y complete media (45% DMEM without L-glutamine, 45% F-12 medium, 10% FBS, 10 ml sodium pyruvate, 10 ml Pen-strep glutamine, 1.5 mg/l sodium bicarbonate and 0.1 mM non-essential amino acids). Chinese hamster ovary (CHO) cells were propagated in 85% DMEM without L-glutamine, 15% FBS, 10 ml Pen-strep glutamine, 1.5 mg/l sodium bicarbonate and 0.1 mM non-essential amino acids.

2. Small Interfering RNA (siRNA) Production

To design STIM siRNAs, STIM1 and STIM2 cDNA sequences were examined for AA(N19)TT sequences with a GC content of about 45-60%, and without a stretch of three G nucleotides in either the sense or antisense strand. Based on these parameters, two human STIM1 siRNAs were synthesized (Dharmacon Research, Lafayette, Colo.), with sense strands corresponding to nucleotides 1140-1160 (huSTIM1-1140; SEQ ID NO:43) and 1414-1434 (huSTIM1-1414; SEQ ID NO:44). Two human STIM2 siRNAs were also synthesized, with sense strands corresponding to nucleotides 1550-1570 (huSTIM2-1550; SEQ ID NO:45) and 2560-2580 (huSTIM2-2560; SEQ ID NO:46), as well as two hamster STIM1 siRNAs, with sense strands corresponding to nucleotides 114-134 (rSTIM1-114; SEQ ID NO:91) and nucleotides 614-634 (rSTIM1-614; SEQ ID NO:92).

3. Conditions for RNAi in Mammalian Cell Culture

For experiments in 6-well dishes, cells were plated on poly-D-lysine (PDL)-coated dishes at the following densities: HEK293 cells at 300,000 cells/well, SH-SY5Y cells at 700,000 cells/well, and CHO cells at 300,000 cells/well on a PDL coated 6-well dish. For experiments in T-75 flasks, ten times as many cells were plated.

On day 0, cells were transfected with siRNA using the TransMessenger Transfection Reagent™ kit (Qiagen) according to the following procedure. Four microliters of Enhancer R (Qiagen) were diluted with 90 EC-R buffer (Qiagen), and 6.7 μl of siRNA (0.3 mg/ml; 20 μM) was added. The solution was mixed by pipetting or briefly vortexing, and then incubated 5 minutes at room temperature. Eight microliters of TransMessenger (Qiagen) was then added. The solution was mixed by pipetting or briefly vortexing, and then incubated a further 10 minutes at room temperature. While the transfection complexes were forming, the cells were washed with PBS. Nine-hundred microliters of RPMI media was added to the transfection complexes, mixed, and added directly to the cells. The cells were incubated with the transfection complexes for 3 hours at 37° C. The transfection complexes were then removed, the cells washed with PBS, and the media replaced with HEK, SY5Y or CHO complete media, as appropriate for the cell type. The cells were then incubated at 37° C. For experiments performed in T-75 flasks, all reagent volumes were increased 6-fold.

On day 2, the cells were harvested by trypsinization, counted and replated on PDL-coated plates. For cell calcium measurements, cells were replated in a 384-well plate at a density of 40,000 cells/well. For western blot or RT-PCR analysis, cells were replated in a 6-well dish at a density of 1,000,000 cells/well. On day 3, cells were assayed for cytosolic calcium levels, as described below. Cell lysates were generated to analyze protein levels by western blot, and RNA was isolated to analyze message levels by RT-PCR, as described below.

B. Analysis of STIM1 Gene Silencing by RT-PCR and Western Blot

1. RT-PCR Analysis

To confirm RNAi-mediated silencing of STIM1, RNA was isolated using an RNeasy™ kit from Qiagen, and RT-PCR used to monitor STIM1 mRNA levels. A reduction in STIM1 mRNA levels in HEK293 or SH-SY5Y cells treated with either of huSTIM1-1140 or huSTIM1-1414 siRNAs, relative to control cells, was observed. Likewise, a reduction in STIM1 mRNA in CHO cells treated with either rSTIM1-114 or rSTIM1-614 siRNAs, relative to control cells, was observed. For further assays, the huSTIM1-1140 siRNA was used for RNAi in human cells, and rSTIM1-114 siRNA was used for RNAi in CHO cells.

2. Western Blot Analysis

For analysis of STIM1 protein levels, cells were lysed in a suitable volume of lysis buffer (50 mM HEPES, (pH 7.2), 150 mM NaCl, 10% glycerol, 1% TritonX-100, 1.5 mM MgCl2, 1 mM EDTA, 10 mM Na-pyrophosphate and Complete Protease inhibitor (Roche)). Lysates were incubated on ice for 5 minutes, collected, and centrifuged at 13,000 rpm for 10 minutes in a microfuge. Supernatants were transferred to a fresh tube and protein concentration determined using the BCA Protein Assay kit (Pierce) using BSA as a standard. Cell extracts were loaded on SDS-PAGE gels and subjected to western blot analysis using an anti-STIM1 antibody (BD Biosciences).

The results of the western blot analysis indicated that STIM1 protein levels were significantly reduced in STIM1 siRNA-treated cells relative to control cells.

C. Measurement of Cytosolic Calcium

Control cells and cells subjected to RNAi for the silencing of STIM1 were analyzed for possible effects of gene silencing on cytosolic calcium using a fluorescent-based assay.

1. Evaluation of Thapsigargin-Induced Store-Operated Calcium Entry

Cells plated in 384-well plates were loaded for 45 min with FLUO-4-AM (5 μM) in a Hanks-buffered salt solution. Cells were washed and placed in a nominally $Ca^{2+}$- and $Mg^{2+}$-free Hanks solution. One minute later, 1 μM thapsigargin (Tg) was added to inhibit the ER $Ca^{2+}$ pump and discharge intracellular $Ca^{2+}$ stores. Fifteen minutes after addition of Tg, store-operated calcium entry was initiated by adding external $Ca^{2+}$ to a final concentration of 1.8 mM. The calcium response was monitored for a further 10-15 minutes. Calcium levels were monitored throughout the assay using a FLIPR384 (Molecular Devices fluorimetric imaging plate reader for high throughput screening). Analysis of the data revealed a significant reduction in thapsigargin-induced store-operated calcium entry in HEK293, SH-SY5Y and CHO cells treated with STIM1 siRNA, relative to control cells. A small but variable reduction in thapsigargin-induced ER calcium release was also observed in some experiments (see FIG. 2). The above experiment was repeated to assess thapsigargin-induced store-operated barium entry, as a surrogate for store-operated calcium entry. The procedure was identical, except that instead of adding external $Ca^{2+}$, store-operated barium entry was initiated by adding external $Ba^{2+}$ to a final concentration of 10 mM. Barium levels were monitored using the FLIPR384. The results indicated that thapsigargin-induced store-operated barium entry is reduced in cells treated with STIM1 siRNA relative to control cells.

2. Evaluation of Agonist-Induced Store-Operated Calcium Entry

Cells plated in 384-well plates were loaded for 45 min with FLUO-4-AM (5 μM) in a Hanks-buffered salt solution. Cells were washed and placed in a nominally $Ca^{2+}$- and $Mg^{2+}$-free free Hanks solution. One minute later, the muscarinic receptor agonist methacholine was added to a final concentration of 300 μM to deplete ER calcium stores. Five minutes later, store-operated calcium entry was initiated by adding external $Ca^{2+}$ to a final concentration of 1.8 mM. The calcium response was monitored for a further five minutes. Calcium levels were monitored throughout the assay using a FLIPR384 (Molecular Devices fluorimetric imaging plate reader for high throughput screening).

Analysis of the data revealed that methacholine-induced store-operated calcium entry was reduced in cells treated with STIM1 siRNA relative to control cells. STIM1 siRNA also had a possible effect on re-uptake of calcium following ER calcium release, and/or other calcium buffering mechanisms, as evidenced by a difference in the decay slope after methacholine addition in STIM1 siRNA-treated cells compared to control cells (see FIG. 3).

The above experiment was repeated to assess agonist-induced store-operated barium ion entry, as a surrogate for store-operated calcium entry. The procedure was identical, except that instead of adding external $Ca^{2+}$, store-operated barium entry was initiated by adding external $Ba^{2+}$ to a final concentration of 10 mM. Barium levels were monitored using the FLIPR384. The results indicated that methacholine-induced store-operated barium entry is reduced in cells treated with STIM1 siRNA relative to control cells.

Example 3

In Vitro Screening for Agents that Modulate Intracellular Calcium Levels

This Example describes fluorescence-based assays that were used for screening for agents that modulate intracellular calcium.

A. Assay Protocol

SH-SY5Y human neuroblastoma cells plated in 384-well plates were loaded for 45 min with FLUO-4-AM (2 μM final concentration) in a Hanks-buffered salt solution. Cells were washed and placed in a nominally $Ca^{2+}$- and $Mg^{2+}$-free Hanks solution. One minute later, a test agent or vehicle was added. After a 15 minute incubation period, 1 μM thapsigargin (Tg) was added to inhibit the ER $Ca^{2+}$ pump and discharge intracellular $Ca^{2+}$ stores. Fifteen minutes after addition of Tg, store-operated calcium entry was initiated by adding external $Ca^{2+}$ to a final concentration of 1.8 mM and the cells monitored for a further 10-15 minutes. Calcium levels were monitored throughout the assay using a FLIPR384 (Molecular Devices fluorimetric imaging plate reader for high throughput screening).

In an alternative screening assay procedure, one minute after washing out the FLUO-4-AM, 1 μM Tg was added to the SH-SY5Y cells. Fifteen minutes after addition of Tg, test compound or vehicle was added, followed by another 15 minute incubation in $Ca^{2+}$-free buffer. Store-operated calcium entry was then initiated by adding external $Ca^{2+}$ to a final concentration of 1.8 mM and the response monitored for a further 10-15 minutes.

A similar screening assay procedure was used with HEK293 and CHO cells. The screening assay can alternatively use external Ba2+ (final concentration of 10 mM) in place of external $Ca^{2+}$. In this case, thapsigargin-induced store-operated Ba2+ entry serves as a surrogate for store-operated $Ca^{2+}$ entry.

B. Data Analysis

The kinetic data from the FLIPR384 were analyzed and then stored in a relational database (ActivityBase; IDBS). Ten quantitative parameters were calculated that define various aspects of the store-operated calcium entry response. These parameters are as follows:

Mean Basal: basal fluorescence (relative fluorescence units, RFU) readings averaged over 30 seconds prior to addition of $Ca^{2+}$ to initiate store-operated calcium entry Up slope: linear regression of the increase in RFU from 2 to 60 sec after addition of $Ca^{2+}$ Up rate constant (Up K): the rate constant derived from first-order association of RFUs from 2 seconds to peak response Peak: the peak RFU (single point) achieved after addition of $Ca^{2+}$ Time to peak: the time at which the peak RFU is achieved Peak/Basal: the difference between peak and mean basal RFU Decay slope: linear regression of the decrease in RFU from the peak to the end of the measurement period Decay rate constant (Decay K): the rate constant derived from first-order decay of RFUs from the peak to the end of the measurement period.

Area under the curve (AUC): area under the curve from the addition of $Ca^{2+}$ to the end of the measurement period.

Combinations of these parameters were queried to identify agents that produce at least a 50% change from vehicle control. Active agents identified from these queries were retested under identical conditions to confirm their activity. Agents with confirmed activity were then analyzed for concentration-dependent effects, and subsequently, those agents displaying concentration-dependent effects were categorized as agents that modulate intracellular calcium.

Example 4

Characterization of cDNAs Encoding Rodent Reference STIM1s

This Example describes the procedure used to clone and sequence cDNA encoding Chinese hamster and rat STIM1 partial sequences and reference STIM1.

To clone Chinese hamster STIM1, mRNA was isolated from CHO cells. cDNA was generated from the isolated mRNA using random hexamer primers. PCR primers were designed based on the human STIM1 cDNA sequence to amplify overlapping fragments of human STIM1 cDNA. PCR reactions were performed on the CHO cell cDNA using these primers. The resulting PCR products were then sequenced. The overlapping nucleotide sequences of the PCR products were assembled to yield a partial hamster STIM1 cDNA sequence corresponding to SEQ ID NO: 95 and encoding SEQ ID NO:96. To clone rat STIM 1, mRNA was isolated from RBL 2H3 rat mast cells. By a similar procedure as described above, a partial rat STIM1 cDNA sequence (SEQ ID NO:97) was obtained encoding SEQ ID NO: 98.

To construct reference STIM1, the partial hamster sequence, nucleotides 21-2019 of SEQ ID NO:51 was extended with *Rattus norvegicus* chromosome 1 WGS supercontig sequence. This partial hamster STIM1 nucleotide sequence encodes amino acids 8-673 of SEQ ID NO:52. The nucleotides encoding the N- and C-termini of rat STIM1 were predicted from BLAST alignments of the 5' and 3' regions, respectively, of cloned hamster STIM1 with the *Rattus norvegicus* chromosome 1 WGS supercontig sequence having GenBank Accession No. NW_043388. The complete reference STIM1 nucleotide sequence corresponds to SEQ ID NO:51 and encodes SEQ ID NO:52.

Example 5

Evaluation of Human STIM2 in Intracellular Calcium Modulation

The effect of RNAi-mediated knockdown of STIM2 on store-operated calcium entry was examined, essentially as described in Example 2. siRNAs specific for STIM2 were designed and tested for message reduction by RT-PCR. Store-operated calcium entry was then evaluated in HEK293 cells transfected with either a control siRNA, an siRNA targeting STIM1 or an siRNA targeting STIM2. Knockdown of STIM1 by RNAi decreased both $Ca^{2+}$ and $Ba^{2+}$ entry into cells following thapsigargin-induced store depletion, as described in Example 2. In contrast, there was no effect on either $Ca^{2+}$ or $Ba^{2+}$ entry in cells treated with the siRNA for STIM2.

Example 6

Specificity of Effect of STIM1 Modulation on Store-Operated Calcium Entry

STIM1 siRNAs were transfected into SH-SY5Y cells and assayed for store-operated calcium entry (SOCE), $Ca^{2+}$ entry mediated through voltage-gated calcium channels (VGCCs), and membrane potential. SH-SY5Y cells express both N- and L-type VGCCs that can be activated by KCl. Cells treated with the STIM1 siRNA displayed a reduction in SOCE to less than 50% of control levels, similar to what was observed in Example 2. To assess effects on $Ca^{2+}$ entry mediated by VGCCs, Fluo-4-loaded cells bathed in a $Ca^{2+}$-containing buffer were challenged with increasing concentrations of external KCl to depolarize cells and activate VGCCs.

RNAi mediated knockdown of STIM1 had no significant effect on the peak of the KCl induced $Ca^{2+}$ signal, indicating that knockdown of STIM1 does not have a general effect on $Ca^{2+}$ entry mechanisms.

The effect of STIM1 knockdown on membrane potential was also examined in SH-SY5Y cells, under conditions similar to those used to measure VGCC activity. Control cells and cells transfected with STIM1 siRNA were loaded with the membrane potential sensitive dye, DiBAC. Cells were then washed in calcium free buffer and then challenged with increasing concentrations of KCl.

STIM1 knockdown produced no detectable effect on the resting membrane potential or the response to depolarization by KCl, indicating that the effect of STIM1 RNAi on SOCE was not due to a collapse in membrane potential. Thus, STIM1 modulation is specific for store-operated calcium entry.

Example 7

Evaluation of Effect of Recombinant Expression of Human STIM1 on Intracellular Calcium Generation of Stable Cell Lines Overexpressing Human STIM1.

A human STIM1 expression construct was prepared by inserting the 2.7-kb BamH1 fragment from IMAGE clone 4899542 (Research Genetics/Invitrogen) (SEQ ID NO: 94) into the BamH1 site of the pcDNA3.1/Zeo expression vector (Invitrogen Corp., California). The pcDNA3.1/Zeo expression vector contains a CMV promoter, T7 promoter priming site, multiple cloning site, BGH reverse priming site, BGH polyadenylation signal, f1 origin, SV40 promoter and origin, EM7 promoter, a zeocin resistance gene, SV40 polyadenylation sequence, pUC origin, bla promoter and ampicillin (bla) resistance gene. SEQ ID NO: 94 contains the complete human STIM1 coding sequence as well as 49 nucleotides of 5' untranslated sequence and 586 nucleotides of 3' untranslated sequence. SEQ ID NO: 94 also contains a silent polymorphism (CCC->CCT) relative to SEQ ID NO: 3 in the codon that encodes PRO675. Plasmid clone pcDNA[STIM1/542-5] was confirmed by sequencing.

For stable cell lines overexpressing STIM1, pcDNA [STIM1/542-5] was transfected into $3 \times 10^5$ HEK293 cells using Effectene (QIAGEN) transfection reagent following the manufacturer's protocol. Forty-eight hours after transfection, cells were harvested and replated under selection with 250 µg/ml Zeocin (Invitrogen). Colonies were selected, amplified, and evaluated for expression of STIM1 mRNA and protein by RT-PCR and western blot, respectively. Limiting dilution of the STIM1 overexpressing colonies generated individual clones.

Evaluation of Store-Operated Calcium Entry.

Multiple subclones were isolated that expressed elevated levels of STIM1 protein, one of which (referred to as HEK [STIM1]) expresses STIM1 at levels greater than 100-fold compared to HEK-Zeo controls. In multiple subclones, overexpression of STIM1 resulted in constitutive activation of a $Ca^{2+}$ entry pathway in the absence of thapsigargin or agonist induced store depletion. An example of this effect is shown for clone HEK[STIM1] (FIG. 4 panel A). Thus, when STIM1-overexpressing cells were treated with vehicle (DMSO) instead of thapsigargin in $Ca^{2+}$-free buffer, readdition of external $Ca^{2+}$ resulted in $Ca^{2+}$ entry with kinetics qualitatively similar to the kinetics of thapsigargin-dependent $Ca^{2+}$ entry in control cells.

In addition to activation of SOCE in the absence of store depletion, stable overexpression of STIM1 enhanced SOCE activated by thapsigargin (FIG. 4 panel B). However, a significant decrease in the amplitude and kinetics of the thapsigargin-mediated release of calcium from the internal stores was also observed. Calcium entry was also increased when stores were depleted by the muscarinic agonists carbachol or methylcholine. Thus, stable overexpression of STIM1 reduces the thapsigargin-mediated discharge of calcium from the internal stores and enhances SOCE when elicited by either thapsigargin or agonists to deplete the internal calcium stores. To exclude clonal variations in the results, similar experiments were performed with a second clone with similar results. These results were dependent on STIM1 overexpression, because overexpression of huAPP, an unrelated single pass transmembrane protein, had no detectable effect on TG-dependent or TG-independent SOCE in HEK293 cells.

Profiles of $Ca^{2+}$, $Sr^{2+}$ and $Ba^{2+}$ entry. The relative cation permeability was assessed in HEK-Zeo and in HEK[STIM1] cells. Cells were loaded with Fluo-4 and treated with thapsigargin to discharge intracellular $Ca^{2+}$ stores (HEK-Zeo cells), or vehicle-treated (both HEK-Zeo and HEK[STIM1] cells). After 15 minutes, 10 mM $BaCl_2$ (final concentration), 10 mM $SrCl_2$ (final concentration), or 1.8 mM $CaCl_2$ (final concentration) was added to elicit cation influx. To quantify the rate of cation influx, the first 30 seconds of data following cation addition was analyzed by linear regression.

In HEK-Zeo cells, treatment with thapsigargin to deplete intracellular $Ca^{2+}$ stores resulted in a greater increase in the initial rate of $Ca^{2+}$ and $Sr^{2+}$ entry compared to $Ba^{2+}$ entry. To test whether the cation entry pathway activated by STIM1 overexpression in HEK293 cells is similar to the endogenous store-operated pathway, the profile of $Ca^{2+}$-, $Ba^{2+}$, and $Sr^{2+}$-entry was assessed in the absence of store-depletion. HEK [STIM1] cells displayed a similar pattern of response compared to HEK-Zeo cells stimulated with thapsigargin, wherein the initial rates of $Ca^{2+}$ and $Sr^{2+}$ entry were markedly increased compared to $Ba^{2+}$.

Thus, the profile of STIM1-induced $Ca^{2+}$, $Sr^{2+}$, and $Ba^{2+}$ entry resembles the profile of endogenous store-operated cation entry in response to store-depletion.

Example 8

Modulation of Intracellular Calcium by a SOCE Inhibitor in STIM1-Overexpressing Cells Store-operated calcium entry is sensitive to the inhibitor 2-aminoethoxydiphenyl borate (2-APB). To test whether the $Ca^{2+}$ entry pathway constitutively activated by STIM1 overexpression is pharmacologically similar to endogenous SOCE, HEK[STIM1] cells were pre-incubated with increasing doses of 2-APB and STIM1-induced $Ca^{2+}$ entry was measured. Thapsigargin-mediated store depletion of both HEK-Zeo control cells and HEK[STIM1] cells followed by readdition of external calcium resulted in inhibition by 2-APB with similar $IC_{50}$ values of 11.8 µM and 10.5 µM, respectively. Treatment of HEK[STIM1] cells with 2-APB and examining calcium entry in the absence of store depletion resulted in a biphasic effect of 2-APB on calcium entry. The constitutive calcium entry was inhibited with an $IC_{50}$ value of 10.8 µM, similar to that reported for endogenous SOCE. However, at lower concentrations of 2-APB, calcium entry was potentiated. The ability to both potentiate and inhibit calcium entry is a property of 2-APB that has previously been shown to occur with the calcium release activated calcium (CRAC) channel.

Thus, overexpression of STIM1 in HEK293 cells confers a CRAC-like property to constitutive $Ca^{2+}$ entry measured in HEK293 cells. Accordingly, assays to identify agents that modulate intracellular calcium can optionally be performed in cells overexpressing STIM1 in the absence of intracellular calcium depletion protocols.

Example 9

Effect of STIM1 RNAi on Degranulation, Cytokine Release and CCE in Mast Cells The effect of STIM4 modulation on degranulation, cytokine release and CCE in mast cells was assessed. RBL-2H3 rat mast cells were electroporated with siRNA STIM1-r114 (SEQ ID NO:91), using the Bio-Rad Gene Pulser electroporator. Three days after transfection, cells were analyzed for levels of rat STIM1 protein as well as for effects on biological properties of mast cells.

To assess STIM1 protein levels, protein extracts were generated and resolved by SDS-PAGE and analyzed by western blot. Using a monoclonal antibody to STIM1 (anti-GOK), which cross-reacts with rat STIM1, levels of STIM1 were knocked down greater than 50% relative to control samples (cells transfected with a non-silencing, scrambled siRNA).

To assess degranulation and cytokine release, cells were plated and stimulated with 20 nM thapsigargin/20 nm TPA for 20 hr. Media was collected and assayed for the release of the inflammatory mediator β-hexosaminidase or for the release of the cytokine TNF-α. The β-hexosaminidase enzymatic assay was performed by adding 200 µl 1 mM p-nitrophenyl-acetyl-glucosamide substrate (Sigma #N9376) in 0.05M Na Citrate (pH 4.5) to 50 µl of conditioned media, incubating for 60' at 37° C., then adding 500 µl 0.05M Na Carbonate, 0.05M Na bicarbonate pH 10.5, mixing thoroughly, and reading the absorbance at 405 nm in a Biorad plate reader. The TNF-α release assay was performed using the Rat Tumor Necrosis Factor-α Ultrasensitive ELISA Kit from Biosource. Cells transfected with STIM1-r114 siRNA showed a decrease in both β-hexosaminidase activity and TNF-α release relative to control cells.

To assess calcium entry, cells were plated in a 384-well plate, loaded with the calcium sensitive dye Fluo-4-AM, placed in a FLIPR384 and assayed for calcium entry. Cells were stimulated with 1 µM TG in calcium free buffer for 15 minutes and then 2 mM calcium was added. Cells treated with STIM1-r114 siRNA showed a decrease in calcium entry upon store-depletion protocols, relative to control cells.

Thus, RNAi-mediated knockdown of STIM1 in rat mast cells reduces TG-induced calcium entry as well as TG/TPA-induced degranulation and cytokine release.

Example 10

Effect of STIM1 RNAi on Cytokine Secretion

Cytokine Secretion in PHA-Stimulated T cells. In Jurkat T cells, T cell receptor (TCR) stimulation leads to activation of the CRAC channel and subsequent gene expression and cytokine release. If STIM1 plays an important role in CRAC channel function, then one would predict that cytokine release in response to TCR stimulation with PHA would be affected by knockdown of STIM1 in Jurkat T cells.

To test this prediction, a stable Jurkat T cell line expressing a short hairpin siRNA to suppress expression of STIM1 was generated as follows. Oligonucleotides corresponding to the STIM1-1140 siRNA (sense oligo, 5'-GAT CCC GGC TCT GGA TAC AGT GCT CTT CAA GAG AGA GCA CTG TAT CCA GAG CCT TTT TTG GAA A-3' SEQ ID NO: 99; antisense oligo, 5'-AGC TTT TCC AAA AAA GGC TCT GGA TAC AGT GCT CTC TCT TGA AGA GCA CTG TAT CCA GAG CCG G-3' SEQ ID NO: 100) were annealed and ligated into pSilencer 2.1-U6 neo (Ambion) according to the manufacturer's protocol. Correct inserts were verified by DNA sequencing. For the control, a non-silencing scrambled siRNA (Negative Control oligo; Ambion) was generated as above. $2 \times 10^6$ Jurkat T cells were electroporated with 5 µg plasmid using a Bio-Rad Gene Pulser (140V, 30 msec, 4 pulses). Two days after transfection, cells were harvested and resuspended in media containing G-418 selection at a concentration of $1 \times 10^4$ cells/ml. 1 ml of cells/well was plated in 24-well plates. Stable pools of cells expressing the short hairpin loop constructs were characterized for STIM1 expression by western blot, and one of these pools was designated Jurkat clone 4A5. Stable pools of Jurkat cells expressing scrambled siRNA were also generated (Jurkat Negative Control, clone 2A4).

To measure IL-2 secretion from Jurkat T cells, cells were plated in a 96 well plate at a density of $1.5 \times 10^5$ cells/well. Cells were stimulated with 2.5 µg/ml PHA lectin+80 nM TPA for 20 hours. The media was collected and analyzed for IL-2 levels by ELISA (BioSource) according to the manufacturer's protocols.

Either Jurkat clone 4A5 or Jurkat Negative Control pools were stimulated with PHA/TPA, a combination of lectin and phorbol ester used for stimulating Jurkat cells for cytokine release studies. IL-2 secretion in control cells required PHA/TPA stimulation. In cells expressing the STIM1-1140 short hairpin siRNA, secretion of IL-2 upon stimulation was completely blocked.

To assess the effect of STIM1 knockdown on calcium entry, cells were loaded with the calcium sensitive dye fluo4-AM and stimulated with PHA. STIM1 knockdown cells showed a delay in calcium entry upon stimulation as well as a sustained reduction in the level of cytosolic calcium throughout the stimulation protocol. Thus, modulation of STIM1 levels in Jurkat T-cells affects both PHA-dependent calcium entry and cytokine release.

Cytokine Secretion in T Cells Activated by Other Stimuli.

IL-2 stimulation can be elicited by several stimuli that act through different pathways. anti-OKT3 activates cells through the CD3 receptor, whereas thapsigargin (TG), ionomycin and TPA activate cells through non-TCR mechanisms. PHA activates cells through the TCR, as described above.

Negative control cells and clone 4A5 cells were plated in a 96-well plate and stimulated with either vehicle (0.005% DMSO)+80 nM TPA, 1.25 µg/ml anti-OKT3 +80 nM TPA, 2.5 µg/ml PHA+80 nM TPA, 0.5 µM TG+80 nM TPA, or 1 µM ionomycin for 20 hours. IL-2 secretion was measured by ELISA (BioSource).

In control cells, there was a modest level of IL-2 secretion by anti-OKT3/TPA stimulation and a significant level of IL-2 release by PHA/TPA, TG/TPA, and ionomycin/TPA. In clone 4A5 Jurkat cells (where STIM1 protein levels were lower) there were barely detectable levels of IL-2 secretion upon stimulation by any of these agents.

To examine stimulus-induced calcium entry in these cells, either negative control cells or clone 4A4 cells were loaded with Fluo-4-AM and analyzed for calcium entry as described above. Cells were stimulated with vehicle (0.005% DMSO), 1.25 µg/ml anti-OKT3, 0.5 µM TG, or 2.5 µg/ml PHA in calcium containing buffer. As described above, cells stimulated with PHA showed an inhibition in the rate of calcium entry as well as a sustained reduction in the level of calcium. The results upon PHA stimulation were also seen in single cell imaging experiments. In imaging experiments the delay in calcium entry was much greater than seen in the FLIPR$^{384}$ experiments. A similar decrease in the level of the sustained calcium plateau upon stimulation was also seen.

When stimulated with anti-OKT3, STIM1 knockdown cells (clone 4A5) showed an increase in the amplitude of calcium entry, but no increase in the rate of calcium entry relative to control cells. STIM1 knockdown had very little effect on the rate of calcium entry or the sustained level in TG stimulated cells.

Thus, STIM1 knockdown reduces IL-2 secretion under some conditions where CCE entry is not affected. This suggests that modulation of STIM1 can have effects on CCE-independent gene expression or secretion, including specific effects on CCE-independent IL-2 expression or IL-2 secretion.

Since modifications will be apparent to those of skill in this art, it is intended that this invention be limited only by the scope of the appended claims.

What is claimed:

1. A composition for an intracellular calcium modulator assay, comprising: a recombinant cell that expresses an exogenous polynucleotide encoding a polypeptide comprising an amino acid sequence at least 90% identical to the amino acid sequence of a human or rodent Stromal Interacting Molecule (STIM) 1 protein of SEQ ID NO:4, 10, or 52, wherein the recombinant protein retains human or rodent STIM 1 intracellular calcium-modulating activity; and an exogenous agent that provides for reduction of calcium levels in an intracellular store, wherein the exogenous agent that provides for reduction of calcium levels in an intracellular store is in contact with the recombinant cell, and is selected from the group consisting of: an antagonist of the endoplasmic reticulum calcium ATPase pump, an agonist of a G-protein coupled receptor that activates phospholipase C, IP3, phospholipase C, an agonist of a ryanodine receptor, an ionophore, N,N,N',N'-tetrakis(2-pyridylmethyl)ethylenediamine (TPEN), 1,2-bis(2-amino-phenoxy)ethane-N,N,N,N'-tetraacetic acid (BAPTA) and ethylene glycol tetraacetic acid (EGTA).

2. The composition of claim 1, wherein the recombinant polypeptide comprises an amino acid sequence at least 95% identical to the amino acid sequence of SEQ ID NO:10.

3. The composition of claim 1, wherein the recombinant polypeptide comprises an amino acid sequence at least 95% identical the amino acid sequence of SEQ ID NO:4.

4. The composition of claim 3, wherein the recombinant polypeptide comprises the amino acid sequence of SEQ ID NO:4, 10 or 52.

5. The composition of claim 1, wherein the exogenous agent that provides for reduction of calcium levels in an intracellular store is selected from among IP3, phospholipase C, thapsigargin, cyclic ADP ribose, ionomycin, caffeine, ryanodine, cyclopiazonic acid, N,N,N',N'-tetrakis(2-pyridylmethyl)ethylenediamine (TPEN), di-tert-butyl-hydroquinone, histamine, muscarine, carbachol, substance P, bradykinin, serotonin, uridine triphosphate (UTP) and glutamate.

6. The composition of claim 1, wherein the recombinant cell is a human recombinant cell, a mouse recombinant cell, a rodent recombinant cell, an insect recombinant cell, or a xenopus recombinant cell.

7. The composition of claim 1, wherein the recombinant ceil is a mammalian recombinant cell.

8. The composition of claim 1, wherein the recombinant cell is a human recombinant cell.

9. The composition of claim 1, wherein the exogenous agent that provides for reduction of calcium levels in an intracellular store comprises thapsigargin, caffeine, or ryanodine.

10. The composition of claim 5, wherein the exogenous agent that provides for reduction of calcium levels in an intracellular store comprises thapsigargin.

11. The composition of claim 5, wherein the exogenous agent that provides for reduction of calcium levels in an intracellular store comprises ryanodine.

12. The composition of claim 1, wherein the recombinant polypeptide comprises an amino acid sequence at least 95% identical the amino acid sequence of SEQ ID NO: 52.

13. A composition comprising:
(i) a recombinant cell that expresses an exogenous polynucleotide encoding a polypeptide comprising an amino acid sequence at least 90% identical to the amino acid sequence of a human or rodent stromal interacting molecule (STIM) 1 protein of SEQ ID NO:4, 10, or 52, wherein the recombinant protein retains human or rodent STIM 1 intracellular calcium-modulating activity;
(ii) an exogenous agent that provides for reduction of calcium levels in an intracellular store, wherein the exogenous agent is selected from the group consisting of: an antagonist of the endoplasmic reticulum calcium ATPase pump, an agonist of a G-protein coupled receptor that activates phospholipase C, IP3, phospholipase C, an agonist of a ryanodine receptor, an ionophore, N,N,N',N'-tetrakis(2-pyridylmethyl)ethylenediamine (TPEN), 1,2-bis(2-amino-phenoxy)ethane-N,N,N,N'-tetraacetic acid (BAPTA) and ethylene glycol tetraacetic acid (EGTA); and
(iii) a test agent to be assayed for its ability to modulate intracellular calcium in the recombinant cell.

* * * * *

UNITED STATES PATENT AND TRADEMARK OFFICE
CERTIFICATE OF CORRECTION

PATENT NO. : 7,645,588 B2  Page 1 of 1
APPLICATION NO. : 10/547720
DATED : January 12, 2010
INVENTOR(S) : Roos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 104

<210> SEQ ID NO 1
<211> LENGTH: 1713
<212> TYPE: DNA
<213> ORGANISM: Drosophila melanogaster
<220> FEATURE:
<221> NAME/KEY: CDS
<222> LOCATION: (1)...(1713)
<223> OTHER INFORMATION: Dm223 Protein
<300> PUBLICATION INFORMATION:
<308> DATABASE ACCESSION NUMBER: Genbank AE003500
<309> DATABASE ENTRY DATE: 2002-09-13

<400> SEQUENCE: 1 atg cga aag aat acc att tgg aac tac tct tta ata ttc ttc tgc tgt        48
```

```
Met Arg Lys Asn Thr Ile Trp Asn Tyr Ser Leu Ile Phe Phe Cys Cys
 1               5                  10                  15 gtg ctg aag agc ata agt acg cta gat cat ggc ccg cac aca gta tca         96
Val Leu Lys Ser Ile Ser Thr Leu Asp His Gly Pro His Thr Val Ser
             20                  25                  30 gtc gat tcg aat cga cac aac aca cag cat cag tat aag caa aat ccc        144
Val Asp Ser Asn Arg His Asn Thr Gln His Gln Tyr Lys Gln Asn Pro
         35                  40                  45 aat gtt gcc tca caa cgt cac tca tcc cac gaa tct ggt cag agt tta        192
Asn Val Ala Ser Gln Arg His Ser Ser His Glu Ser Gly Gln Ser Leu
     50                  55                  60 cac aat tcg caa tcg gaa cat gtc acc cat att gcc gca tcg cac gcc        240
His Asn Ser Gln Ser Glu His Val Thr His Ile Ala Ala Ser His Ala
 65                  70                  75                  80 gga agc ggc gga gag cac tcc act cat ttg gcg caa aat ctg cac agg        288
Gly Ser Gly Gly Glu His Ser Thr His Leu Ala Gln Asn Leu His Arg
                 85                  90                  95 agc tca tat aat ctt ctg agc gag gcc atg tcc cag gct gtc agc aat        336
Ser Ser Tyr Asn Leu Leu Ser Glu Ala Met Ser Gln Ala Val Ser Asn
            100                 105                 110 gaa ttt agt tcc atg gga agt ggt tca gcg gat gga gcg tgt gct gct        384
Glu Phe Ser Ser Met Gly Ser Gly Ser Ala Asp Gly Ala Cys Ala Ala
        115                 120                 125 gat gat ttt gat tgc tac agt gga agt gtt cag gat cgc ttt ggc atg        432
Asp Asp Phe Asp Cys Tyr Ser Gly Ser Val Gln Asp Arg Phe Gly Met
130                 135                 140 gag gct att gcc agc ttg cat cgt cag cta gat gat gac gat aat gga        480
Glu Ala Ile Ala Ser Leu His Arg Gln Leu Asp Asp Asp Asp Asn Gly
145                 150                 155                 160 aac atc gat ctg agc gag tcc gat gac ttt ttg cgg gag gaa ttg aag        528
Asn Ile Asp Leu Ser Glu Ser Asp Asp Phe Leu Arg Glu Glu Leu Lys
                165                 170                 175 tac gac tcg ggc tac gaa aag cgg cag aaa gcg ttt cac ttc aat gac        576
Tyr Asp Ser Gly Tyr Glu Lys Arg Gln Lys Ala Phe His Phe Asn Asp
            180                 185                 190 gat atg cat ata tcg gtc aaa gaa ctt tgg gag gcc tgg ctc aga tcg        624
Asp Met His Ile Ser Val Lys Glu Leu Trp Glu Ala Trp Leu Arg Ser
        195                 200                 205 gag gtg cat aat tgg acc atc gag cag acc acc gat tgg ctg gct cag        672
Glu Val His Asn Trp Thr Ile Glu Gln Thr Thr Asp Trp Leu Ala Gln
210                 215                 220 tcc gtt cag ctg ccg caa tac gtt gat ctg ttc aaa tta cac aag gtt        720
Ser Val Gln Leu Pro Gln Tyr Val Asp Leu Phe Lys Leu His Lys Val
225                 230                 235                 240 act ggc gct gcc ttg cca aga ttg gct gtg aat aat ctt cag tat gtt        768
Thr Gly Ala Ala Leu Pro Arg Leu Ala Val Asn Asn Leu Gln Tyr Val
                245                 250                 255 ggc aat gta ctt ggc atc aaa gac cct ata cac aaa caa aaa atc tca        816
Gly Asn Val Leu Gly Ile Lys Asp Pro Ile His Lys Gln Lys Ile Ser
            260                 265                 270 ttg aag gca atg gat gtg gtt ctg ttt ggg cca ccg aga gaa act ggt        864
Leu Lys Ala Met Asp Val Val Leu Phe Gly Pro Pro Arg Glu Thr Gly
        275                 280                 285 acc cgc tgg aaa gac tac ata ttg gta aca ctg ttg ctt agt gct att        912
Thr Arg Trp Lys Asp Tyr Ile Leu Val Thr Leu Leu Leu Ser Ala Ile
290                 295                 300 att ggt tgt tgg tac gcc tat cag caa aat aag aat gcc aaa cgg cat        960
Ile Gly Cys Trp Tyr Ala Tyr Gln Gln Asn Lys Asn Ala Lys Arg His
305                 310                 315                 320
```

```
ctg cgt cga atg gcc cag gat atg gag gga ttg cag agg gct gag caa      1008
Leu Arg Arg Met Ala Gln Asp Met Glu Gly Leu Gln Arg Ala Glu Gln
                325                 330                 335 agt cta cag gag atg cag aag gaa cta gaa cgg gcc aga atg gag cag      1056
Ser Leu Gln Glu Met Gln Lys Glu Leu Glu Arg Ala Arg Met Glu Gln
            340                 345                 350 gaa aat gtg gca aca gaa aaa cta gat ttg gag cgt cgt cta aaa gaa      1104
Glu Asn Val Ala Thr Glu Lys Leu Asp Leu Glu Arg Arg Leu Lys Glu
        355                 360                 365 gcg ccc act ctc agt tca tcg aac tcg gat ttg gaa gtt cag cag ctg      1152
Ala Pro Thr Leu Ser Ser Ser Asn Ser Asp Leu Glu Val Gln Gln Leu
    370                 375                 380 aaa aag gaa atc gag atg ttg cgc aac gaa ttg tcc cgc gcc gaa ttc      1200
Lys Lys Glu Ile Glu Met Leu Arg Asn Glu Leu Ser Arg Ala Glu Phe
385                 390                 395                 400 gag cta gta gac aac tgc tgg tca ccg ccg cca caa ctg caa tca tgg      1248
Glu Leu Val Asp Asn Cys Trp Ser Pro Pro Pro Gln Leu Gln Ser Trp
                405                 410                 415 ctt caa tac aca tat gaa cta gaa agt aag aat cat cag aag aag cgc      1296
Leu Gln Tyr Thr Tyr Glu Leu Glu Ser Lys Asn His Gln Lys Lys Arg
            420                 425                 430 acg tcg gct gag aag cag cta cag tcg gcc aga gag gct tgt gag aaa      1344
Thr Ser Ala Glu Lys Gln Leu Gln Ser Ala Arg Glu Ala Cys Glu Lys
        435                 440                 445 ttg cgt aag aaa cgg tca agt ttg gtg ggt gcg ttc gtt tcc acg cac      1392
Leu Arg Lys Lys Arg Ser Ser Leu Val Gly Ala Phe Val Ser Thr His
    450                 455                 460 gga aag agt att gat gat gtg gat cgg tcg att gtt gag gca cgg aat      1440
Gly Lys Ser Ile Asp Asp Val Asp Arg Ser Ile Val Glu Ala Arg Asn
465                 470                 475                 480 gcc ctc gga gat gta aca aac gag ctg caa gaa cga ctg cat cgc tgg      1488
Ala Leu Gly Asp Val Thr Asn Glu Leu Gln Glu Arg Leu His Arg Trp
                485                 490                 495 aag caa atc gag acg tgc ctt ggc tta aac att gtg aac aac aat ggt      1536
Lys Gln Ile Glu Thr Cys Leu Gly Leu Asn Ile Val Asn Asn Asn Gly
            500                 505                 510 ctg ccc tac ttg gag aat gtt ctg tac ggt cga aat ggg ggc tta caa      1584
Leu Pro Tyr Leu Glu Asn Val Leu Tyr Gly Arg Asn Gly Gly Leu Gln
        515                 520                 525 agt tcc atg ggc atg agt tca acc aag ggt tct aga gca cgt att acc      1632
Ser Ser Met Gly Met Ser Ser Thr Lys Gly Ser Arg Ala Arg Ile Thr
    530                 535                 540 aac agc acc gaa gac ctg gac gat gag tcc ata caa ggt aag ctg aat      1680
Asn Ser Thr Glu Asp Leu Asp Asp Glu Ser Ile Gln Gly Lys Leu Asn
545                 550                 555                 560 ttt gag aac ttt tcg ctg ctt gcc acg gaa taa                          1713
Phe Glu Asn Phe Ser Leu Leu Ala Thr Glu  *
                565                 570

<210> SEQ ID NO 2
<211> LENGTH: 570
<212> TYPE: PRT
<213> ORGANISM: Drosophila melanogaster
<300> PUBLICATION INFORMATION:
<308> DATABASE ACCESSION NUMBER: Genbank AAF48542
<309> DATABASE ENTRY DATE: 2002-09-13

<400> SEQUENCE: 2

Met Arg Lys Asn Thr Ile Trp Asn Tyr Ser Leu Ile Phe Phe Cys Cys
1               5                   10                  15

Val Leu Lys Ser Ile Ser Thr Leu Asp His Gly Pro His Thr Val Ser
```

```
                     20                  25                  30
Val Asp Ser Asn Arg His Asn Thr Gln His Gln Tyr Lys Gln Asn Pro
             35                  40                  45

Asn Val Ala Ser Gln Arg His Ser Ser His Glu Ser Gly Gln Ser Leu
         50                  55                  60

His Asn Ser Gln Ser Glu His Val Thr His Ile Ala Ala Ser His Ala
 65                  70                  75                  80

Gly Ser Gly Gly Glu His Ser Thr His Leu Ala Gln Asn Leu His Arg
                 85                  90                  95

Ser Ser Tyr Asn Leu Leu Ser Glu Ala Met Ser Gln Ala Val Ser Asn
            100                 105                 110

Glu Phe Ser Ser Met Gly Ser Gly Ser Ala Asp Gly Ala Cys Ala Ala
            115                 120                 125

Asp Asp Phe Asp Cys Tyr Ser Gly Ser Val Gln Asp Arg Phe Gly Met
            130                 135                 140

Glu Ala Ile Ala Ser Leu His Arg Gln Leu Asp Asp Asp Asn Gly
145                 150                 155                 160

Asn Ile Asp Leu Ser Glu Ser Asp Asp Phe Leu Arg Glu Glu Leu Lys
                165                 170                 175

Tyr Asp Ser Gly Tyr Glu Lys Arg Gln Lys Ala Phe His Phe Asn Asp
            180                 185                 190

Asp Met His Ile Ser Val Lys Glu Leu Trp Glu Ala Trp Leu Arg Ser
            195                 200                 205

Glu Val His Asn Trp Thr Ile Glu Gln Thr Thr Asp Trp Leu Ala Gln
            210                 215                 220

Ser Val Gln Leu Pro Gln Tyr Val Asp Leu Phe Lys Leu His Lys Val
225                 230                 235                 240

Thr Gly Ala Ala Leu Pro Arg Leu Ala Val Asn Asn Leu Gln Tyr Val
                245                 250                 255

Gly Asn Val Leu Gly Ile Lys Asp Pro Ile His Lys Gln Lys Ile Ser
            260                 265                 270

Leu Lys Ala Met Asp Val Val Leu Phe Gly Pro Pro Arg Glu Thr Gly
            275                 280                 285

Thr Arg Trp Lys Asp Tyr Ile Leu Val Thr Leu Leu Leu Ser Ala Ile
            290                 295                 300

Ile Gly Cys Trp Tyr Ala Tyr Gln Gln Asn Lys Asn Ala Lys Arg His
305                 310                 315                 320

Leu Arg Arg Met Ala Gln Asp Met Glu Gly Leu Gln Arg Ala Glu Gln
                325                 330                 335

Ser Leu Gln Glu Met Gln Lys Glu Leu Glu Arg Ala Arg Met Glu Gln
            340                 345                 350

Glu Asn Val Ala Thr Glu Lys Leu Asp Leu Glu Arg Arg Leu Lys Glu
            355                 360                 365

Ala Pro Thr Leu Ser Ser Ser Asn Ser Asp Leu Glu Val Gln Gln Leu
            370                 375                 380

Lys Lys Glu Ile Glu Met Leu Arg Asn Glu Leu Ser Arg Ala Glu Phe
385                 390                 395                 400

Glu Leu Val Asp Asn Cys Trp Ser Pro Pro Gln Leu Gln Ser Trp
                405                 410                 415

Leu Gln Tyr Thr Tyr Glu Leu Glu Ser Lys Asn His Gln Lys Lys Arg
            420                 425                 430

Thr Ser Ala Glu Lys Gln Leu Gln Ser Ala Arg Glu Ala Cys Glu Lys
            435                 440                 445
```

```
Leu Arg Lys Lys Arg Ser Ser Leu Val Gly Ala Phe Val Ser Thr His
    450                 455                 460

Gly Lys Ser Ile Asp Asp Val Asp Arg Ser Ile Val Glu Ala Arg Asn
465                 470                 475                 480

Ala Leu Gly Asp Val Thr Asn Glu Leu Gln Glu Arg Leu His Arg Trp
                485                 490                 495

Lys Gln Ile Glu Thr Cys Leu Gly Leu Asn Ile Val Asn Asn Asn Gly
            500                 505                 510

Leu Pro Tyr Leu Glu Asn Val Leu Tyr Gly Arg Asn Gly Gly Leu Gln
        515                 520                 525

Ser Ser Met Gly Met Ser Ser Thr Lys Gly Ser Arg Ala Arg Ile Thr
    530                 535                 540

Asn Ser Thr Glu Asp Leu Asp Asp Glu Ser Ile Gln Gly Lys Leu Asn
545                 550                 555                 560

Phe Glu Asn Phe Ser Leu Leu Ala Thr Glu
                565                 570

<210> SEQ ID NO 3
<211> LENGTH: 2058
<212> TYPE: DNA
<213> ORGANISM: Homo sapiens
<220> FEATURE:
<221> NAME/KEY: CDS
<222> LOCATION: (1)...(2058)
<223> OTHER INFORMATION: STIM1
<300> PUBLICATION INFORMATION:
<308> DATABASE ACCESSION NUMBER: Genbank U52426
<309> DATABASE ENTRY DATE: 1997-07-18

<400> SEQUENCE: 3 atg gat gta tgc gtc cgt ctt gcc ctg tgg ctc ctc tgg ggg ctc ctc        48
Met Asp Val Cys Val Arg Leu Ala Leu Trp Leu Leu Trp Gly Leu Leu
1               5                   10                  15 ctg cac cag ggc cag agc ctc agc cat agt cac agt gag aag gcg aca        96
Leu His Gln Gly Gln Ser Leu Ser His Ser His Ser Glu Lys Ala Thr
            20                  25                  30 gga acc agc tcg ggg gcc aac tct gag gag tcc act gca gca gag ttt       144
Gly Thr Ser Ser Gly Ala Asn Ser Glu Glu Ser Thr Ala Ala Glu Phe
        35                  40                  45 tgc cga att gac aag ccc ctg tgt cac agt gag gat gag aaa ctc agc       192
Cys Arg Ile Asp Lys Pro Leu Cys His Ser Glu Asp Glu Lys Leu Ser
    50                  55                  60 ttc gag gca gtc cgt aac atc cac aaa ctg atg gac gat gat gcc aat       240
Phe Glu Ala Val Arg Asn Ile His Lys Leu Met Asp Asp Asp Ala Asn
65                  70                  75                  80 ggt gat gtg gat gtg gaa gaa agt gat gag ttc ctg agg gaa gac ctc       288
Gly Asp Val Asp Val Glu Glu Ser Asp Glu Phe Leu Arg Glu Asp Leu
                85                  90                  95 aat tac cat gac cca aca gtg aaa cac agc acc ttc cat ggt gag gat       336
Asn Tyr His Asp Pro Thr Val Lys His Ser Thr Phe His Gly Glu Asp
            100                 105                 110 aag ctc atc agc gtg gag gac ctg tgg aag gca tgg aag tca tca gaa       384
Lys Leu Ile Ser Val Glu Asp Leu Trp Lys Ala Trp Lys Ser Ser Glu
        115                 120                 125 gta tac aat tgg acc gtg gat gag gtg gta cag tgg ctg atc aca tat       432
Val Tyr Asn Trp Thr Val Asp Glu Val Val Gln Trp Leu Ile Thr Tyr
    130                 135                 140 gtg gag ctg cct cag tat gag gag acc ttc cgg aag ctg cag ctc agt       480
Val Glu Leu Pro Gln Tyr Glu Glu Thr Phe Arg Lys Leu Gln Leu Ser
145                 150                 155                 160
```

```
ggc cat gcc atg cca agg ctg gct gtc acc aac acc acc atg aca ggg      528
Gly His Ala Met Pro Arg Leu Ala Val Thr Asn Thr Thr Met Thr Gly
            165                 170                 175 act gtg ctg aag atg aca gac cgg agt cat cgg cag aag ctg cag ctg      576
Thr Val Leu Lys Met Thr Asp Arg Ser His Arg Gln Lys Leu Gln Leu
        180                 185                 190 aag gct ctg gat aca gtg ctc ttt ggg cct cct ctc ttg act cgc cat      624
Lys Ala Leu Asp Thr Val Leu Phe Gly Pro Pro Leu Leu Thr Arg His
            195                 200                 205 aat cac ctc aag gac ttc atg ctg gtg gtg tct atc gtt att ggt gtg      672
Asn His Leu Lys Asp Phe Met Leu Val Val Ser Ile Val Ile Gly Val
    210                 215                 220 ggc ggc tgc tgg ttt gcc tat atc cag aac cgt tac tcc aag gag cac      720
Gly Gly Cys Trp Phe Ala Tyr Ile Gln Asn Arg Tyr Ser Lys Glu His
225                 230                 235                 240 atg aag aag atg atg aag gac ttg gag ggg tta cac cga gct gag cag      768
Met Lys Lys Met Met Lys Asp Leu Glu Gly Leu His Arg Ala Glu Gln
                245                 250                 255 agt ctg cat gac ctt cag gaa agg ctg cac aag gcc cag gag gag cac      816
Ser Leu His Asp Leu Gln Glu Arg Leu His Lys Ala Gln Glu Glu His
            260                 265                 270 cgc aca gtg gag gtg gag aag gtc cat ctg gaa aag aag ctg cgc gat      864
Arg Thr Val Glu Val Glu Lys Val His Leu Glu Lys Lys Leu Arg Asp
        275                 280                 285 gag atc aac ctt gct aag cag gaa gcc cag cgg ctg aag gag ctg cgg      912
Glu Ile Asn Leu Ala Lys Gln Glu Ala Gln Arg Leu Lys Glu Leu Arg
    290                 295                 300 gag ggt act gag aat gag cgg agc cgc caa aaa tat gct gag gag gag      960
Glu Gly Thr Glu Asn Glu Arg Ser Arg Gln Lys Tyr Ala Glu Glu Glu
305                 310                 315                 320 ttg gag cag gtt cgg gag gcc ttg agg aaa gca gag aag gag cta gaa     1008
Leu Glu Gln Val Arg Glu Ala Leu Arg Lys Ala Glu Lys Glu Leu Glu
                325                 330                 335 tct cac agc tca tgg tat gct cca gag gcc ctt cag aag tgg ctg cag     1056
Ser His Ser Ser Trp Tyr Ala Pro Glu Ala Leu Gln Lys Trp Leu Gln
            340                 345                 350 ctg aca cat gag gtg gag gtg caa tat tac aac atc aag aag caa aat     1104
Leu Thr His Glu Val Glu Val Gln Tyr Tyr Asn Ile Lys Lys Gln Asn
        355                 360                 365 gct gag aag cag ctg ctg gtg gcc aag gag ggg gct gag aag ata aaa     1152
Ala Glu Lys Gln Leu Leu Val Ala Lys Glu Gly Ala Glu Lys Ile Lys
    370                 375                 380 aag aag aga aac aca ctc ttt ggc acc ttc cac gtg gcc cac agc tct     1200
Lys Lys Arg Asn Thr Leu Phe Gly Thr Phe His Val Ala His Ser Ser
385                 390                 395                 400 tcc ctg gat gat gta gat cat aaa att cta aca gct aag caa gca ctg     1248
Ser Leu Asp Asp Val Asp His Lys Ile Leu Thr Ala Lys Gln Ala Leu
                405                 410                 415 agc gag gtg aca gca gca ttg cgg gag cgc ctg cac cgc tgg caa cag     1296
Ser Glu Val Thr Ala Ala Leu Arg Glu Arg Leu His Arg Trp Gln Gln
            420                 425                 430 atc gag atc ctc tgt ggc ttc cag att gtc aac aac cct ggc atc cac     1344
Ile Glu Ile Leu Cys Gly Phe Gln Ile Val Asn Asn Pro Gly Ile His
        435                 440                 445 tca ctg gtg gct gcc ctc aac ata gac ccc agc tgg atg ggc agt aca     1392
Ser Leu Val Ala Ala Leu Asn Ile Asp Pro Ser Trp Met Gly Ser Thr
    450                 455                 460 cgc ccc aac cct gct cac ttc atc atg act gac gac gtg gat gac atg     1440
Arg Pro Asn Pro Ala His Phe Ile Met Thr Asp Asp Val Asp Asp Met
```

```
                                                                          -continued
       465                470                475                480 gat gag gag att gtg tct ccc ttg tcc atg cag tcc cct agc ctg cag      1488
Asp Glu Glu Ile Val Ser Pro Leu Ser Met Gln Ser Pro Ser Leu Gln
                        485                490                495 agc agt gtt cgg cag cgc ctg acg gag cca cag cat ggc ctg gga tct      1536
Ser Ser Val Arg Gln Arg Leu Thr Glu Pro Gln His Gly Leu Gly Ser
                500                505                510 cag agg gat ttg acc cat tcc gat tcg gag tcc tcc ctc cac atg agt      1584
Gln Arg Asp Leu Thr His Ser Asp Ser Glu Ser Ser Leu His Met Ser
            515                520                525 gac cgc cag cgt gtg gcc ccc aaa cct cct cag atg agc cgt gct gca      1632
Asp Arg Gln Arg Val Ala Pro Lys Pro Pro Gln Met Ser Arg Ala Ala
        530                535                540 gac gag gct ctc aat gcc atg act tcc aat gga cgc cac cgg ctg atc      1680
Asp Glu Ala Leu Asn Ala Met Thr Ser Asn Gly Arg His Arg Leu Ile
545                550                555                560 gag ggg gtc cac cca ggg tct ctg gtg gag aaa ctg cct gac agc cct      1728
Glu Gly Val His Pro Gly Ser Leu Val Glu Lys Leu Pro Asp Ser Pro
                    565                570                575 gcc ctg gcc aag aag gca tta ctg gcg ctg aac cat ggg ctg gac aag      1776
Ala Leu Ala Lys Lys Ala Leu Leu Ala Leu Asn His Gly Leu Asp Lys
                580                585                590 gcc cac agc ctg atg gag ctg agc ccc tca gcc cca cct ggt ggc tct      1824
Ala His Ser Leu Met Glu Leu Ser Pro Ser Ala Pro Pro Gly Gly Ser
            595                600                605 cca cat ttg gat tct tcc cgt tct cac agc ccc agc tcc cca gac cca      1872
Pro His Leu Asp Ser Ser Arg Ser His Ser Pro Ser Ser Pro Asp Pro
        610                615                620 gac aca cca tct cca gtt ggg gac agc cga gcc ctg caa gcc agc cga      1920
Asp Thr Pro Ser Pro Val Gly Asp Ser Arg Ala Leu Gln Ala Ser Arg
625                630                635                640 aac aca cgc att ccc cac ctg gct ggc aag aag gct gtg gct gag gag      1968
Asn Thr Arg Ile Pro His Leu Ala Gly Lys Lys Ala Val Ala Glu Glu
                    645                650                655 gat aat ggc tct att ggc gag gaa aca gac tcc agc cca ggc cgg aag      2016
Asp Asn Gly Ser Ile Gly Glu Glu Thr Asp Ser Ser Pro Gly Arg Lys
                660                665                670 aag ttt cct ctc aaa atc ttt aag aag cct ctt aag aag tag              2058
Lys Phe Pro Leu Lys Ile Phe Lys Lys Pro Leu Lys Lys  *
            675                680                685

<210> SEQ ID NO 4
<211> LENGTH: 685
<212> TYPE: PRT
<213> ORGANISM: Homo sapiens
<300> PUBLICATION INFORMATION:
<308> DATABASE ACCESSION NUMBER: Genbank AAC51627
<309> DATABASE ENTRY DATE: 1997-07-18

<400> SEQUENCE: 4

Met Asp Val Cys Val Arg Leu Ala Leu Trp Leu Leu Trp Gly Leu Leu
 1               5                  10                  15

Leu His Gln Gly Gln Ser Leu Ser His Ser His Ser Glu Lys Ala Thr
                20                  25                  30

Gly Thr Ser Ser Gly Ala Asn Ser Glu Glu Ser Thr Ala Ala Glu Phe
            35                  40                  45

Cys Arg Ile Asp Lys Pro Leu Cys His Ser Glu Asp Glu Lys Leu Ser
        50                  55                  60

Phe Glu Ala Val Arg Asn Ile His Lys Leu Met Asp Asp Asp Ala Asn
65                  70                  75                  80
```

-continued

```
Gly Asp Val Asp Val Glu Glu Ser Asp Glu Phe Leu Arg Glu Asp Leu
                 85                  90                  95
Asn Tyr His Asp Pro Thr Val Lys His Ser Thr Phe His Gly Glu Asp
            100                 105                 110
Lys Leu Ile Ser Val Glu Asp Leu Trp Lys Ala Trp Lys Ser Ser Glu
        115                 120                 125
Val Tyr Asn Trp Thr Val Asp Glu Val Val Gln Trp Leu Ile Thr Tyr
    130                 135                 140
Val Glu Leu Pro Gln Tyr Glu Glu Thr Phe Arg Lys Leu Gln Leu Ser
145                 150                 155                 160
Gly His Ala Met Pro Arg Leu Ala Val Thr Asn Thr Thr Met Thr Gly
                165                 170                 175
Thr Val Leu Lys Met Thr Asp Arg Ser His Arg Gln Lys Leu Gln Leu
            180                 185                 190
Lys Ala Leu Asp Thr Val Leu Phe Gly Pro Pro Leu Leu Thr Arg His
        195                 200                 205
Asn His Leu Lys Asp Phe Met Leu Val Val Ser Ile Val Ile Gly Val
    210                 215                 220
Gly Gly Cys Trp Phe Ala Tyr Ile Gln Asn Arg Tyr Ser Lys Glu His
225                 230                 235                 240
Met Lys Lys Met Met Lys Asp Leu Glu Gly Leu His Arg Ala Glu Gln
                245                 250                 255
Ser Leu His Asp Leu Gln Glu Arg Leu His Lys Ala Gln Glu Glu His
            260                 265                 270
Arg Thr Val Glu Val Glu Lys Val His Leu Glu Lys Lys Leu Arg Asp
        275                 280                 285
Glu Ile Asn Leu Ala Lys Gln Glu Ala Gln Arg Leu Lys Glu Leu Arg
    290                 295                 300
Glu Gly Thr Glu Asn Glu Arg Ser Arg Gln Lys Tyr Ala Glu Glu Glu
305                 310                 315                 320
Leu Glu Gln Val Arg Glu Ala Leu Arg Lys Ala Glu Lys Glu Leu Glu
                325                 330                 335
Ser His Ser Ser Trp Tyr Ala Pro Glu Ala Leu Gln Lys Trp Leu Gln
            340                 345                 350
Leu Thr His Glu Val Glu Val Gln Tyr Tyr Asn Ile Lys Lys Gln Asn
        355                 360                 365
Ala Glu Lys Gln Leu Leu Val Ala Lys Glu Gly Ala Glu Lys Ile Lys
    370                 375                 380
Lys Lys Arg Asn Thr Leu Phe Gly Thr Phe His Val Ala His Ser Ser
385                 390                 395                 400
Ser Leu Asp Asp Val Asp His Lys Ile Leu Thr Ala Lys Gln Ala Leu
                405                 410                 415
Ser Glu Val Thr Ala Ala Leu Arg Glu Arg Leu His Arg Trp Gln Gln
            420                 425                 430
Ile Glu Ile Leu Cys Gly Phe Gln Ile Val Asn Asn Pro Gly Ile His
        435                 440                 445
Ser Leu Val Ala Ala Leu Asn Ile Asp Pro Ser Trp Met Gly Ser Thr
    450                 455                 460
Arg Pro Asn Pro Ala His Phe Ile Met Thr Asp Asp Val Asp Asp Met
465                 470                 475                 480
Asp Glu Glu Ile Val Ser Pro Leu Ser Met Gln Ser Pro Ser Leu Gln
                485                 490                 495
```

```
Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Ser Arg Ala Ala
    530                 535                 540

Asp Glu Ala Leu Asn Ala Met Thr Ser Asn Gly Arg His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Ala Leu Leu Ala Leu Asn His Gly Leu Asp Lys
            580                 585                 590

Ala His Ser Leu Met Glu Leu Ser Pro Ser Ala Pro Pro Gly Gly Ser
        595                 600                 605

Pro His Leu Asp Ser Ser Arg Ser His Ser Pro Ser Ser Pro Asp Pro
    610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 5
<211> LENGTH: 2241
<212> TYPE: DNA
<213> ORGANISM: Homo sapiens
<220> FEATURE:
<221> NAME/KEY: CDS
<222> LOCATION: (1)...(2241)
<223> OTHER INFORMATION: STIM2
<300> PUBLICATION INFORMATION:
<308> DATABASE ACCESSION NUMBER: Genbank AF328905
<309> DATABASE ENTRY DATE: 2001-07-31

<400> SEQUENCE: 5 ttg ctg gtg ctc ggg ctg ctg gta gcc gga gcg gcg gac gga tgc gag      48
Leu Leu Val Leu Gly Leu Leu Val Ala Gly Ala Ala Asp Gly Cys Glu
  1               5                  10                  15 ctt gtg ccc cgg cac ctc cgc ggg cgg cgg gcg act ggc tct gcc gca      96
Leu Val Pro Arg His Leu Arg Gly Arg Arg Ala Thr Gly Ser Ala Ala
             20                  25                  30 act gcc gcc tcc tct ccc gcc gcg gcg gcc ggc gat agc ccg gcg ctc     144
Thr Ala Ala Ser Ser Pro Ala Ala Ala Ala Gly Asp Ser Pro Ala Leu
         35                  40                  45 atg aca gat ccc tgc atg tca ctg agt cca cca tgc ttt aca gaa gaa     192
Met Thr Asp Pro Cys Met Ser Leu Ser Pro Pro Cys Phe Thr Glu Glu
     50                  55                  60 gac aga ttt agt ctg gaa gct ctt caa aca ata cat aaa caa atg gat     240
Asp Arg Phe Ser Leu Glu Ala Leu Gln Thr Ile His Lys Gln Met Asp
 65                  70                  75                  80 gat gac aaa gat ggt gga att gaa gta gag gaa agt gat gaa ttc atc     288
Asp Asp Lys Asp Gly Gly Ile Glu Val Glu Glu Ser Asp Glu Phe Ile
                 85                  90                  95 aga gaa gat atg aaa tat aaa gat gct act aat aaa cac agc cat ctg     336
Arg Glu Asp Met Lys Tyr Lys Asp Ala Thr Asn Lys His Ser His Leu
            100                 105                 110
```

```
cac aga gaa gat aaa cat ata acg att gag gat tta tgg aaa cga tgg      384
His Arg Glu Asp Lys His Ile Thr Ile Glu Asp Leu Trp Lys Arg Trp
            115                 120                 125 aaa aca tca gaa gtt cat aat tgg acc ctt gaa gac act ctt cag tgg      432
Lys Thr Ser Glu Val His Asn Trp Thr Leu Glu Asp Thr Leu Gln Trp
130                 135                 140 ttg ata gag ttt gtt gaa cta ccc caa tat gag aag aat ttt aga gac      480
Leu Ile Glu Phe Val Glu Leu Pro Gln Tyr Glu Lys Asn Phe Arg Asp
145                 150                 155                 160 aac aat gtc aaa gga acg aca ctt ccc agg ata gca gtg cac gaa cct      528
Asn Asn Val Lys Gly Thr Thr Leu Pro Arg Ile Ala Val His Glu Pro
                165                 170                 175 tca ttt atg atc tcc cag ttg aaa atc agt gac cgg agt cac aga caa      576
Ser Phe Met Ile Ser Gln Leu Lys Ile Ser Asp Arg Ser His Arg Gln
            180                 185                 190 aaa ctt cag ctc aag gca ttg gat gtg gtt ttg ttt gga cct cta aca      624
Lys Leu Gln Leu Lys Ala Leu Asp Val Val Leu Phe Gly Pro Leu Thr
        195                 200                 205 cgc cca cct cat aac tgg atg aaa gat ttt atc ctc aca gtt tct ata      672
Arg Pro Pro His Asn Trp Met Lys Asp Phe Ile Leu Thr Val Ser Ile
    210                 215                 220 gta att ggt gtt gga ggc tgc tgg ttt gct tat acg cag aat aag aca      720
Val Ile Gly Val Gly Gly Cys Trp Phe Ala Tyr Thr Gln Asn Lys Thr
225                 230                 235                 240 tca aaa gaa cat gtt gca aaa atg atg aaa gat tta gag agc tta caa      768
Ser Lys Glu His Val Ala Lys Met Met Lys Asp Leu Glu Ser Leu Gln
                245                 250                 255 act gca gag caa agt cta atg gac tta caa gag agg ctt gaa aag gca      816
Thr Ala Glu Gln Ser Leu Met Asp Leu Gln Glu Arg Leu Glu Lys Ala
            260                 265                 270 cag gaa gaa aac aga aat gtt gct gta gaa aag caa aat tta gag cgc      864
Gln Glu Glu Asn Arg Asn Val Ala Val Glu Lys Gln Asn Leu Glu Arg
        275                 280                 285 aaa atg atg gat gaa atc aat tat gca aag gag gag gct tgt cgg ctg      912
Lys Met Met Asp Glu Ile Asn Tyr Ala Lys Glu Glu Ala Cys Arg Leu
    290                 295                 300 aga gag cta agg gag gga gct gaa tgt gaa ttg agt aga cgt cag tat      960
Arg Glu Leu Arg Glu Gly Ala Glu Cys Glu Leu Ser Arg Arg Gln Tyr
305                 310                 315                 320 gca gaa cag gaa ttg gaa cag gtt cgc atg gct ctg aaa aag gcc gaa     1008
Ala Glu Gln Glu Leu Glu Gln Val Arg Met Ala Leu Lys Lys Ala Glu
                325                 330                 335 aaa gaa ttt gaa ctg aga agc agt tgg tct gtt cca gat gca ctt cag     1056
Lys Glu Phe Glu Leu Arg Ser Ser Trp Ser Val Pro Asp Ala Leu Gln
            340                 345                 350 aaa tgg ctt cag tta aca cat gaa gta gaa gtg caa tac tac aat att     1104
Lys Trp Leu Gln Leu Thr His Glu Val Glu Val Gln Tyr Tyr Asn Ile
        355                 360                 365 aaa aga caa aac gct gaa atg cag cta gct att gct aaa gat gag gca     1152
Lys Arg Gln Asn Ala Glu Met Gln Leu Ala Ile Ala Lys Asp Glu Ala
    370                 375                 380 gaa aaa att aaa aag aag aga agc aca gtc ttt ggg act ctg cac gtt     1200
Glu Lys Ile Lys Lys Lys Arg Ser Thr Val Phe Gly Thr Leu His Val
385                 390                 395                 400 gca cac agc tcc tcc cta gat gag gta gac cac aaa att ctg gaa gca     1248
Ala His Ser Ser Ser Leu Asp Glu Val Asp His Lys Ile Leu Glu Ala
                405                 410                 415 aag aaa gct ctc tct gag ttg aca act tgt tta cga gaa cga ctt ttt     1296
Lys Lys Ala Leu Ser Glu Leu Thr Thr Cys Leu Arg Glu Arg Leu Phe
            420                 425                 430
```

```
cgc tgg caa caa att gag aag atc tgt ggc ttt cag ata gcc cat aac    1344
Arg Trp Gln Gln Ile Glu Lys Ile Cys Gly Phe Gln Ile Ala His Asn
        435                 440                 445 tca gga ctc ccc agc ctg acc tct tcc ctt tat tct gat cac agc tgg    1392
Ser Gly Leu Pro Ser Leu Thr Ser Ser Leu Tyr Ser Asp His Ser Trp
    450                 455                 460 gtg gtg atg ccc aga gtc tcc att cca ccc tat cca att gct gga gga    1440
Val Val Met Pro Arg Val Ser Ile Pro Pro Tyr Pro Ile Ala Gly Gly
465                 470                 475                 480 gtt gat gac tta gat gaa gac aca ccc cca ata gtg tca caa ttt ccc    1488
Val Asp Asp Leu Asp Glu Asp Thr Pro Pro Ile Val Ser Gln Phe Pro
                485                 490                 495 ggg acc atg gct aaa cct cct gga tca tta gcc aga agc agc agc ctg    1536
Gly Thr Met Ala Lys Pro Pro Gly Ser Leu Ala Arg Ser Ser Ser Leu
            500                 505                 510 tgc cgt tca cgc cgc agc att gtg ccg tcc tcg cct cag cct cag cga    1584
Cys Arg Ser Arg Arg Ser Ile Val Pro Ser Ser Pro Gln Pro Gln Arg
        515                 520                 525 gct cag ctt gct cca cac gcc ccc cac ccg tca cac cct cgg cac cct    1632
Ala Gln Leu Ala Pro His Ala Pro His Pro Ser His Pro Arg His Pro
    530                 535                 540 cac cac ccg caa cac aca cca cac tcc ttg cct tcc cct gat cca gat    1680
His His Pro Gln His Thr Pro His Ser Leu Pro Ser Pro Asp Pro Asp
545                 550                 555                 560 atc ctc tca gtg tca agt tgc cct gcg ctt tat cga aat gaa gag gag    1728
Ile Leu Ser Val Ser Ser Cys Pro Ala Leu Tyr Arg Asn Glu Glu Glu
                565                 570                 575 gaa gag gcc att tac ttc tct gct gaa aag caa tgg gaa gtg cca gac    1776
Glu Glu Ala Ile Tyr Phe Ser Ala Glu Lys Gln Trp Glu Val Pro Asp
            580                 585                 590 aca gct tca gaa tgt gac tcc tta aat tct tcc att gga agg aaa cag    1824
Thr Ala Ser Glu Cys Asp Ser Leu Asn Ser Ser Ile Gly Arg Lys Gln
        595                 600                 605 tct cct cct tta agc ctc gag ata tac caa aca tta tct ccg cga aag    1872
Ser Pro Pro Leu Ser Leu Glu Ile Tyr Gln Thr Leu Ser Pro Arg Lys
    610                 615                 620 ata tca aga gat gag gtg tcc cta gag gat tcc tcc cga ggg gat tcg    1920
Ile Ser Arg Asp Glu Val Ser Leu Glu Asp Ser Ser Arg Gly Asp Ser
625                 630                 635                 640 cct gta act gtg gat gtg tct tgg ggt tct ccc gac tgt gta ggt ctg    1968
Pro Val Thr Val Asp Val Ser Trp Gly Ser Pro Asp Cys Val Gly Leu
                645                 650                 655 aca gaa act aag agt atg atc ttc agt cct gca agc aaa gtg tac aat    2016
Thr Glu Thr Lys Ser Met Ile Phe Ser Pro Ala Ser Lys Val Tyr Asn
            660                 665                 670 ggc att ttg gag aaa tcc tgt agc atg aac cag ctt tcc agt ggc atc    2064
Gly Ile Leu Glu Lys Ser Cys Ser Met Asn Gln Leu Ser Ser Gly Ile
        675                 680                 685 ccg gtg cct aaa cct cgc cac aca tca tgt tcc tca gct ggc aac gac    2112
Pro Val Pro Lys Pro Arg His Thr Ser Cys Ser Ser Ala Gly Asn Asp
    690                 695                 700 agt aaa cca gtt cag gaa gcc cca agt gtt gcc aga ata agc agc atc    2160
Ser Lys Pro Val Gln Glu Ala Pro Ser Val Ala Arg Ile Ser Ser Ile
705                 710                 715                 720 cca cat gac ctt tgt cat aat gga gag aaa agc aag cca tca aaa       2208
Pro His Asp Leu Cys His Asn Gly Glu Lys Ser Lys Lys Pro Ser Lys
                725                 730                 735 atc aaa agc ctt ttt aag aag aaa tct aag tga                       2241
Ile Lys Ser Leu Phe Lys Lys Lys Ser Lys  *
```

740             745

<210> SEQ ID NO 6
<211> LENGTH: 746
<212> TYPE: PRT
<213> ORGANISM: Homo sapiens
<300> PUBLICATION INFORMATION:
<308> DATABASE ACCESSION NUMBER: Genbank AAK82337
<309> DATABASE ENTRY DATE: 2001-07-31

<400> SEQUENCE: 6

Leu Leu Val Leu Gly Leu Leu Val Ala Gly Ala Asp Gly Cys Glu
 1               5                  10                  15

Leu Val Pro Arg His Leu Arg Gly Arg Arg Ala Thr Gly Ser Ala Ala
            20                  25                  30

Thr Ala Ser Ser Pro Ala Ala Ala Gly Asp Ser Pro Ala Leu
         35                  40                  45

Met Thr Asp Pro Cys Met Ser Leu Ser Pro Pro Cys Phe Thr Glu Glu
 50                  55                  60

Asp Arg Phe Ser Leu Glu Ala Leu Gln Thr Ile His Lys Gln Met Asp
65                   70                  75                  80

Asp Asp Lys Asp Gly Gly Ile Glu Val Glu Glu Ser Asp Glu Phe Ile
                 85                  90                  95

Arg Glu Asp Met Lys Tyr Lys Asp Ala Thr Asn Lys His Ser His Leu
             100                 105                 110

His Arg Glu Asp Lys His Ile Thr Ile Glu Asp Leu Trp Lys Arg Trp
         115                 120                 125

Lys Thr Ser Glu Val His Asn Trp Thr Leu Glu Asp Thr Leu Gln Trp
    130                 135                 140

Leu Ile Glu Phe Val Glu Leu Pro Gln Tyr Glu Lys Asn Phe Arg Asp
145                 150                 155                 160

Asn Asn Val Lys Gly Thr Thr Leu Pro Arg Ile Ala Val His Glu Pro
                165                 170                 175

Ser Phe Met Ile Ser Gln Leu Lys Ile Ser Asp Arg Ser His Arg Gln
            180                 185                 190

Lys Leu Gln Leu Lys Ala Leu Asp Val Val Leu Phe Gly Pro Leu Thr
        195                 200                 205

Arg Pro Pro His Asn Trp Met Lys Asp Phe Ile Leu Thr Val Ser Ile
    210                 215                 220

Val Ile Gly Val Gly Gly Cys Trp Phe Ala Tyr Thr Gln Asn Lys Thr
225                 230                 235                 240

Ser Lys Glu His Val Ala Lys Met Met Lys Asp Leu Glu Ser Leu Gln
                245                 250                 255

Thr Ala Glu Gln Ser Leu Met Asp Leu Gln Glu Arg Leu Glu Lys Ala
            260                 265                 270

Gln Glu Glu Asn Arg Asn Val Ala Val Glu Lys Gln Asn Leu Glu Arg
        275                 280                 285

Lys Met Met Asp Glu Ile Asn Tyr Ala Lys Glu Glu Ala Cys Arg Leu
    290                 295                 300

Arg Glu Leu Arg Glu Gly Ala Glu Cys Glu Leu Ser Arg Arg Gln Tyr
305                 310                 315                 320

Ala Glu Gln Glu Leu Glu Gln Val Arg Met Ala Leu Lys Lys Ala Glu
                325                 330                 335

Lys Glu Phe Glu Leu Arg Ser Ser Trp Ser Val Pro Asp Ala Leu Gln
            340                 345                 350

-continued

```
Lys Trp Leu Gln Leu Thr His Glu Val Glu Val Gln Tyr Tyr Asn Ile
        355                 360                 365

Lys Arg Gln Asn Ala Glu Met Gln Leu Ala Ile Ala Lys Asp Glu Ala
        370                 375                 380

Glu Lys Ile Lys Lys Arg Ser Thr Val Phe Gly Thr Leu His Val
385                 390                 395                 400

Ala His Ser Ser Ser Leu Asp Glu Val Asp His Lys Ile Leu Glu Ala
                405                 410                 415

Lys Lys Ala Leu Ser Glu Leu Thr Thr Cys Leu Arg Glu Arg Leu Phe
            420                 425                 430

Arg Trp Gln Gln Ile Glu Lys Ile Cys Gly Phe Gln Ile Ala His Asn
            435                 440                 445

Ser Gly Leu Pro Ser Leu Thr Ser Ser Leu Tyr Ser Asp His Ser Trp
    450                 455                 460

Val Val Met Pro Arg Val Ser Ile Pro Pro Tyr Pro Ile Ala Gly Gly
465                 470                 475                 480

Val Asp Asp Leu Asp Glu Asp Thr Pro Pro Ile Val Ser Gln Phe Pro
                485                 490                 495

Gly Thr Met Ala Lys Pro Pro Gly Ser Leu Ala Arg Ser Ser Ser Leu
            500                 505                 510

Cys Arg Ser Arg Arg Ser Ile Val Pro Ser Ser Pro Gln Pro Gln Arg
            515                 520                 525

Ala Gln Leu Ala Pro His Ala Pro His Pro Ser His Pro Arg His Pro
        530                 535                 540

His His Pro Gln His Thr Pro His Ser Leu Pro Ser Pro Asp Pro Asp
545                 550                 555                 560

Ile Leu Ser Val Ser Ser Cys Pro Ala Leu Tyr Arg Asn Glu Glu Glu
                565                 570                 575

Glu Glu Ala Ile Tyr Phe Ser Ala Glu Lys Gln Trp Glu Val Pro Asp
            580                 585                 590

Thr Ala Ser Glu Cys Asp Ser Leu Asn Ser Ser Ile Gly Arg Lys Gln
            595                 600                 605

Ser Pro Pro Leu Ser Leu Glu Ile Tyr Gln Thr Leu Ser Pro Arg Lys
    610                 615                 620

Ile Ser Arg Asp Glu Val Ser Leu Glu Asp Ser Ser Arg Gly Asp Ser
625                 630                 635                 640

Pro Val Thr Val Asp Val Ser Trp Gly Ser Pro Asp Cys Val Gly Leu
                645                 650                 655

Thr Glu Thr Lys Ser Met Ile Phe Ser Pro Ala Ser Lys Val Tyr Asn
            660                 665                 670

Gly Ile Leu Glu Lys Ser Cys Ser Met Asn Gln Leu Ser Ser Gly Ile
        675                 680                 685

Pro Val Pro Lys Pro Arg His Thr Ser Cys Ser Ser Ala Gly Asn Asp
    690                 695                 700

Ser Lys Pro Val Gln Glu Ala Pro Ser Val Ala Arg Ile Ser Ser Ile
705                 710                 715                 720

Pro His Asp Leu Cys His Asn Gly Glu Lys Ser Lys Lys Pro Ser Lys
                725                 730                 735

Ile Lys Ser Leu Phe Lys Lys Lys Ser Lys
            740                 745
```

<210> SEQ ID NO 7
<211> LENGTH: 1410
<212> TYPE: DNA

<213> ORGANISM: Anopheles gambiae str. PEST
<300> PUBLICATION INFORMATION:
<308> DATABASE ACCESSION NUMBER: Genbank AAAB01008846
<309> DATABASE ENTRY DATE: 2002-06-20

<400> SEQUENCE: 7

```
cgcaactcct acaccgtgct gagccaagcg atgtcccagg cagttcatca cgaattcggc      60
acgtacggga gcggggcgat ggccggcgat gccggcagtg cctgcacgat cgacgacatc     120
gactgtctgg cgcaccacga ccagctcggg atggaagcga tccgttcgtt gcatcagcag     180
ctcgatgacg atgataacgg tgacatcgat ctttccgaat ctgacgactt tctgagggaa     240
gaactgaagt acgactcggg ctacgagaag cgccacaagg cgttccactt caacgacgac     300
atgcacatct cggtgaagga gctgtgggaa gcgtggctcc gatcggaggt gcacaactgg     360
acggtggatc agacgaccga gtggctggcg cagagcgtcc agctgcccca gtacgtgccc     420
ctgttccggc tgcacaaggt gaccgggaag gtgctgcccc ggctggccgt gaacaacatg     480
cactacgtca gcaacgtgct cgggataaag gatccgatcc acaagcagaa gatagcgctc     540
aaagcgatgg atgccgtcct gttcgggcca ccgcgtgaaa ctggaacccg gtggaaagat     600
ctgctgctcg tcacgctcct tctgacggcc atcatcggca gctggtatgc gtatcatcag     660
aacaagagcg ccaaaataca catccgccgc atggcgaagg atgtggaggg tttgctgaag     720
gcggaagtcg ccctgaaaga gatgcagaag gagctggaac aggcccggat cgagcaggag     780
aacgtgggca aggaaaagat ggatctcgag cggcgcctcc gcgaggcgcc gaccctgtcc     840
tcctccagct ccgacctgga gctgcagcag ctgaagcagg agatcgaggt gctgcggtcc     900
gagctgaacc gggcggaggt ggagatccac gaccactgct ggacgccgcc gcaggggctg     960
cagagctggc tgcagctgac gtacgagctg agaacaagc accacatccg caagcgcatc    1020
atggcggaga gcagctcga gcaggcgagg gaagcgtgcg agaagctgcg caagaagcgc    1080
tccagcctgg tcggtgcgtt cgtgtcgacg cacggcaaaa gcatcgacga cgtcgaccgg    1140
agcatcgtcg aggcgcgcaa cgcgctcaac gacgtgacga cgatctgca ggagcggatg    1200
caccggtgga gcagatcga aacgatgctc gggttcggca tcgtcaacaa cagcggcatc    1260
gcgcacctgg agaatctgct ctacaatcgc aacggcgtcg ctggcaaaac gtaccgatcg    1320
cgactgtcga gtagccagga cgatctggac gatgattccg tgcaaggtaa gccgatcagc    1380
tttgacaatt tttcaatgtt ctcgtcggag                                    1410
```

<210> SEQ ID NO 8
<211> LENGTH: 470
<212> TYPE: PRT
<213> ORGANISM: Anopheles gambiae str. PEST
<300> PUBLICATION INFORMATION:
<308> DATABASE ACCESSION NUMBER: Genbank EAA06485
<309> DATABASE ENTRY DATE: 2002-06-20

<400> SEQUENCE: 8

```
Arg Asn Ser Tyr Thr Val Leu Ser Gln Ala Met Ser Gln Ala Val His
  1               5                  10                  15

His Glu Phe Gly Thr Tyr Gly Ser Gly Ala Met Ala Gly Asp Ala Gly
             20                  25                  30

Ser Ala Cys Thr Ile Asp Asp Ile Asp Cys Leu Ala His His Asp Gln
         35                  40                  45

Leu Gly Met Glu Ala Ile Arg Ser Leu His Gln Gln Leu Asp Asp Asp
     50                  55                  60

Asp Asn Gly Asp Ile Asp Leu Ser Glu Ser Asp Asp Phe Leu Arg Glu
```

-continued

```
               65                  70                  75                  80
          Glu Leu Lys Tyr Asp Ser Gly Tyr Glu Lys Arg His Lys Ala Phe His
                               85                  90                  95
          Phe Asn Asp Asp Met His Ile Ser Val Lys Glu Leu Trp Glu Ala Trp
                              100                 105                 110
          Leu Arg Ser Glu Val His Asn Trp Thr Val Asp Gln Thr Thr Glu Trp
                              115                 120                 125
          Leu Ala Gln Ser Val Gln Leu Pro Gln Tyr Val Pro Leu Phe Arg Leu
                              130                 135                 140
          His Lys Val Thr Gly Lys Val Leu Pro Arg Leu Ala Val Asn Asn Met
          145                 150                 155                 160
          His Tyr Val Ser Asn Val Leu Gly Ile Lys Asp Pro Ile His Lys Gln
                              165                 170                 175
          Lys Ile Ala Leu Lys Ala Met Asp Ala Val Leu Phe Gly Pro Pro Arg
                              180                 185                 190
          Glu Thr Gly Thr Arg Trp Lys Asp Leu Leu Val Thr Leu Leu Leu
                              195                 200                 205
          Thr Ala Ile Ile Gly Ser Trp Tyr Ala Tyr His Gln Asn Lys Ser Ala
          210                 215                 220
          Lys Ile His Ile Arg Arg Met Ala Lys Asp Val Glu Gly Leu Leu Lys
          225                 230                 235                 240
          Ala Glu Val Ala Leu Lys Glu Met Gln Lys Glu Leu Glu Gln Ala Arg
                              245                 250                 255
          Ile Glu Gln Glu Asn Val Gly Lys Glu Lys Met Asp Leu Glu Arg Arg
                              260                 265                 270
          Leu Arg Glu Ala Pro Thr Leu Ser Ser Ser Ser Asp Leu Glu Leu
                              275                 280                 285
          Gln Gln Leu Lys Gln Glu Ile Glu Val Leu Arg Ser Glu Leu Asn Arg
                              290                 295                 300
          Ala Glu Val Glu Ile His Asp His Cys Trp Thr Pro Pro Gln Gly Leu
          305                 310                 315                 320
          Gln Ser Trp Leu Gln Leu Thr Tyr Glu Leu Glu Asn Lys His His Ile
                              325                 330                 335
          Arg Lys Arg Ile Met Ala Glu Lys Gln Leu Glu Gln Ala Arg Glu Ala
                              340                 345                 350
          Cys Glu Lys Leu Arg Lys Lys Arg Ser Ser Leu Val Gly Ala Phe Val
                              355                 360                 365
          Ser Thr His Gly Lys Ser Ile Asp Asp Val Asp Arg Ser Ile Val Glu
                              370                 375                 380
          Ala Arg Asn Ala Leu Asn Asp Val Thr Asn Asp Leu Gln Glu Arg Met
          385                 390                 395                 400
          His Arg Trp Lys Gln Ile Glu Thr Met Leu Gly Phe Gly Ile Val Asn
                              405                 410                 415
          Asn Ser Gly Ile Ala His Leu Glu Asn Leu Leu Tyr Asn Arg Asn Gly
                              420                 425                 430
          Val Ala Gly Lys Thr Tyr Arg Ser Arg Leu Ser Ser Ser Gln Asp Asp
                              435                 440                 445
          Leu Asp Asp Asp Ser Val Gln Gly Lys Pro Ile Ser Phe Asp Asn Phe
          450                 455                 460
          Ser Met Phe Ser Ser Glu
          465                 470

<210> SEQ ID NO 9
```

```
<211> LENGTH: 2058
<212> TYPE: DNA
<213> ORGANISM: Mus musculus
<220> FEATURE:
<221> NAME/KEY: CDS
<222> LOCATION: (1)...(2058)
<223> OTHER INFORMATION: STIM1
<300> PUBLICATION INFORMATION:
<308> DATABASE ACCESSION NUMBER: Genbank NM_009287
<309> DATABASE ENTRY DATE: 2002-01-07

<400> SEQUENCE: 9 atg gat gtg tgc gcc cgt ctt gcc ctg tgg ctt ctt tgg ggg ctc ctt      48
Met Asp Val Cys Ala Arg Leu Ala Leu Trp Leu Leu Trp Gly Leu Leu
 1               5                  10                  15 ctg cat cag ggc cag agt ctc agc cat agt cac agt gaa aag aat aca      96
Leu His Gln Gly Gln Ser Leu Ser His Ser His Ser Glu Lys Asn Thr
             20                  25                  30 gga gct agc tcc ggg gcg act tct gaa gag tct acc gaa gca gag ttt     144
Gly Ala Ser Ser Gly Ala Thr Ser Glu Glu Ser Thr Glu Ala Glu Phe
         35                  40                  45 tgc cga att gac aag ccc ctg tgc cac agt gag gat gag aag ctc agc     192
Cys Arg Ile Asp Lys Pro Leu Cys His Ser Glu Asp Glu Lys Leu Ser
     50                  55                  60 ttt gag gcc gtc cga aac atc cat aag ctg atg gat gac gat gcc aat     240
Phe Glu Ala Val Arg Asn Ile His Lys Leu Met Asp Asp Asp Ala Asn
 65                  70                  75                  80 ggt gat gtg gat gtg gaa gaa agt gat gag ttc cta agg gaa gac ctc     288
Gly Asp Val Asp Val Glu Glu Ser Asp Glu Phe Leu Arg Glu Asp Leu
                 85                  90                  95 aat tac cat gac cca aca gtg aaa cat agc acc ttc cat ggt gag gat     336
Asn Tyr His Asp Pro Thr Val Lys His Ser Thr Phe His Gly Glu Asp
            100                 105                 110 aag ctt atc agc gtg gag gac ctg tgg aag gcg tgg aag tca tca gaa     384
Lys Leu Ile Ser Val Glu Asp Leu Trp Lys Ala Trp Lys Ser Ser Glu
        115                 120                 125 gtg tac aac tgg act gtg gat gag gtg ata cag tgg ctc att acg tat     432
Val Tyr Asn Trp Thr Val Asp Glu Val Ile Gln Trp Leu Ile Thr Tyr
    130                 135                 140 gtg gag ctg cca cag tat gag gaa acc ttc cgg aag ttg cag ctt act     480
Val Glu Leu Pro Gln Tyr Glu Glu Thr Phe Arg Lys Leu Gln Leu Thr
145                 150                 155                 160 ggc cac gcc atg cca agg cta gca gta acc aac acc acc atg aca ggg     528
Gly His Ala Met Pro Arg Leu Ala Val Thr Asn Thr Thr Met Thr Gly
                165                 170                 175 act gta ctg aag atg aca gat cgg agc cac agg cag aag ctg cag ctg     576
Thr Val Leu Lys Met Thr Asp Arg Ser His Arg Gln Lys Leu Gln Leu
            180                 185                 190 aag gcc ctg gac aca gtg ctg ttt ggg cct cct ctc ttg act cgg cat     624
Lys Ala Leu Asp Thr Val Leu Phe Gly Pro Pro Leu Leu Thr Arg His
        195                 200                 205 aat cac ctg aag gac ttc atg ctg gtg gtg tct atc gtt att ggt gtg     672
Asn His Leu Lys Asp Phe Met Leu Val Val Ser Ile Val Ile Gly Val
    210                 215                 220 ggt ggc tgc tgg ttt gcc tat atc cag aac cgt tac tct aag gag cac     720
Gly Gly Cys Trp Phe Ala Tyr Ile Gln Asn Arg Tyr Ser Lys Glu His
225                 230                 235                 240 atg aag aaa atg atg aag gat ctg gaa ggg tta cac cgg gct gag cag     768
Met Lys Lys Met Met Lys Asp Leu Glu Gly Leu His Arg Ala Glu Gln
                245                 250                 255 agt ctg cat gac ctt cag gaa agg ctg cac aag gcc cag gag gag cac     816
Ser Leu His Asp Leu Gln Glu Arg Leu His Lys Ala Gln Glu Glu His
```

-continued

|  | 260 |  |  |  | 265 |  |  |  | 270 |  |  |  |
|---|---|---|---|---|---|---|---|---|---|---|---|---|
| cga | act | gtg | gaa | gta | gag | aag | gtc | cac | ctg | gag | aag | aag | ctg | cga | gat | 864 |
| Arg | Thr | Val | Glu | Val | Glu | Lys | Val | His | Leu | Glu | Lys | Lys | Leu | Arg | Asp |  |
|  |  | 275 |  |  |  |  | 280 |  |  |  |  | 285 |  |  |  |  |

| gag | atc | aac | ctt | gcc | aag | cag | gaa | gct | cag | cgg | ctg | aag | gag | ctg | agg | 912 |
| Glu | Ile | Asn | Leu | Ala | Lys | Gln | Glu | Ala | Gln | Arg | Leu | Lys | Glu | Leu | Arg |  |
| 290 |  |  |  |  | 295 |  |  |  |  | 300 |  |  |  |  |  |  |

| gag | ggt | act | gag | aat | gag | agg | agc | cgt | caa | aaa | tat | gct | gag | gaa | gag | 960 |
| Glu | Gly | Thr | Glu | Asn | Glu | Arg | Ser | Arg | Gln | Lys | Tyr | Ala | Glu | Glu | Glu |  |
| 305 |  |  |  |  | 310 |  |  |  |  | 315 |  |  |  |  | 320 |  |

| ctg | gag | cag | gtt | cgg | gag | gcc | ttg | agg | aaa | tca | gag | aag | gag | ctg | gaa | 1008 |
| Leu | Glu | Gln | Val | Arg | Glu | Ala | Leu | Arg | Lys | Ser | Glu | Lys | Glu | Leu | Glu |  |
|  |  |  |  | 325 |  |  |  |  | 330 |  |  |  |  | 335 |  |  |

| tca | cac | agc | tca | tgg | tat | gct | cct | gag | gcc | ctg | cag | aag | tgg | ctg | cag | 1056 |
| Ser | His | Ser | Ser | Trp | Tyr | Ala | Pro | Glu | Ala | Leu | Gln | Lys | Trp | Leu | Gln |  |
|  |  |  | 340 |  |  |  |  | 345 |  |  |  |  | 350 |  |  |  |

| ctg | acc | cat | gag | gtg | gag | gtg | cag | tac | tac | aac | atc | aag | aag | caa | aat | 1104 |
| Leu | Thr | His | Glu | Val | Glu | Val | Gln | Tyr | Tyr | Asn | Ile | Lys | Lys | Gln | Asn |  |
|  |  | 355 |  |  |  |  | 360 |  |  |  |  | 365 |  |  |  |  |

| gca | gag | agg | cag | ctg | ctg | gtg | gcc | aag | gag | ggg | gct | gag | aaa | ata | aaa | 1152 |
| Ala | Glu | Arg | Gln | Leu | Leu | Val | Ala | Lys | Glu | Gly | Ala | Glu | Lys | Ile | Lys |  |
| 370 |  |  |  |  | 375 |  |  |  |  | 380 |  |  |  |  |  |  |

| aag | aag | aga | aac | acg | ctt | ttt | ggt | acc | ttc | cat | gtg | gcc | cac | agc | tct | 1200 |
| Lys | Lys | Arg | Asn | Thr | Leu | Phe | Gly | Thr | Phe | His | Val | Ala | His | Ser | Ser |  |
| 385 |  |  |  |  | 390 |  |  |  |  | 395 |  |  |  |  | 400 |  |

| tcc | ctg | gat | gat | gtg | gat | cat | aaa | atc | cta | act | gct | aag | caa | gct | ctg | 1248 |
| Ser | Leu | Asp | Asp | Val | Asp | His | Lys | Ile | Leu | Thr | Ala | Lys | Gln | Ala | Leu |  |
|  |  |  |  | 405 |  |  |  |  | 410 |  |  |  |  | 415 |  |  |

| agt | gag | gtg | aca | gcg | gca | ctg | agg | gag | cgc | ctg | cac | cgg | tgg | cag | cag | 1296 |
| Ser | Glu | Val | Thr | Ala | Ala | Leu | Arg | Glu | Arg | Leu | His | Arg | Trp | Gln | Gln |  |
|  |  |  | 420 |  |  |  |  | 425 |  |  |  |  | 430 |  |  |  |

| atc | gag | atc | ctc | tgc | ggt | ttc | cag | att | gtc | aat | aac | ccc | ggc | atc | cac | 1344 |
| Ile | Glu | Ile | Leu | Cys | Gly | Phe | Gln | Ile | Val | Asn | Asn | Pro | Gly | Ile | His |  |
|  |  | 435 |  |  |  |  | 440 |  |  |  |  | 445 |  |  |  |  |

| tcc | ttg | gtg | gct | gct | ctc | aac | atc | gac | ccc | agc | tgg | atg | ggc | agc | acc | 1392 |
| Ser | Leu | Val | Ala | Ala | Leu | Asn | Ile | Asp | Pro | Ser | Trp | Met | Gly | Ser | Thr |  |
| 450 |  |  |  |  | 455 |  |  |  |  | 460 |  |  |  |  |  |  |

| cgc | cct | aac | ccc | gcc | cac | ttc | atc | atg | act | gac | gat | gtg | gat | gac | atg | 1440 |
| Arg | Pro | Asn | Pro | Ala | His | Phe | Ile | Met | Thr | Asp | Asp | Val | Asp | Asp | Met |  |
| 465 |  |  |  |  | 470 |  |  |  |  | 475 |  |  |  |  | 480 |  |

| gat | gag | gag | att | gtg | tcg | ccc | ttg | tcc | atg | cag | tcc | ccc | agc | ctg | cag | 1488 |
| Asp | Glu | Glu | Ile | Val | Ser | Pro | Leu | Ser | Met | Gln | Ser | Pro | Ser | Leu | Gln |  |
|  |  |  |  | 485 |  |  |  |  | 490 |  |  |  |  | 495 |  |  |

| agc | agt | gtc | cgg | cag | cgc | ctg | acg | gag | cca | cag | ctt | ggc | ctg | gga | tct | 1536 |
| Ser | Ser | Val | Arg | Gln | Arg | Leu | Thr | Glu | Pro | Gln | Leu | Gly | Leu | Gly | Ser |  |
|  |  |  | 500 |  |  |  |  | 505 |  |  |  |  | 510 |  |  |  |

| cag | agg | gat | ttg | acc | cat | tcc | gat | tcg | gag | tcc | tcc | ctc | cac | atg | agt | 1584 |
| Gln | Arg | Asp | Leu | Thr | His | Ser | Asp | Ser | Glu | Ser | Ser | Leu | His | Met | Ser |  |
|  |  | 515 |  |  |  |  | 520 |  |  |  |  | 525 |  |  |  |  |

| gac | cgc | cag | cgt | gtg | gcc | ccc | aag | cct | cct | cag | atg | ggc | cgt | gct | gca | 1632 |
| Asp | Arg | Gln | Arg | Val | Ala | Pro | Lys | Pro | Pro | Gln | Met | Gly | Arg | Ala | Ala |  |
| 530 |  |  |  |  | 535 |  |  |  |  | 540 |  |  |  |  |  |  |

| gat | gaa | gct | ctc | aat | gcc | atg | cct | tcc | aat | ggc | agc | cat | cgg | ctg | att | 1680 |
| Asp | Glu | Ala | Leu | Asn | Ala | Met | Pro | Ser | Asn | Gly | Ser | His | Arg | Leu | Ile |  |
| 545 |  |  |  |  | 550 |  |  |  |  | 555 |  |  |  |  | 560 |  |

| gag | ggg | gtc | cat | cca | gga | tct | ctg | gtg | gag | aaa | ctg | cct | gac | agc | cct | 1728 |
| Glu | Gly | Val | His | Pro | Gly | Ser | Leu | Val | Glu | Lys | Leu | Pro | Asp | Ser | Pro |  |
|  |  |  |  | 565 |  |  |  |  | 570 |  |  |  |  | 575 |  |  |

| gct | ctg | gcc | aag | aag | aca | ttt | atg | gcg | ttg | aac | cat | ggc | cta | gac | aag | 1776 |

-continued

```
                Ala Leu Ala Lys Lys Thr Phe Met Ala Leu Asn His Gly Leu Asp Lys
                            580                 585                 590 gcc cac agc ctg atg gag ctg aac ccc tca gtc cca cct ggt ggc tcc        1824
Ala His Ser Leu Met Glu Leu Asn Pro Ser Val Pro Pro Gly Gly Ser
            595                 600                 605 cca ctt ttg gat tct tcc cat tct ctt agc ccc agt tcc cca gac cca        1872
Pro Leu Leu Asp Ser Ser His Ser Leu Ser Pro Ser Ser Pro Asp Pro
610                 615                 620 gac acg cca tct cca gtt ggg gac aac cga gct ctg cag ggt agc cga        1920
Asp Thr Pro Ser Pro Val Gly Asp Asn Arg Ala Leu Gln Gly Ser Arg
625                 630                 635                 640 aac aca cga att ccc cac ttg gct ggc aag aag gca atg gct gag gag        1968
Asn Thr Arg Ile Pro His Leu Ala Gly Lys Lys Ala Met Ala Glu Glu
                645                 650                 655 gat aat ggt tcc att ggt gag gag aca gac tcc agt cca ggc agg aag        2016
Asp Asn Gly Ser Ile Gly Glu Glu Thr Asp Ser Ser Pro Gly Arg Lys
            660                 665                 670 aag ttt cct ctc aaa att ttt aag aag cct ctt aag aag tag                2058
Lys Phe Pro Leu Lys Ile Phe Lys Lys Pro Leu Lys Lys *
        675                 680                 685

<210> SEQ ID NO 10
<211> LENGTH: 685
<212> TYPE: PRT
<213> ORGANISM: Mus musculus
<300> PUBLICATION INFORMATION:
<308> DATABASE ACCESSION NUMBER: NP_033313
<309> DATABASE ENTRY DATE: 2002-01-07

<400> SEQUENCE: 10

Met Asp Val Cys Ala Arg Leu Ala Leu Trp Leu Leu Trp Gly Leu Leu
 1               5                  10                  15

Leu His Gln Gly Gln Ser Leu Ser His Ser His Ser Glu Lys Asn Thr
            20                  25                  30

Gly Ala Ser Ser Gly Ala Thr Ser Glu Glu Ser Thr Glu Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Ile Gln Trp Leu Ile Thr Tyr
    130                 135                 140

Val Glu Leu Pro Gln Tyr Glu Glu Thr Phe Arg Lys Leu Gln Leu Thr
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220
```

```
Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
            245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
            275                 280                 285

Glu Ile Asn Leu Ala Lys Gln Glu Ala Gln Arg Leu Lys Glu Leu Arg
290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ser Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
            355                 360                 365

Ala Glu Arg Gln Leu Leu Val Ala Lys Glu Gly Ala Glu Lys Ile Lys
370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
            435                 440                 445

Ser Leu Val Ala Ala Leu Asn Ile Asp Pro Ser Trp Met Gly Ser Thr
450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln Leu Gly Leu Gly Ser
            500                 505                 510

Gln Arg Asp Leu Thr His Ser Asp Ser Glu Ser Ser Leu His Met Ser
            515                 520                 525

Asp Arg Gln Arg Val Ala Pro Lys Pro Pro Gln Met Gly Arg Ala Ala
530                 535                 540

Asp Glu Ala Leu Asn Ala Met Pro Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Thr Phe Met Ala Leu Asn His Gly Leu Asp Lys
            580                 585                 590

Ala His Ser Leu Met Glu Leu Asn Pro Ser Val Pro Pro Gly Gly Ser
            595                 600                 605

Pro Leu Leu Asp Ser Ser His Ser Leu Ser Pro Ser Ser Pro Asp Pro
610                 615                 620

Asp Thr Pro Ser Pro Val Gly Asp Asn Arg Ala Leu Gln Gly Ser Arg
625                 630                 635                 640
```

```
Asn Thr Arg Ile Pro His Leu Ala Gly Lys Lys Ala Met Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 11
<211> LENGTH: 1944
<212> TYPE: DNA
<213> ORGANISM: Mus musculus
<220> FEATURE:
<221> NAME/KEY: CDS
<222> LOCATION: (1)...(1944)
<223> OTHER INFORMATION: STIM2
<300> PUBLICATION INFORMATION:
<308> DATABASE ACCESSION NUMBER: Genbank XM_132038
<309> DATABASE ENTRY DATE: 2002-10-09

<400> SEQUENCE: 11
```

| | | | | | | | | | | | | | | | | |
|---|---|---|---|---|---|---|---|---|---|---|---|---|---|---|---|---|
| atg | aaa | tat | aaa | gat | gct | acg | aat | aaa | cat | agt | cac | ctg | cac | aga | gaa | 48 |
| Met | Lys | Tyr | Lys | Asp | Ala | Thr | Asn | Lys | His | Ser | His | Leu | His | Arg | Glu | |
| 1 | | | | 5 | | | | | 10 | | | | | 15 | | |
| gat | aag | cac | ata | act | gtt | gag | gat | ttg | tgg | aaa | cag | tgg | aaa | aca | tca | 96 |
| Asp | Lys | His | Ile | Thr | Val | Glu | Asp | Leu | Trp | Lys | Gln | Trp | Lys | Thr | Ser | |
| | | | 20 | | | | | 25 | | | | | 30 | | | |
| gaa | gtt | cac | aat | tgg | aca | ctt | gag | gat | acc | ctg | cag | tgg | tta | ata | gaa | 144 |
| Glu | Val | His | Asn | Trp | Thr | Leu | Glu | Asp | Thr | Leu | Gln | Trp | Leu | Ile | Glu | |
| | 35 | | | | | 40 | | | | | 45 | | | | | |
| ttt | gtt | gaa | ctg | cca | caa | tat | gag | aag | aat | ttt | agg | gat | aat | aat | gtg | 192 |
| Phe | Val | Glu | Leu | Pro | Gln | Tyr | Glu | Lys | Asn | Phe | Arg | Asp | Asn | Asn | Val | |
| 50 | | | | | 55 | | | | | 60 | | | | | | |
| aag | gga | aca | aca | ctc | ccc | agg | ata | gca | gtt | cat | gaa | act | tca | ttt | atg | 240 |
| Lys | Gly | Thr | Thr | Leu | Pro | Arg | Ile | Ala | Val | His | Glu | Thr | Ser | Phe | Met | |
| 65 | | | | 70 | | | | | 75 | | | | | 80 | | |
| att | tcc | cag | ttg | aaa | atc | agc | gac | cga | agt | cac | aga | cag | aaa | ctc | caa | 288 |
| Ile | Ser | Gln | Leu | Lys | Ile | Ser | Asp | Arg | Ser | His | Arg | Gln | Lys | Leu | Gln | |
| | | | | 85 | | | | | 90 | | | | | 95 | | |
| ctc | aaa | gcc | ctg | gat | gtg | gtt | ctg | ttt | ggg | cct | ctg | aca | cgc | cca | cct | 336 |
| Leu | Lys | Ala | Leu | Asp | Val | Val | Leu | Phe | Gly | Pro | Leu | Thr | Arg | Pro | Pro | |
| | | | 100 | | | | | 105 | | | | | 110 | | | |
| cat | aac | tgg | atg | aag | gat | ttt | att | ctc | aca | att | tcc | ata | gta | att | ggt | 384 |
| His | Asn | Trp | Met | Lys | Asp | Phe | Ile | Leu | Thr | Ile | Ser | Ile | Val | Ile | Gly | |
| | 115 | | | | | 120 | | | | | 125 | | | | | |
| gtt | ggg | ggt | tgt | tgg | ttt | gct | tat | aca | caa | aat | aag | aca | tca | aag | gaa | 432 |
| Val | Gly | Gly | Cys | Trp | Phe | Ala | Tyr | Thr | Gln | Asn | Lys | Thr | Ser | Lys | Glu | |
| 130 | | | | | 135 | | | | | 140 | | | | | | |
| cat | gtt | gca | aaa | atg | atg | aaa | gac | tta | gag | agt | ctg | cag | act | gca | gag | 480 |
| His | Val | Ala | Lys | Met | Met | Lys | Asp | Leu | Glu | Ser | Leu | Gln | Thr | Ala | Glu | |
| 145 | | | | | 150 | | | | | 155 | | | | | 160 | |
| cag | agt | ctc | atg | gac | tta | caa | gag | aga | ctt | gaa | aag | gca | cag | gaa | gaa | 528 |
| Gln | Ser | Leu | Met | Asp | Leu | Gln | Glu | Arg | Leu | Glu | Lys | Ala | Gln | Glu | Glu | |
| | | | | 165 | | | | | 170 | | | | | 175 | | |
| aac | aga | act | gtt | gct | gta | gaa | aag | caa | aat | ctg | gaa | cgg | aaa | atg | atg | 576 |
| Asn | Arg | Thr | Val | Ala | Val | Glu | Lys | Gln | Asn | Leu | Glu | Arg | Lys | Met | Met | |
| | | | 180 | | | | | 185 | | | | | 190 | | | |
| gat | gaa | atc | aac | tat | gcc | aag | gag | gag | gcc | tgt | cgg | ctg | cgg | gag | ctg | 624 |
| Asp | Glu | Ile | Asn | Tyr | Ala | Lys | Glu | Glu | Ala | Cys | Arg | Leu | Arg | Glu | Leu | |
| | 195 | | | | | 200 | | | | | 205 | | | | | |
| agg | gag | ggc | gca | gag | tgt | gag | ctg | agc | agg | cgc | cag | tat | gca | gag | cag | 672 |
| Arg | Glu | Gly | Ala | Glu | Cys | Glu | Leu | Ser | Arg | Arg | Gln | Tyr | Ala | Glu | Gln | |
| 210 | | | | | 215 | | | | | 220 | | | | | | |

-continued

| | |
|---|---|
| gaa ctg gag cag gtc cgc atg gct cta aaa aag gcc gaa aag gag ttt<br>Glu Leu Glu Gln Val Arg Met Ala Leu Lys Lys Ala Glu Lys Glu Phe<br>225                           230                        235                    240 | 720 |
| gaa ctg aga agc agc tgg tct gtc cct gac gca cta cag aaa tgg ctt<br>Glu Leu Arg Ser Ser Trp Ser Val Pro Asp Ala Leu Gln Lys Trp Leu<br>                      245                        250                    255 | 768 |
| cag cta aca cac gaa gtt gaa gta cag tac tac aat att aag agg caa<br>Gln Leu Thr His Glu Val Glu Val Gln Tyr Tyr Asn Ile Lys Arg Gln<br>260                        265                        270 | 816 |
| aat gct gag atg cag cta gcc atc gct aag gac gag gca gaa aaa att<br>Asn Ala Glu Met Gln Leu Ala Ile Ala Lys Asp Glu Ala Glu Lys Ile<br>        275                        280                    285 | 864 |
| aaa aag aag aga agc aca gtc ttt ggg acc ctg cac gtt gca cac agc<br>Lys Lys Lys Arg Ser Thr Val Phe Gly Thr Leu His Val Ala His Ser<br>290                           295                        300 | 912 |
| tcc tcc ctg gac gaa gta gac cac aag att ctg gaa gcc aag aaa gcc<br>Ser Ser Leu Asp Glu Val Asp His Lys Ile Leu Glu Ala Lys Lys Ala<br>305                        310                        315                    320 | 960 |
| ctc tct gag ctg acc acg tgc ttg cga gaa cgg ctt ttt cgc tgg cag<br>Leu Ser Glu Leu Thr Thr Cys Leu Arg Glu Arg Leu Phe Arg Trp Gln<br>                      325                        330                    335 | 1008 |
| cag att gag aag atc tgt ggc ttt cag ata gct cac aac tct ggg ctc<br>Gln Ile Glu Lys Ile Cys Gly Phe Gln Ile Ala His Asn Ser Gly Leu<br>340                           345                        350 | 1056 |
| ccc agt ctc acc tcc tct ctg tac tct gac cac agc tgg gtg gtg atg<br>Pro Ser Leu Thr Ser Ser Leu Tyr Ser Asp His Ser Trp Val Val Met<br>        355                        360                    365 | 1104 |
| cct aga gtc tcc att cca ccc tac cct att gct gga gga gtt gat gac<br>Pro Arg Val Ser Ile Pro Pro Tyr Pro Ile Ala Gly Gly Val Asp Asp<br>370                           375                        380 | 1152 |
| ctc gat gaa gac aca ccc cca atc gtg cca cag ttt cca ggg acc gtg<br>Leu Asp Glu Asp Thr Pro Pro Ile Val Pro Gln Phe Pro Gly Thr Val<br>385                        390                        395                    400 | 1200 |
| gct aaa cct gca gga tct tta gcc aga agc agt agt tta tgc cgc tct<br>Ala Lys Pro Ala Gly Ser Leu Ala Arg Ser Ser Ser Leu Cys Arg Ser<br>                      405                        410                    415 | 1248 |
| cgt cgc agc atc gtg cca tcc tcc cca cag tct cag cga gct cag ctt<br>Arg Arg Ser Ile Val Pro Ser Ser Pro Gln Ser Gln Arg Ala Gln Leu<br>420                           425                        430 | 1296 |
| cct gct cat gct cct ctg gca gcc cac cct cgg cac cct cac cat ccg<br>Pro Ala His Ala Pro Leu Ala Ala His Pro Arg His Pro His His Pro<br>        435                        440                    445 | 1344 |
| cag cat ccc cag cac tcg ttg cct tcc cca gat cca gac atc ctg tct<br>Gln His Pro Gln His Ser Leu Pro Ser Pro Asp Pro Asp Ile Leu Ser<br>450                        455                        460 | 1392 |
| gtg tca agt tgc cct gct ctg tat cgg aac gaa gag gag gag gag gct<br>Val Ser Ser Cys Pro Ala Leu Tyr Arg Asn Glu Glu Glu Glu Glu Ala<br>465                        470                        475                    480 | 1440 |
| atc tac ttc act gct gag aaa caa tgg gaa gtg cca gac aca gct tca<br>Ile Tyr Phe Thr Ala Glu Lys Gln Trp Glu Val Pro Asp Thr Ala Ser<br>                      485                        490                    495 | 1488 |
| gaa tgt gac tcc tta aac tct tcc agt ggg aga aaa ccg tct ccc cct<br>Glu Cys Asp Ser Leu Asn Ser Ser Ser Gly Arg Lys Pro Ser Pro Pro<br>500                        505                        510 | 1536 |
| tca agc ctt gag atg tac caa aca ttg tct tcc cga aaa atc tca aga<br>Ser Ser Leu Glu Met Tyr Gln Thr Leu Ser Ser Arg Lys Ile Ser Arg<br>                  515                        520                    525 | 1584 |
| gac gag ctt tcc ctg gag gac tct tcc agg ggg gag tca ccc gtg aca<br>Asp Glu Leu Ser Leu Glu Asp Ser Ser Arg Gly Glu Ser Pro Val Thr | 1632 |

-continued

```
        530                 535                 540
gca gat gtc tcc cgg ggc tcc cct gag tgt gtg ggt ctg acg gag acc      1680
Ala Asp Val Ser Arg Gly Ser Pro Glu Cys Val Gly Leu Thr Glu Thr
545                 550                 555                 560 aag agc atg atc ttc agc cct gca agc aga gtg tac aat ggc atc ctg      1728
Lys Ser Met Ile Phe Ser Pro Ala Ser Arg Val Tyr Asn Gly Ile Leu
                565                 570                 575 gag aaa tcc tgc agc atg cac cag ctc tcc agc ggc atc ccg gtg cct      1776
Glu Lys Ser Cys Ser Met His Gln Leu Ser Ser Gly Ile Pro Val Pro
            580                 585                 590 cat ccc cga cac aca tcg tgc tcc tca gcc ggc aat gat agc aag cca      1824
His Pro Arg His Thr Ser Cys Ser Ser Ala Gly Asn Asp Ser Lys Pro
        595                 600                 605 gtt cag gaa gcc tcg aat gtt tcc aga gta agc agc atc cca cat gac      1872
Val Gln Glu Ala Ser Asn Val Ser Arg Val Ser Ser Ile Pro His Asp
    610                 615                 620 ctc tgt cat aat ggt gag aaa agc aaa aag cca tcc aaa atc aaa agc      1920
Leu Cys His Asn Gly Glu Lys Ser Lys Lys Pro Ser Lys Ile Lys Ser
625                 630                 635                 640 ctt ttc aag aag aag tct aag tga                                       1944
Leu Phe Lys Lys Lys Ser Lys *
            645

<210> SEQ ID NO 12
<211> LENGTH: 647
<212> TYPE: PRT
<213> ORGANISM: Mus musculus
<300> PUBLICATION INFORMATION:
<308> DATABASE ACCESSION NUMBER: Genbank XP_132038
<309> DATABASE ENTRY DATE: 2002-10-09

<400> SEQUENCE: 12

Met Lys Tyr Lys Asp Ala Thr Asn Lys His Ser His Leu His Arg Glu
 1               5                  10                  15

Asp Lys His Ile Thr Val Glu Asp Leu Trp Lys Gln Trp Lys Thr Ser
            20                  25                  30

Glu Val His Asn Trp Thr Leu Glu Asp Thr Leu Gln Trp Leu Ile Glu
        35                  40                  45

Phe Val Glu Leu Pro Gln Tyr Glu Lys Asn Phe Arg Asp Asn Asn Val
    50                  55                  60

Lys Gly Thr Thr Leu Pro Arg Ile Ala Val His Glu Thr Ser Phe Met
65                  70                  75                  80

Ile Ser Gln Leu Lys Ile Ser Asp Arg Ser His Arg Gln Lys Leu Gln
                85                  90                  95

Leu Lys Ala Leu Asp Val Val Leu Phe Gly Pro Leu Thr Arg Pro Pro
            100                 105                 110

His Asn Trp Met Lys Asp Phe Ile Leu Thr Ile Ser Ile Val Ile Gly
        115                 120                 125

Val Gly Gly Cys Trp Phe Ala Tyr Thr Gln Asn Lys Thr Ser Lys Glu
    130                 135                 140

His Val Ala Lys Met Met Lys Asp Leu Glu Ser Leu Gln Thr Ala Glu
145                 150                 155                 160

Gln Ser Leu Met Asp Leu Gln Glu Arg Leu Glu Lys Ala Gln Glu Glu
                165                 170                 175

Asn Arg Thr Val Ala Val Glu Lys Gln Asn Leu Glu Arg Lys Met Met
            180                 185                 190

Asp Glu Ile Asn Tyr Ala Lys Glu Glu Ala Cys Arg Leu Arg Glu Leu
        195                 200                 205
```

-continued

```
Arg Glu Gly Ala Glu Cys Glu Leu Ser Arg Arg Gln Tyr Ala Glu Gln
    210                 215                 220

Glu Leu Glu Gln Val Arg Met Ala Leu Lys Lys Ala Glu Lys Glu Phe
225                 230                 235                 240

Glu Leu Arg Ser Ser Trp Ser Val Pro Asp Ala Leu Gln Lys Trp Leu
                245                 250                 255

Gln Leu Thr His Glu Val Glu Val Gln Tyr Tyr Asn Ile Lys Arg Gln
            260                 265                 270

Asn Ala Glu Met Gln Leu Ala Ile Ala Lys Asp Glu Ala Glu Lys Ile
        275                 280                 285

Lys Lys Lys Arg Ser Thr Val Phe Gly Thr Leu His Val Ala His Ser
    290                 295                 300

Ser Ser Leu Asp Glu Val Asp His Lys Ile Leu Glu Ala Lys Lys Ala
305                 310                 315                 320

Leu Ser Glu Leu Thr Thr Cys Leu Arg Glu Arg Leu Phe Arg Trp Gln
                325                 330                 335

Gln Ile Glu Lys Ile Cys Gly Phe Gln Ile Ala His Asn Ser Gly Leu
            340                 345                 350

Pro Ser Leu Thr Ser Ser Leu Tyr Ser Asp His Ser Trp Val Val Met
        355                 360                 365

Pro Arg Val Ser Ile Pro Pro Tyr Pro Ile Ala Gly Gly Val Asp Asp
    370                 375                 380

Leu Asp Glu Asp Thr Pro Pro Ile Val Pro Gln Phe Pro Gly Thr Val
385                 390                 395                 400

Ala Lys Pro Ala Gly Ser Leu Ala Arg Ser Ser Ser Leu Cys Arg Ser
                405                 410                 415

Arg Arg Ser Ile Val Pro Ser Ser Pro Gln Ser Gln Arg Ala Gln Leu
            420                 425                 430

Pro Ala His Ala Pro Leu Ala Ala His Pro Arg His Pro His His Pro
        435                 440                 445

Gln His Pro Gln His Ser Leu Pro Ser Pro Asp Pro Asp Ile Leu Ser
    450                 455                 460

Val Ser Ser Cys Pro Ala Leu Tyr Arg Asn Glu Glu Glu Glu Glu Ala
465                 470                 475                 480

Ile Tyr Phe Thr Ala Glu Lys Gln Trp Glu Val Pro Asp Thr Ala Ser
                485                 490                 495

Glu Cys Asp Ser Leu Asn Ser Ser Gly Arg Lys Pro Ser Pro Pro Pro
            500                 505                 510

Ser Ser Leu Glu Met Tyr Gln Thr Leu Ser Ser Arg Lys Ile Ser Arg
    515                 520                 525

Asp Glu Leu Ser Leu Glu Asp Ser Ser Arg Gly Glu Ser Pro Val Thr
530                 535                 540

Ala Asp Val Ser Arg Gly Ser Pro Glu Cys Val Gly Leu Thr Glu Thr
545                 550                 555                 560

Lys Ser Met Ile Phe Ser Pro Ala Ser Arg Val Tyr Asn Gly Ile Leu
                565                 570                 575

Glu Lys Ser Cys Ser Met His Gln Leu Ser Ser Gly Ile Pro Val Pro
            580                 585                 590

His Pro Arg His Thr Ser Cys Ser Ser Ala Gly Asn Asp Ser Lys Pro
    595                 600                 605

Val Gln Glu Ala Ser Asn Val Ser Arg Val Ser Ser Ile Pro His Asp
610                 615                 620
```

```
Leu Cys His Asn Gly Glu Lys Ser Lys Pro Ser Lys Ile Lys Ser
625                 630                 635                 640

Leu Phe Lys Lys Lys Ser Lys
                645

<210> SEQ ID NO 13
<211> LENGTH: 1593
<212> TYPE: DNA
<213> ORGANISM: Caenorhabditis elegans
<220> FEATURE:
<221> NAME/KEY: CDS
<222> LOCATION: (1)...(1593)
<223> OTHER INFORMATION: C-STIM
<300> PUBLICATION INFORMATION:
<308> DATABASE ACCESSION NUMBER: Genbank NM_064796
<309> DATABASE ENTRY DATE: 2001-12-03

<400> SEQUENCE: 13 atg ggt aga gtt tcg tgg att att gcc tta tat ctt aca atc aac gtg      48
Met Gly Arg Val Ser Trp Ile Ile Ala Leu Tyr Leu Thr Ile Asn Val
 1               5                  10                  15 gtt att gtt gtt aat gga gat cgg gtg act aga aat gtt gaa gta acg      96
Val Ile Val Val Asn Gly Asp Arg Val Thr Arg Asn Val Glu Val Thr
             20                  25                  30 gcg gaa gaa gaa aaa ata cgg gat aaa ttg gga tat gaa gcg att aga     144
Ala Glu Glu Glu Lys Ile Arg Asp Lys Leu Gly Tyr Glu Ala Ile Arg
         35                  40                  45 gat att cat cga gac atg gac gat gat cat tcg ggt tca atc gat cga     192
Asp Ile His Arg Asp Met Asp Asp Asp His Ser Gly Ser Ile Asp Arg
     50                  55                  60 aat gaa tcg act ggg ttt atg aaa gaa gat atg caa atg cgt gga tcc     240
Asn Glu Ser Thr Gly Phe Met Lys Glu Asp Met Gln Met Arg Gly Ser
 65                  70                  75                  80 gaa cga act aga cgg gag aat aag ttc cat ggc gac gac gat gcg att     288
Glu Arg Thr Arg Arg Glu Asn Lys Phe His Gly Asp Asp Asp Ala Ile
                 85                  90                  95 act gta gac gat ctg tgg gag gcc tgg ttt gag agt atc gag aga act     336
Thr Val Asp Asp Leu Trp Glu Ala Trp Phe Glu Ser Ile Glu Arg Thr
            100                 105                 110 tgg acg aat gaa agg ctc gtc gaa tgg ctc atc aac gac gta aac ctt     384
Trp Thr Asn Glu Arg Leu Val Glu Trp Leu Ile Asn Asp Val Asn Leu
        115                 120                 125 ccc agc att gtt gaa gca gta aaa gcc aag aaa att gat ggg aag att     432
Pro Ser Ile Val Glu Ala Val Lys Ala Lys Lys Ile Asp Gly Lys Ile
    130                 135                 140 ctt cca aga ttt gca tct cca aat tcg gac ttt ttg aac aaa gaa ctt     480
Leu Pro Arg Phe Ala Ser Pro Asn Ser Asp Phe Leu Asn Lys Glu Leu
145                 150                 155                 160 ggc ata aaa tcg tcg gtt tat cgt caa aaa ctt cgt ttg aac tcg ttg     528
Gly Ile Lys Ser Ser Val Tyr Arg Gln Lys Leu Arg Leu Asn Ser Leu
                165                 170                 175 gat gtt gta ctt ttt ggg tat aag gat aat aat aat cga aca aag gat     576
Asp Val Val Leu Phe Gly Tyr Lys Asp Asn Asn Asn Arg Thr Lys Asp
            180                 185                 190 att cta ttg gcg ttt ttg gca ctt ctc cta aca tca ctc atc ttt tta     624
Ile Leu Leu Ala Phe Leu Ala Leu Leu Leu Thr Ser Leu Ile Phe Leu
        195                 200                 205 tac gtc cgc caa aaa caa aag gct cag caa aaa gtc aat gaa tta tca     672
Tyr Val Arg Gln Lys Gln Lys Ala Gln Gln Lys Val Asn Glu Leu Ser
    210                 215                 220 aat aag ttg acc gaa ctg aaa tgt atg gaa acc gaa ttt gaa gat gtt     720
Asn Lys Leu Thr Glu Leu Lys Cys Met Glu Thr Glu Phe Glu Asp Val
```

```
                  225                 230                 235                 240
cag aaa atg ttg aat gac gag aga agt aaa cga tca att tcc gat gga        768
Gln Lys Met Leu Asn Asp Glu Arg Ser Lys Arg Ser Ile Ser Asp Gly
                245                 250                 255 gtt gtg aat cac aca gaa atg gag aac ctc cgt gtc cag ctg gaa gaa        816
Val Val Asn His Thr Glu Met Glu Asn Leu Arg Val Gln Leu Glu Glu
                260                 265                 270 gcc gaa cga cgg ctt gaa gcg aat tcg aat ggt tct caa gct cct ctt        864
Ala Glu Arg Arg Leu Glu Ala Asn Ser Asn Gly Ser Gln Ala Pro Leu
                275                 280                 285 gca ctt cag cca ttg ctt aga aga act tgc gag aat gag atg gct ttt        912
Ala Leu Gln Pro Leu Leu Arg Arg Thr Cys Glu Asn Glu Met Ala Phe
            290                 295                 300 ctg gaa aag cag aga caa gat tgc ttc aag gaa atg aaa gag gcc atc        960
Leu Glu Lys Gln Arg Gln Asp Cys Phe Lys Glu Met Lys Glu Ala Ile
305                 310                 315                 320 gaa atg gtg gat cgt cta cag aaa aag caa gga agt gta ctt tcc tcg       1008
Glu Met Val Asp Arg Leu Gln Lys Lys Gln Gly Ser Val Leu Ser Ser
                325                 330                 335 ttg aaa ttg gca act gga gca gct tcc acg tcg gat caa gtc gat tcg       1056
Leu Lys Leu Ala Thr Gly Ala Ala Ser Thr Ser Asp Gln Val Asp Ser
                340                 345                 350 aag att ttc gcg ttg aaa agt cga atg gaa aaa atc cac aca ttg aca       1104
Lys Ile Phe Ala Leu Lys Ser Arg Met Glu Lys Ile His Thr Leu Thr
                355                 360                 365 cgt gaa act caa gaa cga tgg ctt caa att gaa tca ctt tgc ggt ttt       1152
Arg Glu Thr Gln Glu Arg Trp Leu Gln Ile Glu Ser Leu Cys Gly Phe
370                 375                 380 cca ctt cta tat tta aat gaa acc gaa cat atc aat cga tca att gcc       1200
Pro Leu Leu Tyr Leu Asn Glu Thr Glu His Ile Asn Arg Ser Ile Ala
385                 390                 395                 400 tca tca cat ttc tac aat aaa agt cat gaa ggt tcc tcc tct tcc ggc       1248
Ser Ser His Phe Tyr Asn Lys Ser His Glu Gly Ser Ser Ser Ser Gly
                405                 410                 415 tca att tca aat gct cat tca aat ccc aat gca gtt aat tca aat ttt       1296
Ser Ile Ser Asn Ala His Ser Asn Pro Asn Ala Val Asn Ser Asn Phe
                420                 425                 430 gtg aaa aaa gtg tca ccg cca att cca cct tcc caa caa act gca aat       1344
Val Lys Lys Val Ser Pro Pro Ile Pro Pro Ser Gln Gln Thr Ala Asn
                435                 440                 445 ctt cga ttt gtt ccc acc gag caa agt gat agt att cat tct gaa gac       1392
Leu Arg Phe Val Pro Thr Glu Gln Ser Asp Ser Ile His Ser Glu Asp
450                 455                 460 acg tca cca att gtc gaa gac gtg gca att tcc aga agc tta act caa       1440
Thr Ser Pro Ile Val Glu Asp Val Ala Ile Ser Arg Ser Leu Thr Gln
465                 470                 475                 480 gac cta gct gaa gct gat atg cag tca ata gta tcc ggt tct aca aat       1488
Asp Leu Ala Glu Ala Asp Met Gln Ser Ile Val Ser Gly Ser Thr Asn
                485                 490                 495 ggc tcg ggc tcc gta gct gct ctt aaa aag cga aaa gga att ttc ccg       1536
Gly Ser Gly Ser Val Ala Ala Leu Lys Lys Arg Lys Gly Ile Phe Pro
                500                 505                 510 aaa ctt ttc cgc cga aat aca tcg aaa tct agc agt ctg ggt ggc act       1584
Lys Leu Phe Arg Arg Asn Thr Ser Lys Ser Ser Ser Leu Gly Gly Thr
                515                 520                 525 tct aat taa                                                           1593
Ser Asn  *
530
```

<210> SEQ ID NO 14
<211> LENGTH: 530
<212> TYPE: PRT
<213> ORGANISM: Caenorhabditis elegans
<300> PUBLICATION INFORMATION:
<308> DATABASE ACCESSION NUMBER: Genbank NP_497197
<309> DATABASE ENTRY DATE: 2001-12-03

<400> SEQUENCE: 14

```
Met Gly Arg Val Ser Trp Ile Ile Ala Leu Tyr Leu Thr Ile Asn Val
 1               5                  10                  15

Val Ile Val Val Asn Gly Asp Arg Val Thr Arg Asn Val Glu Val Thr
             20                  25                  30

Ala Glu Glu Glu Lys Ile Arg Asp Lys Leu Gly Tyr Glu Ala Ile Arg
         35                  40                  45

Asp Ile His Arg Asp Met Asp Asp His Ser Gly Ser Ile Asp Arg
 50                  55                  60

Asn Glu Ser Thr Gly Phe Met Lys Glu Asp Met Gln Met Arg Gly Ser
65                  70                  75                  80

Glu Arg Thr Arg Arg Glu Asn Lys Phe His Gly Asp Asp Ala Ile
                 85                  90                  95

Thr Val Asp Asp Leu Trp Glu Ala Trp Phe Glu Ser Ile Glu Arg Thr
            100                 105                 110

Trp Thr Asn Glu Arg Leu Val Glu Trp Leu Ile Asn Asp Val Asn Leu
        115                 120                 125

Pro Ser Ile Val Glu Ala Val Lys Ala Lys Ile Asp Gly Lys Ile
130                 135                 140

Leu Pro Arg Phe Ala Ser Pro Asn Ser Asp Phe Leu Asn Lys Glu Leu
145                 150                 155                 160

Gly Ile Lys Ser Ser Val Tyr Arg Gln Lys Leu Arg Leu Asn Ser Leu
                165                 170                 175

Asp Val Val Leu Phe Gly Tyr Lys Asp Asn Asn Asn Arg Thr Lys Asp
            180                 185                 190

Ile Leu Leu Ala Phe Leu Ala Leu Leu Leu Thr Ser Leu Ile Phe Leu
        195                 200                 205

Tyr Val Arg Gln Lys Gln Lys Ala Gln Gln Lys Val Asn Glu Leu Ser
    210                 215                 220

Asn Lys Leu Thr Glu Leu Lys Cys Met Glu Thr Glu Phe Glu Asp Val
225                 230                 235                 240

Gln Lys Met Leu Asn Asp Glu Arg Ser Lys Arg Ser Ile Ser Asp Gly
                245                 250                 255

Val Val Asn His Thr Glu Met Glu Asn Leu Arg Val Gln Leu Glu Glu
            260                 265                 270

Ala Glu Arg Arg Leu Glu Ala Asn Ser Asn Gly Ser Gln Ala Pro Leu
        275                 280                 285

Ala Leu Gln Pro Leu Leu Arg Arg Thr Cys Gly Asn Glu Met Ala Phe
    290                 295                 300

Leu Glu Lys Gln Arg Gln Asp Cys Phe Lys Glu Met Lys Glu Ala Ile
305                 310                 315                 320

Glu Met Val Asp Arg Leu Gln Lys Lys Gln Gly Ser Val Leu Ser Ser
                325                 330                 335

Leu Lys Leu Ala Thr Gly Ala Ala Ser Thr Ser Asp Gln Val Asp Ser
            340                 345                 350

Lys Ile Phe Ala Leu Lys Ser Arg Met Glu Lys Ile His Thr Leu Thr
        355                 360                 365
```

```
Arg Glu Thr Gln Glu Arg Trp Leu Gln Ile Glu Ser Leu Cys Gly Phe
    370                 375                 380

Pro Leu Leu Tyr Leu Asn Glu Thr Glu His Ile Asn Arg Ser Ile Ala
385                 390                 395                 400

Ser Ser His Phe Tyr Asn Lys Ser His Glu Gly Ser Ser Ser Ser Gly
                405                 410                 415

Ser Ile Ser Asn Ala His Ser Asn Pro Asn Ala Val Asn Ser Asn Phe
            420                 425                 430

Val Lys Lys Val Ser Pro Pro Ile Pro Pro Ser Gln Gln Thr Ala Asn
        435                 440                 445

Leu Arg Phe Val Pro Thr Glu Gln Ser Asp Ser Ile His Ser Glu Asp
    450                 455                 460

Thr Ser Pro Ile Val Glu Asp Val Ala Ile Ser Arg Ser Leu Thr Gln
465                 470                 475                 480

Asp Leu Ala Glu Ala Asp Met Gln Ser Ile Val Ser Gly Ser Thr Asn
                485                 490                 495

Gly Ser Gly Ser Val Ala Ala Leu Lys Lys Arg Lys Gly Ile Phe Pro
            500                 505                 510

Lys Leu Phe Arg Arg Asn Thr Ser Lys Ser Ser Ser Leu Gly Gly Thr
        515                 520                 525

Ser Asn
    530

<210> SEQ ID NO 15
<211> LENGTH: 50
<212> TYPE: DNA
<213> ORGANISM: Artificial Sequence
<220> FEATURE:
<223> OTHER INFORMATION: Dm000223 U2 PCR Primer

<400> SEQUENCE: 15
gaattaatac gactcactat agggagatat aggaactaga acgggccaga        50

<210> SEQ ID NO 16
<211> LENGTH: 46
<212> TYPE: DNA
<213> ORGANISM: Artificial Sequence
<220> FEATURE:
<223> OTHER INFORMATION: Dm000223 L2 PCR Primer

<400> SEQUENCE: 16
aattaaccct cactaaaggg agaaacattc tccaagtagg gcagac            46

<210> SEQ ID NO 17
<211> LENGTH: 51
<212> TYPE: DNA
<213> ORGANISM: Artificial Sequence
<220> FEATURE:
<223> OTHER INFORMATION: Dm223 U55 PCR Primer

<400> SEQUENCE: 17
gaattaatac gactcactat agggagattt gtaaacttat aagaaaccga g        51

<210> SEQ ID NO 18
<211> LENGTH: 44
<212> TYPE: DNA
<213> ORGANISM: Artificial Sequence
<220> FEATURE:
<223> OTHER INFORMATION: Dm223 L556 PCR Primer

<400> SEQUENCE: 18
```

-continued aattaaccct cactaaaggg agaccaaagc gatcctgaac actt    44

```
<210> SEQ ID NO 19
<211> LENGTH: 24
<212> TYPE: DNA
<213> ORGANISM: Artificial Sequence
<220> FEATURE:
<223> OTHER INFORMATION: Dm000223 U3 PCR Primer

<400> SEQUENCE: 19
```
tttgattgct acagtggaag tgtt    24

```
<210> SEQ ID NO 20
<211> LENGTH: 24
<212> TYPE: DNA
<213> ORGANISM: Artificial Sequence
<220> FEATURE:
<223> OTHER INFORMATION: Dm000223 L3 PCR Primer

<400> SEQUENCE: 20
```
tttggcattc ttattttgct gata    24

```
<210> SEQ ID NO 21
<211> LENGTH: 23
<212> TYPE: DNA
<213> ORGANISM: Artificial Sequence
<220> FEATURE:
<223> OTHER INFORMATION: Dm000223 U4 PCR Primer

<400> SEQUENCE: 21
```
aactagattt ggagcgtcgt cta    23

```
<210> SEQ ID NO 22
<211> LENGTH: 24
<212> TYPE: DNA
<213> ORGANISM: Artificial Sequence
<220> FEATURE:
<223> OTHER INFORMATION: Dm000223 L4 PCR Primer

<400> SEQUENCE: 22
```
cacatcatca atactctttc cgtg    24

```
<210> SEQ ID NO 23
<211> LENGTH: 583
<212> TYPE: DNA
<213> ORGANISM: Artificial Sequence
<220> FEATURE:
<223> OTHER INFORMATION: cDNA Sequence of the dsRNA product of Dm223
      U2/Dm223 L2

<400> SEQUENCE: 23
```
gaattaatac gactcactat agggagatat aggaactaga acgggccaga atggagcagg    60
aaaatgtggc aacagaaaaa ctagatttgg agcgtcgtct aaaagaagcg cccactctca    120
gttcatcgaa ctcggatttg gaagttcagc agctgaaaaa ggaaatcgag atgttgcgca    180
acgaattgtc ccgcgccgaa ttcgagctag tagacaactg ctggtcaccg ccgccacaac    240
tgcaatcatg gcttcaatac acatatgaac tagaaagtaa gaatcatcag aagaagcgca    300
cgtcggctga gaagcagcta cagtcggcca gagaggcttg tgagaaattg cgtaagaaac    360
ggtcaagttt ggtgggtgcg ttcgtttcca cgcacggaaa gagtattgat gatgtggatc    420
ggtcgattgt tgaggcacgg aatgccctcg gagatgtaac aaacgagctg caagaacgac    480
tgcatcgctg gaagcaaatc gagacgtgcc ttggcttaaa cattgtgaac aacaatggtc    540

```
tgccctactt ggagaatgtt tctcccttta gtgagggtta att              583
```

<210> SEQ ID NO 24
<211> LENGTH: 572
<212> TYPE: DNA
<213> ORGANISM: Artificial Sequence
<220> FEATURE:
<223> OTHER INFORMATION: cDNA Sequence of the dsRNA product of
      Dm223 U55 / Dm223 L556

<400> SEQUENCE: 24

```
gaattaatac gactcactat agggagattt gtaaacttat aagaaaccga gccgatttac    60
cgatttaaag gagacatatg cgataatttg tattgaagaa gtccgcacac aattcgtaac   120
aatgcgaaag aataccattt ggaactactc tttaatattc ttctgctgtg tgctgaagag   180
cataagtacg ctagatcatg gcccgcacac agtatcagtc gattcgaatc gacacaacac   240
acagcatcag tataagcaaa atcccaatgt tgcctcacaa cgtcactcat cccacgaatc   300
tggtcagagt ttacacaatt cgcaatcgga acatgtcacc catattgccg catcgcacgc   360
cggaagcggc ggagagcact ccactcattt ggcgcaaaat ctgcacagga gctcatataa   420
tcttctgagc gaggccatgt cccaggctgt cagcaatgaa tttagttcca tgggaagtgg   480
ttcagcggat ggagcgtgtg ctgctgatga ttttgattgc tacagtggaa gtgttcagga   540
tcgctttggt ctccctttag tgagggttaa tt                                 572
```

<210> SEQ ID NO 25
<211> LENGTH: 16
<212> TYPE: DNA
<213> ORGANISM: Artificial Sequence
<220> FEATURE:
<223> OTHER INFORMATION: Hs STIM1 U1472 PCR Primer

<400> SEQUENCE: 25

```
gcgggagggt actgag                                                    16
```

<210> SEQ ID NO 26
<211> LENGTH: 21
<212> TYPE: DNA
<213> ORGANISM: Artificial Sequence
<220> FEATURE:
<223> OTHER INFORMATION: Hs STIM1 L1985 PCR Primer

<400> SEQUENCE: 26

```
tccatgtcat ccacgtcgtc a                                              21
```

<210> SEQ ID NO 27
<211> LENGTH: 21
<212> TYPE: DNA
<213> ORGANISM: Artificial Sequence
<220> FEATURE:
<223> OTHER INFORMATION: Hs STIM1 U1846 PCR Primer

<400> SEQUENCE: 27

```
accgctggca acagatcgag a                                              21
```

<210> SEQ ID NO 28
<211> LENGTH: 16
<212> TYPE: DNA
<213> ORGANISM: Artificial Sequence
<220> FEATURE:
<223> OTHER INFORMATION: Hs STIM1 L2305 PCR Primer

<400> SEQUENCE: 28
agcgccagta atgcct 16

<210> SEQ ID NO 29
<211> LENGTH: 21
<212> TYPE: DNA
<213> ORGANISM: Artificial Sequence
<220> FEATURE:
<223> OTHER INFORMATION: Hs STIM2 U1710 PCR Primer

<400> SEQUENCE: 29
gtctttggga ctctgcacgt t 21

<210> SEQ ID NO 30
<211> LENGTH: 19
<212> TYPE: DNA
<213> ORGANISM: Artificial Sequence
<220> FEATURE:
<223> OTHER INFORMATION: Hs STIM2 L2219 PCR Primer

<400> SEQUENCE: 30
cgcagggcaa cttgacact 19

<210> SEQ ID NO 31
<211> LENGTH: 18
<212> TYPE: DNA
<213> ORGANISM: Artificial Sequence
<220> FEATURE:
<223> OTHER INFORMATION: Hs STIM2 U2159 PCR Primer

<400> SEQUENCE: 31
ccctcaccac ccgcaaca 18

<210> SEQ ID NO 32
<211> LENGTH: 21
<212> TYPE: DNA
<213> ORGANISM: Artificial Sequence
<220> FEATURE:
<223> OTHER INFORMATION: Hs STIM2 L2600 PCR Primer

<400> SEQUENCE: 32
gatgtgtggc gaggtttagg c 21

<210> SEQ ID NO 33
<211> LENGTH: 24
<212> TYPE: DNA
<213> ORGANISM: Artificial Sequence
<220> FEATURE:
<223> OTHER INFORMATION: Hs STIM U624 Sequencing Primer

<400> SEQUENCE: 33
gccagagcct cagccatagt caca 24

<210> SEQ ID NO 34
<211> LENGTH: 21
<212> TYPE: DNA
<213> ORGANISM: Artificial Sequence
<220> FEATURE:
<223> OTHER INFORMATION: Hs STIM U899 Sequencing Primer

<400> SEQUENCE: 34
gataagctca tcagcgtgga g 21

<210> SEQ ID NO 35
<211> LENGTH: 24
<212> TYPE: DNA
<213> ORGANISM: Artificial Sequence

```
<220> FEATURE:
<223> OTHER INFORMATION: Hs STIM U1296 Sequencing Primer

<400> SEQUENCE: 35
tgatgaagga cttggagggg ttac                                              24

<210> SEQ ID NO 36
<211> LENGTH: 23
<212> TYPE: DNA
<213> ORGANISM: Artificial Sequence
<220> FEATURE:
<223> OTHER INFORMATION: Hs STIM U1508 Sequencing Primer

<400> SEQUENCE: 36
aaatatgctg aggaggagtt gga                                               23

<210> SEQ ID NO 37
<211> LENGTH: 24
<212> TYPE: DNA
<213> ORGANISM: Artificial Sequence
<220> FEATURE:
<223> OTHER INFORMATION: Hs STIM U1911 Sequencing Primer

<400> SEQUENCE: 37
cactggtggc tgccctcaac atag                                              24

<210> SEQ ID NO 38
<211> LENGTH: 22
<212> TYPE: DNA
<213> ORGANISM: Artificial Sequence
<220> FEATURE:
<223> OTHER INFORMATION: Hs STIM L1148 Sequencing Primer

<400> SEQUENCE: 38
gcccaaagag cactgtatcc ag                                                22

<210> SEQ ID NO 39
<211> LENGTH: 24
<212> TYPE: DNA
<213> ORGANISM: Artificial Sequence
<220> FEATURE:
<223> OTHER INFORMATION: Hs STIM L1400 Sequencing Primer

<400> SEQUENCE: 39
cagcttcttt tccagatgga cctt                                              24

<210> SEQ ID NO 40
<211> LENGTH: 22
<212> TYPE: DNA
<213> ORGANISM: Artificial Sequence
<220> FEATURE:
<223> OTHER INFORMATION: Hs STIM L1814 Sequencing Primer

<400> SEQUENCE: 40
gcaatgctgc tgtcacctcg ct                                                22

<210> SEQ ID NO 41
<211> LENGTH: 24
<212> TYPE: DNA
<213> ORGANISM: Artificial Sequence
<220> FEATURE:
<223> OTHER INFORMATION: Hs STIM L2013 Sequencing Primer

<400> SEQUENCE: 41
gcatggacaa gggagacaca atct                                              24
```

-continued

<210> SEQ ID NO 42
<211> LENGTH: 19
<212> TYPE: DNA
<213> ORGANISM: Artificial Sequence
<220> FEATURE:
<223> OTHER INFORMATION: Hs STIM L2403 Sequencing Primer

<400> SEQUENCE: 42
gggctgtgag aacgggaag                                          19

<210> SEQ ID NO 43
<211> LENGTH: 21
<212> TYPE: RNA
<213> ORGANISM: Artificial Sequence
<220> FEATURE:
<223> OTHER INFORMATION: Hs STIM1 1140-1161 siRNA

<400> SEQUENCE: 43
aaggcucugg auacagugcu c                                       21

<210> SEQ ID NO 44
<211> LENGTH: 21
<212> TYPE: RNA
<213> ORGANISM: Artificial Sequence
<220> FEATURE:
<223> OTHER INFORMATION: Hs STIM1 1414-1435 siRNA

<400> SEQUENCE: 44
aagaagcugc gcgaugagau c                                       21

<210> SEQ ID NO 45
<211> LENGTH: 21
<212> TYPE: RNA
<213> ORGANISM: Artificial Sequence
<220> FEATURE:
<223> OTHER INFORMATION: Hs STIM2 1550-1571 siRNA

<400> SEQUENCE: 45
aacugagaag caguuggucu g                                       21

<210> SEQ ID NO 46
<211> LENGTH: 21
<212> TYPE: RNA
<213> ORGANISM: Artificial Sequence
<220> FEATURE:
<223> OTHER INFORMATION: Hs STIM2 2560-2581 siRNA

<400> SEQUENCE: 46
aauccuguag caugaaccag c                                       21

<210> SEQ ID NO 47
<211> LENGTH: 27
<212> TYPE: DNA
<213> ORGANISM: Artificial Sequence
<220> FEATURE:
<223> OTHER INFORMATION: 5' T7 Polymerase Binding Site

<400> SEQUENCE: 47
gaattaatac gactcactat agggaga                                 27

<210> SEQ ID NO 48
<211> LENGTH: 23
<212> TYPE: DNA
<213> ORGANISM: Artificial Sequence
<220> FEATURE:
<223> OTHER INFORMATION: 5' T3 Polymerase Binding Site

```
<400> SEQUENCE: 48
aattaaccct cactaaaggg aga                                          23

<210> SEQ ID NO 49
<211> LENGTH: 2058
<212> TYPE: DNA
<213> ORGANISM: Homo sapiens
<220> FEATURE:
<221> NAME/KEY: CDS
<222> LOCATION: (1)...(2058)
<223> OTHER INFORMATION: Unknown protein MGC: 29566
<300> PUBLICATION INFORMATION:
<308> DATABASE ACCESSION NUMBER: Genbank BC021300
<309> DATABASE ENTRY DATE: 2002-05-20

<400> SEQUENCE: 49 atg gat gta tgc gtc cgt ctt gcc ctg tgg ctc ctc tgg gga ctc ctc    48
Met Asp Val Cys Val Arg Leu Ala Leu Trp Leu Leu Trp Gly Leu Leu
 1               5                  10                  15 ctg cac cag ggc cag agc ctc agc cat agt cac agt gag aag gcg aca    96
Leu His Gln Gly Gln Ser Leu Ser His Ser His Ser Glu Lys Ala Thr
             20                  25                  30 gga acc agc tcg ggg gcc aac tct gag gag tcc act gca gca gag ttt   144
Gly Thr Ser Ser Gly Ala Asn Ser Glu Glu Ser Thr Ala Ala Glu Phe
         35                  40                  45 tgc cga att gac aag ccc ctg tgt cac agt gag gat gag aaa ctc agc   192
Cys Arg Ile Asp Lys Pro Leu Cys His Ser Glu Asp Glu Lys Leu Ser
     50                  55                  60 ttc gag gca gtc cgt aac atc cac aaa ctg atg gac gat gat gcc aat   240
Phe Glu Ala Val Arg Asn Ile His Lys Leu Met Asp Asp Asp Ala Asn
 65                  70                  75                  80 ggt gat gtg gat gtg gaa gaa agt gat gag ttc ctg agg gaa gac ctc   288
Gly Asp Val Asp Val Glu Glu Ser Asp Glu Phe Leu Arg Glu Asp Leu
                 85                  90                  95 aat tac cat gac cca aca gtg aaa cac agc acc ttc cat ggt gag gat   336
Asn Tyr His Asp Pro Thr Val Lys His Ser Thr Phe His Gly Glu Asp
            100                 105                 110 aag ctc atc agc gtg gag gac ctg tgg aag gca tgg aag tca tca gaa   384
Lys Leu Ile Ser Val Glu Asp Leu Trp Lys Ala Trp Lys Ser Ser Glu
        115                 120                 125 gta tac aat tgg acc gtg gat gag gtg gta cag tgg ctg atc aca tat   432
Val Tyr Asn Trp Thr Val Asp Glu Val Val Gln Trp Leu Ile Thr Tyr
    130                 135                 140 gtg gag ctg cct cag tat gag gag acc ttc cgg aag ctg cag ctc agt   480
Val Glu Leu Pro Gln Tyr Glu Glu Thr Phe Arg Lys Leu Gln Leu Ser
145                 150                 155                 160 ggc cat gcc atg cca agg ctg gct gtc acc aac acc acc atg aca ggg   528
Gly His Ala Met Pro Arg Leu Ala Val Thr Asn Thr Thr Met Thr Gly
                165                 170                 175 act gtg ctg aag atg aca gac cgg agt cat cgg cag aag ctg cag ctg   576
Thr Val Leu Lys Met Thr Asp Arg Ser His Arg Gln Lys Leu Gln Leu
            180                 185                 190 aag gct ctg gat aca gtg ctc ttt ggg cct cct ctc ttg act cgc cat   624
Lys Ala Leu Asp Thr Val Leu Phe Gly Pro Pro Leu Leu Thr Arg His
        195                 200                 205 aat cac ctc aag gac ttc atg ctg gtg gtg tct atc gtt att ggt gtg   672
Asn His Leu Lys Asp Phe Met Leu Val Val Ser Ile Val Ile Gly Val
    210                 215                 220 ggc ggc tgc tgg ttt gcc tat atc cag aac cgt tac tcc aag gag cac   720
Gly Gly Cys Trp Phe Ala Tyr Ile Gln Asn Arg Tyr Ser Lys Glu His
225                 230                 235                 240
```

| | | |
|---|---|---|
| atg aag aag atg atg aag gac ttg gag ggg tta cac cga gct gag cag<br>Met Lys Lys Met Met Lys Asp Leu Glu Gly Leu His Arg Ala Glu Gln<br>245 250 255 | | 768 |
| agt ctg cat gac ctt cag gaa agg ctg cac aag gcc cag gag gag cac<br>Ser Leu His Asp Leu Gln Glu Arg Leu His Lys Ala Gln Glu Glu His<br>260 265 270 | | 816 |
| cgc aca gtg gag gtg gag aag gtc cat ctg gaa aag aag ctg cgc gat<br>Arg Thr Val Glu Val Glu Lys Val His Leu Glu Lys Lys Leu Arg Asp<br>275 280 285 | | 864 |
| gag atc aac ctt gct aag cag gaa gcc cag cgg ctg aag gag ctg cgg<br>Glu Ile Asn Leu Ala Lys Gln Glu Ala Gln Arg Leu Lys Glu Leu Arg<br>290 295 300 | | 912 |
| gag ggt act gag aat gag cgg agc cgc caa aaa tat gct gag gag gag<br>Glu Gly Thr Glu Asn Glu Arg Ser Arg Gln Lys Tyr Ala Glu Glu Glu<br>305 310 315 320 | | 960 |
| ttg gag cag gtt cgg gag gcc ttg agg aaa gca gag aag gag cta gaa<br>Leu Glu Gln Val Arg Glu Ala Leu Arg Lys Ala Glu Lys Glu Leu Glu<br>325 330 335 | | 1008 |
| tct cac agc tca tgg tat gct cca gag gcc ctt cag aag tgg ctg cag<br>Ser His Ser Ser Trp Tyr Ala Pro Glu Ala Leu Gln Lys Trp Leu Gln<br>340 345 350 | | 1056 |
| ctg aca cat gag gtg gag gtg caa tat tac aac atc aag aag caa aat<br>Leu Thr His Glu Val Glu Val Gln Tyr Tyr Asn Ile Lys Lys Gln Asn<br>355 360 365 | | 1104 |
| gct gag aag cag ctg ctg gtg gcc aag gag ggg gct gag aag ata aaa<br>Ala Glu Lys Gln Leu Leu Val Ala Lys Glu Gly Ala Glu Lys Ile Lys<br>370 375 380 | | 1152 |
| aag aag aga aac aca ctc ttt ggc acc ttc cac gtg gcc cac agc tct<br>Lys Lys Arg Asn Thr Leu Phe Gly Thr Phe His Val Ala His Ser Ser<br>385 390 395 400 | | 1200 |
| tcc ctg gat gat gta gat cat aaa att cta aca gct aag caa gca ctg<br>Ser Leu Asp Asp Val Asp His Lys Ile Leu Thr Ala Lys Gln Ala Leu<br>405 410 415 | | 1248 |
| agc gag gtg aca gca gca ttg cgg gag cgc ctg cac cgc tgg caa cag<br>Ser Glu Val Thr Ala Ala Leu Arg Glu Arg Leu His Arg Trp Gln Gln<br>420 425 430 | | 1296 |
| atc gag atc ctc tgt ggc ttc cag att gtc aac aac cct ggc atc cac<br>Ile Glu Ile Leu Cys Gly Phe Gln Ile Val Asn Asn Pro Gly Ile His<br>435 440 445 | | 1344 |
| tca ctg gtg gct gcc ctc aac ata gac ccc agc tgg atg ggc agt aca<br>Ser Leu Val Ala Ala Leu Asn Ile Asp Pro Ser Trp Met Gly Ser Thr<br>450 455 460 | | 1392 |
| cgc ccc aac cct gct cac ttc atc atg act gac gac gtg gat gac atg<br>Arg Pro Asn Pro Ala His Phe Ile Met Thr Asp Asp Val Asp Asp Met<br>465 470 475 480 | | 1440 |
| gat gag gag att gtg tct ccc ttg tcc atg cag tcc cct agc ctg cag<br>Asp Glu Glu Ile Val Ser Pro Leu Ser Met Gln Ser Pro Ser Leu Gln<br>485 490 495 | | 1488 |
| agc agt gtt cgg cag cgc ctg acg gag cca cag cat ggc ctg gga tct<br>Ser Ser Val Arg Gln Arg Leu Thr Glu Pro Gln His Gly Leu Gly Ser<br>500 505 510 | | 1536 |
| cag agg gat ttg acc cat tcc gat tcg gag tcc tcc ctc cac atg agt<br>Gln Arg Asp Leu Thr His Ser Asp Ser Glu Ser Ser Leu His Met Ser<br>515 520 525 | | 1584 |
| gac cgc cag cgt gtg gcc ccc aaa cct cct cag atg agc cgt gct gca<br>Asp Arg Gln Arg Val Ala Pro Lys Pro Pro Gln Met Ser Arg Ala Ala<br>530 535 540 | | 1632 |
| gac gag gct ctc aat gcc atg act tcc aat ggc agc cac cgg ctg atc<br>Asp Glu Ala Leu Asn Ala Met Thr Ser Asn Gly Ser His Arg Leu Ile | | 1680 |

```
                545                 550                 555                 560
gag ggg gtc cac cca ggg tct ctg gtg gag aaa ctg cct gac agc cct      1728
Glu Gly Val His Pro Gly Ser Leu Val Glu Lys Leu Pro Asp Ser Pro
                565                 570                 575 gcc ctg gcc aag aag gca tta ctg gcg ctg aac cat ggg ctg gac aag      1776
Ala Leu Ala Lys Lys Ala Leu Leu Ala Leu Asn His Gly Leu Asp Lys
                580                 585                 590 gcc cac agc ctg atg gag ctg agc ccc tca gcc cca cct ggt ggc tct      1824
Ala His Ser Leu Met Glu Leu Ser Pro Ser Ala Pro Pro Gly Gly Ser
                595                 600                 605 cca cat ttg gat tct tcc cgt tct cac agc ccc agc tcc cca gac cca      1872
Pro His Leu Asp Ser Ser Arg Ser His Ser Pro Ser Ser Pro Asp Pro
                610                 615                 620 gac aca cca tct cca gtt ggg gac agc cga gcc ctg caa gcc agc cga      1920
Asp Thr Pro Ser Pro Val Gly Asp Ser Arg Ala Leu Gln Ala Ser Arg
625                 630                 635                 640 aac aca cgc att ccc cac ctg gct ggc aag aag gct gtg gct gag gag      1968
Asn Thr Arg Ile Pro His Leu Ala Gly Lys Lys Ala Val Ala Glu Glu
                645                 650                 655 gat aat ggc tct att ggc gag gaa aca gac tcc agc cca ggc cgg aag      2016
Asp Asn Gly Ser Ile Gly Glu Glu Thr Asp Ser Ser Pro Gly Arg Lys
                660                 665                 670 aag ttt ccc ctc aaa atc ttt aag aag cct ctt aag aag tag              2058
Lys Phe Pro Leu Lys Ile Phe Lys Lys Pro Leu Lys Lys *
                675                 680                 685

<210> SEQ ID NO 50
<211> LENGTH: 685
<212> TYPE: PRT
<213> ORGANISM: Homo sapiens
<300> PUBLICATION INFORMATION:
<308> DATABASE ACCESSION NUMBER: Genbank AAH21300
<309> DATABASE ENTRY DATE: 2002-05-20

<400> SEQUENCE: 50

Met Asp Val Cys Val Arg Leu Ala Leu Trp Leu Leu Trp Gly Leu Leu
 1               5                  10                  15

Leu His Gln Gly Gln Ser Leu Ser His Ser His Ser Glu Lys Ala Thr
                20                  25                  30

Gly Thr Ser Ser Gly Ala Asn Ser Glu Glu Ser Thr Ala Ala Glu Phe
            35                  40                  45

Cys Arg Ile Asp Lys Pro Leu Cys His Ser Glu Asp Glu Lys Leu Ser
        50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
                100                 105                 110

Lys Leu Ile Ser Val Glu Asp Leu Trp Lys Ala Trp Lys Ser Ser Glu
            115                 120                 125

Val Tyr Asn Trp Thr Val Asp Glu Val Val Gln Trp Leu Ile Thr Tyr
        130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
```

-continued

```
               180                 185                 190
Lys Ala Leu Asp Thr Val Leu Phe Gly Pro Pro Leu Leu Thr Arg His
            195                 200                 205
Asn His Leu Lys Asp Phe Met Leu Val Val Ser Ile Val Ile Gly Val
            210                 215                 220
Gly Gly Cys Trp Phe Ala Tyr Ile Gln Asn Arg Tyr Ser Lys Glu His
225                 230                 235                 240
Met Lys Lys Met Met Lys Asp Leu Glu Gly Leu His Arg Ala Glu Gln
                    245                 250                 255
Ser Leu His Asp Leu Gln Glu Arg Leu His Lys Ala Gln Glu Glu His
                260                 265                 270
Arg Thr Val Glu Val Glu Lys Val His Leu Glu Lys Lys Leu Arg Asp
            275                 280                 285
Glu Ile Asn Leu Ala Lys Gln Glu Ala Gln Arg Leu Lys Glu Leu Arg
            290                 295                 300
Glu Gly Thr Glu Asn Glu Arg Ser Arg Gln Lys Tyr Ala Glu Glu Glu
305                 310                 315                 320
Leu Glu Gln Val Arg Glu Ala Leu Arg Lys Ala Glu Lys Glu Leu Glu
                    325                 330                 335
Ser His Ser Ser Trp Tyr Ala Pro Glu Ala Leu Gln Lys Trp Leu Gln
                340                 345                 350
Leu Thr His Glu Val Glu Val Gln Tyr Tyr Asn Ile Lys Lys Gln Asn
                355                 360                 365
Ala Glu Lys Gln Leu Leu Val Ala Lys Glu Gly Ala Glu Lys Ile Lys
            370                 375                 380
Lys Lys Arg Asn Thr Leu Phe Gly Thr Phe His Val Ala His Ser Ser
385                 390                 395                 400
Ser Leu Asp Asp Val Asp His Lys Ile Leu Thr Ala Lys Gln Ala Leu
                    405                 410                 415
Ser Glu Val Thr Ala Ala Leu Arg Glu Arg Leu His Arg Trp Gln Gln
                420                 425                 430
Ile Glu Ile Leu Cys Gly Phe Gln Ile Val Asn Asn Pro Gly Ile His
            435                 440                 445
Ser Leu Val Ala Ala Leu Asn Ile Asp Pro Ser Trp Met Gly Ser Thr
            450                 455                 460
Arg Pro Asn Pro Ala His Phe Ile Met Thr Asp Asp Val Asp Asp Met
465                 470                 475                 480
Asp Glu Glu Ile Val Ser Pro Leu Ser Met Gln Ser Pro Ser Leu Gln
                    485                 490                 495
Ser Ser Val Arg Gln Arg Leu Thr Glu Pro Gln His Gly Leu Gly Ser
                500                 505                 510
Gln Arg Asp Leu Thr His Ser Asp Ser Glu Ser Ser Leu His Met Ser
            515                 520                 525
Asp Arg Gln Arg Val Ala Pro Lys Pro Gln Met Ser Arg Ala Ala
            530                 535                 540
Asp Glu Ala Leu Asn Ala Met Thr Ser Asn Gly Ser His Arg Leu Ile
545                 550                 555                 560
Glu Gly Val His Pro Gly Ser Leu Val Glu Lys Leu Pro Asp Ser Pro
                    565                 570                 575
Ala Leu Ala Lys Lys Ala Leu Ala Leu Asn His Gly Leu Asp Lys
                580                 585                 590
Ala His Ser Leu Met Glu Leu Ser Pro Ala Pro Pro Gly Gly Ser
                595                 600                 605
```

```
Pro His Leu Asp Ser Ser Arg Ser His Ser Pro Ser Ser Pro Asp Pro
    610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 51
<211> LENGTH: 2058
<212> TYPE: DNA
<213> ORGANISM: Rattus norvegicus
<220> FEATURE:
<221> NAME/KEY: CDS
<222> LOCATION: (1)...(2058)
<223> OTHER INFORMATION: Stromal interaction molecule 1
<309> DATABASE ENTRY DATE: -  -

<400> SEQUENCE: 51
```

| | | | | | | | | | | | | | | | | |
|---|---|---|---|---|---|---|---|---|---|---|---|---|---|---|---|---|
| atg | gat | gtg | tgc | gct | cgt | ctt | gcc | ctg | tgg | ctt | ctt | tgg | ggg | ctc | ctc | 48 |
| Met | Asp | Val | Cys | Ala | Arg | Leu | Ala | Leu | Trp | Leu | Leu | Trp | Gly | Leu | Leu | |
| 1 | | | | 5 | | | | | 10 | | | | | 15 | | |
| ctg | cat | cag | ggc | cat | agc | ctt | agc | cat | agt | cac | agc | gaa | aag | aat | aca | 96 |
| Leu | His | Gln | Gly | His | Ser | Leu | Ser | His | Ser | His | Ser | Glu | Lys | Asn | Thr | |
| | | | 20 | | | | | 25 | | | | | 30 | | | |
| gga | gcc | ggc | tct | ggg | acg | act | tca | gag | gag | tcc | act | gaa | gca | gag | ttt | 144 |
| Gly | Ala | Gly | Ser | Gly | Thr | Thr | Ser | Glu | Glu | Ser | Thr | Glu | Ala | Glu | Phe | |
| | | 35 | | | | | 40 | | | | | 45 | | | | |
| tgc | cgg | att | gac | aag | ccc | ctg | tgc | cac | agt | gag | gat | gat | aag | ctc | agc | 192 |
| Cys | Arg | Ile | Asp | Lys | Pro | Leu | Cys | His | Ser | Glu | Asp | Asp | Lys | Leu | Ser | |
| | 50 | | | | | 55 | | | | | 60 | | | | | |
| ttc | gag | gct | gtc | cgc | aat | att | cac | aag | ctg | atg | gat | gat | gat | gcc | aac | 240 |
| Phe | Glu | Ala | Val | Arg | Asn | Ile | His | Lys | Leu | Met | Asp | Asp | Asp | Ala | Asn | |
| 65 | | | | | 70 | | | | | 75 | | | | | 80 | |
| ggt | gat | gtg | gat | gtg | gaa | gaa | agt | gat | gag | ttc | cta | agg | gaa | gac | ctc | 288 |
| Gly | Asp | Val | Asp | Val | Glu | Glu | Ser | Asp | Glu | Phe | Leu | Arg | Glu | Asp | Leu | |
| | | | | 85 | | | | | 90 | | | | | 95 | | |
| aat | tac | cat | gat | ccg | aca | gtg | aag | cac | agc | acc | ttc | cat | ggc | gag | gat | 336 |
| Asn | Tyr | His | Asp | Pro | Thr | Val | Lys | His | Ser | Thr | Phe | His | Gly | Glu | Asp | |
| | | | 100 | | | | | 105 | | | | | 110 | | | |
| aag | ctt | atc | agc | gtg | gag | gat | ctg | tgg | aag | gca | tgg | aag | tca | tca | gaa | 384 |
| Lys | Leu | Ile | Ser | Val | Glu | Asp | Leu | Trp | Lys | Ala | Trp | Lys | Ser | Ser | Glu | |
| | | 115 | | | | | 120 | | | | | 125 | | | | |
| gtg | tac | aac | tgg | act | gtc | gat | gag | gtg | ata | cag | tgg | ctg | att | acg | tat | 432 |
| Val | Tyr | Asn | Trp | Thr | Val | Asp | Glu | Val | Ile | Gln | Trp | Leu | Ile | Thr | Tyr | |
| | 130 | | | | | 135 | | | | | 140 | | | | | |
| gtg | gag | cta | cct | cag | tat | gag | gag | acc | ttc | cgg | aag | ttg | caa | ctt | act | 480 |
| Val | Glu | Leu | Pro | Gln | Tyr | Glu | Glu | Thr | Phe | Arg | Lys | Leu | Gln | Leu | Thr | |
| 145 | | | | | 150 | | | | | 155 | | | | | 160 | |
| ggc | cat | gcc | atg | cca | agg | cta | gct | gta | acc | aat | acc | acc | atg | aca | ggg | 528 |
| Gly | His | Ala | Met | Pro | Arg | Leu | Ala | Val | Thr | Asn | Thr | Thr | Met | Thr | Gly | |
| | | | | 165 | | | | | 170 | | | | | 175 | | |
| act | gta | ctg | aag | atg | aca | gat | cgg | agc | cac | agg | cag | aag | cta | cag | ctg | 576 |
| Thr | Val | Leu | Lys | Met | Thr | Asp | Arg | Ser | His | Arg | Gln | Lys | Leu | Gln | Leu | |
| | | | 180 | | | | | 185 | | | | | 190 | | | |
| aag | gcc | ctg | gat | aca | gtg | ctc | ttt | ggg | cct | cct | ctc | ttg | act | cga | cat | 624 |
| Lys | Ala | Leu | Asp | Thr | Val | Leu | Phe | Gly | Pro | Pro | Leu | Leu | Thr | Arg | His | |

-continued

|  |  | 195 |  |  |  | 200 |  |  |  | 205 |  |  |  |  |
|---|---|---|---|---|---|---|---|---|---|---|---|---|---|---|
| aat | cac | ctc | aag | gac | ttc | atg | ctg | gtg | gtg | tct | att | gtt | att | ggt gtg | 672 |
| Asn | His | Leu | Lys | Asp | Phe | Met | Leu | Val | Val | Ser | Ile | Val | Ile | Gly Val |
|  |  | 210 |  |  |  | 215 |  |  |  | 220 |  |  |  |  |

| ggc | ggc | tgc | tgg | ttt | gcc | tat | att | cag | aac | cgt | tac | tcc | aag | gag cac | 720 |
| Gly | Gly | Cys | Trp | Phe | Ala | Tyr | Ile | Gln | Asn | Arg | Tyr | Ser | Lys | Glu His |
| 225 |  |  |  |  | 230 |  |  |  |  | 235 |  |  |  | 240 |

| atg | aag | aag | atg | atg | aaa | gat | ctg | gaa | ggg | tta | cac | cga | gct | gag cag | 768 |
| Met | Lys | Lys | Met | Met | Lys | Asp | Leu | Glu | Gly | Leu | His | Arg | Ala | Glu Gln |
|  |  |  |  | 245 |  |  |  |  | 250 |  |  |  |  | 255 |

| agt | ctg | cat | gac | ctg | cag | gaa | agg | ctc | cac | aag | gcc | cag | gag | gag cac | 816 |
| Ser | Leu | His | Asp | Leu | Gln | Glu | Arg | Leu | His | Lys | Ala | Gln | Glu | Glu His |
|  |  |  | 260 |  |  |  |  | 265 |  |  |  |  | 270 |  |

| cgc | aca | gtg | gaa | gta | gag | aag | gtc | cat | ctg | gag | aag | aag | ctg | cgt gat | 864 |
| Arg | Thr | Val | Glu | Val | Glu | Lys | Val | His | Leu | Glu | Lys | Lys | Leu | Arg Asp |
|  |  | 275 |  |  |  |  | 280 |  |  |  |  | 285 |  |  |

| gag | atc | aat | gtt | gcc | aag | cag | gaa | gct | cag | agg | ctg | aag | gag | ctg agg | 912 |
| Glu | Ile | Asn | Val | Ala | Lys | Gln | Glu | Ala | Gln | Arg | Leu | Lys | Glu | Leu Arg |
|  | 290 |  |  |  |  | 295 |  |  |  |  | 300 |  |  |  |

| gag | ggt | act | gag | aat | gag | agg | agc | cgc | caa | aaa | tat | gcc | gag | gaa gag | 960 |
| Glu | Gly | Thr | Glu | Asn | Glu | Arg | Ser | Arg | Gln | Lys | Tyr | Ala | Glu | Glu Glu |
| 305 |  |  |  |  | 310 |  |  |  |  | 315 |  |  |  | 320 |

| ctg | gag | cag | gtt | cgg | gag | gcc | ttg | agg | aaa | gca | gag | aag | gag | ctg gaa | 1008 |
| Leu | Glu | Gln | Val | Arg | Glu | Ala | Leu | Arg | Lys | Ala | Glu | Lys | Glu | Leu Glu |
|  |  |  |  | 325 |  |  |  |  | 330 |  |  |  |  | 335 |

| tca | cac | agc | tca | tgg | tat | gct | cct | gag | gcc | ctt | cag | aag | tgg | ttg cag | 1056 |
| Ser | His | Ser | Ser | Trp | Tyr | Ala | Pro | Glu | Ala | Leu | Gln | Lys | Trp | Leu Gln |
|  |  |  | 340 |  |  |  |  | 345 |  |  |  |  | 350 |  |

| ctg | acg | cat | gag | gtg | gag | gtg | cag | tac | tac | aac | atc | aag | aag | caa aat | 1104 |
| Leu | Thr | His | Glu | Val | Glu | Val | Gln | Tyr | Tyr | Asn | Ile | Lys | Lys | Gln Asn |
|  |  | 355 |  |  |  |  | 360 |  |  |  |  | 365 |  |  |

| gcc | gag | aag | cag | ctg | ctg | gtg | gcc | aag | gag | ggg | gct | gag | aaa | ata aaa | 1152 |
| Ala | Glu | Lys | Gln | Leu | Leu | Val | Ala | Lys | Glu | Gly | Ala | Glu | Lys | Ile Lys |
|  | 370 |  |  |  |  | 375 |  |  |  |  | 380 |  |  |  |

| aag | aag | aga | aac | acg | ctt | ttt | ggt | acc | ttc | cat | gtg | gcc | cac | agc tcc | 1200 |
| Lys | Lys | Arg | Asn | Thr | Leu | Phe | Gly | Thr | Phe | His | Val | Ala | His | Ser Ser |
| 385 |  |  |  |  | 390 |  |  |  |  | 395 |  |  |  | 400 |

| tcc | ctg | gat | gat | gtg | gat | cat | aag | atc | tta | act | gct | aag | caa | gca ctg | 1248 |
| Ser | Leu | Asp | Asp | Val | Asp | His | Lys | Ile | Leu | Thr | Ala | Lys | Gln | Ala Leu |
|  |  |  |  | 405 |  |  |  |  | 410 |  |  |  |  | 415 |

| agc | gag | gtg | aca | gca | gca | ctg | agg | gag | cgt | ctg | cac | cgg | tgg | cag cag | 1296 |
| Ser | Glu | Val | Thr | Ala | Ala | Leu | Arg | Glu | Arg | Leu | His | Arg | Trp | Gln Gln |
|  |  |  | 420 |  |  |  |  | 425 |  |  |  |  | 430 |  |

| att | gag | atc | ctc | tgt | ggc | ttc | cag | att | gtc | aat | aac | cct | ggc | atc cac | 1344 |
| Ile | Glu | Ile | Leu | Cys | Gly | Phe | Gln | Ile | Val | Asn | Asn | Pro | Gly | Ile His |
|  |  | 435 |  |  |  |  | 440 |  |  |  |  | 445 |  |  |

| tcc | ttg | gtg | gct | gcc | ctc | aac | ata | gac | ccc | agc | tgg | atg | ggc | agt act | 1392 |
| Ser | Leu | Val | Ala | Ala | Leu | Asn | Ile | Asp | Pro | Ser | Trp | Met | Gly | Ser Thr |
|  | 450 |  |  |  |  | 455 |  |  |  |  | 460 |  |  |  |

| cgg | cct | aac | cct | gcc | cac | ttc | atc | atg | act | gac | gat | gtg | gat | gac atg | 1440 |
| Arg | Pro | Asn | Pro | Ala | His | Phe | Ile | Met | Thr | Asp | Asp | Val | Asp | Asp Met |
| 465 |  |  |  |  | 470 |  |  |  |  | 475 |  |  |  | 480 |

| gat | gag | gag | atc | gtg | tcg | ccc | ttg | tcc | atg | cag | tcc | ccc | agc | ctg cag | 1488 |
| Asp | Glu | Glu | Ile | Val | Ser | Pro | Leu | Ser | Met | Gln | Ser | Pro | Ser | Leu Gln |
|  |  |  |  | 485 |  |  |  |  | 490 |  |  |  |  | 495 |

| agc | agt | gtc | cgg | cag | cgc | ctg | acg | gag | cca | cag | cat | ggc | ctg | gga tct | 1536 |
| Ser | Ser | Val | Arg | Gln | Arg | Leu | Thr | Glu | Pro | Gln | His | Gly | Leu | Gly Ser |
|  |  |  | 500 |  |  |  |  | 505 |  |  |  |  | 510 |  |

| cag | agg | gat | ttg | acc | cat | tcc | gat | tcg | gag | tcc | tcc | ctc | cac | acg agt | 1584 |

```
Gln Arg Asp Leu Thr His Ser Asp Ser Glu Ser Ser Leu His Thr Ser
            515                 520                 525 gac cgc cag cgt gtg gcc ccc aag cct cct cag atg ggc cgt gct gca       1632
Asp Arg Gln Arg Val Ala Pro Lys Pro Pro Gln Met Gly Arg Ala Ala
530                 535                 540 gat gag gct ctc aat gcc acg tct tcc aat ggt agc cat cgg ctg att       1680
Asp Glu Ala Leu Asn Ala Thr Ser Ser Asn Gly Ser His Arg Leu Ile
545                 550                 555                 560 gag ggg gtc cat cca gga tct ctg gtg gag aaa ctg cct gac agc cct       1728
Glu Gly Val His Pro Gly Ser Leu Val Glu Lys Leu Pro Asp Ser Pro
                565                 570                 575 gct ctg gcc aag aag aca atc ctg gcg ctg aac cat ggc cta gat aag       1776
Ala Leu Ala Lys Lys Thr Ile Leu Ala Leu Asn His Gly Leu Asp Lys
            580                 585                 590 gcc cac agc ctg atg gag ctg aac ccc tca gtc cca cct ggt ggc tcc       1824
Ala His Ser Leu Met Glu Leu Asn Pro Ser Val Pro Pro Gly Gly Ser
        595                 600                 605 cca ctt ttg gat tct tcc cat tct cat agt gcc agt tcc cca gac cca       1872
Pro Leu Leu Asp Ser Ser His Ser His Ser Ala Ser Ser Pro Asp Pro
610                 615                 620 gac aca cct tca cca att ggg gat agc cga gct ctg cag ggt agc cga       1920
Asp Thr Pro Ser Pro Ile Gly Asp Ser Arg Ala Leu Gln Gly Ser Arg
625                 630                 635                 640 aac aca cga att ccc cac ttg gct ggc aag aag gct gtg gct gag gag       1968
Asn Thr Arg Ile Pro His Leu Ala Gly Lys Lys Ala Val Ala Glu Glu
                645                 650                 655 gat aat ggt tct att ggt gag gag aca gac tct agc cca ggc agg aag       2016
Asp Asn Gly Ser Ile Gly Glu Glu Thr Asp Ser Ser Pro Gly Arg Lys
            660                 665                 670 aag ttt ccc ctc aaa att ttt aag aag cct ctt aag aag tag               2058
Lys Phe Pro Leu Lys Ile Phe Lys Lys Pro Leu Lys Lys *
        675                 680                 685

<210> SEQ ID NO 52
<211> LENGTH: 685
<212> TYPE: PRT
<213> ORGANISM: Rattus norvegicus
<300> PUBLICATION INFORMATION:
<308> DATABASE ACCESSION NUMBER: Genbank XP_011967
<309> DATABASE ENTRY DATE: 2002-08-01

<400> SEQUENCE: 52

Met Asp Val Cys Ala Arg Leu Ala Leu Trp Leu Leu Trp Gly Leu Leu
 1               5                  10                  15

Leu His Gln Gly His Ser Leu Ser His Ser His Ser Glu Lys Asn Thr
            20                  25                  30

Gly Ala Gly Ser Gly Thr Thr Ser Glu Glu Ser Thr Glu Ala Glu Phe
        35                  40                  45

Cys Arg Ile Asp Lys Pro Leu Cys His Ser Glu Asp Asp Lys Leu Ser
    50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Ile Gln Trp Leu Ile Thr Tyr
```

```
                130                 135                 140
Val Glu Leu Pro Gln Tyr Glu Glu Thr Phe Arg Lys Leu Gln Leu Thr
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Thr Arg His
        195                 200                 205

Asn His Leu Lys Asp Phe Met Leu Val Val Ser Ile Val Ile Gly Val
210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Val Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Lys Gln Leu Leu Val Ala Lys Glu Gly Ala Glu Lys Ile Lys
    370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
    450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Thr Ser
        515                 520                 525

Asp Arg Gln Arg Val Ala Pro Lys Pro Pro Gln Met Gly Arg Ala Ala
    530                 535                 540

Asp Glu Ala Leu Asn Ala Thr Ser Ser Asn Gly Ser His Arg Leu Ile
545                 550                 555                 560
```

```
Glu Gly Val His Pro Gly Ser Leu Val Glu Lys Leu Pro Asp Ser Pro
                565                 570                 575

Ala Leu Ala Lys Lys Thr Ile Leu Ala Leu Asn His Gly Leu Asp Lys
            580                 585                 590

Ala His Ser Leu Met Glu Leu Asn Pro Ser Val Pro Pro Gly Gly Ser
        595                 600                 605

Pro Leu Leu Asp Ser Ser His Ser His Ser Ala Ser Ser Pro Asp Pro
    610                 615                 620

Asp Thr Pro Ser Pro Ile Gly Asp Ser Arg Ala Leu Gln Gly Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Pro Leu Lys Lys
        675                 680                 685

<210> SEQ ID NO 53
<211> LENGTH: 2058
<212> TYPE: DNA
<213> ORGANISM: Mus musculus
<220> FEATURE:
<221> NAME/KEY: CDS
<222> LOCATION: (1)...(2058)
<223> OTHER INFORMATION: Unknown protein MGC: 13964
<300> PUBLICATION INFORMATION:
<308> DATABASE ACCESSION NUMBER: Genbank BC021644
<309> DATABASE ENTRY DATE: 2002-09-20

<400> SEQUENCE: 53 atg gat gtg tgc gcc cgt ctt gcc ctg tgg ctt ctt tgg ggg ctc ctt        48
Met Asp Val Cys Ala Arg Leu Ala Leu Trp Leu Leu Trp Gly Leu Leu
1               5                   10                  15 ctg cat cag ggc cag agt ctc agc cat agt cac agt gaa aag aat aca        96
Leu His Gln Gly Gln Ser Leu Ser His Ser His Ser Glu Lys Asn Thr
            20                  25                  30 gga gct agc tcc ggg gcg act tct gaa gag tct acc gaa gca gag ttt       144
Gly Ala Ser Ser Gly Ala Thr Ser Glu Glu Ser Thr Glu Ala Glu Phe
        35                  40                  45 tgc cga att gac aag ccc ctg tgc cac agt gag gat gag aag ctc agc       192
Cys Arg Ile Asp Lys Pro Leu Cys His Ser Glu Asp Glu Lys Leu Ser
50                  55                  60 ttt gag gcc gtc cga aac atc cat aag ctg atg gat gac gat gcc aat       240
Phe Glu Ala Val Arg Asn Ile His Lys Leu Met Asp Asp Asp Ala Asn
65                  70                  75                  80 ggt gat gtg gat gtg gaa gaa agt gat gag ttc cta agg gaa gac ctc       288
Gly Asp Val Asp Val Glu Glu Ser Asp Glu Phe Leu Arg Glu Asp Leu
                85                  90                  95 aat tac cat gac cca aca gtg aaa cat agc acc ttc cat ggt gag gat       336
Asn Tyr His Asp Pro Thr Val Lys His Ser Thr Phe His Gly Glu Asp
            100                 105                 110 aag ctt atc agc gtg gag gac ctg tgg aag gcg tgg aaa tca tca gaa       384
Lys Leu Ile Ser Val Glu Asp Leu Trp Lys Ala Trp Lys Ser Ser Glu
        115                 120                 125 gtg tac aac tgg act gtg gat gag gtg ata cag tgg ctc att acg tat       432
Val Tyr Asn Trp Thr Val Asp Glu Val Ile Gln Trp Leu Ile Thr Tyr
    130                 135                 140 gtg gag ctg cca cag tat gag gag acc ttc cgg aag ttg cag ctt act       480
Val Glu Leu Pro Gln Tyr Glu Glu Thr Phe Arg Lys Leu Gln Leu Thr
145                 150                 155                 160
```

-continued

| | |
|---|---|
| ggc cac gcc atg cca agg cta gca gta acc aac acc acc atg aca ggg<br>Gly His Ala Met Pro Arg Leu Ala Val Thr Asn Thr Thr Met Thr Gly<br>165                     170                   175 | 528 |
| act gta ctg aag atg aca gat cgg agc cac agg cag aag ctg cag ctg<br>Thr Val Leu Lys Met Thr Asp Arg Ser His Arg Gln Lys Leu Gln Leu<br>    180                     185                   190 | 576 |
| aag gcc ctg gac aca gtg ctg ttt ggg cct cct ctc ttg act cgg cat<br>Lys Ala Leu Asp Thr Val Leu Phe Gly Pro Pro Leu Leu Thr Arg His<br>195                     200                   205 | 624 |
| aat cac ctg aag gac ttc atg ctg gtg gtg tct atc gtt att ggt gtg<br>Asn His Leu Lys Asp Phe Met Leu Val Val Ser Ile Val Ile Gly Val<br>    210                     215                   220 | 672 |
| ggt ggc tgc tgg ttt gcc tat atc cag aac cgt tac tct aag gag cac<br>Gly Gly Cys Trp Phe Ala Tyr Ile Gln Asn Arg Tyr Ser Lys Glu His<br>225                     230                   235               240 | 720 |
| atg aag aaa atg atg aag gat ctg gaa ggg tta cac cgg gct gag cag<br>Met Lys Lys Met Met Lys Asp Leu Glu Gly Leu His Arg Ala Glu Gln<br>                   245                   250                   255 | 768 |
| agt ctg cat gac ctt cag gaa agg ctg cac aag gcc cag gag gag cac<br>Ser Leu His Asp Leu Gln Glu Arg Leu His Lys Ala Gln Glu Glu His<br>    260                     265                   270 | 816 |
| cga act gtg gaa gta gag aaa gtc cac ctg gag aag aag ctg cga gat<br>Arg Thr Val Glu Val Glu Lys Val His Leu Glu Lys Lys Leu Arg Asp<br>275                     280                   285 | 864 |
| gag atc aac ctt gcc aag cag gaa gct cag cgg ctg aag gag ctg agg<br>Glu Ile Asn Leu Ala Lys Gln Glu Ala Gln Arg Leu Lys Glu Leu Arg<br>    290                     295                   300 | 912 |
| gag ggt act gag aat gag agg agc cgt caa aaa tat gct gag gaa gag<br>Glu Gly Thr Glu Asn Glu Arg Ser Arg Gln Lys Tyr Ala Glu Glu Glu<br>305                     310                   315               320 | 960 |
| ctg gag cag gtt cgg gag gcc ttg agg aaa gca gag aag gag ctg gaa<br>Leu Glu Gln Val Arg Glu Ala Leu Arg Lys Ala Glu Lys Glu Leu Glu<br>                   325                   330                   335 | 1008 |
| tca cac agc tca tgg tat gct cct gag gcc ctg cag aag tgg ctg cag<br>Ser His Ser Ser Trp Tyr Ala Pro Glu Ala Leu Gln Lys Trp Leu Gln<br>         340                   345                   350 | 1056 |
| ctg acc cat gag gtg gag gtg cag tac tac aac atc aag aag caa aat<br>Leu Thr His Glu Val Glu Val Gln Tyr Tyr Asn Ile Lys Lys Gln Asn<br>                355                   360                   365 | 1104 |
| gca gag agg cag ctg ctg gtg gcc aag gag ggg gct gag aaa ata aaa<br>Ala Glu Arg Gln Leu Leu Val Ala Lys Glu Gly Ala Glu Lys Ile Lys<br>370                     375                   380 | 1152 |
| aag aag aga aac acg ctt ttt ggt acc ttc cat gtg gcc cac agc tct<br>Lys Lys Arg Asn Thr Leu Phe Gly Thr Phe His Val Ala His Ser Ser<br>385                     390                   395               400 | 1200 |
| tcc ctg gat gat gtg gat cat aaa atc cta act gct aag caa gct ctg<br>Ser Leu Asp Asp Val Asp His Lys Ile Leu Thr Ala Lys Gln Ala Leu<br>                   405                   410                   415 | 1248 |
| agt gag gtg aca gcg gca ctg agg gag cgc ctg cac cgg tgg cag cag<br>Ser Glu Val Thr Ala Ala Leu Arg Glu Arg Leu His Arg Trp Gln Gln<br>               420                   425                   430 | 1296 |
| atc gag atc ctc tgc ggt ttc cag att gtc aat aac ccc ggc atc cac<br>Ile Glu Ile Leu Cys Gly Phe Gln Ile Val Asn Asn Pro Gly Ile His<br>                   435                   440                   445 | 1344 |
| tcc ttg gtg gct gct ctc aac atc gac ccc agc tgg atg ggc agc acc<br>Ser Leu Val Ala Ala Leu Asn Ile Asp Pro Ser Trp Met Gly Ser Thr<br>450                     455                   460 | 1392 |
| cgc cct aac ccc gcc cac ttc atc atg act gac gat gtg gat gac atg<br>Arg Pro Asn Pro Ala His Phe Ile Met Thr Asp Asp Val Asp Asp Met | 1440 |

```
                    465                 470                 475                 480
gat gag gag att gtg tcg ccc ttg tcc atg cag tcc ccc agc ctg cag          1488
Asp Glu Glu Ile Val Ser Pro Leu Ser Met Gln Ser Pro Ser Leu Gln
                        485                 490                 495 agc agt gtc cgg cag cgc ctg acg gag cca cag ctt ggc ctg gga tct          1536
Ser Ser Val Arg Gln Arg Leu Thr Glu Pro Gln Leu Gly Leu Gly Ser
            500                 505                 510 cag agg gat ttg acc cat tcc gat tcg gag tcc tcc ctc cac atg agt          1584
Gln Arg Asp Leu Thr His Ser Asp Ser Glu Ser Ser Leu His Met Ser
        515                 520                 525 gac cgc cag cgt gtg gcc ccc aag cct cct cag atg ggc cgt gct gca          1632
Asp Arg Gln Arg Val Ala Pro Lys Pro Pro Gln Met Gly Arg Ala Ala
    530                 535                 540 gat gaa gct ctc aat gcc atg cct tcc aat ggc agc cat cgg ctg att          1680
Asp Glu Ala Leu Asn Ala Met Pro Ser Asn Gly Ser His Arg Leu Ile
545                 550                 555                 560 gag ggg gtc cat cca gga tct ctg gtg gag aaa ctg cct gac agc cct          1728
Glu Gly Val His Pro Gly Ser Leu Val Glu Lys Leu Pro Asp Ser Pro
                    565                 570                 575 gct ctg gcc aag aag aca ttt atg gcg ttg aac cat ggc cta gac aag          1776
Ala Leu Ala Lys Lys Thr Phe Met Ala Leu Asn His Gly Leu Asp Lys
                580                 585                 590 gcc cac agc ctg atg gag ctg aac ccc tca gtc cca cct ggt ggc tcc          1824
Ala His Ser Leu Met Glu Leu Asn Pro Ser Val Pro Pro Gly Gly Ser
            595                 600                 605 cca ctt ttg gat tct tcc cat tct ctt agc ccc agt tcc cca gac cca          1872
Pro Leu Leu Asp Ser Ser His Ser Leu Ser Pro Ser Ser Pro Asp Pro
        610                 615                 620 gac aca cca tct cca gtt ggg gac aac cga gct ctg cag ggt agc cga          1920
Asp Thr Pro Ser Pro Val Gly Asp Asn Arg Ala Leu Gln Gly Ser Arg
625                 630                 635                 640 aac aca cga att ccc cac ttg gct ggc aag aag gca atg gct gag gag          1968
Asn Thr Arg Ile Pro His Leu Ala Gly Lys Lys Ala Met Ala Glu Glu
                    645                 650                 655 gat aat ggt tcc att ggt gag gag aca gac tcc agt cca ggc agg aag          2016
Asp Asn Gly Ser Ile Gly Glu Glu Thr Asp Ser Ser Pro Gly Arg Lys
                660                 665                 670 aag ttt cct ctc aaa att ttt aag aag cct ctt aag aag tag              2058
Lys Phe Pro Leu Lys Ile Phe Lys Lys Pro Leu Lys Lys *
            675                 680                 685

<210> SEQ ID NO 54
<211> LENGTH: 685
<212> TYPE: PRT
<213> ORGANISM: Mus musculus
<300> PUBLICATION INFORMATION:
<308> DATABASE ACCESSION NUMBER: Genbank AAH21644
<309> DATABASE ENTRY DATE: 2002-09-20

<400> SEQUENCE: 54

Met Asp Val Cys Ala Arg Leu Ala Leu Trp Leu Leu Trp Gly Leu Leu
1               5                   10                  15

Leu His Gln Gly Gln Ser Leu Ser His Ser His Ser Glu Lys Asn Thr
                20                  25                  30

Gly Ala Ser Ser Gly Ala Thr Ser Glu Glu Ser Thr Glu Ala Glu Phe
            35                  40                  45

Cys Arg Ile Asp Lys Pro Leu Cys His Ser Glu Asp Glu Lys Leu Ser
        50                  55                  60

Phe Glu Ala Val Arg Asn Ile His Lys Leu Met Asp Asp Asp Ala Asn
65                  70                  75                  80
```

-continued

```
Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Ile Gln Trp Leu Ile Thr Tyr
    130                 135                 140

Val Glu Leu Pro Gln Tyr Glu Thr Phe Arg Lys Leu Gln Leu Thr
145                 150                 155                 160

Gly His Ala Met Pro Arg Leu Ala Val Thr Asn Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Leu Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Arg Gln Leu Leu Val Ala Lys Glu Gly Ala Glu Lys Ile Lys
    370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
    450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
                485                 490                 495
```

| | | | | | | | | | | | | |
|---|---|---|---|---|---|---|---|---|---|---|---|---|
| Ser | Ser | Val | Arg | Gln | Arg | Leu | Thr | Glu | Pro | Gln | Leu | Gly | Leu | Gly | Ser |
| | | | 500 | | | | | 505 | | | | 510 | |

Ser Ser Val Arg Gln Arg Leu Thr Glu Pro Gln Leu Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Gly Arg Ala Ala
        530                 535                 540

Asp Glu Ala Leu Asn Ala Met Pro Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Thr Phe Met Ala Leu Asn His Gly Leu Asp Lys
            580                 585                 590

Ala His Ser Leu Met Glu Leu Asn Pro Ser Val Pro Pro Gly Gly Ser
        595                 600                 605

Pro Leu Leu Asp Ser Ser His Ser Leu Ser Pro Ser Ser Pro Asp Pro
    610                 615                 620

Asp Thr Pro Ser Pro Val Gly Asp Asn Arg Ala Leu Gln Gly Ser Arg
625                 630                 635                 640

Asn Thr Arg Ile Pro His Leu Ala Gly Lys Lys Ala Met Ala Glu Glu
                645                 650                 655

Asp Asn Gly Ser Ile Gly Glu Glu Thr Asp Ser Ser Pro Gly Arg Lys
                660                 665                 670

Lys Phe Pro Leu Lys Ile Phe Lys Pro Leu Lys Lys
            675                 680                 685

<210> SEQ ID NO 55
<211> LENGTH: 2058
<212> TYPE: DNA
<213> ORGANISM: Mus musculus
<220> FEATURE:
<221> NAME/KEY: CDS
<222> LOCATION: (1)...(2058)
<223> OTHER INFORMATION: Stromal Cell Protein
<300> PUBLICATION INFORMATION:
<308> DATABASE ACCESSION NUMBER: Genbank U47323
<309> DATABASE ENTRY DATE: 1996-08-16

<400> SEQUENCE: 55

```
atg gat gtg tgc gcc cgt ctt gcc ctg tgg ctt ctt tgg ggg ctc ctt        48
Met Asp Val Cys Ala Arg Leu Ala Leu Trp Leu Leu Trp Gly Leu Leu
  1               5                  10                  15 ctg cat cag ggc cag agt ctc agc cat agt cac agt gaa aag aat aca        96
Leu His Gln Gly Gln Ser Leu Ser His Ser His Ser Glu Lys Asn Thr
             20                  25                  30 gga gct agc tcc ggg gcg act tct gaa gag tct acc gaa gca gag ttt       144
Gly Ala Ser Ser Gly Ala Thr Ser Glu Glu Ser Thr Glu Ala Glu Phe
         35                  40                  45 tgc cga att gac aag ccc ctg tgc cac agt gag gat gag aag ctc agc       192
Cys Arg Ile Asp Lys Pro Leu Cys His Ser Glu Asp Glu Lys Leu Ser
     50                  55                  60 ttt gag gcc gtc cga aac atc cat aag ctg atg gat gac gat gcc aat       240
Phe Glu Ala Val Arg Asn Ile His Lys Leu Met Asp Asp Asp Ala Asn
 65                  70                  75                  80 ggt gat gtg gat gtg gaa gaa agt gat gag ttc cta agg gaa gac ctc       288
Gly Asp Val Asp Val Glu Glu Ser Asp Glu Phe Leu Arg Glu Asp Leu
                 85                  90                  95 aat tac cat gac cca aca gtg aaa cat agc acc ttc cat ggt gag gat       336
Asn Tyr His Asp Pro Thr Val Lys His Ser Thr Phe His Gly Glu Asp
            100                 105                 110
```

```
aag ctt atc agc gtg gag gac ctg tgg aag gcg tgg aag tca tca gaa      384
Lys Leu Ile Ser Val Glu Asp Leu Trp Lys Ala Trp Lys Ser Ser Glu
        115                 120                 125 gtg tac aac tgg act gtg gat gag gtg ata cag tgg ctc att acg tat      432
Val Tyr Asn Trp Thr Val Asp Glu Val Ile Gln Trp Leu Ile Thr Tyr
130                 135                 140 gtg gag ctg cca cag tat gag gaa acc ttc cgg aag ttg cag ctt act      480
Val Glu Leu Pro Gln Tyr Glu Glu Thr Phe Arg Lys Leu Gln Leu Thr
145                 150                 155                 160 ggc cac gcc atg cca agg cta gca gta acc aac acc atg aca ggg          528
Gly His Ala Met Pro Arg Leu Ala Val Thr Asn Thr Met Thr Gly
                165                 170                 175 act gta ctg aag atg aca gat cgg agc cac agg cag aag ctg cag ctg      576
Thr Val Leu Lys Met Thr Asp Arg Ser His Arg Gln Lys Leu Gln Leu
            180                 185                 190 aag gcc ctg gac aca gtg ctg ttt ggg cct cct ctc ttg act cgg cat      624
Lys Ala Leu Asp Thr Val Leu Phe Gly Pro Pro Leu Leu Thr Arg His
        195                 200                 205 aat cac ctg aag gac ttc atg ctg gtg gtg tct atc gtt att ggt gtg      672
Asn His Leu Lys Asp Phe Met Leu Val Val Ser Ile Val Ile Gly Val
    210                 215                 220 ggt ggc tgc tgg ttt gcc tat atc cag aac cgt tac tct aag gag cac      720
Gly Gly Cys Trp Phe Ala Tyr Ile Gln Asn Arg Tyr Ser Lys Glu His
225                 230                 235                 240 atg aag aaa atg atg aag gat ctg gaa ggg tta cac cgg gct gag cag      768
Met Lys Lys Met Met Lys Asp Leu Glu Gly Leu His Arg Ala Glu Gln
                245                 250                 255 agt ctg cat gac ctt cag gaa agg ctg cac aag gcc cag gag gag cac      816
Ser Leu His Asp Leu Gln Glu Arg Leu His Lys Ala Gln Glu Glu His
            260                 265                 270 cga act gtg gaa gta gag aag gtc cac ctg gag aag aag ctg cga gat      864
Arg Thr Val Glu Val Glu Lys Val His Leu Glu Lys Lys Leu Arg Asp
        275                 280                 285 gag atc aac ctt gcc aag cag gaa gct cag cgg ctg aag gag ctg agg      912
Glu Ile Asn Leu Ala Lys Gln Glu Ala Gln Arg Leu Lys Glu Leu Arg
    290                 295                 300 gag ggt act gag aat gag agg agc cgt caa aaa tat gct gag gaa gag      960
Glu Gly Thr Glu Asn Glu Arg Ser Arg Gln Lys Tyr Ala Glu Glu Glu
305                 310                 315                 320 ctg gag cag gtt cgg gag gcc ttg agg aaa tca gag aag gag ctg gaa     1008
Leu Glu Gln Val Arg Glu Ala Leu Arg Lys Ser Glu Lys Glu Leu Glu
                325                 330                 335 tca cac agc tca tgg tat gct cct gag gcc ctg cag aag tgg ctg cag     1056
Ser His Ser Ser Trp Tyr Ala Pro Glu Ala Leu Gln Lys Trp Leu Gln
            340                 345                 350 ctg acc cat gag gtg gag gtg cag tac tac aac atc aag aag caa aat     1104
Leu Thr His Glu Val Glu Val Gln Tyr Tyr Asn Ile Lys Lys Gln Asn
        355                 360                 365 gca gag agg cag ctg ctg gtg gcc aag gag ggg gct gag aaa ata aaa     1152
Ala Glu Arg Gln Leu Leu Val Ala Lys Glu Gly Ala Glu Lys Ile Lys
    370                 375                 380 aag aag aga aac acg ctt ttt ggt acc ttc cat gtg gcc cac agc tct     1200
Lys Lys Arg Asn Thr Leu Phe Gly Thr Phe His Val Ala His Ser Ser
385                 390                 395                 400 tcc ctg gat gat gtg gat cat aaa atc cta act gct aag caa gct ctg     1248
Ser Leu Asp Asp Val Asp His Lys Ile Leu Thr Ala Lys Gln Ala Leu
                405                 410                 415 agt gag gtg aca gcg gca ctg agg gag cgc ctg cac cgg tgg cag cag     1296
Ser Glu Val Thr Ala Ala Leu Arg Glu Arg Leu His Arg Trp Gln Gln
            420                 425                 430
```

```
atc gag atc ctc tgc ggt ttc cag att gtc aat aac ccc ggc atc cac      1344
Ile Glu Ile Leu Cys Gly Phe Gln Ile Val Asn Asn Pro Gly Ile His
            435                 440                 445 tcc ttg gtg gct gct ctc aac atc gac ccc agc tgg atg ggc agc acc      1392
Ser Leu Val Ala Ala Leu Asn Ile Asp Pro Ser Trp Met Gly Ser Thr
450                 455                 460 cgc cct aac ccc gcc cac ttc atc atg act gac gat gtg gat gac atg      1440
Arg Pro Asn Pro Ala His Phe Ile Met Thr Asp Asp Val Asp Asp Met
465                 470                 475                 480 gat gag gag att gtg tcg ccc ttg tcc atg cag tcc ccc agc ctg cag      1488
Asp Glu Glu Ile Val Ser Pro Leu Ser Met Gln Ser Pro Ser Leu Gln
                485                 490                 495 agc agt gtc cgg cag cgc ctg acg gag cca cag ctt ggc ctg gga tct      1536
Ser Ser Val Arg Gln Arg Leu Thr Glu Pro Gln Leu Gly Leu Gly Ser
            500                 505                 510 cag agg gat ttg acc cat tcc gat tcg gag tcc tcc ctc cac atg agt      1584
Gln Arg Asp Leu Thr His Ser Asp Ser Glu Ser Ser Leu His Met Ser
        515                 520                 525 gac cgc cag cgt gtg gcc ccc aag cct cct cag atg ggc cgt gct gca      1632
Asp Arg Gln Arg Val Ala Pro Lys Pro Pro Gln Met Gly Arg Ala Ala
530                 535                 540 gat gaa gct ctc aat gcc atg cct tcc aat ggc agc cat cgg ctg att      1680
Asp Glu Ala Leu Asn Ala Met Pro Ser Asn Gly Ser His Arg Leu Ile
545                 550                 555                 560 gag ggg gtc cat cca gga tct ctg gtg gag aaa ctg cct gac agc cct      1728
Glu Gly Val His Pro Gly Ser Leu Val Glu Lys Leu Pro Asp Ser Pro
                565                 570                 575 gct ctg gcc aag aag aca ttt atg gcg ttg aac cat ggc cta gac aag      1776
Ala Leu Ala Lys Lys Thr Phe Met Ala Leu Asn His Gly Leu Asp Lys
            580                 585                 590 gcc cac agc ctg atg gag ctg aac ccc tca gtc cca cct ggt ggc tcc      1824
Ala His Ser Leu Met Glu Leu Asn Pro Ser Val Pro Pro Gly Gly Ser
        595                 600                 605 cca ctt ttg gat tct tcc cat tct ctt agc ccc agt tcc cca gac cca      1872
Pro Leu Leu Asp Ser Ser His Ser Leu Ser Pro Ser Ser Pro Asp Pro
610                 615                 620 gac acg cca tct cca gtt ggg gac aac cga gct ctg cag ggt agc cga      1920
Asp Thr Pro Ser Pro Val Gly Asp Asn Arg Ala Leu Gln Gly Ser Arg
625                 630                 635                 640 aac aca cga att ccc cac ttg gct ggc aag aag gca atg gct gag gag      1968
Asn Thr Arg Ile Pro His Leu Ala Gly Lys Lys Ala Met Ala Glu Glu
                645                 650                 655 gat aat ggt tcc att ggt gag gag aca gac tcc agt cca ggc agg aag      2016
Asp Asn Gly Ser Ile Gly Glu Glu Thr Asp Ser Ser Pro Gly Arg Lys
            660                 665                 670 aag ttt cct ctc aaa att ttt aag aag cct ctt aag aag tag               2058
Lys Phe Pro Leu Lys Ile Phe Lys Lys Pro Leu Lys Lys *
        675                 680                 685

<210> SEQ ID NO 56
<211> LENGTH: 685
<212> TYPE: PRT
<213> ORGANISM: Mus musculus
<300> PUBLICATION INFORMATION:
<308> DATABASE ACCESSION NUMBER: Genbank AAC52715
<309> DATABASE ENTRY DATE: 1996-08-16

<400> SEQUENCE: 56

Met Asp Val Cys Ala Arg Leu Ala Leu Trp Leu Leu Trp Gly Leu Leu
1               5                   10                  15
```

-continued

```
Leu His Gln Gly Gln Ser Leu Ser His Ser His Ser Glu Lys Asn Thr
         20                  25                  30
Gly Ala Ser Ser Gly Ala Thr Ser Glu Glu Ser Thr Glu Ala Glu Phe
         35                  40                  45
Cys Arg Ile Asp Lys Pro Leu Cys His Ser Glu Asp Glu Lys Leu Ser
 50                  55                  60
Phe Glu Ala Val Arg Asn Ile His Lys Leu Met Asp Asp Ala Asn
 65                  70                  75                  80
Gly Asp Val Asp Val Glu Glu Ser Asp Glu Phe Leu Arg Glu Asp Leu
                 85                  90                  95
Asn Tyr His Asp Pro Thr Val Lys His Ser Thr Phe His Gly Glu Asp
             100                 105                 110
Lys Leu Ile Ser Val Glu Asp Leu Trp Lys Ala Trp Lys Ser Ser Glu
         115                 120                 125
Val Tyr Asn Trp Thr Val Asp Glu Val Ile Gln Trp Leu Ile Thr Tyr
     130                 135                 140
Val Glu Leu Pro Gln Tyr Glu Glu Thr Phe Arg Lys Leu Gln Leu Thr
145                 150                 155                 160
Gly His Ala Met Pro Arg Leu Ala Val Thr Asn Thr Thr Met Thr Gly
                 165                 170                 175
Thr Val Leu Lys Met Thr Asp Arg Ser His Arg Gln Lys Leu Gln Leu
             180                 185                 190
Lys Ala Leu Asp Thr Val Leu Phe Gly Pro Pro Leu Leu Thr Arg His
         195                 200                 205
Asn His Leu Lys Asp Phe Met Leu Val Val Ser Ile Val Ile Gly Val
     210                 215                 220
Gly Gly Cys Trp Phe Ala Tyr Ile Gln Asn Arg Tyr Ser Lys Glu His
225                 230                 235                 240
Met Lys Lys Met Met Lys Asp Leu Glu Gly Leu His Arg Ala Glu Gln
                 245                 250                 255
Ser Leu His Asp Leu Gln Glu Arg Leu His Lys Ala Gln Glu Glu His
             260                 265                 270
Arg Thr Val Glu Val Glu Lys Val His Leu Glu Lys Lys Leu Arg Asp
         275                 280                 285
Glu Ile Asn Leu Ala Lys Gln Glu Ala Gln Arg Leu Lys Glu Leu Arg
     290                 295                 300
Glu Gly Thr Glu Asn Glu Arg Ser Arg Gln Lys Tyr Ala Glu Glu Glu
305                 310                 315                 320
Leu Glu Gln Val Arg Glu Ala Leu Arg Lys Ser Lys Glu Leu Glu
                 325                 330                 335
Ser His Ser Ser Trp Tyr Ala Pro Glu Ala Leu Gln Lys Trp Leu Gln
             340                 345                 350
Leu Thr His Glu Val Glu Val Gln Tyr Tyr Asn Ile Lys Lys Gln Asn
         355                 360                 365
Ala Glu Arg Gln Leu Leu Val Ala Lys Glu Gly Ala Glu Lys Ile Lys
     370                 375                 380
Lys Lys Arg Asn Thr Leu Phe Gly Thr Phe His Val Ala His Ser Ser
385                 390                 395                 400
Ser Leu Asp Asp Val Asp His Lys Ile Leu Thr Ala Lys Gln Ala Leu
                 405                 410                 415
Ser Glu Val Thr Ala Ala Leu Arg Glu Arg Leu His Arg Trp Gln Gln
             420                 425                 430
Ile Glu Ile Leu Cys Gly Phe Gln Ile Val Asn Asn Pro Gly Ile His
```

```
                435                 440                 445
Ser Leu Val Ala Ala Leu Asn Ile Asp Pro Ser Trp Met Gly Ser Thr
    450                 455                 460

Arg Pro Asn Pro Ala His Phe Ile Met Thr Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln Leu Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Gly Arg Ala Ala
    530                 535                 540

Asp Glu Ala Leu Asn Ala Met Pro Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Thr Phe Met Ala Leu Asn His Gly Leu Asp Lys
            580                 585                 590

Ala His Ser Leu Met Glu Leu Asn Pro Ser Val Pro Pro Gly Gly Ser
        595                 600                 605

Pro Leu Leu Asp Ser Ser His Ser Leu Ser Pro Ser Ser Pro Asp Pro
    610                 615                 620

Asp Thr Pro Ser Pro Val Gly Asp Asn Arg Ala Leu Gln Gly Ser Arg
625                 630                 635                 640

Asn Thr Arg Ile Pro His Leu Ala Gly Lys Lys Ala Met Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 57
<211> LENGTH: 2310
<212> TYPE: DNA
<213> ORGANISM: Homo sapiens
<300> PUBLICATION INFORMATION:
<308> DATABASE ACCESSION NUMBER: Genbank AL136577
<309> DATABASE ENTRY DATE: 2002-03-20

<400> SEQUENCE: 57
cgccttcatc ccgcctcgac tcctggccca gcgtggggct ggctgctgcg gcggcggcgc    60
tgggctgcgt tgctggtgct cgggctgctg gtacccggag cggcggacgg atgcgagctt   120
gtgccccggc acctccgcgg gcggcgggcg actggctctg ccgcaactgc cgcctcctct   180
cccgccgcgc cggccggcga tagcccggcg ctcatgacag atccctgcat gtcactgagt   240
ccaccatgct ttacagaaga agacagattt agtctggaag ctcttcaaac aatacataaa   300
caaatggatg atgacaaaga tggtggaatt gaagtagagg aaagtgatga attcatcaga   360
gaagatatga aatataaaga tgctactaat aaacacagcc atctgcacag agaagataaa   420
catataacga ttgaggattt atggaaacga tggaaaacat cagaagttca taattggacc   480
cttgaagaca ctcttcagtg gttgatagag tttgttgaac taccccaata tgagaagaat   540
tttagagaca caatgtcaa aggaacgaca cttcccagga tagcagtgca cgaaccttca   600
tttatgatct cccagttgaa aatcagtgac cggagtcaca gacaaaaact tcagctcaag   660
```

```
gcattggatg tggttttgtt tggacctcta acacgcccac ctcataactg gatgaaagat      720
tttatcctca cagtttctat agtaattggt gttggaggct gctggtttgc ttatacgcag      780
aataagacat caaagaaaca tgttgcaaaa atgatgaaag atttagagag cttacaaact      840
gcagagcaaa gtctaatgga cttacaagag aggcttgaaa aggcacagga agaaaacaga      900
aatgttgctg tagaaaagca aaatttagag cgcaaaatga tggatgaaat caattatgca      960
aaggaggagg cttgtcggct gagagagcta agggagggag ctgaatgtga attgagtaga     1020
cgtcagtatg cagaacagga attggaacag gttcgcatgg ctctgaaaaa ggccgaaaaa     1080
gaatttgaac tgagaagcag ttggtctgtt ccagatgcac ttcagaaatg gcttcagtta     1140
acacatgaag tagaagtgca atactacaat attaaaagac aaaacgctga atgcagcta      1200 gctattgcta aagatgaggc agaaaaaatt aaaaagaaga aagcacagt ctttgggact      1260 ctgcacgttg cacacagctc ctccctagat gaggtagacc acaaaattct ggaagcaaag     1320
aaagctctct ctgagttgac aacttgttta cgagaacgac ttttcgctg gcaacaaatt      1380 gagaagatct gtggctttca gatagcccat aactcaggac tccccagcct gacctcttcc     1440
ctttattctg atcacagctg ggtggtgatg cccagagtct ccattccacc ctatccaatt     1500
gctggaggag ttgatgactt agatgaagac acaccccaa tagtgtcaca atttcccggg      1560
accatggcta aacctcctgg atcattagcc agaagcagca gcctgtgccg ttcacgccgc     1620
agcattgtgc cgtcctcgcc tcagcctcag cgagctcagc ttgctccaca cgcccccac      1680 ccgtcacacc ctcggcaccc tcaccacccg caacacacac cacactcctt gccttcccct     1740
gatccagata tcctctcagt gtcaagttgc cctgcgcttt atcgaaatga agaggaggaa     1800
gaggccattt acttctctgc tgaaaagcaa tgggaagtgc cagacacagc ttcagaatgt     1860
gactccttaa attcttccat tggaaggaaa cagtctcctc ctttaagcct cgagatatac     1920
caaacattat ctccgcgaaa gatatcaaga gatgaggtgt ccctagagga ttcctcccga     1980
ggggattcgc ctgtaactgt ggatgtgtct tggggttctc ccgactgtgt aggtctgaca     2040
gaaactaaga gtatgatctt cagtcctgca agcaaagtgt acaatggcat tttggagaaa     2100
tcctgtagca tgaaccagct ttccagtggc atcccggtgc ctaaacctcg ccacacatca     2160
tgttcctcag ctggcaacga cagtaaacca gttcaggaag ccccaagtgt tgccagaata     2220
agcagcatcc cacatgacct ttgtcataat ggagagaaaa gcaaaaagcc atcaaaaatc     2280
aaaagccttt ttaagaagaa atctaagtga                                       2310
```

<210> SEQ ID NO 58
<211> LENGTH: 769
<212> TYPE: PRT
<213> ORGANISM: Homo sapiens
<300> PUBLICATION INFORMATION:
<308> DATABASE ACCESSION NUMBER: Genbank CAB66512
<309> DATABASE ENTRY DATE: 2002-03-20

<400> SEQUENCE: 58

```
Arg Leu His Pro Ala Ser Thr Pro Gly Pro Ala Trp Gly Trp Leu Leu
  1               5                  10                  15

Arg Arg Arg Arg Trp Ala Ala Leu Leu Val Leu Gly Leu Leu Val Pro
             20                  25                  30

Gly Ala Ala Asp Gly Cys Glu Leu Val Pro Arg His Leu Arg Gly Arg
         35                  40                  45

Arg Ala Thr Gly Ser Ala Ala Thr Ala Ala Ser Ser Pro Ala Ala Ala
     50                  55                  60
```

-continued

```
Ala Gly Asp Ser Pro Ala Leu Met Thr Asp Pro Cys Met Ser Leu Ser
 65                  70                  75                  80

Pro Pro Cys Phe Thr Glu Glu Asp Arg Phe Ser Leu Glu Ala Leu Gln
                 85                  90                  95

Thr Ile His Lys Gln Met Asp Asp Lys Asp Gly Ile Glu Val
            100                 105                 110

Glu Glu Ser Asp Glu Phe Ile Arg Glu Asp Met Lys Tyr Lys Asp Ala
        115                 120                 125

Thr Asn Lys His Ser His Leu His Arg Glu Asp Lys His Ile Thr Ile
130                 135                 140

Glu Asp Leu Trp Lys Arg Trp Lys Thr Ser Glu Val His Asn Trp Thr
145                 150                 155                 160

Leu Glu Asp Thr Leu Gln Trp Leu Ile Glu Phe Val Glu Leu Pro Gln
                165                 170                 175

Tyr Glu Lys Asn Phe Arg Asp Asn Val Lys Gly Thr Thr Leu Pro
                180                 185                 190

Arg Ile Ala Val His Glu Pro Ser Phe Met Ile Ser Gln Leu Lys Ile
            195                 200                 205

Ser Asp Arg Ser His Arg Gln Lys Leu Gln Leu Lys Ala Leu Asp Val
    210                 215                 220

Val Leu Phe Gly Pro Leu Thr Arg Pro Pro His Asn Trp Met Lys Asp
225                 230                 235                 240

Phe Ile Leu Thr Val Ser Ile Val Gly Val Gly Gly Cys Trp Phe
                245                 250                 255

Ala Tyr Thr Gln Asn Lys Thr Ser Lys Glu His Val Ala Lys Met Met
            260                 265                 270

Lys Asp Leu Glu Ser Leu Gln Thr Ala Glu Gln Ser Leu Met Asp Leu
        275                 280                 285

Gln Glu Arg Leu Glu Lys Ala Gln Glu Glu Asn Arg Asn Val Ala Val
    290                 295                 300

Glu Lys Gln Asn Leu Glu Arg Lys Met Met Asp Glu Ile Asn Tyr Ala
305                 310                 315                 320

Lys Glu Glu Ala Cys Arg Leu Arg Glu Leu Arg Glu Gly Ala Glu Cys
                325                 330                 335

Glu Leu Ser Arg Arg Gln Tyr Ala Glu Gln Glu Leu Glu Gln Val Arg
            340                 345                 350

Met Ala Leu Lys Lys Ala Glu Lys Glu Phe Glu Leu Arg Ser Ser Trp
        355                 360                 365

Ser Val Pro Asp Ala Leu Gln Lys Trp Leu Gln Leu Thr His Glu Val
    370                 375                 380

Glu Val Gln Tyr Tyr Asn Ile Lys Arg Gln Asn Ala Glu Met Gln Leu
385                 390                 395                 400

Ala Ile Ala Lys Asp Glu Ala Glu Lys Ile Lys Lys Lys Arg Ser Thr
                405                 410                 415

Val Phe Gly Thr Leu His Val Ala His Ser Ser Ser Leu Asp Glu Val
            420                 425                 430

Asp His Lys Ile Leu Glu Ala Lys Lys Ala Leu Ser Glu Leu Thr Thr
        435                 440                 445

Cys Leu Arg Glu Arg Leu Phe Arg Trp Gln Gln Ile Glu Lys Ile Cys
    450                 455                 460

Gly Phe Gln Ile Ala His Asn Ser Gly Leu Pro Ser Leu Thr Ser Ser
465                 470                 475                 480
```

```
Leu Tyr Ser Asp His Ser Trp Val Val Met Pro Arg Val Ser Ile Pro
                485                 490                 495

Pro Tyr Pro Ile Ala Gly Gly Val Asp Asp Leu Asp Glu Asp Thr Pro
            500                 505                 510

Pro Ile Val Ser Gln Phe Pro Gly Thr Met Ala Lys Pro Pro Gly Ser
        515                 520                 525

Leu Ala Arg Ser Ser Ser Leu Cys Arg Ser Arg Arg Ser Ile Val Pro
    530                 535                 540

Ser Ser Pro Gln Pro Gln Arg Ala Gln Leu Ala Pro His Ala Pro His
545                 550                 555                 560

Pro Ser His Pro Arg His Pro His His Pro Gln His Thr Pro His Ser
                565                 570                 575

Leu Pro Ser Pro Asp Pro Asp Ile Leu Ser Val Ser Ser Cys Pro Ala
            580                 585                 590

Leu Tyr Arg Asn Glu Glu Glu Glu Ala Ile Tyr Phe Ser Ala Glu
        595                 600                 605

Lys Gln Trp Glu Val Pro Asp Thr Ala Ser Glu Cys Asp Ser Leu Asn
    610                 615                 620

Ser Ser Ile Gly Arg Lys Gln Ser Pro Pro Leu Ser Leu Glu Ile Tyr
625                 630                 635                 640

Gln Thr Leu Ser Pro Arg Lys Ile Ser Arg Asp Glu Val Ser Leu Glu
                645                 650                 655

Asp Ser Ser Arg Gly Asp Ser Pro Val Thr Val Asp Val Ser Trp Gly
            660                 665                 670

Ser Pro Asp Cys Val Gly Leu Thr Glu Thr Lys Ser Met Ile Phe Ser
        675                 680                 685

Pro Ala Ser Lys Val Tyr Asn Gly Ile Leu Glu Lys Ser Cys Ser Met
    690                 695                 700

Asn Gln Leu Ser Ser Gly Ile Pro Val Pro Lys Pro Arg His Thr Ser
705                 710                 715                 720

Cys Ser Ser Ala Gly Asn Asp Ser Lys Pro Val Gln Glu Ala Pro Ser
                725                 730                 735

Val Ala Arg Ile Ser Ser Ile Pro His Asp Leu Cys His Asn Gly Glu
            740                 745                 750

Lys Ser Lys Lys Pro Ser Lys Ile Lys Ser Leu Phe Lys Lys Lys Ser
        755                 760                 765

Lys

<210> SEQ ID NO 59
<211> LENGTH: 2457
<212> TYPE: DNA
<213> ORGANISM: Homo sapiens
<300> PUBLICATION INFORMATION:
<308> DATABASE ACCESSION NUMBER: Genbank AB040915
<309> DATABASE ENTRY DATE: 2001-02-22
<312> PUBLICATION DATE: -  -

<400> SEQUENCE: 59
gggaccaggc tggcgcccgg cgggagcccg tgtctgaggc ggcggggcg gccggaggag      60 tcgccggcgg cggtggtggc gcctcgcgga gccggcgagc tgcaggcggc cggggcgccg     120
ctgcgctttc acccggcttc tcctcggcgc cttcatcccg cctcgactcc tggcccagcg     180
tggggctggc tgctgcggcg gcggcgctgg gctgcgttgc tggtgctcgg gctgctggta     240
gccggagcgg cggacggatg cgagcttgtg cccccggcac ctccgcgggcg gcgggcgact     300 ggctctgccg caactgccgc ctcctctccc gccgcggcgg ccggcgatag cccggcgctc     360
```

```
atgacagatc cctgcatgtc actgagtcca ccatgcttta cagaagaaga cagatttagt    420
ctggaagctc ttcaaacaat acataaacaa atggatgatg acaaagatgg tggaattgaa    480
gtagaggaaa gtgatgaatt catcagagaa gatatgaaat ataaagatgc tactaataaa    540
cacagccatc tgcacagaga agataaacat ataacgattg aggatttatg gaaacgatgg    600
aaaacatcag aagttcataa ttggaccctt gaagacactc ttcagtggtt gatagagttt    660
gttgaactac cccaatatga aagaattttt agagacaaca atgtcaaagg aacgacactt    720
cccaggatag cagtgcacga accttcattt atgatctccc agttgaaaat cagtgaccgg    780
agtcacagac aaaaacttca gctcaaggca ttggatgtgg ttttgtttgg acctctaaca    840
cgcccacctc ataactggat gaaagatttt atcctcacag tttctatagt aattggtgtt    900
ggaggctgct ggtttgctta tacgcagaat aagacatcaa agaacatgt  tgcaaaaatg    960 atgaaagatt tagagagctt acaaactgca gagcaaagtc taatggactt acaagagagg   1020
cttgaaaagg cacaggaaga aaacagaaat gttgctgtag aaaagcaaaa tttagagcgc   1080
aaaatgatgg atgaaatcaa ttatgcaaag gaggaggctt gtcggctgag agagctaagg   1140
gagggagctg aatgtgaatt gagtagacgt cagtatgcag aacaggaatt ggaacaggtt   1200
cgcatggctc tgaaaaaggc cgaaaaagaa tttgaactga gaagcagttg gtctgttcca   1260
gatgcacttc agaaatggct tcagttaaca catgaagtag aagtgcaata ctacaatatt   1320
aaaagacaaa acgctgaaat gcagctagct attgctaaag atgaggcaga aaaaattaaa   1380
aagaagagaa gcacagtctt tgggactctg cacgttgcac acagctcctc cctagatgag   1440
gtagaccaca aaattctgga agcaaagaaa gctctctctg agttgacaac ttgtttacga   1500
gaacgacttt ttcgctggca acaaattgag aagatctgtg gctttcagat agcccataac   1560
tcaggactcc ccagcctgac ctcttccctt tattctgatc acagctgggt ggtgatgccc   1620
agagtctcca ttccaccccta tccaattgct ggaggagttg atgacttaga tgaagacaca   1680
cccccaatag tgtcacaatt tcccgggacc atggctaaac ctcctggatc attagccaga   1740
agcagcagcc tgtgccgttc acgccgcagc attgtgccgt cctcgcctca gcctcagcga   1800
gctcagcttg ctccacacgc cccccacccg tcacaccctc ggcaccctca ccacccgcaa   1860
cacacaccac actccttgcc ttcccctgat ccagatatcc tctcagtgtc aagttgccct   1920
gcgctttatc gaaatgaaga ggaggaagag gccatttact tctctgctga aaagcaatgg   1980
gaagtgccag acacagcttc agaatgtgac tccttaaatt cttccattgg aaggaaacag   2040
tctcctcctt taagcctcga gatataccaa acattatctc cgcgaaagat atcaagagat   2100
gaggtgtccc tagaggattc ctcccgaggg gattcgcctg taactgtgga tgtgtcttgg   2160
ggttctcccg actgtgtagg tctgacagaa actaagagta tgatcttcag tcctgcaagc   2220
aaagtgtaca atggcatttt ggagaaatcc tgtagcatga accagctttc cagtggcatc   2280
ccggtgccta aacctcgcca cacatcatgt tcctcagctg gcaacgacag taaaccagtt   2340
caggaagccc caagtgttgc cagaataagc agcatcccac atgaccttg tcataatgga    2400 gagaaaagca aaaagccatc aaaaatcaaa agccttttta agaagaaatc taagtga      2457
```

<210> SEQ ID NO 60  
<211> LENGTH: 818  
<212> TYPE: PRT  
<213> ORGANISM: Homo sapiens  
<300> PUBLICATION INFORMATION:  
<308> DATABASE ACCESSION NUMBER: Genbank BAA96006  
<309> DATABASE ENTRY DATE: 2001-02-22

-continued

```
<400> SEQUENCE: 60

Gly Thr Arg Leu Ala Pro Gly Gly Ser Pro Cys Leu Arg Arg Gly
 1               5                  10                  15

Arg Pro Glu Glu Ser Pro Ala Ala Val Val Ala Pro Arg Gly Ala Gly
                20                  25                  30

Glu Leu Gln Ala Ala Gly Ala Pro Leu Arg Phe His Pro Ala Ser Pro
            35                  40                  45

Arg Arg Leu His Pro Ala Ser Thr Pro Gly Pro Ala Trp Gly Trp Leu
50                  55                  60

Leu Arg Arg Arg Arg Trp Ala Ala Leu Leu Val Gly Leu Leu Val
65                  70                  75                  80

Ala Gly Ala Ala Asp Gly Cys Glu Leu Val Pro Arg His Leu Arg Gly
                85                  90                  95

Arg Arg Ala Thr Gly Ser Ala Ala Thr Ala Ala Ser Ser Pro Ala Ala
                100                 105                 110

Ala Ala Gly Asp Ser Pro Ala Leu Met Thr Asp Pro Cys Met Ser Leu
            115                 120                 125

Ser Pro Pro Cys Phe Thr Glu Glu Asp Arg Phe Ser Leu Glu Ala Leu
130                 135                 140

Gln Thr Ile His Lys Gln Met Asp Asp Lys Asp Gly Gly Ile Glu
145                 150                 155                 160

Val Glu Glu Ser Asp Glu Phe Ile Arg Glu Asp Met Lys Tyr Lys Asp
                165                 170                 175

Ala Thr Asn Lys His Ser His Leu His Arg Glu Asp Lys His Ile Thr
            180                 185                 190

Ile Glu Asp Leu Trp Lys Arg Trp Lys Thr Ser Glu Val His Asn Trp
        195                 200                 205

Thr Leu Glu Asp Thr Leu Gln Trp Leu Ile Glu Phe Val Glu Leu Pro
210                 215                 220

Gln Tyr Glu Lys Asn Phe Arg Asp Asn Asn Val Lys Gly Thr Thr Leu
225                 230                 235                 240

Pro Arg Ile Ala Val His Glu Pro Ser Phe Met Ile Ser Gln Leu Lys
                245                 250                 255

Ile Ser Asp Arg Ser His Arg Gln Lys Leu Gln Leu Lys Ala Leu Asp
            260                 265                 270

Val Val Leu Phe Gly Pro Leu Thr Arg Pro Pro His Asn Trp Met Lys
        275                 280                 285

Asp Phe Ile Leu Thr Val Ser Ile Val Ile Gly Val Gly Gly Cys Trp
290                 295                 300

Phe Ala Tyr Thr Gln Asn Lys Thr Ser Lys Glu His Val Ala Lys Met
305                 310                 315                 320

Met Lys Asp Leu Glu Ser Leu Gln Thr Ala Glu Gln Ser Leu Met Asp
                325                 330                 335

Leu Gln Glu Arg Leu Glu Lys Ala Gln Glu Glu Asn Arg Asn Val Ala
            340                 345                 350

Val Glu Lys Gln Asn Leu Glu Arg Lys Met Met Asp Glu Ile Asn Tyr
        355                 360                 365

Ala Lys Glu Glu Ala Cys Arg Leu Arg Glu Leu Arg Glu Gly Ala Glu
370                 375                 380

Cys Glu Leu Ser Arg Arg Gln Tyr Ala Glu Gln Glu Leu Glu Gln Val
385                 390                 395                 400

Arg Met Ala Leu Lys Lys Ala Glu Lys Glu Phe Glu Leu Arg Ser Ser
```

```
                405                 410                 415
Trp Ser Val Pro Asp Ala Leu Gln Lys Trp Leu Gln Leu Thr His Glu
                420                 425                 430

Val Glu Val Gln Tyr Tyr Asn Ile Lys Arg Gln Asn Ala Glu Met Gln
                435                 440                 445

Leu Ala Ile Ala Lys Asp Glu Ala Glu Lys Ile Lys Lys Lys Arg Ser
                450                 455                 460

Thr Val Phe Gly Thr Leu His Val Ala His Ser Ser Ser Leu Asp Glu
465                 470                 475                 480

Val Asp His Lys Ile Leu Glu Ala Lys Lys Ala Leu Ser Glu Leu Thr
                485                 490                 495

Thr Cys Leu Arg Glu Arg Leu Phe Arg Trp Gln Gln Ile Glu Lys Ile
                500                 505                 510

Cys Gly Phe Gln Ile Ala His Asn Ser Gly Leu Pro Ser Leu Thr Ser
                515                 520                 525

Ser Leu Tyr Ser Asp His Ser Trp Val Val Met Pro Arg Val Ser Ile
                530                 535                 540

Pro Pro Tyr Pro Ile Ala Gly Gly Val Asp Asp Leu Asp Glu Asp Thr
545                 550                 555                 560

Pro Pro Ile Val Ser Gln Phe Pro Gly Thr Met Ala Lys Pro Pro Gly
                565                 570                 575

Ser Leu Ala Arg Ser Ser Ser Leu Cys Arg Ser Arg Arg Ser Ile Val
                580                 585                 590

Pro Ser Ser Pro Gln Pro Gln Arg Ala Gln Leu Ala Pro His Ala Pro
                595                 600                 605

His Pro Ser His Pro Arg His Pro His His Pro Gln His Thr Pro His
                610                 615                 620

Ser Leu Pro Ser Pro Asp Pro Asp Ile Leu Ser Val Ser Ser Cys Pro
625                 630                 635                 640

Ala Leu Tyr Arg Asn Glu Glu Glu Glu Ala Ile Tyr Phe Ser Ala
                645                 650                 655

Glu Lys Gln Trp Glu Val Pro Asp Thr Ala Ser Glu Cys Asp Ser Leu
                660                 665                 670

Asn Ser Ser Ile Gly Arg Lys Gln Ser Pro Pro Leu Ser Leu Glu Ile
                675                 680                 685

Tyr Gln Thr Leu Ser Pro Arg Lys Ile Ser Arg Asp Glu Val Ser Leu
                690                 695                 700

Glu Asp Ser Ser Arg Gly Asp Ser Pro Val Thr Val Asp Val Ser Trp
705                 710                 715                 720

Gly Ser Pro Asp Cys Val Gly Leu Thr Glu Thr Lys Ser Met Ile Phe
                725                 730                 735

Ser Pro Ala Ser Lys Val Tyr Asn Gly Ile Leu Glu Lys Ser Cys Ser
                740                 745                 750

Met Asn Gln Leu Ser Ser Gly Ile Pro Val Pro Lys Pro Arg His Thr
                755                 760                 765

Ser Cys Ser Ser Ala Gly Asn Asp Ser Lys Pro Val Gln Glu Ala Pro
                770                 775                 780

Ser Val Ala Arg Ile Ser Ser Ile Pro His Asp Leu Cys His Asn Gly
785                 790                 795                 800

Glu Lys Ser Lys Lys Pro Ser Lys Ile Lys Ser Leu Phe Lys Lys Lys
                805                 810                 815

Ser Lys
```

<210> SEQ ID NO 61
<211> LENGTH: 1677
<212> TYPE: DNA
<213> ORGANISM: Homo sapiens
<300> PUBLICATION INFORMATION:
<308> DATABASE ACCESSION NUMBER: Genbank BC015659
<309> DATABASE ENTRY DATE: 2001-10-09

<400> SEQUENCE: 61

```
ggcacgaggc aaaaacttca gctcaaggca ttggatgtgg ttttgtttgg acctctaaca      60
cgcccacctc ataactggat gaaagatttt atcctcacag tttctatagt aattggtgtt     120
ggaggctgct ggtttgctta tacgcagaat aagacatcaa agaacatgt tgcaaaaatg      180
atgaaagatt tagagagctt acaaactgca gagcaaagtc taatggactt acaagagagg     240
cttgaaaagg cacaggaaga aacagaaat gttgctgtag aaaagcaaaa tttagagcgc      300
aaaatgatgg atgaaatcaa ttatgcaaag gaggaggctt gtcggctgag agagctaagg     360
gagggagctg aatgtgaatt gagtagacgt cagtatgcag aacaggaatt ggaacaggtt     420
cgcatggctc tgaaaaaggc cgaaaaagaa tttgaactga aagcagttg gtctgttcca      480
gatgcacttc agaaatggct tcagttaaca catgaagtag aagtgcaata ctacaatatt     540
aaaagacaaa acgctgaaat gcagctagct attgctaaag atgaggcaga aaaaattaaa     600
aagaagagaa gcacagtctt tgggactctg cacgttgcac acagctcctc cctagatgag     660
gtagaccaca aaattctgga agcaaagaaa gctctctctg agttgacaac ttgtttacga     720
gaacgacttt ttcgctggca acaaattgag aagatctgtg gctttcagat agcccataac     780
tcaggactcc ccagcctgac ctcttccctt tattctgatc acagctgggt ggtgatgccc     840
agagtctcca ttccacccta tccaattgct ggaggagttg atgacttaga tgaagacaca     900
cccccaatag tgtcacaatt tcccgggacc atggctaaac ctcctggatc attagccaga     960
agcagcagcc tgtgccgttc acgccgcagc attgtgccgt cctcgcctca gcctcagcga    1020
gctcagcttg ctccacacgc cccccacccg tcacaccctc ggcaccctca ccacccgcaa    1080
cacacaccac actccttgcc ttcccctgat ccagatatcc tctcagtgtc aagttgccct    1140
gcgctttatc gaaatgaaga ggaggaagag gccatttact tctctgctga aaagcaatgg    1200
gaagtgccag acacagcttc agaatgtgac tccttaaatt cttccattgg aaggaaacag    1260
tctcctcctt taagcctcga gataaccaa acattatctc cgcgaaagat atcaagagat    1320
gaggtgtccc tagaggattc ctcccgaggg gattcgcctg taactgtgga tgtgtcttgg    1380
ggttctcccg actgtgtagg tctgacagaa actaagagta tgatcttcag tcctgcaagc    1440
aaagtgtaca atggcatttt ggagaaatcc tgtagcatga accagctttc cagtggcatc    1500
ccggtgccta aacctcgcca cacatcatgt tcctcagctg gcaacgacag taaaccagtt    1560
caggaagccc caagtgttgc cagaataagc agcatcccac atgacctttg tcataatgga    1620
gagaaaagca aaaagccatc aaaaatcaaa agccttttta agaagaaatc taagtga       1677
```

<210> SEQ ID NO 62
<211> LENGTH: 558
<212> TYPE: PRT
<213> ORGANISM: Homo sapiens
<300> PUBLICATION INFORMATION:
<308> DATABASE ACCESSION NUMBER: Genbank AAH15659
<309> DATABASE ENTRY DATE: 2001-10-09

<400> SEQUENCE: 62

Gly Thr Arg Gln Lys Leu Gln Leu Lys Ala Leu Asp Val Val Leu Phe

-continued

```
              1               5                  10                 15
Gly Pro Leu Thr Arg Pro His Asn Trp Met Lys Asp Phe Ile Leu
                 20                  25                 30
Thr Val Ser Ile Val Ile Gly Val Gly Gly Cys Trp Phe Ala Tyr Thr
                 35                  40                 45
Gln Asn Lys Thr Ser Lys Glu His Val Ala Lys Met Met Lys Asp Leu
     50                  55                  60
Glu Ser Leu Gln Thr Ala Glu Gln Ser Leu Met Asp Leu Gln Glu Arg
 65                  70                  75                  80
Leu Glu Lys Ala Gln Glu Glu Asn Arg Asn Val Ala Val Glu Lys Gln
                 85                  90                  95
Asn Leu Glu Arg Lys Met Met Asp Glu Ile Asn Tyr Ala Lys Glu Glu
                100                 105                 110
Ala Cys Arg Leu Arg Glu Leu Arg Glu Gly Ala Glu Cys Glu Leu Ser
                115                 120                 125
Arg Arg Gln Tyr Ala Glu Gln Glu Leu Glu Gln Val Arg Met Ala Leu
                130                 135                 140
Lys Lys Ala Glu Lys Glu Phe Glu Leu Arg Ser Ser Trp Ser Val Pro
145                 150                 155                 160
Asp Ala Leu Gln Lys Trp Leu Gln Leu Thr His Glu Val Glu Val Gln
                165                 170                 175
Tyr Tyr Asn Ile Lys Arg Gln Asn Ala Glu Met Gln Leu Ala Ile Ala
                180                 185                 190
Lys Asp Glu Ala Glu Lys Ile Lys Lys Arg Ser Thr Val Phe Gly
                195                 200                 205
Thr Leu His Val Ala His Ser Ser Ser Leu Asp Glu Val Asp His Lys
                210                 215                 220
Ile Leu Glu Ala Lys Lys Ala Leu Ser Glu Leu Thr Thr Cys Leu Arg
225                 230                 235                 240
Glu Arg Leu Phe Arg Trp Gln Gln Ile Glu Lys Ile Cys Gly Phe Gln
                245                 250                 255
Ile Ala His Asn Ser Gly Leu Pro Ser Leu Thr Ser Ser Leu Tyr Ser
                260                 265                 270
Asp His Ser Trp Val Val Met Pro Arg Val Ser Ile Pro Pro Tyr Pro
                275                 280                 285
Ile Ala Gly Gly Val Asp Asp Leu Asp Glu Asp Thr Pro Pro Ile Val
                290                 295                 300
Ser Gln Phe Pro Gly Thr Met Ala Lys Pro Pro Gly Ser Leu Ala Arg
305                 310                 315                 320
Ser Ser Ser Leu Cys Arg Ser Arg Ser Ile Val Pro Ser Ser Pro
                325                 330                 335
Gln Pro Gln Arg Ala Gln Leu Ala Pro His Ala Pro His Pro Ser His
                340                 345                 350
Pro Arg His Pro His His Pro Gln His Thr Pro His Ser Leu Pro Ser
                355                 360                 365
Pro Asp Pro Asp Ile Leu Ser Val Ser Ser Cys Pro Ala Leu Tyr Arg
                370                 375                 380
Asn Glu Glu Glu Glu Ala Ile Tyr Phe Ser Ala Glu Lys Gln Trp
385                 390                 395                 400
Glu Val Pro Asp Thr Ala Ser Glu Cys Asp Ser Leu Asn Ser Ser Ile
                405                 410                 415
Gly Arg Lys Gln Ser Pro Pro Leu Ser Leu Glu Ile Tyr Gln Thr Leu
                420                 425                 430
```

```
-continued

Ser Pro Arg Lys Ile Ser Arg Asp Glu Val Ser Leu Glu Asp Ser Ser
        435                 440                 445

Arg Gly Asp Ser Pro Val Thr Val Asp Val Ser Trp Gly Ser Pro Asp
    450                 455                 460

Cys Val Gly Leu Thr Glu Thr Lys Ser Met Ile Phe Ser Pro Ala Ser
465                 470                 475                 480

Lys Val Tyr Asn Gly Ile Leu Glu Lys Ser Cys Ser Met Asn Gln Leu
                485                 490                 495

Ser Ser Gly Ile Pro Val Pro Lys Pro Arg His Thr Ser Cys Ser Ser
            500                 505                 510

Ala Gly Asn Asp Ser Lys Pro Val Gln Glu Ala Pro Ser Val Ala Arg
        515                 520                 525

Ile Ser Ser Ile Pro His Asp Leu Cys His Asn Gly Glu Lys Ser Lys
    530                 535                 540

Lys Pro Ser Lys Ile Lys Ser Leu Phe Lys Lys Lys Ser Lys
545                 550                 555

<210> SEQ ID NO 63
<211> LENGTH: 1593
<212> TYPE: DNA
<213> ORGANISM: Caenorhabditis elegans
<220> FEATURE:
<221> NAME/KEY: CDS
<222> LOCATION: (1)...(1593)
<223> OTHER INFORMATION: Hypothetical protein Y55B1BM.1a
<300> PUBLICATION INFORMATION:
<308> DATABASE ACCESSION NUMBER: Genbank AC024823
<309> DATABASE ENTRY DATE: 2002-05-29

<400> SEQUENCE: 63 atg ggt aga gtt tcg tgg att att gcc tta tat ctt aca atc aac gtg      48
Met Gly Arg Val Ser Trp Ile Ile Ala Leu Tyr Leu Thr Ile Asn Val
1               5                   10                  15 gtt att gtt gtt aat gga gat cgg gtg act aga aat gtt gaa gta acg      96
Val Ile Val Val Asn Gly Asp Arg Val Thr Arg Asn Val Glu Val Thr
            20                  25                  30 gcg gaa gaa gaa aaa ata cgg gat aaa ttg gga tat gaa gcg att aga     144
Ala Glu Glu Glu Lys Ile Arg Asp Lys Leu Gly Tyr Glu Ala Ile Arg
        35                  40                  45 gat att cat cga gac atg gac gat gat cat tcg ggt tca atc gat cga     192
Asp Ile His Arg Asp Met Asp Asp Asp His Ser Gly Ser Ile Asp Arg
    50                  55                  60 aat gaa tcg act ggg ttt atg aaa gaa gat atg caa atg cgt gga tcc     240
Asn Glu Ser Thr Gly Phe Met Lys Glu Asp Met Gln Met Arg Gly Ser
65                  70                  75                  80 gaa cga act aga cgg gag aat aag ttc cat ggc gac gac gat gcg att     288
Glu Arg Thr Arg Arg Glu Asn Lys Phe His Gly Asp Asp Asp Ala Ile
                85                  90                  95 act gta gac gat ctg tgg gag gcc tgg ttt gag agt atc gag aga act     336
Thr Val Asp Asp Leu Trp Glu Ala Trp Phe Glu Ser Ile Glu Arg Thr
            100                 105                 110 tgg acg aat gaa agg ctc gtc gaa tgg ctc atc aac gac gta aac ctt     384
Trp Thr Asn Glu Arg Leu Val Glu Trp Leu Ile Asn Asp Val Asn Leu
        115                 120                 125 ccc agc att gtt gaa gca gta aaa gcc aag aaa att gat ggg aag att     432
Pro Ser Ile Val Glu Ala Val Lys Ala Lys Lys Ile Asp Gly Lys Ile
    130                 135                 140 ctt cca aga ttt gca tct cca aat tcg gac ttt ttg aac aaa gaa ctt     480
Leu Pro Arg Phe Ala Ser Pro Asn Ser Asp Phe Leu Asn Lys Glu Leu
145                 150                 155                 160
```

```
ggc ata aaa tcg tcg gtt tat cgt caa aaa ctt cgt ttg aac tcg ttg      528
Gly Ile Lys Ser Ser Val Tyr Arg Gln Lys Leu Arg Leu Asn Ser Leu
        165                 170                 175 gat gtt gta ctt ttt ggg tat aag gat aat aat aat cga aca aag gat      576
Asp Val Val Leu Phe Gly Tyr Lys Asp Asn Asn Asn Arg Thr Lys Asp
            180                 185                 190 att cta ttg gcg ttt ttg gca ctt ctc cta aca tca ctc atc ttt tta      624
Ile Leu Leu Ala Phe Leu Ala Leu Leu Leu Thr Ser Leu Ile Phe Leu
                195                 200                 205 tac gtc cgc caa aaa caa aag gct cag caa aaa gtc aat gaa tta tca      672
Tyr Val Arg Gln Lys Gln Lys Ala Gln Gln Lys Val Asn Glu Leu Ser
    210                 215                 220 aat aag ttg acc gaa ctg aaa tgt atg gaa acc gaa ttt gaa gat gtt      720
Asn Lys Leu Thr Glu Leu Lys Cys Met Glu Thr Glu Phe Glu Asp Val
225                 230                 235                 240 cag aaa atg ttg aat gac gag aga agt aaa cga tca att tcc gat gga      768
Gln Lys Met Leu Asn Asp Glu Arg Ser Lys Arg Ser Ile Ser Asp Gly
                245                 250                 255 gtt gtg aat cac aca gaa atg gag aac ctc cgt gtc cag ctg gaa gaa      816
Val Val Asn His Thr Glu Met Glu Asn Leu Arg Val Gln Leu Glu Glu
            260                 265                 270 gcc gaa cga cgg ctt gaa gcg aat tcg aat ggt tct caa gct cct ctt      864
Ala Glu Arg Arg Leu Glu Ala Asn Ser Asn Gly Ser Gln Ala Pro Leu
        275                 280                 285 gca ctt cag cca ttg ctt aga aga act tgc gag aat gag atg gct ttt      912
Ala Leu Gln Pro Leu Leu Arg Arg Thr Cys Glu Asn Glu Met Ala Phe
    290                 295                 300 ctg gaa aag cag aga caa gat tgc ttc aag gaa atg aaa gag gcc atc      960
Leu Glu Lys Gln Arg Gln Asp Cys Phe Lys Glu Met Lys Glu Ala Ile
305                 310                 315                 320 gaa atg gtg gat cgt cta cag aaa aag caa gga agt gta ctt tcc tcg     1008
Glu Met Val Asp Arg Leu Gln Lys Lys Gln Gly Ser Val Leu Ser Ser
                325                 330                 335 ttg aaa ttg gca act gga gca gct tcc acg tcg gat caa gtc gat tcg     1056
Leu Lys Leu Ala Thr Gly Ala Ala Ser Thr Ser Asp Gln Val Asp Ser
            340                 345                 350 aag att ttc gcg ttg aaa agt cga atg gaa aaa atc cac aca ttg aca     1104
Lys Ile Phe Ala Leu Lys Ser Arg Met Glu Lys Ile His Thr Leu Thr
        355                 360                 365 cgt gaa act caa gaa cga tgg ctt caa att gaa tca ctt tgc ggt ttt     1152
Arg Glu Thr Gln Glu Arg Trp Leu Gln Ile Glu Ser Leu Cys Gly Phe
    370                 375                 380 cca ctt cta tat tta aat gaa acc gaa cat atc aat cga tca att gcc     1200
Pro Leu Leu Tyr Leu Asn Glu Thr Glu His Ile Asn Arg Ser Ile Ala
385                 390                 395                 400 tca tca cat ttc tac aat aaa agt cat gaa ggt tcc tcc tct tcc ggc     1248
Ser Ser His Phe Tyr Asn Lys Ser His Glu Gly Ser Ser Ser Ser Gly
                405                 410                 415 tca att tca aat gct cat tca aat ccc aat gca gtt aat tca aat ttt     1296
Ser Ile Ser Asn Ala His Ser Asn Pro Asn Ala Val Asn Ser Asn Phe
            420                 425                 430 gtg aaa aaa gtg tca ccg cca att cca cct tcc caa caa act gca aat     1344
Val Lys Lys Val Ser Pro Pro Ile Pro Pro Ser Gln Gln Thr Ala Asn
        435                 440                 445 ctt cga ttt gtt ccc acc gag caa agt gat agt att cat tct gaa gac     1392
Leu Arg Phe Val Pro Thr Glu Gln Ser Asp Ser Ile His Ser Glu Asp
    450                 455                 460 acg tca cca att gtc gaa gac gtg gca att tcc aga agc tta act caa     1440
Thr Ser Pro Ile Val Glu Asp Val Ala Ile Ser Arg Ser Leu Thr Gln
```

```
                465                 470                 475                 480
gac cta gct gaa gct gat atg cag tca ata gta tcc ggt tct aca aat      1488
Asp Leu Ala Glu Ala Asp Met Gln Ser Ile Val Ser Gly Ser Thr Asn
                    485                 490                 495 ggc tcg ggc tcc gta gct gct ctt aaa aag cga aaa gga att ttc ccg      1536
Gly Ser Gly Ser Val Ala Ala Leu Lys Lys Arg Lys Gly Ile Phe Pro
            500                 505                 510 aaa ctt ttc cgc cga aat aca tcg aaa tct agc agt ctg ggt ggc act      1584
Lys Leu Phe Arg Arg Asn Thr Ser Lys Ser Ser Ser Leu Gly Gly Thr
        515                 520                 525 tct aat taa                                                           1593
Ser Asn *
    530

<210> SEQ ID NO 64
<211> LENGTH: 530
<212> TYPE: PRT
<213> ORGANISM: Caenorhabditis elegans
<300> PUBLICATION INFORMATION:
<308> DATABASE ACCESSION NUMBER: Genbank AAF59596
<309> DATABASE ENTRY DATE: 2002-05-29

<400> SEQUENCE: 64

Met Gly Arg Val Ser Trp Ile Ile Ala Leu Tyr Leu Thr Ile Asn Val
 1               5                  10                  15

Val Ile Val Val Asn Gly Asp Arg Val Thr Arg Asn Val Glu Val Thr
             20                  25                  30

Ala Glu Glu Lys Ile Arg Asp Lys Leu Gly Tyr Glu Ala Ile Arg
         35                  40                  45

Asp Ile His Arg Asp Met Asp Asp His Ser Gly Ser Ile Asp Arg
     50                  55                  60

Asn Glu Ser Thr Gly Phe Met Lys Glu Asp Met Gln Met Arg Gly Ser
 65                  70                  75                  80

Glu Arg Thr Arg Arg Glu Asn Lys Phe His Gly Asp Asp Ala Ile
                 85                  90                  95

Thr Val Asp Asp Leu Trp Glu Ala Trp Phe Glu Ser Ile Glu Arg Thr
            100                 105                 110

Trp Thr Asn Glu Arg Leu Val Glu Trp Leu Ile Asn Asp Val Asn Leu
        115                 120                 125

Pro Ser Ile Val Glu Ala Val Lys Ala Lys Lys Ile Asp Gly Lys Ile
    130                 135                 140

Leu Pro Arg Phe Ala Ser Pro Asn Ser Asp Phe Leu Asn Lys Glu Leu
145                 150                 155                 160

Gly Ile Lys Ser Ser Val Tyr Arg Gln Lys Leu Arg Leu Asn Ser Leu
                165                 170                 175

Asp Val Val Leu Phe Gly Tyr Lys Asp Asn Asn Asn Arg Thr Lys Asp
            180                 185                 190

Ile Leu Leu Ala Phe Leu Ala Leu Leu Thr Ser Leu Ile Phe Leu
        195                 200                 205

Tyr Val Arg Gln Lys Gln Lys Ala Gln Lys Val Asn Glu Leu Ser
    210                 215                 220

Asn Lys Leu Thr Glu Leu Lys Cys Met Glu Thr Glu Phe Glu Asp Val
225                 230                 235                 240

Gln Lys Met Leu Asn Asp Glu Arg Ser Lys Arg Ser Ile Ser Asp Gly
                245                 250                 255

Val Val Asn His Thr Glu Met Glu Asn Leu Arg Val Gln Leu Glu Glu
            260                 265                 270
```

```
Ala Glu Arg Arg Leu Glu Ala Asn Ser Asn Gly Ser Gln Ala Pro Leu
            275                 280                 285

Ala Leu Gln Pro Leu Leu Arg Arg Thr Cys Glu Asn Glu Met Ala Phe
        290                 295                 300

Leu Glu Lys Gln Arg Gln Asp Cys Phe Lys Glu Met Lys Glu Ala Ile
305                 310                 315                 320

Glu Met Val Asp Arg Leu Gln Lys Lys Gln Gly Ser Val Leu Ser Ser
                325                 330                 335

Leu Lys Leu Ala Thr Gly Ala Ala Ser Thr Ser Asp Gln Val Asp Ser
            340                 345                 350

Lys Ile Phe Ala Leu Lys Ser Arg Met Glu Lys Ile His Thr Leu Thr
        355                 360                 365

Arg Glu Thr Gln Glu Arg Trp Leu Gln Ile Glu Ser Leu Cys Gly Phe
    370                 375                 380

Pro Leu Leu Tyr Leu Asn Glu Thr Glu His Ile Asn Arg Ser Ile Ala
385                 390                 395                 400

Ser Ser His Phe Tyr Asn Lys Ser His Glu Gly Ser Ser Ser Ser Gly
                405                 410                 415

Ser Ile Ser Asn Ala His Ser Asn Pro Asn Ala Val Asn Ser Asn Phe
            420                 425                 430

Val Lys Lys Val Ser Pro Pro Ile Pro Pro Ser Gln Gln Thr Ala Asn
        435                 440                 445

Leu Arg Phe Val Pro Thr Glu Gln Ser Asp Ser Ile His Ser Glu Asp
    450                 455                 460

Thr Ser Pro Ile Val Glu Asp Val Ala Ile Ser Arg Ser Leu Thr Gln
465                 470                 475                 480

Asp Leu Ala Glu Ala Asp Met Gln Ser Ile Val Ser Gly Ser Thr Asn
                485                 490                 495

Gly Ser Gly Ser Val Ala Ala Leu Lys Lys Arg Lys Gly Ile Phe Pro
            500                 505                 510

Lys Leu Phe Arg Arg Asn Thr Ser Lys Ser Ser Ser Leu Gly Gly Thr
        515                 520                 525

Ser Asn
530

<210> SEQ ID NO 65
<211> LENGTH: 1533
<212> TYPE: DNA
<213> ORGANISM: Caenorhabditis elegans
<220> FEATURE:
<221> NAME/KEY: CDS
<222> LOCATION: (1)...(1533)
<223> OTHER INFORMATION: Hypothetical protein Y55B1BM.1b
<300> PUBLICATION INFORMATION:
<308> DATABASE ACCESSION NUMBER: Genbank AC024823
<309> DATABASE ENTRY DATE: 2002-05-29

<400> SEQUENCE: 65 atg ggt aga gtt tcg tgg att att gcc tta tat ctt aca atc aac gtg      48
Met Gly Arg Val Ser Trp Ile Ile Ala Leu Tyr Leu Thr Ile Asn Val
 1               5                  10                  15 gtt att gtt gtt aat gga gat cgg gtg act aga aat gtt gaa gta acg      96
Val Ile Val Val Asn Gly Asp Arg Val Thr Arg Asn Val Glu Val Thr
             20                  25                  30 gcg gaa gaa gaa aaa ata cgg gat aaa ttg gga tat gaa gcg att aga     144
Ala Glu Glu Glu Lys Ile Arg Asp Lys Leu Gly Tyr Glu Ala Ile Arg
         35                  40                  45
```

-continued

| | |
|---|---|
| gat att cat cga gac atg gac gat cat tcg ggt tca atc gat cga<br>Asp Ile His Arg Asp Met Asp Asp His Ser Gly Ser Ile Asp Arg<br>50          55                  60 | 192 |
| aat gaa tcg act ggg ttt atg aaa gaa gat atg caa atg cgt gga tcc<br>Asn Glu Ser Thr Gly Phe Met Lys Glu Asp Met Gln Met Arg Gly Ser<br>65              70                  75                  80 | 240 |
| gaa cga act aga cgg gag aat aag ttc cat ggc gac gac gat gcg att<br>Glu Arg Thr Arg Arg Glu Asn Lys Phe His Gly Asp Asp Asp Ala Ile<br>              85                  90                  95 | 288 |
| act gta gac gat ctg tgg gag gcc tgg ttt gag agt atc gag aga act<br>Thr Val Asp Asp Leu Trp Glu Ala Trp Phe Glu Ser Ile Glu Arg Thr<br>          100                 105                 110 | 336 |
| tgg acg aat gaa agg ctc gtc gaa tgg ctc atc aac gac gta aac ctt<br>Trp Thr Asn Glu Arg Leu Val Glu Trp Leu Ile Asn Asp Val Asn Leu<br>      115                 120                 125 | 384 |
| ccc agc att gtt gaa gca gta aaa gcc aag aaa att gat ggg aag att<br>Pro Ser Ile Val Glu Ala Val Lys Ala Lys Lys Ile Asp Gly Lys Ile<br>130                 135                 140 | 432 |
| ctt cca aga ttt gca tct cca aat tcg gac ttt ttg aac aaa gaa ctt<br>Leu Pro Arg Phe Ala Ser Pro Asn Ser Asp Phe Leu Asn Lys Glu Leu<br>145                 150                 155                 160 | 480 |
| ggc ata aaa tcg tcg gtt tat cgt caa aaa ctt cgt ttg aac tcg ttg<br>Gly Ile Lys Ser Ser Val Tyr Arg Gln Lys Leu Arg Leu Asn Ser Leu<br>              165                 170                 175 | 528 |
| gat gtt gta ctt ttt ggg tat aag gat aat aat aat cga aca aag gat<br>Asp Val Val Leu Phe Gly Tyr Lys Asp Asn Asn Asn Arg Thr Lys Asp<br>          180                 185                 190 | 576 |
| att cta ttg gcg ttt ttg gca ctt ctc cta aca tca ctc atc ttt tta<br>Ile Leu Leu Ala Phe Leu Ala Leu Leu Leu Thr Ser Leu Ile Phe Leu<br>      195                 200                 205 | 624 |
| tac gtc cgc caa aaa caa aag gct cag caa aaa gtc aat gaa tta tca<br>Tyr Val Arg Gln Lys Gln Lys Ala Gln Gln Lys Val Asn Glu Leu Ser<br>210                 215                 220 | 672 |
| aat aag ttg acc gaa ctg aaa tgt atg gaa acc gaa ttt gaa gat gtt<br>Asn Lys Leu Thr Glu Leu Lys Cys Met Glu Thr Glu Phe Glu Asp Val<br>225                 230                 235                 240 | 720 |
| cag aaa atg ttg aat gac gag aga agt aaa cga tca att tcc gat gga<br>Gln Lys Met Leu Asn Asp Glu Arg Ser Lys Arg Ser Ile Ser Asp Gly<br>              245                 250                 255 | 768 |
| gtt gtg aat cac aca gaa atg gag aac ctc cgt gtc cag ctg gaa gaa<br>Val Val Asn His Thr Glu Met Glu Asn Leu Arg Val Gln Leu Glu Glu<br>          260                 265                 270 | 816 |
| gcc gaa cga cgg ctt gaa gcg aat tcg aat ggt tct caa gct cct ctt<br>Ala Glu Arg Arg Leu Glu Ala Asn Ser Asn Gly Ser Gln Ala Pro Leu<br>      275                 280                 285 | 864 |
| gca ctt cag cca ttg ctt aga aga act tgc gag aat gag atg gct ttt<br>Ala Leu Gln Pro Leu Leu Arg Arg Thr Cys Glu Asn Glu Met Ala Phe<br>290                 295                 300 | 912 |
| ctg gaa aag cag aga caa gat tgc ttc aag gaa atg aaa gag gcc atc<br>Leu Glu Lys Gln Arg Gln Asp Cys Phe Lys Glu Met Lys Glu Ala Ile<br>305                 310                 315                 320 | 960 |
| gaa atg gtg gat cgt cta cag aaa aag caa gga agt gta ctt tcc tcg<br>Glu Met Val Asp Arg Leu Gln Lys Lys Gln Gly Ser Val Leu Ser Ser<br>              325                 330                 335 | 1008 |
| ttg aaa ttg gca act gga gca gct tcc acg tcg gat caa gtc gat tcg<br>Leu Lys Leu Ala Thr Gly Ala Ala Ser Thr Ser Asp Gln Val Asp Ser<br>          340                 345                 350 | 1056 |
| aag att ttc gcg ttg aaa agt cga atg gaa aaa atc cac aca ttg aca<br>Lys Ile Phe Ala Leu Lys Ser Arg Met Glu Lys Ile His Thr Leu Thr<br>      355                 360                 365 | 1104 |

```
cgt gaa act caa gaa cga tgg ctt caa att gaa tca ctt tgc ggt ttt    1152
Arg Glu Thr Gln Glu Arg Trp Leu Gln Ile Glu Ser Leu Cys Gly Phe
    370                 375                 380 cca ctt cta tat tta aat ggt tcc tcc tct tcc ggc tca att tca aat    1200
Pro Leu Leu Tyr Leu Asn Gly Ser Ser Ser Ser Gly Ser Ile Ser Asn
385                 390                 395                 400 gct cat tca aat ccc aat gca gtt aat tca aat ttt gtg aaa aaa gtg    1248
Ala His Ser Asn Pro Asn Ala Val Asn Ser Asn Phe Val Lys Lys Val
                405                 410                 415 tca ccg cca att cca cct tcc caa caa act gca aat ctt cga ttt gtt    1296
Ser Pro Pro Ile Pro Pro Ser Gln Gln Thr Ala Asn Leu Arg Phe Val
            420                 425                 430 ccc acc gag caa agt gat agt att cat tct gaa gac acg tca cca att    1344
Pro Thr Glu Gln Ser Asp Ser Ile His Ser Glu Asp Thr Ser Pro Ile
        435                 440                 445 gtc gaa gac gtg gca att tcc aga agc tta act caa gac cta gct gaa    1392
Val Glu Asp Val Ala Ile Ser Arg Ser Leu Thr Gln Asp Leu Ala Glu
    450                 455                 460 gct gat atg cag tca ata gta tcc ggt tct aca aat ggc tcg ggc tcc    1440
Ala Asp Met Gln Ser Ile Val Ser Gly Ser Thr Asn Gly Ser Gly Ser
465                 470                 475                 480 gta gct gct ctt aaa aag cga aaa gga att ttc ccg aaa ctt ttc cgc    1488
Val Ala Ala Leu Lys Lys Arg Lys Gly Ile Phe Pro Lys Leu Phe Arg
                485                 490                 495 cga aat aca tcg aaa tct agc agt ctg ggt ggc act tct aat taa       1533
Arg Asn Thr Ser Lys Ser Ser Ser Leu Gly Gly Thr Ser Asn *
            500                 505                 510

<210> SEQ ID NO 66
<211> LENGTH: 510
<212> TYPE: PRT
<213> ORGANISM: Caenorhabditis elegans
<300> PUBLICATION INFORMATION:
<308> DATABASE ACCESSION NUMBER: Genbank AAL32257
<309> DATABASE ENTRY DATE: 2002-05-29

<400> SEQUENCE: 66

Met Gly Arg Val Ser Trp Ile Ile Ala Leu Tyr Leu Thr Ile Asn Val
1               5                   10                  15

Val Ile Val Val Asn Gly Asp Arg Val Thr Arg Asn Val Glu Val Thr
            20                  25                  30

Ala Glu Glu Lys Ile Arg Asp Lys Leu Gly Tyr Glu Ala Ile Arg
        35                  40                  45

Asp Ile His Arg Asp Met Asp Asp His Ser Gly Ser Ile Asp Arg
    50                  55                  60

Asn Glu Ser Thr Gly Phe Met Lys Glu Asp Met Gln Met Arg Gly Ser
65                  70                  75                  80

Glu Arg Thr Arg Arg Glu Asn Lys Phe His Gly Asp Asp Ala Ile
                85                  90                  95

Thr Val Asp Asp Leu Trp Glu Ala Trp Phe Glu Ser Ile Glu Arg Thr
            100                 105                 110

Trp Thr Asn Glu Arg Leu Val Glu Trp Leu Ile Asn Asp Val Asn Leu
        115                 120                 125

Pro Ser Ile Val Glu Ala Val Lys Ala Lys Ile Asp Gly Lys Ile
    130                 135                 140

Leu Pro Arg Phe Ala Ser Pro Asn Ser Asp Phe Leu Asn Lys Glu Leu
145                 150                 155                 160

Gly Ile Lys Ser Ser Val Tyr Arg Gln Lys Leu Arg Leu Asn Ser Leu
```

```
                165                 170                 175
Asp Val Val Leu Phe Gly Tyr Lys Asp Asn Asn Arg Thr Lys Asp
            180                 185                 190
Ile Leu Leu Ala Phe Leu Ala Leu Leu Thr Ser Leu Ile Phe Leu
            195                 200                 205
Tyr Val Arg Gln Lys Gln Lys Ala Gln Gln Lys Val Asn Glu Leu Ser
    210                 215                 220
Asn Lys Leu Thr Glu Leu Lys Cys Met Glu Thr Glu Phe Glu Asp Val
225                 230                 235                 240
Gln Lys Met Leu Asn Asp Glu Arg Ser Lys Arg Ser Ile Ser Asp Gly
                245                 250                 255
Val Val Asn His Thr Glu Met Glu Asn Leu Arg Val Gln Leu Glu Glu
            260                 265                 270
Ala Glu Arg Arg Leu Glu Ala Asn Ser Asn Gly Ser Gln Ala Pro Leu
        275                 280                 285
Ala Leu Gln Pro Leu Leu Arg Arg Thr Cys Glu Asn Glu Met Ala Phe
        290                 295                 300
Leu Glu Lys Gln Arg Gln Asp Cys Phe Lys Glu Met Lys Glu Ala Ile
305                 310                 315                 320
Glu Met Val Asp Arg Leu Gln Lys Lys Gln Gly Ser Val Leu Ser Ser
                325                 330                 335
Leu Lys Leu Ala Thr Gly Ala Ala Ser Thr Ser Asp Gln Val Asp Ser
            340                 345                 350
Lys Ile Phe Ala Leu Lys Ser Arg Met Glu Lys Ile His Thr Leu Thr
        355                 360                 365
Arg Glu Thr Gln Glu Arg Trp Leu Gln Ile Glu Ser Leu Cys Gly Phe
    370                 375                 380
Pro Leu Leu Tyr Leu Asn Gly Ser Ser Ser Gly Ser Ile Ser Asn
385                 390                 395                 400
Ala His Ser Asn Pro Asn Ala Val Asn Ser Asn Phe Val Lys Val
                405                 410                 415
Ser Pro Pro Ile Pro Pro Ser Gln Gln Thr Ala Asn Leu Arg Phe Val
            420                 425                 430
Pro Thr Glu Gln Ser Asp Ser Ile His Ser Glu Asp Thr Ser Pro Ile
        435                 440                 445
Val Glu Asp Val Ala Ile Ser Arg Ser Leu Thr Gln Asp Leu Ala Glu
    450                 455                 460
Ala Asp Met Gln Ser Ile Val Ser Gly Ser Thr Asn Gly Ser Gly Ser
465                 470                 475                 480
Val Ala Ala Leu Lys Lys Arg Lys Gly Ile Phe Pro Lys Leu Phe Arg
            485                 490                 495
Arg Asn Thr Ser Lys Ser Ser Ser Leu Gly Gly Thr Ser Asn
        500                 505                 510

<210> SEQ ID NO 67
<211> LENGTH: 437
<212> TYPE: DNA
<213> ORGANISM: Mus musculus
<300> PUBLICATION INFORMATION:
<308> DATABASE ACCESSION NUMBER: Genbank AF328907
<309> DATABASE ENTRY DATE: 2001-07-31

<400> SEQUENCE: 67
gacaaggacg gcgggatcga agtggacgag agtgatgagt ttatcagaga agatatgaaa     60
tataaagatg ctacgaataa acatagtcac ctgcacagag aagataagca cataactgtt    120
```

```
gaggatttgt ggaaacagtg gaaaacatca gaagttcaca attggacact tgaggatacc    180
ctgcagtggt taatagaatt tgttgaactg ccacaatatg agaagaattt tagggataat    240
aatgtgaagg gaacaacact ccccaggata gcagttcatg aaacttcatt tatgatttcc    300
cagttgaaaa tcagcgaccg aagtcacaga cagaaactcc aactcaaagc cctggatgtg    360
gttctgtttg ggcctctgac acgcccacct cataactgga tgaaggattt tattctcaca    420
atttccatag taattgg                                                  437
```

```
<210> SEQ ID NO 68
<211> LENGTH: 146
<212> TYPE: PRT
<213> ORGANISM: Mus musculus
<300> PUBLICATION INFORMATION:
<308> DATABASE ACCESSION NUMBER: Genbank AAK82339
<309> DATABASE ENTRY DATE: 2001-07-31

<400> SEQUENCE: 68

Asp Lys Asp Gly Gly Ile Glu Val Asp Glu Ser Asp Glu Phe Ile Arg
 1               5                  10                  15

Glu Asp Met Lys Tyr Lys Asp Ala Thr Asn Lys His Ser His Leu His
            20                  25                  30

Arg Glu Asp Lys His Ile Thr Val Glu Asp Leu Trp Lys Gln Trp Lys
        35                  40                  45

Thr Ser Glu Val His Asn Trp Thr Leu Glu Asp Thr Leu Gln Trp Leu
    50                  55                  60

Ile Glu Phe Val Glu Leu Pro Gln Tyr Glu Lys Asn Phe Arg Asp Asn
65                  70                  75                  80

Asn Val Lys Gly Thr Thr Leu Pro Arg Ile Ala Val His Glu Thr Ser
                85                  90                  95

Phe Met Ile Ser Gln Leu Lys Ile Ser Asp Arg Ser His Arg Gln Lys
            100                 105                 110

Leu Gln Leu Lys Ala Leu Asp Val Val Leu Phe Gly Pro Leu Thr Arg
        115                 120                 125

Pro Pro His Asn Trp Met Lys Asp Phe Ile Leu Thr Ile Ser Ile Val
    130                 135                 140

Ile Gly
145
```

```
<210> SEQ ID NO 69
<211> LENGTH: 933
<212> TYPE: DNA
<213> ORGANISM: Homo sapiens
<220> FEATURE:
<221> NAME/KEY: CDS
<222> LOCATION: (1)...(933)
<223> OTHER INFORMATION: Unnamed protein product
<300> PUBLICATION INFORMATION:
<308> DATABASE ACCESSION NUMBER: Genbank AK023369
<309> DATABASE ENTRY DATE: 2002-08-01

<400> SEQUENCE: 69 atg gct ctg aaa aag gcc gaa aaa gaa ttt gaa ctg aga agc agt tgg    48
Met Ala Leu Lys Lys Ala Glu Lys Glu Phe Glu Leu Arg Ser Ser Trp
 1               5                  10                  15 tct gtt cca gat gca ctt cag aaa tgg ctt cag tta aca cat gaa gta    96
Ser Val Pro Asp Ala Leu Gln Lys Trp Leu Gln Leu Thr His Glu Val
            20                  25                  30 gaa gtg caa tac tac aat att aaa aga caa aac gct gaa atg cag cta    144
Glu Val Gln Tyr Tyr Asn Ile Lys Arg Gln Asn Ala Glu Met Gln Leu
```

```
              35                  40                  45
gct att gct aaa gat gag gca gaa aaa att aaa aag aag aga agc aca    192
Ala Ile Ala Lys Asp Glu Ala Glu Lys Ile Lys Lys Lys Arg Ser Thr
     50                  55                  60 gtc ttt ggg act ctg cac gtt gca cac agc tcc tcc cta gat gag gta    240
Val Phe Gly Thr Leu His Val Ala His Ser Ser Ser Leu Asp Glu Val
 65                  70                  75                  80 gac cac aaa att ctg gaa gca aag aaa gct ctc tct gag ttg aca act    288
Asp His Lys Ile Leu Glu Ala Lys Lys Ala Leu Ser Glu Leu Thr Thr
                 85                  90                  95 tgt tta cga gaa cga ctt ttt cgc tgg caa caa att gag aag atc tgt    336
Cys Leu Arg Glu Arg Leu Phe Arg Trp Gln Gln Ile Glu Lys Ile Cys
            100                 105                 110 ggc ttt cag ata gcc cat aac tca gga ctc ccc agc ctg acc tct tcc    384
Gly Phe Gln Ile Ala His Asn Ser Gly Leu Pro Ser Leu Thr Ser Ser
        115                 120                 125 ctt tat tct gat cac agc tgg gtg gtg atg ccc aga gtc tcc att cca    432
Leu Tyr Ser Asp His Ser Trp Val Val Met Pro Arg Val Ser Ile Pro
    130                 135                 140 ccc tat cca att gct gga gga gtt gat gac tta gat gaa gac aca ccc    480
Pro Tyr Pro Ile Ala Gly Gly Val Asp Asp Leu Asp Glu Asp Thr Pro
145                 150                 155                 160 cca ata gtg tca caa ttt ccc ggg acc atg gct aaa cct cct gga tca    528
Pro Ile Val Ser Gln Phe Pro Gly Thr Met Ala Lys Pro Pro Gly Ser
                165                 170                 175 tta gcc aga agc agc agc ctg tgc cgt tca cgc cgc agc att gtg ccg    576
Leu Ala Arg Ser Ser Ser Leu Cys Arg Ser Arg Arg Ser Ile Val Pro
            180                 185                 190 tcc tcg cct cag cct cag cga gct cag ctt gct cca cac gcc ccc cac    624
Ser Ser Pro Gln Pro Gln Arg Ala Gln Leu Ala Pro His Ala Pro His
        195                 200                 205 ccg tca cac cct cgg cac cct cac cac ccg caa cac aca cca cac tcc    672
Pro Ser His Pro Arg His Pro His His Pro Gln His Thr Pro His Ser
    210                 215                 220 ttg cct tcc cct gat cca gat atc ctc tca gtg tca agt tgc cct gcg    720
Leu Pro Ser Pro Asp Pro Asp Ile Leu Ser Val Ser Ser Cys Pro Ala
225                 230                 235                 240 ctt tat cga aat gaa gag gag gaa gag gcc att tac ttc tct gct gaa    768
Leu Tyr Arg Asn Glu Glu Glu Glu Glu Ala Ile Tyr Phe Ser Ala Glu
                245                 250                 255 aag caa tgg aac aca agg gag tgt gca gct gga gac agc cag gga cca    816
Lys Gln Trp Asn Thr Arg Glu Cys Ala Ala Gly Asp Ser Gln Gly Pro
            260                 265                 270 cat gta cac ggc ctg gta cgc ttt gac aag gac ttt gga tct tac tct    864
His Val His Gly Leu Val Arg Phe Asp Lys Asp Phe Gly Ser Tyr Ser
        275                 280                 285 gag tat gag aga aag cac tgg gaa gtt tca agg aag tgc cag aca cag    912
Glu Tyr Glu Arg Lys His Trp Glu Val Ser Arg Lys Cys Gln Thr Gln
    290                 295                 300 ctt cag aat gtg act cct taa                                        933
Leu Gln Asn Val Thr Pro *
305                 310

<210> SEQ ID NO 70
<211> LENGTH: 310
<212> TYPE: PRT
<213> ORGANISM: Homo sapiens
<300> PUBLICATION INFORMATION:
<308> DATABASE ACCESSION NUMBER: Genbank BAB14545
<309> DATABASE ENTRY DATE: 2002-08-01
```

<400> SEQUENCE: 70

```
Met Ala Leu Lys Lys Ala Glu Lys Glu Phe Glu Leu Arg Ser Ser Trp
  1               5                  10                  15

Ser Val Pro Asp Ala Leu Gln Lys Trp Leu Gln Leu Thr His Glu Val
             20                  25                  30

Glu Val Gln Tyr Tyr Asn Ile Lys Arg Gln Asn Ala Glu Met Gln Leu
         35                  40                  45

Ala Ile Ala Lys Asp Glu Ala Glu Lys Ile Lys Lys Arg Ser Thr
     50                  55                  60

Val Phe Gly Thr Leu His Val Ala His Ser Ser Leu Asp Glu Val
 65                  70                  75                  80

Asp His Lys Ile Leu Glu Ala Lys Lys Ala Leu Ser Glu Leu Thr Thr
                 85                  90                  95

Cys Leu Arg Glu Arg Leu Phe Arg Trp Gln Gln Ile Glu Lys Ile Cys
            100                 105                 110

Gly Phe Gln Ile Ala His Asn Ser Gly Leu Pro Ser Leu Thr Ser Ser
            115                 120                 125

Leu Tyr Ser Asp His Ser Trp Val Val Met Pro Arg Val Ser Ile Pro
    130                 135                 140

Pro Tyr Pro Ile Ala Gly Gly Val Asp Asp Leu Asp Glu Asp Thr Pro
145                 150                 155                 160

Pro Ile Val Ser Gln Phe Pro Gly Thr Met Ala Lys Pro Pro Gly Ser
                165                 170                 175

Leu Ala Arg Ser Ser Ser Leu Cys Arg Ser Arg Arg Ser Ile Val Pro
            180                 185                 190

Ser Ser Pro Gln Pro Gln Arg Ala Gln Leu Ala Pro His Ala Pro His
        195                 200                 205

Pro Ser His Pro Arg His Pro His Pro Gln His Thr Pro His Ser
    210                 215                 220

Leu Pro Ser Pro Asp Pro Asp Ile Leu Ser Val Ser Ser Cys Pro Ala
225                 230                 235                 240

Leu Tyr Arg Asn Glu Glu Glu Glu Ala Ile Tyr Phe Ser Ala Glu
                245                 250                 255

Lys Gln Trp Asn Thr Arg Glu Cys Ala Ala Gly Asp Ser Gln Gly Pro
            260                 265                 270

His Val His Gly Leu Val Arg Phe Asp Lys Asp Phe Gly Ser Tyr Ser
        275                 280                 285

Glu Tyr Glu Arg Lys His Trp Glu Val Ser Arg Lys Cys Gln Thr Gln
    290                 295                 300

Leu Gln Asn Val Thr Pro
305                 310
```

<210> SEQ ID NO 71
<211> LENGTH: 1899
<212> TYPE: DNA
<213> ORGANISM: Rattus norvegicus
<220> FEATURE:
<221> NAME/KEY: CDS
<222> LOCATION: (1)...(1899)
<223> OTHER INFORMATION: Similar to STIM 2 precursor

<400> SEQUENCE: 71

```
atg aac ttg gct gta gtt cac aat tgg acg ctt gag gat acc ctg cag      48
Met Asn Leu Ala Val Val His Asn Trp Thr Leu Glu Asp Thr Leu Gln
  1               5                  10                  15 tgg ttg ata gaa ttt gtt gaa ctc cca caa tac gag aag aat ttt agg      96
```

```
                                                           -continued

Trp Leu Ile Glu Phe Val Glu Leu Pro Gln Tyr Glu Lys Asn Phe Arg
            20                  25                  30 gat aat aat gtg aaa gga aca aca ctt ccc agg ata gca gtt cat gaa     144
Asp Asn Asn Val Lys Gly Thr Thr Leu Pro Arg Ile Ala Val His Glu
            35                  40                  45 act tca ttt atg att tcc cag ttg aaa atc agt gac cgg agt cac aga     192
Thr Ser Phe Met Ile Ser Gln Leu Lys Ile Ser Asp Arg Ser His Arg
 50                  55                  60 cag aaa ctt caa ctc aaa gca ctg gat gtg gtt ttg ttt ggg cct ctg     240
Gln Lys Leu Gln Leu Lys Ala Leu Asp Val Val Leu Phe Gly Pro Leu
 65                  70                  75                  80 aca cgc cca cct cat aat tgg atg aag gat ttt att ctc aca att tcc     288
Thr Arg Pro Pro His Asn Trp Met Lys Asp Phe Ile Leu Thr Ile Ser
                 85                  90                  95 ata gta att ggc gtt gga ggt tgt tgg ttt gct tat aca caa aat aag     336
Ile Val Ile Gly Val Gly Gly Cys Trp Phe Ala Tyr Thr Gln Asn Lys
                100                 105                 110 aca tca aag gaa cat gtt gca aag atg atg aaa gac tta gaa agc cta     384
Thr Ser Lys Glu His Val Ala Lys Met Met Lys Asp Leu Glu Ser Leu
            115                 120                 125 caa acc gca gag cag agc ctc atg gac tta cag gag aga ctt gaa aag     432
Gln Thr Ala Glu Gln Ser Leu Met Asp Leu Gln Glu Arg Leu Glu Lys
130                 135                 140 gca cag gaa gaa aac aga act gtt gct gtc gaa aag caa aat ctg gaa     480
Ala Gln Glu Glu Asn Arg Thr Val Ala Val Glu Lys Gln Asn Leu Glu
145                 150                 155                 160 cga aag atg atg gat gaa atc aac tac gcc aag gag gag gcc tgc cgg     528
Arg Lys Met Met Asp Glu Ile Asn Tyr Ala Lys Glu Glu Ala Cys Arg
                165                 170                 175 ctg cgg gag ctg agg gag ggc gca gag tgt gag ctg agc agg cgc cag     576
Leu Arg Glu Leu Arg Glu Gly Ala Glu Cys Glu Leu Ser Arg Arg Gln
            180                 185                 190 tat gcg gag cag gag ctg gag cag gtc cgc atg gct cta aaa aag gct     624
Tyr Ala Glu Gln Glu Leu Glu Gln Val Arg Met Ala Leu Lys Lys Ala
        195                 200                 205 gaa aag gag ttt gaa ctg aga agc agc tgg tct gtc cct gat gca ctg     672
Glu Lys Glu Phe Glu Leu Arg Ser Ser Trp Ser Val Pro Asp Ala Leu
210                 215                 220 cag aaa tgg ctt cag cta aca cac gag gtt gaa gta cag tac tat aat     720
Gln Lys Trp Leu Gln Leu Thr His Glu Val Glu Val Gln Tyr Tyr Asn
225                 230                 235                 240 att aag agg cag aat gcc gag atg cag cta gcc atc gct aag gac gag     768
Ile Lys Arg Gln Asn Ala Glu Met Gln Leu Ala Ile Ala Lys Asp Glu
                245                 250                 255 gca gaa aaa att aaa aag aaa aga agc aca gtc ttt ggg acc ctg cat     816
Ala Glu Lys Ile Lys Lys Lys Arg Ser Thr Val Phe Gly Thr Leu His
            260                 265                 270 gtt gca cac agc tcc tcc ctg gat gaa gta gac cac aag att ctg gaa     864
Val Ala His Ser Ser Ser Leu Asp Glu Val Asp His Lys Ile Leu Glu
        275                 280                 285 gcc aag aaa gca ctc tct gag ctg acg aca tgt ttg cga gaa cgg ctt     912
Ala Lys Lys Ala Leu Ser Glu Leu Thr Thr Cys Leu Arg Glu Arg Leu
    290                 295                 300 ttt cgc tgg cag cag att gag aag atc tgt ggc ttt cag ata gct cac     960
Phe Arg Trp Gln Gln Ile Glu Lys Ile Cys Gly Phe Gln Ile Ala His
305                 310                 315                 320 aac tct ggc ctc ccc agt ctc acc tcc tct ctg tac tct gac cac agc    1008
Asn Ser Gly Leu Pro Ser Leu Thr Ser Ser Leu Tyr Ser Asp His Ser
                325                 330                 335
```

```
tgg gtg gtg atg cct aga gtc tcc att cca cct tac cct att gcg gga    1056
Trp Val Val Met Pro Arg Val Ser Ile Pro Pro Tyr Pro Ile Ala Gly
        340                 345                 350 gga gtc gat gac ctg gat gaa gat aca ccc cca ata gtg tca cag ttt    1104
Gly Val Asp Asp Leu Asp Glu Asp Thr Pro Pro Ile Val Ser Gln Phe
    355                 360                 365 cca gtg gag gag gaa gag gca gtg act ctt cag ggg gag gaa gga gca    1152
Pro Val Glu Glu Glu Glu Ala Val Thr Leu Gln Gly Glu Glu Gly Ala
370                 375                 380 gct tgg acc gtg gct aag cct gct ggg tct tta gcc aga agc agt agt    1200
Ala Trp Thr Val Ala Lys Pro Ala Gly Ser Leu Ala Arg Ser Ser Ser
385                 390                 395                 400 tta tgc cgc tct cgt cga agc att gtg cca tcc tcc cca cag tct cag    1248
Leu Cys Arg Ser Arg Arg Ser Ile Val Pro Ser Ser Pro Gln Ser Gln
                405                 410                 415 cga gct cag ctt cct gca cat gct cct ctg gca gcc cac cct cgg cac    1296
Arg Ala Gln Leu Pro Ala His Ala Pro Leu Ala Ala His Pro Arg His
            420                 425                 430 cct cac cat ccc cag cac tca tta cct tcc cca gat cca gac att ctc    1344
Pro His His Pro Gln His Ser Leu Pro Ser Pro Asp Pro Asp Ile Leu
        435                 440                 445 tct gtg tca agt tgc cct gct ctg tat cgg aac gaa gaa gag gag gag    1392
Ser Val Ser Ser Cys Pro Ala Leu Tyr Arg Asn Glu Glu Glu Glu Glu
    450                 455                 460 gct atc tac ttc act gct gag aaa caa tgg gag gta cca gac aca gct    1440
Ala Ile Tyr Phe Thr Ala Glu Lys Gln Trp Glu Val Pro Asp Thr Ala
465                 470                 475                 480 tca gaa tgt gac tcc tta aac tct tcc att ggg aga aaa cag tct cct    1488
Ser Glu Cys Asp Ser Leu Asn Ser Ser Ile Gly Arg Lys Gln Ser Pro
                485                 490                 495 cct tca agc ctt gag ata tac caa aca ttg tct tct cga aaa ata tca    1536
Pro Ser Ser Leu Glu Ile Tyr Gln Thr Leu Ser Ser Arg Lys Ile Ser
            500                 505                 510 aga gac gag ctt tcc ctg gag gac tct tcc agg ggg gac tca ccc gtg    1584
Arg Asp Glu Leu Ser Leu Glu Asp Ser Ser Arg Gly Asp Ser Pro Val
        515                 520                 525 aca gca gat gtc tcc cgg ggc tcc cct gag tgt gtg ggc ctg acg gaa    1632
Thr Ala Asp Val Ser Arg Gly Ser Pro Glu Cys Val Gly Leu Thr Glu
    530                 535                 540 acc aag agc atg atc ttc agc cct gcg agc aga gtg tac aac ggc atc    1680
Thr Lys Ser Met Ile Phe Ser Pro Ala Ser Arg Val Tyr Asn Gly Ile
545                 550                 555                 560 ctg gag aag tcc tgc agc atg cac cag ctc tct agt ggc atc ccg gtg    1728
Leu Glu Lys Ser Cys Ser Met His Gln Leu Ser Ser Gly Ile Pro Val
                565                 570                 575 cct aat cct cga cac acg tcc tgc tcc ttg gct ggc agt gac agc aag    1776
Pro Asn Pro Arg His Thr Ser Cys Ser Leu Ala Gly Ser Asp Ser Lys
            580                 585                 590 cca gtt cag gaa gcc tcc agc gtt tcc aga gta ggc agc atc ccg cac    1824
Pro Val Gln Glu Ala Ser Ser Val Ser Arg Val Gly Ser Ile Pro His
        595                 600                 605 gac ctt tgt cat aat ggt gag aaa agc aaa aag cca tca aaa atc aaa    1872
Asp Leu Cys His Asn Gly Glu Lys Ser Lys Lys Pro Ser Lys Ile Lys
    610                 615                 620 agc ctt ttc aag aag aag tcc aag tga                                1899
Ser Leu Phe Lys Lys Lys Ser Lys *
625                 630

<210> SEQ ID NO 72
<211> LENGTH: 632
```

```
<212> TYPE: PRT
<213> ORGANISM: Rattus norvegicus

<400> SEQUENCE: 72

Met Asn Leu Ala Val Val His Asn Trp Thr Leu Glu Asp Thr Leu Gln
 1               5                  10                  15

Trp Leu Ile Glu Phe Val Glu Leu Pro Gln Tyr Glu Lys Asn Phe Arg
             20                  25                  30

Asp Asn Val Lys Gly Thr Thr Leu Pro Arg Ile Ala Val His Glu
         35                  40                  45

Thr Ser Phe Met Ile Ser Gln Leu Lys Ile Ser Asp Arg Ser His Arg
     50                  55                  60

Gln Lys Leu Gln Leu Lys Ala Leu Asp Val Val Leu Phe Gly Pro Leu
65                  70                  75                  80

Thr Arg Pro Pro His Asn Trp Met Lys Asp Phe Ile Leu Thr Ile Ser
                 85                  90                  95

Ile Val Ile Gly Val Gly Gly Cys Trp Phe Ala Tyr Thr Gln Asn Lys
            100                 105                 110

Thr Ser Lys Glu His Val Ala Lys Met Met Lys Asp Leu Glu Ser Leu
        115                 120                 125

Gln Thr Ala Glu Gln Ser Leu Met Asp Leu Gln Glu Arg Leu Glu Lys
    130                 135                 140

Ala Gln Glu Glu Asn Arg Thr Val Ala Val Glu Lys Gln Asn Leu Glu
145                 150                 155                 160

Arg Lys Met Met Asp Glu Ile Asn Tyr Ala Lys Glu Glu Ala Cys Arg
                165                 170                 175

Leu Arg Glu Leu Arg Glu Gly Ala Glu Cys Glu Leu Ser Arg Arg Gln
            180                 185                 190

Tyr Ala Glu Gln Glu Leu Glu Gln Val Arg Met Ala Leu Lys Lys Ala
        195                 200                 205

Glu Lys Glu Phe Glu Leu Arg Ser Ser Trp Ser Val Pro Asp Ala Leu
    210                 215                 220

Gln Lys Trp Leu Gln Leu Thr His Glu Val Glu Val Gln Tyr Tyr Asn
225                 230                 235                 240

Ile Lys Arg Gln Asn Ala Glu Met Gln Leu Ala Ile Ala Lys Asp Glu
                245                 250                 255

Ala Glu Lys Ile Lys Lys Arg Ser Thr Val Phe Gly Thr Leu His
            260                 265                 270

Val Ala His Ser Ser Ser Leu Asp Glu Val Asp His Lys Ile Leu Glu
        275                 280                 285

Ala Lys Lys Ala Leu Ser Glu Leu Thr Thr Cys Leu Arg Glu Arg Leu
    290                 295                 300

Phe Arg Trp Gln Gln Ile Glu Lys Ile Cys Gly Phe Gln Ile Ala His
305                 310                 315                 320

Asn Ser Gly Leu Pro Ser Leu Thr Ser Ser Leu Tyr Ser Asp His Ser
                325                 330                 335

Trp Val Val Met Pro Arg Val Ser Ile Pro Pro Tyr Pro Ile Ala Gly
            340                 345                 350

Gly Val Asp Asp Leu Asp Glu Asp Thr Pro Pro Ile Val Ser Gln Phe
        355                 360                 365

Pro Val Glu Glu Glu Glu Ala Val Thr Leu Gln Gly Glu Glu Gly Ala
    370                 375                 380

Ala Trp Thr Val Ala Lys Pro Ala Gly Ser Leu Ala Arg Ser Ser Ser
385                 390                 395                 400
```

```
Leu Cys Arg Ser Arg Arg Ser Ile Val Pro Ser Ser Gln Ser Gln
            405                 410                 415

Arg Ala Gln Leu Pro Ala His Ala Pro Leu Ala Ala His Pro Arg His
        420                 425                 430

Pro His His Pro Gln His Ser Leu Pro Ser Pro Asp Pro Asp Ile Leu
    435                 440                 445

Ser Val Ser Ser Cys Pro Ala Leu Tyr Arg Asn Glu Glu Glu Glu
    450                 455                 460

Ala Ile Tyr Phe Thr Ala Glu Lys Gln Trp Glu Val Pro Asp Thr Ala
465                 470                 475                 480

Ser Glu Cys Asp Ser Leu Asn Ser Ser Ile Gly Arg Lys Gln Ser Pro
                485                 490                 495

Pro Ser Ser Leu Glu Ile Tyr Gln Thr Leu Ser Ser Arg Lys Ile Ser
            500                 505                 510

Arg Asp Glu Leu Ser Leu Glu Asp Ser Ser Arg Gly Asp Ser Pro Val
        515                 520                 525

Thr Ala Asp Val Ser Arg Gly Ser Pro Glu Cys Val Gly Leu Thr Glu
    530                 535                 540

Thr Lys Ser Met Ile Phe Ser Pro Ala Ser Arg Val Tyr Asn Gly Ile
545                 550                 555                 560

Leu Glu Lys Ser Cys Ser Met His Gln Leu Ser Ser Gly Ile Pro Val
                565                 570                 575

Pro Asn Pro Arg His Thr Ser Cys Ser Leu Ala Gly Ser Asp Ser Lys
            580                 585                 590

Pro Val Gln Glu Ala Ser Ser Val Ser Arg Val Gly Ser Ile Pro His
        595                 600                 605

Asp Leu Cys His Asn Gly Glu Lys Ser Lys Lys Pro Ser Lys Ile Lys
    610                 615                 620

Ser Leu Phe Lys Lys Lys Ser Lys
625                 630

<210> SEQ ID NO 73
<211> LENGTH: 1533
<212> TYPE: DNA
<213> ORGANISM: Caenorhabditis elegans
<220> FEATURE:
<221> NAME/KEY: CDS
<222> LOCATION: (1)...(1533)
<223> OTHER INFORMATION: Putative membrane protein
<300> PUBLICATION INFORMATION:
<308> DATABASE ACCESSION NUMBER: Genbank NM_171065
<309> DATABASE ENTRY DATE: 2002-11-22

<400> SEQUENCE: 73 atg ggt aga gtt tcg tgg att att gcc tta tat ctt aca atc aac gtg     48
Met Gly Arg Val Ser Trp Ile Ile Ala Leu Tyr Leu Thr Ile Asn Val
 1               5                  10                  15 gtt att gtt gtt aat gga gat cgg gtg act aga aat gtt gaa gta acg     96
Val Ile Val Val Asn Gly Asp Arg Val Thr Arg Asn Val Glu Val Thr
             20                  25                  30 gcg gaa gaa gaa aaa ata cgg gat aaa ttg gga tat gaa gcg att aga    144
Ala Glu Glu Glu Lys Ile Arg Asp Lys Leu Gly Tyr Glu Ala Ile Arg
         35                  40                  45 gat att cat cga gac atg gac gat cat tcg ggt tca atc gat cga        192
Asp Ile His Arg Asp Met Asp Asp His Ser Gly Ser Ile Asp Arg
     50                  55                  60 aat gaa tcg act ggg ttt atg aaa gaa gat atg caa atg cgt gga tcc    240
Asn Glu Ser Thr Gly Phe Met Lys Glu Asp Met Gln Met Arg Gly Ser
```

-continued

```
                65                  70                  75                  80 gaa cga act aga cgg gag aat aag ttc cat ggc gac gac gat gcg att   288
Glu Arg Thr Arg Arg Glu Asn Lys Phe His Gly Asp Asp Asp Ala Ile
                    85                  90                  95 act gta gac gat ctg tgg gag gcc tgg ttt gag agt atc gag aga act   336
Thr Val Asp Asp Leu Trp Glu Ala Trp Phe Glu Ser Ile Glu Arg Thr
                100                 105                 110 tgg acg aat gaa agg ctc gtc gaa tgg ctc atc aac gac gta aac ctt   384
Trp Thr Asn Glu Arg Leu Val Glu Trp Leu Ile Asn Asp Val Asn Leu
            115                 120                 125 ccc agc att gtt gaa gca gta aaa gcc aag aaa att gat ggg aag att   432
Pro Ser Ile Val Glu Ala Val Lys Ala Lys Lys Ile Asp Gly Lys Ile
        130                 135                 140 ctt cca aga ttt gca tct cca aat tcg gac ttt ttg aac aaa gaa ctt   480
Leu Pro Arg Phe Ala Ser Pro Asn Ser Asp Phe Leu Asn Lys Glu Leu
145                 150                 155                 160 ggc ata aaa tcg tcg gtt tat cgt caa aaa ctt cgt ttg aac tcg ttg   528
Gly Ile Lys Ser Ser Val Tyr Arg Gln Lys Leu Arg Leu Asn Ser Leu
                165                 170                 175 gat gtt gta ctt ttt ggg tat aag gat aat aat aat cga aca aag gat   576
Asp Val Val Leu Phe Gly Tyr Lys Asp Asn Asn Asn Arg Thr Lys Asp
                180                 185                 190 att cta ttg gcg ttt ttg gca ctt ctc cta aca tca ctc atc ttt tta   624
Ile Leu Leu Ala Phe Leu Ala Leu Leu Leu Thr Ser Leu Ile Phe Leu
            195                 200                 205 tac gtc cgc caa aaa caa aag gct cag caa aaa gtc aat gaa tta tca   672
Tyr Val Arg Gln Lys Gln Lys Ala Gln Gln Lys Val Asn Glu Leu Ser
        210                 215                 220 aat aag ttg acc gaa ctg aaa tgt atg gaa acc gaa ttt gaa gat gtt   720
Asn Lys Leu Thr Glu Leu Lys Cys Met Glu Thr Glu Phe Glu Asp Val
225                 230                 235                 240 cag aaa atg ttg aat gac gag aga agt aaa cga tca att tcc gat gga   768
Gln Lys Met Leu Asn Asp Glu Arg Ser Lys Arg Ser Ile Ser Asp Gly
                245                 250                 255 gtt gtg aat cac aca gaa atg gag aac ctc cgt gtc cag ctg gaa gaa   816
Val Val Asn His Thr Glu Met Glu Asn Leu Arg Val Gln Leu Glu Glu
                260                 265                 270 gcc gaa cga cgg ctt gaa gcg aat tcg aat ggt tct caa gct cct ctt   864
Ala Glu Arg Arg Leu Glu Ala Asn Ser Asn Gly Ser Gln Ala Pro Leu
            275                 280                 285 gca ctt cag cca ttg ctt aga aga act tgc gag aat gag atg gct ttt   912
Ala Leu Gln Pro Leu Leu Arg Arg Thr Cys Glu Asn Glu Met Ala Phe
        290                 295                 300 ctg gaa aag cag aga caa gat tgc ttc aag gaa atg aaa gag gcc atc   960
Leu Glu Lys Gln Arg Gln Asp Cys Phe Lys Glu Met Lys Glu Ala Ile
305                 310                 315                 320 gaa atg gtg gat cgt cta cag aaa aag caa gga agt gta ctt tcc tcg   1008
Glu Met Val Asp Arg Leu Gln Lys Lys Gln Gly Ser Val Leu Ser Ser
                325                 330                 335 ttg aaa ttg gca act gga gca gct tcc acg tcg gat caa gtc gat tcg   1056
Leu Lys Leu Ala Thr Gly Ala Ala Ser Thr Ser Asp Gln Val Asp Ser
                340                 345                 350 aag att ttc gcg ttg aaa agt cga atg gaa aaa atc cac aca ttg aca   1104
Lys Ile Phe Ala Leu Lys Ser Arg Met Glu Lys Ile His Thr Leu Thr
            355                 360                 365 cgt gaa act caa gaa cga tgg ctt caa att gaa tca ctt tgc ggt ttt   1152
Arg Glu Thr Gln Glu Arg Trp Leu Gln Ile Glu Ser Leu Cys Gly Phe
        370                 375                 380 cca ctt cta tat tta aat ggt tcc tcc tct tcc ggc tca att tca aat   1200
```

```
Pro Leu Leu Tyr Leu Asn Gly Ser Ser Ser Gly Ser Ile Ser Asn
385                 390                 395                 400 gct cat tca aat ccc aat gca gtt aat tca aat ttt gtg aaa aaa gtg    1248
Ala His Ser Asn Pro Asn Ala Val Asn Ser Asn Phe Val Lys Lys Val
                    405                 410                 415 tca ccg cca att cca cct tcc caa caa act gca aat ctt cga ttt gtt    1296
Ser Pro Pro Ile Pro Pro Ser Gln Gln Thr Ala Asn Leu Arg Phe Val
                420                 425                 430 ccc acc gag caa agt gat agt att cat tct gaa gac acg tca cca att    1344
Pro Thr Glu Gln Ser Asp Ser Ile His Ser Glu Asp Thr Ser Pro Ile
            435                 440                 445 gtc gaa gac gtg gca att tcc aga agc tta act caa gac cta gct gaa    1392
Val Glu Asp Val Ala Ile Ser Arg Ser Leu Thr Gln Asp Leu Ala Glu
        450                 455                 460 gct gat atg cag tca ata gta tcc ggt tct aca aat ggc tcg ggc tcc    1440
Ala Asp Met Gln Ser Ile Val Ser Gly Ser Thr Asn Gly Ser Gly Ser
465                 470                 475                 480 gta gct gct ctt aaa aag cga aaa gga att ttc ccg aaa ctt ttc cgc    1488
Val Ala Ala Leu Lys Lys Arg Lys Gly Ile Phe Pro Lys Leu Phe Arg
                485                 490                 495 cga aat aca tcg aaa tct agc agt ctg ggt ggc act tct aat taa        1533
Arg Asn Thr Ser Lys Ser Ser Ser Leu Gly Gly Thr Ser Asn *
            500                 505                 510
```

<210> SEQ ID NO 74
<211> LENGTH: 510
<212> TYPE: PRT
<213> ORGANISM: Caenorhabditis elegans
<300> PUBLICATION INFORMATION:
<308> DATABASE ACCESSION NUMBER: Genbank NP_741073
<309> DATABASE ENTRY DATE: 2002-11-22

<400> SEQUENCE: 74

```
Met Gly Arg Val Ser Trp Ile Ile Ala Leu Tyr Leu Thr Ile Asn Val
1               5                   10                  15

Val Ile Val Val Asn Gly Asp Arg Val Thr Arg Asn Val Glu Val Thr
                20                  25                  30

Ala Glu Glu Lys Ile Arg Asp Lys Leu Gly Tyr Glu Ala Ile Arg
            35                  40                  45

Asp Ile His Arg Asp Met Asp Asp His Ser Gly Ser Ile Asp Arg
        50                  55                  60

Asn Glu Ser Thr Gly Phe Met Lys Glu Asp Met Gln Met Arg Gly Ser
65                  70                  75                  80

Glu Arg Thr Arg Arg Glu Asn Lys Phe His Gly Asp Asp Ala Ile
                85                  90                  95

Thr Val Asp Asp Leu Trp Glu Ala Trp Phe Glu Ser Ile Glu Arg Thr
            100                 105                 110

Trp Thr Asn Glu Arg Leu Val Glu Trp Leu Ile Asn Asp Val Asn Leu
        115                 120                 125

Pro Ser Ile Val Glu Ala Val Lys Ala Lys Lys Ile Asp Gly Lys Ile
130                 135                 140

Leu Pro Arg Phe Ala Ser Pro Asn Ser Asp Phe Leu Asn Lys Glu Leu
145                 150                 155                 160

Gly Ile Lys Ser Ser Val Tyr Arg Gln Lys Leu Arg Leu Asn Ser Leu
                165                 170                 175

Asp Val Val Leu Phe Gly Tyr Lys Asp Asn Asn Asn Arg Thr Lys Asp
            180                 185                 190

Ile Leu Leu Ala Phe Leu Ala Leu Leu Leu Thr Ser Leu Ile Phe Leu
```

-continued

```
                 195                 200                 205
Tyr Val Arg Gln Lys Gln Lys Ala Gln Gln Lys Val Asn Glu Leu Ser
    210                 215                 220

Asn Lys Leu Thr Glu Leu Lys Cys Met Glu Thr Glu Phe Glu Asp Val
225                 230                 235                 240

Gln Lys Met Leu Asn Asp Glu Arg Ser Lys Arg Ser Ile Ser Asp Gly
                245                 250                 255

Val Val Asn His Thr Glu Met Glu Asn Leu Arg Val Gln Leu Glu Glu
            260                 265                 270

Ala Glu Arg Arg Leu Glu Ala Asn Ser Asn Gly Ser Gln Ala Pro Leu
        275                 280                 285

Ala Leu Gln Pro Leu Leu Arg Arg Thr Cys Glu Asn Glu Met Ala Phe
    290                 295                 300

Leu Glu Lys Gln Arg Gln Asp Cys Phe Lys Glu Met Lys Glu Ala Ile
305                 310                 315                 320

Glu Met Val Asp Arg Leu Gln Lys Lys Gln Gly Ser Val Leu Ser Ser
                325                 330                 335

Leu Lys Leu Ala Thr Gly Ala Ala Ser Thr Ser Asp Gln Val Asp Ser
            340                 345                 350

Lys Ile Phe Ala Leu Lys Ser Arg Met Glu Lys Ile His Thr Leu Thr
        355                 360                 365

Arg Glu Thr Gln Glu Arg Trp Leu Gln Ile Glu Ser Leu Cys Gly Phe
    370                 375                 380

Pro Leu Leu Tyr Leu Asn Gly Ser Ser Ser Gly Ser Ile Ser Asn
385                 390                 395                 400

Ala His Ser Asn Pro Asn Ala Val Asn Ser Asn Phe Val Lys Lys Val
                405                 410                 415

Ser Pro Pro Ile Pro Pro Ser Gln Gln Thr Ala Asn Leu Arg Phe Val
            420                 425                 430

Pro Thr Glu Gln Ser Asp Ser Ile His Ser Glu Asp Thr Ser Pro Ile
        435                 440                 445

Val Glu Asp Val Ala Ile Ser Arg Ser Leu Thr Gln Asp Leu Ala Glu
    450                 455                 460

Ala Asp Met Gln Ser Ile Val Ser Gly Ser Thr Asn Gly Ser Gly Ser
465                 470                 475                 480

Val Ala Ala Leu Lys Lys Arg Lys Gly Ile Phe Pro Lys Leu Phe Arg
                485                 490                 495

Arg Asn Thr Ser Lys Ser Ser Ser Leu Gly Gly Thr Ser Asn
            500                 505                 510
```

<210> SEQ ID NO 75
<211> LENGTH: 1713
<212> TYPE: DNA
<213> ORGANISM: Drosophila melanogaster
<220> FEATURE:
<221> NAME/KEY: CDS
<222> LOCATION: (1)...(1713)
<223> OTHER INFORMATION: DSTIM
<300> PUBLICATION INFORMATION:
<308> DATABASE ACCESSION NUMBER: Genbank NM_078633
<309> DATABASE ENTRY DATE: 2002-12-04

<400> SEQUENCE: 75

```
atg cga aag aat acc att tgg aac tac tct tta ata ttc ttc tgc tgt      48
Met Arg Lys Asn Thr Ile Trp Asn Tyr Ser Leu Ile Phe Phe Cys Cys
1               5                   10                  15 gtg ctg aag agc ata agt acg cta gat cat ggc ccg cac aca gta tca      96
```

```
                Val Leu Lys Ser Ile Ser Thr Leu Asp His Gly Pro His Thr Val Ser
                             20                  25                  30 gtc gat tcg aat cga cac aac aca cag cat cag tat aag caa aat ccc         144
Val Asp Ser Asn Arg His Asn Thr Gln His Gln Tyr Lys Gln Asn Pro
         35                  40                  45 aat gtt gcc tca caa cgt cac tca tcc cac gaa tct ggt cag agt tta         192
Asn Val Ala Ser Gln Arg His Ser Ser His Glu Ser Gly Gln Ser Leu
 50                  55                  60 cac aat tcg caa tcg gaa cat gtc acc cat att gcc gca tcg cac gcc         240
His Asn Ser Gln Ser Glu His Val Thr His Ile Ala Ala Ser His Ala
 65                  70                  75                  80 gga agc ggc gga gag cac tcc act cat ttg gcg caa aat ctg cac agg         288
Gly Ser Gly Gly Glu His Ser Thr His Leu Ala Gln Asn Leu His Arg
             85                  90                  95 agc tca tat aat ctt ctg agc gag gcc atg tcc cag gct gtc agc aat         336
Ser Ser Tyr Asn Leu Leu Ser Glu Ala Met Ser Gln Ala Val Ser Asn
            100                 105                 110 gaa ttt agt tcc atg gga agt ggt tca gcg gat gga gcg tgt gct gct         384
Glu Phe Ser Ser Met Gly Ser Gly Ser Ala Asp Gly Ala Cys Ala Ala
        115                 120                 125 gat gat ttt gat tgc tac agt gga agt gtt cag gat cgc ttt ggc atg         432
Asp Asp Phe Asp Cys Tyr Ser Gly Ser Val Gln Asp Arg Phe Gly Met
130                 135                 140 gag gct att gcc agc ttg cat cgt cag cta gat gat gac gat aat gga         480
Glu Ala Ile Ala Ser Leu His Arg Gln Leu Asp Asp Asp Asp Asn Gly
145                 150                 155                 160 aac atc gat ctg agc gag tcc gat gac ttt ttg cgg gag gaa ttg aag         528
Asn Ile Asp Leu Ser Glu Ser Asp Asp Phe Leu Arg Glu Glu Leu Lys
                165                 170                 175 tac gac tcg ggc tac gaa aag cgg cag aaa gcg ttt cac ttc aat gac         576
Tyr Asp Ser Gly Tyr Glu Lys Arg Gln Lys Ala Phe His Phe Asn Asp
            180                 185                 190 gat atg cat ata tcg gtc aaa gaa ctt tgg gag gcc tgg ctc aga tcg         624
Asp Met His Ile Ser Val Lys Glu Leu Trp Glu Ala Trp Leu Arg Ser
        195                 200                 205 gag gtg cat aat tgg acc atc gag cag acc acc gat tgg ctg gct cag         672
Glu Val His Asn Trp Thr Ile Glu Gln Thr Thr Asp Trp Leu Ala Gln
210                 215                 220 tcc gtt cag ctg ccg caa tac gtt gat ctg ttc aaa tta cac aag gtt         720
Ser Val Gln Leu Pro Gln Tyr Val Asp Leu Phe Lys Leu His Lys Val
225                 230                 235                 240 act ggc gct gcc ttg cca aga ttg gct gtg aat aat ctt cag tat gtt         768
Thr Gly Ala Ala Leu Pro Arg Leu Ala Val Asn Asn Leu Gln Tyr Val
                245                 250                 255 ggc aat gta ctt ggc atc aaa gac cct ata cac aaa caa aaa atc tca         816
Gly Asn Val Leu Gly Ile Lys Asp Pro Ile His Lys Gln Lys Ile Ser
            260                 265                 270 ttg aag gca atg gat gtg gtt ctg ttt ggg cca ccg cga gaa act ggt         864
Leu Lys Ala Met Asp Val Val Leu Phe Gly Pro Pro Arg Glu Thr Gly
        275                 280                 285 acc cgc tgg aaa gac tac ata ttg gta aca ctg ttg ctt agt gct att         912
Thr Arg Trp Lys Asp Tyr Ile Leu Val Thr Leu Leu Leu Ser Ala Ile
290                 295                 300 att ggt tgt tgg tac gcc tat cag caa aat aag aat gcc aaa cgg cat         960
Ile Gly Cys Trp Tyr Ala Tyr Gln Gln Asn Lys Asn Ala Lys Arg His
305                 310                 315                 320 ctg cgt cga atg gcc cag gat atg gag gga ttg cag agg gct gag caa        1008
Leu Arg Arg Met Ala Gln Asp Met Glu Gly Leu Gln Arg Ala Glu Gln
                325                 330                 335
```

```
agt cta cag gag atg cag aag gaa cta gaa cgg gcc aga atg gag cag    1056
Ser Leu Gln Glu Met Gln Lys Glu Leu Glu Arg Ala Arg Met Glu Gln
        340                 345                 350 gaa aat gtg gca aca gaa aaa cta gat ttg gag cgt cgt cta aaa gaa    1104
Glu Asn Val Ala Thr Glu Lys Leu Asp Leu Glu Arg Arg Leu Lys Glu
355                 360                 365 gcg ccc act ctc agt tca tcg aac tcg gat ttg gaa gtt cag cag ctg    1152
Ala Pro Thr Leu Ser Ser Ser Asn Ser Asp Leu Glu Val Gln Gln Leu
    370                 375                 380 aaa aag gaa atc gag atg ttg cgc aac gaa ttg tcc cgc gcc gaa ttc    1200
Lys Lys Glu Ile Glu Met Leu Arg Asn Glu Leu Ser Arg Ala Glu Phe
385                 390                 395                 400 gag cta gta gac aac tgc tgg tca ccg ccg cca caa ctg caa tca tgg    1248
Glu Leu Val Asp Asn Cys Trp Ser Pro Pro Pro Gln Leu Gln Ser Trp
                405                 410                 415 ctt caa tac aca tat gaa cta gaa agt aag aat cat cag aag aag cgc    1296
Leu Gln Tyr Thr Tyr Glu Leu Glu Ser Lys Asn His Gln Lys Lys Arg
            420                 425                 430 acg tcg gct gag aag cag cta cag tcg gcc aga gag gct tgt gag aaa    1344
Thr Ser Ala Glu Lys Gln Leu Gln Ser Ala Arg Glu Ala Cys Glu Lys
        435                 440                 445 ttg cgt aag aaa cgg tca agt ttg gtg ggt gcg ttc gtt tcc acg cac    1392
Leu Arg Lys Lys Arg Ser Ser Leu Val Gly Ala Phe Val Ser Thr His
450                 455                 460 gga aag agt att gat gat gtg gat cgg tcg att gtt gag gca cgg aat    1440
Gly Lys Ser Ile Asp Asp Val Asp Arg Ser Ile Val Glu Ala Arg Asn
465                 470                 475                 480 gcc ctc gga gat gta aca aac gag ctg caa gaa cga ctg cat cgc tgg    1488
Ala Leu Gly Asp Val Thr Asn Glu Leu Gln Glu Arg Leu His Arg Trp
                485                 490                 495 aag caa atc gag acg tgc ctt ggc tta aac att gtg aac aac aat ggt    1536
Lys Gln Ile Glu Thr Cys Leu Gly Leu Asn Ile Val Asn Asn Asn Gly
            500                 505                 510 ctg ccc tac ttg gag aat gtt ctg tac ggt cga aat ggg ggc tta caa    1584
Leu Pro Tyr Leu Glu Asn Val Leu Tyr Gly Arg Asn Gly Gly Leu Gln
        515                 520                 525 agt tcc atg ggc atg agt tca acc aag ggt tct aga gca cgt att acc    1632
Ser Ser Met Gly Met Ser Ser Thr Lys Gly Ser Arg Ala Arg Ile Thr
530                 535                 540 aac agc acc gaa gac ctg gac gat gag tcc ata caa ggt aag ctg aat    1680
Asn Ser Thr Glu Asp Leu Asp Asp Glu Ser Ile Gln Gly Lys Leu Asn
545                 550                 555                 560 ttt gag aac ttt tcg ctg ctt gcc acg gaa taa                        1713
Phe Glu Asn Phe Ser Leu Leu Ala Thr Glu *
                565                 570
```

<210> SEQ ID NO 76
<211> LENGTH: 570
<212> TYPE: PRT
<213> ORGANISM: Drosophila melanogaster
<300> PUBLICATION INFORMATION:
<308> DATABASE ACCESSION NUMBER: Genbank NP_523357
<309> DATABASE ENTRY DATE: 2002-12-04

<400> SEQUENCE: 76

```
Met Arg Lys Asn Thr Ile Trp Asn Tyr Ser Leu Ile Phe Phe Cys Cys
 1               5                  10                  15

Val Leu Lys Ser Ile Ser Thr Leu Asp His Gly Pro His Thr Val Ser
            20                  25                  30

Val Asp Ser Asn Arg His Asn Thr Gln His Gln Tyr Lys Gln Asn Pro
        35                  40                  45
```

```
Asn Val Ala Ser Gln Arg His Ser His Glu Ser Gly Gln Ser Leu
 50                  55                  60

His Asn Ser Gln Ser Glu His Val Thr His Ile Ala Ala Ser His Ala
 65                  70                  75                  80

Gly Ser Gly Gly Glu His Ser Thr His Leu Ala Gln Asn Leu His Arg
                 85                  90                  95

Ser Ser Tyr Asn Leu Leu Ser Glu Ala Met Ser Gln Ala Val Ser Asn
            100                 105                 110

Glu Phe Ser Ser Met Gly Ser Gly Ser Ala Asp Gly Ala Cys Ala Ala
            115                 120                 125

Asp Asp Phe Asp Cys Tyr Ser Gly Ser Val Gln Asp Arg Phe Gly Met
130                 135                 140

Glu Ala Ile Ala Ser Leu His Arg Gln Leu Asp Asp Asp Asn Gly
145                 150                 155                 160

Asn Ile Asp Leu Ser Glu Ser Asp Asp Phe Leu Arg Glu Glu Leu Lys
                165                 170                 175

Tyr Asp Ser Gly Tyr Glu Lys Arg Gln Lys Ala Phe His Phe Asn Asp
            180                 185                 190

Asp Met His Ile Ser Val Lys Glu Leu Trp Glu Ala Trp Leu Arg Ser
            195                 200                 205

Glu Val His Asn Trp Thr Ile Glu Gln Thr Thr Asp Trp Leu Ala Gln
            210                 215                 220

Ser Val Gln Leu Pro Gln Tyr Val Asp Leu Phe Lys Leu His Lys Val
225                 230                 235                 240

Thr Gly Ala Ala Leu Pro Arg Leu Ala Val Asn Asn Leu Gln Tyr Val
                245                 250                 255

Gly Asn Val Leu Gly Ile Lys Asp Pro Ile His Lys Gln Lys Ile Ser
            260                 265                 270

Leu Lys Ala Met Asp Val Val Leu Phe Gly Pro Pro Arg Glu Thr Gly
            275                 280                 285

Thr Arg Trp Lys Asp Tyr Ile Leu Val Thr Leu Leu Leu Ser Ala Ile
290                 295                 300

Ile Gly Cys Trp Tyr Ala Tyr Gln Gln Asn Lys Asn Ala Lys Arg His
305                 310                 315                 320

Leu Arg Arg Met Ala Gln Asp Met Glu Gly Leu Gln Arg Ala Glu Gln
                325                 330                 335

Ser Leu Gln Glu Met Gln Lys Glu Leu Glu Arg Ala Arg Met Glu Gln
            340                 345                 350

Glu Asn Val Ala Thr Glu Lys Leu Asp Leu Glu Arg Arg Leu Lys Glu
            355                 360                 365

Ala Pro Thr Leu Ser Ser Ser Asn Ser Asp Leu Glu Val Gln Gln Leu
            370                 375                 380

Lys Lys Glu Ile Glu Met Leu Arg Asn Glu Leu Ser Arg Ala Glu Phe
385                 390                 395                 400

Glu Leu Val Asp Asn Cys Trp Ser Pro Pro Gln Leu Gln Ser Trp
                405                 410                 415

Leu Gln Tyr Thr Tyr Glu Leu Glu Ser Lys Asn His Gln Lys Lys Arg
            420                 425                 430

Thr Ser Ala Glu Lys Gln Leu Gln Ser Ala Arg Glu Ala Cys Glu Lys
            435                 440                 445

Leu Arg Lys Lys Arg Ser Ser Leu Val Gly Ala Phe Val Ser Thr His
450                 455                 460
```

```
Gly Lys Ser Ile Asp Asp Val Asp Arg Ser Ile Val Glu Ala Arg Asn
465                 470                 475                 480

Ala Leu Gly Asp Val Thr Asn Glu Leu Gln Glu Arg Leu His Arg Trp
                485                 490                 495

Lys Gln Ile Glu Thr Cys Leu Gly Leu Asn Ile Val Asn Asn Asn Gly
            500                 505                 510

Leu Pro Tyr Leu Glu Asn Val Leu Tyr Gly Arg Asn Gly Gly Leu Gln
        515                 520                 525

Ser Ser Met Gly Met Ser Ser Thr Lys Gly Ser Arg Ala Arg Ile Thr
    530                 535                 540

Asn Ser Thr Glu Asp Leu Asp Asp Glu Ser Ile Gln Gly Lys Leu Asn
545                 550                 555                 560

Phe Glu Asn Phe Ser Leu Leu Ala Thr Glu
                565                 570

<210> SEQ ID NO 77
<211> LENGTH: 1713
<212> TYPE: DNA
<213> ORGANISM: Drosophila melanogaster
<220> FEATURE:
<221> NAME/KEY: CDS
<222> LOCATION: (1)...(1713)
<223> OTHER INFORMATION: DSTIM-like Protein
<300> PUBLICATION INFORMATION:
<308> DATABASE ACCESSION NUMBER: Genbank AF328906
<309> DATABASE ENTRY DATE: 2001-07-31

<400> SEQUENCE: 77 atg cga aag aat acc att tgg aac tac tct tta ata ttc ttc tgc tgt       48
Met Arg Lys Asn Thr Ile Trp Asn Tyr Ser Leu Ile Phe Phe Cys Cys
 1               5                  10                  15 gtg ctg aag agc ata agt acg cta gat cat ggc ccg cac aca gta tca       96
Val Leu Lys Ser Ile Ser Thr Leu Asp His Gly Pro His Thr Val Ser
             20                  25                  30 gtc gat tcg aat cga cac aac aca cag cat cag tat aag caa aat ccc      144
Val Asp Ser Asn Arg His Asn Thr Gln His Gln Tyr Lys Gln Asn Pro
         35                  40                  45 aat gtt gcc tca caa cgt cac tca tcc cac gaa tct ggt cag agt tta      192
Asn Val Ala Ser Gln Arg His Ser Ser His Glu Ser Gly Gln Ser Leu
     50                  55                  60 cac aat tcg caa tcg gaa cat gtc acc cat att gcc gca tcg cac gcc      240
His Asn Ser Gln Ser Glu His Val Thr His Ile Ala Ala Ser His Ala
 65                  70                  75                  80 gga agc ggc gga gag cac tcc act cat ttg gcg caa aat ctg cac agg      288
Gly Ser Gly Gly Glu His Ser Thr His Leu Ala Gln Asn Leu His Arg
                 85                  90                  95 agc tca tat aat ctt ctg agc gag gcc atg tcc cag gct gtc agc aat      336
Ser Ser Tyr Asn Leu Leu Ser Glu Ala Met Ser Gln Ala Val Ser Asn
            100                 105                 110 gaa ttt agt tcc atg gga agt ggt tca gcg gat gga gcg tgt gct gct      384
Glu Phe Ser Ser Met Gly Ser Gly Ser Ala Asp Gly Ala Cys Ala Ala
        115                 120                 125 gat gat ttt gat tgc tac agt gga agt gtt cag gat cgc ttt ggc atg      432
Asp Asp Phe Asp Cys Tyr Ser Gly Ser Val Gln Asp Arg Phe Gly Met
    130                 135                 140 gag gct att gcc agc ttg cat cgt cag cta gat gat gac gat aat gga      480
Glu Ala Ile Ala Ser Leu His Arg Gln Leu Asp Asp Asp Asp Asn Gly
145                 150                 155                 160 aac atc gat ctg agc gag tcc gat gac ttt ttg cgg gag gaa ttg aag      528
Asn Ile Asp Leu Ser Glu Ser Asp Asp Phe Leu Arg Glu Glu Leu Lys
                165                 170                 175
```

|  |  |
|---|---|
| tac gac tcg ggc tac gaa aag cgg cag aaa gcg ttt cac ttc aat gac<br>Tyr Asp Ser Gly Tyr Glu Lys Arg Gln Lys Ala Phe His Phe Asn Asp<br>          180                   185               190 | 576 |
| gat atg cat ata tcg gtc aaa gaa ctt tgg gag gcc tgg ctc aga tcg<br>Asp Met His Ile Ser Val Lys Glu Leu Trp Glu Ala Trp Leu Arg Ser<br>195                  200               205 | 624 |
| gag gtg cat aat tgg acc atc gag cag acc acc gat tgg ctg gct cag<br>Glu Val His Asn Trp Thr Ile Glu Gln Thr Thr Asp Trp Leu Ala Gln<br>         210                 215               220 | 672 |
| tcc gtt cag ctg ccg caa tac gtt gat ctg ttc aaa tta cac aag gtt<br>Ser Val Gln Leu Pro Gln Tyr Val Asp Leu Phe Lys Leu His Lys Val<br>225                  230               235               240 | 720 |
| act ggc gct gcc ttg cca aga ttg gct gtg aat aat ctt cag tat gtt<br>Thr Gly Ala Ala Leu Pro Arg Leu Ala Val Asn Asn Leu Gln Tyr Val<br>                245               250               255 | 768 |
| ggc aat gta ctt ggc atc aaa gac cct ata cac aaa caa aaa atc tca<br>Gly Asn Val Leu Gly Ile Lys Asp Pro Ile His Lys Gln Lys Ile Ser<br>         260                 265               270 | 816 |
| ttg aag gca atg gat gtg gtt ctg ttt ggg cca ccg cga gaa act ggt<br>Leu Lys Ala Met Asp Val Val Leu Phe Gly Pro Pro Arg Glu Thr Gly<br>                275               280               285 | 864 |
| acc cgc tgg aaa gac tac ata ttg gta aca ctg ttg ctt agt gct att<br>Thr Arg Trp Lys Asp Tyr Ile Leu Val Thr Leu Leu Leu Ser Ala Ile<br>290                  295               300 | 912 |
| att ggt tgt tgg tac gcc tat cag caa aat aag aat gcc aaa cgg cat<br>Ile Gly Cys Trp Tyr Ala Tyr Gln Gln Asn Lys Asn Ala Lys Arg His<br>305                  310               315               320 | 960 |
| ctg cgt cga atg gcc cag gat atg gag gga ttg cag agg gct gag caa<br>Leu Arg Arg Met Ala Gln Asp Met Glu Gly Leu Gln Arg Ala Glu Gln<br>                325               330               335 | 1008 |
| agt cta cag gag atg cag aag gaa cta gaa cgg gcc aga atg gag cag<br>Ser Leu Gln Glu Met Gln Lys Glu Leu Glu Arg Ala Arg Met Glu Gln<br>         340                 345               350 | 1056 |
| gaa aat gtg gca aca gaa aaa cta gat ttg gag cgt cgt cta aaa gaa<br>Glu Asn Val Ala Thr Glu Lys Leu Asp Leu Glu Arg Arg Leu Lys Glu<br>355                  360               365 | 1104 |
| gcg ccc act ctc agt tca tcg aac tcg gat ttg gaa gtt cag cag ctg<br>Ala Pro Thr Leu Ser Ser Ser Asn Ser Asp Leu Glu Val Gln Gln Leu<br>         370                 375               380 | 1152 |
| aaa aag gaa atc gag atg ttg cgc aac gaa ttg tcc cgc gcc gaa ttc<br>Lys Lys Glu Ile Glu Met Leu Arg Asn Glu Leu Ser Arg Ala Glu Phe<br>385                  390               395               400 | 1200 |
| gag cta gta gac aac tgc tgg tca ccg ccg cca caa ctg caa tca tgg<br>Glu Leu Val Asp Asn Cys Trp Ser Pro Pro Pro Gln Leu Gln Ser Trp<br>                405               410               415 | 1248 |
| ctt caa tac aca tat gaa cta gaa agt aag aat cat cag aag aag cgc<br>Leu Gln Tyr Thr Tyr Glu Leu Glu Ser Lys Asn His Gln Lys Lys Arg<br>         420                 425               430 | 1296 |
| acg tcg gct gag aag cag cta cag tcg gcc aga gag gct tgt gag aaa<br>Thr Ser Ala Glu Lys Gln Leu Gln Ser Ala Arg Glu Ala Cys Glu Lys<br>                435               440               445 | 1344 |
| ttg cgt aag aaa cgg tca agt ttg gtg ggt gcg ttc gtt tcc acg cac<br>Leu Arg Lys Lys Arg Ser Ser Leu Val Gly Ala Phe Val Ser Thr His<br>450                  455               460 | 1392 |
| gga aag agt att gat gat gtg gat cgg tcg att gtt gag gca cgg aat<br>Gly Lys Ser Ile Asp Asp Val Asp Arg Ser Ile Val Glu Ala Arg Asn<br>465                  470               475               480 | 1440 |
| gcc ctc gga gat gta aca aac gag ctg caa gaa cga ctg cat cgc tgg<br>Ala Leu Gly Asp Val Thr Asn Glu Leu Gln Glu Arg Leu His Arg Trp | 1488 |

-continued

```
                    485                 490                 495
aag caa atc gag acg tgc ctt ggc tta aac att gtg aac aac aat ggt      1536
Lys Gln Ile Glu Thr Cys Leu Gly Leu Asn Ile Val Asn Asn Asn Gly
                500                 505                 510 ctg ccc tac ttg gag aat gtt ctg tac ggt cga aat ggg ggc tta caa      1584
Leu Pro Tyr Leu Glu Asn Val Leu Tyr Gly Arg Asn Gly Gly Leu Gln
            515                 520                 525 agt tcc atg ggc atg agt tca acc aag ggt tct aga gca cgt att acc      1632
Ser Ser Met Gly Met Ser Ser Thr Lys Gly Ser Arg Ala Arg Ile Thr
        530                 535                 540 aac agc acc gaa gac ctg gac gat gag tcc ata caa ggt aag ctg aat      1680
Asn Ser Thr Glu Asp Leu Asp Asp Glu Ser Ile Gln Gly Lys Leu Asn
545                 550                 555                 560 ttt gag aac ttt tcg ctg ctt gcc acg gaa taa                          1713
Phe Glu Asn Phe Ser Leu Leu Ala Thr Glu  *
                565                 570
```

<210> SEQ ID NO 78
<211> LENGTH: 570
<212> TYPE: PRT
<213> ORGANISM: Drosophila melanogaster
<300> PUBLICATION INFORMATION:
<308> DATABASE ACCESSION NUMBER: Genbank AAK82338
<309> DATABASE ENTRY DATE: 2001-07-31

<400> SEQUENCE: 78

```
Met Arg Lys Asn Thr Ile Trp Asn Tyr Ser Leu Ile Phe Phe Cys Cys
1               5                  10                  15

Val Leu Lys Ser Ile Ser Thr Leu Asp His Gly Pro His Thr Val Ser
            20                  25                  30

Val Asp Ser Asn Arg His Asn Thr Gln His Gln Tyr Lys Gln Asn Pro
        35                  40                  45

Asn Val Ala Ser Gln Arg His Ser Ser His Glu Ser Gly Gln Ser Leu
    50                  55                  60

His Asn Ser Gln Ser Glu His Val Thr His Ile Ala Ala Ser His Ala
65                  70                  75                  80

Gly Ser Gly Gly Glu His Ser Thr His Leu Ala Gln Asn Leu His Arg
                85                  90                  95

Ser Ser Tyr Asn Leu Leu Ser Glu Ala Met Ser Gln Ala Val Ser Asn
            100                 105                 110

Glu Phe Ser Ser Met Gly Ser Gly Ser Ala Asp Gly Ala Cys Ala Ala
        115                 120                 125

Asp Asp Phe Asp Cys Tyr Ser Gly Ser Val Gln Asp Arg Phe Gly Met
    130                 135                 140

Glu Ala Ile Ala Ser Leu His Arg Gln Leu Asp Asp Asp Asn Gly
145                 150                 155                 160

Asn Ile Asp Leu Ser Glu Ser Asp Phe Leu Arg Glu Glu Leu Lys
                165                 170                 175

Tyr Asp Ser Gly Tyr Glu Lys Arg Gln Lys Ala Phe His Phe Asn Asp
            180                 185                 190

Asp Met His Ile Ser Val Lys Glu Leu Trp Glu Ala Trp Leu Arg Ser
        195                 200                 205

Glu Val His Asn Trp Thr Ile Glu Gln Thr Thr Asp Trp Leu Ala Gln
    210                 215                 220

Ser Val Gln Leu Pro Gln Tyr Val Asp Leu Phe Lys Leu His Lys Val
225                 230                 235                 240

Thr Gly Ala Ala Leu Pro Arg Leu Ala Val Asn Asn Leu Gln Tyr Val
```

-continued

```
                245                 250                 255
Gly Asn Val Leu Gly Ile Lys Asp Pro Ile His Lys Gln Lys Ile Ser
                260                 265                 270
Leu Lys Ala Met Asp Val Val Leu Phe Gly Pro Pro Arg Glu Thr Gly
                275                 280                 285
Thr Arg Trp Lys Asp Tyr Ile Leu Val Thr Leu Leu Leu Ser Ala Ile
                290                 295                 300
Ile Gly Cys Trp Tyr Ala Tyr Gln Gln Asn Lys Asn Ala Lys Arg His
305                 310                 315                 320
Leu Arg Arg Met Ala Gln Asp Met Glu Gly Leu Gln Arg Ala Glu Gln
                325                 330                 335
Ser Leu Gln Glu Met Gln Lys Glu Leu Glu Arg Ala Arg Met Glu Gln
                340                 345                 350
Glu Asn Val Ala Thr Glu Lys Leu Asp Leu Glu Arg Arg Leu Lys Glu
                355                 360                 365
Ala Pro Thr Leu Ser Ser Ser Asn Ser Asp Leu Glu Val Gln Gln Leu
                370                 375                 380
Lys Lys Glu Ile Glu Met Leu Arg Asn Glu Leu Ser Arg Ala Glu Phe
385                 390                 395                 400
Glu Leu Val Asp Asn Cys Trp Ser Pro Pro Gln Leu Gln Ser Trp
                405                 410                 415
Leu Gln Tyr Thr Tyr Glu Leu Glu Ser Lys Asn His Gln Lys Lys Arg
                420                 425                 430
Thr Ser Ala Glu Lys Gln Leu Gln Ser Ala Arg Glu Ala Cys Glu Lys
                435                 440                 445
Leu Arg Lys Lys Arg Ser Ser Leu Val Gly Ala Phe Val Ser Thr His
                450                 455                 460
Gly Lys Ser Ile Asp Asp Val Asp Arg Ser Ile Val Glu Ala Arg Asn
465                 470                 475                 480
Ala Leu Gly Asp Val Thr Asn Glu Leu Gln Glu Arg Leu His Arg Trp
                485                 490                 495
Lys Gln Ile Glu Thr Cys Leu Gly Leu Asn Ile Val Asn Asn Asn Gly
                500                 505                 510
Leu Pro Tyr Leu Glu Asn Val Leu Tyr Gly Arg Asn Gly Gly Leu Gln
                515                 520                 525
Ser Ser Met Gly Met Ser Ser Thr Lys Gly Ser Arg Ala Arg Ile Thr
                530                 535                 540
Asn Ser Thr Glu Asp Leu Asp Asp Glu Ser Ile Gln Gly Lys Leu Asn
545                 550                 555                 560
Phe Glu Asn Phe Ser Leu Leu Ala Thr Glu
                565                 570
```

<210> SEQ ID NO 79
<211> LENGTH: 1713
<212> TYPE: DNA
<213> ORGANISM: Drosophila melanogaster
<220> FEATURE:
<221> NAME/KEY: CDS
<222> LOCATION: (1)...(1713)
<223> OTHER INFORMATION: Drosophila melanogaster LD45776
<300> PUBLICATION INFORMATION:
<308> DATABASE ACCESSION NUMBER: Genbank AY069686
<309> DATABASE ENTRY DATE: 2001-12-17

<400> SEQUENCE: 79

```
atg cga aag aat acc att tgg aac tac tct tta ata ttc ttc tgc tgt      48
Met Arg Lys Asn Thr Ile Trp Asn Tyr Ser Leu Ile Phe Phe Cys Cys
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
gtg ctg aag agc ata agt acg cta gat cat ggc ccg cac aca gta tca         96
Val Leu Lys Ser Ile Ser Thr Leu Asp His Gly Pro His Thr Val Ser
             20                  25                  30 gtc gat tcg aat cga cac aac aca cag cat cag tat aag caa aat ccc        144
Val Asp Ser Asn Arg His Asn Thr Gln His Gln Tyr Lys Gln Asn Pro
         35                  40                  45 aat gtt gcc tca caa cgt cac tca tcc cac gaa tct ggt cag agt tta        192
Asn Val Ala Ser Gln Arg His Ser Ser His Glu Ser Gly Gln Ser Leu
     50                  55                  60 cac aat tcg caa tcg gaa cat gtc acc cat att gcc gca tcg cac gcc        240
His Asn Ser Gln Ser Glu His Val Thr His Ile Ala Ala Ser His Ala
 65                  70                  75                  80 gga agc ggc gga gag cac tcc act cat ttg gcg caa aat ctg cac agg        288
Gly Ser Gly Gly Glu His Ser Thr His Leu Ala Gln Asn Leu His Arg
                 85                  90                  95 agc tca tat aat ctt ctg agc gag gcc atg tcc cag gct gtc agc aat        336
Ser Ser Tyr Asn Leu Leu Ser Glu Ala Met Ser Gln Ala Val Ser Asn
            100                 105                 110 gaa ttt agt tcc atg gga agt ggt tca gcg gat gga gcg tgt gct gct        384
Glu Phe Ser Ser Met Gly Ser Gly Ser Ala Asp Gly Ala Cys Ala Ala
        115                 120                 125 gat gat ttt gat tgc tac agt gga agt gtt cag gat cgc ttt ggc atg        432
Asp Asp Phe Asp Cys Tyr Ser Gly Ser Val Gln Asp Arg Phe Gly Met
    130                 135                 140 gag gct att gcc agc ttg cat cgt cag cta gat gat gac gat aat gga        480
Glu Ala Ile Ala Ser Leu His Arg Gln Leu Asp Asp Asp Asp Asn Gly
145                 150                 155                 160 aac atc gat ctg agc gag tcc gat gac ttt ttg cgg gag gaa ttg aag        528
Asn Ile Asp Leu Ser Glu Ser Asp Asp Phe Leu Arg Glu Glu Leu Lys
                165                 170                 175 tac gac tcg ggc tac gaa aag cgg cag aaa gcg ttt cac ttc aat gac        576
Tyr Asp Ser Gly Tyr Glu Lys Arg Gln Lys Ala Phe His Phe Asn Asp
            180                 185                 190 gat atg cat ata tcg gtc aaa gaa ctt tgg gag gcc tgg ctc aga tcg        624
Asp Met His Ile Ser Val Lys Glu Leu Trp Glu Ala Trp Leu Arg Ser
        195                 200                 205 gag gtg cat aat tgg acc atc gag cag acc acc gat tgg ctg gct cag        672
Glu Val His Asn Trp Thr Ile Glu Gln Thr Thr Asp Trp Leu Ala Gln
    210                 215                 220 tcc gtt cag ctg ccg caa tac gtt gat ctg ttc aaa tta cac aag gtt        720
Ser Val Gln Leu Pro Gln Tyr Val Asp Leu Phe Lys Leu His Lys Val
225                 230                 235                 240 act ggc gct gcc ttg cca aga ttg gct gtg aat aat ctt cag tat gtt        768
Thr Gly Ala Ala Leu Pro Arg Leu Ala Val Asn Asn Leu Gln Tyr Val
                245                 250                 255 ggc aat gta ctt ggc atc aaa gac cct ata cac aaa caa aaa atc tca        816
Gly Asn Val Leu Gly Ile Lys Asp Pro Ile His Lys Gln Lys Ile Ser
            260                 265                 270 ttg aag gca atg gat gtg gtt ctg ttt ggg cca ccg cga gaa act ggt        864
Leu Lys Ala Met Asp Val Val Leu Phe Gly Pro Pro Arg Glu Thr Gly
        275                 280                 285 acc cgc tgg aaa gac tac ata ttg gta aca ctg ttg ctt agt gct att        912
Thr Arg Trp Lys Asp Tyr Ile Leu Val Thr Leu Leu Leu Ser Ala Ile
    290                 295                 300 att ggt tgt tgg tac gcc tat cag caa aat aag aat gcc aaa cgg cat        960
Ile Gly Cys Trp Tyr Ala Tyr Gln Gln Asn Lys Asn Ala Lys Arg His
305                 310                 315                 320 ctg cgt cga atg gcc cag gat atg gag gga ttg cag agg gct gag caa       1008
```

```
                                                     -continued

Leu Arg Arg Met Ala Gln Asp Met Glu Gly Leu Gln Arg Ala Glu Gln
                325                 330                 335 agt cta cag gag atg cag aag gaa cta gaa cgg gcc aga atg gag cag       1056
Ser Leu Gln Glu Met Gln Lys Glu Leu Glu Arg Ala Arg Met Glu Gln
            340                 345                 350 gaa aat gtg gca aca gaa aaa cta gat ttg gag cgt cgt cta aaa gaa       1104
Glu Asn Val Ala Thr Glu Lys Leu Asp Leu Glu Arg Arg Leu Lys Glu
        355                 360                 365 gcg ccc act ctc agt tca tcg aac tcg gat ttg gaa gtt cag cag ctg       1152
Ala Pro Thr Leu Ser Ser Ser Asn Ser Asp Leu Glu Val Gln Gln Leu
    370                 375                 380 aaa aag gaa atc gag atg ttg cgc aac gaa ttg tcc cgc gcc gaa ttc       1200
Lys Lys Glu Ile Glu Met Leu Arg Asn Glu Leu Ser Arg Ala Glu Phe
385                 390                 395                 400 gag cta gta gac aac tgc tgg tca ccg ccg cca caa ctg caa tca tgg       1248
Glu Leu Val Asp Asn Cys Trp Ser Pro Pro Pro Gln Leu Gln Ser Trp
                405                 410                 415 ctt caa tac aca tat gaa cta gaa agt aag aat cat cag aag aag cgc       1296
Leu Gln Tyr Thr Tyr Glu Leu Glu Ser Lys Asn His Gln Lys Lys Arg
            420                 425                 430 acg tcg gct gag aag cag cta cag tcg gcc aga gag gct tgt gag aaa       1344
Thr Ser Ala Glu Lys Gln Leu Gln Ser Ala Arg Glu Ala Cys Glu Lys
        435                 440                 445 ttg cgt aag aaa cgg tca agt ttg gtg ggt gcg ttc gtt tcc acg cac       1392
Leu Arg Lys Lys Arg Ser Ser Leu Val Gly Ala Phe Val Ser Thr His
    450                 455                 460 gga aag agt att gat gat gtg gat cgg tcg att gtt gag gca cgg aat       1440
Gly Lys Ser Ile Asp Asp Val Asp Arg Ser Ile Val Glu Ala Arg Asn
465                 470                 475                 480 gcc ctc gga gat gta aca aac gag ctg caa gaa cga ctg cat cgc tgg       1488
Ala Leu Gly Asp Val Thr Asn Glu Leu Gln Glu Arg Leu His Arg Trp
                485                 490                 495 aag caa atc gag acg tgc ctt ggc tta aac att gtg aac aac aat ggt       1536
Lys Gln Ile Glu Thr Cys Leu Gly Leu Asn Ile Val Asn Asn Asn Gly
            500                 505                 510 ctg ccc tac ttg gag aat gtt ctg tac ggt cga aat ggg gga tta caa       1584
Leu Pro Tyr Leu Glu Asn Val Leu Tyr Gly Arg Asn Gly Gly Leu Gln
        515                 520                 525 agt tcc atg ggc atg agt tca acc aag ggt tct aga gca cgt att acc       1632
Ser Ser Met Gly Met Ser Ser Thr Lys Gly Ser Arg Ala Arg Ile Thr
    530                 535                 540 aac agc acc gaa gac ctg gac gat gag tcc ata caa ggt aag ctg aat       1680
Asn Ser Thr Glu Asp Leu Asp Asp Glu Ser Ile Gln Gly Lys Leu Asn
545                 550                 555                 560 ttt gag aac ttt tcg ctg ctt gcc acg gaa taa                           1713
Phe Glu Asn Phe Ser Leu Leu Ala Thr Glu  *
                565                 570

<210> SEQ ID NO 80
<211> LENGTH: 570
<212> TYPE: PRT
<213> ORGANISM: Drosophila melanogaster
<300> PUBLICATION INFORMATION:
<308> DATABASE ACCESSION NUMBER: Genbank AAL39831
<309> DATABASE ENTRY DATE: 2001-12-17

<400> SEQUENCE: 80

Met Arg Lys Asn Thr Ile Trp Asn Tyr Ser Leu Ile Phe Phe Cys Cys
1               5                   10                  15

Val Leu Lys Ser Ile Ser Thr Leu Asp His Gly Pro His Thr Val Ser
            20                  25                  30
```

-continued

```
Val Asp Ser Asn Arg His Asn Thr Gln His Gln Tyr Lys Gln Asn Pro
         35                  40                  45
Asn Val Ala Ser Gln Arg His Ser Ser His Glu Ser Gly Gln Ser Leu
 50                  55                  60
His Asn Ser Gln Ser Glu His Val Thr His Ile Ala Ala Ser His Ala
 65                  70                  75                  80
Gly Ser Gly Gly Glu His Ser Thr His Leu Ala Gln Asn Leu His Arg
                 85                  90                  95
Ser Ser Tyr Asn Leu Leu Ser Glu Ala Met Ser Gln Ala Val Ser Asn
            100                 105                 110
Glu Phe Ser Ser Met Gly Ser Gly Ser Ala Asp Gly Ala Cys Ala Ala
            115                 120                 125
Asp Asp Phe Asp Cys Tyr Ser Gly Ser Val Gln Asp Arg Phe Gly Met
130                 135                 140
Glu Ala Ile Ala Ser Leu His Arg Gln Leu Asp Asp Asp Asp Asn Gly
145                 150                 155                 160
Asn Ile Asp Leu Ser Glu Ser Asp Asp Phe Leu Arg Glu Glu Leu Lys
                165                 170                 175
Tyr Asp Ser Gly Tyr Glu Lys Arg Gln Lys Ala Phe His Phe Asn Asp
            180                 185                 190
Asp Met His Ile Ser Val Lys Glu Leu Trp Glu Ala Trp Leu Arg Ser
            195                 200                 205
Glu Val His Asn Trp Thr Ile Glu Gln Thr Thr Asp Trp Leu Ala Gln
210                 215                 220
Ser Val Gln Leu Pro Gln Tyr Val Asp Leu Phe Lys Leu His Lys Val
225                 230                 235                 240
Thr Gly Ala Ala Leu Pro Arg Leu Ala Val Asn Asn Leu Gln Tyr Val
                245                 250                 255
Gly Asn Val Leu Gly Ile Lys Asp Pro Ile His Lys Gln Lys Ile Ser
            260                 265                 270
Leu Lys Ala Met Asp Val Val Leu Phe Gly Pro Pro Arg Glu Thr Gly
            275                 280                 285
Thr Arg Trp Lys Asp Tyr Ile Leu Val Thr Leu Leu Leu Ser Ala Ile
290                 295                 300
Ile Gly Cys Trp Tyr Ala Tyr Gln Gln Asn Lys Asn Ala Lys Arg His
305                 310                 315                 320
Leu Arg Arg Met Ala Gln Asp Met Glu Gly Leu Gln Arg Ala Glu Gln
                325                 330                 335
Ser Leu Gln Glu Met Gln Lys Glu Leu Glu Arg Ala Arg Met Glu Gln
            340                 345                 350
Glu Asn Val Ala Thr Glu Lys Leu Asp Leu Glu Arg Arg Leu Lys Glu
            355                 360                 365
Ala Pro Thr Leu Ser Ser Asn Ser Asp Leu Glu Val Gln Gln Leu
370                 375                 380
Lys Lys Glu Ile Glu Met Leu Arg Asn Glu Leu Ser Arg Ala Glu Phe
385                 390                 395                 400
Glu Leu Val Asp Asn Cys Trp Ser Pro Pro Gln Leu Gln Ser Trp
                405                 410                 415
Leu Gln Tyr Thr Tyr Glu Leu Glu Ser Lys Asn His Gln Lys Lys Arg
            420                 425                 430
Thr Ser Ala Glu Lys Gln Leu Gln Ser Ala Arg Glu Ala Cys Glu Lys
            435                 440                 445
```

-continued

```
Leu Arg Lys Lys Arg Ser Ser Leu Val Gly Ala Phe Val Ser Thr His
    450                 455                 460

Gly Lys Ser Ile Asp Asp Val Asp Arg Ser Ile Val Glu Ala Arg Asn
465                 470                 475                 480

Ala Leu Gly Asp Val Thr Asn Glu Leu Gln Glu Arg Leu His Arg Trp
                485                 490                 495

Lys Gln Ile Glu Thr Cys Leu Gly Leu Asn Ile Val Asn Asn Asn Gly
                500                 505                 510

Leu Pro Tyr Leu Glu Asn Val Leu Tyr Gly Arg Asn Gly Gly Leu Gln
            515                 520                 525

Ser Ser Met Gly Met Ser Ser Thr Lys Gly Ser Arg Ala Arg Ile Thr
    530                 535                 540

Asn Ser Thr Glu Asp Leu Asp Asp Glu Ser Ile Gln Gly Lys Leu Asn
545                 550                 555                 560

Phe Glu Asn Phe Ser Leu Leu Ala Thr Glu
                565                 570

<210> SEQ ID NO 81
<211> LENGTH: 570
<212> TYPE: PRT
<213> ORGANISM: Drosophila melanogaster
<300> PUBLICATION INFORMATION:
<308> DATABASE ACCESSION NUMBER: Swiss Prot P83094
<309> DATABASE ENTRY DATE: 2002-06-01

<400> SEQUENCE: 81

Met Arg Lys Asn Thr Ile Trp Asn Tyr Ser Leu Ile Phe Phe Cys Cys
1               5                   10                  15

Val Leu Lys Ser Ile Ser Thr Leu Asp His Gly Pro His Thr Val Ser
            20                  25                  30

Val Asp Ser Asn Arg His Asn Thr Gln His Gln Tyr Lys Gln Asn Pro
        35                  40                  45

Asn Val Ala Ser Gln Arg His Ser Ser His Glu Ser Gly Gln Ser Leu
    50                  55                  60

His Asn Ser Gln Ser Glu His Val Thr His Ile Ala Ala Ser His Ala
65                  70                  75                  80

Gly Ser Gly Gly Glu His Ser Thr His Leu Ala Gln Asn Leu His Arg
                85                  90                  95

Ser Ser Tyr Asn Leu Leu Ser Glu Ala Met Ser Gln Ala Val Ser Asn
            100                 105                 110

Glu Phe Ser Ser Met Gly Ser Gly Ser Ala Asp Gly Ala Cys Ala Ala
        115                 120                 125

Asp Asp Phe Asp Cys Tyr Ser Gly Ser Val Gln Asp Arg Phe Gly Met
    130                 135                 140

Glu Ala Ile Ala Ser Leu His Arg Gln Leu Asp Asp Asp Asn Gly
145                 150                 155                 160

Asn Ile Asp Leu Ser Glu Ser Asp Asp Phe Leu Arg Glu Glu Leu Lys
                165                 170                 175

Tyr Asp Ser Gly Tyr Glu Lys Arg Gln Lys Ala Phe His Phe Asn Asp
            180                 185                 190

Asp Met His Ile Ser Val Lys Glu Leu Trp Glu Ala Trp Leu Arg Ser
        195                 200                 205

Glu Val His Asn Trp Thr Ile Glu Gln Thr Thr Asp Trp Leu Ala Gln
    210                 215                 220

Ser Val Gln Leu Pro Gln Tyr Val Asp Leu Phe Lys Leu His Lys Val
225                 230                 235                 240
```

-continued

```
Thr Gly Ala Ala Leu Pro Arg Leu Ala Val Asn Asn Leu Gln Tyr Val
                245                 250                 255
Gly Asn Val Leu Gly Ile Lys Asp Pro Ile His Lys Gln Lys Ile Ser
            260                 265                 270
Leu Lys Ala Met Asp Val Val Leu Phe Gly Pro Pro Arg Glu Thr Gly
        275                 280                 285
Thr Arg Trp Lys Asp Tyr Ile Leu Val Thr Leu Leu Ser Ala Ile
    290                 295                 300
Ile Gly Cys Trp Tyr Ala Tyr Gln Gln Asn Lys Asn Ala Lys Arg His
305                 310                 315                 320
Leu Arg Arg Met Ala Gln Asp Met Glu Gly Leu Gln Arg Ala Glu Gln
                325                 330                 335
Ser Leu Gln Glu Met Gln Lys Glu Leu Glu Arg Ala Arg Met Glu Gln
            340                 345                 350
Glu Asn Val Ala Thr Glu Lys Leu Asp Leu Glu Arg Arg Leu Lys Glu
        355                 360                 365
Ala Pro Thr Leu Ser Ser Asn Ser Asp Leu Glu Val Gln Gln Leu
    370                 375                 380
Lys Lys Glu Ile Glu Met Leu Arg Asn Glu Leu Ser Arg Ala Glu Phe
385                 390                 395                 400
Glu Leu Val Asp Asn Cys Trp Ser Pro Pro Gln Leu Gln Ser Trp
                405                 410                 415
Leu Gln Tyr Thr Tyr Glu Leu Glu Ser Lys Asn His Gln Lys Lys Arg
            420                 425                 430
Thr Ser Ala Glu Lys Gln Leu Gln Ser Ala Arg Glu Ala Cys Glu Lys
        435                 440                 445
Leu Arg Lys Lys Arg Ser Ser Leu Val Gly Ala Phe Val Ser Thr His
    450                 455                 460
Gly Lys Ser Ile Asp Asp Val Asp Arg Ser Ile Val Glu Ala Arg Asn
465                 470                 475                 480
Ala Leu Gly Asp Val Thr Asn Glu Leu Gln Glu Arg Leu His Arg Trp
                485                 490                 495
Lys Gln Ile Glu Thr Cys Leu Gly Leu Asn Ile Val Asn Asn Asn Gly
            500                 505                 510
Leu Pro Tyr Leu Glu Asn Val Leu Tyr Gly Arg Asn Gly Gly Leu Gln
        515                 520                 525
Ser Ser Met Gly Met Ser Ser Thr Lys Gly Ser Arg Ala Arg Ile Thr
    530                 535                 540
Asn Ser Thr Glu Asp Leu Asp Asp Glu Ser Ile Gln Gly Lys Leu Asn
545                 550                 555                 560
Phe Glu Asn Phe Ser Leu Leu Ala Thr Glu
                565                 570
```

<210> SEQ ID NO 82
<211> LENGTH: 2058
<212> TYPE: DNA
<213> ORGANISM: Homo sapiens
<220> FEATURE:
<221> NAME/KEY: CDS
<222> LOCATION: (1)...(2058)
<223> OTHER INFORMATION: STIM-1
<300> PUBLICATION INFORMATION:
<308> DATABASE ACCESSION NUMBER: Genbank NM_003156
<309> DATABASE ENTRY DATE: 2002-05-22

<400> SEQUENCE: 82

-continued

| | |
|---|---|
| atg gat gta tgc gtc cgt ctt gcc ctg tgg ctc ctc tgg gga ctc ctc<br>Met Asp Val Cys Val Arg Leu Ala Leu Trp Leu Leu Trp Gly Leu Leu<br>1                        5                      10                    15 | 48 |
| ctg cac cag ggc cag agc ctc agc cat agt cac agt gag aag gcg aca<br>Leu His Gln Gly Gln Ser Leu Ser His Ser His Ser Glu Lys Ala Thr<br>                20                      25                    30 | 96 |
| gga acc agc tcg ggg gcc aac tct gag gag tcc act gca gca gag ttt<br>Gly Thr Ser Ser Gly Ala Asn Ser Glu Glu Ser Thr Ala Ala Glu Phe<br>      35                      40                    45 | 144 |
| tgc cga att gac aag ccc ctg tgt cac agt gag gat gag aaa ctc agc<br>Cys Arg Ile Asp Lys Pro Leu Cys His Ser Glu Asp Glu Lys Leu Ser<br>50                      55                    60 | 192 |
| ttc gag gca gtc cgt aac atc cac aaa ctg atg gac gat gat gcc aat<br>Phe Glu Ala Val Arg Asn Ile His Lys Leu Met Asp Asp Asp Ala Asn<br>65                      70                    75                    80 | 240 |
| ggt gat gtg gat gtg gaa gaa agt gat gag ttc ctg agg gaa gac ctc<br>Gly Asp Val Asp Val Glu Glu Ser Asp Glu Phe Leu Arg Glu Asp Leu<br>                85                      90                    95 | 288 |
| aat tac cat gac cca aca gtg aaa cac agc acc ttc cat ggt gag gat<br>Asn Tyr His Asp Pro Thr Val Lys His Ser Thr Phe His Gly Glu Asp<br>                100                   105                 110 | 336 |
| aag ctc atc agc gtg gag gac ctg tgg aag gca tgg aag tca tca gaa<br>Lys Leu Ile Ser Val Glu Asp Leu Trp Lys Ala Trp Lys Ser Ser Glu<br>                115                   120                 125 | 384 |
| gta tac aat tgg acc gtg gat gag gtg gta cag tgg ctg atc aca tat<br>Val Tyr Asn Trp Thr Val Asp Glu Val Val Gln Trp Leu Ile Thr Tyr<br>      130                      135                   140 | 432 |
| gtg gag ctg cct cag tat gag gag acc ttc cgg aag ctg cag ctc agt<br>Val Glu Leu Pro Gln Tyr Glu Glu Thr Phe Arg Lys Leu Gln Leu Ser<br>145                      150                   155                 160 | 480 |
| ggc cat gcc atg cca agg ctg gct gtc acc aac acc acc atg aca ggg<br>Gly His Ala Met Pro Arg Leu Ala Val Thr Asn Thr Thr Met Thr Gly<br>                     165                   170                 175 | 528 |
| act gtg ctg aag atg aca gac cgg agt cat cgg cag aag ctg cag ctg<br>Thr Val Leu Lys Met Thr Asp Arg Ser His Arg Gln Lys Leu Gln Leu<br>                180                   185                 190 | 576 |
| aag gct ctg gat aca gtg ctc ttt ggg cct cct ctc ttg act cgc cat<br>Lys Ala Leu Asp Thr Val Leu Phe Gly Pro Pro Leu Leu Thr Arg His<br>            195                   200                 205 | 624 |
| aat cac ctc aag gac ttc atg ctg gtg gtg tct atc gtt att ggt gtg<br>Asn His Leu Lys Asp Phe Met Leu Val Val Ser Ile Val Ile Gly Val<br>210                      215                   220 | 672 |
| ggc ggc tgc tgg ttt gcc tat atc cag aac cgt tac tcc aag gag cac<br>Gly Gly Cys Trp Phe Ala Tyr Ile Gln Asn Arg Tyr Ser Lys Glu His<br>225                      230                   235                 240 | 720 |
| atg aag aag atg atg aag gac ttg gag ggg tta cac cga gct gag cag<br>Met Lys Lys Met Met Lys Asp Leu Glu Gly Leu His Arg Ala Glu Gln<br>                     245                   250                 255 | 768 |
| agt ctg cat gac ctt cag gaa agg ctg cac aag gcc cag gag gag cac<br>Ser Leu His Asp Leu Gln Glu Arg Leu His Lys Ala Gln Glu Glu His<br>                260                   265                 270 | 816 |
| cgc aca gtg gag gtg gag aag gtc cat ctg gaa aag aag ctg cgc gat<br>Arg Thr Val Glu Val Glu Lys Val His Leu Glu Lys Lys Leu Arg Asp<br>            275                   280                 285 | 864 |
| gag atc aac ctt gct aag cag gaa gcc cag cgg ctg aag gag ctg cgg<br>Glu Ile Asn Leu Ala Lys Gln Glu Ala Gln Arg Leu Lys Glu Leu Arg<br>      290                      295                   300 | 912 |
| gag ggt act gag aat gag cgg agc cgc caa aaa tat gct gag gag gag<br>Glu Gly Thr Glu Asn Glu Arg Ser Arg Gln Lys Tyr Ala Glu Glu Glu<br>305                      310                   315                 320 | 960 |

-continued

| | | |
|---|---|---|
| ttg gag cag gtt cgg gag gcc ttg agg aaa gca gag aag gag cta gaa<br>Leu Glu Gln Val Arg Glu Ala Leu Arg Lys Ala Glu Lys Glu Leu Glu<br>325                           330                      335 | | 1008 |
| tct cac agc tca tgg tat gct cca gag gcc ctt cag aag tgg ctg cag<br>Ser His Ser Ser Trp Tyr Ala Pro Glu Ala Leu Gln Lys Trp Leu Gln<br>         340                      345                      350 | | 1056 |
| ctg aca cat gag gtg gag gtg caa tat tac aac atc aag aag caa aat<br>Leu Thr His Glu Val Glu Val Gln Tyr Tyr Asn Ile Lys Lys Gln Asn<br>              355                      360                    365 | | 1104 |
| gct gag aag cag ctg ctg gtg gcc aag gag ggg gct gag aag ata aaa<br>Ala Glu Lys Gln Leu Leu Val Ala Lys Glu Gly Ala Glu Lys Ile Lys<br>370                           375                      380 | | 1152 |
| aag aag aga aac aca ctc ttt ggc acc ttc cac gtg gcc cac agc tct<br>Lys Lys Arg Asn Thr Leu Phe Gly Thr Phe His Val Ala His Ser Ser<br>385                         390                      395                    400 | | 1200 |
| tcc ctg gat gat gta gat cat aaa att cta aca gct aag caa gca ctg<br>Ser Leu Asp Asp Val Asp His Lys Ile Leu Thr Ala Lys Gln Ala Leu<br>                     405                      410                    415 | | 1248 |
| agc gag gtg aca gca gca ttg cgg gag cgc ctg cac cgc tgg caa cag<br>Ser Glu Val Thr Ala Ala Leu Arg Glu Arg Leu His Arg Trp Gln Gln<br>              420                      425                    430 | | 1296 |
| atc gag atc ctc tgt ggc ttc cag att gtc aac aac cct ggc atc cac<br>Ile Glu Ile Leu Cys Gly Phe Gln Ile Val Asn Asn Pro Gly Ile His<br>                     435                      440                    445 | | 1344 |
| tca ctg gtg gct gcc ctc aac ata gac ccc agc tgg atg ggc agt aca<br>Ser Leu Val Ala Ala Leu Asn Ile Asp Pro Ser Trp Met Gly Ser Thr<br>450                           455                      460 | | 1392 |
| cgc ccc aac cct gct cac ttc atc atg act gac gac gtg gat gac atg<br>Arg Pro Asn Pro Ala His Phe Ile Met Thr Asp Asp Val Asp Asp Met<br>465                           470                      475                    480 | | 1440 |
| gat gag gag att gtg tct ccc ttg tcc atg cag tcc cct agc ctg cag<br>Asp Glu Glu Ile Val Ser Pro Leu Ser Met Gln Ser Pro Ser Leu Gln<br>                     485                      490                    495 | | 1488 |
| agc agt gtt cgg cag cgc ctg acg gag cca cag cat ggc ctg gga tct<br>Ser Ser Val Arg Gln Arg Leu Thr Glu Pro Gln His Gly Leu Gly Ser<br>              500                      505                    510 | | 1536 |
| cag agg gat ttg acc cat tcc gat tcg gag tcc tcc ctc cac atg agt<br>Gln Arg Asp Leu Thr His Ser Asp Ser Glu Ser Ser Leu His Met Ser<br>                     515                      520                    525 | | 1584 |
| gac cgc cag cgt gtg gcc ccc aaa cct cct cag atg agc cgt gct gca<br>Asp Arg Gln Arg Val Ala Pro Lys Pro Pro Gln Met Ser Arg Ala Ala<br>530                           535                      540 | | 1632 |
| gac gag gct ctc aat gcc atg act tcc aat ggc agc cac cgg ctg atc<br>Asp Glu Ala Leu Asn Ala Met Thr Ser Asn Gly Ser His Arg Leu Ile<br>545                           550                      555                    560 | | 1680 |
| gag ggg gtc cac cca ggg tct ctg gtg gag aaa ctg cct gac agc cct<br>Glu Gly Val His Pro Gly Ser Leu Val Glu Lys Leu Pro Asp Ser Pro<br>                       565                      570                    575 | | 1728 |
| gcc ctg gcc aag aag gca tta ctg gcg ctg aac cat ggg ctg gac aag<br>Ala Leu Ala Lys Lys Ala Leu Leu Ala Leu Asn His Gly Leu Asp Lys<br>                    580                      585                    590 | | 1776 |
| gcc cac agc ctg atg gag ctg agc ccc tca gcc cca cct ggt ggc tct<br>Ala His Ser Leu Met Glu Leu Ser Pro Ser Ala Pro Pro Gly Gly Ser<br>              595                      600                    605 | | 1824 |
| cca cat ttg gat tct tcc cgt tct cac agc ccc agc tcc cca gac cca<br>Pro His Leu Asp Ser Ser Arg Ser His Ser Pro Ser Ser Pro Asp Pro<br>610                           615                      620 | | 1872 |
| gac aca cca tct cca gtt ggg gac agc cga gcc ctg caa gcc agc cga<br>Asp Thr Pro Ser Pro Val Gly Asp Ser Arg Ala Leu Gln Ala Ser Arg | | 1920 |

```
                    625                 630                 635                 640
aac aca cgc att ccc cac ctg gct ggc aag aag gct gtg gct gag gag                    1968
Asn Thr Arg Ile Pro His Leu Ala Gly Lys Lys Ala Val Ala Glu Glu
                645                 650                 655 gat aat ggc tct att ggc gag gaa aca gac tcc agc cca ggc cgg aag                    2016
Asp Asn Gly Ser Ile Gly Glu Glu Thr Asp Ser Ser Pro Gly Arg Lys
                660                 665                 670 aag ttt cct ctc aaa atc ttt aag aag cct ctt aag aag tag                            2058
Lys Phe Pro Leu Lys Ile Phe Lys Lys Pro Leu Lys Lys  *
                675                 680                 685

<210> SEQ ID NO 83
<211> LENGTH: 685
<212> TYPE: PRT
<213> ORGANISM: Homo sapiens
<300> PUBLICATION INFORMATION:
<308> DATABASE ACCESSION NUMBER: Genbank NP_003147
<309> DATABASE ENTRY DATE: 2002-05-22

<400> SEQUENCE: 83

Met Asp Val Cys Val Arg Leu Ala Leu Trp Leu Leu Trp Gly Leu Leu
  1               5                  10                  15

Leu His Gln Gly Gln Ser Leu Ser His Ser His Ser Glu Lys Ala Thr
                 20                  25                  30

Gly Thr Ser Ser Gly Ala Asn Ser Glu Glu Ser Thr Ala Ala Glu Phe
             35                  40                  45

Cys Arg Ile Asp Lys Pro Leu Cys His Ser Glu Asp Glu Lys Leu Ser
         50                  55                  60

Phe Glu Ala Val Arg Asn Ile His Lys Leu Met Asp Asp Ala Asn
 65                  70                  75                  80

Gly Asp Val Asp Val Glu Glu Ser Asp Glu Phe Leu Arg Glu Asp Leu
                 85                  90                  95

Asn Tyr His Asp Pro Thr Val Lys His Ser Thr Phe His Gly Glu Asp
                100                 105                 110

Lys Leu Ile Ser Val Glu Asp Leu Trp Lys Ala Trp Lys Ser Ser Glu
            115                 120                 125

Val Tyr Asn Trp Thr Val Asp Glu Val Val Gln Trp Leu Ile Thr Tyr
        130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285
```

```
Glu Ile Asn Leu Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Lys Gln Leu Leu Val Ala Lys Glu Gly Ala Glu Lys Ile Lys
370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Pro Gly Ile His
        435                 440                 445

Ser Leu Val Ala Ala Leu Asn Ile Asp Pro Ser Trp Met Gly Ser Thr
450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Ser Arg Ala Ala
530                 535                 540

Asp Glu Ala Leu Asn Ala Met Thr Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Ala Leu Leu Ala Leu Asn His Gly Leu Asp Lys
            580                 585                 590

Ala His Ser Leu Met Glu Leu Ser Pro Ser Ala Pro Pro Gly Gly Ser
        595                 600                 605

Pro His Leu Asp Ser Ser Arg Ser His Ser Pro Ser Pro Asp Pro
610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 84
<211> LENGTH: 685
<212> TYPE: PRT
```

<213> ORGANISM: Homo sapiens
<300> PUBLICATION INFORMATION:
<308> DATABASE ACCESSION NUMBER: Swiss Prot Q13586
<309> DATABASE ENTRY DATE: 2002-06-01

<400> SEQUENCE: 84

Met Asp Val Cys Val Arg Leu Ala Leu Trp Leu Leu Trp Gly Leu Leu
1               5                   10                  15

Leu His Gln Gly Gln Ser Leu Ser His Ser His Ser Glu Lys Ala Thr
            20                  25                  30

Gly Thr Ser Ser Gly Ala Asn Ser Glu Glu Ser Thr Ala Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Val Gln Trp Leu Ile Thr Tyr
    130                 135                 140

Val Glu Leu Pro Gln Tyr Glu Glu Thr Phe Arg Lys Leu Gln Leu Ser
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Leu Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Lys Gln Leu Leu Val Ala Lys Glu Gly Ala Glu Lys Ile Lys
    370                 375                 380

-continued

```
Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
            405                 410                 415

Ser Glu Val Thr Ala Ala Leu Arg Glu Arg Leu His Arg Trp Gln Gln
        420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
    450                 455                 460

Arg Pro Asn Pro Ala His Phe Ile Met Thr Asp Val Asp Asp Met
465                 470                 475                 480

Asp Glu Glu Ile Val Ser Pro Leu Ser Met Gln Ser Pro Ser Leu Gln
                485                 490                 495

Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Ser Arg Ala Ala
    530                 535                 540

Asp Glu Ala Leu Asn Ala Met Thr Ser Asn Gly Arg His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Ala Leu Ala Leu Asn His Gly Leu Asp Lys
            580                 585                 590

Ala His Ser Leu Met Glu Leu Ser Pro Ser Ala Pro Pro Gly Gly Ser
        595                 600                 605

Pro His Leu Asp Ser Ser Arg Ser His Ser Pro Ser Pro Asp Pro
    610                 615                 620

Asp Thr Pro Ser Pro Val Gly Asp Ser Arg Ala Leu Gln Ala Ser Arg
625                 630                 635                 640

Asn Thr Arg Ile Pro His Leu Ala Gly Lys Lys Ala Val Ala Glu Glu
                645                 650                 655

Asp Asn Gly Ser Ile Gly Glu Gly Thr Asp Ser Ser Pro Gly Arg Lys
            660                 665                 670

Lys Phe Pro Leu Lys Ile Phe Lys Pro Leu Lys Lys
        675                 680                 685

<210> SEQ ID NO 85
<211> LENGTH: 685
<212> TYPE: PRT
<213> ORGANISM: Mus musculus
<300> PUBLICATION INFORMATION:
<308> DATABASE ACCESSION NUMBER: Swiss Prot P70302
<309> DATABASE ENTRY DATE: 2002-06-01

<400> SEQUENCE: 85

Met Asp Val Cys Ala Arg Leu Ala Leu Trp Leu Leu Trp Gly Leu Leu
1                   5                   10                  15

Leu His Gln Gly Gln Ser Leu Ser His Ser His Ser Glu Lys Asn Thr
            20                  25                  30

Gly Ala Ser Ser Gly Ala Thr Ser Glu Glu Ser Thr Glu Ala Glu Phe
        35                  40                  45

Cys Arg Ile Asp Lys Pro Leu Cys His Ser Glu Asp Glu Lys Leu Ser
    50                  55                  60
```

-continued

```
Phe Glu Ala Val Arg Asn Ile His Lys Leu Met Asp Asp Ala Asn
 65                  70                  75                  80

Gly Asp Val Asp Val Glu Ser Asp Glu Phe Leu Arg Glu Asp Leu
                 85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Ile Gln Trp Leu Ile Thr Tyr
    130                 135                 140

Val Glu Leu Pro Gln Tyr Glu Glu Thr Phe Arg Lys Leu Gln Leu Thr
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
    210                 215                 220

Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
                245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
        275                 280                 285

Glu Ile Asn Leu Ala Lys Gln Glu Ala Gln Arg Leu Lys Glu Leu Arg
    290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ser Lys Glu Leu Glu
                325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
        355                 360                 365

Ala Glu Arg Gln Leu Leu Val Ala Lys Glu Gly Ala Glu Lys Ile Lys
    370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
                405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
        435                 440                 445

Ser Leu Val Ala Ala Leu Asn Ile Asp Pro Ser Trp Met Gly Ser Thr
    450                 455                 460

Arg Pro Asn Pro Ala His Phe Ile Met Thr Asp Asp Val Asp Met
465                 470                 475                 480
```

-continued

```
Asp Glu Glu Ile Val Ser Pro Leu Ser Met Gln Ser Pro Ser Leu Gln
                485                 490                 495

Ser Ser Val Arg Gln Arg Leu Thr Glu Pro Gln Leu Gly Leu Gly Ser
            500                 505                 510

Gln Arg Asp Leu Thr His Ser Asp Ser Glu Ser Ser Leu His Met Ser
        515                 520                 525

Asp Arg Gln Arg Val Ala Pro Lys Pro Pro Gln Met Gly Arg Ala Ala
    530                 535                 540

Asp Glu Ala Leu Asn Ala Met Pro Ser Asn Gly Ser His Arg Leu Ile
545                 550                 555                 560

Glu Gly Val His Pro Gly Ser Leu Val Glu Lys Leu Pro Asp Ser Pro
                565                 570                 575

Ala Leu Ala Lys Lys Thr Phe Met Ala Leu Asn His Gly Leu Asp Lys
            580                 585                 590

Ala His Ser Leu Met Glu Leu Asn Pro Ser Val Pro Pro Gly Gly Ser
        595                 600                 605

Pro Leu Leu Asp Ser Ser His Ser Leu Ser Pro Ser Ser Pro Asp Pro
    610                 615                 620

Asp Thr Pro Ser Pro Val Gly Asp Asn Arg Ala Leu Gln Gly Ser Arg
625                 630                 635                 640

Asn Thr Arg Ile Pro His Leu Ala Gly Lys Lys Ala Met Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 86
<211> LENGTH: 2241
<212> TYPE: DNA
<213> ORGANISM: Homo sapiens
<220> FEATURE:
<221> NAME/KEY: CDS
<222> LOCATION: (1)...(2241)
<223> OTHER INFORMATION: STIM-2
<300> PUBLICATION INFORMATION:
<308> DATABASE ACCESSION NUMBER: Genbank NM_020860
<309> DATABASE ENTRY DATE: 2003-01-15

<400> SEQUENCE: 86 atg ctg gtg ctc ggg ctg ctg gta gcc gga gcg gcg gac gga tgc gag     48
Met Leu Val Leu Gly Leu Leu Val Ala Gly Ala Ala Asp Gly Cys Glu
 1               5                  10                  15 ctt gtg ccc cgg cac ctc cgc ggg cgg cgg gcg act ggc tct gcc gca     96
Leu Val Pro Arg His Leu Arg Gly Arg Arg Ala Thr Gly Ser Ala Ala
                20                  25                  30 act gcc gcc tcc tct ccc gcc gcg gcg gcc ggc gat agc ccg gcg ctc    144
Thr Ala Ala Ser Ser Pro Ala Ala Ala Ala Gly Asp Ser Pro Ala Leu
            35                  40                  45 atg aca gat ccc tgc atg tca ctg agt cca cca tgc ttt aca gaa gaa    192
Met Thr Asp Pro Cys Met Ser Leu Ser Pro Pro Cys Phe Thr Glu Glu
        50                  55                  60 gac aga ttt agt ctg gaa gct ctt caa aca ata cat aaa caa atg gat    240
Asp Arg Phe Ser Leu Glu Ala Leu Gln Thr Ile His Lys Gln Met Asp
 65                 70                  75                  80 gat gac aaa gat ggt gga att gaa gta gag gaa agt gat gaa ttc atc    288
Asp Asp Lys Asp Gly Gly Ile Glu Val Glu Glu Ser Asp Glu Phe Ile
                85                  90                  95 aga gaa gat atg aaa tat aaa gat gct act aat aaa cac agc cat ctg    336
```

-continued

```
                Arg Glu Asp Met Lys Tyr Lys Asp Ala Thr Asn Lys His Ser His Leu
                            100                 105                 110 cac aga gaa gat aaa cat ata acg att gag gat tta tgg aaa cga tgg            384
His Arg Glu Asp Lys His Ile Thr Ile Glu Asp Leu Trp Lys Arg Trp
            115                 120                 125 aaa aca tca gaa gtt cat aat tgg acc ctt gaa gac act ctt cag tgg            432
Lys Thr Ser Glu Val His Asn Trp Thr Leu Glu Asp Thr Leu Gln Trp
130                 135                 140 ttg ata gag ttt gtt gaa cta ccc caa tat gag aag aat ttt aga gac            480
Leu Ile Glu Phe Val Glu Leu Pro Gln Tyr Glu Lys Asn Phe Arg Asp
145                 150                 155                 160 aac aat gtc aaa gga acg aca ctt ccc agg ata gca gtg cac gaa cct            528
Asn Asn Val Lys Gly Thr Thr Leu Pro Arg Ile Ala Val His Glu Pro
                165                 170                 175 tca ttt atg atc tcc cag ttg aaa atc agt gac cgg agt cac aga caa            576
Ser Phe Met Ile Ser Gln Leu Lys Ile Ser Asp Arg Ser His Arg Gln
                180                 185                 190 aaa ctt cag ctc aag gca ttg gat gtg gtt ttg ttt gga cct cta aca            624
Lys Leu Gln Leu Lys Ala Leu Asp Val Val Leu Phe Gly Pro Leu Thr
            195                 200                 205 cgc cca cct cat aac tgg atg aaa gat ttt atc ctc aca gtt tct ata            672
Arg Pro Pro His Asn Trp Met Lys Asp Phe Ile Leu Thr Val Ser Ile
210                 215                 220 gta att ggt gtt gga ggc tgc tgg ttt gct tat acg cag aat aag aca            720
Val Ile Gly Val Gly Gly Cys Trp Phe Ala Tyr Thr Gln Asn Lys Thr
225                 230                 235                 240 tca aaa gaa cat gtt gca aaa atg atg aaa gat tta gag agc tta caa            768
Ser Lys Glu His Val Ala Lys Met Met Lys Asp Leu Glu Ser Leu Gln
                245                 250                 255 act gca gag caa agt cta atg gac tta caa gag agg ctt gaa aag gca            816
Thr Ala Glu Gln Ser Leu Met Asp Leu Gln Glu Arg Leu Glu Lys Ala
            260                 265                 270 cag gaa gaa aac aga aat gtt gct gta gaa aag caa aat tta gag cgc            864
Gln Glu Glu Asn Arg Asn Val Ala Val Glu Lys Gln Asn Leu Glu Arg
        275                 280                 285 aaa atg atg gat gaa atc aat tat gca aag gag gag gct tgt cgg ctg            912
Lys Met Met Asp Glu Ile Asn Tyr Ala Lys Glu Glu Ala Cys Arg Leu
290                 295                 300 aga gag cta agg gag gga gct gaa tgt gaa ttg agt aga cgt cag tat            960
Arg Glu Leu Arg Glu Gly Ala Glu Cys Glu Leu Ser Arg Arg Gln Tyr
305                 310                 315                 320 gca gaa cag gaa ttg gaa cag gtt cgc atg gct ctg aaa aag gcc gaa           1008
Ala Glu Gln Glu Leu Glu Gln Val Arg Met Ala Leu Lys Lys Ala Glu
                325                 330                 335 aaa gaa ttt gaa ctg aga agc agt tgg tct gtt cca gat gca ctt cag           1056
Lys Glu Phe Glu Leu Arg Ser Ser Trp Ser Val Pro Asp Ala Leu Gln
            340                 345                 350 aaa tgg ctt cag tta aca cat gaa gta gaa gtg caa tac tac aat att           1104
Lys Trp Leu Gln Leu Thr His Glu Val Glu Val Gln Tyr Tyr Asn Ile
        355                 360                 365 aaa aga caa aac gct gaa atg cag cta gct att gct aaa gat gag gca           1152
Lys Arg Gln Asn Ala Glu Met Gln Leu Ala Ile Ala Lys Asp Glu Ala
370                 375                 380 gaa aaa att aaa aag aag aga agc aca gtc ttt ggg act ctg cac gtt           1200
Glu Lys Ile Lys Lys Lys Arg Ser Thr Val Phe Gly Thr Leu His Val
385                 390                 395                 400 gca cac agc tcc tcc cta gat gag gta gac cac aaa att ctg gaa gca           1248
Ala His Ser Ser Ser Leu Asp Glu Val Asp His Lys Ile Leu Glu Ala
                405                 410                 415
```

```
aag aaa gct ctc tct gag ttg aca act tgt tta cga gaa cga ctt ttt    1296
Lys Lys Ala Leu Ser Glu Leu Thr Thr Cys Leu Arg Glu Arg Leu Phe
            420                 425                 430 cgc tgg caa caa att gag aag atc tgt ggc ttt cag ata gcc cat aac    1344
Arg Trp Gln Gln Ile Glu Lys Ile Cys Gly Phe Gln Ile Ala His Asn
        435                 440                 445 tca gga ctc ccc agc ctg acc tct tcc ctt tat tct gat cac agc tgg    1392
Ser Gly Leu Pro Ser Leu Thr Ser Ser Leu Tyr Ser Asp His Ser Trp
    450                 455                 460 gtg gtg atg ccc aga gtc tcc att cca ccc tat cca att gct gga gga    1440
Val Val Met Pro Arg Val Ser Ile Pro Pro Tyr Pro Ile Ala Gly Gly
465                 470                 475                 480 gtt gat gac tta gat gaa gac aca ccc cca ata gtg tca caa ttt ccc    1488
Val Asp Asp Leu Asp Glu Asp Thr Pro Pro Ile Val Ser Gln Phe Pro
                485                 490                 495 ggg acc atg gct aaa cct cct gga tca tta gcc aga agc agc agc ctg    1536
Gly Thr Met Ala Lys Pro Pro Gly Ser Leu Ala Arg Ser Ser Ser Leu
            500                 505                 510 tgc cgt tca cgc cgc agc att gtg ccg tcc tcg cct cag cct cag cga    1584
Cys Arg Ser Arg Arg Ser Ile Val Pro Ser Ser Pro Gln Pro Gln Arg
        515                 520                 525 gct cag ctt gct cca cac gcc ccc cac ccg tca cac cct cgg cac cct    1632
Ala Gln Leu Ala Pro His Ala Pro His Pro Ser His Pro Arg His Pro
    530                 535                 540 cac cac ccg caa cac aca cca cac tcc ttg cct tcc cct gat cca gat    1680
His His Pro Gln His Thr Pro His Ser Leu Pro Ser Pro Asp Pro Asp
545                 550                 555                 560 atc ctc tca gtg tca agt tgc cct gcg ctt tat cga aat gaa gag gag    1728
Ile Leu Ser Val Ser Ser Cys Pro Ala Leu Tyr Arg Asn Glu Glu Glu
                565                 570                 575 gaa gag gcc att tac ttc tct gct gaa aag caa tgg gaa gtg cca gac    1776
Glu Glu Ala Ile Tyr Phe Ser Ala Glu Lys Gln Trp Glu Val Pro Asp
            580                 585                 590 aca gct tca gaa tgt gac tcc tta aat tct tcc att gga agg aaa cag    1824
Thr Ala Ser Glu Cys Asp Ser Leu Asn Ser Ser Ile Gly Arg Lys Gln
        595                 600                 605 tct cct cct tta agc ctc gag ata tac caa aca tta tct ccg cga aag    1872
Ser Pro Pro Leu Ser Leu Glu Ile Tyr Gln Thr Leu Ser Pro Arg Lys
    610                 615                 620 ata tca aga gat gag gtg tcc cta gag gat tcc tcc cga ggg gat tcg    1920
Ile Ser Arg Asp Glu Val Ser Leu Glu Asp Ser Ser Arg Gly Asp Ser
625                 630                 635                 640 cct gta act gtg gat gtg tct tgg ggt tct ccc gac tgt gta ggt ctg    1968
Pro Val Thr Val Asp Val Ser Trp Gly Ser Pro Asp Cys Val Gly Leu
                645                 650                 655 aca gaa act aag agt atg atc ttc agt cct gca agc aaa gtg tac aat    2016
Thr Glu Thr Lys Ser Met Ile Phe Ser Pro Ala Ser Lys Val Tyr Asn
            660                 665                 670 ggc att ttg gag aaa tcc tgt agc atg aac cag ctt tcc agt ggc atc    2064
Gly Ile Leu Glu Lys Ser Cys Ser Met Asn Gln Leu Ser Ser Gly Ile
        675                 680                 685 ccg gtg cct aaa cct cgc cac aca tca tgt tcc tca gct ggc aac gac    2112
Pro Val Pro Lys Pro Arg His Thr Ser Cys Ser Ser Ala Gly Asn Asp
    690                 695                 700 agt aaa cca gtt cag gaa gcc cca agt gtt gcc aga ata agc agc atc    2160
Ser Lys Pro Val Gln Glu Ala Pro Ser Val Ala Arg Ile Ser Ser Ile
705                 710                 715                 720 cca cat gac ctt tgt cat aat gga gag aaa agc aag aag cca tca aaa    2208
Pro His Asp Leu Cys His Asn Gly Glu Lys Ser Lys Lys Pro Ser Lys
                725                 730                 735
```

```
atc aaa agc ctt ttt aag aag aaa tct aag tga                                    2241
Ile Lys Ser Leu Phe Lys Lys Lys Ser Lys *
        740                 745
```

<210> SEQ ID NO 87
<211> LENGTH: 746
<212> TYPE: PRT
<213> ORGANISM: Homo sapiens
<300> PUBLICATION INFORMATION:
<308> DATABASE ACCESSION NUMBER: Genbank NP_065911
<309> DATABASE ENTRY DATE: 2003-01-15

<400> SEQUENCE: 87

```
Met Leu Val Leu Gly Leu Leu Val Ala Gly Ala Ala Asp Gly Cys Glu
 1               5                  10                  15

Leu Val Pro Arg His Leu Arg Gly Arg Arg Ala Thr Gly Ser Ala Ala
             20                  25                  30

Thr Ala Ala Ser Ser Pro Ala Ala Ala Gly Asp Ser Pro Ala Leu
         35                  40                  45

Met Thr Asp Pro Cys Met Ser Leu Ser Pro Pro Cys Phe Thr Glu Glu
 50                  55                  60

Asp Arg Phe Ser Leu Glu Ala Leu Gln Thr Ile His Lys Gln Met Asp
 65                  70                  75                  80

Asp Asp Lys Asp Gly Gly Ile Glu Val Glu Ser Asp Glu Phe Ile
                 85                  90                  95

Arg Glu Asp Met Lys Tyr Lys Asp Ala Thr Asn Lys His Ser His Leu
             100                 105                 110

His Arg Glu Asp Lys His Ile Thr Ile Glu Asp Leu Trp Lys Arg Trp
         115                 120                 125

Lys Thr Ser Glu Val His Asn Trp Thr Leu Glu Asp Thr Leu Gln Trp
     130                 135                 140

Leu Ile Glu Phe Val Glu Leu Pro Gln Tyr Glu Lys Asn Phe Arg Asp
145                 150                 155                 160

Asn Asn Val Lys Gly Thr Thr Leu Pro Arg Ile Ala Val His Glu Pro
                 165                 170                 175

Ser Phe Met Ile Ser Gln Leu Lys Ile Ser Asp Arg Ser His Arg Gln
             180                 185                 190

Lys Leu Gln Leu Lys Ala Leu Asp Val Val Leu Phe Gly Pro Leu Thr
         195                 200                 205

Arg Pro Pro His Asn Trp Met Lys Asp Phe Ile Leu Thr Val Ser Ile
     210                 215                 220

Val Ile Gly Val Gly Gly Cys Trp Phe Ala Tyr Thr Gln Asn Lys Thr
225                 230                 235                 240

Ser Lys Glu His Val Ala Lys Met Met Lys Asp Leu Glu Ser Leu Gln
                 245                 250                 255

Thr Ala Glu Gln Ser Leu Met Asp Leu Gln Glu Arg Leu Glu Lys Ala
             260                 265                 270

Gln Glu Glu Asn Arg Asn Val Ala Val Glu Lys Gln Asn Leu Glu Arg
         275                 280                 285

Lys Met Met Asp Glu Ile Asn Tyr Ala Lys Glu Ala Cys Arg Leu
     290                 295                 300

Arg Glu Leu Arg Glu Gly Ala Glu Cys Glu Leu Ser Arg Arg Gln Tyr
305                 310                 315                 320

Ala Glu Gln Glu Leu Glu Gln Val Arg Met Ala Leu Lys Lys Ala Glu
                 325                 330                 335
```

-continued

```
Lys Glu Phe Glu Leu Arg Ser Ser Trp Ser Val Pro Asp Ala Leu Gln
                340                 345                 350

Lys Trp Leu Gln Leu Thr His Glu Val Glu Val Gln Tyr Tyr Asn Ile
                355                 360                 365

Lys Arg Gln Asn Ala Glu Met Gln Leu Ala Ile Ala Lys Asp Glu Ala
            370                 375                 380

Glu Lys Ile Lys Lys Arg Ser Thr Val Phe Gly Thr Leu His Val
385                 390                 395                 400

Ala His Ser Ser Ser Leu Asp Glu Val Asp His Lys Ile Leu Glu Ala
                405                 410                 415

Lys Lys Ala Leu Ser Glu Leu Thr Thr Cys Leu Arg Glu Arg Leu Phe
            420                 425                 430

Arg Trp Gln Gln Ile Glu Lys Ile Cys Gly Phe Gln Ile Ala His Asn
                435                 440                 445

Ser Gly Leu Pro Ser Leu Thr Ser Ser Leu Tyr Ser Asp His Ser Trp
        450                 455                 460

Val Val Met Pro Arg Val Ser Ile Pro Pro Tyr Pro Ile Ala Gly Gly
465                 470                 475                 480

Val Asp Asp Leu Asp Glu Asp Thr Pro Pro Ile Val Ser Gln Phe Pro
                485                 490                 495

Gly Thr Met Ala Lys Pro Pro Gly Ser Leu Ala Arg Ser Ser Ser Leu
            500                 505                 510

Cys Arg Ser Arg Arg Ser Ile Val Pro Ser Pro Gln Pro Gln Arg
                515                 520                 525

Ala Gln Leu Ala Pro His Ala Pro His Pro Ser His Pro Arg His Pro
        530                 535                 540

His His Pro Gln His Thr Pro His Ser Leu Pro Ser Pro Asp Pro Asp
545                 550                 555                 560

Ile Leu Ser Val Ser Ser Cys Pro Ala Leu Tyr Arg Asn Glu Glu Glu
                565                 570                 575

Glu Glu Ala Ile Tyr Phe Ser Ala Glu Lys Gln Trp Glu Val Pro Asp
            580                 585                 590

Thr Ala Ser Glu Cys Asp Ser Leu Asn Ser Ser Ile Gly Arg Lys Gln
                595                 600                 605

Ser Pro Pro Leu Ser Leu Glu Ile Tyr Gln Thr Leu Ser Pro Arg Lys
        610                 615                 620

Ile Ser Arg Asp Glu Val Ser Leu Glu Asp Ser Ser Arg Gly Asp Ser
625                 630                 635                 640

Pro Val Thr Val Asp Val Ser Trp Gly Ser Pro Asp Cys Val Gly Leu
                645                 650                 655

Thr Glu Thr Lys Ser Met Ile Phe Ser Pro Ala Ser Lys Val Tyr Asn
            660                 665                 670

Gly Ile Leu Glu Lys Ser Cys Ser Met Asn Gln Leu Ser Ser Gly Ile
                675                 680                 685

Pro Val Pro Lys Pro Arg His Thr Ser Cys Ser Ser Ala Gly Asn Asp
        690                 695                 700

Ser Lys Pro Val Gln Glu Ala Pro Ser Val Ala Arg Ile Ser Ser Ile
705                 710                 715                 720

Pro His Asp Leu Cys His Asn Gly Glu Lys Ser Lys Lys Pro Ser Lys
                725                 730                 735

Ile Lys Ser Leu Phe Lys Lys Ser Lys
            740                 745
```

```
<210> SEQ ID NO 88
<211> LENGTH: 746
<212> TYPE: PRT
<213> ORGANISM: Homo sapiens
<300> PUBLICATION INFORMATION:
<308> DATABASE ACCESSION NUMBER: Swiss Prot Q9P246
<309> DATABASE ENTRY DATE: 2002-06-01

<400> SEQUENCE: 88
```

| | | | | | | | | | | | | | | | |
|---|---|---|---|---|---|---|---|---|---|---|---|---|---|---|---|
| Met | Leu | Val | Leu | Gly | Leu | Leu | Val | Ala | Gly | Ala | Ala | Asp | Gly | Cys | Glu |
| 1 | | | | 5 | | | | | 10 | | | | | 15 | |
| Leu | Val | Pro | Arg | His | Leu | Arg | Gly | Arg | Arg | Ala | Thr | Gly | Ser | Ala | Ala |
| | | | 20 | | | | | 25 | | | | | 30 | | |
| Thr | Ala | Ala | Ser | Ser | Pro | Ala | Ala | Ala | Gly | Asp | Ser | Pro | Ala | Leu | |
| | | 35 | | | | | 40 | | | | | 45 | | | |
| Met | Thr | Asp | Pro | Cys | Met | Ser | Leu | Ser | Pro | Pro | Cys | Phe | Thr | Glu | Glu |
| | 50 | | | | | 55 | | | | | 60 | | | | |
| Asp | Arg | Phe | Ser | Leu | Glu | Ala | Leu | Gln | Thr | Ile | His | Lys | Gln | Met | Asp |
| 65 | | | | | 70 | | | | | 75 | | | | | 80 |
| Asp | Asp | Lys | Asp | Gly | Gly | Ile | Glu | Val | Glu | Glu | Ser | Asp | Glu | Phe | Ile |
| | | | | 85 | | | | | 90 | | | | | 95 | |
| Arg | Glu | Asp | Met | Lys | Tyr | Lys | Asp | Ala | Thr | Asn | Lys | His | Ser | His | Leu |
| | | | 100 | | | | | 105 | | | | | 110 | | |
| His | Arg | Glu | Asp | Lys | His | Ile | Thr | Ile | Glu | Asp | Leu | Trp | Lys | Arg | Trp |
| | | 115 | | | | | 120 | | | | | 125 | | | |
| Lys | Thr | Ser | Glu | Val | His | Asn | Trp | Thr | Leu | Glu | Asp | Thr | Leu | Gln | Trp |
| | 130 | | | | | 135 | | | | | 140 | | | | |
| Leu | Ile | Glu | Phe | Val | Glu | Leu | Pro | Gln | Tyr | Glu | Lys | Asn | Phe | Arg | Asp |
| 145 | | | | | 150 | | | | | 155 | | | | | 160 |
| Asn | Asn | Val | Lys | Gly | Thr | Thr | Leu | Pro | Arg | Ile | Ala | Val | His | Glu | Pro |
| | | | | 165 | | | | | 170 | | | | | 175 | |
| Ser | Phe | Met | Ile | Ser | Gln | Leu | Lys | Ile | Ser | Asp | Arg | Ser | His | Arg | Gln |
| | | | 180 | | | | | 185 | | | | | 190 | | |
| Lys | Leu | Gln | Leu | Lys | Ala | Leu | Asp | Val | Val | Leu | Phe | Gly | Pro | Leu | Thr |
| | | 195 | | | | | 200 | | | | | 205 | | | |
| Arg | Pro | Pro | His | Asn | Trp | Met | Lys | Asp | Phe | Ile | Leu | Thr | Val | Ser | Ile |
| | 210 | | | | | 215 | | | | | 220 | | | | |
| Val | Ile | Gly | Val | Gly | Gly | Cys | Trp | Phe | Ala | Tyr | Thr | Gln | Asn | Lys | Thr |
| 225 | | | | | 230 | | | | | 235 | | | | | 240 |
| Ser | Lys | Glu | His | Val | Ala | Lys | Met | Met | Lys | Asp | Leu | Glu | Ser | Leu | Gln |
| | | | | 245 | | | | | 250 | | | | | 255 | |
| Thr | Ala | Glu | Gln | Ser | Leu | Met | Asp | Leu | Gln | Glu | Arg | Leu | Glu | Lys | Ala |
| | | | 260 | | | | | 265 | | | | | 270 | | |
| Gln | Glu | Glu | Asn | Arg | Asn | Val | Ala | Val | Glu | Lys | Gln | Asn | Leu | Glu | Arg |
| | | 275 | | | | | 280 | | | | | 285 | | | |
| Lys | Met | Met | Asp | Glu | Ile | Asn | Tyr | Ala | Lys | Glu | Ala | Cys | Arg | Leu | |
| | 290 | | | | | 295 | | | | | 300 | | | | |
| Arg | Glu | Leu | Arg | Glu | Gly | Ala | Glu | Cys | Glu | Leu | Ser | Arg | Arg | Gln | Tyr |
| 305 | | | | | 310 | | | | | 315 | | | | | 320 |
| Ala | Glu | Gln | Glu | Leu | Glu | Gln | Val | Arg | Met | Ala | Leu | Lys | Lys | Ala | Glu |
| | | | | 325 | | | | | 330 | | | | | 335 | |
| Lys | Glu | Phe | Glu | Leu | Arg | Ser | Ser | Trp | Ser | Val | Pro | Asp | Ala | Leu | Gln |
| | | | 340 | | | | | 345 | | | | | 350 | | |
| Lys | Trp | Leu | Gln | Leu | Thr | His | Glu | Val | Glu | Val | Gln | Tyr | Tyr | Asn | Ile |
| | | 355 | | | | | 360 | | | | | 365 | | | |

```
Lys Arg Gln Asn Ala Glu Met Gln Leu Ala Ile Ala Lys Asp Glu Ala
    370                 375                 380

Glu Lys Ile Lys Lys Arg Ser Thr Val Phe Gly Thr Leu His Val
385                 390                 395                 400

Ala His Ser Ser Ser Leu Asp Glu Val Asp His Lys Ile Leu Glu Ala
                405                 410                 415

Lys Lys Ala Leu Ser Glu Leu Thr Thr Cys Leu Arg Glu Arg Leu Phe
            420                 425                 430

Arg Trp Gln Gln Ile Glu Lys Ile Cys Gly Phe Gln Ile Ala His Asn
        435                 440                 445

Ser Gly Leu Pro Ser Leu Thr Ser Ser Leu Tyr Ser Asp His Ser Trp
    450                 455                 460

Val Val Met Pro Arg Val Ser Ile Pro Pro Tyr Pro Ile Ala Gly Gly
465                 470                 475                 480

Val Asp Asp Leu Asp Glu Asp Thr Pro Ile Val Ser Gln Phe Pro
                485                 490                 495

Gly Thr Met Ala Lys Pro Pro Gly Ser Leu Ala Arg Ser Ser Ser Leu
                500                 505                 510

Cys Arg Ser Arg Arg Ser Ile Val Pro Ser Ser Pro Gln Pro Gln Arg
            515                 520                 525

Ala Gln Leu Ala Pro His Ala Pro His Pro Ser His Pro Arg His Pro
        530                 535                 540

His His Pro Gln His Thr Pro His Ser Leu Pro Ser Pro Asp Pro Asp
545                 550                 555                 560

Ile Leu Ser Val Ser Ser Cys Pro Ala Leu Tyr Arg Asn Glu Glu Glu
                565                 570                 575

Glu Glu Ala Ile Tyr Phe Ser Ala Glu Lys Gln Trp Glu Val Pro Asp
            580                 585                 590

Thr Ala Ser Glu Cys Asp Ser Leu Asn Ser Ser Ile Gly Arg Lys Gln
        595                 600                 605

Ser Pro Pro Leu Ser Leu Glu Ile Tyr Gln Thr Leu Ser Pro Arg Lys
    610                 615                 620

Ile Ser Arg Asp Glu Val Ser Leu Glu Asp Ser Ser Arg Gly Asp Ser
625                 630                 635                 640

Pro Val Thr Val Asp Val Ser Trp Gly Ser Pro Asp Cys Val Gly Leu
                645                 650                 655

Thr Glu Thr Lys Ser Met Ile Phe Ser Pro Ala Ser Lys Val Tyr Asn
            660                 665                 670

Gly Ile Leu Glu Lys Ser Cys Ser Met Asn Gln Leu Ser Ser Gly Ile
        675                 680                 685

Pro Val Pro Lys Pro Arg His Thr Ser Cys Ser Ser Ala Gly Asn Asp
    690                 695                 700

Ser Lys Pro Val Gln Glu Ala Pro Ser Val Ala Arg Ile Ser Ser Ile
705                 710                 715                 720

Pro His Asp Leu Cys His Asn Gly Glu Lys Ser Lys Pro Ser Lys
                725                 730                 735

Ile Lys Ser Leu Phe Lys Lys Ser Lys
            740                 745

<210> SEQ ID NO 89
<211> LENGTH: 2058
<212> TYPE: DNA
<213> ORGANISM: Artificial Sequence
<220> FEATURE:
<223> OTHER INFORMATION: STIM Consensus Sequence
```

<220> FEATURE:
<221> NAME/KEY: CDS
<222> LOCATION: (1)...(2058)
<223> OTHER INFORMATION: STIM Consensus Sequence
<220> FEATURE:
<221> NAME/KEY: misc_feature
<222> LOCATION: 108,197,203,621,861,1062,1107,1392,1654,1749
<223> OTHER INFORMATION: n is a, t, g or c

<400> SEQUENCE: 89

```
atg gat gtg tgc gcc cgt ctt gcc ctg tgg ctt ctt tgg ggg ctc ctc      48
Met Asp Val Cys Ala Arg Leu Ala Leu Trp Leu Leu Trp Gly Leu Leu
 1               5                  10                  15 ctg cat cag ggc cag agc ctc agc cat agt cac agt gaa aag aat aca      96
Leu His Gln Gly Gln Ser Leu Ser His Ser His Ser Glu Lys Asn Thr
             20                  25                  30 gga gcc agc tcn ggg gcg act tct gag gag tcc act gaa gca gag ttt     144
Gly Ala Ser Ser Gly Ala Thr Ser Glu Glu Ser Thr Glu Ala Glu Phe
         35                  40                  45 tgc cga att gac aag ccc ctg tgc cac agt gag gat gag aag ctc agc     192
Cys Arg Ile Asp Lys Pro Leu Cys His Ser Glu Asp Glu Lys Leu Ser
     50                  55                  60 ttc gag gcn gtc cgn aac atc cac aag ctg atg gat gat gat gcc aat     240
Phe Glu Ala Val Arg Asn Ile His Lys Leu Met Asp Asp Asp Ala Asn
 65                  70                  75                  80 ggt gat gtg gat gtg gaa gaa agt gat gag ttc cta agg gaa gac ctc     288
Gly Asp Val Asp Val Glu Glu Ser Asp Glu Phe Leu Arg Glu Asp Leu
                 85                  90                  95 aat tac cat gac cca aca gtg aaa cac agc acc ttc cat ggt gag gat     336
Asn Tyr His Asp Pro Thr Val Lys His Ser Thr Phe His Gly Glu Asp
            100                 105                 110 aag ctt atc agc gtg gag gac ctg tgg aag gca tgg aag tca tca gaa     384
Lys Leu Ile Ser Val Glu Asp Leu Trp Lys Ala Trp Lys Ser Ser Glu
        115                 120                 125 gtg tac aac tgg act gtg gat gag gtg ata cag tgg ctg att acg tat     432
Val Tyr Asn Trp Thr Val Asp Glu Val Ile Gln Trp Leu Ile Thr Tyr
    130                 135                 140 gtg gag ctg cct cag tat gag gag acc ttc cgg aag ttg cag ctt act     480
Val Glu Leu Pro Gln Tyr Glu Glu Thr Phe Arg Lys Leu Gln Leu Thr
145                 150                 155                 160 ggc cat gcc atg cca agg cta gct gta acc aac acc acc atg aca ggg     528
Gly His Ala Met Pro Arg Leu Ala Val Thr Asn Thr Thr Met Thr Gly
                165                 170                 175 act gta ctg aag atg aca gat cgg agc cac agg cag aag ctg cag ctg     576
Thr Val Leu Lys Met Thr Asp Arg Ser His Arg Gln Lys Leu Gln Leu
            180                 185                 190 aag gcc ctg gat aca gtg ctc ttt ggg cct cct ctc ttg act cgn cat     624
Lys Ala Leu Asp Thr Val Leu Phe Gly Pro Pro Leu Leu Thr Arg His
        195                 200                 205 aat cac ctc aag gac ttc atg ctg gtg gtg tct atc gtt att ggt gtg     672
Asn His Leu Lys Asp Phe Met Leu Val Val Ser Ile Val Ile Gly Val
    210                 215                 220 ggc ggc tgc tgg ttt gcc tat atc cag aac cgt tac tcc aag gag cac     720
Gly Gly Cys Trp Phe Ala Tyr Ile Gln Asn Arg Tyr Ser Lys Glu His
225                 230                 235                 240 atg aag aag atg atg aag gat ctg gaa ggg tta cac cga gct gag cag     768
Met Lys Lys Met Met Lys Asp Leu Glu Gly Leu His Arg Ala Glu Gln
                245                 250                 255 agt ctg cat gac ctt cag gaa agg ctg cac aag gcc cag gag gag cac     816
Ser Leu His Asp Leu Gln Glu Arg Leu His Lys Ala Gln Glu Glu His
            260                 265                 270
```

```
cgc aca gtg gaa gta gag aag gtc cat ctg gag aag aag ctg cgn gat      864
Arg Thr Val Glu Val Glu Lys Val His Leu Glu Lys Lys Leu Arg Asp
        275                 280                 285 gag atc aac ctt gcc aag cag gaa gct cag cgg ctg aag gag ctg agg      912
Glu Ile Asn Leu Ala Lys Gln Glu Ala Gln Arg Leu Lys Glu Leu Arg
    290                 295                 300 gag ggt act gag aat gag agg agc cgc caa aaa tat gct gag gaa gag      960
Glu Gly Thr Glu Asn Glu Arg Ser Arg Gln Lys Tyr Ala Glu Glu Glu
305                 310                 315                 320 ctg gag cag gtt cgg gag gcc ttg agg aaa gca gag aag gag ctg gaa     1008
Leu Glu Gln Val Arg Glu Ala Leu Arg Lys Ala Glu Lys Glu Leu Glu
            325                 330                 335 tca cac agc tca tgg tat gct cct gag gcc ctt cag aag tgg ctg cag     1056
Ser His Ser Ser Trp Tyr Ala Pro Glu Ala Leu Gln Lys Trp Leu Gln
                340                 345                 350 ctg acn cat gag gtg gag gtg cag tac tac aac atc aag aag caa aat     1104
Leu Thr His Glu Val Glu Val Gln Tyr Tyr Asn Ile Lys Lys Gln Asn
        355                 360                 365 gcn gag aag cag ctg ctg gtg gcc aag gag ggg gct gag aaa ata aaa     1152
Ala Glu Lys Gln Leu Leu Val Ala Lys Glu Gly Ala Glu Lys Ile Lys
370                 375                 380 aag aag aga aac acg ctt ttt ggt acc ttc cat gtg gcc cac agc tct     1200
Lys Lys Arg Asn Thr Leu Phe Gly Thr Phe His Val Ala His Ser Ser
385                 390                 395                 400 tcc ctg gat gat gtg gat cat aaa atc cta act gct aag caa gca ctg     1248
Ser Leu Asp Asp Val Asp His Lys Ile Leu Thr Ala Lys Gln Ala Leu
            405                 410                 415 agc gag gtg aca gca gca ctg agg gag cgc ctg cac cgg tgg cag cag     1296
Ser Glu Val Thr Ala Ala Leu Arg Glu Arg Leu His Arg Trp Gln Gln
                420                 425                 430 atc gag atc ctc tgt ggc ttc cag att gtc aat aac cct ggc atc cac     1344
Ile Glu Ile Leu Cys Gly Phe Gln Ile Val Asn Asn Pro Gly Ile His
        435                 440                 445 tcc ttg gtg gct gcc ctc aac ata gac ccc agc tgg atg ggc agt acn     1392
Ser Leu Val Ala Ala Leu Asn Ile Asp Pro Ser Trp Met Gly Ser Thr
    450                 455                 460 cgc cct aac cct gcc cac ttc atc atg act gac gat gtg gat gac atg     1440
Arg Pro Asn Pro Ala His Phe Ile Met Thr Asp Asp Val Asp Asp Met
465                 470                 475                 480 gat gag gag att gtg tcg ccc ttg tcc atg cag tcc ccc agc ctg cag     1488
Asp Glu Glu Ile Val Ser Pro Leu Ser Met Gln Ser Pro Ser Leu Gln
            485                 490                 495 agc agt gtc cgg cag cgc ctg acg gag cca cag cat ggc ctg gga tct     1536
Ser Ser Val Arg Gln Arg Leu Thr Glu Pro Gln His Gly Leu Gly Ser
                500                 505                 510 cag agg gat ttg acc cat tcc gat tcg gag tcc tcc ctc cac atg agt     1584
Gln Arg Asp Leu Thr His Ser Asp Ser Glu Ser Ser Leu His Met Ser
        515                 520                 525 gac cgc cag cgt gtg gcc ccc aag cct cct cag atg ggc cgt gct gca     1632
Asp Arg Gln Arg Val Ala Pro Lys Pro Pro Gln Met Gly Arg Ala Ala
    530                 535                 540 gat gag gct ctc aat gcc atg nct tcc aat ggc agc cat cgg ctg att     1680
Asp Glu Ala Leu Asn Ala Met Xaa Ser Asn Gly Ser His Arg Leu Ile
545                 550                 555                 560 gag ggg gtc cat cca gga tct ctg gtg gag aaa ctg cct gac agc cct     1728
Glu Gly Val His Pro Gly Ser Leu Val Glu Lys Leu Pro Asp Ser Pro
            565                 570                 575 gct ctg gcc aag aag aca ttn ctg gcg ctg aac cat ggc cta gac aag     1776
Ala Leu Ala Lys Lys Thr Xaa Leu Ala Leu Asn His Gly Leu Asp Lys
                580                 585                 590
```

```
gcc cac agc ctg atg gag ctg aac ccc tca gtc cca cct ggt ggc tcc    1824
Ala His Ser Leu Met Glu Leu Asn Pro Ser Val Pro Pro Gly Gly Ser
        595                 600                 605 cca ctt ttg gat tct tcc cat tct cat agc ccc agt tcc cca gac cca    1872
Pro Leu Leu Asp Ser Ser His Ser His Ser Pro Ser Ser Pro Asp Pro
    610                 615                 620 gac aca cca tct cca gtt ggg gac agc cga gct ctg cag ggt agc cga    1920
Asp Thr Pro Ser Pro Val Gly Asp Ser Arg Ala Leu Gln Gly Ser Arg
625                 630                 635                 640 aac aca cga att ccc cac ttg gct ggc aag aag gct gtg gct gag gag    1968
Asn Thr Arg Ile Pro His Leu Ala Gly Lys Lys Ala Val Ala Glu Glu
                645                 650                 655 gat aat ggt tct att ggt gag gag aca gac tcc agc cca ggc agg aag    2016
Asp Asn Gly Ser Ile Gly Glu Glu Thr Asp Ser Ser Pro Gly Arg Lys
            660                 665                 670 aag ttt cct ctc aaa att ttt aag aag cct ctt aag aag tag            2058
Lys Phe Pro Leu Lys Ile Phe Lys Lys Pro Leu Lys Lys *
        675                 680                 685
```

<210> SEQ ID NO 90
<211> LENGTH: 685
<212> TYPE: PRT
<213> ORGANISM: Artificial Sequence
<220> FEATURE:
<223> OTHER INFORMATION: STIM Consensus Sequence
<220> FEATURE:
<221> NAME/KEY: VARIANT
<222> LOCATION: 552, 583
<223> OTHER INFORMATION: Xaa is any amino acid

<400> SEQUENCE: 90

```
Met Asp Val Cys Ala Arg Leu Ala Leu Trp Leu Leu Trp Gly Leu Leu
 1               5                  10                  15

Leu His Gln Gly Gln Ser Leu Ser His Ser His Ser Glu Lys Asn Thr
            20                  25                  30

Gly Ala Ser Ser Gly Ala Thr Ser Glu Glu Ser Thr Glu Ala Glu Phe
        35                  40                  45

Cys Arg Ile Asp Lys Pro Leu Cys His Ser Glu Asp Glu Lys Leu Ser
    50                  55                  60

Phe Glu Ala Val Arg Asn Ile His Lys Leu Met Asp Asp Ala Asn
65                  70                  75                  80

Gly Asp Val Asp Val Glu Glu Ser Asp Glu Phe Leu Arg Glu Asp Leu
                85                  90                  95

Asn Tyr His Asp Pro Thr Val Lys His Ser Thr Phe His Gly Glu Asp
            100                 105                 110

Lys Leu Ile Ser Val Glu Asp Leu Trp Lys Ala Trp Lys Ser Ser Glu
        115                 120                 125

Val Tyr Asn Trp Thr Val Asp Glu Val Ile Gln Trp Leu Ile Thr Tyr
    130                 135                 140

Val Glu Leu Pro Gln Tyr Glu Glu Thr Phe Arg Lys Leu Gln Leu Thr
145                 150                 155                 160

Gly His Ala Met Pro Arg Leu Ala Val Thr Asn Thr Thr Met Thr Gly
                165                 170                 175

Thr Val Leu Lys Met Thr Asp Arg Ser His Arg Gln Lys Leu Gln Leu
            180                 185                 190

Lys Ala Leu Asp Thr Val Leu Phe Gly Pro Pro Leu Leu Thr Arg His
        195                 200                 205

Asn His Leu Lys Asp Phe Met Leu Val Val Ser Ile Val Ile Gly Val
```

-continued

```
            210                 215                 220
Gly Gly Cys Trp Phe Ala Tyr Ile Gln Asn Arg Tyr Ser Lys Glu His
225                 230                 235                 240

Met Lys Lys Met Met Lys Asp Leu Glu Gly Leu His Arg Ala Glu Gln
            245                 250                 255

Ser Leu His Asp Leu Gln Glu Arg Leu His Lys Ala Gln Glu Glu His
            260                 265                 270

Arg Thr Val Glu Val Glu Lys Val His Leu Glu Lys Lys Leu Arg Asp
            275                 280                 285

Glu Ile Asn Leu Ala Lys Gln Glu Ala Gln Arg Leu Lys Glu Leu Arg
290                 295                 300

Glu Gly Thr Glu Asn Glu Arg Ser Arg Gln Lys Tyr Ala Glu Glu Glu
305                 310                 315                 320

Leu Glu Gln Val Arg Glu Ala Leu Arg Lys Ala Glu Lys Glu Leu Glu
            325                 330                 335

Ser His Ser Ser Trp Tyr Ala Pro Glu Ala Leu Gln Lys Trp Leu Gln
            340                 345                 350

Leu Thr His Glu Val Glu Val Gln Tyr Tyr Asn Ile Lys Lys Gln Asn
            355                 360                 365

Ala Glu Lys Gln Leu Leu Val Ala Lys Glu Gly Ala Glu Lys Ile Lys
            370                 375                 380

Lys Lys Arg Asn Thr Leu Phe Gly Thr Phe His Val Ala His Ser Ser
385                 390                 395                 400

Ser Leu Asp Asp Val Asp His Lys Ile Leu Thr Ala Lys Gln Ala Leu
            405                 410                 415

Ser Glu Val Thr Ala Ala Leu Arg Glu Arg Leu His Arg Trp Gln Gln
            420                 425                 430

Ile Glu Ile Leu Cys Gly Phe Gln Ile Val Asn Asn Pro Gly Ile His
            435                 440                 445

Ser Leu Val Ala Ala Leu Asn Ile Asp Pro Ser Trp Met Gly Ser Thr
            450                 455                 460

Arg Pro Asn Pro Ala His Phe Ile Met Thr Asp Asp Val Asp Asp Met
465                 470                 475                 480

Asp Glu Glu Ile Val Ser Pro Leu Ser Met Gln Ser Pro Ser Leu Gln
            485                 490                 495

Ser Ser Val Arg Gln Arg Leu Thr Glu Pro Gln His Gly Leu Gly Ser
            500                 505                 510

Gln Arg Asp Leu Thr His Ser Asp Ser Glu Ser Ser Leu His Met Ser
            515                 520                 525

Asp Arg Gln Arg Val Ala Pro Lys Pro Pro Gln Met Gly Arg Ala Ala
            530                 535                 540

Asp Glu Ala Leu Asn Ala Met Xaa Ser Asn Gly Ser His Arg Leu Ile
545                 550                 555                 560

Glu Gly Val His Pro Gly Ser Leu Val Glu Lys Leu Pro Asp Ser Pro
            565                 570                 575

Ala Leu Ala Lys Lys Thr Xaa Leu Ala Leu Asn His Gly Leu Asp Lys
            580                 585                 590

Ala His Ser Leu Met Glu Leu Asn Pro Ser Val Pro Pro Gly Gly Ser
            595                 600                 605

Pro Leu Leu Asp Ser Ser His Ser His Ser Pro Ser Ser Pro Asp Pro
            610                 615                 620

Asp Thr Pro Ser Pro Val Gly Asp Ser Arg Ala Leu Gln Gly Ser Arg
625                 630                 635                 640
```

```
Asn Thr Arg Ile Pro His Leu Ala Gly Lys Lys Ala Val Ala Glu Glu
                645                 650                 655

Asp Asn Gly Ser Ile Gly Glu Glu Thr Asp Ser Ser Pro Gly Arg Lys
            660                 665                 670

Lys Phe Pro Leu Lys Ile Phe Lys Lys Pro Leu Lys Lys
        675                 680                 685

<210> SEQ ID NO 91
<211> LENGTH: 21
<212> TYPE: RNA
<213> ORGANISM: Artificial Sequence
<220> FEATURE:
<223> OTHER INFORMATION: ratSTIM1-114 Primer

<400> SEQUENCE: 91
aagcagaguu uugccggauu g                                              21

<210> SEQ ID NO 92
<211> LENGTH: 21
<212> TYPE: RNA
<213> ORGANISM: Artificial Sequence
<220> FEATURE:
<223> OTHER INFORMATION: ratSTIM1-614 siRNA

<400> SEQUENCE: 92
aaggacuuca ugcugguggu g                                              21

<210> SEQ ID NO 93
<211> LENGTH: 2129
<212> TYPE: DNA
<213> ORGANISM: Homo sapiens
<220> FEATURE:
<221> NAME/KEY: misc_feature
<222> LOCATION: 1719, 1732, 1761, 1846, 2030
<223> OTHER INFORMATION: n is a, c, t or g
<300> PUBLICATION INFORMATION:
<308> DATABASE ACCESSION NUMBER: Genbank AF139917
<309> DATABASE ENTRY DATE: 2000-03-13

<400> SEQUENCE: 93
gagctcctgg atttaagcga tcatccccccc tcagcctgct gagtagctgg gaccacagaa    60
gccagatacc actcatggct aattaaaaaa atttttttg tagagatggg ggtcccactg     120
tgtttcccag gctggtcttg aactcatggg ctcaagtaat cctcccactt tggcctccca    180
gagtgctggg attagagata tgagtcactg cacccagccc catcttctct taatgacact    240
ccagcaatac taggcccatc tttctgcctg ctctccacag tccccaccac tccgtattac    300
tcctacctac ttttcttaat tgaattacct acctgcccat tttgccattt gaatttaaga    360
cccctggctc agagaatagg tctaggagaa cctaggtagg gtttcaactg ttctggtcaa    420
ttttccaata ttccggtatt agttttagt atctgagtgt tcaagtgaat taactcatgt    480
aatccagctt ttacagagaa cttactatgt gcagggtcta tggctgggtc ctagtgtcac    540
agagatgaat aaggcacagt ctctgacctg aaaagtggca atcactatct gttggggag    600 gggcagacag atgtaatggt ccaattttgg ccacagactg attttgaagg ggtgggcaga    660
gtaaaagttt ctaaggagac acattgagct gtatctggaa gagtaagaga ccagctacat    720
gaggaactgg gagcaggcga gagtgtttca tgcagaagca acagcagata caaaggctgt    780
gaggtggctg agtttgacgt ggttaggaac ttaacgaagg ctagtgtgac aggagcttaa    840
cagagccggg agagtggtag taggttacat tagccatgta ttttttatc aacggcctaa    900
```

```
ccccttaagcc aggcagctgt tgggcaaatt cgtgttccca gtcttcaggg gccttgctca    960
gaacaggtag ctggtttagc actgtcagtc agaggaggga ctgggcctga tccttttcccc   1020 tgcgtctggt gccaaggaca gggtagggca cagaggtttc agtcaagatc tgctgacagc   1080
acgcttgaga agagaacagg aagtgcaggc tttgttgaag gaggctcagg cgtggctctg   1140
tcttctttgg cgcactcatt ctcaagtcgc tgacacctcc tccaccagag aggtagctgg   1200
gagaatgaga tgcagggagg aagcatttac aggccccacc gaaaaacctt aaagggctga   1260
gagcttgagg gcaggtagga aaagggctt tgagagctaa gggagggcat cccacttagc    1320
ttggagggga agggaggcgg ggtcgggaaa gcagatggca ccctttagcc cagactcaag   1380
gaatgtgtag gggaatttta gctagagtgg tttggacatt tcattttgct ttctggcatc   1440
atcatttcct cagaaaacac tcgcaggccc cagtggccct cgtgggcctc ccccggggcg    1500
ggtcttagct tcactcggca accctctgca aaagagcagg ccctcccagg agcgccgagt   1560
cctgtctgca gtttgctgat tttcccacca ggggccgctg cgcatgggcg acgaagcgcg   1620
cgggttccca agccgcagag aggcggaagc cgattggttg tcaggcgagg cgcgagggcg   1680
gagcctggga actggccggg agttggggc tggagctcnc ccccgggccg anccgggtcg     1740
ggctgttgtc gcctcaggca nctcctggga ggctaacgtc gtgtcctggg cctctgttta   1800
gacagctcta gaactgaggc gagtggagca gcaccaaggc ccggagatcg gggcagggca   1860
gctgctgtcg ccgccgccgc aggcctgagt tacctgagta actgcgggtc agggacccgc   1920
ccgacggccc gcggttggcg ctgganactc tcggtgggga aagggaagct gggacttgat   1980
cctttgcgcg ggatcctggc aaagactagc gcgggccggg ggtccgggan agcccgctag   2040
gggcggggat tccggggagc cgtcttcacc ggttattccg ggatccagct gggcgctggg   2100
gctggcccgg gcttcgctgg ggaccgggc                                     2129

<210> SEQ ID NO 94
<211> LENGTH: 2694
<212> TYPE: DNA
<213> ORGANISM: Artificial Sequence
<220> FEATURE:
<223> OTHER INFORMATION: STIM1 Overexpression Construct

<400> SEQUENCE: 94
ggatcccgag gtgtccacat cagacgcatg ttgactgaga cctagagtca tggatgtatg      60
cgtccgtctt gccctgtggc tcctctgggg actcctcctg caccagggcc agagcctcag    120
ccatagtcac agtgagaagg cgacaggaac cagctcgggg gccaactctg aggagtccac    180
tgcagcagag ttttgccgaa ttgacaagcc cctgtgtcac agtgaggatg agaaactcag    240
cttcgaggca gtccgtaaca tccacaaact gatggacgat gatgccaatg gtgatgtgga    300
tgtggaagaa agtgatgagt tcctgaggga agacctcaat taccatgacc aacagtgaa    360 acacagcacc ttccatggtg aggataagct catcagcgtg gaggacctgt ggaaggcatg   420
gaagtcatca gaagtataca attggaccgt ggatgaggtg gtacagtggc tgatcacata   480
tgtggagctg cctcagtatg aggagacctt ccggaagctg cagctcagtg ccatgccat    540 gccaaggctg gctgtcacca acaccaccat gacagggact gtgctgaaga tgacagaccg   600
gagtcatcgg cagaagctgc agctgaaggc tctggatcaca gtgctctttg gcctcctct    660 cttgactcgc cataatcacc tcaaggactt catgctggtg gtgtctatcg ttattggtgt   720
gggcggctgc tggtttgcct atatccagaa ccgttactcc aaggagcaca tgaagaagat   780
gatgaaggac ttgagggggt tacaccgagc tgagcagagt ctgcatgacc ttcaggaaag   840
```

```
gctgcacaag gcccaggagg agcaccgcac agtggaggtg gagaaggtcc atctggaaaa      900
gaagctgcgc gatgagatca accttgctaa gcaggaagcc cagcggctga aggagctgcg      960
ggagggtact gagaatgagc ggagccgcca aaaatatgct gaggaggagt tggagcaggt     1020
tcgggaggcc ttgaggaaag cagagaagga gctagaatct cacagctcat ggtatgctcc     1080
agaggccctt cagaagtggc tgcagctgac acatgaggtg gaggtgcaat attacaacat     1140
caagaagcaa aatgctgaga agcagctgct ggtggccaag gagggggctg agaagataaa     1200
aaagaagaga aacacactct ttggcacctt ccacgtggcc cacagctctt ccctggatga     1260
tgtagatcat aaaattctaa cagctaagca agcactgagc gaggtgacag cagcattgcg     1320
ggagcgcctg caccgctggc aacagatcga gatcctctgt ggcttccaga ttgtcaacaa     1380
ccctggcatc cactcactgg tggctgccct caacatagac cccagctgga tgggcagtac     1440
acgcccaac cctgctcact tcatcatgac tgacgacgtg gatgacatgg atgaggagat     1500
tgtgtctccc ttgtccatgc agtcccctag cctgcagagc agtgttcggc agcgcctgac     1560
ggagccacag catggcctgg gatctcgagg ggatttgacc cattccgatt cggagtcctc     1620
cctccacatg agtgaccgcc agcgtgtggc ccccaaacct cctcagatga gccgtgctgc     1680
agacgaggct ctcaatgcca tgacttccaa tggcagccac cggctgatcg agggggtcca     1740
cccagggtct ctggtggaga aactgcctga cagccctgcc ctggccaaga aggcattact     1800
ggcgctgaac catgggctgg acaaggccca cagcctgatg gagctgagcc cctcagcccc     1860
acctggtggc tctccacatt tggattcttc ccgttctcac agcccagct ccccagaccc     1920
agacacacca tctccagttg gggacagccg agccctgcaa gccagccgaa acacacgcat     1980
tccccacctg gctggcaaga aggctgtggc tgaggaggat aatggctcta ttggcgagga     2040
aacagactcc agcccaggcc ggaagaagtt tcccctcaaa atctttaaga agcctcttaa     2100
gaagtaggca ggatggggtg gcagtaaagg gacagcttgt ccttccctgg gtgttctgtc     2160
tctccttccc tcccttcctt caagataact ggccccaaga gtggggcatg ggaagggctg     2220
gtccaggggt ctgggcactg tacatacctg cccctcatc cttgggtcct tcattattat      2280
ttattaactg accaccatgg cctgcctgcc ctgcctccgt cccaaccatg ggctgctgct     2340
gtcactccct ctccacttca gtgcatgtct tagttgctgt tccctcagct cccagctcca     2400
cctctgggt tcagcttctg tctctgctgt cccagttttg aggtttggtt tcttgtttct      2460
gtctcttgct ttcaggctcc tccctcccac cactccccaa cttcccctag cagttgcagg     2520
gaagatagga cgagtagctt ctgacatgtg tgcctcagat ctgttccacc ccactcacag     2580
tggttctgtt tgctccagac tggggctagg gcctaatctt tgaagtttgt tctttggtat     2640
tgatgtgggt cagaaggagc ctcatcctaa tctcactcag gcctccaggg atcc           2694

<210> SEQ ID NO 95
<211> LENGTH: 1999
<212> TYPE: DNA
<213> ORGANISM: Chinese hamster
<220> FEATURE:
<221> NAME/KEY: CDS
<222> LOCATION: (2)...(1999)

<400> SEQUENCE: 95 t gcc ctg tgg ctt ctt tgg ggg ctc ctc ctg cat cag ggc cat agc ctt      49
  Ala Leu Trp Leu Leu Trp Gly Leu Leu Leu His Gln Gly His Ser Leu
   1               5                  10                  15 agc cat agt cac agc gaa aag aat aca gga gcc ggc tct ggg acg act        97
```

|  |  |
|---|---|
| Ser His Ser His Ser Glu Lys Asn Thr Gly Ala Gly Ser Gly Thr Thr<br>            20                25                30 | |
| tca gag gag tcc act gaa gca gag ttt tgc cgg att gac aag ccc ctg<br>Ser Glu Glu Ser Thr Glu Ala Glu Phe Cys Arg Ile Asp Lys Pro Leu<br>    35                    40                45 | 145 |
| tgc cac agt gag gat gat aag ctc agc ttc gag gct gtc cgc aat att<br>Cys His Ser Glu Asp Asp Lys Leu Ser Phe Glu Ala Val Arg Asn Ile<br>      50                 55              60 | 193 |
| cac aag ctg atg gat gat gat gcc aac ggt gat gtg gat gtg gaa gaa<br>His Lys Leu Met Asp Asp Asp Ala Asn Gly Asp Val Asp Val Glu Glu<br>65               70                75              80 | 241 |
| agt gat gag ttc cta agg gaa gac ctc aat tac cat gat ccg aca gtg<br>Ser Asp Glu Phe Leu Arg Glu Asp Leu Asn Tyr His Asp Pro Thr Val<br>               85                90              95 | 289 |
| aag cac agc acc ttc cat ggc gag gat aag ctt atc agc gtg gag gat<br>Lys His Ser Thr Phe His Gly Glu Asp Lys Leu Ile Ser Val Glu Asp<br>           100                105             110 | 337 |
| ctg tgg aag gca tgg aag tca tca gaa gtg tac aac tgg act gtc gat<br>Leu Trp Lys Ala Trp Lys Ser Ser Glu Val Tyr Asn Trp Thr Val Asp<br>        115                 120              125 | 385 |
| gag gtg ata cag tgg ctg att acg tat gtg gag cta cct cag tat gag<br>Glu Val Ile Gln Trp Leu Ile Thr Tyr Val Glu Leu Pro Gln Tyr Glu<br>130                 135                140 | 433 |
| gag acc ttc cgg aag ttg caa ctt act ggc cat gcc atg cca agg cta<br>Glu Thr Phe Arg Lys Leu Gln Leu Thr Gly His Ala Met Pro Arg Leu<br>145               150                155             160 | 481 |
| gct gta acc aat acc acc atg aca ggg act gta ctg aag atg aca gat<br>Ala Val Thr Asn Thr Thr Met Thr Gly Thr Val Leu Lys Met Thr Asp<br>               165                170             175 | 529 |
| cgg agc cac agg cag aag cta cag ctg aag gcc ctg gat aca gtg ctc<br>Arg Ser His Arg Gln Lys Leu Gln Leu Lys Ala Leu Asp Thr Val Leu<br>           180                185             190 | 577 |
| ttt ggg cct cct ctc ttg act cga cat aat cac ctc aag gac ttc atg<br>Phe Gly Pro Pro Leu Leu Thr Arg His Asn His Leu Lys Asp Phe Met<br>        195               200              205 | 625 |
| ctg gtg gtg tct att gtt att ggt gtg ggc ggc tgc tgg ttt gcc tat<br>Leu Val Val Ser Ile Val Ile Gly Val Gly Gly Cys Trp Phe Ala Tyr<br>210                 215                220 | 673 |
| att cag aac cgt tac tcc aag gag cac atg aag aag atg atg aaa gat<br>Ile Gln Asn Arg Tyr Ser Lys Glu His Met Lys Lys Met Met Lys Asp<br>225               230                235             240 | 721 |
| ctg gaa ggg tta cac cga gct gag cag agt ctg cat gac ctg cag gaa<br>Leu Glu Gly Leu His Arg Ala Glu Gln Ser Leu His Asp Leu Gln Glu<br>               245                250             255 | 769 |
| agg ctc cac aag gcc cag gag gag cac cgc aca gtg gaa gta gag aag<br>Arg Leu His Lys Ala Gln Glu Glu His Arg Thr Val Glu Val Glu Lys<br>        260             265              270 | 817 |
| gtc cat ctg gag aag aag ctg cgt gat gag atc aat gtt gcc aag cag<br>Val His Leu Glu Lys Lys Leu Arg Asp Glu Ile Asn Val Ala Lys Gln<br>           275                280             285 | 865 |
| gaa gct cag agg ctg aag gag ctg agg gag ggt act gag aat gag agg<br>Glu Ala Gln Arg Leu Lys Glu Leu Arg Glu Gly Thr Glu Asn Glu Arg<br>290                 295                300 | 913 |
| agc cgc caa aaa tat gcc gag gaa gag ctg gag cag gtt cgg gag gcc<br>Ser Arg Gln Lys Tyr Ala Glu Glu Glu Leu Glu Gln Val Arg Glu Ala<br>305               310                315             320 | 961 |
| ttg agg aaa gca gag aag gag ctg gaa tca cac agc tca tgg tat gct<br>Leu Arg Lys Ala Glu Lys Glu Leu Glu Ser His Ser Ser Trp Tyr Ala<br>        325               330              335 | 1009 |

```
cct gag gcc ctt cag aag tgg ttg cag ctg acg cat gag gtg gag gtg    1057
Pro Glu Ala Leu Gln Lys Trp Leu Gln Leu Thr His Glu Val Glu Val
        340                 345                 350 cag tac tac aac atc aag aag caa aat gcc gag aag cag ctg ctg gtg    1105
Gln Tyr Tyr Asn Ile Lys Lys Gln Asn Ala Glu Lys Gln Leu Leu Val
                355                 360                 365 gcc aag gag ggg gct gag aaa ata aaa aag aag aga aac acg ctt ttt    1153
Ala Lys Glu Gly Ala Glu Lys Ile Lys Lys Lys Arg Asn Thr Leu Phe
370                 375                 380 ggt acc ttc cat gtg gcc cac agc tcc tcc ctg gat gat gtg gat cat    1201
Gly Thr Phe His Val Ala His Ser Ser Ser Leu Asp Asp Val Asp His
385                 390                 395                 400 aag atc tta act gct aag caa gca ctg agc gag gtg aca gca gca ctg    1249
Lys Ile Leu Thr Ala Lys Gln Ala Leu Ser Glu Val Thr Ala Ala Leu
                405                 410                 415 agg gag cgt ctg cac cgg tgg cag cag att gag atc ctc tgt ggc ttc    1297
Arg Glu Arg Leu His Arg Trp Gln Gln Ile Glu Ile Leu Cys Gly Phe
                420                 425                 430 cag att gtc aat aac cct ggc atc cac tcc ttg gtg gct gcc ctc aac    1345
Gln Ile Val Asn Asn Pro Gly Ile His Ser Leu Val Ala Ala Leu Asn
            435                 440                 445 ata gac ccc agc tgg atg ggc agt act cgg cct aac cct gcc cac ttc    1393
Ile Asp Pro Ser Trp Met Gly Ser Thr Arg Pro Asn Pro Ala His Phe
450                 455                 460 atc atg act gac gat gtg gat gac atg gat gag gag atc gtg tcg ccc    1441
Ile Met Thr Asp Asp Val Asp Asp Met Asp Glu Glu Ile Val Ser Pro
465                 470                 475                 480 ttg tcc atg cag tcc ccc agc ctg cag agc agt gtc cgg cag cgc ctg    1489
Leu Ser Met Gln Ser Pro Ser Leu Gln Ser Ser Val Arg Gln Arg Leu
                485                 490                 495 acg gag cca cag cat ggc ctg gga tct cag agg gat ttg acc cat tcc    1537
Thr Glu Pro Gln His Gly Leu Gly Ser Gln Arg Asp Leu Thr His Ser
                500                 505                 510 gat tcg gag tcc tcc ctc cac acg agt gac cgc cag cgt gtg gcc ccc    1585
Asp Ser Glu Ser Ser Leu His Thr Ser Asp Arg Gln Arg Val Ala Pro
            515                 520                 525 aag cct cct cag atg ggc cgt gct gca gat gag gct ctc aat gcc acg    1633
Lys Pro Pro Gln Met Gly Arg Ala Ala Asp Glu Ala Leu Asn Ala Thr
530                 535                 540 tct tcc aat ggt agc cat cgg ctg att gag ggg gtc cat cca gga tct    1681
Ser Ser Asn Gly Ser His Arg Leu Ile Glu Gly Val His Pro Gly Ser
545                 550                 555                 560 ctg gtg gag aaa ctg cct gac agc cct gct ctg gcc aag aag aca atc    1729
Leu Val Glu Lys Leu Pro Asp Ser Pro Ala Leu Ala Lys Lys Thr Ile
                565                 570                 575 ctg gcg ctg aac cat ggc cta gat aag gcc cac agc ctg atg gag ctg    1777
Leu Ala Leu Asn His Gly Leu Asp Lys Ala His Ser Leu Met Glu Leu
                580                 585                 590 aac ccc tca gtc cca cct ggt ggc tcc cca ctt ttg gat tct tcc cat    1825
Asn Pro Ser Val Pro Pro Gly Gly Ser Pro Leu Leu Asp Ser Ser His
            595                 600                 605 tct cat agt gcc agt tcc cca gac cca gac aca cct tca cca att ggg    1873
Ser His Ser Ala Ser Ser Pro Asp Pro Asp Thr Pro Ser Pro Ile Gly
610                 615                 620 gat agc cga gct ctg cag ggt agc cga aac aca cga att ccc cac ttg    1921
Asp Ser Arg Ala Leu Gln Gly Ser Arg Asn Thr Arg Ile Pro His Leu
625                 630                 635                 640 gct ggc aag aag gct gtg gct gag gag gat aat ggt tct att ggt gag    1969
Ala Gly Lys Lys Ala Val Ala Glu Glu Asp Asn Gly Ser Ile Gly Glu
                645                 650                 655
```

```
gag aca gac tct agc cca ggc agg aag aag                              1999
Glu Thr Asp Ser Ser Pro Gly Arg Lys Lys
        660                 665
```

<210> SEQ ID NO 96
<211> LENGTH: 666
<212> TYPE: PRT
<213> ORGANISM: Chinese hamster

<400> SEQUENCE: 96

```
Ala Leu Trp Leu Leu Trp Gly Leu Leu Leu His Gln Gly His Ser Leu
 1               5                  10                  15

Ser His Ser His Ser Glu Lys Asn Thr Gly Ala Gly Ser Gly Thr Thr
            20                  25                  30

Ser Glu Glu Ser Thr Glu Ala Glu Phe Cys Arg Ile Asp Lys Pro Leu
        35                  40                  45

Cys His Ser Glu Asp Asp Lys Leu Ser Phe Glu Ala Val Arg Asn Ile
    50                  55                  60

His Lys Leu Met Asp Asp Ala Asn Gly Asp Val Asp Val Glu Glu
65                  70                  75                  80

Ser Asp Glu Phe Leu Arg Glu Asp Leu Asn Tyr His Asp Pro Thr Val
                85                  90                  95

Lys His Ser Thr Phe His Gly Glu Asp Lys Leu Ile Ser Val Glu Asp
            100                 105                 110

Leu Trp Lys Ala Trp Lys Ser Ser Glu Val Tyr Asn Trp Thr Val Asp
        115                 120                 125

Glu Val Ile Gln Trp Leu Ile Thr Tyr Val Glu Leu Pro Gln Tyr Glu
    130                 135                 140

Glu Thr Phe Arg Lys Leu Gln Leu Thr Gly His Ala Met Pro Arg Leu
145                 150                 155                 160

Ala Val Thr Asn Thr Thr Met Thr Gly Thr Val Leu Lys Met Thr Asp
                165                 170                 175

Arg Ser His Arg Gln Lys Leu Gln Leu Lys Ala Leu Asp Thr Val Leu
            180                 185                 190

Phe Gly Pro Pro Leu Leu Thr Arg His Asn His Leu Lys Asp Phe Met
        195                 200                 205

Leu Val Val Ser Ile Val Ile Gly Val Gly Gly Cys Trp Phe Ala Tyr
    210                 215                 220

Ile Gln Asn Arg Tyr Ser Lys Glu His Met Lys Lys Met Met Lys Asp
225                 230                 235                 240

Leu Glu Gly Leu His Arg Ala Glu Gln Ser Leu His Asp Leu Gln Glu
                245                 250                 255

Arg Leu His Lys Ala Gln Glu Glu His Arg Thr Val Glu Val Glu Lys
            260                 265                 270

Val His Leu Glu Lys Lys Leu Arg Asp Glu Ile Asn Val Ala Lys Gln
        275                 280                 285

Glu Ala Gln Arg Leu Lys Glu Leu Arg Glu Gly Thr Glu Asn Glu Arg
    290                 295                 300

Ser Arg Gln Lys Tyr Ala Glu Glu Leu Glu Gln Val Arg Glu Ala
305                 310                 315                 320

Leu Arg Lys Ala Glu Lys Glu Leu Glu Ser His Ser Ser Trp Tyr Ala
                325                 330                 335

Pro Glu Ala Leu Gln Lys Trp Leu Gln Leu Thr His Glu Val Glu Val
            340                 345                 350
```

```
Gln Tyr Tyr Asn Ile Lys Lys Gln Asn Ala Glu Lys Gln Leu Leu Val
            355                 360                 365
Ala Lys Glu Gly Ala Glu Lys Ile Lys Lys Arg Asn Thr Leu Phe
    370                 375                 380
Gly Thr Phe His Val Ala His Ser Ser Ser Leu Asp Asp Val Asp His
385                 390                 395                 400
Lys Ile Leu Thr Ala Lys Gln Ala Leu Ser Glu Val Thr Ala Ala Leu
                405                 410                 415
Arg Glu Arg Leu His Arg Trp Gln Gln Ile Glu Ile Leu Cys Gly Phe
            420                 425                 430
Gln Ile Val Asn Asn Pro Gly Ile His Ser Leu Val Ala Ala Leu Asn
            435                 440                 445
Ile Asp Pro Ser Trp Met Gly Ser Thr Arg Pro Asn Pro Ala His Phe
450                 455                 460
Ile Met Thr Asp Asp Val Asp Asp Met Asp Glu Glu Ile Val Ser Pro
465                 470                 475                 480
Leu Ser Met Gln Ser Pro Ser Leu Gln Ser Ser Val Arg Gln Arg Leu
                485                 490                 495
Thr Glu Pro Gln His Gly Leu Gly Ser Gln Arg Asp Leu Thr His Ser
            500                 505                 510
Asp Ser Glu Ser Ser Leu His Thr Ser Asp Arg Gln Arg Val Ala Pro
        515                 520                 525
Lys Pro Pro Gln Met Gly Arg Ala Ala Asp Glu Ala Leu Asn Ala Thr
    530                 535                 540
Ser Ser Asn Gly Ser His Arg Leu Ile Glu Gly Val His Pro Gly Ser
545                 550                 555                 560
Leu Val Glu Lys Leu Pro Asp Ser Pro Ala Leu Ala Lys Lys Thr Ile
                565                 570                 575
Leu Ala Leu Asn His Gly Leu Asp Lys Ala His Ser Leu Met Glu Leu
            580                 585                 590
Asn Pro Ser Val Pro Pro Gly Gly Ser Pro Leu Leu Asp Ser Ser His
        595                 600                 605
Ser His Ser Ala Ser Ser Pro Asp Pro Asp Thr Pro Ser Pro Ile Gly
    610                 615                 620
Asp Ser Arg Ala Leu Gln Gly Ser Arg Asn Thr Arg Ile Pro His Leu
625                 630                 635                 640
Ala Gly Lys Lys Ala Val Ala Glu Glu Asp Asn Gly Ser Ile Gly Glu
                645                 650                 655
Glu Thr Asp Ser Ser Pro Gly Arg Lys Lys
            660                 665

<210> SEQ ID NO 97
<211> LENGTH: 1636
<212> TYPE: DNA
<213> ORGANISM: Rattus norvegicus

<400> SEQUENCE: 97
gattacgtat gtggagctgc cacagtatga ggagactttc cggaagttgc agcttactgg      60
ccatgccatg ccaaggctag ctgtaacaaa caccaccatg acagggactg tcctgaagat     120
gacagaccgg agccacaggc agaagctgca gctgaaggct ctggacacag tgctgttcgg     180
gcctcctctc ttgactcgcc acaatcacct gaaggacttc atgctggtgg tatctatcgt     240
gattggtgtg ggtggctgct ggtttgccta tatccagaac cgttactcta aggagcacat     300
gaagaaaatg atgaaggatc tggaaggatt gcaccgagct gagcagagtc tgcatgacct     360
```

-continued

```
tcaggaaagg ctgcacaagg cccaggagga gcaccgaaca gtggaagtag agaaggtcca      420
cctggagaag aagctgcgtg acgagatcaa tcttgccaag caggaagctc agcggctgaa      480
ggagctgagg gagggtaccg agaatgagag gagccgccaa aaatatgctg aggaagagct      540
ggagcaggtt cgggaggctt tgaggaaagc agagaaggag ctggaatcac acagctcctg      600
gtatgctcct gaggccctgc agaagtggct gcagctgaca catgaggtgg aggtgcagta      660
ctacaacatc aagaagcaaa atgcagagag gcagctgctg gtggccaagg aggggctga      720 gaaaataaaa aagaagagaa acacgctttt tggtaccttc catgtggccc acagctcgtc      780
cctggatgac gtggatcata aaatcttaac tgctaagcag gcactgagtg aggtgacagc      840
agccctgagg gagcgcctgc accggtggca gcagatcgag atcctctgtg gtttccagat      900
tgtcaataac cctggcatcc actccttggt ggccgcgctc aacatagatc ccagctggat      960
gggcagtacc cgcccttaacc ctgcccactt catcatgact gacgatgtgg atgcatggat      1020
tgaggagatc gtgtcgccct gtccatgca gtccccagc ctgcagagca gtgtccggca      1080
gcgcctgacg gagccacagc atggcctggg atctcagagg gatttgaccc attccgattc      1140
ggagtcctcc ctccacacga gtgaccgcca gcgtgtggcc cccaagcctc ctcagatggg      1200
ccgtgctgca gatgaggctc tcaatgccac gtcttccaat ggtagccatc ggctgattga      1260
gggggtccat ccaggatctc tggtggagaa actgcctgac agccctgctc tggccaagaa      1320
gacaatcctg gcgctgaacc atggcctaga taaggcccac agcctgatgg agctgaaccc      1380
ctcagtccca cctggtggct ccccactttt ggattcttcc cattctcata gccccagctc      1440
cccagaccca gacacaccat ctccagttgg ggacagccga gccctgcagg gtagccgaaa      1500
cacacgaatt ccccacttgg ctggcaagaa ggctatggct gaggaggata atggctctat      1560
tggtgaggag acagactcta gtccaggcag gaagaagttt cccctcaaaa ttttaagaa      1620 gcctcttaag aagtag                                                     1636
```

<210> SEQ ID NO 98
<211> LENGTH: 544
<212> TYPE: PRT
<213> ORGANISM: Rattus norvegicus

<400> SEQUENCE: 98

```
Ile Thr Tyr Val Glu Leu Pro Gln Tyr Glu Glu Thr Phe Arg Lys Leu
 1               5                  10                  15

Gln Leu Thr Gly His Ala Met Pro Arg Leu Ala Val Thr Asn Thr Thr
            20                  25                  30

Met Thr Gly Thr Val Leu Lys Met Thr Asp Arg Ser His Arg Gln Lys
        35                  40                  45

Leu Gln Leu Lys Ala Leu Asp Thr Val Leu Phe Gly Pro Pro Leu Leu
    50                  55                  60

Thr Arg His Asn His Leu Lys Asp Phe Met Leu Val Val Ser Ile Val
65                  70                  75                  80

Ile Gly Val Gly Gly Cys Trp Phe Ala Tyr Ile Gln Asn Arg Tyr Ser
                85                  90                  95

Lys Glu His Met Lys Lys Met Met Lys Asp Leu Glu Gly Leu His Arg
            100                 105                 110

Ala Glu Gln Ser Leu His Asp Leu Gln Glu Arg Leu His Lys Ala Gln
        115                 120                 125

Glu Glu His Arg Thr Val Glu Val Glu Lys Val His Leu Glu Lys Lys
    130                 135                 140
```

-continued

```
Leu Arg Asp Glu Ile Asn Leu Ala Lys Gln Glu Ala Gln Arg Leu Lys
145                 150                 155                 160

Glu Leu Arg Glu Gly Thr Glu Asn Glu Arg Ser Arg Gln Lys Tyr Ala
            165                 170                 175

Glu Glu Glu Leu Glu Gln Val Arg Glu Ala Leu Arg Lys Ala Glu Lys
        180                 185                 190

Glu Leu Glu Ser His Ser Ser Trp Tyr Ala Pro Glu Ala Leu Gln Lys
    195                 200                 205

Trp Leu Gln Leu Thr His Glu Val Glu Val Gln Tyr Tyr Asn Ile Lys
210                 215                 220

Lys Gln Asn Ala Glu Arg Gln Leu Leu Val Ala Lys Glu Gly Ala Glu
225                 230                 235                 240

Lys Ile Lys Lys Lys Arg Asn Thr Leu Phe Gly Thr Phe His Val Ala
                245                 250                 255

His Ser Ser Ser Leu Asp Asp Val Asp His Lys Ile Leu Thr Ala Lys
            260                 265                 270

Gln Ala Leu Ser Glu Val Thr Ala Ala Leu Arg Glu Arg Leu His Arg
        275                 280                 285

Trp Gln Gln Ile Glu Ile Leu Cys Gly Phe Gln Ile Val Asn Asn Pro
    290                 295                 300

Gly Ile His Ser Leu Val Ala Ala Leu Asn Ile Asp Pro Ser Trp Met
305                 310                 315                 320

Gly Ser Thr Arg Pro Asn Pro Ala His Phe Ile Met Thr Asp Asp Val
                325                 330                 335

Asp Asp Met Asp Glu Glu Ile Val Ser Pro Leu Ser Met Gln Ser Pro
            340                 345                 350

Ser Leu Gln Ser Ser Val Arg Gln Arg Leu Thr Glu Pro Gln His Gly
        355                 360                 365

Leu Gly Ser Gln Arg Asp Leu Thr His Ser Asp Ser Glu Ser Ser Leu
    370                 375                 380

His Thr Ser Asp Arg Gln Arg Val Ala Pro Lys Pro Pro Gln Met Gly
385                 390                 395                 400

Arg Ala Ala Asp Glu Ala Leu Asn Ala Thr Ser Ser Asn Gly Ser His
                405                 410                 415

Arg Leu Ile Glu Gly Val His Pro Gly Ser Leu Val Glu Lys Leu Pro
            420                 425                 430

Asp Ser Pro Ala Leu Ala Lys Lys Thr Ile Leu Ala Leu Asn His Gly
        435                 440                 445

Leu Asp Lys Ala His Ser Leu Met Glu Leu Asn Pro Ser Val Pro Pro
    450                 455                 460

Gly Gly Ser Pro Leu Leu Asp Ser Ser His Ser His Ser Pro Ser Ser
465                 470                 475                 480

Pro Asp Pro Asp Thr Pro Ser Pro Val Gly Asp Ser Arg Ala Leu Gln
                485                 490                 495

Gly Ser Arg Asn Thr Arg Ile Pro His Leu Ala Gly Lys Lys Ala Met
            500                 505                 510

Ala Glu Glu Asp Asn Gly Ser Ile Gly Glu Glu Thr Asp Ser Ser Pro
        515                 520                 525

Gly Arg Lys Lys Phe Pro Leu Lys Ile Phe Lys Lys Pro Leu Lys Lys
    530                 535                 540
```

<210> SEQ ID NO 99
<211> LENGTH: 64

<210> SEQ ID NO 99
<211> LENGTH: 64
<212> TYPE: DNA
<213> ORGANISM: Artificial Sequence
<220> FEATURE:
<223> OTHER INFORMATION: STIM1-1140 hairpin siRNA sense oligo

<400> SEQUENCE: 99
gatcccggct ctggatacag tgctcttcaa gagagagcac tgtatccaga gccttttttg    60
gaaa    64

<210> SEQ ID NO 100
<211> LENGTH: 64
<212> TYPE: DNA
<213> ORGANISM: Artificial Sequence
<220> FEATURE:
<223> OTHER INFORMATION: STIM1-1140 hairpin siRNA antisense oligo

<400> SEQUENCE: 100
agcttttcca aaaaggctc tggatacagt gctctctctt gaagagcact gtatccagag    60
ccgg    64

<210> SEQ ID NO 101
<211> LENGTH: 22
<212> TYPE: PRT
<213> ORGANISM: Artificial Sequence
<220> FEATURE:
<223> OTHER INFORMATION: human STIM1 peptide

<400> SEQUENCE: 101

His Lys Leu Met Asp Asp Asp Ala Asn Gly Asp Val Asp Val Glu Glu
1               5                   10                  15

Ser Asp Glu Phe Leu Arg
            20

<210> SEQ ID NO 102
<211> LENGTH: 22
<212> TYPE: PRT
<213> ORGANISM: Artificial Sequence
<220> FEATURE:
<223> OTHER INFORMATION: human STIM2 peptide

<400> SEQUENCE: 102

His Lys Gln Met Asp Asp Asp Lys Asp Gly Gly Ile Glu Val Glu Glu
1               5                   10                  15

Ser Asp Glu Phe Ile Arg
            20

<210> SEQ ID NO 103
<211> LENGTH: 22
<212> TYPE: PRT
<213> ORGANISM: Artificial Sequence
<220> FEATURE:
<223> OTHER INFORMATION: D. melanogaster STIM peptide

<400> SEQUENCE: 103

His Arg Gln Leu Asp Asp Asp Asn Gly Asn Ile Asp Leu Ser Glu
1               5                   10                  15

Ser Asp Asp Phe Leu Arg
            20

<210> SEQ ID NO 104
<211> LENGTH: 22
<212> TYPE: PRT
<213> ORGANISM: Artificial Sequence
<220> FEATURE:

```
<223> OTHER INFORMATION: C. elegans STIM peptide

<400> SEQUENCE: 104

His Arg Asp Met Asp Asp His Ser Gly Ser Ile Asp Arg Asn Glu
1               5                   10                  15

Ser Phe Gln Phe Met Lys
            20
```